United States Patent
Larsen et al.

(10) Patent No.: US 12,060,357 B2
(45) Date of Patent: Aug. 13, 2024

(54) 9-SUBSTITUTED AMINO TRIAZOLO QUINAZOLINE DERIVATIVES AS ADENOSINE RECEPTOR ANTAGONISTS, PHARMACEUTICAL COMPOSITIONS AND THEIR USE

(71) Applicant: Merck Sharp & Dohme LLC, Rahway, NJ (US)

(72) Inventors: Matthew A. Larsen, Templeton, CA (US); Amjad Ali, Freehold, NJ (US); Jared Cumming, Winchester, MA (US); Duane DeMong, Hanover, MA (US); Qiaolin Deng, Edison, NJ (US); Thomas H. Graham, Somerville, MA (US); Elisabeth Hennessy, Weston, MA (US); Andrew J. Hoover, Boston, MA (US); Ping Liu, Westfield, NJ (US); Kun Liu, Needham, MA (US); Umar Faruk Mansoor, Hopkinton, MA (US); Jianping Pan, Monmouth Junction, NJ (US); Christopher W. Plummer, Cranford, NJ (US); Aaron Sather, Melrose, MA (US); Uma Swaminathan, Auburndale, MA (US); Huijun Wang, Westfield, NJ (US); Yonglian Zhang, East Brunswick, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/657,515

(22) Filed: Mar. 31, 2022

(65) Prior Publication Data

US 2022/0220117 A1    Jul. 14, 2022

Related U.S. Application Data

(62) Division of application No. 16/695,367, filed on Nov. 26, 2019, now Pat. No. 11,312,719.

(60) Provisional application No. 62/774,077, filed on Nov. 30, 2018.

(51) Int. Cl.
C07D 487/04    (2006.01)
C07K 16/28    (2006.01)

(52) U.S. Cl.
CPC ........ C07D 487/04 (2013.01); C07K 16/2818 (2013.01)

(58) Field of Classification Search
CPC .... A61P 35/00; C07D 487/04; C07K 16/2818
See application file for complete search history.

(56) References Cited

U.S. PATENT DOCUMENTS

| | | | |
|---|---|---|---|
| 3,957,766 A | 5/1976 | Berger et al. |
| 4,713,383 A | 12/1987 | Francis et al. |
| 6,630,475 B2 | 10/2003 | Neustadt et al. |
| RE44,205 E | 5/2013 | Neustadt et al. |
| 10,870,663 B2 | 12/2020 | Dunham et al. |
| 11,104,675 B2 | 8/2021 | Jones et al. |
| 11,117,899 B2 | 9/2021 | Chen et al. |
| 11,312,705 B2 | 4/2022 | Lu et al. |
| 2001/0016954 A1 | 8/2001 | Atkinson et al. |
| 2004/0012471 A1 | 1/2004 | Kojima et al. |
| 2006/0037003 A1 | 2/2006 | Long et al. |
| 2006/0058320 A1 | 3/2006 | Iida et al. |
| 2014/0101113 A1 | 4/2014 | Zhang et al. |
| 2014/0101120 A1 | 4/2014 | Bryant |

(Continued)

FOREIGN PATENT DOCUMENTS

| | | |
|---|---|---|
| DE | 2109577 A1 | 9/1972 |
| EC | 1997SP2189 A | 7/1997 |

(Continued)

OTHER PUBLICATIONS

U.S. Appl. No. 16/695,367, filed Nov. 26, 2019.

(Continued)

*Primary Examiner* — Rei Tsang Shiao
(74) *Attorney, Agent, or Firm* — Sanjeev K. Mahanta; Alysia Finnegan

(57) ABSTRACT

In its many embodiments, the present invention provides certain 9-substituted amino triazolo quinazoline compounds of the structural Formula (I):

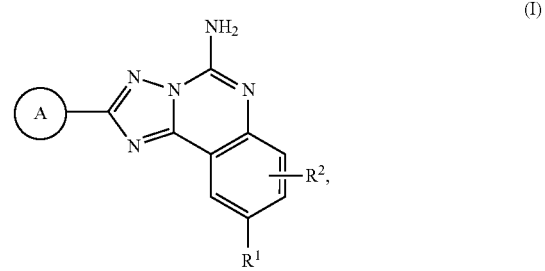

and pharmaceutically acceptable salts thereof, wherein, ring A, $R^1$ and $R^2$ are as defined herein, pharmaceutical compositions comprising one or more such compounds (alone and in combination with one or more other therapeutically active agents), and methods for their preparation and use, alone and in combination with other therapeutic agents, as antagonists of A2a and/or A2b receptors, and in the treatment of a variety of diseases, conditions, or disorders that are mediated, at least in part, by the adenosine A2a receptor and/or the adenosine A2b receptor.

28 Claims, No Drawings

(56) References Cited

U.S. PATENT DOCUMENTS

| | | |
|---|---|---|
| 2018/0362530 A1 | 12/2018 | Ali |
| 2022/0017501 A1 | 1/2022 | Burns et al. |
| 2022/0183295 A1 | 6/2022 | Burns et al. |

FOREIGN PATENT DOCUMENTS

| | | |
|---|---|---|
| EC | 2002SP4364 A | 11/2002 |
| WO | 1998003511 A1 | 1/1998 |
| WO | 2001092264 A1 | 12/2001 |
| WO | 2003032996 A1 | 4/2003 |
| WO | 03048165 A1 | 6/2003 |
| WO | 2003048164 A2 | 6/2003 |
| WO | 2004029056 A1 | 4/2004 |
| WO | 2004092177 A1 | 10/2004 |
| WO | 2005044819 A1 | 5/2005 |
| WO | 2005054245 A2 | 6/2005 |
| WO | 2005103055 A1 | 11/2005 |
| WO | 2006068954 A2 | 6/2006 |
| WO | 2007035542 A1 | 3/2007 |
| WO | 2007038284 A1 | 4/2007 |
| WO | 2008002596 A2 | 1/2008 |
| WO | 2008121748 A2 | 10/2008 |
| WO | 2008149168 A1 | 12/2008 |
| WO | 2009077741 A2 | 6/2009 |
| WO | 2009111442 A1 | 9/2009 |
| WO | 2011060207 A1 | 5/2011 |
| WO | 20120135084 A1 | 10/2012 |
| WO | 2014101113 A1 | 7/2014 |
| WO | 2014101120 A1 | 7/2014 |
| WO | 2014101373 A1 | 7/2014 |
| WO | 2014105664 A1 | 7/2014 |
| WO | 2014105666 A1 | 7/2014 |
| WO | 2015027431 A1 | 3/2015 |
| WO | 2015031221 A1 | 3/2015 |
| WO | 2016081290 A1 | 5/2016 |
| WO | 2016089796 A1 | 6/2016 |
| WO | 2016126570 A1 | 8/2016 |
| WO | 2016/209787 A1 | 12/2016 |
| WO | 2016200717 A1 | 12/2016 |
| WO | 2017008205 A1 | 1/2017 |
| WO | 2017011214 A1 | 1/2017 |
| WO | 2018136700 A1 | 7/2018 |
| WO | 2018166493 A1 | 9/2018 |
| WO | 2018184590 A1 | 10/2018 |
| WO | 2019002606 A1 | 1/2019 |
| WO | 2019118313 A1 | 6/2019 |
| WO | 2019222677 A1 | 11/2019 |
| WO | 2020106558 A1 | 5/2020 |
| WO | 2020106560 A1 | 5/2020 |
| WO | 2020112706 A1 | 6/2020 |

OTHER PUBLICATIONS

Adenot, M., Interest of cluster significance analysis in structure-affinity relationahips for non-xanthine heterocyclic antagonists of adenosine, Eur. J. Med. Chem., 1997, 493-504, 32.

Fishman, P., Adenosine Receptors and Cancer, Handbook of Experimental Pharmacology, 2009, 399-441, 193.

Gessi, Stefania et al., Inhibition of A2A Adenosine Receptor Signaling in Cancer Cells Proliferation by the Novel Antagonist TP455, Frontiers in Pharmacology, 2017, 1-13, 8.

Neustadt, B.R. et al., Potent and selective adeonsine A2A receptor antagonists: 1,2,4-Triazolo[l,5-c]pyrimidines, Bioorganic & Medicinal Chemistry Letters, 2009, 967-971, 19.

Vu, C.B. et al., Tramino derivatives of triazolotriazine and triazolopyrimidine as adenosine A2A receptor antagonists, Bioorganic & Medicinal Chemistry Letters, 2004, 4835-4838, 14.

Francis, John E. et al., Structure-Activity Profile of a Series of Novel Triazoloquinazoline Adenosine Antagonists, J. Med. Chem., 1988, 1014-1020, 31.

9-SUBSTITUTED AMINO TRIAZOLO QUINAZOLINE DERIVATIVES AS ADENOSINE RECEPTOR ANTAGONISTS, PHARMACEUTICAL COMPOSITIONS AND THEIR USE

CROSS-REFERENCE TO RELATED APPLICATIONS

This application is a Divisional of co-pending U.S. application Ser. No. 16/695,367, filed on Nov. 26, 2019, which claims priority to U.S. Provisional Patent Application No. 62/774,077, filed on Nov. 30, 2018, the content of each of which is hereby incorporated by reference herein in its entirety.

FIELD OF THE INVENTION

The present invention relates to novel compounds that inhibit at least one of the A2a and A2b adenosine receptors, and pharmaceutically acceptable salts thereof, and compositions comprising such compound(s) and salts, methods for the synthesis of such compounds, and their use in the treatment of a variety of diseases, conditions, or disorders that are mediated, at least in part, by the adenosine A2a receptor and/or the adenosine A2b receptor. Such diseases, conditions, and disorders include but are not limited to cancer and immune-related disorders. The invention further relates to combination therapies, including but not limited to a combination comprising a compound of the invention and a PD-1 antagonist.

BACKGROUND OF THE INVENTION

Adenosine is a purine nucleoside compound comprised of adenine and ribofuranose, a ribose sugar molecule. Adenosine occurs naturally in mammals and plays important roles in various biochemical processes, including energy transfer (as adenosine triphosphate and adenosine monophosphate) and signal transduction (as cyclic adenosine monophosphate). Adenosine also plays a causative role in processes associated with vasodilation, including cardiac vasodilation. It also acts as a neuromodulator (e.g., it is thought to be involved in promoting sleep). In addition to its involvement in these biochemical processes, adenosine is used as a therapeutic antiarrhythmic agent to treat supraventricular tachycardia and other indications.

The adenosine receptors are a class of purinergic G protein-coupled receptors with adenosine as the endogenous ligand. The four types of adenosine receptors in humans are referred to as A1, A2a, A2b, and A3. Modulation of A1 has been proposed for the management and treatment of neurological disorders, asthma, and heart and renal failure, among others. Modulation of A3 has been proposed for the management and treatment of asthma and chronic obstructive pulmonary diseases, glaucoma, cancer, stroke, and other indications. Modulation of the A2a and A2b receptors are also believed to be of potential therapeutic use.

In the central nervous system, A2a antagonists are believed to exhibit antidepressant properties and to stimulate cognitive functions. A2a receptors are present in high density in the basal ganglia, known to be important in the control of movement. Hence, A2a receptor antagonists are believed to be useful in the treatment of depression and to improve motor impairment due to neurodegenerative diseases such as Parkinson's disease, senile dementia (as in Alzheimer's disease), and in various psychoses of organic origin.

In the immune system, adenosine signaling through A2a receptors and A2b receptors, expressed on a variety of immune cells and endothelial cells, has been established as having an important role in protecting tissues during inflammatory responses. In this way (and others), tumors have been shown to evade host responses by inhibiting immune function and promoting tolerance. (See, e.g., Fishman, P., et al., Handb. Exp. Pharmacol. (2009) 193:399-441). Moreover, A2a and A2b cell surface adenosine receptors have been found to be upregulated in various tumor cells. Thus, antagonists of the A2a and/or A2b adenosine receptors represent a new class of promising oncology therapeutics. For example, activation of A2a adenosine receptors results in the inhibition of the immune response to tumors by a variety of cell types, including but not limited to: the inhibition of natural killer cell cytotoxicity, the inhibition of tumor-specific CD4+/CD8+ activity, promoting the generation of LAG-3 and Foxp3+ regulatory T-cells, and mediating the inhibition of regulatory T-cells. Adenosine A2a receptor inhibition has also been shown to increase the efficacy of PD-1 inhibitors through enhanced anti-tumor T cell responses. As each of these immunosuppressive pathways has been identified as a mechanism by which tumors evade host responses, a cancer immunotherapeutic regimen that includes an antagonist of the A2a and/or A2b receptors, alone or together with one or more other therapeutic agents designed to mitigate immune suppression, may result in enhanced tumor immunotherapy. (See, e.g., P. Beavis, et al., Cancer Immunol. Res. DOI: 10.1158/2326-6066. CIR-14-0211, Feb. 11, 2015; Willingham, S B., et al., Cancer Immunol. Res., 6(10), 1136-49; and Leone R D, et al., Cancer Immunol. Immunother., August 2018, Vol. 67, Issue 8, 1271-1284).

Cancer cells release ATP into the tumor microenvironment when treated with chemotherapy and radiation therapy, which is subsequently converted to adenosine. (See Martins, I., et al., Cell Cycle, vol. 8, issue 22, pp. 3723 to 3728.) The adenosine can then bind to A2a receptors and blunt the anti-tumor immune response through mechanisms such as those described above. The administration of A2a receptor antagonists during chemotherapy or radiation therapy has been proposed to lead to the expansion of the tumor-specific T-cells while simultaneously preventing the induction of tumor-specific regulatory T-cells. (Young, A., et al., Cancer Discovery (2014) 4:879-888).

The combination of an A2a receptor antagonist with anti-tumor vaccines is believed to provide at least an additive therapeutic effect in view of their different mechanisms of action. Further, A2a receptor antagonists may be useful in combination with checkpoint blockers. By way of example, the combination of a PD-1 inhibitor and an adenosine A2a receptor inhibitor is thought to mitigate the ability of tumors to inhibit the activity of tumor-specific effector T-cells. (See, e.g., Willingham, S B., et al., Cancer Immunol. Res.; 6(10), 1136-49; Leone, R D., et al., Cancer Immunol. Immunother., August 2018, Vol. 67, Issue 8, pp. 1271-1284; Fishman, P., et al., Handb. Exp. Pharmacol. (2009) 193:399-441; and Sitkovsky, M V., et al., (2014) Cancer Immunol. Res 2:598-605.)

The A2b receptor is a G protein-coupled receptor found in various cell types. A2b receptors require higher concentrations of adenosine for activation than the other adenosine receptor subtypes, including A2a. (Fredholm, B B., et al., Biochem. Pharmacol. (2001) 61:443-448). Conditions which activate A2b have been seen, for example, in tumors where hypoxia is observed. The A2b receptor may thus play an important role in pathophysiological conditions associated with massive adenosine release. While the pathway(s) associated with A2b receptor-mediated inhibition are not well understood, it is believed that the inhibition of A2b receptors (alone or together with A2a receptors) may block pro-tumorigenic functions of adenosine in the tumor microenvironment, including suppression of T-cell function and angiogenesis, and thus expand the types of cancers treatable by the inhibition of these receptors.

A2b receptors are expressed primarily on myeloid cells. The engagement of A2b receptors on myeloid derived suppressor cells (MDSCs) results in their expansion in vitro (Ryzhov, S. et al., J. Immunol. 2011, 187:6120-6129). MDSCs suppress T-cell proliferation and anti-tumor immune responses. Selective inhibitors of A2b receptors and A2b receptor knockouts have been shown to inhibit tumor growth in mouse models by increasing MDSCs in the tumor microenvironment (Iannone, R., et al., Neoplasia Vol. 13 No. 12, (2013) pp. 1400-1409; Ryzhov, S., et al., Neoplasia (2008) 10: 987-995). Thus, A2b receptor inhibition has become an attractive biological target for the treatment of a variety of cancers involving myeloid cells. Examples of cancers that express A2b receptors can be readily obtained through analysis of the publicly available TCGA database. Such cancers include lung, colorectal, head and neck, and cervical cancer, among others, and are discussed in further detail below.

Angiogenesis plays an important role in tumor growth. The angiogenesis process is highly regulated by a variety of factors and is triggered by adenosine under particular circumstances that are associated with hypoxia. The A2b receptor is expressed in human microvascular endothelial cells, where it plays an important role in the regulation of the expression of angiogenic factors such as the vascular endothelial growth factor (VEGF). In certain tumor types, hypoxia has been observed to cause an upregulation of the A2b receptors, suggesting that inhibition of A2b receptors may limit tumor growth by limiting the oxygen supply to the tumor cells. Furthermore, experiments involving adenylate cyclase activation indicate that A2b receptors are the sole adenosine receptor subtype in certain tumor cells, suggesting that A2b receptor antagonists may exhibit effects on particular tumor types. (See, e.g., Feoktistov, I., et al., (2003) Circ. Res. 92:485-492; and P. Fishman, P., et al., Handb. Exp. Pharmacol. (2009) 193:399-441).

In view of their promising and varied therapeutic potential, there remains a need in the art for potent and selective inhibitors of the A2a and/or A2b adenosine receptors, for use alone or in combination with other therapeutic agents. The present invention addresses this and other needs.

SUMMARY OF THE INVENTION

In one aspect, the present invention provides compounds (hereinafter referred to as compounds of the invention) which, surprisingly and advantageously, have been found to be inhibitors of the adenosine A2a receptor and/or the adenosine A2b receptor. The compounds of the invention have a structure in accordance with the structural Formula (I):

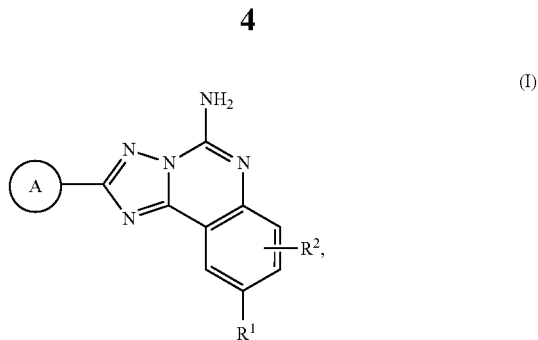

or a pharmaceutically acceptable salt thereof, wherein ring A, $R^1$, and $R^2$ are as defined below.

In another aspect, the present invention provides pharmaceutical compositions comprising at least one compound of the invention, or a pharmaceutically acceptable salt thereof, in a pharmaceutically acceptable carrier or diluent. Such compositions according to the invention may optionally further include one or more additional therapeutic agents as described herein.

In another aspect, the present invention provides a method for treating or preventing a disease, condition, or disorder that is mediated, at least in part, by the adenosine A2a receptor and/or the adenosine A2b receptor in a subject (e.g., an animal or human) in need thereof, said method comprising administering to the subject a therapeutically effective amount of at least one compound of the invention, or a pharmaceutically acceptable salt thereof, alone or in combination with one or more additional therapeutic agents. These and other aspects and embodiments of the invention are described more fully below.

DETAILED DESCRIPTION OF THE INVENTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I):

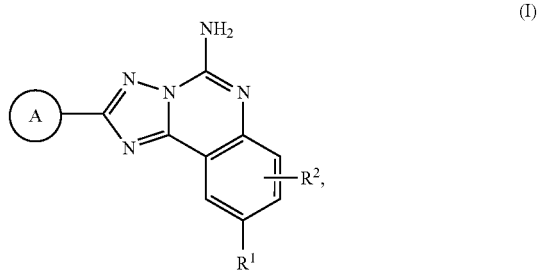

or a pharmaceutically acceptable salt thereof, wherein:
$R^1$ is selected from F, Cl, $(C_1\text{-}C_6)$alkyl, and $O(C_1\text{-}C_6)$alkyl;
$R^2$ is selected from H, F, Cl, $(C_1\text{-}C_6)$alkyl, and $O(C_1\text{-}C_6)$alkyl;

ring A is a moiety selected from:

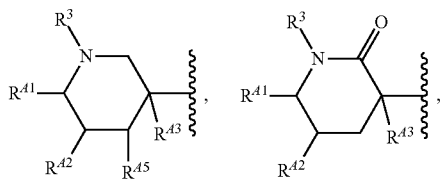

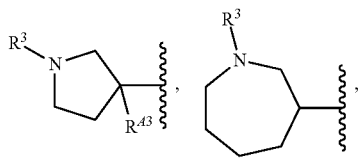

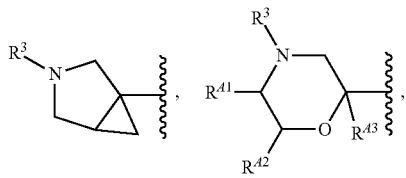

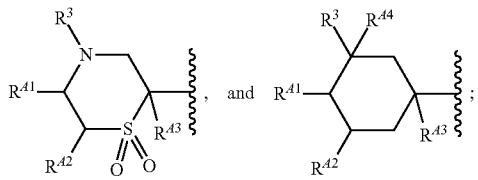

R³ is selected from pyrazolyl, triazolyl, and pyridinyl, wherein said pyrazolyl and said triazolyl, are substituted with 1 or 2 $R^{3A}$ groups, and wherein said pyridinyl is substituted with 1, 2, or 3 $R^{3A}$ groups, wherein:

each $R^{3A}$ is independently selected from $(C_1-C_6)$alkyl, $O(C_1-C_6)$alkyl, $(C_1-C_6)$alkyl-OH, $(C_1-C_6)$haloalkyl, $O(C_1-C_6)$haloalkyl, oxo, $(C_1-C_4)$alkylC(O)$(C_1-C_3)$alkyl, $(C_1-C_4)$alkylCH(OH)$(C_1-C_3)$alkyl, $(C_1-C_4)$alkylS(O)$_2(C_1-C_3)$alkyl, —$(CH_2)_n(C_3-C_7)$cycloalkyl, and —$(CH_2)_n$4-7 membered monocyclic heterocycloalkyl comprising 1 or 2 ring heteroatoms selected from oxygen and nitrogen, wherein said $(C_3-C_7)$cycloalkyl, and said 4-7 membered monocyclic heterocycloalkyl are each unsubstituted or substituted with 1, 2, or 3 groups independently selected from F, Cl, OH, $(C_1-C_6)$alkyl, and $(C_1-C_6)$haloalkyl;

n is 0, 1, or 2;

$R^{41}$ is selected from H, and $(C_1-C_4)$alkyl;

$R^{42}$ is selected from H, F, and $(C_1-C_4)$alkyl;

$R^{43}$ is selected from H, F, and $(C_1-C_4)$alkyl;

$R^{44}$ is selected from H and OH; and $R^{45}$ is selected from H, F, and $(C_1-C_4)$alkyl.

In another embodiment, the compounds of the invention have the structural Formula (I.1):

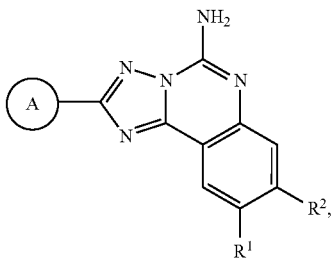

(I.1)

or a pharmaceutically acceptable salt thereof, wherein ring A, $R^1$, and $R^2$ are as defined in Formula (I).

In another embodiment, the compounds of the invention have the structural Formula (I.2):

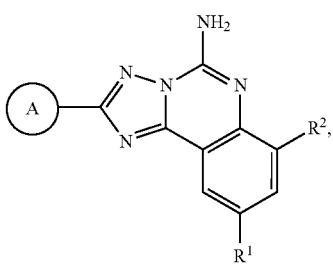

(I.2)

or a pharmaceutically acceptable salt thereof, wherein ring A, $R^1$, and $R^2$ are as defined in Formula (I).

In another embodiment, in each of Formulas (I), (I.1), and (I.2):

$R^1$ is selected from F, Cl, and $OCH_3$;

$R^2$ is selected from H, F, Cl, $CH_3$, and $OCH_3$.

In another embodiment, in each of Formulas (I), (I.1), and (I.2):

$R^1$ is F; and $R^2$ is selected from H, F, Cl, $CH_3$, and $OCH_3$.

In another embodiment, in each of Formulas (I), (I.1), and (I.2):

$R^1$ is Cl; and $R^2$ is selected from H, F, Cl, $CH_3$, and $OCH_3$.

In another embodiment, in each of Formulas (I), (I.1), and (I.2):

$R^1$ is F; and $R^2$ is $OCH_3$.

In another embodiment, in each of Formulas (I), (I.1), and (I.2):

$R^1$ is F; and $R^2$ is F.

In another embodiment, in each of Formulas (I), (I.1), and (I.2):

$R^1$ is F; and $R^2$ is H.

In another embodiment, in each of Formulas (I), (I.1), and (I.2):

ring A is a moiety selected from:

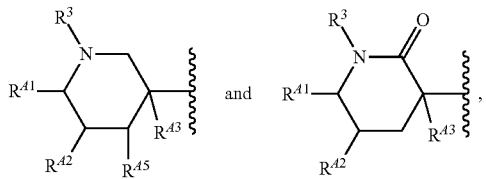

wherein R³, R^{A1}, R^{A2}, R^{A3}, and R^{A5} are as defined in Formula (I); and wherein R¹ and R² are as defined in Formula (I) or as defined in any of the alternative embodiments of R¹ and R² described above.

In another embodiment, in each of Formulas (I), (I.1), and (I.2):

ring A is a moiety selected from:

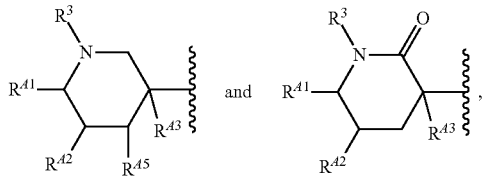

wherein:
R³ is selected from

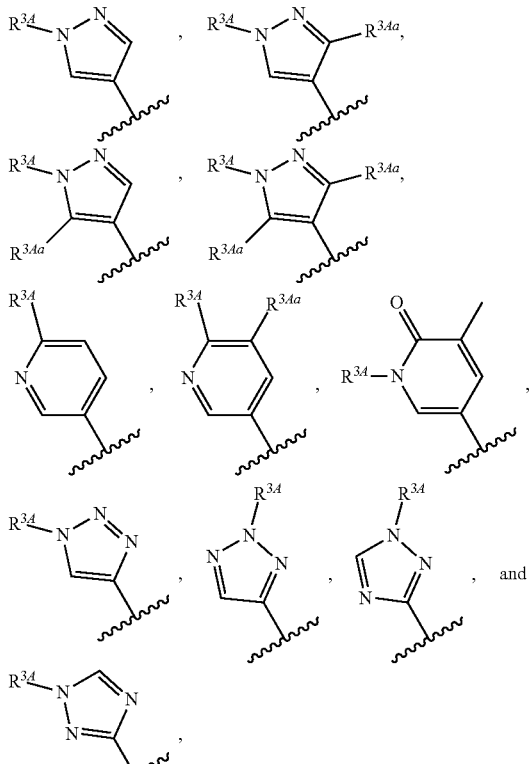

wherein:
each R^{3A} is as defined in Formula (I);
each R^{Aa} is independently selected from $(C_1-C_4)$alkyl, $O(C_1-C_4)$alkyl, $(C_1-C_4)$haloalkyl, and $O(C_1-C_4)$haloalkyl;
R^{A1}, R^{A2}, R^{A3}, and R^{A5} are as defined in Formula (I); and
R¹ and R² are as defined in Formula (I) or as defined in any of the alternative embodiments of R¹ and R² described above.

In another embodiment, in each of Formulas (I), (I.1), and (I.2):

ring A is a moiety selected from:

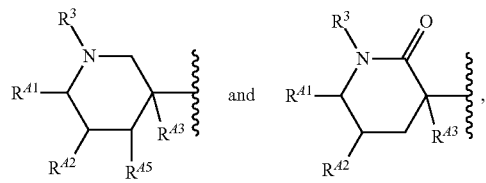

wherein:
R³ is selected from

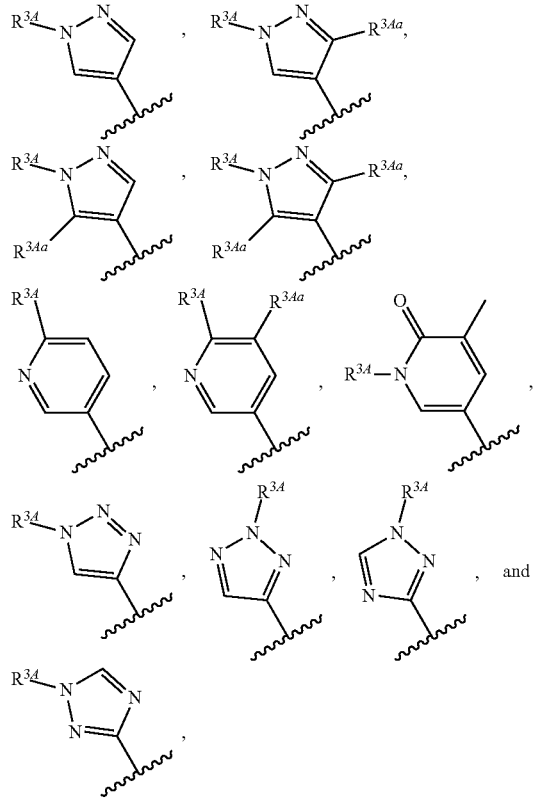

wherein:
each R^{3A} is a moiety selected from:

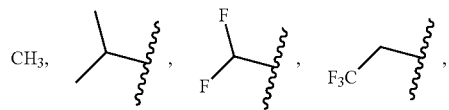

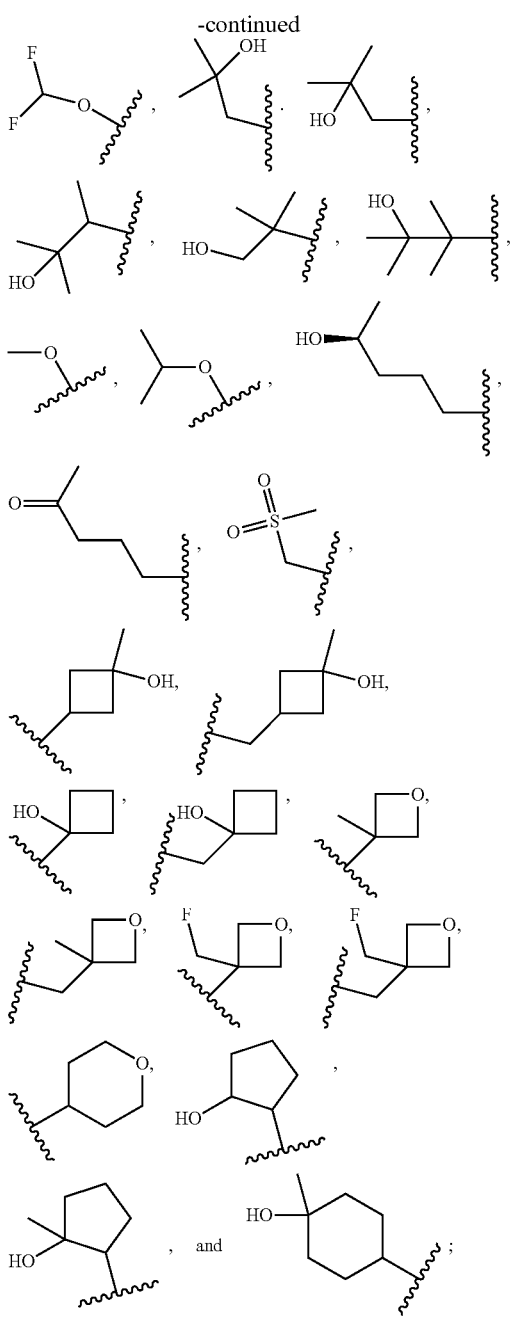

each $R^{3Aa}$ is independently selected from $(C_1-C_4)$alkyl, $O(C_1-C_4)$alkyl, $(C_1-C_4)$haloalkyl, and $O(C_1-C_4)$haloalkyl;

$R^{A1}$, $R^{A2}$, $R^{A3}$, and $R^{A5}$ are as defined in Formula (I); and $R^1$ and $R^2$ are as defined in Formula (I) or as defined in any of the alternative embodiments of $R^1$ and $R^2$ described above.

In an alternative of the immediately preceding embodiment:

$R^{A1}$ is selected from H, CH$_3$, and CH$_2$CH$_3$;

$R^{A2}$ is selected from H, F, CH$_3$, and CH$_2$CH$_3$;

$R^{A3}$ is selected from H and F; and $R^{A5}$ is H.

In another alternative of the immediately preceding embodiment:

$R^{A1}$ is selected from H and CH$_3$;

$R^{A2}$ is H;

$R^{A3}$ is H; and $R^{A5}$ is H.

In another alternative of the immediately preceding embodiment:

$R^{A1}$ is H;

$R^{A2}$ is H;

$R^{A3}$ is H; and $R^{A5}$ is H.

In another embodiment, in each of Formulas (I), (I.1), and (I.2):

ring A is the moiety:

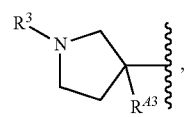

wherein $R^3$ and $R^{A3}$ are as defined in Formula (I); and wherein $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

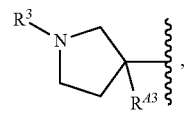

wherein:

$R^3$ is selected from

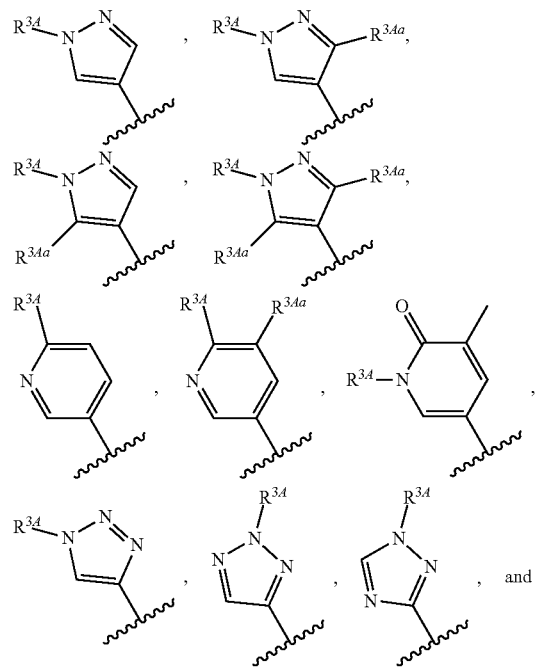

-continued

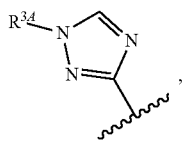

wherein:

each $R^{3A}$ is as defined in Formula (I);

each $R^{3Aa}$ is independently selected from $(C_1-C_4)$alkyl, $O(C_1-C_4)$alkyl, $(C_1-C_4)$haloalkyl, and $O(C_1-C_4)$haloalkyl;

$R^{43}$ is as defined in Formula (I); and $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

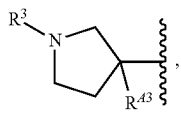

wherein:

$R^3$ is selected from

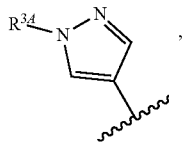

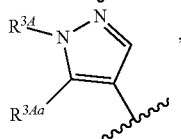

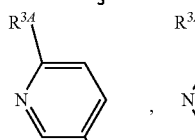

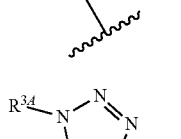

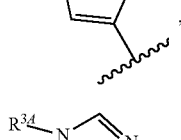

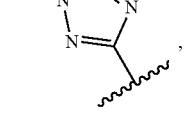

wherein:

each $R^{3A}$ is a moiety selected from:

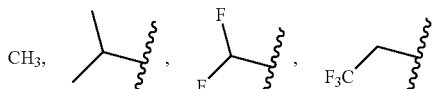

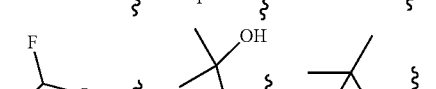

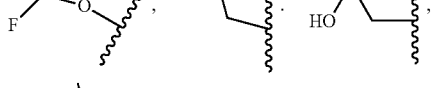

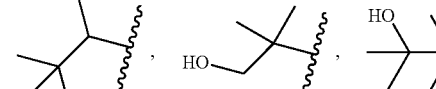

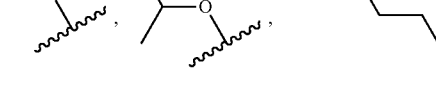

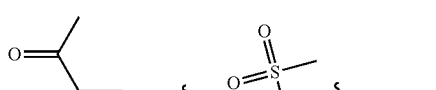

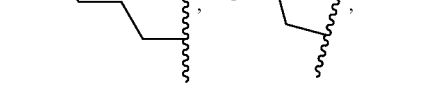

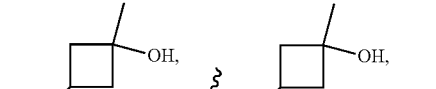

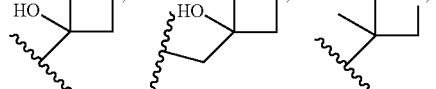

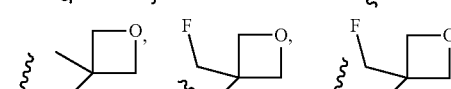

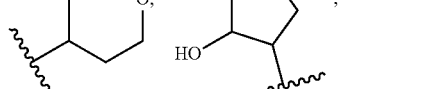

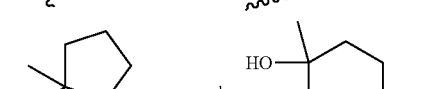

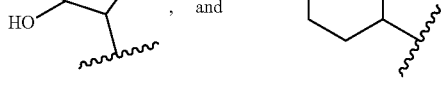

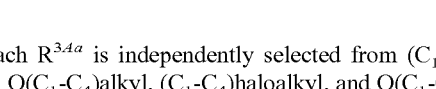

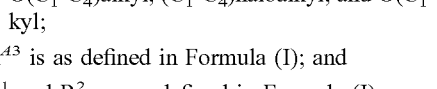

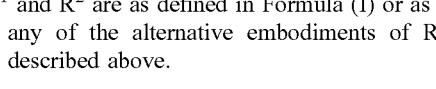

each $R^{3Aa}$ is independently selected from $(C_1-C_4)$alkyl, $O(C_1-C_4)$alkyl, $(C_1-C_4)$haloalkyl, and $O(C_1-C_4)$haloalkyl;

$R^{43}$ is as defined in Formula (I); and $R^1$ and $R^2$ are as defined in Formula (I) or as defined in any of the alternative embodiments of $R^1$ and $R^2$ described above.

In an alternative of the immediately preceding embodiment:

$R^{43}$ is selected from H and F.

In another alternative of the immediately preceding embodiment:

$R^{43}$ is H.

In another embodiment, in each of Formulas (I), (I.1), and (I.2):

ring A is the moiety:

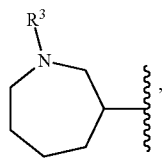

wherein $R^3$ is as defined in Formula (I); and wherein $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

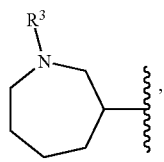

wherein:

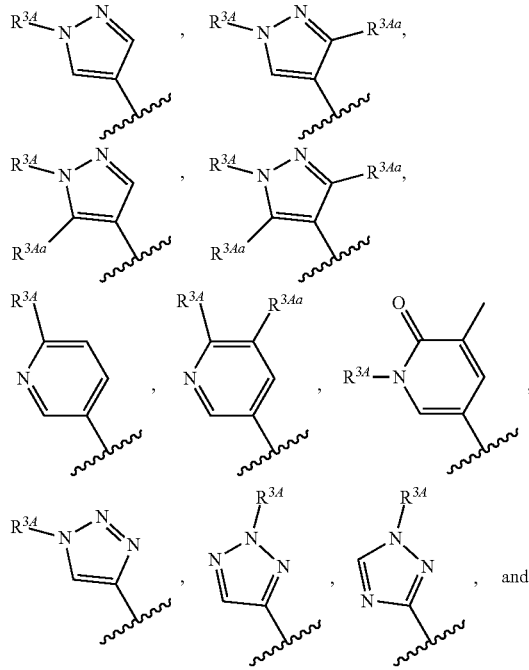

$R^3$ is selected from

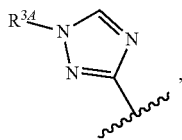

wherein:

each $R^{3A}$ is as defined in Formula (I);

each $R^{3Aa}$ is independently selected from $(C_1\text{-}C_4)$alkyl, $O(C_1\text{-}C_4)$alkyl, $(C_1\text{-}C_4)$haloalkyl, and $O(C_1\text{-}C_4)$haloalkyl; and $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

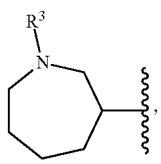

wherein:

$R^3$ is selected from

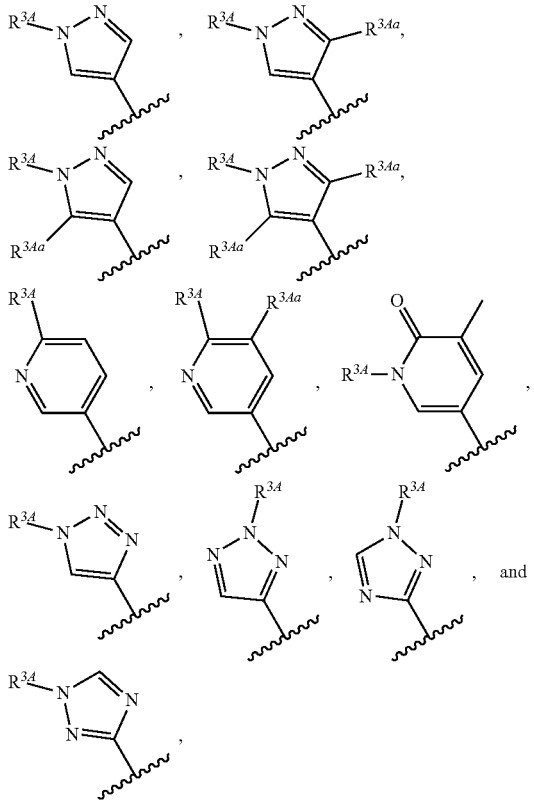

wherein:

each $R^{3A}$ is a moiety selected from:

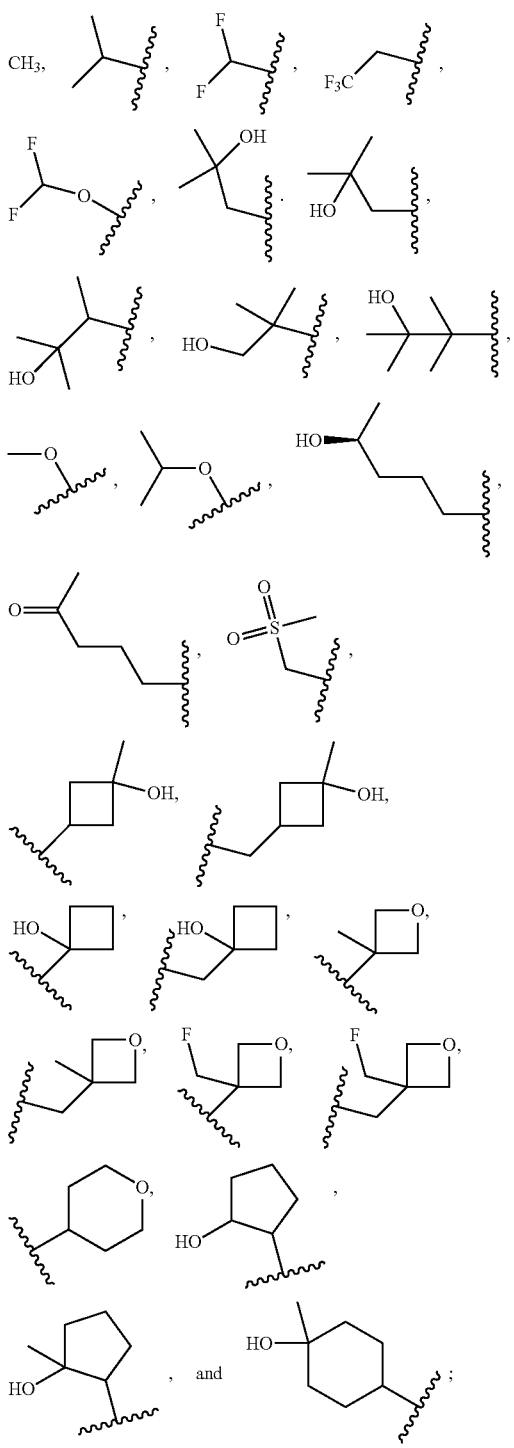

each $R^{3Aa}$ is independently selected from $(C_1-C_4)$alkyl, $O(C_1-C_4)$alkyl, $(C_1-C_4)$haloalkyl, and $O(C_1-C_4)$haloalkyl; and $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

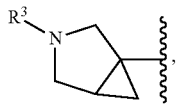

wherein $R^3$ is as defined in Formula (I); and wherein $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

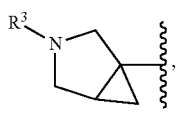

wherein:

$R^3$ is selected from

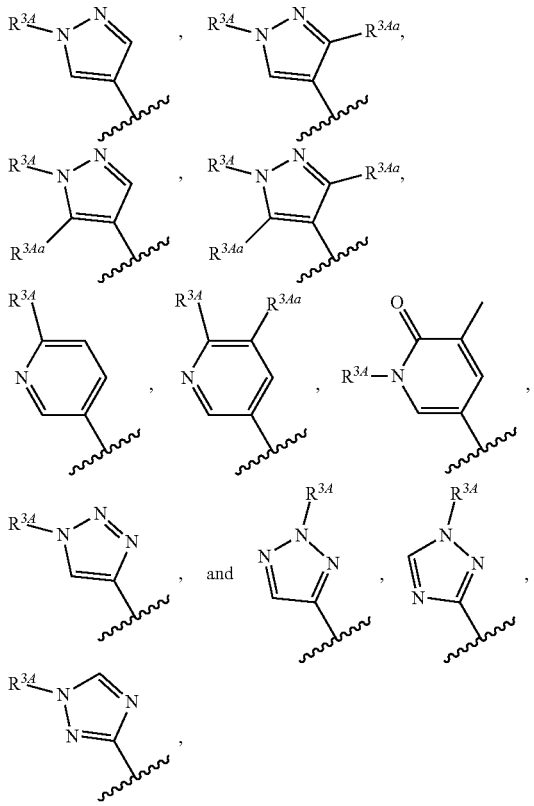

wherein:

each $R^{3A}$ is as defined in Formula (I);

each $R^{3Aa}$ is independently selected from $(C_1-C_4)$alkyl, $O(C_1-C_4)$alkyl, $(C_1-C_4)$haloalkyl, and $O(C_1-C_4)$haloalkyl; and $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

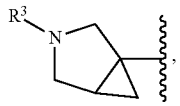

wherein:

R³ is selected from

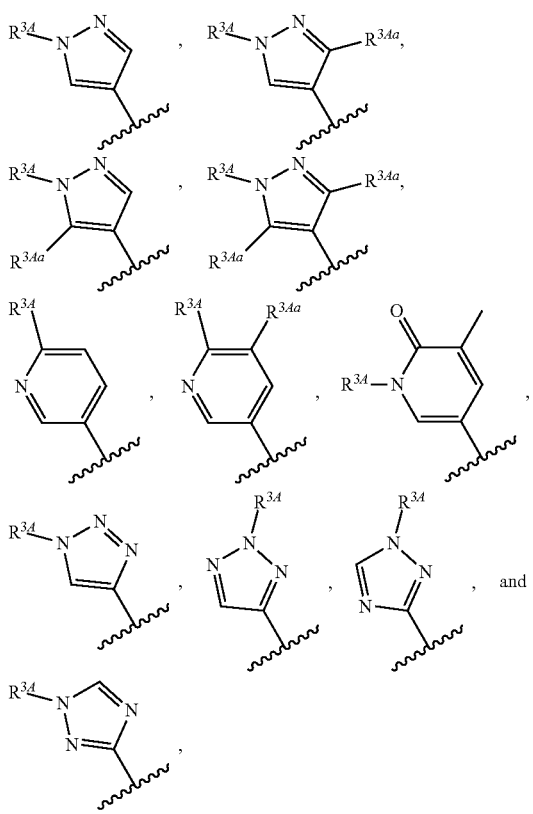

wherein:

each R³ᴬ is a moiety selected from:

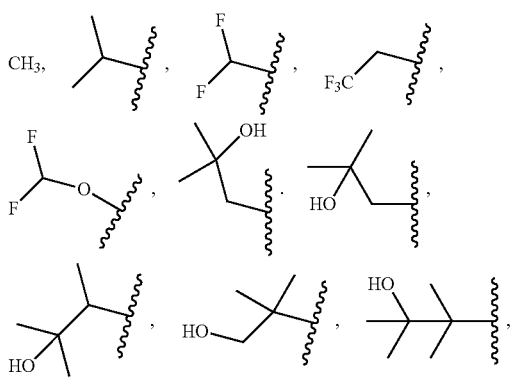

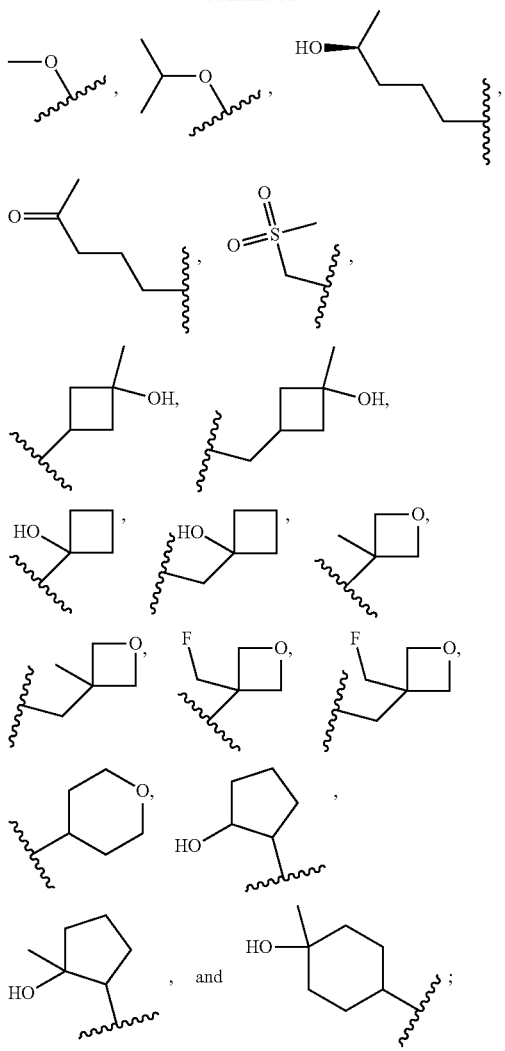

each R³ᴬᵃ is independently selected from $(C_1-C_4)$alkyl, $O(C_1-C_4)$alkyl, $(C_1-C_4)$haloalkyl, and $O(C_1-C_4)$haloalkyl; and R¹ and R² are as defined in Formula (I) or as defined in any of the alternative embodiments of R¹ and R² described above.

In another embodiment, in each of Formulas (I), (I.1), and (I.2):

ring A is the moiety:

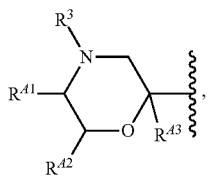

wherein R³, R^{A1}, R^{A2}, and R^{A3} are as defined in Formula (I); and wherein R¹ and R² are as defined in Formula (I) or as defined in any of the alternative embodiments of R¹ and R² described above.

In another embodiment, in each of Formulas (I), (I.1), and (I.2):

ring A is the moiety:

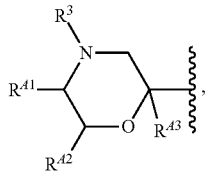

wherein:

$R^3$ is selected from

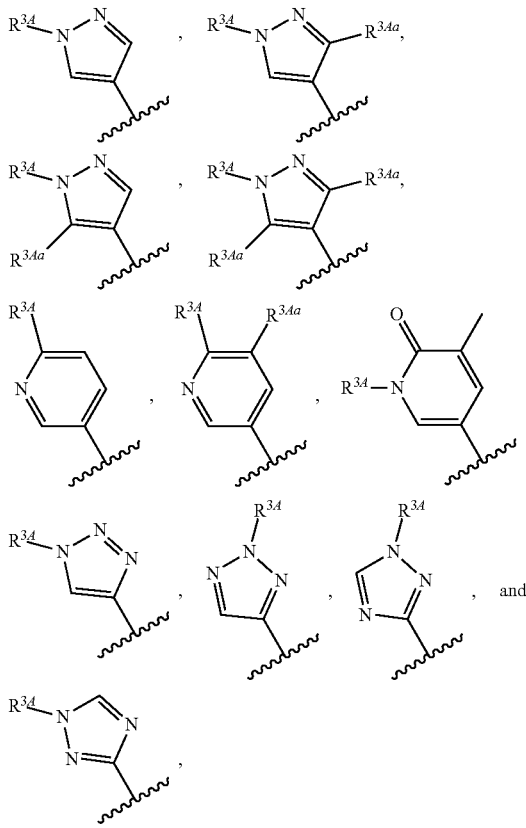

wherein:
- each $R^{3A}$ is as defined in Formula (I);
- each $R^{3Aa}$ is independently selected from $(C_1-C_4)$alkyl, $O(C_1-C_4)$alkyl, $(C_1-C_4)$haloalkyl, and $O(C_1-C_4)$haloalkyl;
- $R^{A1}$, $R^{A2}$, and $R^{A3}$ are as defined in Formula (I); and
- $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

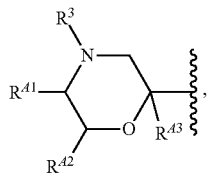

wherein:

$R^3$ is selected from

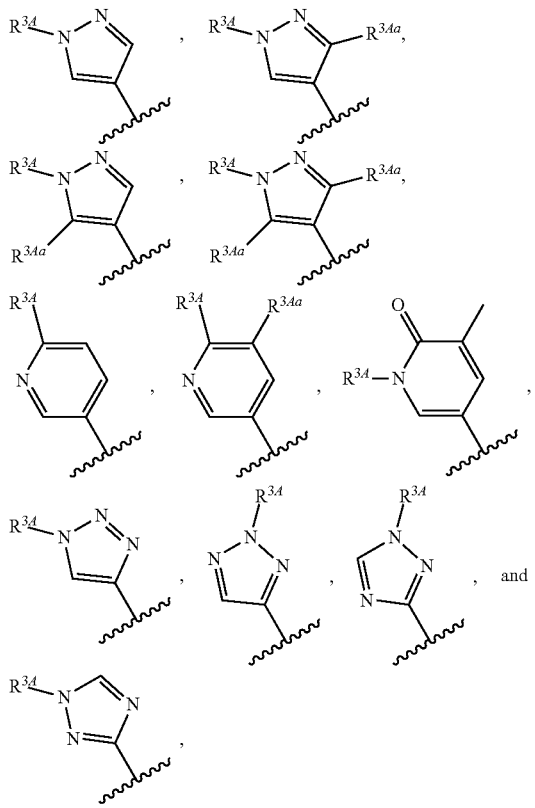

wherein:
each $R^{3A}$ is a moiety selected from:

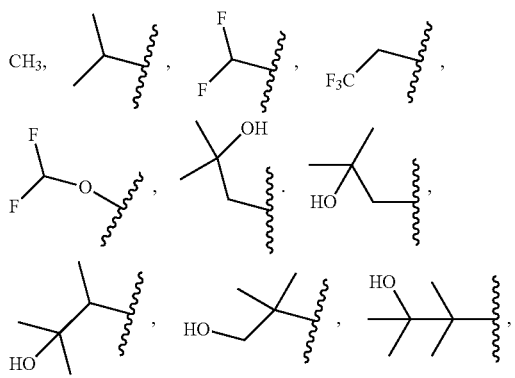

-continued

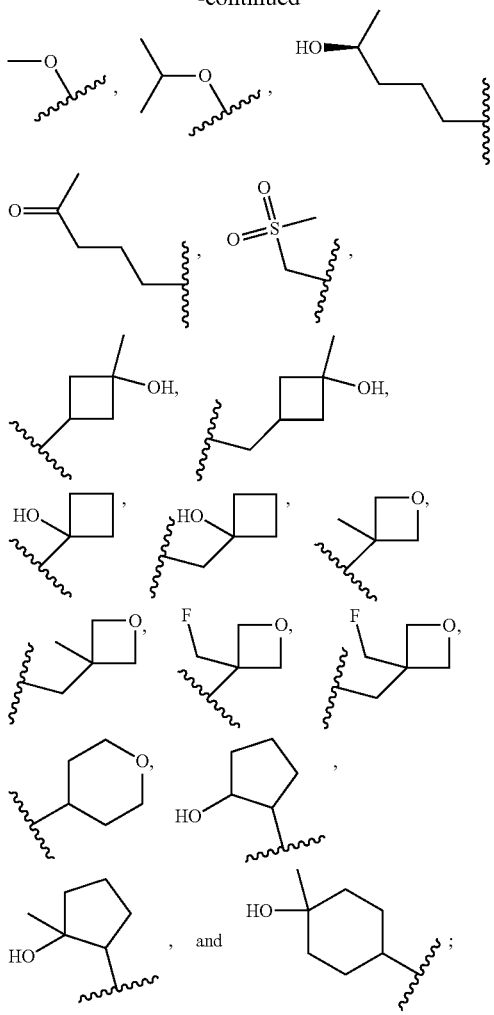

each $R^{3Aa}$ is independently selected from $(C_1-C_4)$alkyl, $O(C_1-C_4)$alkyl, $(C_1-C_4)$haloalkyl, and $O(C_1-C_4)$haloalkyl;

$R^{A1}$, $R^{A2}$, and $R^{A3}$ are as defined in Formula (I); and $R^1$ and $R^2$ are as defined in Formula (I) or as defined in any of the alternative embodiments of $R^1$ and $R^2$ described above.

In an alternative of the immediately preceding embodiment:

$R^{A1}$ is selected from H, CH$_3$, and CH$_2$CH$_3$;

$R^{A2}$ is selected from H, F, CH$_3$, and CH$_2$CH$_3$; and $R^{A3}$ is selected from H and F.

In another alternative of the immediately preceding embodiment:

$R^{A1}$ is selected from H and CH$_3$;

$R^{A2}$ is H; and $R^{A3}$ is H.

In another alternative of the immediately preceding embodiment:

$R^{A1}$ is H;

$R^{A2}$ is H; and $R^{A3}$ is H.

In another embodiment, in each of Formulas (I), (I.1), and (I.2):

ring A is the moiety:

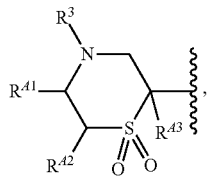

wherein $R^3$, $R^{A1}$, $R^{A2}$, and $R^{A3}$ are as defined in Formula (I); and wherein $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

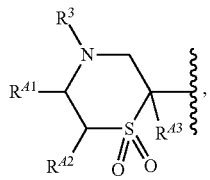

wherein:

$R^3$ is selected from

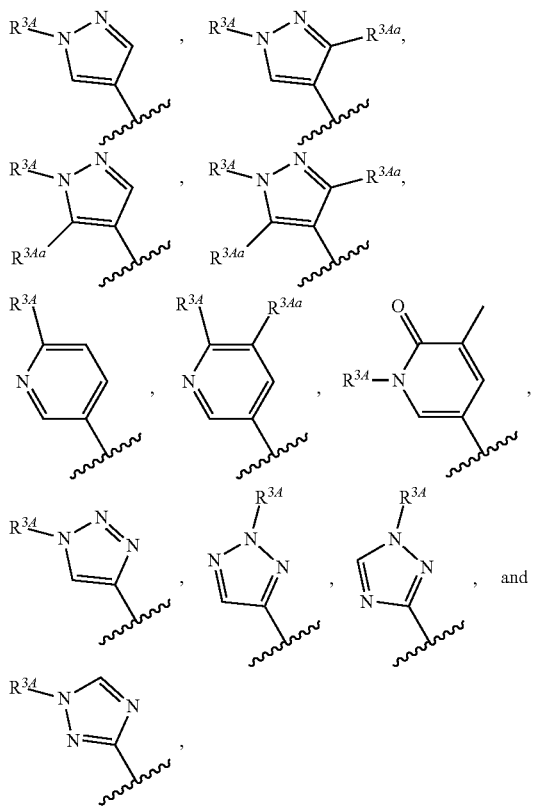

and wherein:

each $R^{3A}$ is as defined in Formula (I);

each $R^{3Aa}$ is independently selected from $(C_1-C_4)$alkyl, $O(C_1-C_4)$alkyl, $(C_1-C_4)$haloalkyl, and $O(C_1-C_4)$haloalkyl;

$R^{A1}$, $R^{A2}$, and $R^{A3}$ are as defined in Formula (I); and $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

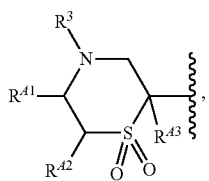

wherein:

$R^3$ is selected from

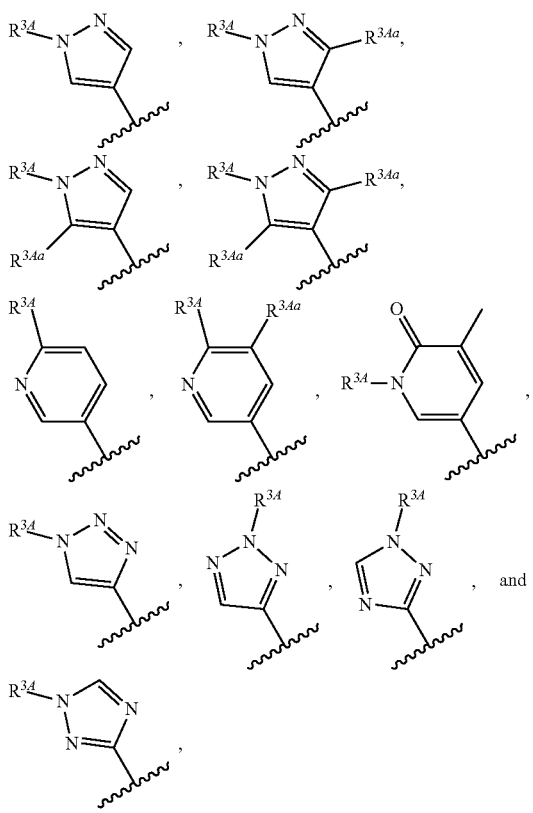

wherein:

each $R^{3A}$ is a moiety selected from:

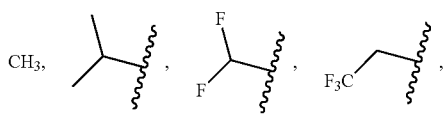

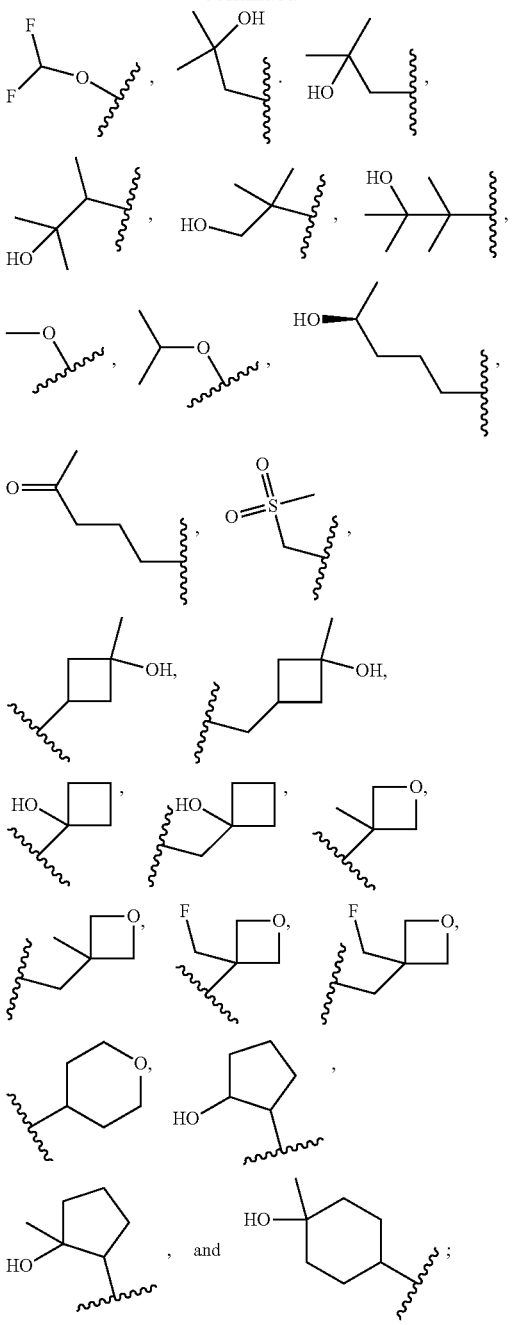

each $R^{3Aa}$ is independently selected from $(C_1-C_4)$alkyl, $O(C_1-C_4)$alkyl, $(C_1-C_4)$haloalkyl, and $O(C_1-C_4)$haloalkyl;

$R^{A1}$, $R^{A2}$, and $R^{A3}$ are as defined in Formula (I); and $R^1$ and $R^2$ are as defined in Formula (I) or as defined in any of the alternative embodiments of $R^1$ and $R^2$ described above.

In an alternative of the immediately preceding embodiment:

$R^{A1}$ is selected from H, $CH_3$, and $CH_2CH_3$;

$R^{A2}$ is selected from H, F, $CH_3$, and $CH_2CH_3$; and $R^{A3}$ is selected from H and F.

In another alternative of the immediately preceding embodiment:

$R^{A1}$ is selected from H and $CH_3$;

$R^{A2}$ is H; and $R^{A3}$ is H.

In another alternative of the immediately preceding embodiment:

$R^{A1}$ is H;

$R^{A2}$ is H; and $R^{A3}$ is H.

In another embodiment, in each of Formulas (I), (I.1), and (I.2):

ring A is the moiety:

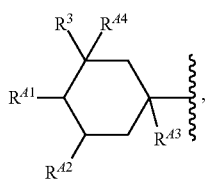

wherein $R^3$, $R^{A1}$, $R^{A2}$, $R^{A3}$ and $R^{A4}$ are as defined in Formula (I); and wherein $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

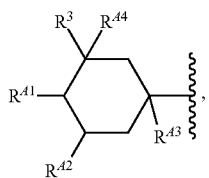

wherein:

$R^3$ is selected from

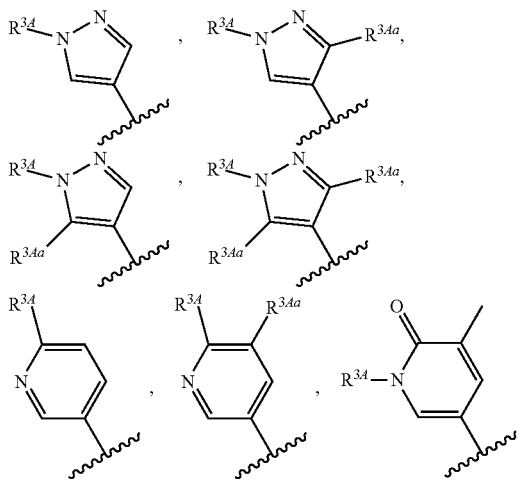

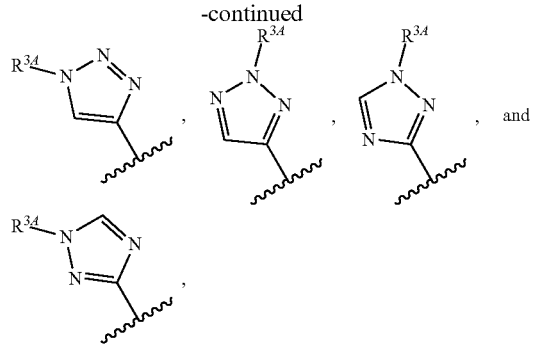

wherein:

each $R^{3A}$ is as defined in Formula (I);

each $R^{3Aa}$ is independently selected from $(C_1-C_4)$alkyl, $O(C_1-C_4)$alkyl, $(C_1-C_4)$haloalkyl, and $O(C_1-C_4)$haloalkyl;

$R^{A1}$, $R^{A2}$, $R^{A3}$ and $R^{A4}$ re as defined in Formula (I); and $R^1$ and $R^2$ are as defined in Formula (I) or as defined in any of the alternative embodiments of $R^1$ and $R^2$ described above.

In another embodiment, in each of Formulas (I), (I.1), and (I.2):

ring A is the moiety:

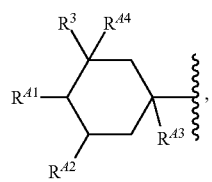

wherein:

$R^3$ is selected from

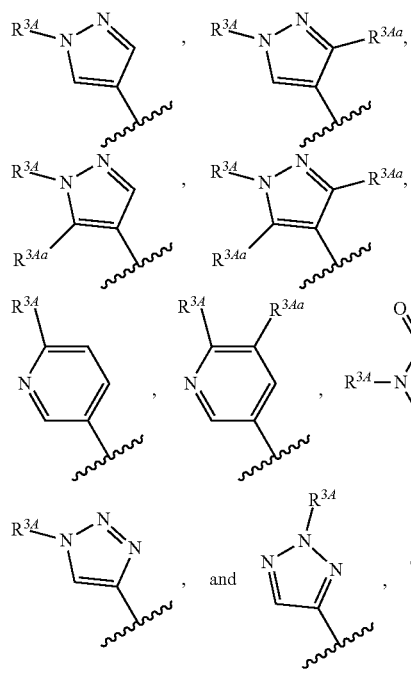

-continued

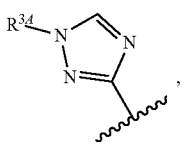

wherein:

each $R^{3A}$ is a moiety selected from:

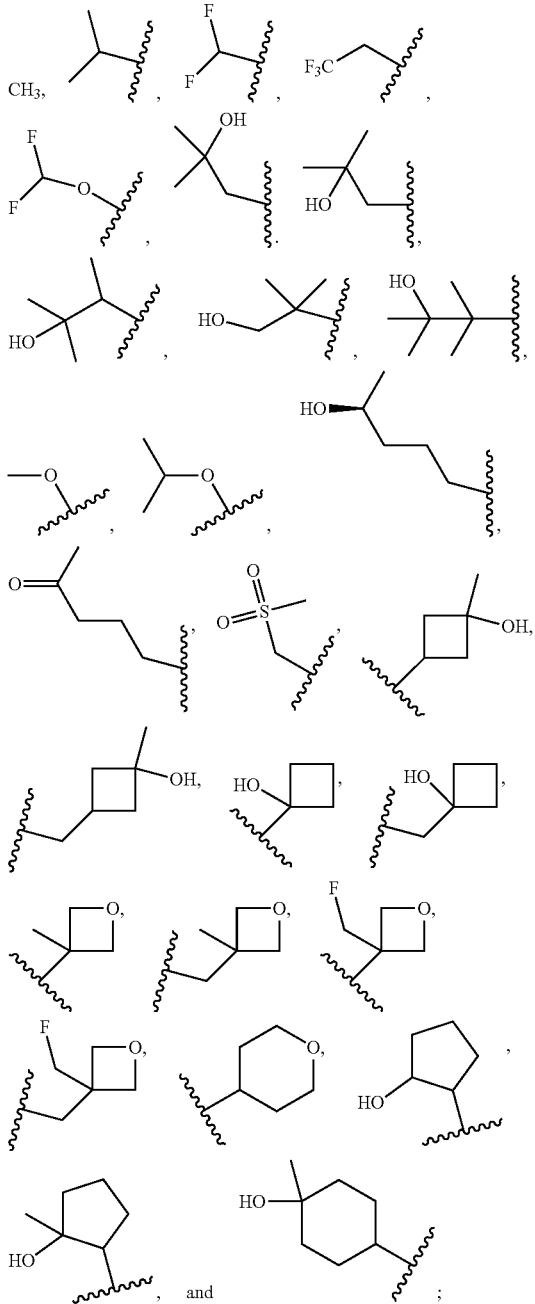

each $R^{4a}$ is independently selected from $(C_1-C_4)$alkyl, $O(C_1-C_4)$alkyl, $(C_1-C_4)$haloalkyl, and $O(C_1-C_4)$haloalkyl;

$R^{41}$; $R^{42}$; $R^{43}$ and $R^{44}$ re as defined in Formula (I); and $R^1$ and $R^2$ are as defined in Formula (I) or as defined in any of the alternative embodiments of $R^1$ and $R^2$ described above.

In an alternative of the immediately preceding embodiment:
$R^{41}$ is selected from H, $CH_3$, and $CH_2CH_3$;
$R^{42}$ is selected from H, F, $CH_3$, and $CH_2CH_3$;
$R^{43}$ is selected from H and F; and
$R^{44}$ is selected from H and OH.

In an alternative of the immediately preceding embodiment:
$R^{41}$ is H;
$R^{42}$ is H;
$R^{43}$ is H; and
$R^{44}$ is selected from H and OH.

In another embodiment, the compounds of the invention comprise those compounds identified herein as examples in the tables below, and pharmaceutically acceptable salts thereof.

In another aspect, the present invention provides pharmaceutical compositions comprising a pharmaceutically acceptable carrier and a compound of the invention or a pharmaceutically acceptable salt thereof. Such compositions according to the invention may optionally further include one or more additional therapeutic agents as described herein.

In another aspect, the present invention provides a method for the manufacture of a medicament or a composition which may be useful for treating diseases, conditions, or disorders that are mediated, at least in part, by the adenosine A2a receptor and/or the adenosine A2b receptor, comprising combining a compound of the invention with one or more pharmaceutically acceptable carriers.

In another aspect, the present invention provides a method for treating or preventing a disease, condition, or disorder that is mediated, at least in part, by the adenosine A2a receptor and/or the adenosine A2b receptor in a subject (e.g., an animal or human) in need thereof, said method comprising administering to the subject in need thereof a therapeutically effective amount of at least one compound of the invention, or a pharmaceutically acceptable salt thereof, alone or in combination with one or more additional therapeutic agents. Specific non-limiting examples of such diseases, conditions, and disorders are described herein.

Oncology

In some embodiments, the disease, condition or disorder is a cancer. Any cancer for which a PD-1 antagonist and/or an A2a and/or A2b inhibitor are thought to be useful by those of ordinary skill in the art are contemplated as cancers treatable by this embodiment, either as a monotherapy or in combination with other therapeutic agents discussed below. Cancers that express high levels of A2a receptors or A2b receptors are among those cancers contemplated as treatable by the compounds of the invention. Examples of cancers that express high levels of A2a and/or A2b receptors may be discerned by those of ordinary skill in the art by reference to the Cancer Genome Atlas (TCGA) database. Non-limiting examples of cancers that express high levels of A2a receptors include cancers of the kidney, breast, lung, and liver. Non-limiting examples of cancers that express high levels of the A2b receptor include lung, colorectal, head & neck cancer, and cervical cancer.

Thus, one embodiment provides a method of treating cancer comprising administering an effective amount of a compound of the invention, or a pharmaceutically acceptable salt thereof, to a subject in need of such treatment, wherein said cancer is a cancer that expresses a high level of A2a receptor. A related embodiment provides a method of treating cancer comprising administering an effective amount of a compound of the invention, or a pharmaceutically acceptable salt thereof, to a subject in need of such treatment, wherein said cancer is selected from kidney (or renal) cancer, breast cancer, lung cancer, and liver cancer.

Another embodiment provides a method of treating cancer comprising administering an effective amount of a compound of the invention, or a pharmaceutically acceptable salt thereof, to a subject in need of such treatment, wherein said cancer is a cancer that expresses a high level of A2b receptor. A related embodiment provides a method of treating cancer comprising administering an effective amount of a compound of the invention, or a pharmaceutically acceptable salt thereof, to a subject in need of such treatment, wherein said cancer is selected from lung cancer, colorectal cancer, head & neck cancer, and cervical cancer.

Additional non-limiting examples of cancers which may be treatable by administration of a compound of the invention (alone or in combination with one or more additional agents described below) include cancers of the prostate (including but not limited to metastatic castration resistant prostate cancer), colon, rectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including but not limited to small cell lung cancer, non-small cell lung cancer, and lung adenocarcinoma), adrenal gland, thyroid, kidney, or bone. Additional cancers treatable by a compound of the invention include glioblastoma, mesothelioma, renal cell carcinoma, gastric carcinoma, sarcoma, choriocarcinoma, cutaneous basocellular carcinoma, and testicular seminoma, and Kaposi's sarcoma.

CNS and Neurological Disorders

In other embodiments, the disease, condition or disorder is a central nervous system or a neurological disorder. Non-limiting examples of such diseases, conditions or disorders include movement disorders such as tremors, bradykinesias, gait disorders, dystonias, dyskinesias, tardive dyskinesias, other extrapyramidal syndromes, Parkinson's disease, and disorders associated with Parkinson's disease. The compounds of the invention also have the potential, or are believed to have the potential, for use in preventing or reducing the effect of drugs that cause or worsen such movement disorders.

Infections

In other embodiments, the disease, condition or disorder is an infective disorder. Non-limiting examples of such diseases, conditions or disorders include an acute or chronic viral infection, a bacterial infection, a fungal infection, or a parasitic infection. In one embodiment, the viral infection is human immunodeficiency virus. In another embodiment, the viral infection is cytomegalovirus.

Immune Disease

In other embodiments, the disease, condition or disorder is an immune-related disease, condition or disorder. Non-limiting examples of immune-related diseases, conditions, or disorders include multiple sclerosis and bacterial infections. (See, e.g., Safarzadeh, E. et al., Inflamm Res 2016 65(7):511-20; and Antonioli, L., et al., Immunol Lett S0165-2478(18)30172-X 2018).

Additional Indications

Other diseases, conditions, and disorders that have the potential to be treated or prevented, in whole or in part, by the inhibition of the A2a and/or A2b adenosine receptor(s) are also candidate indications for the compounds of the invention and salts thereof. Non-limiting examples of other diseases, conditions or disorders in which a compound of the invention, or a pharmaceutically acceptable salt thereof, may be useful include the treatment of hypersensitivity reaction to a tumor antigen and the amelioration of one or more complications related to bone marrow transplant or to a peripheral blood stem cell transplant. Thus, in another embodiment, the present invention provides a method for treating a subject receiving a bone marrow transplant or a peripheral blood stem cell transplant by administering to said subject a therapeutically effective amount of a compound of the invention, or a pharmaceutically acceptable salt thereof, sufficient to increase the delayed-type hypersensitivity reaction to tumor antigen, to delay the time-to-relapse of post-transplant malignancy, to increase relapse-free survival time post-transplant, and/or to increase long-term post-transplant survival.

Combination Therapy

In another aspect, the present invention provides methods for the use of a compound of the invention, or a pharmaceutically acceptable salt thereof, (or a pharmaceutically acceptable composition comprising a compound of the invention or pharmaceutically acceptable salt thereof) in combination with one or more additional agents. Such additional agents may have some adenosine A2a and/or A2b receptor activity, or, alternatively, they may function through distinct mechanisms of action. The compounds of the invention may be used in combination with one or more other drugs in the treatment, prevention, suppression or amelioration of diseases or conditions for which the compounds of the invention or the other drugs described herein may have utility, where the combination of the drugs together are safer or more effective than either drug alone. The combination therapy may have an additive or synergistic effect. Such other drug(s) may be administered in an amount commonly used therefore, contemporaneously or sequentially with a compound of the invention or a pharmaceutically acceptable salt thereof. When a compound of the invention is used contemporaneously with one or more other drugs, the pharmaceutical composition may in specific embodiments contain such other drugs and the compound of the invention or its pharmaceutically acceptable salt in separate doses or in unit dosage form. However, the combination therapy may also include therapies in which the compound of the invention or its pharmaceutically acceptable salt and one or more other drugs are administered sequentially, on different or overlapping schedules. It is also contemplated that when used in combination with one or more other active ingredients, the compounds of the invention and the other active ingredients may be used in lower doses than when each is used singly. Accordingly, the pharmaceutical compositions comprising the compounds of the invention include those that contain one or more other active ingredients, in addition to a compound of the invention or a pharmaceutically acceptable salt thereof.

The weight ratio of the compound of the present invention to the second active ingredient may be varied and will depend upon the effective dose of each ingredient. Generally, an effective dose of each will be used. Thus, for example, when a compound of the invention is used in combination with another agent, the weight ratio of the compound of the present invention to the other agent may generally range from about 1000:1 to about 1:1000, in particular embodiments from about 200:1 to about 1:200. Combinations of a compound of the present invention and other active ingredients will generally also be within the aforementioned range, but in each case, an effective dose of each active ingredient should generally be used.

Given the immunosuppressive role of adenosine, the administration of an A2a receptor antagonist, an A2b receptor antagonist, and/or an A2a/A2b receptor dual antagonist according to the invention may enhance the efficacy of immunotherapies such as PD-1 antagonists. Thus, in one embodiment, the additional therapeutic agent comprises an anti-PD-1 antibody. In another embodiment, the additional therapeutic agent is an anti-PD-L1 antibody.

As noted above, PD-1 is recognized as having an important role in immune regulation and the maintenance of peripheral tolerance. PD-1 is moderately expressed on naive T-cells, B-cells and NKT-cells and up-regulated by T-cell and B-cell receptor signaling on lymphocytes, monocytes and myeloid cells (Sharpe et al., Nature Immunology (2007); 8:239-245).

Two known ligands for PD-1, PD-L1 (B7-H1) and PD-L2 (B7-DC) are expressed in human cancers arising in various tissues. In large sample sets of, for example, ovarian, renal, colorectal, pancreatic, and liver cancers, and in melanoma, it was shown that PD-L1 expression correlated with poor prognosis and reduced overall survival irrespective of subsequent treatment. (Dong et al., Nat Med. 8(8):793-800 (2002); Yang et al., Invest Ophthamol Vis Sci. 49: 2518-2525 (2008); Ghebeh et al., Neoplasia 8:190-198 (2006); Hamanishi et al., Proc. Natl. Acad. Sci. USA 104: 3360-3365 (2007); Thompson et al., Cancer 5: 206-211 (2006); Nomi et al., Clin. Cancer Research 13:2151-2157 (2007); Ohigashi et al., Clin. Cancer Research 11: 2947-2953; Inman et al., Cancer 109: 1499-1505 (2007); Shimauchi et al., Int. J. Cancer 121:2585-2590 (2007); Gao et al., Clin. Cancer Research 15: 971-979 (2009); Nakanishi J., Cancer Immunol Immunother. 56: 1173-1182 (2007); and Hino et al., Cancer 00: 1-9 (2010)).

Similarly, PD-1 expression on tumor infiltrating lymphocytes was found to mark dysfunctional T-cells in breast cancer and melanoma (Ghebeh et al., BMC Cancer. 2008 8:5714-15 (2008); and Ahmadzadeh et al., Blood 114: 1537-1544 (2009)) and to correlate with poor prognosis in renal cancer (Thompson et al., Clinical Cancer Research 15: 1757-1761(2007)). Thus, it has been proposed that PD-L1 expressing tumor cells interact with PD-1 expressing T-cells to attenuate T-cell activation and to evade immune surveillance, thereby contributing to an impaired immune response against the tumor.

Immune checkpoint therapies targeting the PD-1 axis have resulted in groundbreaking improvements in clinical response in multiple human cancers (Brahmer, et al., N Engl J Med 2012, 366: 2455-65; Garon et al., N Engl J Med 2015, 372: 2018-28; Hamid et al., N Engl J Med 2013, 369: 134-44; Robert et al., Lancet 2014, 384: 1109-17; Robert et al., N Engl J Med 2015, 372: 2521-32; Robert et al., N Engl J Med 2015, 372: 320-30; Topalian et al., N Engl J Med 2012, 366: 2443-54; Topalian et al., J Clin Oncol 2014, 32: 1020-30; and Wolchok et al., N Engl J Med 2013, 369: 122-33).

"PD-1 antagonist" means any chemical compound or biological molecule that blocks binding of PD-L1 expressed on a cancer cell to PD-1 expressed on an immune cell (T-cell, B-cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment methods, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP 005009. Human PD-L1 and PD-L2 amino acid sequences can be found in NCBI Locus No.: NP_054862 and NP_079515, respectively.

PD-1 antagonists useful in any of the treatment methods, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, scFv and Fv fragments. Examples of PD-1 antagonists include, but are not limited to, pembrolizumab (KEYTRUDA®, Merck and Co., Inc., Kenilworth, NJ, USA). "Pembrolizumab" (formerly known as MK-3475, SCH 900475 and lambrolizumab and sometimes referred to as "pembro") is a humanized IgG4 mAb with the structure described in WHO Drug Information, Vol. 27, No. 2, pages 161-162 (2013). Additional examples of PD-1 antagonists include nivolumab (OPDIVO®, Bristol-Myers Squibb Company, Princeton, NJ, USA), atezolizumab (MPDL3280A; TECENTRIQ®, Genentech, San Francisco, CA, USA), durvalumab (IMFINZI®, Astra Zeneca Pharmaceuticals, LP, Wilmington, DE, and avelumab (BAVENCIO®, Merck KGaA, Darmstadt, Germany and Pfizer, Inc., New York, NY).

Examples of monoclonal antibodies (mAbs) that bind to human PD-1, and useful in the treatment methods, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment methods, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment methods, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010/027827 and WO2011/066342. Specific fusion proteins useful as the PD-1 antagonist in the treatment methods, medicaments and uses of the present invention include AMP-224 (also known as B7-DCIg), which is a PD-L2-FC fusion protein that binds to human PD-1.

Thus, one embodiment provides for a method of treating cancer comprising administering an effective amount of a compound of the invention, or a pharmaceutically acceptable salt thereof, in combination with a PD-1 antagonist to a subject in need thereof. In such embodiments, the compounds of the invention, or a pharmaceutically acceptable salt thereof, and PD-1 antagonist are administered concurrently or sequentially.

Specific non-limiting examples of such cancers in accordance with this embodiment include melanoma (including unresectable or metastatic melanoma), head & neck cancer (including recurrent or metastatic head and neck squamous cell cancer (HNSCC)), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, hepatocellular carcinoma, clear cell kidney cancer, colorectal cancer, breast cancer, squamous cell lung cancer, basal carcinoma, sarcoma, bladder cancer, endometrial cancer, pancreatic cancer, liver cancer, gastrointestinal cancer, multiple myeloma, renal cancer, mesothelioma, ovarian cancer, anal cancer, biliary tract cancer, esophageal cancer, and salivary cancer.

In one embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from unresectable or metastatic melanoma, recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma. In one such embodiment, the agent is a PD-1 antagonist. In one such embodiment, the agent is pembrolizumab. In another such embodiment, the agent is nivolumab. In another such embodiment, the agent is atezolizumab.

Pembrolizumab is approved by the U.S. FDA for the treatment of patients with unresectable or metastatic melanoma and for the treatment of certain patients with recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma, as described in the Prescribing Information for KEYTRUDA™ (Merck & Co., Inc., Whitehouse Station, NJ USA; initial U.S. approval 2014, updated November 2018). In another embodiment, there is provided a method of treating cancer comprising administering an effective amount of a compound of the invention, or a pharmaceutically acceptable salt thereof, to a person in need thereof, in combination with pembrolizumab, wherein said cancer is selected from unresectable or metastatic melanoma, recurrent or metastatic head and neck squamous cell cancer (HNSCC), classical Hodgkin lymphoma (cHL), urothelial carcinoma, gastric cancer, cervical cancer, primary mediastinal large-B-cell lymphoma, microsatellite instability-high (MSI-H) cancer, non-small cell lung cancer, and hepatocellular carcinoma.

In another embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from melanoma, non-small cell lung cancer, head and neck squamous cell cancer (HNSCC), Hodgkin lymphoma, primary mediastinal large B-cell lymphoma, urothelial carcinoma, micro satellite instability-high cancer, gastric cancer, Merkel cell carcinoma, hepatocellular carcinoma, esophageal cancer and cervical cancer. In one such embodiment, the agent is a PD-1 antagonist. In one such embodiment, the agent is pembrolizumab. In another such embodiment, the agent is nivolumab. In another such embodiment, the agent is atezolizumab. In another such embodiment, the agent is durvalumab. In another such embodiment, the agent is avelumab.

In another embodiment, there is provided a method of treating cancer comprising administering an effective amount of a compound of the invention, or a pharmaceutically acceptable salt thereof, to a person in need thereof, in combination with a PD-1 antagonist, wherein said cancer is selected from melanoma, non-small cell lung cancer, small cell lung cancer, head and neck cancer, bladder cancer, breast cancer, gastrointestinal cancer, multiple myeloma, hepatocellular cancer, lymphoma, renal cancer, mesothelioma, ovarian cancer, esophageal cancer, anal cancer, biliary tract cancer, colorectal cancer, cervical cancer, thyroid cancer, and salivary cancer. In one such embodiment, the agent is a PD-1 antagonist. In one such embodiment, the agent is pembrolizumab. In another such embodiment, the agent is nivolumab. In another such embodiment, the agent is atezolizumab. In another such embodiment, the agent is durvalumab. In another such embodiment, the agent is avelumab.

In one embodiment, there is provided a method of treating unresectable or metastatic melanoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating recurrent or metastatic head and neck squamous cell cancer (HNSCC) comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating classical Hodgkin lymphoma (cHL) comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating urothelial carcinoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating gastric cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating cervical cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating primary mediastinal large-B-cell lymphoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating microsatellite instability-high (MSI-H) cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating non-small cell lung cancer comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In one embodiment, there is provided a method of treating hepatocellular carcinoma comprising administering an effective amount of a compound of the invention, or a pharmaceutically acceptable salt thereof, to a person in need thereof, in combination with a PD-1 antagonist. In one such embodiment, the agent is pembrolizumab. In another such embodiment, the agent is nivolumab. In another such embodiment, the agent is atezolizumab.

In another embodiment, the additional therapeutic agent is at least one immunomodulator other than an A2a or A2b receptor inhibitor. Non-limiting examples of immunomodulators include CD40L, B7, B7RP1, anti-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-a/-13, M-CSF, IL-3, GM-CSF, IL-13, anti-IL-10 and indolamine 2,3-dioxygenase 1 (ID01) inhibitors.

In another embodiment, the additional therapeutic agent comprises radiation. Such radiation includes localized radiation therapy and total body radiation therapy.

In another embodiment, the additional therapeutic agent is at least one chemotherapeutic agent. Non-limiting examples of chemotherapeutic agents contemplated for use in combination with the compounds of the invention include: pemetrexed, alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin, carboplatin and oxaliplatin; bioreductive alkylators such as mitomycin, procarbazine, dacarbazine and altretamine); anthracycline-based therapies (e.g., doxorubicin, daunorubicin, epirubicin and idarubicin); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethynyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); luteinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide).

In another embodiment, the additional therapeutic agent is at least one signal transduction inhibitor (STI). Non-limiting examples of signal transduction inhibitors include BCR/ABL kinase inhibitors, epidermal growth factor (EGF) receptor inhibitors, HER-2/neu receptor inhibitors, and farnesyl transferase inhibitors (FTIs).

In another embodiment, the additional therapeutic agent is at least one anti-infective agent. Non-limiting examples of anti-infective agents include cytokines, non-limiting examples of which include granulocyte-macrophage colony stimulating factor (GM-CSF) and an flt3-ligand.

In another embodiment, the present invention provides a method for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackievirus, and human immunodeficiency virus (HIV).

In another embodiment, the present invention provides a method for the treatment of an infective disorder, said method comprising administering to a subject in need thereof an effective amount of a compound of the invention, or a pharmaceutically acceptable salt thereof, in combination with a vaccine. In some embodiments, the vaccine is an anti-viral vaccine, including, for example, an anti-HTV vaccine. Other antiviral agents contemplated for use include an anti-HIV, anti-HPV, anti HCV, anti HSV agents and the like. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-CSF). In another embodiment, the vaccine includes one or more immunogenic peptides and/or dendritic cells.

In another embodiment, the present invention provides for the treatment of an infection by administering a compound of the invention, or a pharmaceutically acceptable salt thereof, and at least one additional therapeutic agent, wherein a symptom of the infection observed after administering both the compound of the invention (or a pharmaceutically acceptable salt thereof) and the additional therapeutic agent is improved over the same symptom of infection observed after administering either alone. In some embodiments, the symptom of infection observed can be reduction in viral load, increase in CD4+ T cell count, decrease in opportunistic infections, increased survival time, eradication of chronic infection, or a combination thereof.

Definitions

As used herein, unless otherwise specified, the following terms have the following meanings.

Unsatisfied valences in the text, schemes, examples, structural formulae, and any Tables herein are assumed to have a hydrogen atom or atoms of sufficient number to satisfy the valences.

When a variable appears more than once in any moiety or in any compound of the invention (e.g., aryl, heterocycle, $N(R)_2$), the selection of moieties defining that variable for each occurrence is independent of its definition at every other occurrence unless specified otherwise in the local variable definition.

As used herein, unless otherwise specified, the term "A2a receptor antagonist" (equivalently, A2a antagonist) and/or "A2b receptor antagonist" (equivalently, A2b antagonist) means a compound exhibiting a potency ($IC_{50}$) of less than about 1 µM with respect to the A2a and/or A2b receptors, respectively, when assayed in accordance with the procedures described herein. Preferred compounds exhibit at least 10-fold selectivity for antagonizing the A2a receptor and/or the A2b receptor over any other adenosine receptor (e.g., A1 or A3).

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administrations.

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

Whether used in reference to a substituent on a compound or a component of a pharmaceutical composition the phrase "one or more", means the same as "at least one".

"Concurrently" and "contemporaneously" both include in their meaning (1) simultaneously in time (e.g., at the same time); and (2) at different times but within the course of a common treatment schedule.

"Consecutively" means one following the other.

"Sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component.

"Effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating a cancer as described herein with one or more of the compounds of the invention optionally in combination with one or more additional agents, "effective amount" (or "therapeutically effective amount") means, for example, providing the amount of at least one compound of the invention that results in a therapeutic response in a patient afflicted with the disease, condition, or disorder, including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition.

"Patient" and "subject" means an animal, such as a mammal (e.g., a human being) and is preferably a human being.

"Prodrug" means compounds that are rapidly transformed, for example, by hydrolysis in blood, in vivo to the parent compound, e.g., conversion of a prodrug of a compound of the invention to a compound of the invention, or to a salt thereof. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention.

The term "substituted" means that one or more of the moieties enumerated as substituents (or, where a list of substituents are not specifically enumerated, the substituents specified elsewhere in this application) for the particular type of substrate to which said substituent is appended, provided that such substitution does not exceed the normal valence rules for the atom in the bonding configuration presented in the substrate, and that the substitution ultimate provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution by a moiety is described (e.g. "optionally substituted") the term means that if substituents are present, one or more of the enumerated (or default) moieties listed as optional substituents for the specified substrate can be present on the substrate in a bonding position normally occupied by the default substituent, for example, a hydrogen atom on an alkyl chain can be substituted by one of the optional substituents, in accordance with the definition of "substituted" presented herein.

"Alkyl" means an aliphatic hydrocarbon group, which may be straight or branched, comprising 1 to 10 carbon atoms. "($C_1$-$C_6$)alkyl" means an aliphatic hydrocarbon group, which may be straight or branched, comprising 1 to 6 carbon atoms. Branched means that one or more lower alkyl groups such as methyl, ethyl or propyl, are attached to a linear alkyl chain. Non-limiting examples of alkyl groups include methyl, ethyl, n-propyl, isopropyl, n-butyl, i-butyl, and t-butyl.

"Haloalkyl" means an alkyl as defined above wherein one or more hydrogen atoms on the alkyl (up to and including each available hydrogen group) is replaced by a halogen atom. As appreciated by those of skill in the art, "halo" or "halogen" as used herein is intended to include chloro (Cl), fluoro (F), bromo (Br) and iodo (I). Chloro (Cl) and fluoro (F) halogens are generally preferred.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridinyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic fully saturated monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyl groups contain 4, 5 or 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

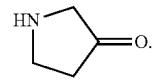

As used herein, the term "monocyclic heterocycloalkyl" refers to monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

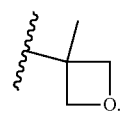

It is noted that in hetero-atom containing ring systems of this invention, there are no hydroxyl groups on carbon atoms adjacent to a N, O or S, and there are no N or S groups on carbon adjacent to another heteroatom.

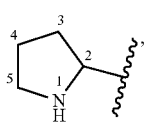

there is no —OH attached directly to carbons marked 2 and 5.

The line ———, as a bond generally indicates a mixture of, or either of, the possible isomers, e.g., containing (R)- and (S)-stereochemistry. For example:

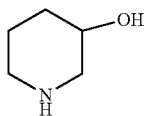

means containing both

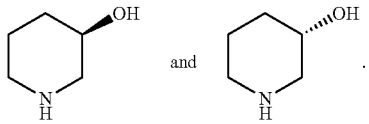

The wavy line ∿∿∿, as used herein, indicates a point of attachment to the rest of the compound. Lines drawn into the ring systems, such as, for example:

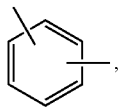

indicate that the indicated line (bond) may be attached to any of the substitutable ring atoms.

"Oxo" is defined as an oxygen atom that is double bonded to a ring carbon in a cycloalkyl, cycloalkenyl, heterocyclyl, heterocyclenyl, or other ring described herein, e.g.,

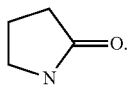

As well known in the art, a bond drawn from a particular atom wherein no moiety is depicted at the terminal end of the bond indicates a methyl group bound through that bond to the atom, unless stated otherwise. For example:

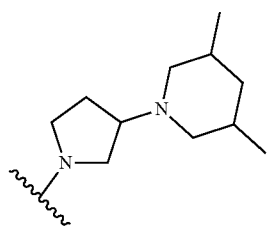 [SMILES: *N1CCC(N2CC(C)CC(C)C2)C1]

represents

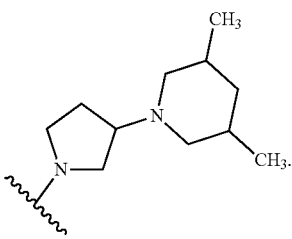 [SMILES: *N1CCC(N2CC(C)CC(C)C2)C1]

One or more compounds of the invention may also exist as, or optionally be converted to, a solvate. Preparation of solvates is generally known. Thus, for example, M. Caira et al., J. Pharmaceutical Sci., 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al., AAPS PharmSciTech., 5(1), article 12 (2004); and A. L. Bingham et al., Chem. Commun., 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

This invention also includes the compounds of the invention in isolated and purified form obtained by routine techniques. Polymorphic forms of the compounds of the invention, and of the salts, solvates and prodrugs of the thereof, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In similar manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imineenamine tautomeric forms, and for example heteroaromatic forms such as the following moieties:

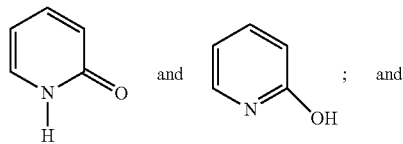

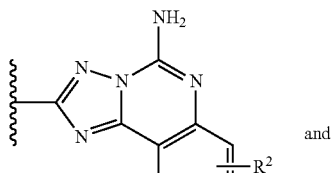

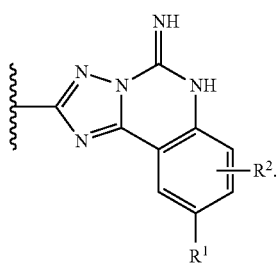

Where a reaction scheme appearing in an example employs a compound having one or more stereocenters, the stereocenters are indicated with an asterisk, as shown below:

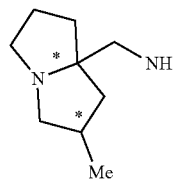 [SMILES: CC1CN2CCCC2(CN)C1]

Accordingly, the above depiction consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

ABC-1
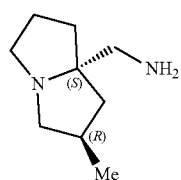

ABC-2
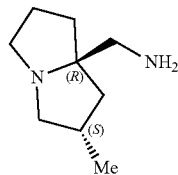

ABC-3
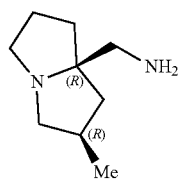

ABC-4
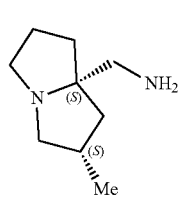

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al., The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), arylalkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the scope of the invention.

A functional group in a compound termed "protected" means that the group is in modified form to preclude undesired side reactions at the protected site when the protected compound is subjected to particular reaction conditions aimed at modifying another region of the molecule. Suitable protecting groups are known, for example, as by reference to standard textbooks, for example, T. W. Greene et al., Protective Groups in organic Synthesis (1991), Wiley, New York.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the Schemes and Examples herein using appropriate isotopically-enriched reagents and/or intermediates.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, and $^{36}$Cl, $^{123}$I and $^{125}$I. It will be appreciated that other isotopes also may be incorporated by known means.

Certain isotopically-labeled compounds of the invention (e.g., those labeled with $^3$H, $^{11}$C and $^{14}$C) are recognized as being particularly useful in compound and/or substrate tissue distribution assays using a variety of known techniques. Tritiated (i.e., $^3$H) and carbon-14 (i.e., $^{14}$C) isotopes are particularly preferred for their ease of preparation and detection. Further, substitution of a naturally abundant isotope with a heavier isotope, for example, substitution of protium with deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

The term "composition" is intended to encompass a product comprising the specified ingredients in the specified amounts, and any product which results, directly or indirectly, from combination of the specified ingredients in the specified amounts.

The term "pharmaceutical composition" as used herein encompasses both the bulk composition and individual dosage units comprised of one, or more than one (e.g., two), pharmaceutically active agents such as, for example, a compound of the present invention (optionally together with an additional agent as described herein), along with any pharmaceutically inactive excipients. As will be appreciated by those of ordinary skill in the art, excipients are any constituent which adapts the composition to a particular route of administration or aids the processing of a composition into a dosage form without itself exerting an active pharmaceutical effect. The bulk composition and each individual dosage unit can contain fixed amounts of the aforesaid one, or more than one, pharmaceutically active agents. The bulk composition is material that has not yet been formed into individual dosage units.

It will be appreciated that pharmaceutical formulations of the invention may comprise more than one compound of the invention (or a pharmaceutically acceptable salt thereof), for example, the combination of two or three compounds of the invention, each present in such a composition by adding to the formulation the desired amount of the compound in a pharmaceutically acceptably pure form. It will be appreciated also that in formulating compositions of the invention, a composition may comprise, in addition to one or more of compounds of the invention, one or more other agents which also have pharmacological activity, as described herein.

While formulations of the invention may be employed in bulk form, it will be appreciated that for most applications the inventive formulations will be incorporated into a dosage form suitable for administration to a patient, each dosage form comprising an amount of the selected formulation which contains an effective amount of one or more compounds of the invention. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions comprising compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, minitablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, $20^{th}$ Edition, (2000), Lippincott Williams & Wilkins, Baltimore, MD.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In accordance with the present invention, antagonism of adenosine A2a and/or A2b receptors is accomplished by administering to a patient in need of such therapy an effective amount of one or more compounds of the invention, or a pharmaceutically acceptable salt thereof.

In some embodiments it is preferred for the compound to be administered in the form of a pharmaceutical composition comprising the compound of the invention, or a salt thereof, and at least one pharmaceutically acceptable carrier (described herein). It will be appreciated that pharmaceutically formulations of the invention may comprise more than one compound of the invention, or a salt thereof, for example, the combination of two or three compounds of the invention, or, additionally or alternatively, another active agent such as those described herein, each present by adding to the formulation the desired amount of the compound or a salt thereof (or agent, where applicable) which has been isolated in a pharmaceutically acceptably pure form.

As mentioned above, administration of a compound of the invention to effect antagonism of A2a and/or A2b receptors is preferably accomplished by incorporating the compound into a pharmaceutical formulation incorporated into a dosage form, for example, one of the above-described dosage forms comprising an effective amount of at least one compound of the invention (e.g., 1, 2 or 3, or 1 or 2, or 1, and usually 1 compound of the invention), or a pharmaceutically acceptable salt thereof. Methods for determining safe and effective administration of compounds which are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, NJ 07645-1742, USA), the Physician's Desk Reference, 56$^{th}$ Edition, 2002 (published by Medical Economics company, Inc. Montvale, NJ 07645-1742), or the Physician's Desk Reference, 57$^{th}$ Edition, 2003 (published by Thompson PDR, Montvale, NJ 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the invention can be administered at a total daily dosage of up to 1,000 mg, which can be administered in one daily dose or can be divided into multiple doses per 24 hour period, for example, two to four doses per day.

As those of ordinary skill in the art will appreciate, an appropriate dosage level for a compound (or compounds) of the invention will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during a treatment cycle.

In general, in whatever form administered, the dosage form administered will contain an amount of at least one compound of the invention, or a salt thereof, which will provide a therapeutically effective serum level of the compound in some form for a suitable period of time such as at least 2 hours, more preferably at least four hours or longer. In general, as is known in the art, dosages of a pharmaceutical composition providing a therapeutically effective serum level of a compound of the invention can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active agents as may be additionally needed or desired in the course of providing treatment. As will be appreciated, the dosage form administered may also be in a form providing an extended release period for the pharmaceutically active compound which will provide a therapeutic serum level for a longer period, necessitating less frequent dosage intervals.

Preparative Examples

The compounds of the present invention can be prepared readily according to the following schemes and specific examples, or modifications thereof, using readily available starting materials, reagents and conventional synthetic procedures. In these reactions, it is also possible to make use of variants which are themselves known to those of ordinary skill in this art but are not mentioned in detail. The general procedures for making the compounds claimed in this invention can be readily understood and appreciated by one skilled in the art from viewing the following Schemes and descriptions.

General Scheme 1

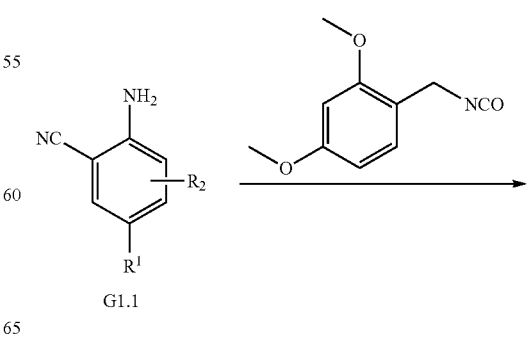

G1.1

-continued

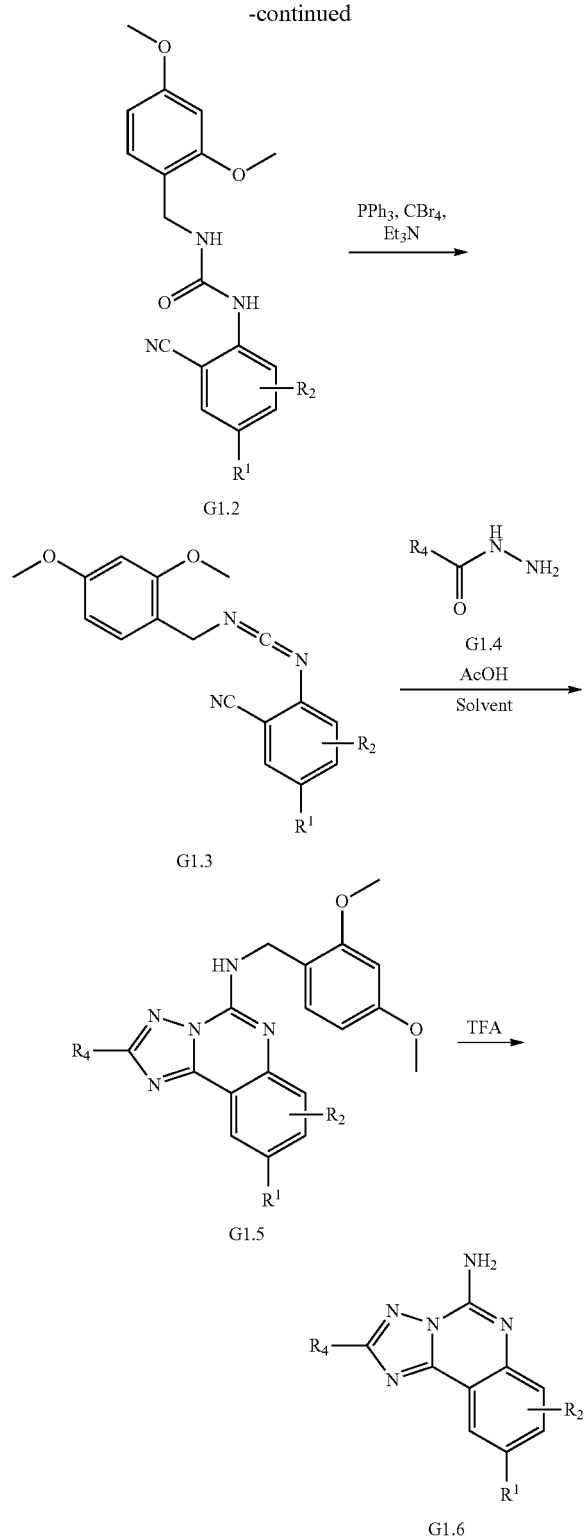

form intermediate ureas G1.2. In the second step, these ureas can be dehydrated to the corresponding carbodiimides G1.3 in the presence of triphenylphosphine, carbon tetrabromide, and triethylamine in a solvent such as dichloromethane. In the third step, treatment of carbodiimides G1.3 with a hydrazide of the type G1.4 in the presence of acetic acid in a solvent such as dichloromethane or dioxane, produces products of the type G1.5. In the fourth step, the 2,4-dimethoxybenzyl group of G1.4 is removed under acidic conditions to provide products of type G1.6, which can be purified by silica gel chromatography, preparative reversed phase HPLC, and/or chiral SFC.

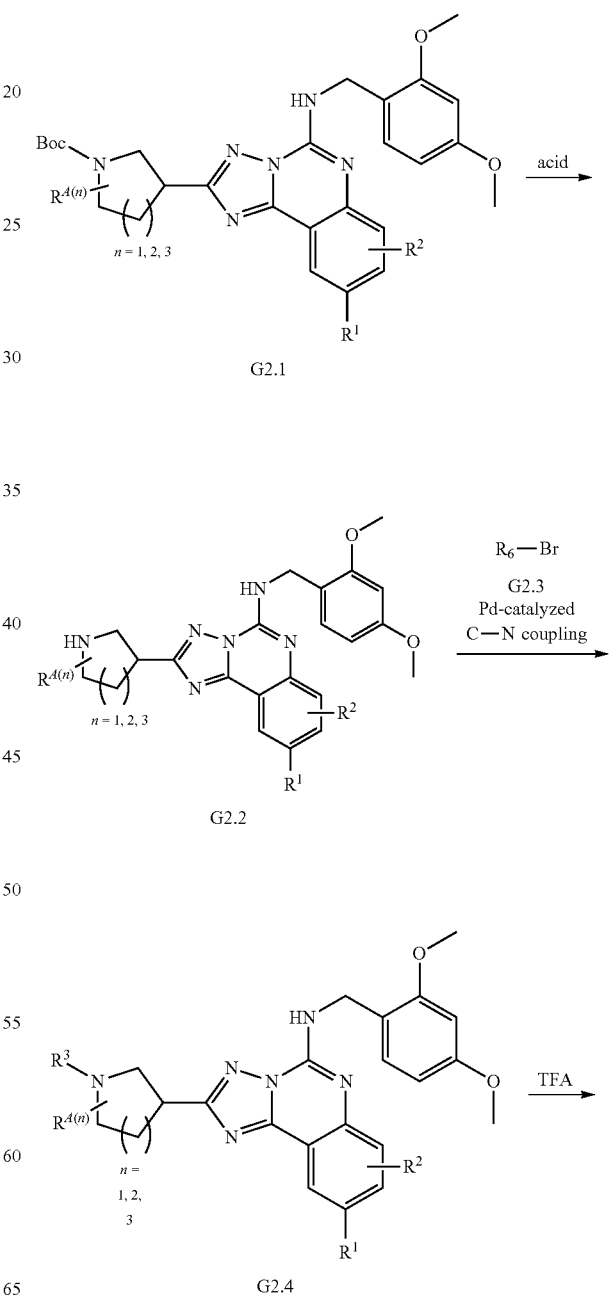

One general strategy for the synthesis of compounds of type G1.6 is via the four-step procedure shown in General Scheme 1, wherein $R_4$ corresponds to ring A in Formula (I) and wherein $R^1$, $R^2$, and ring A are as defined in Formula (I). In the first step, amino benzonitriles G1.1 can be treated with 1-(isocyanatomethyl)-2,4-dimethoxybenzene in solvents such as the combination of dichloromethane and pyridine to

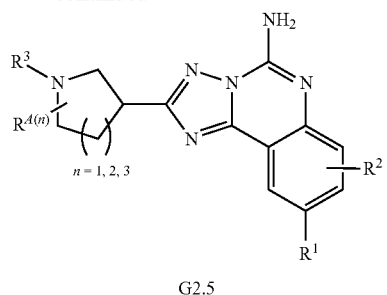

G2.5

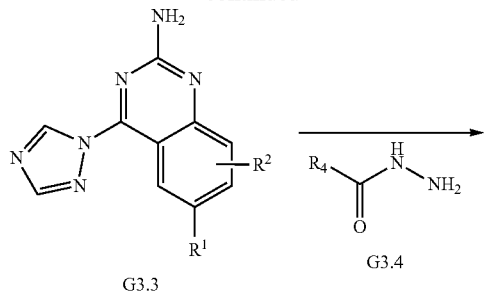

G3.3    G3.4

One general strategy for the synthesis of compounds of type G2.5 is via the three-step procedure shown in General Scheme 2, wherein $R^A(n)$ corresponds to $R^{A1}$, $R^{A2}$, $R^{A3}$, and $R^{A5}$ in Formula (I) and wherein $R^1$, $R^2$, $R^3$ and $R^{A(n)}$ (as $R^{A1}$, $R^{A2}$, $R^{A3}$, and $R^{A5}$) are as defined in Formula (I). In the first step, protected cyclic amines G2.1 can be converted into unprotected amines G2.2 through carefully controlled treatment with acid. Acids such as formic acid in the absence of solvent or hydrochloric acid in the presence of MeOH or DCM, can be used. In the second step, intermediates of type G2.2 can be converted into intermediates of type G2.4 through a transition-metal catalyzed C—N coupling reaction with aryl bromides G2.3. The reaction is performed under deoxygenated conditions with palladium catalysts such as, tert-butyl X-Phos Third Generation Precatalyst, a base such as sodium tert-butoxide, and a solvent such as THF, at the appropriate temperature. In the third step, the 2,4-dimethoxybenzyl group of G2.4 is removed under acidic conditions to provide products of type G2.5, which can be purified by silica gel chromatography, preparative reversed-phase HPLC, and/or chiral SFC.

General Scheme 3

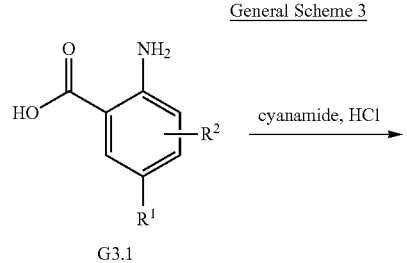

G3.1

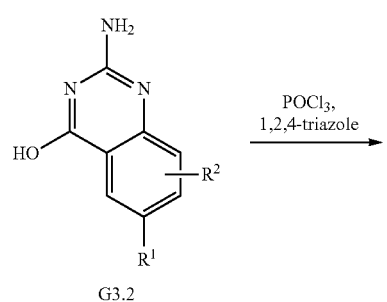

G3.2

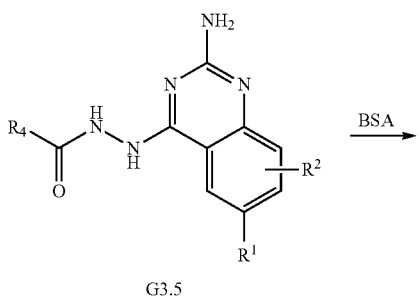

G3.5

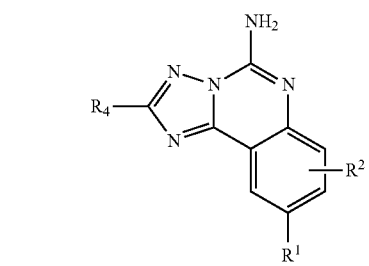

G3.6

One general strategy for the synthesis of compounds of type G3.6 is via a four-step procedure shown in General Scheme 3, wherein $R_4$ corresponds to ring A in Formula (I) and wherein $R^1$, $R^2$, and ring A are as defined in Formula (I). In the first step, amino benzoic acids G3.1 can be converted into amino quinazolines G3.2 via treatment with cyanamide in the presence of aqueous HCl in a solvent such as EtOH. In the second step, intermediates of type G3.2 can be converted into intermediates of type G3.3 through coupling with 1,2,4-triazole, following treatment of G3.2 with phosphorous (V) oxychloride in a solvent such as acetonitrile. In the third step, intermediates of type G3.3 can be treated with hydrazides G3.4 in a solvent such as THF, to provide products of type G3.5. In the fourth step, intermediates of type G3.5 can undergo a rearrangement upon heating in neat N,O-Bis(trimethylsilyl)acetamide (BSA) to form products of type G3.6. Products of type G3.6 can be purified by silica gel chromatography, preparative reversed-phase HPLC, and/or chiral SFC.

General Scheme 4

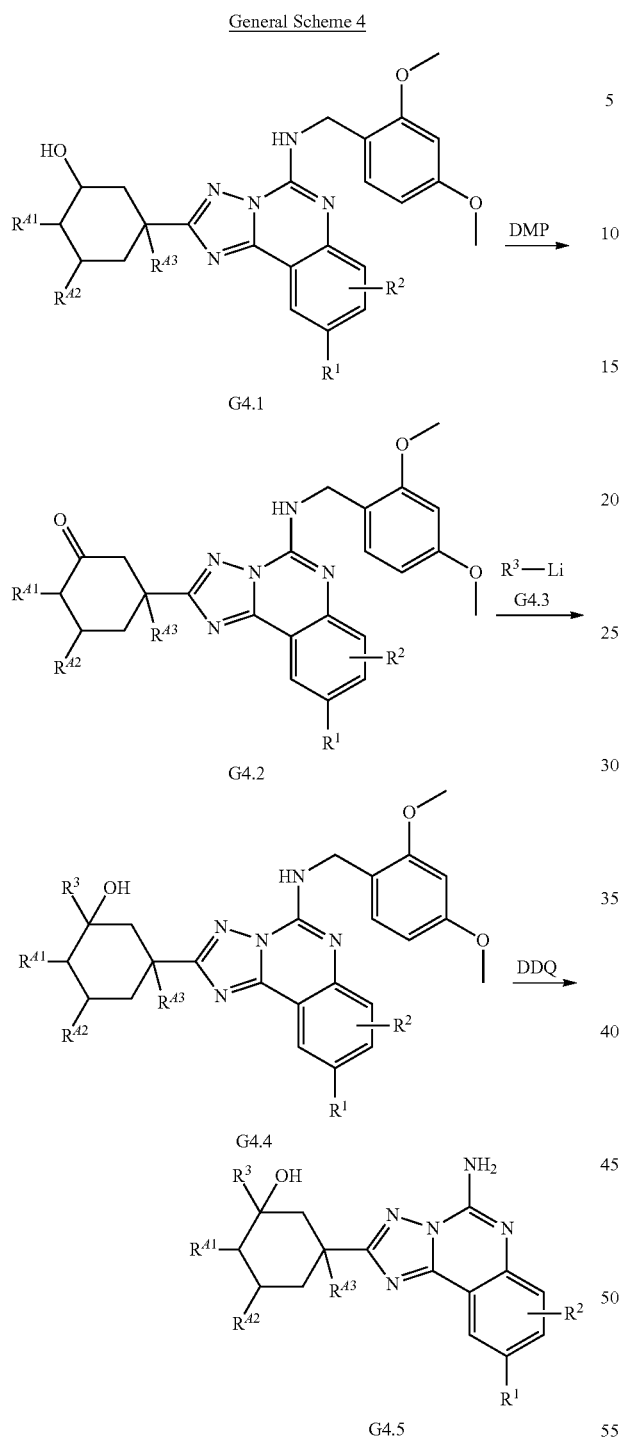

G4.5, which can be purified by silica gel chromatography, preparative reversed-phase HPLC, and/or chiral SFC.

Experimentals

Abbreviations used in the experimentals may include, but are not limited to, the following:

| | |
|---|---|
| 18-crown-6 | 1,4,7,10,13,16-hexaoxacyclooctadecane |
| ° C. | Degrees Celsius |
| AcOH | Acetic acid |
| aq. | Aqueous |
| Atm | Atmospheres |
| $Boc_2O$ | Di-tert-butyl dicarbonate |
| BSA | N,O-Bis(trimethylsilyl)acetamide |
| $CD_3OD$ | Deuterated Methanol-d4 |
| DCM | Dichloromethane |
| DDQ | 2,3-Dichloro-5,6-dicyano-1,4-benzoquinone |
| DEA | Diethylamine |
| DIAD | Diisopropyl diazene-1,2-dicarboxylate |
| DIBAL | Diisobutylaluminium hydride |
| DIPEA | N,N-Diisopropylethylamine |
| DMAP | 4-(dimethylamino)-pyridine |
| DMF | Dimethylformamide |
| DMP | Dess-Martin periodinane |
| DMSO | Dimethyl Sulfoxide |
| DMSO-d6 | Deuterated Dimethyl Sulfoxide |
| dppf | Bis(diphenylphosphino)ferrocene |
| ES | Electrospray Ionization |
| $Et_2O$ | Diethylether |
| EtOAc | Ethyl Acetate |
| EtOH | Ethanol |
| h | Hours |
| HPLC | High Performance Liquid Chromatography |
| M | Molar |
| MeCN | Acetonitrile |
| MeOD-d4 | Deuterated Methanol |
| MeOH | Methanol |
| MHz | Megahertz |
| min | Minutes |
| mL | Milliliters |
| MS | Mass Spectroscopy |
| MsCl | p-Toluenesulfonyl chloride |
| NaH | Sodium hydride |
| NBS | N-Bromosuccinimide |
| nm | Nanometers |
| NMR | Nuclear Magnetic Resonance |
| Pd/C | Palladium on Carbon |
| PPTS | Pyrdinium para-toluenesulfonate |
| p-TsOH | 4-Methylbenzenesulfonic acid |
| Py | Pyridine |
| rac | racemic |
| SFC | Supercritical Fluid (CO2) Chromatography |
| T3P | Tripropyl phosphonic anhydride |
| tBuXPhos-Pd G3 | 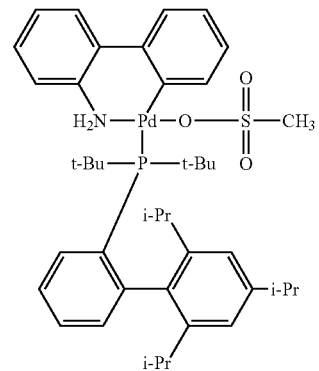 [(2-Di-tert-butylphosphino-2',4',6'-triisopropyl-1,1'-biphenyl)-2-(2'-amino-1,1'-biphenyl)] palladium(II) methanesulfonate CAS# 1447963-75-8 |
| $Tf_2O$ | Trifluoromethanesulfonic anhydride |
| TFA | Trifluoroacetic acid |
| TFE | 2,2,2-Trifluoroethanol |
| THF | Tetrahydrofuran |

One general strategy for the synthesis of compounds of type G4.5 is via a three-step procedure outlined in General Scheme 4, wherein $R^1$, $R^2$, $R^3$, $R^{A1}$, $R^{A2}$, and $R^{A3}$ are defined in Formula (I). Heteroaryl cyclohexanol G4.1 can be converted into the corresponding cyclohexanone G4.2 via oxidation with Dess-Martin periodinane. In the second step, intermediates of type G4.2 can undergo treatment with an $R^3$—Li G4.3 at low temperature, to provide products of type G4.4. In the third step, the 2,4-dimethoxybenzyl group of G2.4 can be removed with DDQ to provide products of type

| | |
|---|---|
| THP | (tetrahydro-2H-pyran-2-yl)oxy |
| TLC | Thin Layer Chromatography |

General Experimental Information:

Unless otherwise noted, all reactions were magnetically stirred and performed under an inert atmosphere such as nitrogen or argon.

Unless otherwise noted, diethyl ether used in the experiments described below was Fisher ACS certified material and stabilized with BHT.

Unless otherwise noted, "degassed" refers to a solvent from which oxygen has been removed, generally by bubbling an inert gas such as nitrogen or argon through the solution for 10 to 15 minutes with an outlet needle to normalize pressure.

Unless otherwise noted, "concentrated" means evaporating the solvent from a solution or mixture using a rotary evaporator or vacuum pump.

Unless otherwise noted, "evaporated" means evaporating using a rotary evaporator or vacuum pump.

Unless otherwise noted, silica gel chromatography was carried out on an ISCO®, Analogix®, or Biotage® automated chromatography system using a commercially available cartridge as the column. Columns were usually filled with silica gel as the stationary phase. Reverse phase preparative HPLC conditions can be found at the end of the experimental section. Aqueous solutions were concentrated on a Genevac® evaporator or were lyophilized.

Unless otherwise noted, proton nuclear magnetic resonance ($^1$H NMR) spectra and proton-decoupled carbon nuclear magnetic resonance ($^{13}$C{$^1$H} NMR) spectra were recorded on 400, 500, or 600 MHz Bruker or Varian NMR spectrometers at ambient temperature. All chemical shifts (δ) were reported in parts per million (ppm). Proton resonances were referenced to residual protium in the NMR solvent, which can include, but is not limited to, CDCl$_3$, DMSO-d$_6$, and MeOD-d$_4$. Carbon resonances are referenced to the carbon resonances of the NMR solvent. Data are represented as follows: chemical shift, multiplicity (br=broad, br s=broad singlet, s=singlet, d=doublet, dd=doublet of doublets, ddd=doublet of doublet of doublets, t=triplet, q=quartet, m=multiplet), coupling constants (J) in Hertz (Hz), integration.

Intermediate 1: rac-3-(4-bromo-1H-pyrazol-1-yl)-2-methylbutan-2-ol

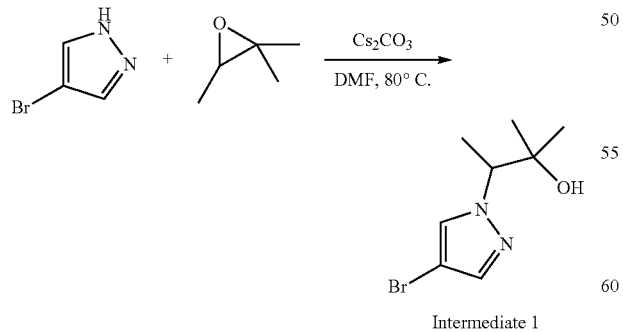

Intermediate 1

To a stirred solution of 4-bromo-1H-pyrazole (1.00 g, 6.80 mmol) in DMF (3.40 ml) was added cesium carbonate (2.22 g, 6.80 mmol) and 2,2,3-trimethyloxirane (820 mg, 9.52 mmol). The mixture was stirred and heated at 90° C. for 4 h. The mixture was cooled to room temperature, filtered, and the solvents of the filtrate were evaporated. The residue was purified by silica gel chromatography with 5-100% EtOAc in hexanes as eluent to afford rac-3-(4-bromo-1H-pyrazol-1-yl)-2-methylbutan-2-ol. LCMS (C$_8$H$_{13}$BrN$_2$O) (ES, m/z) [M+H]$^+$: 233, 235.

The intermediates in the following Table 1 were prepared in a manner similar to that of Intermediate 1 from the appropriate pyrazole and epoxide.

TABLE 1

| Intermediate | Structure Name | Observed m/z [M + H]$^+$ |
|---|---|---|
| 2 | 1-(3-bromo-1H-1,2,4-triazol-1-yl)-2-methylpropan-2-ol? | 220, 222 |
| 3 | 1-(3-bromo-5-methyl-1H-1,2,4-triazol-1-yl)-2-methylpropan-2-ol | 234, 236 |
| 4 | 1-(4-bromo-1H-pyrazol-1-yl)-2-methylpropan-2-ol | 219, 221 |
| 5 | 2-(4-bromo-1H-pyrazol-1-yl)cyclopentan-1-ol | 231, 233 |

TABLE 1-continued

| Intermediate | Structure Name | Observed m/z [M + H]+ |
|---|---|---|
| 6 | 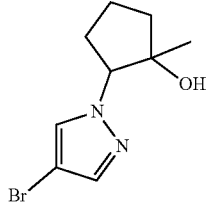 2-(4-bromo-1H-pyrazol-1-yl)-1-methylcyclopentan-1-ol | 245, 247 |
| 7 | 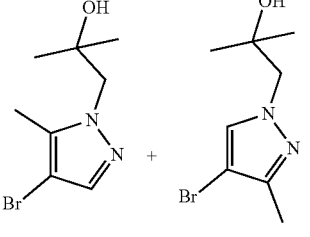 mixture of 1-(4-bromo-3-methyl-1H-pyrazol-1-yl)-2-methylpropan-2-ol and 1-(4-bromo-5-methyl-1H-pyrazol-1-yl)-2-methylpropan-2-ol | ND |
| 8 | 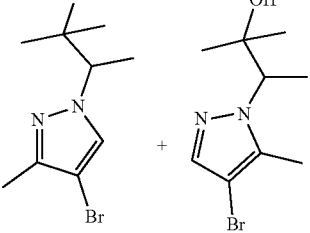 mixture of rac-3-(4-bromo-3-methyl-1H-pyrazol-1-yl)-2-methylbutan-2-ol and rac-3-(4-bromo-5-methyl-1H-pyrazol-1-yl)-2-methylbutan-2-ol | 247, 249 |
| 9 | 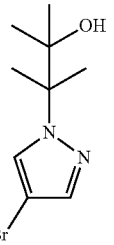 3-(4-bromo-1H-pyrazol-1-yl)-2,3-dimethylbutan-2-ol | 247, 249 |
| 10 | 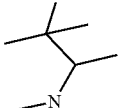 rac-3-(3-bromo-1H-1,2,4-triazol-1-yl)-2-methylbutan-2-ol | 234, 236 |

Intermediate 11: 1-((4-bromo-1H-pyrazol-1-yl)methyl)cyclobutan-1-ol

Step 1: (1-hydroxycyclobutyl)methyl methanesulfonate

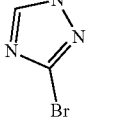

To a stirred solution of 1-(hydroxymethyl)cyclobutan-1-ol (9.00 g, 88.0 mmol) in DCM (260 mL) at 0° C. was added triethylamine (17.2 ml, 123 mmol) followed by methanesulfonyl chloride (7.0 mL, 90 mmol). The mixture was stirred at 0° C. for 10 min. The mixture was then warmed to room temperature and stirred for 15 min. The mixture was then partitioned with water. The layers were separated and the organic layer was washed with brine. The organic layer was dried over anhydrous MgSO₄, filtered, and evaporated to afford (1-hydroxycyclobutyl)methyl methanesulfonate.

Step 2: 1-((4-bromo-1H-pyrazol-1-yl)methyl)cyclobutan-1-ol

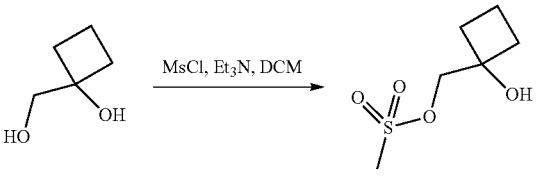

Intermediate 11

To a solution of 4-bromo-1H-pyrazole (7.70 g, 52.4 mmol) in DMF (60 ml) at 0° C. was added NaH (60% in mineral oil, 2.30 g, 57.6 mmol) portionwise. The mixture was stirred at 0° C. under nitrogen for 30 min. To the mixture was added a solution of (1-hydroxycyclobutyl)methyl methanesulfonate (13.1 g, 72.8 mmol) in DMF (20 ml). The mixture was stirred and heated at 90° C. for 16 h. The mixture was quenched with water (70 mL), then extracted with EtOAc three times. The organic layer was dried over anhydrous MgSO$_4$, filtered, and the solvents of the filtrate were evaporated. The residue was purified by silica gel chromatography with 0-30% EtOAc in petroleum ether as eluent, to afford 1-((4-bromo-1H-pyrazol-1-yl)methyl)cyclobutan-1-ol. LCMS (C$_8$H$_{11}$BrN$_2$O) (ES, m/z): 231, 233 [M+H]$^+$.

Intermediate 12: 4-bromo-1-((3-methyloxetan-3-yl)methyl)-1H-pyrazole

Step 1: (3-methyloxetan-3-yl)methyl methanesulfonate

Step 1 of the synthesis of Intermediate 12 was conducted similar to step 1 of the synthesis of Intermediate 11 from the appropriate starting materials to afford (3-methyloxetan-3-yl)methyl methanesulfonate.

Step 2: 4-bromo-1-((3-methyloxetan-3-yl)methyl)-1H-pyrazole

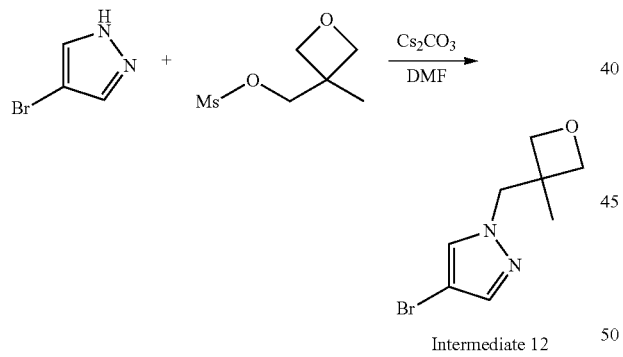

Intermediate 12

To a solution of 4-bromo-1H-pyrazole (5.04 g, 34.3 mmol) in DMF (114 mL) was added (3-methyloxetan-3-yl)methyl methanesulfonate (6.18 g, 34.3 mmol) and cesium carbonate (15.6 g, 48.0 mmol). The mixture was stirred and heated at 60° C. for 6 h. The solvents were evaporated. To the residue was added DCM (100 mL), and the mixture was filtered. The solvents of the filtrate were evaporated. The residue was purified by silica gel chromatography with 0-100% EtOAc in hexane to afford 4-bromo-1-((3-methyloxetan-3-yl)methyl)-1H-pyrazole. LCMS (C$_8$H$_{11}$BrN$_2$O) (ES, m/z): 231, 233 [M+H]$^+$.

Intermediate 13, shown in the following Table 2, was prepared in a manner similar to that of Intermediate 12 from the appropriate starting materials.

TABLE 2

| Intermediate | Structure Name | Observed m/z [M + H]$^+$ |
|---|---|---|
| 13 | 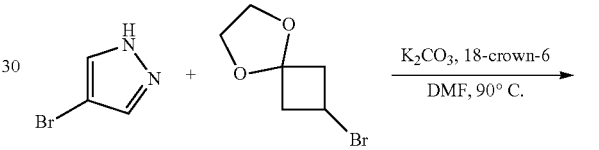<br>4-bromo-1-((3-(fluoromethyl)oxetan-3-yl)methyl)-1H-pyrazole | 249, 251 |

Intermediate 14: (1s,3s)-3-(4-bromo-1H-pyrazol-1-yl)-1-methylcyclobutanol

Step 1: 4-bromo-1-(5,8-dioxaspiro[3.4]octan-2-yl)-1H-pyrazole

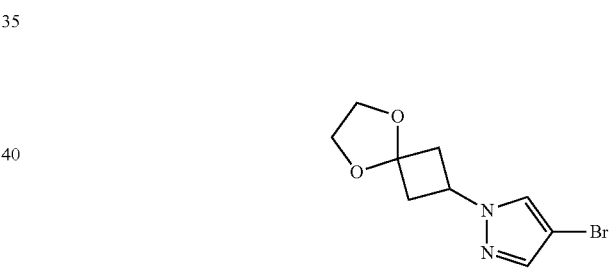

To a solution of 2-bromo-5,8-dioxaspiro[3.4]octane (0.500 g, 2.59 mmol) and 4-bromo-1H-pyrazole (0.761 g, 5.18 mmol) in DMF (2.6 mL) in an 8 mL vial was added potassium carbonate (1.07 g, 7.77 mmol) and 18-crown-6 (0.137 g, 0.518 mmol). The mixture was stirred and heated at 90° C. After 5 min, the mixture was cooled to room temperature, and to the mixture was added additional 4-bromo-1H-pyrazole (400 mg, 2.72 mmol). The mixture was stirred and heated at 90° C. for 48 h. The mixture was then cooled to room temperature and partitioned between EtOAc (25 mL) and water (25 mL). The layers were separated and the organic layer was washed with brine. The two aqueous layers were combined and extracted with EtOAc (15 mL). The organic layers were combined, washed with brine twice, dried over anhydrous Na$_2$SO$_4$, filtered, and the solvents of the filtrate were evaporated. The residue was purified by silica gel chromatography with 0-50% EtOAc in hexanes to afford 4-bromo-1-(5,8-dioxaspiro[3.4]octan-2-yl)-1H-pyrazole.

LCMS (C$_9$H$_{12}$BrN$_2$O$_2$) (ES, m/z): 259, 261 [M+H]$^+$.

Step 2: 3-(4-bromo-1H-pyrazol-1-yl)cyclobutanone

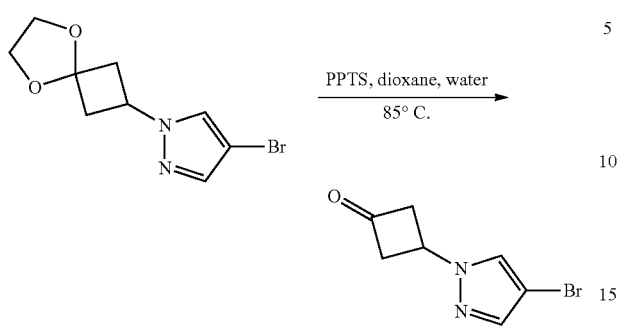

To a solution of 4-bromo-1-(5,8-dioxaspiro[3.4]octan-2-yl)-1H-pyrazole (270 mg, 1.042 mmol) and PPTS (131 mg, 0.521 mmol) in dioxane (2.6 mL) was added water (2.6 mL). The mixture was stirred and heated at 85° C. for 95 h. The mixture was cooled to room temperature. The mixture was partitioned between EtOAc and saturated aqueous sodium bicarbonate. The layers were separated, and the aqueous layer was extracted with EtOAc. The organic layers were combined, washed with brine, dried over anhydrous $Na_2SO_4$, filtered, and the solvents were evaporated. The residue was purified by silica gel chromatography with 0-100% EtOAc in hexane to afford 3-(4-bromo-1H-pyrazol-1-yl)cyclobutanone. LCMS ($C_7H_8BrN_2O$) (ES, m/z): 215, 217 [M+H]$^+$.

Step 3: (1s,3s)-3-(4-bromo-1H-pyrazol-1-yl)-1-methylcyclobutanol

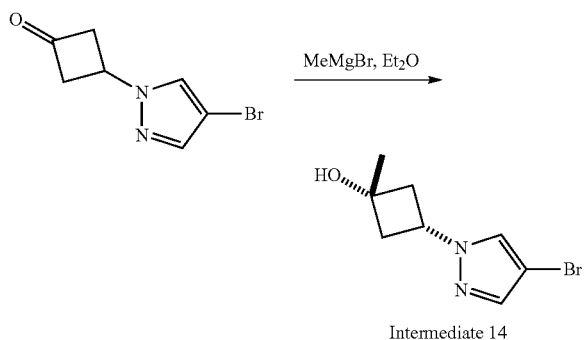

Intermediate 14

A solution of 3-(4-bromo-1H-pyrazol-1-yl)cyclobutanone (129 mg, 0.600 mmol) in diethyl ether (3.5 ml) was cooled to 0° C. To the stirred mixture was added methylmagnesium bromide (3 M in diethyl ether, 0.240 ml, 0.720 mmol) dropwise. The mixture was stirred for 16 h, allowing the ice bath to expire. The mixture was partitioned between EtOAc and 20% aqueous citric acid and stirred for 2 h. The layers were separated and the aqueous layer was extracted with EtOAc. The organic layers were combined, washed with brine, dried over anhydrous $Na_2SO_4$, filtered, and the solvents of the filtrate were evaporated. The residue was purified by silica gel chromatography with 0-60% EtOAc in hexanes as eluent to afford (1s, 3s)-3-(4-bromo-1H-pyrazol-1-yl)-1-methylcyclobutanol. LCMS ($C_8H_{12}BrN_2O$) (ES, m/z): 231, 233 [M+H]$^+$.

Intermediate 15: 4-bromo-1-(tetrahydro-2H-pyran-4-yl)-1H-pyrazole

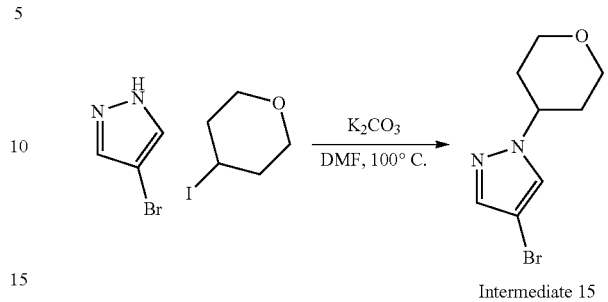

Intermediate 15

To a reaction vial were added 4-bromo-1H-pyrazole (1.50 g, 10.2 mmol), 4-iodotetrahydro-2H-pyran (2.16 g, 10.2 mmol), potassium carbonate (1.41 g, 10.2 mmol) and DMF (15 mL). The mixture was stirred and heated at 100° C. for 16 h. The mixture was purified by silica gel chromatography with 0-50% EtOAc in petroleum ether as eluent, to afford 4-bromo-1-(tetrahydro-2H-pyran-4-yl)-1H-pyrazole. LCMS ($C_8H_{11}BrN_2O$) (ES, m/z): 231, 233 [M+H]$^+$.

Intermediate 16: mixture of 4-bromo-5-methyl-1-trityl-1H-pyrazole and 4-bromo-3-methyl-1-trityl-1H-pyrazole

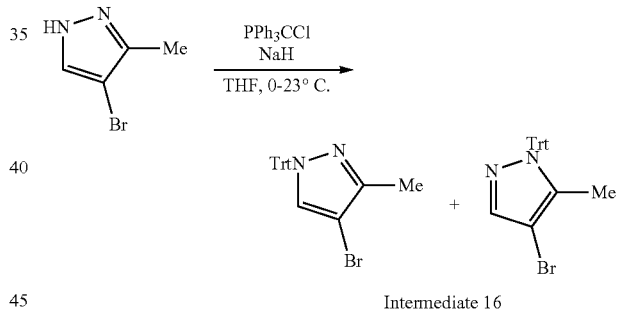

Intermediate 16

To a 200 mL round bottom flask was added 4-bromo-3-methyl-1H-pyrazole (1.00 g, 6.21 mmol) and THF (62.1 ml). The mixture was stirred under an atmosphere of nitrogen. The mixture was cooled at 0° C. To the mixture was added NaH (0.311 g, 7.76 mmol) portionwise. The mixture was slowly warmed to room temperature over 30 min. The mixture was then cooled at 0° C., and to the mixture was added trityl chloride (1.90 g, 6.83 mmol). The mixture was stirred for 16 h at room temperature. The mixture was quenched with water (60 mL) and diluted with EtOAc (60 mL). The layers were separated and the aqueous layer was further extracted with EtOAc (2×50 mL). The combined organic layers were dried over anhydrous $MgSO_4$, filtered, and the solvents of the filtrate were evaporated. The residue was purified by silica gel chromatography with 0-25% EtOAc in hexanes as eluent to afford 4-bromo-3-methyl-1-trityl-1H-pyrazole and 4-bromo-5-methyl-1-trityl-1H-pyrazole as a mixture of regioisomers. LCMS ($C_{23}H_{19}BrN_2$) (ES, m/z): 425, 427 [M+Na]$^+$.

Intermediate 17: 4-bromo-3-(difluoromethyl)-1-trityl-1H-pyrazole

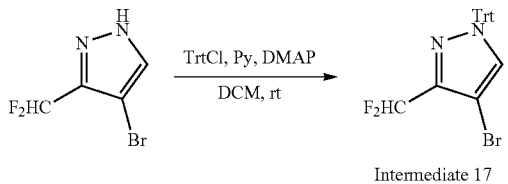

Intermediate 17

To a stirred mixture of 4-bromo-5-(difluoromethyl)-1H-pyrazole (250 mg, 1.27 mmol), trityl chloride (460 mg, 1.65 mmol) and pyridine (201 mg, 2.54 mmol) in DCM (4 mL) was added DMAP (15.5 mg, 0.127 mmol). The mixture was stirred at room temperature for 16 h. The mixture was washed with water (5 mL) and aqueous saturated NH$_4$Cl (5 mL). The organic layer was dried over anhydrous Na$_2$SO$_4$, filtered, and the solvents of the filtrate were evaporated. The residue was purified by silica gel chromatography with 0-50% EtOAc in petroleum ether as eluent to afford 4-bromo-5-(difluoromethyl)-1-trityl-1H-pyrazole. LCMS (C$_{23}$H$_{17}$BrF$_2$N$_2$) (ES, m/z): 461, 463 [M+Na]$^+$.

Intermediate 18: mixture of 4-bromo-3-(difluoromethyl)-1-(tetrahydro-2H-pyran-4-yl)-1H-pyrazole and 4-bromo-5-(difluoromethyl)-1-(tetrahydro-2H-pyran-4-yl)-1H-pyrazole

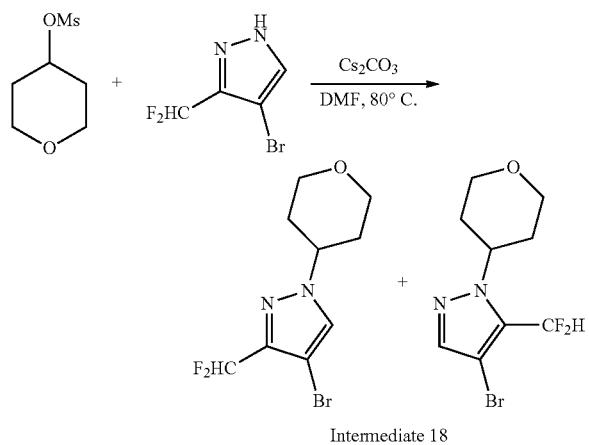

Intermediate 18

To a solution of 4-bromo-5-(difluoromethyl)-1H-pyrazole (240 mg, 1.218 mmol) in DMF (60 ml) were added cesium carbonate (595 mg, 1.828 mmol) and tetrahydro-2H-pyran-4-yl methanesulfonate (329 mg, 1.828 mmol). The mixture was stirred and heated at 80° C. under nitrogen for 3 h. The mixture was cooled to room temperature and diluted with water (100 mL). The mixture was extracted with EtOAc three times. The organic layer was washed with water followed by brine, dried over anhydrous MgSO$_4$, and filtered. The solvents of the filtrate were evaporated. The resulting residue was purified by silica gel chromatography with 0-90% EtOAc in hexanes as eluent to afford a mixture of 4-bromo-3-(difluoromethyl)-1-(tetrahydro-2H-pyran-4-yl)-1H-pyrazole and 4-bromo-5-(difluoromethyl)-1-(tetrahydro-2H-pyran-4-yl)-1H-pyrazole.

Intermediate 19: 2-(4-Bromo-1H-pyrazol-1-yl)-2-methylpropan-1-ol

Step 1: Methyl 2-(4-bromo-1H-pyrazol-1-yl)-2-methylpropanoate

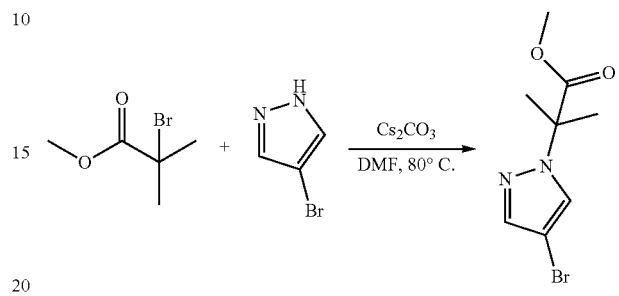

To a solution of 4-bromo-1H-pyrazole (2.00 g, 13.6 mmol) in DMF (20 mL) was added methyl 2-bromo-2-methylpropanoate (1.76 mL, 13.6 mmol) followed by cesium carbonate (8.87 g, 27.2 mmol). The mixture was heated at 80° C. for 18 h. The mixture was filtered, and the filter cake was washed with DCM. The combined filtrates were evaporated. The resulting residue was purified by silica gel chromatography with 10% EtOAc in hexanes as eluent to afford methyl 2-(4-bromo-1H-pyrazol-1-yl)-2-methylpropanoate. LCMS (C$_8$H$_{11}$BrN$_2$O$_2$) (ES, m/z): 247, 249 [M+H]$^+$.

Step 2: 2-(4-bromo-1H-pyrazol-1-yl)-2-methylpropan-1-ol

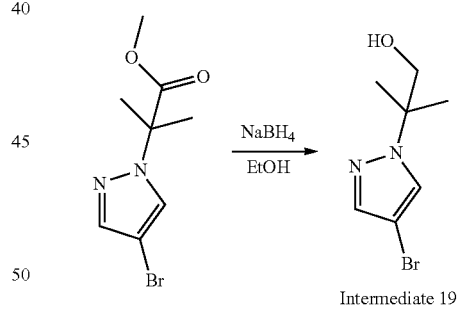

Intermediate 19

To a solution of methyl 2-(4-bromo-1H-pyrazol-1-yl)-2-methylpropanoate (1.74 g, 7.04 mmol) in EtOH (35 ml) was added sodium borohydride (0.799 g, 21.1 mmol) at 0° C. The mixture was stirred at room temperature for 2 h. The mixture was diluted in DCM (50 mL), washed with water and brine solution. The organic layer was dried over anhydrous sodium sulfate, filtered, and the filtrate was evaporated to afford 2-(4-bromo-1H-pyrazol-1-yl)-2-methylpropan-1-ol.

LCMS (C$_7$H$_{11}$BrN$_2$O) (ES, m/z): 219, 221 [M+H]$^+$.

Intermediate 20 in the following Table 3 was prepared in a manner similar to that described for the synthesis of Intermediate 19 from the appropriate starting materials.

TABLE 3

| Intermediate | Structure Name | Observed m/z [M + H]+ |
|---|---|---|
| 20 | 2-(4-bromo-3-methyl-1H-pyrazol-1-yl)-2-methylpropan-1-ol | 233, 235 |

Intermediate 21: 1-(4-bromo-3-cyclopropyl-1H-pyrazol-1-yl)-2-methylpropan-2-ol Step 1: 1-(3-cyclopropyl-1H-pyrazol-1-yl)-2-methylpropan-2-ol

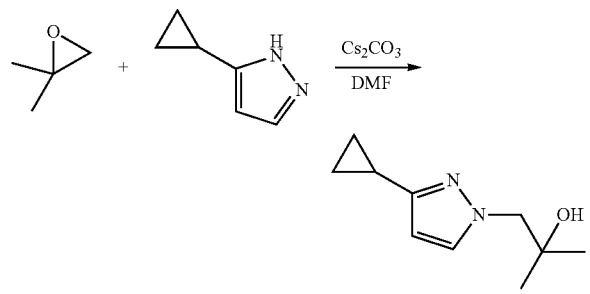

Step 1 of the synthesis of Intermediate 21 was conducted in manner similar to that used in the synthesis of Intermediate 1 from the appropriate starting materials to afford 1-(3-cyclopropyl-1H-pyrazol-1-yl)-2-methylpropan-2-ol.

Step 2: 1-(4-bromo-3-cyclopropyl-1H-pyrazol-1-yl)-2-methylpropan-2-ol

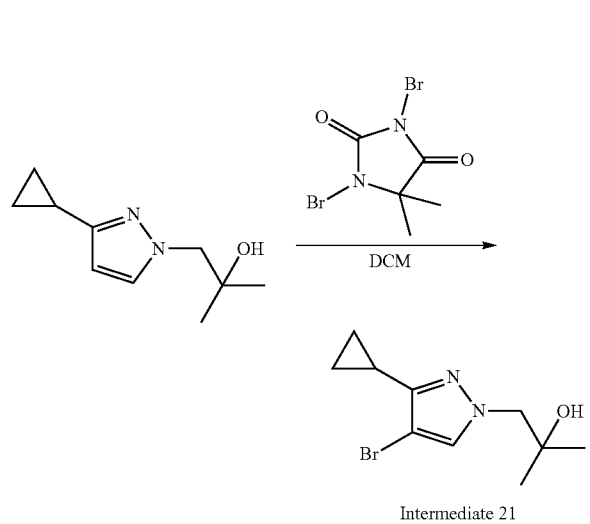

To a solution of 1-(3-cyclopropyl-1H-pyrazol-1-yl)-2-methylpropan-2-ol (1.55 g, 8.60 mmol) in DCM (86 mL) was added 1,3-dibromo-5,5-dimethylhydantoin (1.23 g, 4.30 mmol). The mixture was stirred at room temperature for 30 min. The solvents were evaporated, and the resulting residue was purified by silica gel chromatography with 10-90% EtOAc in hexanes to afford 1-(4-bromo-3-cyclopropyl-1H-pyrazol-1-yl)-2-methylpropan-2-ol. LCMS ($C_{10}H_{15}BrN_2O$) (ES, m/z): 259, 261 [M+H]+.

Intermediate 22: 4-bromo-1-ethyl-3-(((tetrahydro-2H-pyran-2-yl)oxy)methyl)-1H-pyrazole Step 1: (4-bromo-1-ethyl-1H-pyrazol-3-yl)methanol

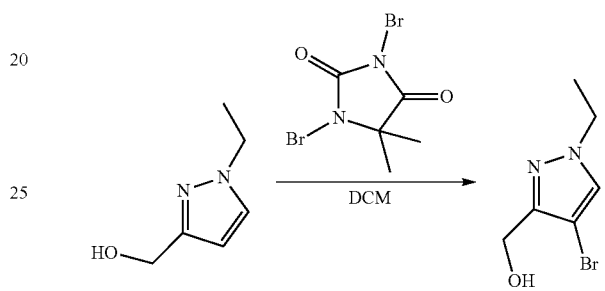

Step 1 of the synthesis of Intermediate 22 was conducted in a manner analogous to step 2 of the synthesis of Intermediate 21 from the appropriate starting materials to afford (4-bromo-1-ethyl-1H-pyrazol-3-yl)methanol. LCMS ($C_6H_9BrN_2O$) (ES, m/z): 205, 207 [M+H]+.

Step 2: rac-4-bromo-1-ethyl-3-(((tetrahydro-2H-pyran-2-yl)oxy)methyl)-1H-pyrazole

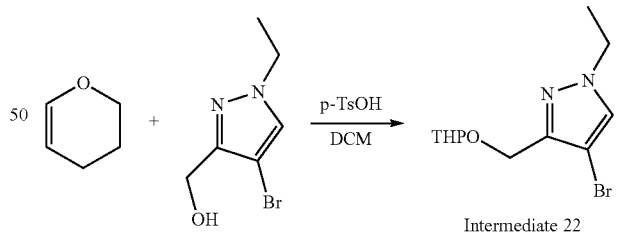

To a stirred solution of (4-bromo-1-ethyl-1H-pyrazol-3-yl)methanol (570 mg, 2.78 mmol) in DCM (27 mL) was added 3,4-dihydro-2H-pyran (468 mg, 5.56 mmol), followed by the addition of 4-methylbenzenesulfonic acid (polymer supported) (239 mg, 1.39 mmol). The mixture was stirred at room temperature for 2 h. The mixture was filtered, and the filtrate was loaded directly onto a silica gel column and purified with 0-60% EtOAc in hexane as eluent to afford rac-4-bromo-1-ethyl-3-(((tetrahydro-2H-pyran-2-yl)oxy)methyl)-1H-pyrazole. LCMS ($C_{11}H_{17}BrN_2O_2$) (ES, m/z): 289, 291 [M+H]+.

Intermediate 23: rac-4-bromo-1-((1-((tetrahydro-2H-pyran-2-yl)oxy)cyclobutyl)methyl)-1H-pyrazole Step 1: rac-(1-((tetrahydro-2H-pyran-2-yl)oxy)cyclobutyl)methyl methanesulfonate

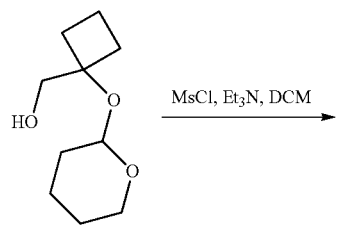

To a stirred solution of rac-(1-((tetrahydro-2H-pyran-2-yl)oxy)cyclobutyl)methanol (8.00 g, 43.0 mmol) in DCM (150 mL) at 0° C. was added triethylamine (8.38 mL, 60.1 mmol) followed by methanesulfonyl chloride (4.02 mL, 51.5 mmol). The mixture was stirred at 0° C. for 10 min and then warmed to room temperature and stirred for 40 min. The mixture was then partitioned with water. The layers were separated, and the organic layer was washed with brine. The organic layer was dried over anhydrous MgSO$_4$, filtered, and evaporated to afford rac-(1-((tetrahydro-2H-pyran-2-yl)oxy)cyclobutyl)methyl methanesulfonate, LCMS ($C_{11}H_{20}O_5S$) (ES, m/z): 287 [M+Na]$^+$.

Step 2: rac-4-bromo-1-((1-((tetrahydro-2H-pyran-2-yl)oxy)cyclobutyl)methyl)-1H-pyrazole

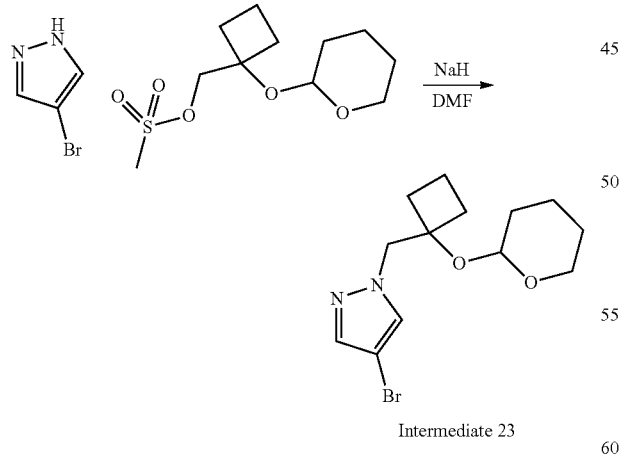

Intermediate 23

To a solution of 4-bromo-1H-pyrazole (5.40 g, 36.7 mmol) in DMF (60 mL) at 0° C. was added NaH (60% in mineral oil, 1.62 g, 40.4 mmol) portionwise. The mixture was stirred at 0° C. under nitrogen for 1 h. To the mixture was added rac-(1-((tetrahydro-2H-pyran-2-yl)oxy)cyclobutyl)methyl methanesulfonate (10.7 g, 40.4 mmol). The mixture was stirred and heated at 90° C. under nitrogen for 16 h. The mixture was quenched with water (200 mL) and extracted with EtOAc three times. The combined organic layers were washed with water followed by brine. The organic layer was dried over anhydrous MgSO$_4$, filtered, and evaporated. The resulting residue was purified by silica gel chromatography with 0-30% EtOAc in petroleum ether as eluent to afford rac-4-bromo-1-((1-((tetrahydro-2H-pyran-2-yl)oxy)cyclobutyl)methyl)-1H-pyrazole (Intermediate 23). LCMS ($C_{13}H_{19}BrN_2O_2$) (ES, m/z): 315, 317 [M+H]$^+$.

Intermediate 24 and Intermediate 25: 1-(4-bromo-3-methyl-1H-pyrazol-1-yl)-2-methylpropan-2-ol and 1-(4-bromo-5-methyl-1H-pyrazol-1-yl)-2-methylpropan-2-ol

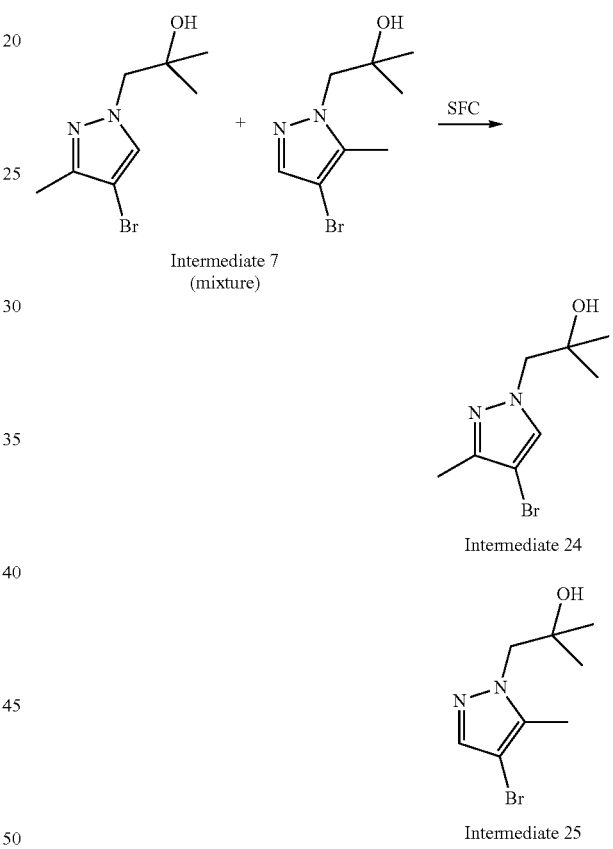

The mixture of 1-(4-bromo-3-methyl-1H-pyrazol-1-yl)-2-methylpropan-2-ol and 1-(4-bromo-5-methyl-1H-pyrazol-1-yl)-2-methylpropan-2-ol (Intermediate 7) was separated by SFC (Chiral Technologies IG 21×250 mm column with 15% (MeOH w/0.1% NH$_4$OH modifier) as cosolvent) to afford 1-(4-bromo-3-methyl-1H-pyrazol-1-yl)-2-methylpropan-2-ol (Intermediate 24, first eluting peak) and 1-(4-bromo-5-methyl-1H-pyrazol-1-yl)-2-methylpropan-2-ol (Intermediate 25, second eluting peak).

For Intermediate 24: LCMS ($C_{13}H_{19}BrN_2O_2$) (ES, m/z): 233, 235 [M+H]$^+$.

For Intermediate 25: LCMS ($C_8H_{13}BrN_2O$) (ES, m/z): 233, 235 [M+H]$^+$.

Intermediate 26 and Intermediate 27 in the following Table 4 were prepared in a manner analogous to the preparation of Intermediate 24 and Intermediate 25 by SFC separation of the racemic mixture Intermediate 1.

TABLE 4

| Intermediate | Structure Name | SFC Conditions | Observed m/z [M + H]+ |
|---|---|---|---|
| 26 | (S or R)-3-(4-bromo-1H-pyrazol-1-yl)-2-methylbutan-2-ol | Peak 1; Chiral Technologies AD-H 50 × 250 mm column with 35% MeOH as co-solvent | 233, 235 |
| 27 | (R or S)-3-(4-bromo-1H-pyrazol-1-yl)-2-methylbutan-2-ol | Peak 2; Chiral Technologies AD-H 50 × 250 mm column with 35% MeOH as co-solvent | 233, 235 |

Intermediate 28: rac-2-(4-bromo-1H-pyrazol-1-yl)cyclobutan-1-one

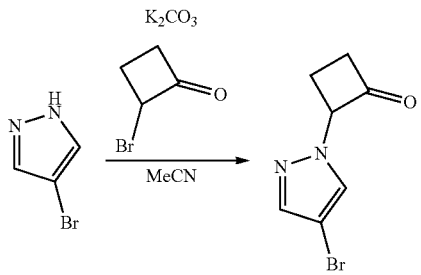

To a solution of 2-bromocyclobutanone (16.2 g, 109 mmol) in MeCN (30 mL) was added 4-bromo-1H-pyrazole (8.00 g, 54.4 mmol) and potassium carbonate (30.1 g, 218 mmol). The mixture was stirred at 20° C. for 10 h. The mixture was filtered, and the solvents of the filtrate were evaporated. The residue was purified by reversed-phase HPLC (Waters SunFire C18 OBD Prep Column, 19 mm×100 mm MeCN/water (with 0.1% TFA modifier) as eluent) to afford rac-2-(4-bromo-1H-pyrazol-1-yl)cyclobutanone. LCMS ($C_7H_7BrN_2O$) (ES, m/z) [M+H]+: 215, 217.

Intermediate 29: 2-(4-bromo-1H-pyrazol-1-yl)-1-methylcyclobutan-1-ol

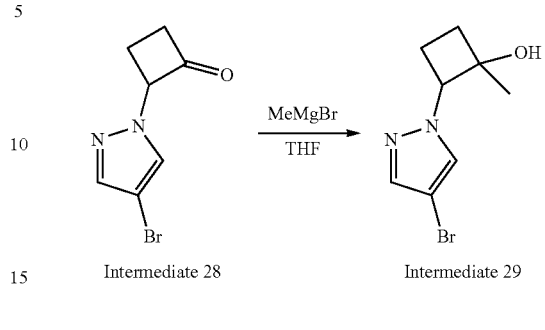

Methylmagnesium bromide (0.248 ml, 0.744 mmol, 3 M in diethyl ether) was added to a stirred mixture of rac-2-(4-bromo-1H-pyrazol-1-yl)cyclobutanone (Intermediate 28) (80.0 mg, 0.372 mmol) in THF (2 mL) at −78° C., and the mixture was stirred at that temperature for 3 h. The reaction was quenched with aqueous saturated $NH_4Cl$ (2 mL), and the desired layer was extracted from the mixture with EtOAc (2×20 mL). The combined organic layers were dried over anhydrous $Na_2SO_4$, filtered, and evaporated. The resulting residue was purified by preparative silica gel TLC with 30% EtOAc in petroleum ether as eluent to afford 2-(4-bromo-1H-pyrazol-1-yl)-1-methylcyclobutanol. LCMS ($C_8H_{11}BrN_2O$) (ES, m/z) [M+H]+: 231, 233.

Intermediate 30: rac-4-bromo-1-(2,2-dimethoxycyclobutyl)-1H-pyrazole

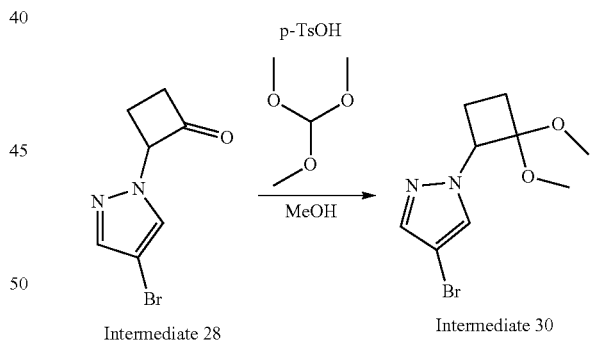

To a stirred mixture of trimethoxymethane (592 mg, 5.58 mmol) and rac-2-(4-bromo-1H-pyrazol-1-yl)cyclobutanone (Intermediate 28) (600 mg, 2.79 mmol) in MeOH (5 mL) was added 4-methylbenzenesulfonic acid hydrate (53.1 mg, 0.279 mmol). The mixture was stirred at 28° C. for 12 h. The mixture was diluted with EtOAc (50 mL) and washed with water (30 mL). The organic layer was dried over anhydrous $Na_2SO_4$, filtered, and the solvents of the filtrate were evaporated. The resulting residue was purified by silica gel chromatography with 0-10% EtOAc in petroleum ether as eluent to afford rac-4-bromo-1-(2,2-dimethoxycyclobutyl)-1H-pyrazole.
LCMS ($C_9H_{13}BrN_2O_2$) (ES, m/z) [M+H]+: 261, 263.

Intermediate 31: mixture of rac-4-bromo-5-methyl-1-((1-((tetrahydro-2H-pyran-2-yl)oxy)cyclobutyl)methyl)-1H-pyrazole and rac-4-bromo-3-methyl-1-((1-((tetrahydro-2H-pyran-2-yl)oxy)cyclobutyl)methyl)-1H-pyrazole

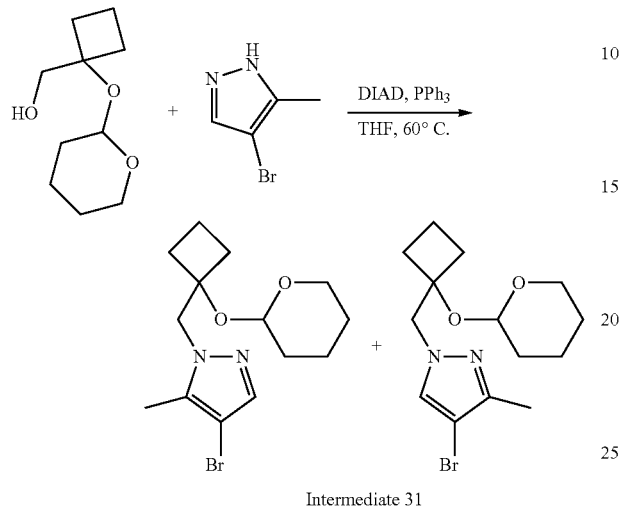

Intermediate 31

To a stirred solution of rac-(1-((tetrahydro-2H-pyran-2-yl)oxy)cyclobutyl)methanol (1.00 g, 5.37 mmol), 4-bromo-5-methyl-1H-pyrazole (0.864 g, 5.37 mmol) and triphenylphosphine (1.41 g, 5.37 mmol) in THF (10.2 mL) was added diisopropyl diazene-1,2-dicarboxylate (1.09 g, 5.37 mmol). The mixture was stirred and heated at 60° C. for 16 h. The solvents were evaporated. The resulting residue was purified by silica gel chromatography with 0-80% EtOAc in hexane to afford a mixture of rac-4-bromo-5-methyl-1-((1-((tetrahydro-2H-pyran-2-yl)oxy)cyclobutyl)methyl)-1H-pyrazole and rac-4-bromo-3-methyl-1-((1-((tetrahydro-2H-pyran-2-yl)oxy)cyclobutyl)methyl)-1H-pyrazole. LCMS ($C_{14}H_{21}BrN_2O_2$) (ES, m/z): 329, 331 [M+H]$^+$.

Intermediate 32: rac-4-bromo-1-(2-((tetrahydro-2H-pyran-2-yl)oxy)cyclopentyl)-1H-pyrazole To a stirred solution of 2-(4-bromo-1H-pyrazol-1-yl)cyclopentanol (Intermediate 5) (3.00 g, 13.0 mmol) in DCM (45 mL) was added 3,4-dihydro-2H-pyran (2.4 mL, 26 mmol), followed by 4-methylbenzenesulfonic acid (polymer-bound, 2.0 g). The mixture was stirred at room temperature for 16 h. The mixture was filtered, and the solvents of the filtrate were evaporated. The residue was purified by reversed-phase C18 chromatography with 0-100% MeCN in water as eluent to afford rac-4-bromo-1-(2-((tetrahydro-2H-pyran-2-yl)oxy)cyclopentyl)-1H-pyrazole. LCMS ($C_{13}H_{19}BrN_2O_2$) (ES, m/z): 315, 317 [M+H]$^+$.

Intermediate 33: 1-(4-amino-1H-pyrazol-1-yl)-2-methylpropan-2-ol

Step 1: 2-methyl-1-(4-nitro-1H-pyrazol-1-yl)propan-2-ol

To a 500 mL round bottom flask was added 4-nitro-1H-pyrazole (15.0 g, 133 mmol), cesium carbonate (64.8 g, 199 mmol), and DMF (195 mL). To the mixture was added 2,2-dimethyloxirane (23.6 mL, 265 mmol). The mixture was heated at 80° C. for 16 h. The mixture was cooled to room temperature. The mixture was filtered and washed with EtOAc. The solvents of the filtrate were evaporated. The resulting residue was purified by silica gel chromatography with 0-80% EtOAc in hexanes, yielding 2-methyl-1-(4-nitro-1H-pyrazol-1-yl)propan-2-ol. LCMS ($C_7H_{11}N_3O_3$) (ES, m/z): 186 [M+H]$^+$.

Step 2: 1-(4-amino-1H-pyrazol-1-yl)-2-methylpropan-2-ol

To a 500 mL flask was added 2-methyl-1-(4-nitro-1H-pyrazol-1-yl)propan-2-ol (18.8 g, 102 mmol), 10% palladium on carbon (1.08 g, 1.01 mmol), and EtOAc (300 mL). The mixture was degassed under vacuum and refilled with nitrogen three times. The mixture was degassed and refilled with hydrogen from a balloon. The mixture was stirred under an atmosphere of hydrogen for 21 h. The mixture was filtered through Celite® (diatomaceous earth). The solvents of the filtrate were evaporated, yielding 1-(4-amino-1H-pyrazol-1-yl)-2-methylpropan-2-ol. LCMS ($C_7H_{13}N_3O$) (ES, m/z): 156 $[M+H]^+$.

Intermediate 34: 2-(4-amino-1H-pyrazol-1-yl)-2-methylpropan-1-ol

Step 1: ethyl 2-methyl-2-(4-nitro-1H-pyrazol-1-yl)propanoate

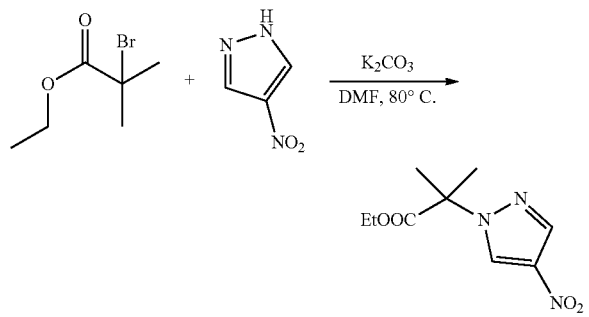

To a stirred mixture of 4-nitro-1H-pyrazole (3.00 g, 26.5 mmol) and ethyl 2-bromo-2-methylpropanoate (5.69 g, 29.2 mmol) in DMF (50 mL) was added $K_2CO_3$ (11.00 g, 80.00 mmol). The mixture was stirred and heated at 80° C. for 10 h. The mixture was cooled, filtered, and the solvents of the filtrate were evaporated. The resulting residue was purified by silica gel chromatography 5-20% EtOAc in petroleum ether as eluent to afford ethyl 2-methyl-2-(4-nitro-1H-pyrazol-1-yl)propanoate. LCMS ($C_9H_{13}N_3O_4$) (ES, m/z): 228 $[M+H]^+$.

Step 2: 2-methyl-2-(4-nitro-1H-pyrazol-1-yl)propan-1-ol

To a stirred mixture of ethyl 2-methyl-2-(4-nitro-1H-pyrazol-1-yl)propanoate (3.00 g, 13.2 mmol) in EtOH (50 mL) was added $NaBH_4$ (0.999 g, 26.4 mmol). The mixture was stirred at room temperature for 2 h. The mixture was diluted with water (40 mL) and extracted with EtOAc (2×50 mL). The combined organic layers were dried over anhydrous $Na_2SO_4$, filtered, and the solvents of the filtrate were evaporated to afford 2-methyl-2-(4-nitro-1H-pyrazol-1-yl)propan-1-ol.

Step 3: 2-(4-amino-1H-pyrazol-1-yl)-2-methylpropan-1-ol

Step 3 of the synthesis of Intermediate 34 was conducted in a manner similar to that of step 2 of the synthesis of Intermediate 33, using 2-methyl-2-(4-nitro-1H-pyrazol-1-yl) propan-1-ol as the starting material, to afford 2-(4-amino-1H-pyrazol-1-yl)-2-methylpropan-1-ol. LCMS ($C_7H_{13}N_3O$) (ES, m/z): 156 $[M+H]^+$.

Intermediate 35: 2-amino-5-fluoro-4-methoxybenzonitrile

Step 1: 2-bromo-4-fluoro-5-methoxyaniline

A solution of 4-fluoro-3-methoxyaniline (350.0 g, 2.48 mol) in EtOAc (3.5 L) was cooled at 0-5° C. To the mixture was added tetra-n-butylammonium tribromide (14.0 kg, 2.90 mol) portionwise. The mixture was warmed to 15° C., and stirred at that temperature for 1 h. The mixture was adjusted to pH 8 with saturated aqueous $Na_2CO_3$. The mixture was extracted with EtOAc and the combined organic layers were washed with water (2×1.5 L) and dried with anhydrous $Na_2SO_4$. The solids were removed by filtration, and the solvents of the filtrate were evaporated. The resulting residue was purified by silica gel chromatography with 0-100% EtOAc in petroleum ether as eluent to afford 2-bromo-4-fluoro-5-methoxyaniline. LCMS ($C_7H_7BrFNO$) (ES, m/z): 220, 222 $[M+H]^+$.

Step 2: 2-amino-5-fluoro-4-methoxybenzonitrile

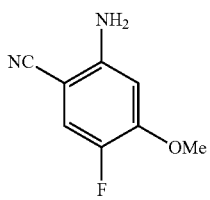

Intermediate 35

To a solution of 2-bromo-4-fluoro-5-methoxyaniline (300 g, 1.36 mol) in DMF (2.1 L) was added Zn(CN)$_2$ (327 g, 2.78 mol) and Pd(PPh$_3$)$_4$ (90.0 g, 0.0778 mol). The mixture was degassed under vacuum and purged with nitrogen. The mixture was stirred and heated at 130° C. for 1 h under nitrogen. The mixture was poured into ice water (4 L). The mixture was extracted with EtOAc (3 L, 2 L, 1 L), and the combined organic layers were washed with brine (2 L, 1.5 L). The organic layer was dried over anhydrous Na$_2$SO$_4$, filtered, and the solvents of the filtrate were evaporated. The resulting residue was purified by silica gel chromatography with 0-100% EtOAc in petroleum ether as eluent to afford 2-amino-5-fluoro-4-methoxybenzonitrile. LCMS (C$_8$H$_7$FN$_2$O) (ES, m/z): 167 [M+H]$^+$.

Intermediate 36: 2-amino-4-chloro-5-fluorobenzonitrile

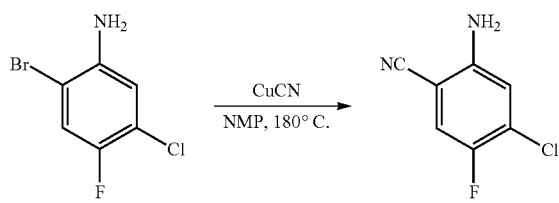

Intermediate 36

To a 20 mL microwave vial was added 2-bromo-5-chloro-4-fluoroaniline (1.00 g, 4.46 mmol), copper(I) cyanide (0.472 g, 4.90 mmol), and NMP (8 mL). The mixture was stirred and heated at 180° C. in a microwave for 1 h. The mixture was diluted in diethyl ether (100 mL) and filtered through Celite® (diatomaceous earth). The filtrate was washed with water (3×100 mL). The organic layer was dried over anhydrous magnesium sulfate, filtered, and the solvents of the filtrate were evaporated, to afford 2-amino-4-chloro-5-fluorobenzonitrile (LCMS (C$_7$H$_4$ClFN$_2$) (ES, m/z): 171 [M+H]$^+$.

Intermediate 37: 2-((((2,4-dimethoxybenzyl)imino)methylene)amino)-5-fluoro-4-methoxybenzonitrile Step 1: 1-(2-Cyano-4-fluoro-5-methoxyphenyl)-3-(2,4-dimethoxybenzyl)urea

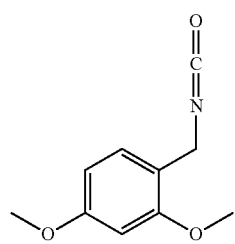

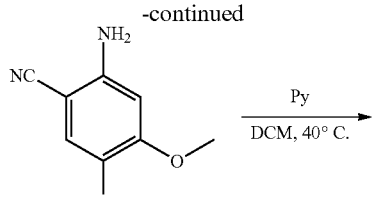

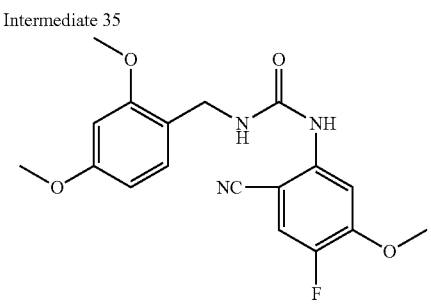

To a 20 mL vial was added 2-amino-5-fluoro-4-methoxybenzonitrile (Intermediate 35) (817 mg, 4.92 mmol), DCM (6 mL), and pyridine (1 mL). The mixture was stirred. To the mixture was added 1-(isocyanatomethyl)-2,4-dimethoxybenzene (1425 mg, 7.380 mmol). The mixture was stirred and heated at 40° C. for 16 h. The solids were collected by filtration and washed with MeOH (3×3 mL), to afford 1-(2-cyano-4-fluoro-5-methoxyphenyl)-3-(2,4-dimethoxybenzyl)urea.

Step 2: 2-((((2,4-Dimethoxybenzyl)imino)methylene)amino)-5-fluoro-4-methoxybenzonitrile

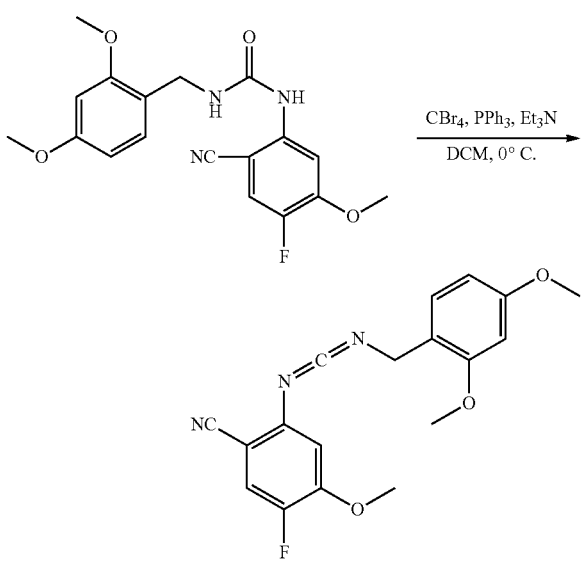

Intermediate 37

To a 100 mL round bottom flask was added 1-(2-cyano-4-fluoro-5-methoxyphenyl)-3-(2,4-dimethoxybenzyl)urea (1.16 g, 3.22 mmol), triphenylphosphine (1.69 g, 6.44 mmol), triethylamine (1.80 ml, 12.9 mmol), and DCM (25 mL). The mixture was stirred and cooled at 0° C. To the mixture was added a solution of carbon tetrabromide (2.14 g, 6.44 mmol) in DCM (5 mL) dropwise. After 30 min, the mixture was concentrated. The resulting residue was purified by silica gel chromatography with 0-70% EtOAc in hexanes as eluent, to afford 2-((((2,4-dimethoxybenzyl)imino)methylene)amino)-5-fluoro-4-methoxybenzonitrile. LCMS ($C_{18}H_{16}FN_3O_3$) (ES, m/z) [M+Na]$^+$: 364.

The intermediates in the following Table 5 were prepared in a manner similar to that of Intermediate 37 from the appropriate intermediates and starting materials.

TABLE 5

| Intermediate | Structure Name | Observed m/z [M + Na]$^+$ |
|---|---|---|
| 38 | 2-((((2,3-dimethoxybenzyl)imino)methylene)amino)-5-fluoro-3-methoxybenzonitrile | 364 |
| 39 | 4-chloro-2-((((2,4-dimethoxybenzyl)imino)methylene)amino)-5-fluorobenzonitrile | 368 |
| 40 | 2-((((2,4-dimethoxybenzyl)imino)methylene)amino)-5-fluoro-4-methylbenzonitrile | 348 |
| 41 | 2-((((2,4-dimethoxybenzyl)imino)methylene)amino)-3,5-difluorobenzonitrile | 352 |
| 42 | 3,5-dichloro-2-((((2,4-dimethoxybenzyl)imino)methylene)amino)benzonitrile | 384 |

Intermediate 43: 1-(tert-butyl) 3-ethyl (R)-piperidine-1,3-dicarboxylate

Intermediate 43

A solution of (R)-ethyl piperidine-3-carboxylate (200.0 g, 1270 mmol), triethylamine (257.5 g, 2540 mmol) and DMAP (15.5 g, 130 mmol) in DCM (2 L) was cooled at 0° C. To the mixture was added di-tert-butyl dicarbonate (305.4 g, 1400 mmol) portionwise. The mixture was stirred at room temperature for 3 h. Then the organic layer was washed with aqueous saturated sodium bicarbonate (3×1 L). The combined organic layers were dried over anhydrous MgSO$_4$, filtered, and the solvents of the filtrate were evaporated to afford 1-(tert-butyl) 3-ethyl (R)-piperidine-1,3-dicarboxylate.

Intermediate 44 in the following Table 6 was prepared in a manner similar to that of Intermediate 43 from the appropriate starting materials.

TABLE 6

| Intermediate | Structure Name | Observed m/z [M + Na]+ |
|---|---|---|
| 44 | 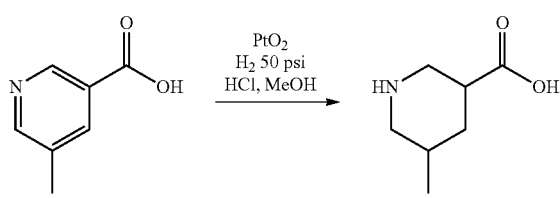<br>1-(tert-butyl) 3-methyl azepane-1,3-dicarboxylate | 280 |

Intermediate 45: 1-(tert-butyl) 3-methyl 5-methylpiperidine-1,3-dicarboxylate Step 1: 5-methylpiperidine-3-carboxylic acid

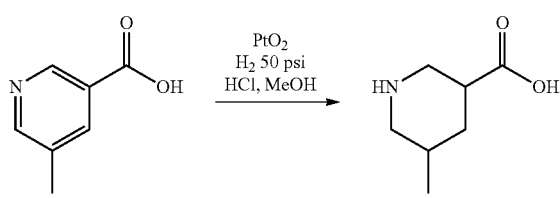

To a stirred mixture of 5-methylnicotinic acid (10 g, 72.9 mmol) and concentrated aqueous HCl (0.599 mL, 7.29 mmol) in MeOH (100 mL) at 20° C. was added platinum (IV) oxide (1.67 g, 7.29 mmol). The mixture was degassed and purged with nitrogen then pressurized to 50 psi with hydrogen. The mixture was stirred for 10 h. The mixture was filtered, and the solvents of the filtrate were evaporated to afford the 5-methylpiperidine-3-carboxylic acid.

Step 2: 1-(tert-butoxycarbonyl)-5-methylpiperidine-3-carboxylic acid

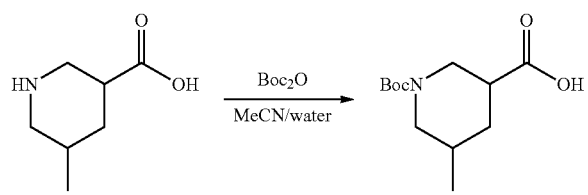

To a stirred mixture of di-tert-butyl dicarbonate (5.84 ml, 25.1 mmol) and 5-methylpiperidine-3-carboxylic acid (3.00 g, 21.0 mmol) in MeCN (20 mL) and water (20 mL) at 20° C. was added sodium bicarbonate (7.04 g, 84.0 mmol). The mixture was stirred at 20° C. for 5 h. The mixture was diluted with water (20 mL), adjusted with concentrated aqueous HCl to pH 5, and extracted with EtOAc (3×30 mL). The combined organic layers were dried over anhydrous Na$_2$SO$_4$, filtered, and the solvents of the filtrate were evaporated to afford 1-(tert-butoxycarbonyl)-5-methylpiperidine-3-carboxylic acid. LCMS (C$_{12}$H$_{21}$NO$_4$) (ES, m/z) [M+H]+: 244.

Step 3: 1-(tert-butyl) 3-methyl 5-methylpiperidine-1,3-dicarboxylate

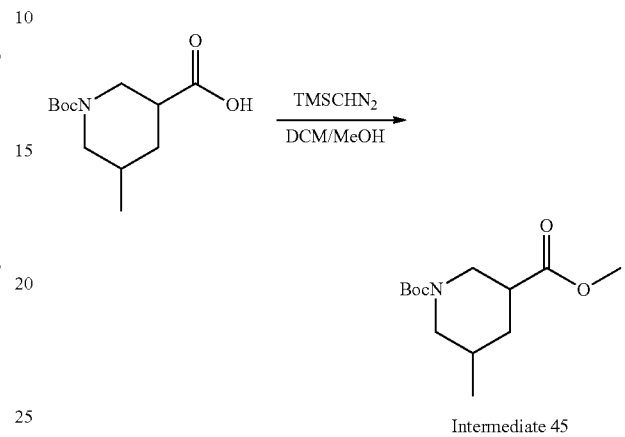

Intermediate 45

To a stirred mixture of 1-(tert-butoxycarbonyl)-5-methylpiperidine-3-carboxylic acid (5.00 g, 20.5 mmol) in DCM (10 mL) and MeOH (10 mL) at 0° C. was added trimethylsilyl-diazomethane (15.4 mL, 30.8 mmol). The mixture was stirred at room temperature for 2 h. The solvents were evaporated to afford 1-tert-butyl 3-methyl 5-methylpiperidine-1,3-dicarboxylate. LCMS (C$_{13}$H$_{23}$NO$_4$) (ES, m/z) [M+H]+: 258.

Intermediate 46: 1-(tert-butyl) 3-methyl 4-methylpiperidine-1,3-dicarboxylate Step 1: Methyl 4-methylpiperidine-3-carboxylate

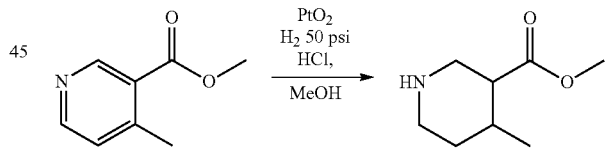

Step 1 of the synthesis of Intermediate 46 was conducted in a manner similar to that of step 1 of the synthesis of Intermediate 45 from the appropriate starting materials to afford methyl 4-methylpiperidine-3-carboxylate. LCMS (C$_8$H$_{15}$NO$_2$) (ES, m/z) [M+H]+: 158.

Step 2: 1-(tert-butyl) 3-methyl 4-methylpiperidine-1,4-dicarboxylate

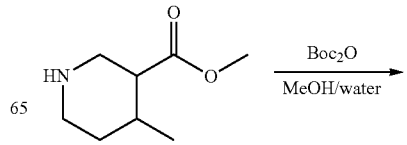

83
-continued

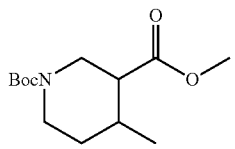

Intermediate 46

Step 2 of the synthesis of Intermediate 46 was conducted in a manner similar to step 2 of the synthesis of Intermediate 45 from the appropriate starting materials, with the exception that the crude material was purified by silica gel chromatography with 0-30% EtOAc in petroleum ether as eluent to afford to 1-(tert-butyl) 3-methyl 4-methylpiperidine-1,4-dicarboxylate. Intermediate 47: mixture of rac,cis-1-(tert-butyl) 3-ethyl-5-fluoropiperidine-1,3-dicarboxylate and rac,trans-1-(tert-butyl) 3-ethyl-5-fluoropiperidine-1,3-dicarboxylate

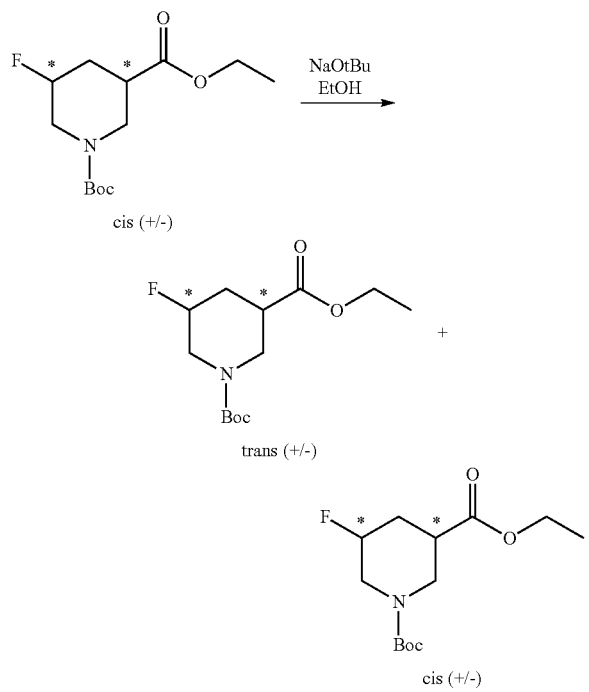

To a 250 mL round bottom flask containing rac, cis-1-(tert-butyl) 3-ethyl-5-fluoropiperidine-1,3-dicarboxylate (2.00 g, 7.26 mmol) was added EtOH (73 mL). To the mixture was added sodium tert-butoxide (7.26 mL, 14.5 mmol) (2 M solution in THF) dropwise with stirring. The mixture was stirred at room temperature for 3 h. The mixture was concentrated to about 10 mL of volume. To the mixture was added EtOAc (10 mL). The solvents were evaporated. The residue was dissolved in EtOAc (60 mL) and washed with water (3×20 mL). The organic layer was dried over anhydrous sodium sulfate, filtered, and the solvents were evaporated to afford a mixture of rac,cis-1-(tert-butyl) 3-ethyl-5-fluoropiperidine-1,3-dicarboxylate and rac,trans-1-(tert-butyl) 3-ethyl-5-fluoropiperidine-1,3-dicarboxylate.

84
Intermediate 48 and 49: methyl (3S,6R)-1-(1-(2-hydroxy-2-methylpropyl)-1H-pyrazol-4-yl)-6-methylpiperidine-3-carboxylate and methyl (3R,6S)-1-(1-(2-hydroxy-2-methylpropyl)-1H-pyrazol-4-yl)-6-methylpiperidine-3-carboxylate

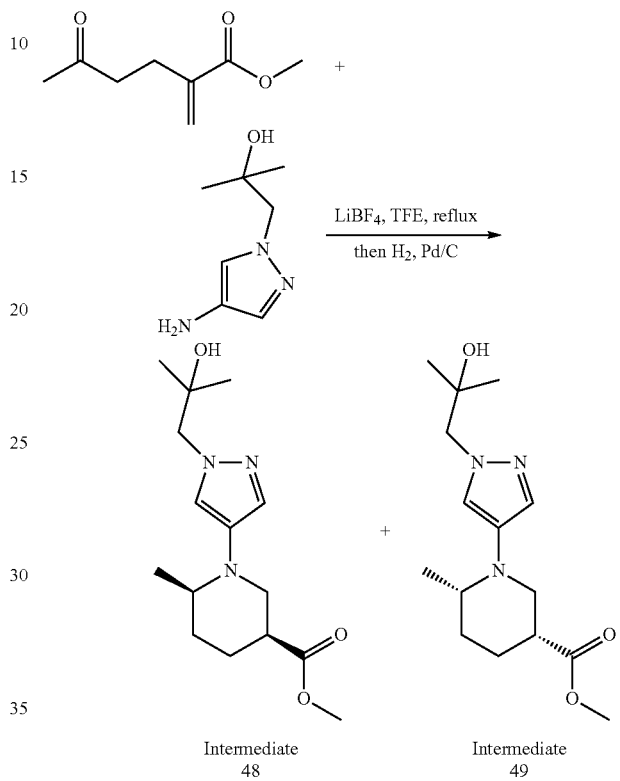

A 100 mL flask was charged with 1-(4-amino-1H-pyrazol-1-yl)-2-methylpropan-2-ol (4.66 g, 30.0 mmol), methyl 2-methylene-5-oxohexanoate[1] (3.12 g, 20.0 mmol), and LiBF$_4$ (1.88 g, 20.0 mmol). To the flask was added TFE (31.2 mL). The flask was fitted with a reflux condenser, which had an inlet for nitrogen. The mixture was heated at reflux for 48 h. The mixture was cooled to room temperature, and to the mixture was added 10% palladium on carbon (0.639 g, 6.00 mmol). The mixture was placed under an atmosphere of hydrogen and stirred at room temperature for 6 h. The mixture was filtered, and the solvents of the filtrate were evaporated. The resulting residue was purified by silica gel chromatography with 0-4% MeOH in DCM as eluent, yielding the racemate with cis relative stereochemistry. The racemic mixture was resolved by chiral SFC (Chiral Technologies AD-H 21×250 mm column with 15% (MeOH w/0.1% NH$_4$OH modifier) as cosolvent), to afford methyl (3S,6R)-1-(1-(2-hydroxy-2-methylpropyl)-1H-pyrazol-4-yl)-6-methylpiperidine-3-carboxylate (Intermediate 48, first eluting peak) and methyl (3R,6S)-1-(1-(2-hydroxy-2-methylpropyl)-1H-pyrazol-4-yl)-6-methylpiperidine-3-carboxylate (Intermediate 49, second eluting peak).

For Intermediate 48: LCMS (C$_{15}$H$_{25}$N$_3$O$_3$) (ES, m/z): 296 [M+H]$^+$. For Intermediate 49: LCMS (C$_{15}$H$_{25}$N$_3$O$_3$) (ES, m/z): 296 [M+H]$^+$. [1]Bizet, V.; Lefebvre, V.; Baudoux, J.; Lasne, M.; Boulange, A.; Leleu, S.; Franck, X.; Rouden, J. Eur. J. Org. Chem. 2011, 4170.

The intermediates in the following Table 7 were prepared in a manner similar to that of Intermediate 48 and Intermediate 49 from the appropriate intermediates and starting materials, with the exception that these compounds were isolated as racemic mixtures of diastereomers that were not resolved by SFC separation.

TABLE 7

| Intermediate | Structure Name | Observed m/z [M + H]+ |
|---|---|---|
| 50 | ethyl 1-(1-(1-hydroxy-2-methylpropan-2-yl)-1H-pyrazol-4-yl)-6-methylpiperidine-3-carboxylate | 310 |
| 51 | methyl 1-(1-(2-hydroxy-2-methylpropyl)-3-methyl-1H-pyrazol-4-yl)-6-methylpiperidine-3-carboxylate | 310 |

Intermediate 52: ethyl 6-ethyl-1-(1-(2-hydroxy-2-methylpropyl)-1H-pyrazol-4-yl)-2-oxopiperidine-3-carboxylate Step 1: diethyl 2-(3-oxopentyl)malonate

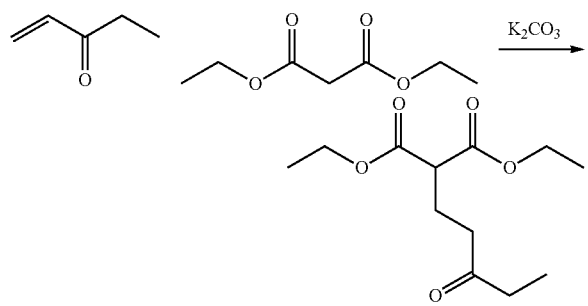

A mixture of diethyl malonate (10.0 g, 62.4 mmol), pent-1-en-3-one (5.78 g, 68.7 mmol) and potassium carbonate (0.863 g, 6.24 mmol) was stirred at room temperature in a sealed tube for 3 days. The resulting mixture was filtered to provide the filtrate, which is neat diethyl 2-(3-oxopentyl)malonate. LCMS ($C_{12}H_{20}O_5$) (ES, m/z): 245 [M+H]+. The crude material was used without further purification.

Step 2: rac-diethyl 2-(3-((1-(2-hydroxy-2-methylpropyl)-1H-pyrazol-4-yl)amino)pentyl)malonate

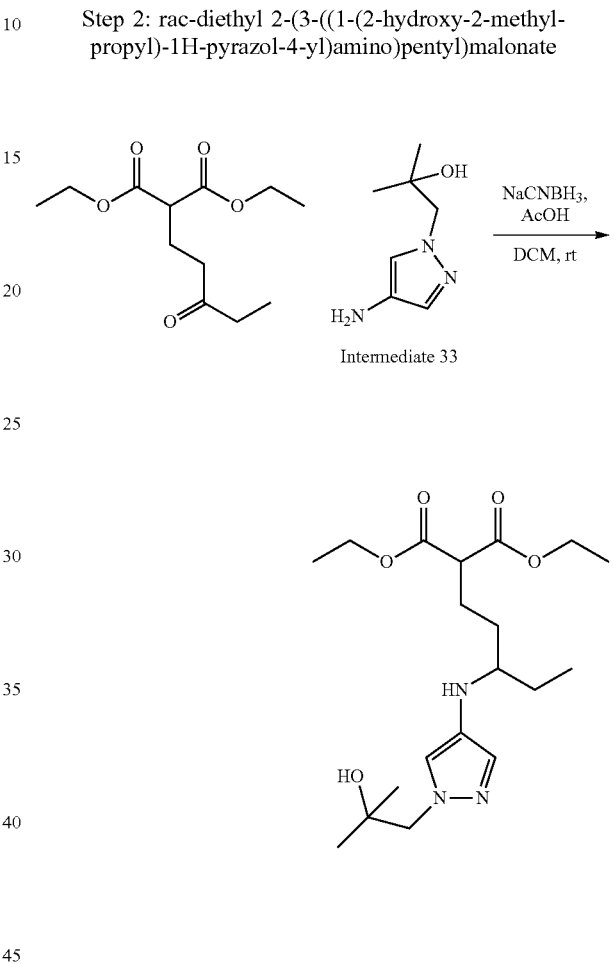

To a stirred solution of 1-(4-amino-1H-pyrazol-1-yl)-2-methylpropan-2-ol (Intermediate 33) (2.00 g, 12.9 mmol) in DCM (129 mL) was added diethyl 2-(3-oxopentyl)malonate (6.93 g, 28.4 mmol) and AcOH (0.077 mL, 1.3 mmol). The mixture was stirred at room temperature for 30 min. To the mixture was added sodium cyanoborohydride (1.62 g, 25.8 mmol) portionwise. The mixture was stirred at room temperature for an additional 30 min. The mixture was quenched with 1 M aqueous HCl (150 mL). The organic layer was separated, and the aqueous layer was extracted with DCM twice more. The combined organic layers were dried over anhydrous $Na_2SO_4$, filtered, and the solvents of the filtrate were evaporated to afford rac-diethyl 2-(3-((1-(2-hydroxy-2-methylpropyl)-1H-pyrazol-4-yl)amino)pentyl)malonate. LCMS ($C_{19}H_{33}N_3O_5$) (ES, m/z): 384 [M+H]+.

Step 3: ethyl 6-ethyl-1-(1-(2-hydroxy-2-methylpropyl)-1H-pyrazol-4-yl)-2-oxopiperidine-3-carboxylate

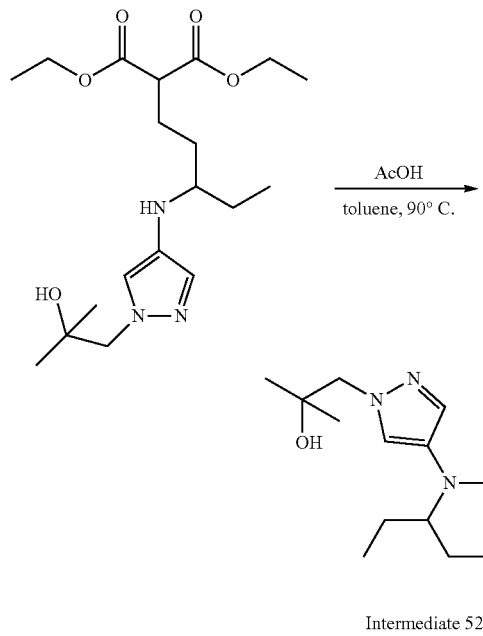

Intermediate 52

To a solution of rac-diethyl 2-(3-((1-(2-hydroxy-2-methylpropyl)-1H-pyrazol-4-yl)amino)pentyl)malonate (1.70 g, 4.43 mmol) in toluene (22 mL) was added AcOH (0.530 mL, 8.87 mmol). The mixture was stirred at 90° C. for 2 days. The mixture was cooled to room temperature, and the solvents were evaporated. The residue was purified by silica gel chromatography with 0-100% EtOAc in hexanes as eluent to afford ethyl 6-ethyl-1-(1-(2-hydroxy-2-methylpropyl)-1H-pyrazol-4-yl)-2-oxopiperidine-3-carboxylate. LCMS ($C_{17}H_{27}N_3O_4$) (ES, m/z): 338 [M+H]$^+$.

Intermediate 53: ethyl 3-hydroxycyclohexanecarboxylate

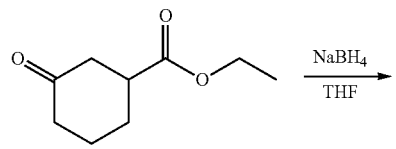

To a solution of ethyl 3-oxocyclohexanecarboxylate (2.00 g, 11.7 mmol) in THF (20 mL) was added a solution of sodium borohydride (0.889 g, 23.5 mmol) in THF (10 mL) at 0° C. The mixture was stirred at 0° C. for 2 h. To the mixture was added water (10 mL), and the mixture was extracted with EtOAc (3×15 mL). The combined organic layers were dried over anhydrous $Na_2SO_4$, filtered, and the solvents of the filtrate were evaporated. The resulting residue was purified by silica gel chromatography with 10-50% EtOAc in petroleum ether as eluent to afford ethyl 3-hydroxycyclohexanecarboxylate.

Intermediate 54: tert-butyl (R)-3-(hydrazinecarbonyl)piperidine-1-carboxylate The solution of (R)-1-tert-butyl 3-ethyl piperidine-1,3-dicarboxylate (320.0 g, 1243 mmol) and hydrazine hydrate (311.3 g, 6217 mmol) in EtOH (1.6 L) was stirred and heated at 80° C. for 16 h. The solvents were evaporated. The resulting residue was purified by silica gel chromatography eluting with DCM to afford tert-butyl (R)-3-(hydrazinecarbonyl)piperidine-1-carboxylate. LCMS ($C_{11}H_{21}N_3O_3$) (ES, m/z): 244 [M+H]$^+$.

The intermediates in the following Table 8 were prepared in a manner similar to that of Intermediate 54 from the appropriate intermediates and starting materials.

TABLE 8

| Intermediate | Structure name | Observed m/z [M + H]$^+$ |
|---|---|---|
| 55 | | 258 |

TABLE 8-continued

| Intermediate | Structure name | Observed m/z [M + H]+ |
|---|---|---|
| | tert-butyl 3-(hydrazinecarbonyl)azepane-1-carboxylate | |
| 56 | tert-butyl 3-(hydrazinecarbonyl)-5-methylpiperidine-1-carboxylate | 258 |
| 57 | tert-butyl 3-(hydrazinecarbonyl)-4-methylpiperidine-1-carboxylate | 258 |
| 58 | tert-butyl 3-fluoro-4-(hydrazinecarbonyl)piperidine-1-carboxylate | 206 [M + H − C$_4$H$_8$]+ |
| 59 | mixture of tert-butyl (3R,5R and 3S,5S)-3-fluoro-5-(hydrazinecarbonyl)piperidine-1-carboxylate and tert-butyl (3S,5R and 3R,5S)-3-fluoro-5-(hydrazinecarbonyl)piperidine-1-carboxylate | 206 [M + H − C$_4$H$_8$]+ |
| 60 | tert-butyl 3-fluoro-3-(hydrazinecarbonyl)pyrrolidine-1-carboxylate | 248 |

TABLE 8-continued
| Intermediate | Structure name | Observed m/z [M + H]+ |
|---|---|---|
| 61 | 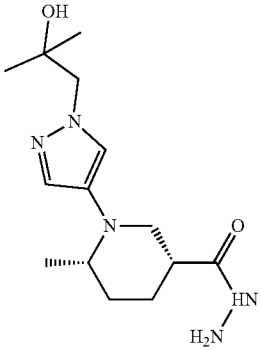 [SMILES: C[C@H]1CC[C@@H](C(=O)NN)CN1c1cnn(CC(C)(C)O)c1]<br>(3R,6S)-1-(1-(2-hydroxy-2-methylpropyl)-1H-pyrazol-4-yl)-6-methylpiperidine-3-carbohydrazide | 296 |
| 62 | 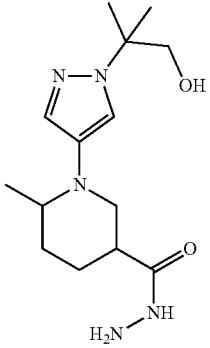 [SMILES: CC1CCC(C(=O)NN)CN1c1cnn(C(C)(C)CO)c1]<br>1-(1-(1-hydroxy-2-methylpropan-2-yl)-1H-pyrazol-4-yl)-6-methylpiperidine-3-carbohydrazide | 296 |
| 63 | 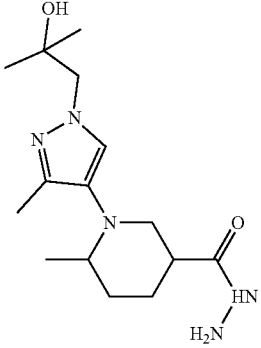 [SMILES: Cc1nn(CC(C)(C)O)cc1N1CC(C(=O)NN)CCC1C]<br>1-(1-(2-hydroxy-2-methylpropyl)-3-methyl-1H-pyrazol-4-yl)-6-methylpiperidine-3-carbohydrazide | 310 |

TABLE 8-continued

| Intermediate | Structure name | Observed m/z [M + H]+ |
|---|---|---|
| 64 | 6-ethyl-1-(1-(2-hydroxy-2-methylpropyl)-1H-pyrazol-4-yl)-2-oxopiperidine-3-carbohydrazide | 324 |
| 65 | 3-hydroxycyclohexane-1-carbohydrazide | 159 |
| 66 | tert-butyl 5-(hydrazinecarbonyl)-2-methylpiperidine-1-carboxylate | 258 |

Intermediate 67: (R)-1-(1-methyl-1H-pyrazol-4-yl)piperidine-3-carbohydrazide

Step 1: ethyl 1-(1-methyl-1H-pyrazol-4-yl)piperidine-3-carboxylate

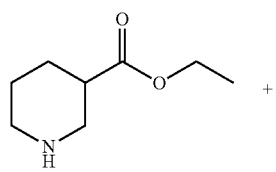

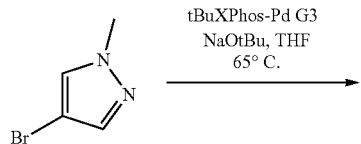

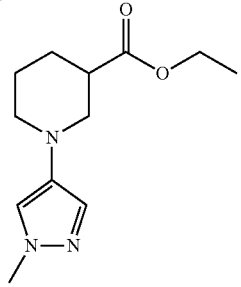

A 40 mL reaction vial was charged with ethyl 1-(1-methyl-1H-pyrazol-4-yl)piperidine-3-carboxylate (1.00 g, 6.36 mmol) and THF (15 mL). To the mixture was added 4-bromo-1-methyl-1H-pyrazole (4.96 mL, 48.0 mmol), followed by tBuXPhos-Pd G3 (2.02 g, 2.54 mmol) and sodium tert-butoxide (4.61 g, 48.0 mmol). Nitrogen was bubbled through the mixture for 10 min. The vial was sealed and heated at 65° C. for 24 h. The mixture was cooled to room temperature and diluted with EtOAc (40 mL). The mixture was filtered through Celite® (diatomaceous earth). The solvents of the filtrate were evaporated. The resulting residue was purified by silica gel chromatography with 0-10% MeOH in DCM to afford ethyl 1-(1-methyl-1H-pyrazol-4-yl)piperidine-3-carboxylate. LCMS ($C_{12}H_{19}N_3O_2$) (ES, m/z): 238 [M+H]+.

Step 2: (R)-1-(1-methyl-1H-pyrazol-4-yl)piperidine-3-carbohydrazide

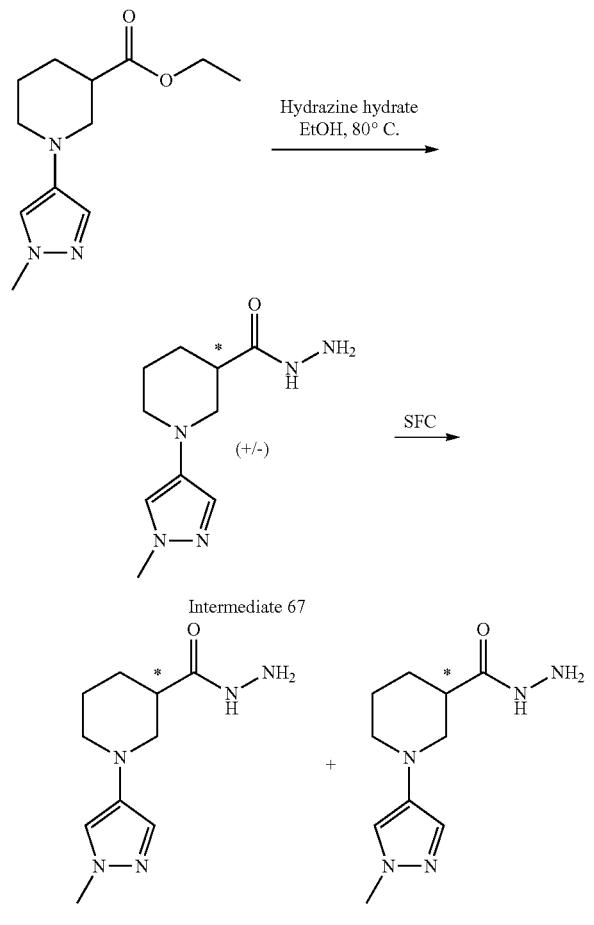

Intermediate 67

Intermediate 67a    Intermediate 67b

A round bottom flask was charged with ethyl 1-(1-methyl-1H-pyrazol-4-yl)piperidine-3-carboxylate (7.72 g, 32.5 mmol) and EtOH (77 mL). To the mixture was added hydrazine hydrate (31.7 mL, 651 mmol). The round bottom flask was fitted with a reflux condenser, and the mixture was heated at 80° C. for 16 h. The mixture was cooled to room temperature, and the solvents were evaporated to afford (R and S)-1-(1-methyl-1H-pyrazol-4-yl)piperidine-3-carbohydrazide (Intermediate 67). The racemic mixture was resolved by chiral SFC separation (Chiral Technologies AD-H 21×250 mm column with 40% (MeOH w/0.25% DEA modifier) as co-solvent to afford (R or S)-1-(1-methyl-1H-pyrazol-4-yl)piperidine-3-carbohydrazide as the first eluting peak and (S or R)-1-(1-methyl-1H-pyrazol-4-yl)piperidine-3-carbohydrazide as the second eluting peak corresponding to Intermediate 67a and Intermediate 67b, respectively. LCMS ($C_{10}H_{17}N_5O$) (ES, m/z): 224 $[M+H]^+$.

Intermediate 68 in the following Table 9 was prepared in a manner similar to that of Intermediate 67, with the exception that no SFC separation was conducted. Thus, the compound was isolated as a mixture of isomers.

TABLE 9

| Intermediate | Structure Name | Observed m/z $[M + H]^+$ |
|---|---|---|
| 68 | 1-(1-(2-hydroxy-2-methylpropyl)-1H-pyrazol-4-yl)-6-methylpiperidine-3-carbohydrazide | 296 |

Intermediate 69: tert-butyl (R)-3-(hydrazinecarbonyl)pyrrolidine-1-carboxylate To a 100 mL round bottom flask was added (R)-1-(tert-butoxycarbonyl)pyrrolidine-3-carboxylic acid (2.00 g, 9.29 mmol) and THF (18.6 mL). To the mixture was added 1,1'-carbonyldiimidazole (1.96 g, 12.1 mmol). The mixture was heated at 60° C. for 30 min. The mixture was cooled to room temperature and transferred to a stirring mixture of hydrazine hydrate (0.447 g, 13.9 mmol) in THF (10 mL) dropwise over 25 min. The mixture was stirred at room temperature for 2 h. The mixture was quenched with water (50 mL) and extracted with EtOAc (2×60 mL). The combined organic layers were dried over anhydrous MgSO₄, filtered, and the solvents of the filtrate were evaporated to afford (R)-tert-butyl 3-(hydrazinecarbonyl)pyrrolidine-1-carboxylate. LCMS ($C_{10}H_{19}N_3O_3$) (ES, m/z): 230 $[M+H]^+$. The intermediates in the following Table 9A were prepared in a manner similar to that of the preparation of Intermediate 60.

TABLE 9A

| Intermediate | Structure Name | Observed m/z [M + H]+ |
|---|---|---|
| 70 | tert-butyl 1-(hydrazinecarbonyl)-3-azabicyclo[3.1.0]hexane-3-carboxylate | 186 [M + H − C$_4$H$_8$]+ |
| 71 | 2-oxopiperidine-3-carbohydrazide | 158 |
| 72 | (R)-tert-butyl 2-(hydrazinecarbonyl)morpholine-4-carboxylate | 268 [M + Na]+ |
| 73 | tert-butyl 2-(hydrazinecarbonyl)thiomorpholine-4-carboxylate 1,1-dioxide | 316 [M + Na]+ |

Intermediate 74: Benzyl 3-fluoro-3-(hydrazinecarbonyl)piperidine-1-carboxylate

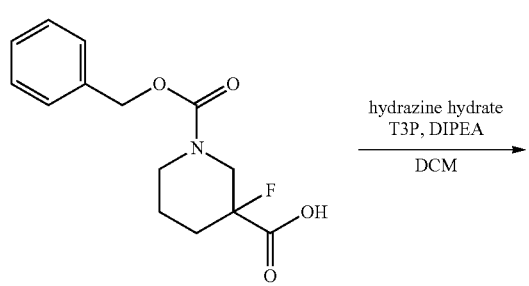

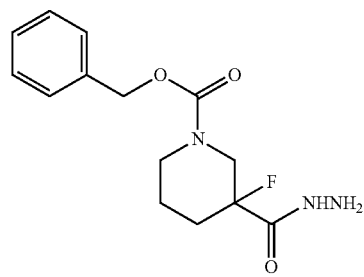

Intermediate 74

To a stirred solution of hydrazine hydrate (0.155 mL, 7.11 mmol), 1-((benzyloxy)carbonyl)-3-fluoropiperidine-3-carboxylic acid (2.00 g, 7.11 mmol) and DIPEA (5.02 ml, 28.4 mmol) in DCM (70 mL) was added tripropyl phosphonic anhydride (50% v/v solution in EtOAc, 6.38 mL, 14.2 mmol) dropwise. The mixture was stirred at room temperature for 12 h. The reaction mixture was quenched by adding saturated aqueous sodium bicarbonate. The mixture was stirred for 5 min, the organic layer was separated, dried over anhydrous Na$_2$SO$_4$, filtered, and the solvents of the filtrate were evaporated to afford benzyl 3-fluoro-3-(hydrazinecarbonyl)piperidine-1-carboxylate. LCMS (C$_{14}$H$_{18}$FN$_3$O$_3$) (ES, m/z): 296 [M+H]+. Intermediate 75 and Intermediate 76: tert-butyl (2R,5S or 2S,5R)-5-(5-((2,4-dimethoxybenzyl)amino)-9-fluoro-8-methoxy-[1,2,4]triazolo[1,5-c]quinazolin-2-yl)-2-methylpiperidine-1-carboxylate and tert-butyl (2S,5R or 2R,5S)-5-(5-((2,4-dimethoxybenzyl)amino)-9-fluoro-8-methoxy-[1,2,4]triazolo[1,5-c]quinazolin-2-yl)-2-methylpiperidine-1-carboxylate

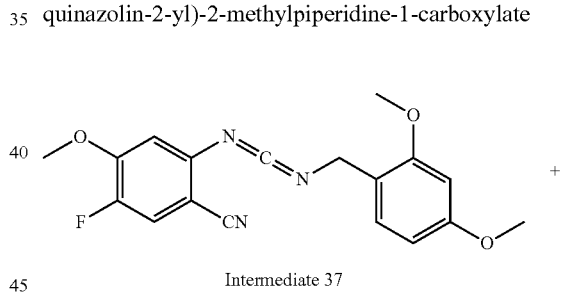

Intermediate 37

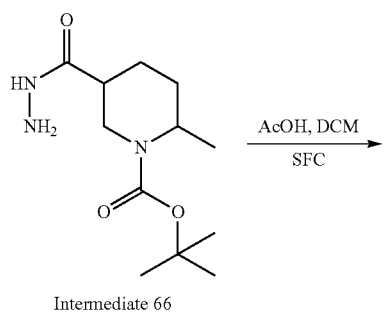

Intermediate 66

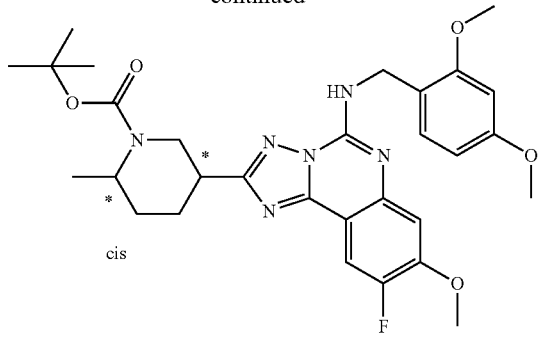

Intermediate 75

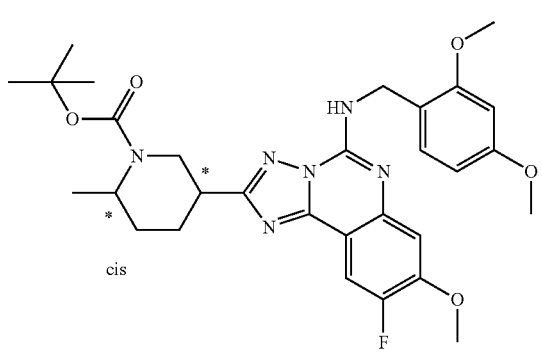

Intermediate 76

A solution of rac,cis-tert-butyl 5-(hydrazinecarbonyl)-2-methylpiperidine-1-carboxylate (Intermediate 66) (5.00 g, 19.4 mmol) in DCM (7 mL) was added AcOH (0.556 ml, 9.72 mmol). The mixture was stirred at room temperature. To the mixture was added 2-((((2,4-dimethoxybenzyl)imino) methylene) amino)-5-fluoro-4-methoxybenzonitrile (Intermediate 37) (6.63 g, 19.4 mmol). The mixture was stirred for 60 h. The mixture was filtered, and the filtrate was loaded directly onto a silica gel column and purified with 0-100% EtOAc in hexane as eluent to provide the racemic tert-butyl (2R,5S and 2S,5R)-5-(5-((2,4-dimethoxybenzyl)amino)-9-fluoro-8-methoxy-[1,2,4]triazolo[1,5-c]quinazolin-2-yl)-2-methylpiperidine-1-carboxylate. The racemic mixture was resolved by chiral SFC (Chiral Technologies AD-H 50×250 mm column, with 35% EtOH as cosolvent) to afford tert-butyl (2R,5S or 2S,5R)-5-(5-((2,4-dimethoxybenzyl)amino)-9-fluoro-8-methoxy-[1,2,4]triazolo[1,5-c]quinazolin-2-yl)-2-methylpiperidine-1-carboxylate (Intermediate 75, first eluting peak) and tert-butyl (2S,5R or 2R,5S)-5-(5-((2,4-dimethoxybenzyl)amino)-9-fluoro-8-methoxy-[1,2,4]triazolo[1,5-c]quinazolin-2-yl)-2-methylpiperidine-1-carboxylate (Intermediate 76, second eluting peak). The intermediates in the following Table 10 were prepared in a manner similar to Intermediate 75 and Intermediate 76, from the appropriate intermediates and starting materials.

TABLE 10

| Intermediate | Structure Name | SFC Conditions | Observed m/z [M + H]+ |
|---|---|---|---|
| 77 | tert-butyl (1R,5R or 1S,5S)-1-(5-((2,4-dimethoxybenzyl)amino)-9-fluoro-8-methoxy-[1,2,4]triazolo[1,5-c]quinazolin-2-yl)-3-azabicyclo[3.1.0]hexane-3-carboxylate | Peak 1; Chiral Technologies AD-H 21 × 25 mm column with 50% (IPA w/ 0.2% DIPA modifier) as co-solvent | 565 |

TABLE 10-continued

| Intermediate | Structure Name | SFC Conditions | Observed m/z [M + H]+ |
|---|---|---|---|
| 78 | 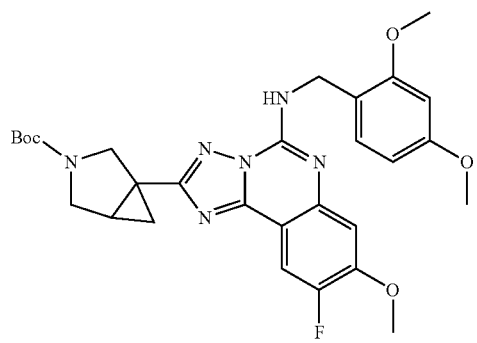 [SMILES: COc1ccc(CNc2nc3cc(OC)c(F)cc3c3nc(C45CC4CN(C(=O)OC(C)(C)C)C5)nn23)c(OC)c1]<br>tert-butyl (1S,5S or 1R,5R)-1-(5-((2,4-dimethoxybenzyl)amino)-9-fluoro-8-methoxy-[1,2,4]triazolo[1,5-c]quinazolin-2-yl)-3-azabicyclo[3.1.0]hexane-3-carboxylate | Peak 2; Chiral Technologies AD-H 21 × 250 mm column with 50% (IPA w/ 0.2% DIPA modifier) as co-solvent | 565 |

Intermediates 79-81: tert-butyl (3S,5R or 3R,5S)-3-(5-((2,4-dimethoxybenzyl)amino)-9-fluoro-8-methoxy-[1,2,4]triazolo[1,5-c]quinazolin-2-yl)-5-fluoropiperidine-1-carboxylate and tert-butyl (3R,5S or 3S,5R)-3-(5-((2,4-dimethoxybenzyl)amino)-9-fluoro-8-methoxy-[1,2,4]triazolo[1,5-c]quinazolin-2-yl)-5-fluoropiperidine-1-carboxylate and tert-butyl (3R,5R and 3S,5S)-3-(5-((2,4-dimethoxybenzyl)amino)-9-fluoro-8-methoxy-[1,2,4]triazolo[1,5-c]quinazolin-2-yl)-5-fluoropiperidine-1-carboxylate

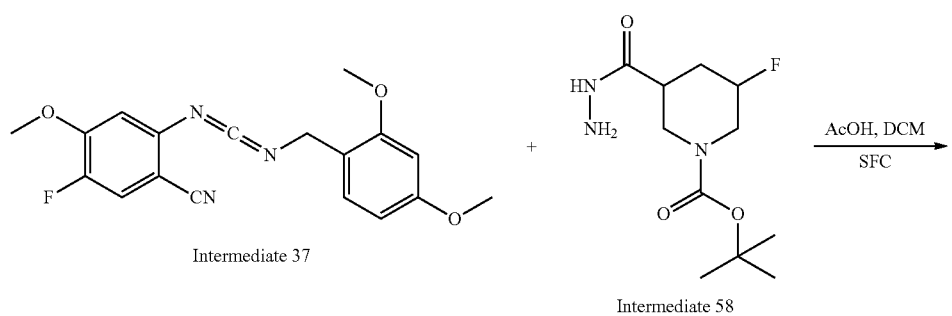

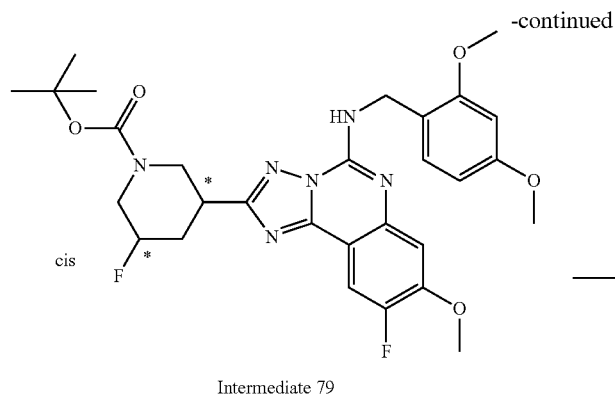

Intermediate 79

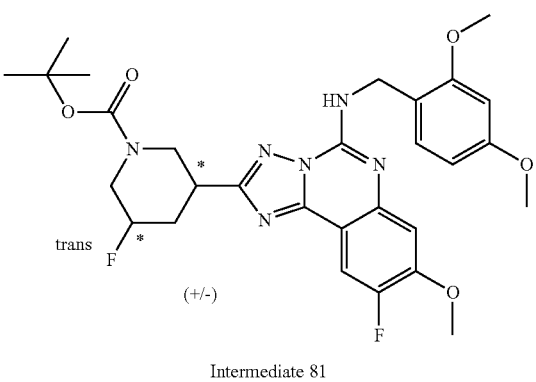

Intermediate 81

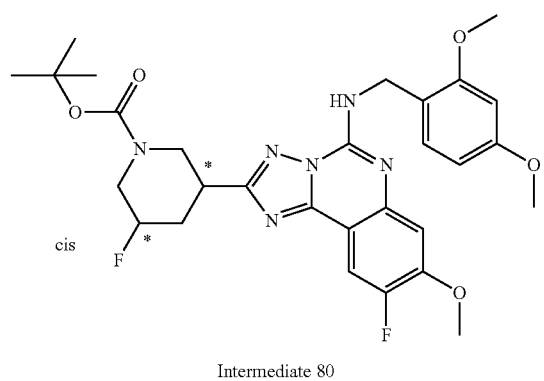

Intermediate 80

Intermediates 79-81 were prepared from Intermediate 37 and Intermediate 58 in a manner similar to that used for the preparation of Intermediate 75 and Intermediate 76. The crude residue was purified by silica gel chromatography with 0-100% EtOAc in hexane as eluent to afford tert-butyl (3S,5R and 3R,5S)-3-(5-((2,4-dimethoxybenzyl)amino)-9-fluoro-8-methoxy-[1,2,4]triazolo[1,5-c]quinazolin-2-yl)-5-fluoropiperidine-1-carboxylate (first eluting peak, mixture of Intermediate 79 and Intermediate 80) and tert-butyl (3R,5R and 3S,5S)-3-(5-((2,4-dimethoxybenzyl)amino)-9-fluoro-8-methoxy-[1,2,4]triazolo[1,5-c]quinazolin-2-yl)-5-fluoropiperidine-1-carboxylate (second eluting peak, Intermediate 81). For Intermediate 81: LCMS ($C_{29}H_{34}F_2N_6O_5$) (ES, m/z): 585 [M+H]$^+$. The mixture of Intermediate 79 and Intermediate 80 was resolved by chiral SFC (Chiral Technologies AD-H 50×250 mm column with 35% MeOH as cosolvent) to afford tert-butyl (3S,5R or 3R,5S)-3-(5-((2,4-dimethoxybenzyl)amino)-9-fluoro-8-methoxy-[1,2,4]triazolo[1,5-c]quinazolin-2-yl)-5-fluoropiperidine-1-carboxylate (Intermediate 79, first eluting peak) and tert-butyl (3R,5S or 3S,5R)-3-(5-((2,4-dimethoxybenzyl)amino)-9-fluoro-8-methoxy-[1,2,4]triazolo[1,5-c]quinazolin-2-yl)-5-fluoropiperidine-1-carboxylate (Intermediate 80, second eluting peak). For Intermediate 79: LCMS ($C_{29}H_{34}F_2N_6O_5$) (ES, m/z): 585 [M+H]$^+$. For Intermediate 80: LCMS ($C_{29}H_{34}F_2N_6O_5$) (ES, m/z): 585 [M+H]$^+$.

Intermediate 82: (R)—N-(2,4-dimethoxybenzyl)-9-fluoro-8-methoxy-2-(piperidin-3-yl)-[1,2,4]triazolo[1,5-c]quinazolin-5-amine Step 1: (R)-tert-butyl 3-(5-((2,4-dimethoxybenzyl)amino)-9-fluoro-8-methoxy-[1,2,4]triazolo[1,5-c]quinazolin-2-yl)piperidine-1-carboxylate

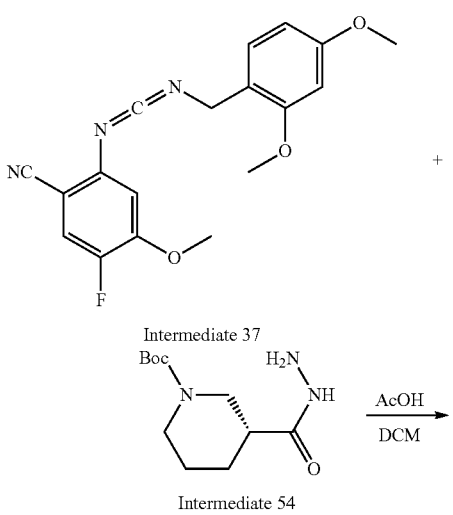

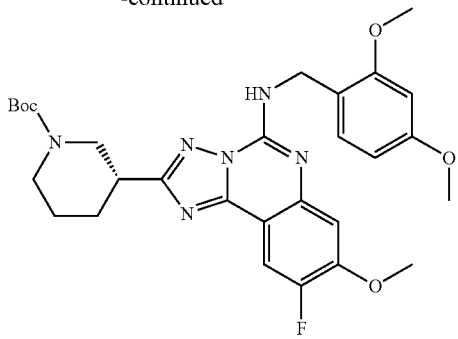

To a 40 mL vial was added (R)-tert-butyl 3-(hydrazinecarbonyl)piperidine-1-carboxylate (Intermediate 54) (596 mg, 2.45 mmol), DCM (7 mL) and AcOH (0.070 ml, 1.2 mmol). To the mixture was added 2-((((2,4-dimethoxybenzyl)imino)methylene)amino)-5-fluoro-4-methoxybenzonitrile (Intermediate 37) (836 mg, 2.45 mmol). The mixture was stirred for 16 h. The solution was loaded onto a silica gel column and purified with 0-80% EtOAc in hexane as eluent to afford (R)-tert-butyl 3-(5-((2,4-dimethoxybenzyl)amino)-9-fluoro-8-methoxy-[1,2,4]triazolo[1,5-c]quinazolin-2-yl)piperidine-1-carboxylate LCMS ($C_{29}H_{35}FN_6O_5$) (ES, m/z) [M+H]$^+$: 567.

Step 2: (R)—N-(2,4-dimethoxybenzyl)-9-fluoro-8-methoxy-2-(piperidin-3-yl)-[1,2,4]triazolo[1,5-c]quinazolin-5-amine

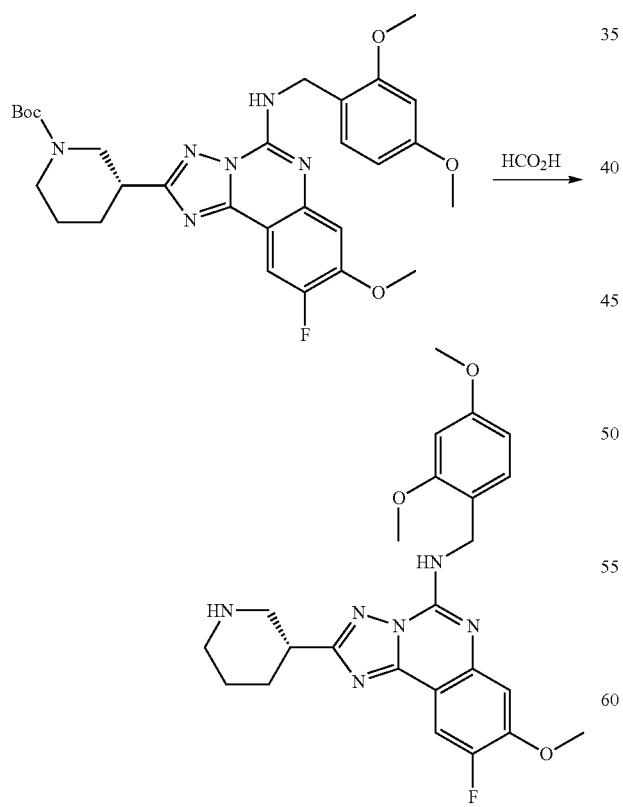

Intermediate 82

To a 20 mL vial was added (R)-tert-butyl 3-(5-((2,4-dimethoxybenzyl)amino)-9-fluoro-8-methoxy-[1,2,4]triazolo[1,5-c]quinazolin-2-yl)piperidine-1-carboxylate (1.40 g, 2.47 mmol) and formic acid (4 mL). The solution was stirred for 16 h. The mixture was diluted with DCM (50 mL) and washed with 2 M aqueous potassium carbonate (75 mL). The mixture was extracted with additional DCM (50 mL). The combined organic layers were dried over sodium sulfate, filtered, and the solvents of the filtrate were evaporated to afford (R)—N-(2,4-dimethoxybenzyl)-9-fluoro-8-methoxy-2-(piperidin-3-yl)-[1,2,4]triazolo[1,5-c]quinazolin-5-amine (Intermediate 82). LCMS ($C_{24}H_{27}FN_6O_3$) (ES, m/z) [M+H]$^+$: 467.

The intermediates in the following Table 11 were synthesized in a manner similar to that used in the preparation of Intermediate 82 from the appropriate intermediates and starting materials. For the synthesis of Intermediate 89, the deprotection step in formic acid (step 2) was not necessary.

TABLE 11

| Intermediate | Structure Name | Observed m/z [M + H]$^+$ |
|---|---|---|
| 83 | 2-(azepan-3-yl)-N-(2,4-dimethoxybenzyl)-9-fluoro-8-methoxy-[1,2,4]triazolo[1,5-c]quinazolin-5-amine | 481 |
| 84 | 2-(azepan-3-yl)-N-(2,4-dimethoxybenzyl)-9-fluoro-7-methoxy-[1,2,4]triazolo[1,5-c]quinazolin-5-amine | 481 |

TABLE 11-continued

| Intermediate | Structure Name | Observed m/z [M + H]+ |
|---|---|---|
| 85 | N-(2,4-dimethoxybenzyl)-9-fluoro-8-methoxy-2-(5-methylpiperidin-3-yl)-[1,2,4]triazolo[1,5-c]quinazolin-5-amine | 481 |
| 86 | N-(2,4-dimethoxybenzyl)-9-fluoro-8-methoxy-2-(4-methylpiperidin-3-yl)-[1,2,4]triazolo[1,5-c]quinazolin-5-amine | 481 |
| 87 | (R)-N-(2,4-dimethoxybenzyl)-9-fluoro-8-methoxy-2-(morpholin-2-yl)-[1,2,4]triazolo[1,5-c]quinazolin-5-amine | 469 |
| 88 | 2-(5-((2,4-dimethoxybenzyl)amino)-9-fluoro-8-methoxy-[1,2,4]triazolo[1,5-c]quinazolin-2-yl)thiomorpholine 1,1-dioxide | 517 |

TABLE 11-continued

| Intermediate | Structure Name | Observed m/z [M + H]+ |
|---|---|---|
| 89 | | 481 |
| | 3-(5-((2,4-dimethoxybenzyl)amino)-9-fluoro-8-methoxy-[1,2,4]triazolo[1,5-c]quinazolin-2-yl)piperidin-2-one | |

Intermediate 90 and Intermediate 91: (S or R)—N-(2,4-dimethoxybenzyl)-9-fluoro-2-(3-fluoropiperidin-3-yl)-7-methoxy-[1,2,4]triazolo[1,5-c]quinazolin-5-amine and (R or S)—N-(2,4-dimethoxybenzyl)-9-fluoro-2-(3-fluoropiperidin-3-yl)-7-methoxy-[1,2,4]triazolo[1,5-c]quinazolin-5-amine Step 1: rac-benzyl 3-(5-((2,4-dimethoxybenzyl)amino)-9-fluoro-7-methoxy-[1,2,4]triazolo[1,5-c]quinazolin-2-yl)-3-fluoropiperidine-1-carboxylate

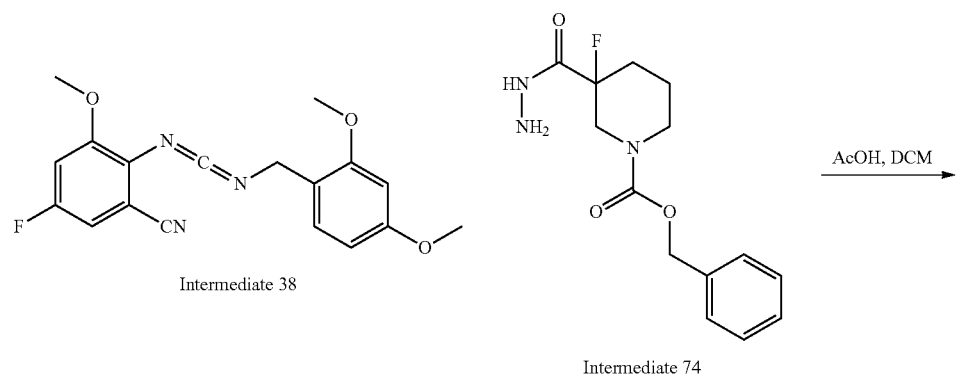

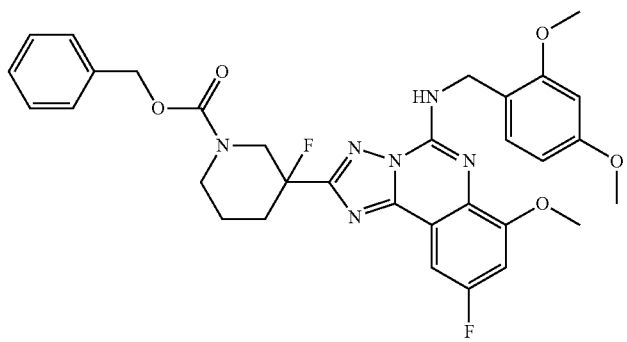

To a stirred solution of rac-benzyl 3-fluoro-3-(hydrazinecarbonyl)piperidine-1-carboxylate (Intermediate 74) (1.73 g, 5.86 mmol) in DCM (25 mL) was added AcOH (0.201 mL, 3.52 mmol). The mixture was stirred at room temperature for 10 min. To the mixture was added 2-((((2,4-dimethoxybenzyl)imino)methylene)amino)-5-fluoro-3-methoxybenzonitrile (Intermediate 38) (2.00 g, 5.86 mmol). The mixture was stirred and heated at 40° C. for 16 h. The mixture was cooled to room temperature. The mixture was diluted with DCM (100 mL) and then washed with saturated aqueous sodium bicarbonate and brine. The organic layer was dried over anhydrous MgSO$_4$, filtered, and the solvents of the filtrate were evaporated. The resulting residue was purified by silica gel chromatography with EtOAc in isohexane as eluent to afford rac-benzyl 3-(5-((2,4-dimethoxybenzyl)amino)-9-fluoro-7-methoxy-[1,2,4]triazolo[1,5-c]quinazolin-2-yl)-3-fluoropiperidine-1-carboxylate. LCMS (C$_{32}$H$_{32}$F$_2$N$_6$O$_5$) (ES, m/z): 619 [M+H]$^+$.

Step 2: (S or R)—N-(2,4-dimethoxybenzyl)-9-fluoro-2-(3-fluoropiperidin-3-yl)-7-methoxy-[1,2,4]triazolo[1,5-c]quinazolin-5-amine and (R or S)—N-(2,4-dimethoxybenzyl)-9-fluoro-2-(3-fluoropiperidin-3-yl)-7-methoxy-[1,2,4]triazolo[1,5-c]quinazolin-5-amine

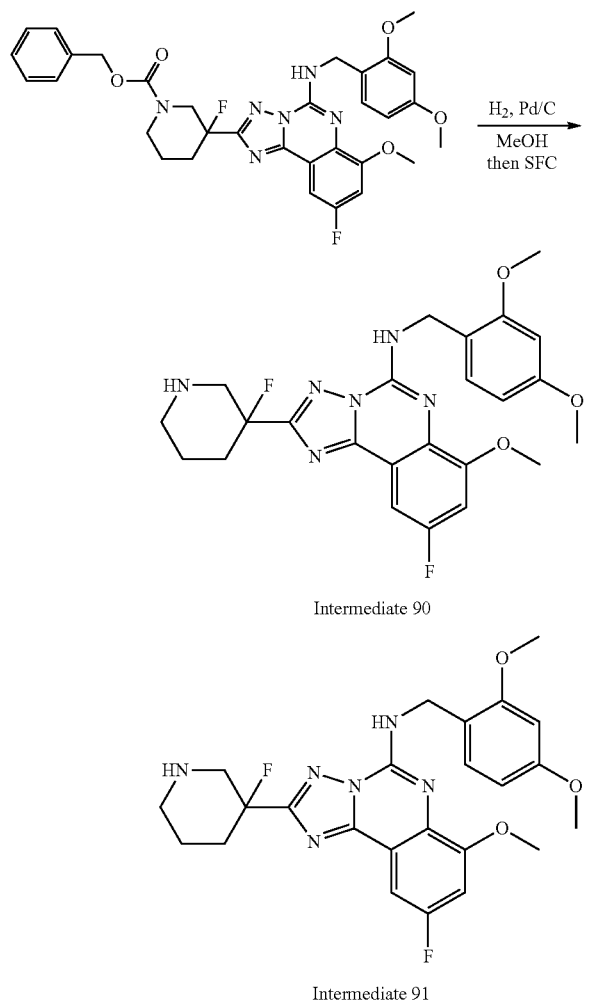

Intermediate 90

Intermediate 91

A 200 mL round bottom flask was charged rac-benzyl 3-(5-((2,4-dimethoxybenzyl)amino)-9-fluoro-7-methoxy-[1,2,4]triazolo[1,5-c]quinazolin-2-yl)-3-fluoropiperidine-1-carboxylate (2.00 g, 3.23 mmol), 10% Pd/C (800 mg, 3.23 mmol), and MeOH (50 mL). The mixture was stirred under an atmosphere of hydrogen for 16 h. The mixture was filtered through Celite® (diatomaceous earth). and the solvents of the filtrate were evaporated. The residue was purified by silica gel chromatography with 0-8% MeOH in DCM (with 0.2% NH$_4$OH) as eluent to afford a racemic mixture that was resolved by chiral SFC separation (Chiral Technologies, IC 20×250 mm column with 50% (EtOH with 0.2% DEA modifier) as cosolvent) to afford (S or R)—N-(2,4-dimethoxybenzyl)-9-fluoro-2-(3-fluoropiperidin-3-yl)-7-methoxy-[1,2,4]triazolo[1,5-c]quinazolin-5-amine (first eluting peak, Intermediate 90) and (R or S)—N-(2,4-dimethoxybenzyl)-9-fluoro-2-(3-fluoropiperidin-3-yl)-7-methoxy-[1,2,4]triazolo[1,5-c]quinazolin-5-amine (second eluting peak, Intermediate 91). For Intermediate 90: LCMS (C$_{24}$H$_{26}$F$_2$N$_6$O$_3$) (ES, m/z): 485 [M+H]$^+$. For Intermediate 91: LCMS (C$_{24}$H$_{26}$F$_2$N$_6$O$_3$) (ES, m/z): 485 [M+H]$^+$.

Intermediate 92: (R)—N-(2,4-dimethoxybenzyl)-9-fluoro-7-methoxy-2-(piperidin-3-yl)-[1,2,4]triazolo[1,5-c]quinazolin-5-amine Step 1: tert-butyl (R)-3-(5-((2,4-dimethoxybenzyl)amino)-9-fluoro-7-methoxy-[1,2,4]triazolo[1,5-c]quinazolin-2-yl)piperidine-1-carboxylate

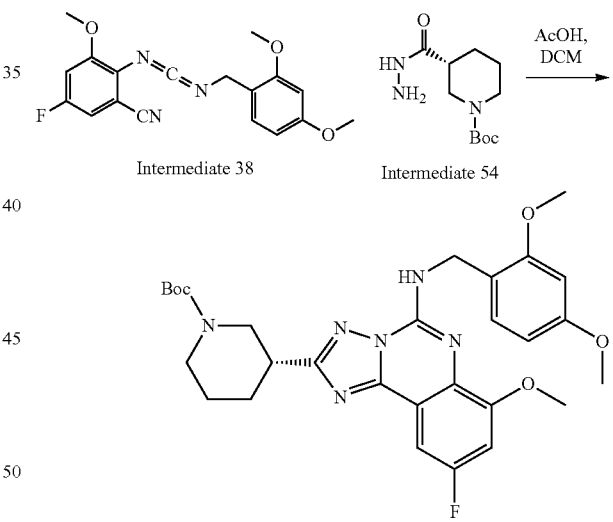

Intermediate 38    Intermediate 54

To a solution of tert-butyl (R)-3-(hydrazinecarbonyl)piperidine-1-carboxylate (Intermediate 54) (1.52 g, 6.25 mmol) in DCM (25 mL) was added AcOH (0.201 mL, 3.52 mmol). The mixture was stirred at room temperature for 10 min. To this mixture was added 2-((((2,4-dimethoxybenzyl)imino)methylene)amino)-5-fluoro-3-methoxybenzonitrile (Intermediate 38) (2.00 g, 5.86 mmol). The mixture was stirred for 16 h. The mixture was diluted with DCM (100 mL), washed with saturated aqueous sodium bicarbonate and brine. The organic layer was dried over anhydrous MgSO$_4$, the solids were removed by filtration, and the solvents of the filtrate were evaporated. The residue was purified by silica gel chromatography with EtOAc in isohexane as eluent to afford tert-butyl (R)-3-(5-((2,4-dimethoxybenzyl)amino)-9-fluoro- 7-methoxy-[1,2,4]triazolo[1,5-c]quinazolin-2-yl)piperidine-1-carboxylate. LCMS ($C_{29}H_{35}FN_6O_5$) (ES, m/z): 567 [M+H]$^+$.

Step 2: (R)—N-(2,4-dimethoxybenzyl)-9-fluoro-7-methoxy-2-(piperidin-3-yl)-[1,2,4]triazolo[1,5-c]quinazolin-5-amine

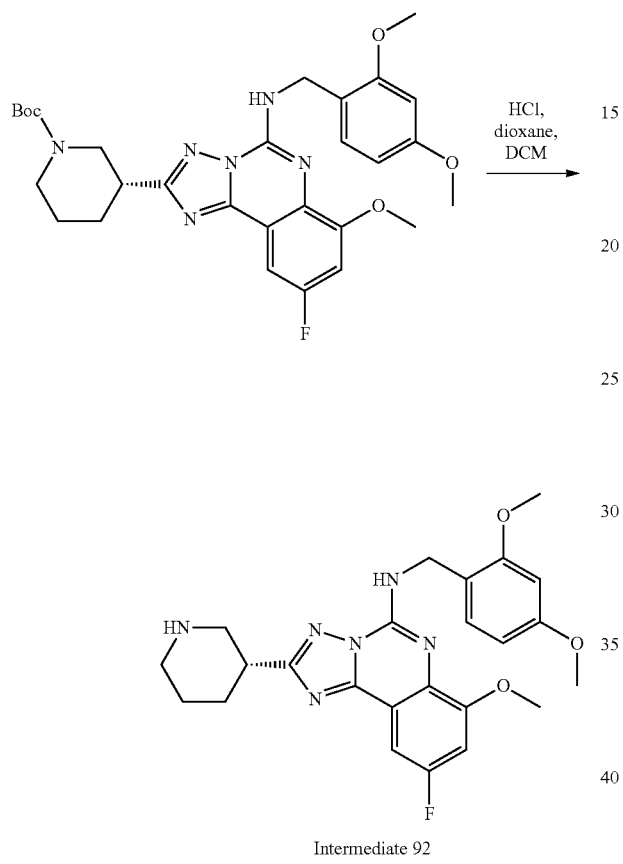

Intermediate 92

To a solution of tert-butyl (R)-3-(5-((2,4-dimethoxybenzyl)amino)-9-fluoro-7-methoxy-[1,2,4]triazolo[1,5-c]quinazolin-2-yl)piperidine-1-carboxylate (2.12 g, 3.74 mmol) in DCM (30 mL) was added 4 M HCl in dioxane (10 mL, 40.0 mmol). The mixture was stirred at room temperature for 2 h. The solvents were evaporated. The residue was purified by silica gel chromatography with 0-8% MeOH in DCM (with 0.2% NH$_4$OH) as eluent to afford (R)—N-(2,4-dimethoxybenzyl)-9-fluoro-7-methoxy-2-(piperidin-3-yl)-[1,2,4]triazolo[1,5-c]quinazolin-5-amine (Intermediate 92). LCMS ($C_{24}H_{27}FN_6O_3$) (ES, m/z): 467 [M+H]$^+$.

The intermediates in the following Table 12 were prepared in a manner similar to that used in the preparation of Intermediate 92 from the appropriate intermediates and starting materials.

TABLE 12

| Intermediate | Structure Name | Observed m/z [M + H]$^+$ |
|---|---|---|
| 93 | (R)-N-(2,4-dimethoxybenzyl)-9-fluoro-8-methoxy-2-(pyrrolidin-3-yl)-[1,2,4]triazolo[1,5-c]quinazolin-5-amine | 453 |
| 94 | N-(2,4-dimethoxybenzyl)-9-fluoro-2-(3-fluoropyrrolidin-3-yl)-8-methoxy-[1,2,4]triazolo[1,5-c]quinazolin-5-amine | 471 |

The intermediates in the following Table 12A were prepared in a manner similar to that used in step 2 of the preparation of Intermediate 92 from the appropriate intermediates and starting materials.

TABLE 12A

| Intermediate | Structure Name | Observed m/z [M + H]+ |
|---|---|---|
| 95 | N-(2,4-dimethoxybenzyl)-9-fluoro-8-methoxy-2-((3R,6S or 3S,6R)-6-methylpiperidin-3-yl)-[1,2,4]triazolo[1,5-c]quinazolin-5-amine | 481 |
| 96 | N-(2,4-dimethoxybenzyl)-9-fluoro-8-methoxy-2-((3S,6R or 3R,6S)-6-methylpiperidin-3-yl)-[1,2,4]triazolo[1,5-c]quinazolin-5-amine | 481 |
| 97 | | 465 |
| 98 | 2-((1R,5R or 1S,5S)-3-azabicyclo[3.1.0]hexan-1-yl)-N-(2,4-dimethoxybenzyl)-9-fluoro-8-methoxy-[1,2,4]triazolo[1,5-c]quinazolin-5-amine | 465 |
| 99 | N-(2,4-dimethoxybenzyl)-9-fluoro-2-((3R,5S or 3S,5R)-5-fluoropiperidin-3-yl)-8-methoxy-[1,2,4]triazolo[1,5-c]quinazolin-5-amine | 485 |

2-((1S,5S or 1R,5R)-3-azabicyclo[3.1.0]hexan-1-yl)-N-(2,4-dimethoxybenzyl)-9-fluoro-8-methoxy-[1,2,4]triazolo[1,5-c]quinazolin-5-amine

TABLE 12A-continued

| Intermediate | Structure Name | Observed m/z [M + H]+ |
|---|---|---|
| 100 | N-(2,4-dimethoxybenzyl)-9-fluoro-2-((3S,5R or 3R,5S)-5-fluoropiperidin-3-yl)-8-methoxy-[1,2,4]triazolo[1,5-c]quinazolin-5-amine (cis) | 485 |
| 101 | N-(2,4-dimethoxybenzyl)-9-fluoro-2-((3R,5R and 3S,5S)-5-fluoropiperidin-3-yl)-8-methoxy-[1,2,4]triazolo[1,5-c]quinazolin-5-amine (trans (+/−)) | 485 |
| 102 | N-(2,4-dimethoxybenzyl)-9-fluoro-2-((3R,5R and 3S,5S)-5-fluoropiperidin-3-yl)-8-methoxy-[1,2,4]triazolo[1,5-c]quinazolin-5-amine (cis (+/−)) | 485 |
| 103 | N-(2,4-dimethoxybenzyl)-9-fluoro-2-((3R,5S and 3S,5R)-5-fluoropiperidin-3-yl)-8-methoxy-[1,2,4]triazolo[1,5-c]quinazolin-5-amine (trans (+/−)) | 485 |

Intermediate 104: rac-N'-(2-amino-6-fluoro-8-methoxyquinazolin-4-yl)-1-(1-methyl-1H-pyrazol-4-yl)piperidine-3-carbohydrazide Step 1: 2-amino-6-fluoro-8-methoxyquinazolin-4-ol To a stirred mixture of 2-amino-5-fluoro-3-methoxybenzoic acid (278 mg, 1.50 mmol) in EtOH (1.5 mL) was added cyanamide (158 mg, 3.75 mmol) and hydrochloric acid (325 μL, 1.95 mmol) (6 M, aqueous). The mixture was heated at reflux for 16 h. The mixture was cooled. The precipitate was collected by filtration and dried under high vacuum to afford 2-amino-6-fluoro-8-methoxyquinazolin-4-ol. LCMS ($C_9H_8FN_3O_2$) (ES, m/z): 210 [M+H]+.

Step 2: 6-fluoro-8-methoxy-4-(1H-1,2,4-triazol-1-yl)quinazolin-2-amine

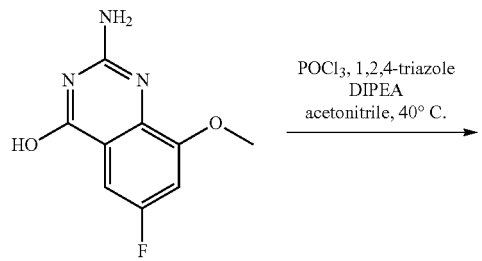

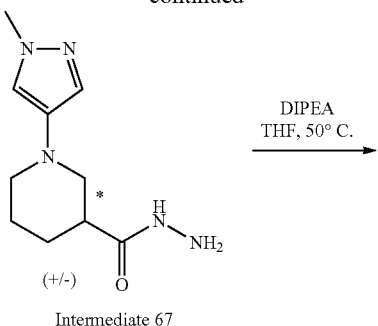

Intermediate 67

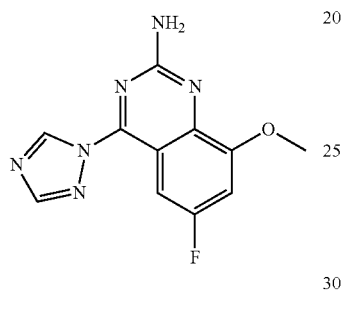

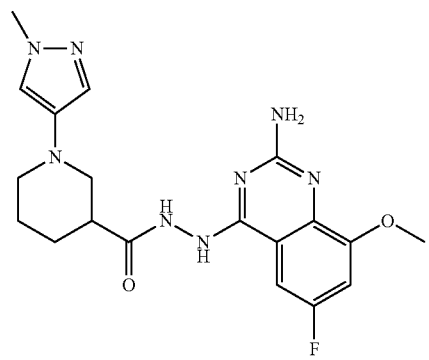

Intermediate 104

POCl₃ (295 µL, 3.16 mmol) was added dropwise over 15 min to a stirred mixture of 1,2,4-triazole (524 mg, 7.59 mmol), 2-amino-6-fluoro-8-methoxyquinazolin-4-ol (264.7 mg, 1.265 mmol), and DIPEA (553 µL, 3.16 mmol) in acetonitrile (5 mL) at room temperature. The mixture was stirred and heated at 40° C. for 3 h and then at room temperature for 16 h. The mixture was filtered through Celite® (diatomaceous earth), washing with acetonitrile and diethyl ether to afford 6-fluoro-8-methoxy-4-(1H-1,2,4-triazol-1-yl)quinazolin-2-amine. LCMS (C₁₁H₉FN₆O) (ES, m/z): 261 [M+H]⁺.

Step 3: rac-N'-(2-amino-6-fluoro-8-methoxyquinazolin-4-yl)-1-(1-methyl-1H-pyrazol-4-yl)piperidine-3-carbohydrazide

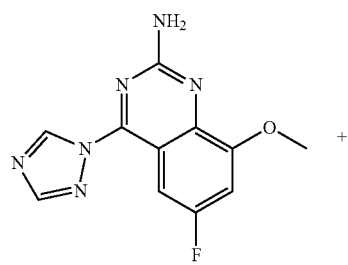

+

A 20 mL reaction vial was charged with 6-fluoro-8-methoxy-4-(1H-1,2,4-triazol-1-yl)quinazolin-2-amine (41.1 mg, 0.158 mmol), (R and S)-1-(1-methyl-1H-pyrazol-4-yl)piperidine-3-carbohydrazide Intermediate 67) (38.8 mg, 0.174 mmol), THF (1 mL) and DIPEA (138 µl, 0.790 mmol). The mixture was stirred and heated at 50° C. for 4 h. The mixture was diluted with ethyl acetate (10 mL) and washed with saturated aqueous sodium bicarbonate (20 mL). The organic layer was dried over anhydrous MgSO₄, filtered, and the solvents of the filtrate were evaporated to afford rac-N'-(2-amino-6-fluoro-8-methoxyquinazolin-4-yl)-1-(1-methyl-1H-pyrazol-4-yl)piperidine-3-carbohydrazide. LCMS (C₁₉H₂₃FN₈O₂) (ES, m/z): 415 [M+H]⁺.

The intermediates in the following Table 13 were prepared from the appropriate starting materials in a manner similar to Intermediate 104, with the exception that the enantiopure hydrazide, Intermediate 67b, was used.

TABLE 13

| Intermediate | Structure Name | Observed m/z [M + H]+ |
|---|---|---|
| 105 | 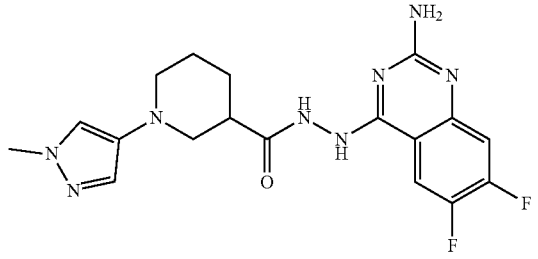 [SMILES: Cn1cc(N2CCCC(C(=O)NNc3nc(N)nc4cc(F)c(F)cc34)C2)cn1]<br>(R os S)-N'-(2-amino-6,7-difluoroquinazolin-4-yl)-1-(1-methyl-1H-pyrazol-4-yl)piperidine-3-carbohydrazide | 403 |
| 106 | 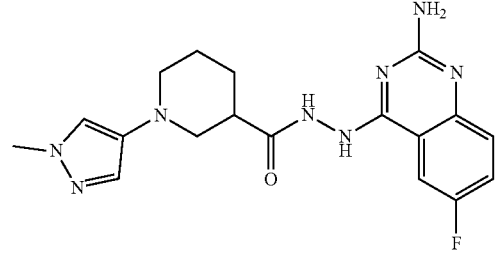 [SMILES: Cn1cc(N2CCCC(C(=O)NNc3nc(N)nc4ccc(F)cc34)C2)cn1]<br>(R or S)-N'-(2-amino-6-fluoroquinazolin-4-yl)-1-(1-methyl-1H-pyrazol-4-yl)piperidine-3-carbohydrazide | 385 |
| 107 | 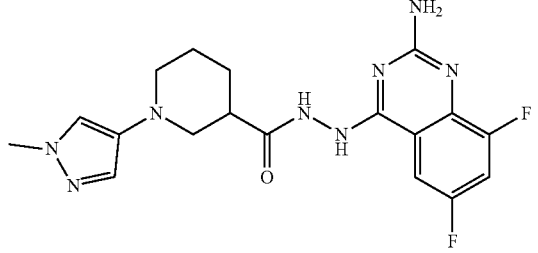 [SMILES: Cn1cc(N2CCCC(C(=O)NNc3nc(N)nc4c(F)cc(F)cc34)C2)cn1]<br>(R or S)-N'-(2-amino-6,8-difluoroquinazolin-4-yl)-1-(1-methyl-1H-pyrazol-4-yl)piperidine-3-carbohydrazide | 403 |
| 108 | 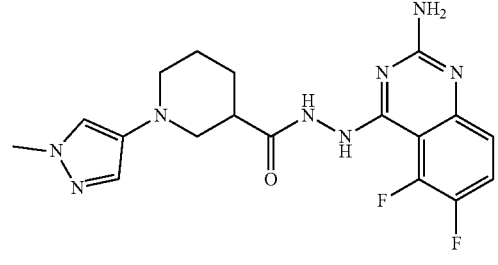 [SMILES: Cn1cc(N2CCCC(C(=O)NNc3nc(N)nc4ccc(F)c(F)c34)C2)cn1]<br>(R or S)-N'-(2-amino-5,6-difluoroquinazolin-4-yl)-1-(1-methyl-1H-pyrazol-4-yl)piperidine-3-carbohydrazide | 403 |

TABLE 13-continued

| Intermediate | Structure Name | Observed m/z [M + H]⁺ |
|---|---|---|
| 109 | (R or S)-N'-(2-amino-6-chloroquinazolin-4-yl)-1-(1-methyl-1H-pyrazol-4-yl)piperidine-3-carbohydrazide | 401 |
| 110 | (R or S)-N'-(2-amino-6-chloro-8-methylquinazolin-4-yl)-1-(1-methyl-1H-pyrazol-4-yl)piperidine-3-carbohydrazide | 415 |
| 111 | (R or S)-N'-(2-amino-6-chloro-8-methoxyquinazolin-4-yl)-1-(1-methyl-1H-pyrazol-4-yl)piperidine-3-carbohydrazide | 431 |
| 112 | (R or S)-N'-(2-amino-6-methoxyquinazolin-4-yl)-1-(1-methyl-1H-pyrazol-4-yl)piperidine-3-carbohydrazide | 397 |

125

Intermediates 113-116: 1-(4-((2R or 2S,5S or 5R)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol and 1-(4-((2S or 2R,5R or 5S)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol and 1-(4-((2S or 2R,5S or 5R)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol and 1-(4-((2R or 2S,5R or 5S)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol Step 1: 3-(5-((2,4-dimethoxybenzyl)amino)-9-fluoro-8-methoxy-[1,2,4]triazolo[1,5-c]quinazolin-2-yl)-6-ethyl-1-(1-(2-hydroxy-2-methylpropyl)-1H-pyrazol-4-yl)piperidin-2-one

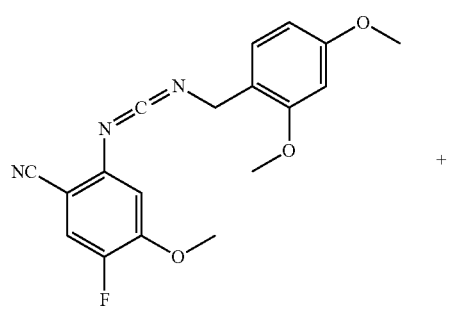

Intermediate 37

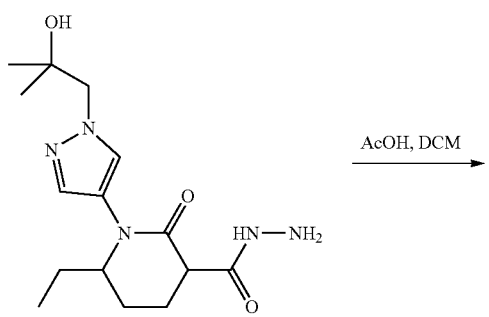

Intermediate 64

126

-continued

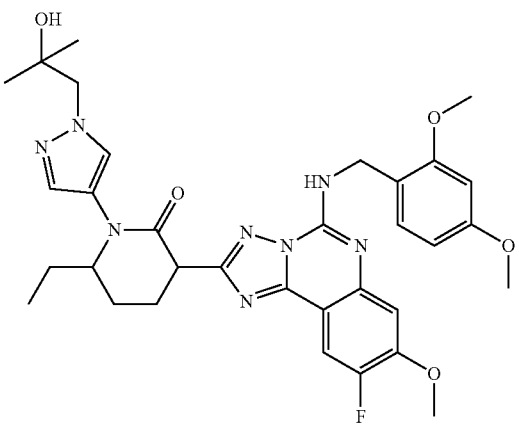

To a solution of 6-ethyl-1-(1-(2-hydroxy-2-methylpropyl)-1H-pyrazol-4-yl)-2-oxopiperidine-3-carbohydrazide (Intermediate 64) (270 mg, 0.835 mmol) in dioxane (7 mL) was added AcOH (0.024 mL, 0.42 mmol). The mixture was stirred at room temperature for 30 min. To this mixture was added 2-((((2,4-dimethoxybenzyl)imino)methylene)amino)-5-fluoro-4-methoxybenzonitrile (Intermediate 37) (285 mg, 0.835 mmol). The mixture was stirred at room temperature for 3 days. The mixture was filtered, and the filtrate was purified by silica gel chromatography with 0-100% 3:1 EtOAc:EtOH in hexanes as eluent to afford 3-(5-((2,4-dimethoxybenzyl)amino)-9-fluoro-8-methoxy-[1,2,4]triazolo[1,5-c]quinazolin-2-yl)-6-ethyl-1-(1-(2-hydroxy-2-methylpropyl)-1H-pyrazol-4-yl)piperidin-2-one. LCMS ($C_{33}H_{39}FN_8O_5$) (ES, m/z): 647 $[M+H]^+$.

Step 2: 1-(4-((2R or 2S,5S or 5R)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol and 1-(4-((2S or 2R,5R or 5S)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol and 1-(4-((2S or 2R,5S or 5R)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol and 1-(4-((2R or 2S,5R or 5S)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol

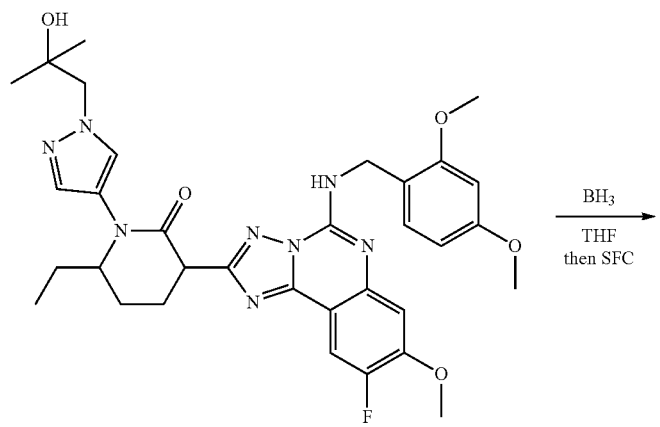

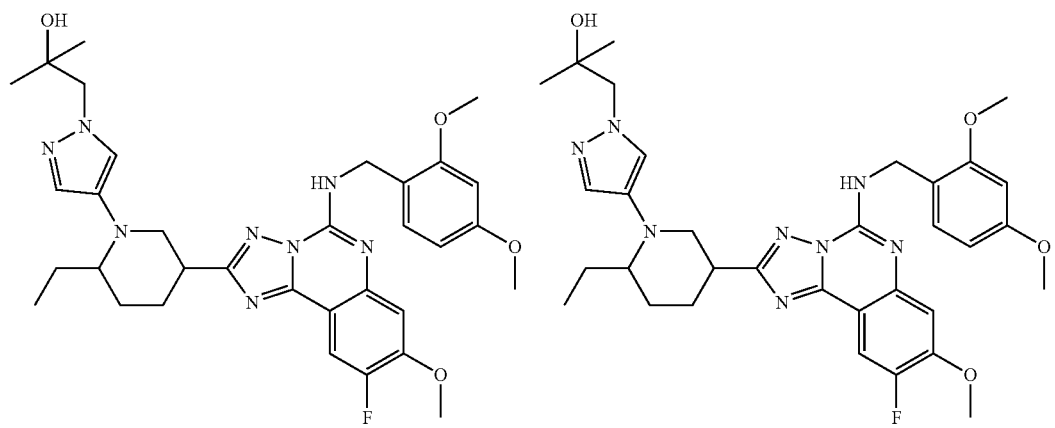

Intermediate 113        Intermediate 115

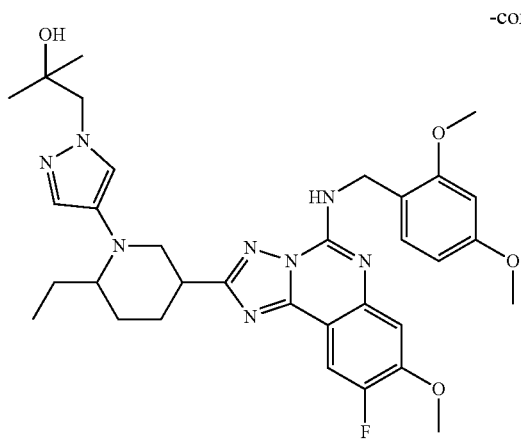

Intermediate 114

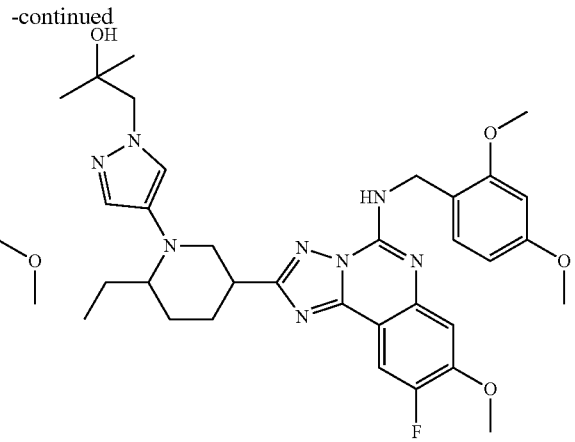

Intermediate 116

To the solution of 3-(5-((2,4-dimethoxybenzyl)amino)-9-fluoro-8-methoxy-[1,2,4]triazolo[1,5-c]quinazolin-2-yl)-6-ethyl-1-(1-(2-hydroxy-2-methylpropyl)-1H-pyrazol-4-yl)piperidin-2-one (320 mg, 0.495 mmol) in THF (4.9 mL) was added borane in THF (1.0 M, 2.47 mL, 2.47 mmol). The mixture was stirred at room temperature for 24 h. The reaction mixture was quenched with MeOH, and then the solvents were evaporated. The resulting residue was purified by preparative reversed-phase HPLC (Waters SunFire C18 OBD Prep Column, 19 mm×100 mm with MeCN/water (with 0.1% TFA) as eluent) to afford two racemic mixtures of the corresponding diastereomers. Each racemate was resolved by chiral SFC.

The first eluting racemate was resolved by chiral SFC separation (Chiral Technologies, AS-H, 21×250 mm column with 50% (IPA+0.2% DIPA) as co-solvent) to afford 1-(4-((2R or 2S,5S or 5R)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol (first eluting peak) and 1-(4-((2S or 2R,5R or 5S)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol (second eluting) corresponding to Intermediate 113 and Intermediate 114, respectively. For Intermediate 113: LCMS ($C_{33}H_{41}FN_8O_4$) (ES, m/z): 634 [M+H]$^+$. For Intermediate 114: LCMS ($C_{33}H_{41}FN_8O_4$) (ES, m/z): 634 [M+H]$^+$.

The second eluting racemate was resolved by chiral SFC separation (AS-H, 21×250 mm column with 50% (IPA+0.2% DIPA) as co-solvent) to afford 1-(4-((2S or 2R,5S or 5R)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol (first eluting peak) and 1-(4-((2R or 2S,5R or 5S)-5-(5-((2,4-dimethoxybenzyl)amino)-9-fluoro-8-methoxy-[1,2,4]triazolo[1,5-c]quinazolin-2-yl)-2-ethylpiperidin-1-yl)-1H-pyrazol-1-yl)-2-methylpropan-2-ol (second eluting peak), corresponding to Intermediate 115 and Intermediate 116, respectively. For Intermediate 115: LCMS ($C_{33}H_{41}FN_8O_4$) (ES, m/z): 634 [M+H]$^+$. For Intermediate 116: LCMS ($C_{33}H_{41}FN_8O_4$) (ES, m/z): 634 [M+H]$^+$.

Intermediate 117: mixture of (R)—N-(2,4-dimethoxybenzyl)-9-fluoro-8-methoxy-2-(1-(3-methyl-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(5-methyl-1H-pyrazol-4-yl)piperidin-3-yl)-[1,2,4]triazolo[1,5-c]quinazolin-5-amine Step 1: mixture of (R)—N-(2,4-dimethoxybenzyl)-9-fluoro-8-methoxy-2-(1-(5-methyl-1-trityl-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(3-methyl-1-trityl-1H-pyrazol-4-yl)piperidin-3-yl)-[1,2,4]triazolo[1,5-c]quinazolin-5-amine

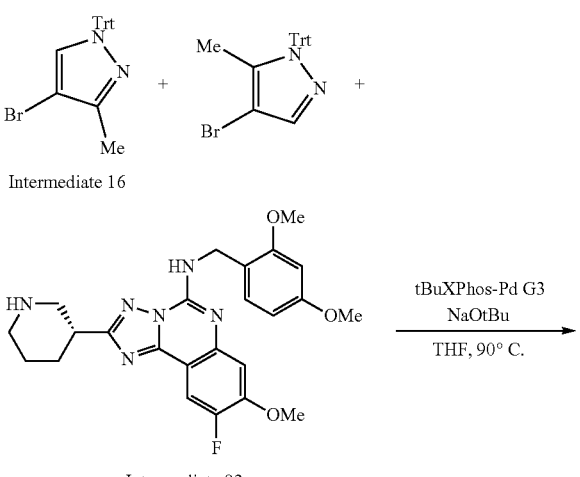

131
-continued

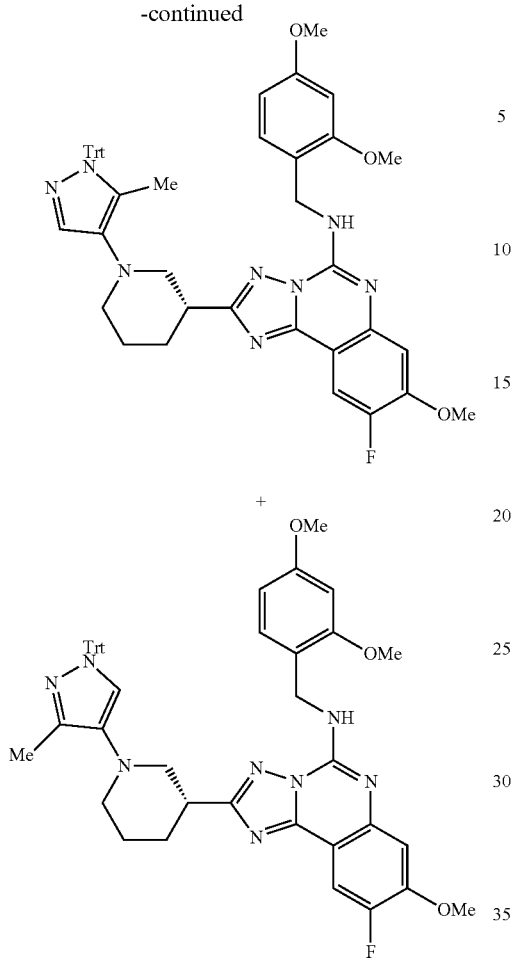

A 20 mL microwave vial was charged with (R)—N-(2,4-dimethoxybenzyl)-9-fluoro-8-methoxy-2-(piperidin-3-yl)-[1,2,4]triazolo[1,5-c]quinazolin-5-amine (Intermediate 82) (500 mg, 1.07 mmol) and THF (6.7 mL). To the mixture was added the mixture of 4-bromo-5-methyl-1-trityl-1H-pyrazole and 4-bromo-3-methyl-1-trityl-1H-pyrazole (Intermediate 16) (865 mg, 2.14 mmol), followed by tBuXPhos-Pd G3 (412 mg, 4.29 mmol) and sodium tert-butoxide (412 mg, 4.29 mmol). Nitrogen was bubbled through the mixture for 10 min. The mixture was stirred and heated at 90° C. for 16 h. The mixture was cooled to room temperature. To the mixture was added Celite® (diatomaceous earth) and saturated aqueous NH$_4$Cl. The mixture was stirred vigorously for 5 min. The mixture was filtered through Celite® (diatomaceous earth) topped with anhydrous MgSO$_4$ and washed with DCM. The solvents of the filtrate were evaporated. The residue was purified by silica gel chromatography with 0-20% MeOH in DCM to afford the mixture of (R)—N-(2,4-dimethoxybenzyl)-9-fluoro-8-methoxy-2-(1-(5-methyl-1-trityl-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(3-methyl-1-trityl-1H-pyrazol-4-yl)piperidin-3-yl)-[1,2,4]triazolo[1,5-c]quinazolin-5-amine. LCMS (C$_{47}$H$_{45}$FN$_8$O$_3$) (ES, m/z): 789 [M+H]$^+$.

132

Step 2: Mixture of (R)—N-(2,4-dimethoxybenzyl)-9-fluoro-8-methoxy-2-(1-(3-methyl-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(5-methyl-1H-pyrazol-4-yl)piperidin-3-yl)-[1,2,4]triazolo[1,5-c]quinazolin-5-amine

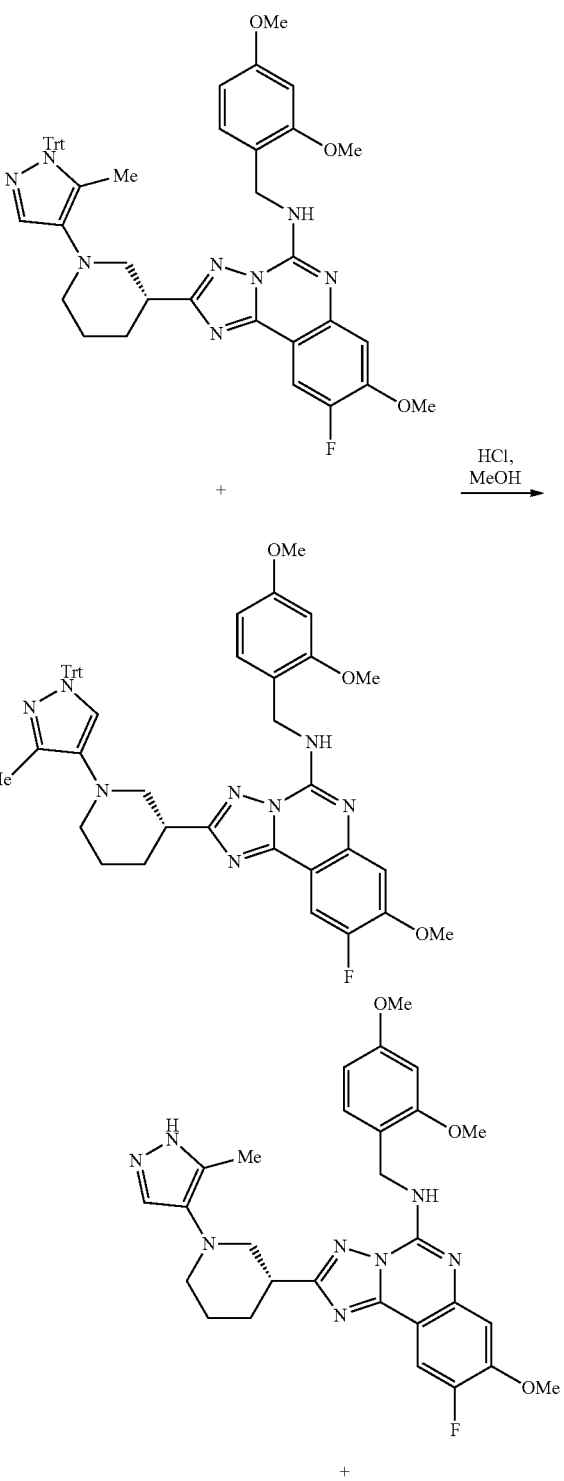

133

-continued

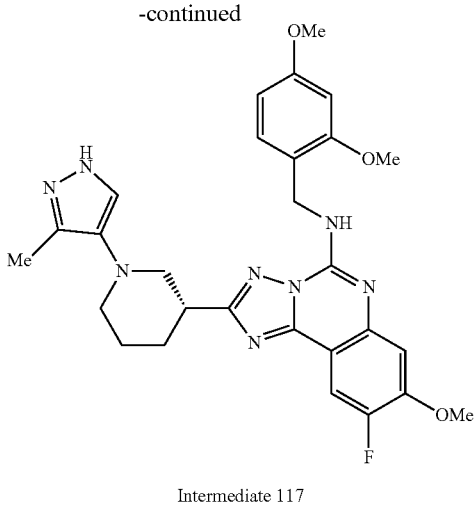

Intermediate 117

To a stirred solution of the mixture of (R)—N-(2,4-dimethoxybenzyl)-9-fluoro-8-methoxy-2-(1-(3-methyl-1-trityl-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(5-methyl-1H-pyrazol-4-yl)piperidin-3-yl)-[1,2,4]triazolo[1,5-c]quinazolin-5-amine (565 mg, 0.716 mmol) in MeOH (7.2 mL) was added a 4 M solution of HCl in dioxane (1.79 mL, 7.16 mmol). The mixture was stirred at room temperature for 1 h. The solvents were evaporated, and the residue was dissolved in DCM (50 mL). To the mixture was added saturated aqueous sodium bicarbonate (50 mL). The biphasic mixture was separated, and the aqueous layer was extracted with additional DCM (50 mL). The combined organic layers were dried over anhydrous MgSO$_4$, filtered, and the solvents of the filtrate were evaporated to afford the mixture of (R)—N-(2,4-dimethoxybenzyl)-9-fluoro-8-methoxy-2-(1-(3-methyl-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(5-methyl-1H-pyrazol-4-yl)piperidin-3-yl)-[1,2,4]triazolo[1,5-c]quinazolin-5-amine. LCMS (C$_{28}$H$_{31}$FN$_8$O$_3$) (ES, m/z): 547 [M+H]$^+$.

The intermediates in the following Table 14 were prepared in a manner similar to that used for the preparation of Intermediate 117, from the appropriate starting materials.

TABLE 14

| Intermediate | Structure Name | Observed m/z [M + H]$^+$ |
|---|---|---|
| 118 | ![structure] (R)-2-(1-(1H-pyrazol-4-yl)piperidin-3-yl)-N-(2,4-dimethoxybenzyl)-9-fluoro-8-methoxy-[1,2,4]triazolo[1,5-c]quinazolin-5-amine | 533 |

TABLE 14-continued

| Intermediate | Structure Name | Observed m/z [M + H]+ |
|---|---|---|
| 119 | 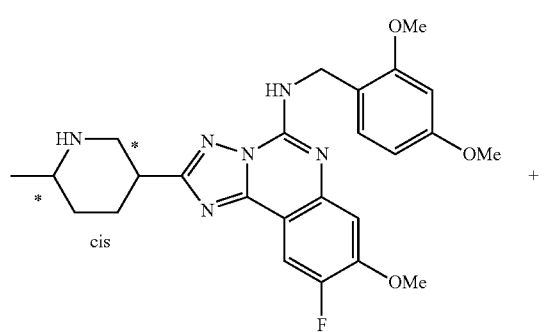<br>(R)-2-(1-(3-(difluoromethyl)-1H-pyrazol-4-yl)piperidin-3-yl)-N-(2,4-dimethoxybenzyl)-9-fluoro-8-methoxy-[1,2,4]triazolo[1,5-c]quinazolin-5-amine | 583 |

Intermediate 120 and Intermediate 121: N-(2,4-dimethoxybenzyl)-9-fluoro-8-methoxy-2-((3R,6S or 3S, 6R)-6-methyl-1-(1-((1R,2R or 1S,2S)-2-((tetrahydro-2H-pyran-2-yl)oxy)cyclopentyl)-1H-pyrazol-4-yl)piperidin-3-yl)-[1,2,4]triazolo[1,5-c]quinazolin-5-amine and N-(2,4-dimethoxybenzyl)-9-fluoro-8-methoxy-2-((3R,6S or 3S, 6R)-6-methyl-1-(1-((1S, 2S or 1R,2R)-2-((tetrahydro-2H-pyran-2-yl)oxy)cyclopentyl)-1H-pyrazol-4-yl)piperidin-3-yl)-[1,2,4]triazolo[1,5-c]quinazolin-5-amine

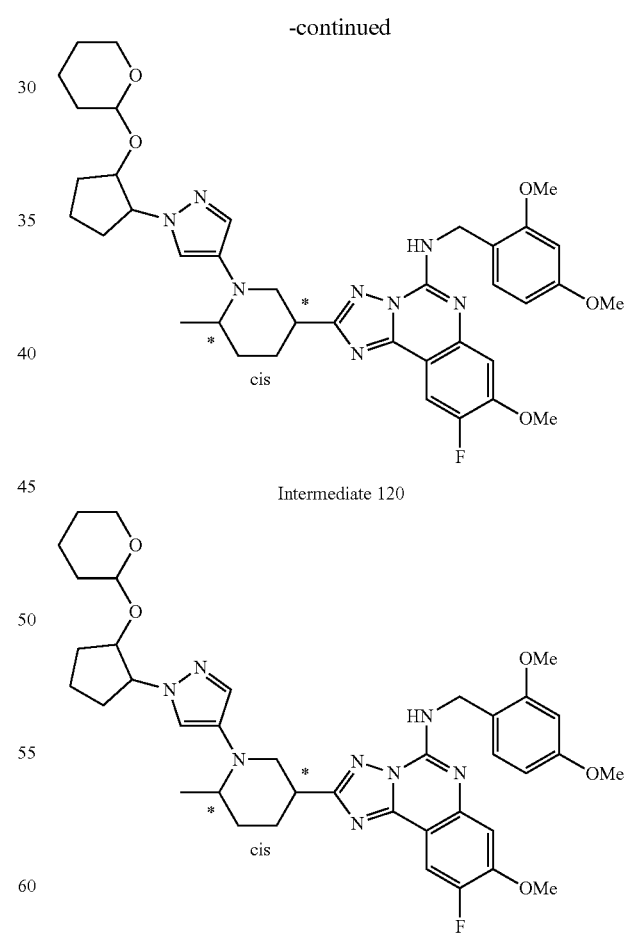

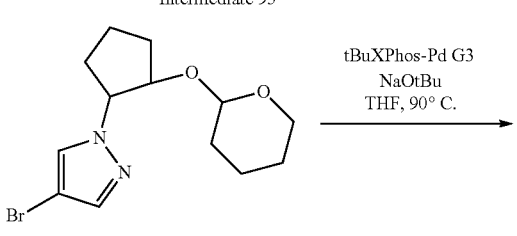

To a reaction vial containing of solution of N-(2,4-dimethoxybenzyl)-9-fluoro-8-methoxy-2-((3R,6S or 3S,6R)-6-methylpiperidin-3-yl)-[1,2,4]triazolo[1,5-c]quinazolin-5-amine (Intermediate 95) (150 mg, 0.312 mmol) in THF (4 mL) was added 4-bromo-1-(2-((tetrahydro-2H-pyran-2-yl)oxy)cyclopentyl)-1H-pyrazole (Intermediate 32) (177 mg, 0.562 mmol), followed by tBuXPhos-Pd G3 (124 mg, 0.156 mmol) and sodium tert-butoxide (105 mg, 1.09 mmol). The mixture was sparged with nitrogen for 10 min. The mixture was stirred and heated at 90° C. for 16 h. To the mixture was added additional 4-bromo-1-(2-((tetrahydro-2H-pyran-2-yl)oxy)cyclopentyl)-1H-pyrazole (Intermediate 32) (88.5 mg, 0.281 mmol), tBuXPhos-Pd G3 (62 mg, 0.078 mmol) and sodium tert-butoxide (52.5 mg, 0.547 mmol). The mixture was stirred and heated at 90° C. for 16 h. The mixture was purified by preparative silica gel TLC with 4% MeOH in DCM as eluent to afford a mixture of isomers. The mixture was resolved by chiral SFC separation (ID 21×250 mm column with 50% (MeOH w/ACN 1:1+0.2% DIPA) as co-solvent) to afford N-(2,4-dimethoxybenzyl)-9-fluoro-8-methoxy-2-((3R,6S or 3S,6R)-6-methyl-1-(1-((1R,2R or 1S,2S)-2-((tetrahydro-2H-pyran-2-yl)oxy)cyclopentyl)-1H-pyrazol-4-yl)piperidin-3-yl)-[1,2,4]triazolo[1,5-c]quinazolin-5-amine (first eluting peak, Intermediate 120) and N-(2,4-dimethoxybenzyl)-9-fluoro-8-methoxy-2-((3R,6S or 3S,6R)-6-methyl-1-(1-((1S,2S or 1R,2R)-2-((tetrahydro-2H-pyran-2-yl)oxy)cyclopentyl)-1H-pyrazol-4-yl)piperidin-3-yl)-[1,2,4]triazolo[1,5-c]quinazolin-5-amine (fourth eluting peak, Intermediate 121), corresponding to Intermediate 120 and Intermediate 121, respectively. (NOTE: peaks 2 and 3 had poor separation). For Intermediate 120: LCMS ($C_{34}H_{47}FN_8O_5$) (ES, m/z): 715 [M+H]$^+$. For Intermediate 121: LCMS ($C_{38}H_{47}FN_8O_5$) (ES, m/z): 715 [M+H]$^+$.

Intermediate 122 and Intermediate 123: 1-(4-((3R, 5S and 3R,5S)-3-(5-((2,4-dimethoxybenzyl)amino)-9-fluoro-8-methoxy-[1,2,4]triazolo[1,5-c]quinazolin-2-yl)-5-methylpiperidin-1-yl)-1H-pyrazol-1-yl)-2-methylpropan-2-ol and 1-(4-((3R,5R and 3S,5S)-3-(5-((2,4-dimethoxybenzyl)amino)-9-fluoro-8-methoxy-[1,2,4]triazolo[1,5-c]quinazolin-2-yl)-5-methylpiperidin-1-yl)-1H-pyrazol-1-yl)-2-methylpropan-2-ol

Intermediate 85

+

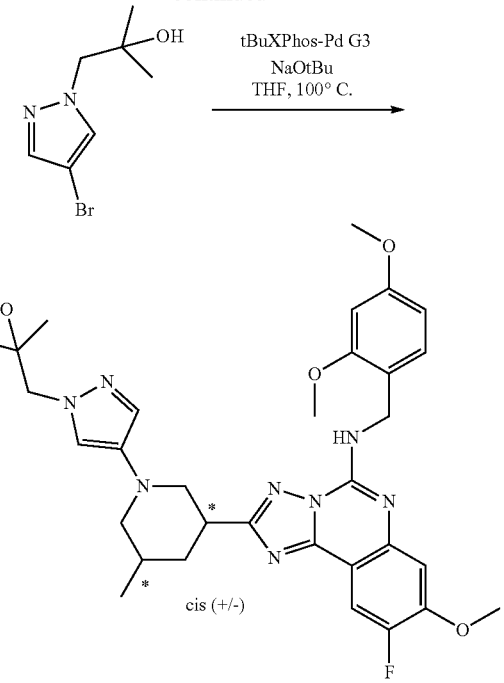

Intermediate 122

+

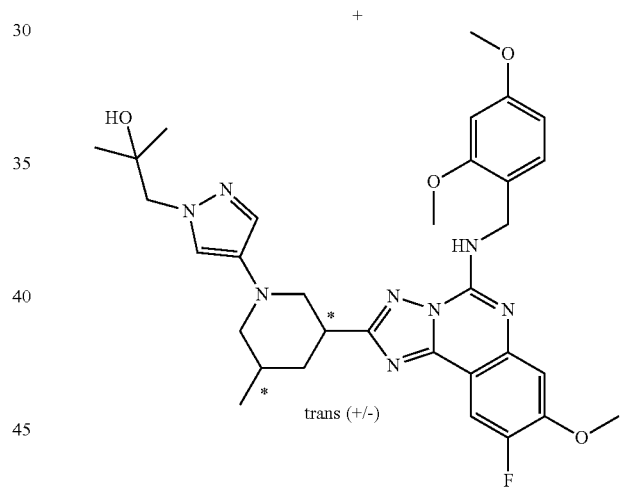

Intermediate 123

To a stirred mixture of sodium tert-butoxide (300 mg, 3.12 mmol), 1-(4-bromo-1H-pyrazol-1-yl)-2-methylpropan-2-ol (Intermediate 4) (274 mg, 1.25 mmol) and N-(2,4-dimethoxybenzyl)-9-fluoro-8-methoxy-2-(5-methylpiperidin-3-yl)-[1,2,4]triazolo[1,5-c]quinazolin-5-amine (Intermediate 85) (300 mg, 0.624 mmol) in THF (2 mL) was added tBuXPhos-Pd G3 (149 mg, 0.187 mmol) under a nitrogen atmosphere in a glove box. The mixture was stirred and heated at 100° C. for 14 h. The mixture was purified by preparative silica gel TLC with 10% MeOH in DCM as eluent to afford the two diastereomers: 1-(4-((3R,5S and 3R,5S)-3-(5-((2,4-dimethoxybenzyl)amino)-9-fluoro-8-methoxy-[1,2,4]triazolo[1,5-c]quinazolin-2-yl)-5-methylpiperidin-1-yl)-1H-pyrazol-1-yl)-2-methylpropan-2-ol and 1-(4-((3R,5R and 3S,5S)-3-(5-((2,4-dimethoxybenzyl)amino)-9-fluoro-8-methoxy-[1,2,4]triazolo[1,5-c]quinazolin-2-yl)-5-methylpiperidin-1-yl)-1H-pyrazol-1-yl)-2-meth-

139 ylpropan-2-ol, corresponding to Intermediate 122 and Intermediate 123, respectively. For Intermediate 122, LCMS ($C_{32}H_{39}FN_8O_4$) (ES, m/z): 619 [M+H]$^+$. For Intermediate 123, LCMS ($C_{32}H_{39}FN_8O_4$) (ES, m/z): 619 [M+H]$^+$.

Intermediate 124: (R)-5-(4-(3-(5-((2,4-dimethoxybenzyl)amino)-9-fluoro-8-methoxy-[1,2,4]triazolo[1,5-c]quinazolin-2-yl)piperidin-1-yl)-1H-pyrazol-1-yl)pentan-2-one

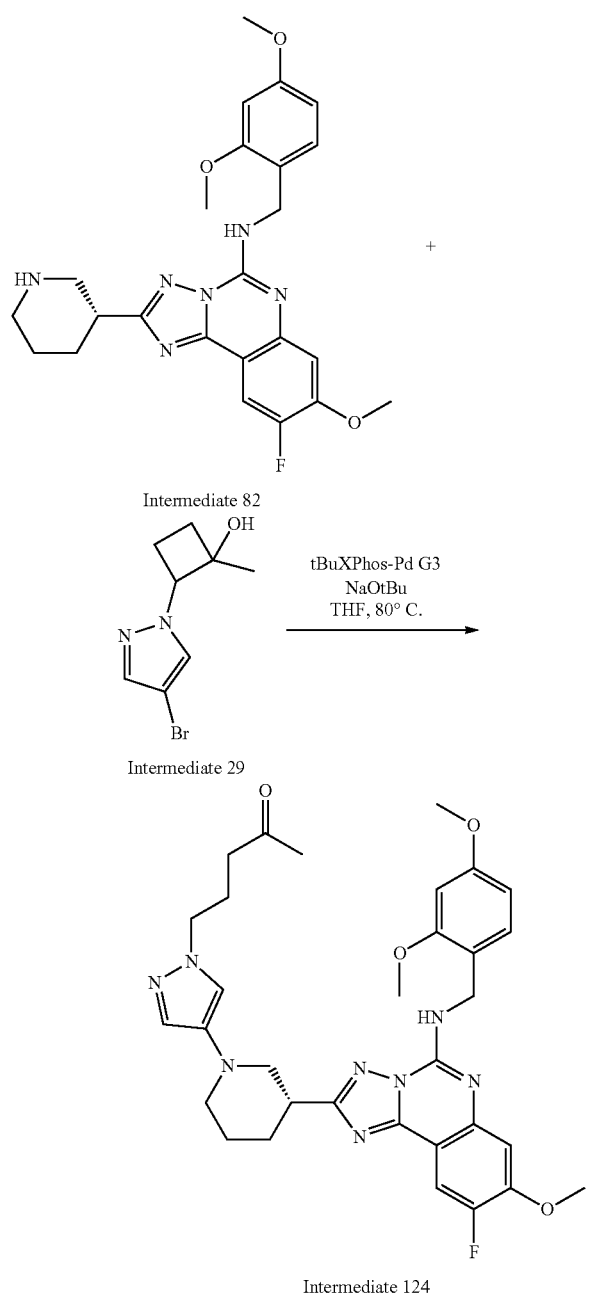

To a stirred mixture of sodium tert-butoxide (66.5 mg, 0.692 mmol), (R)—N-(2,4-dimethoxybenzyl)-9-fluoro-8-methoxy-2-(piperidin-3-yl)-[1,2,4]triazolo[1,5-c]quinazolin-5-amine (Intermediate 82) (89.0 mg, 0.190 mmol), 2-(4-bromo-1H-pyrazol-1-yl)-1-methylcyclobutanol (Intermediate 29) (40.0 mg, 0.173 mmol) in THF (2 mL) was added tBuXPhos-Pd G3 (41.3 mg, 0.0520 mmol). The mixture was stirred and heated at 80° C. for 12 h. The mixture was cooled, diluted with EtOAc (10 mL), and washed with water (10 mL). The organic layer was dried over anhydrous $Na_2SO_4$, filtered, and the solvents of the filtrate were evaporated. The resulting residue was purified by preparative silica gel TLC with EtOAc as eluent, affording the ring-opened product (R)-5-(4-(3-(5-((2,4-dimethoxybenzyl)amino)-9-fluoro-8-methoxy-[1,2,4]triazolo[1,5-c]quinazolin-2-yl)piperidin-1-yl)-1H-pyrazol-1-yl)pentan-2-one. LCMS ($C_{32}H_{37}FN_8O_4$) (ES, m/z): 617 [M+H]$^+$.

Intermediate 125: 2-(4-((R)-3-(5-amino-9-fluoro-8-methoxy-[1,2,4]triazolo[1,5-c]quinazolin-2-yl)piperidin-1-yl)-1H-pyrazol-1-yl)cyclobutan-1-one Step 1: N-(2,4-dimethoxybenzyl)-2-((3R)-1-(1-(2,2-dimethoxycyclobutyl)-1H-pyrazol-4-yl)piperidin-3-yl)-9-fluoro-8-methoxy-[1,2,4]triazolo[1,5-c]quinazolin-5-amine

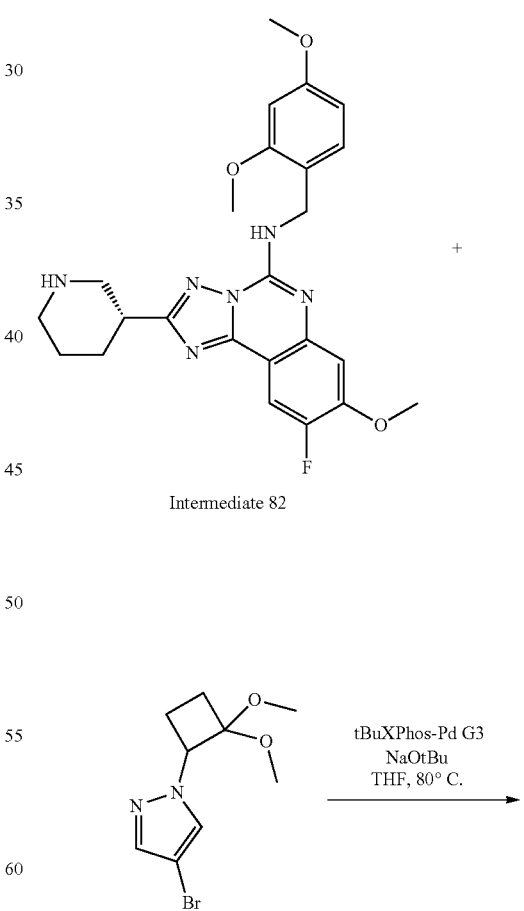

141
-continued

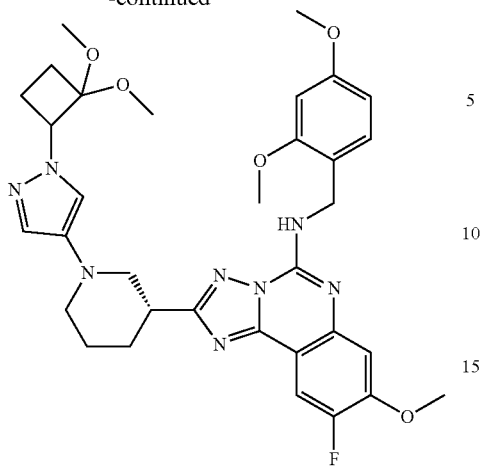

To a stirred mixture of sodium tert-butoxide (177 mg, 1.84 mmol), (R)—N-(2,4-dimethoxybenzyl)-9-fluoro-8-methoxy-2-(piperidin-3-yl)-[1,2,4]triazolo[1,5-c]quinazolin-5-amine (Intermediate 82) (236 mg, 0.506 mmol), 4-bromo-1-(2,2-dimethoxycyclobutyl)-1H-pyrazole (Intermediate 30) (120 mg, 0.460 mmol) in THF (4 mL) was added tBuXPhos-Pd G3 (110 mg, 0.138 mmol). The mixture was stirred and heated at 80° C. for 12 h under nitrogen. The mixture was cooled, diluted with EtOAc (10 mL), and then washed with water (10 mL). The organic layer was dried over anhydrous $Na_2SO_4$, filtered, and the solvents of the filtrate were evaporated. The residue was purified silica gel chromatography with 0-100% EtOAc in petroleum ether as eluent to afford N-(2,4-dimethoxybenzyl)-2-((3R)-1-(1-(2,2-dimethoxycyclobutyl)-1H-pyrazol-4-yl)piperidin-3-yl)-9-fluoro-8-methoxy-[1,2,4]triazolo[1,5-c]quinazolin-5-amine. LCMS ($C_{33}H_{39}FN_8O_5$) (ES, m/z): 647 [M+H]⁺.

Step 2: 2-(4-((R)-3-(5-amino-9-fluoro-8-methoxy-[1,2,4]triazolo[1,5-c]quinazolin-2-yl)piperidin-1-yl)-1H-pyrazol-1-yl)cyclobutan-1-one

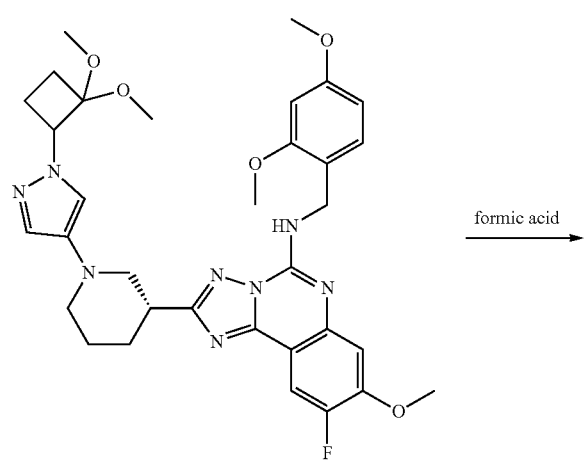

formic acid

142
-continued

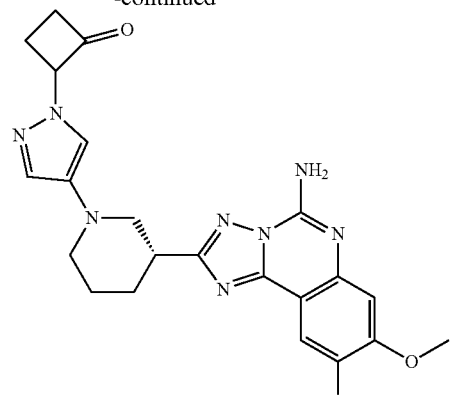

Intermediate 125

A mixture of N-(2,4-dimethoxybenzyl)-2-((3R)-1-(1-(2,2-dimethoxycyclobutyl)-1H-pyrazol-4-yl)piperidin-3-yl)-9-fluoro-8-methoxy-[1,2,4]triazolo[1,5-c]quinazolin-5-amine (130 mg, 0.201 mmol) and formic acid (2 mL) was stirred and heated at 40° C. for 15 h. The mixture was cooled and adjusted to pH=8 with saturated aqueous sodium bicarbonate. The mixture was extracted with DCM (3×10 mL). The combined organic layers were dried over anhydrous $Na_2SO_4$, filtered, and the solvents of the filtrate were evaporated. The residue was purified by preparative silica gel TLC with EtOAc as eluent to afford 2-(4-((R)-3-(5-amino-9-fluoro-8-methoxy-[1,2,4]triazolo[1,5-c]quinazolin-2-yl)piperidin-1-yl)-1H-pyrazol-1-yl)cyclobutan-1-one. LCMS ($C_{22}H_{23}FN_8O_2$) (ES, m/z): 451 [M+H]⁺.

Intermediate 126 and Intermediate 127: rac-(1R or 1S,3R or 3S)-3-(5-amino-9-fluoro-8-methoxy-[1,2,4]triazolo[1,5-c]quinazolin-2-yl)-1-(1-ethyl-1H-pyrazol-4-yl)cyclohexan-1-ol and rac-(1S or 1R,3S or 3R)-3-(5-amino-9-fluoro-8-methoxy-[1,2,4]triazolo[1,5-c]quinazolin-2-yl)-1-(1-ethyl-1H-pyrazol-4-yl)cyclohexan-1-ol Step 1: 3-(5-((2,4-dimethoxybenzyl)amino)-9-fluoro-8-methoxy-[1,2,4]triazolo[1,5-c]quinazolin-2-yl)cyclohexan-1-ol

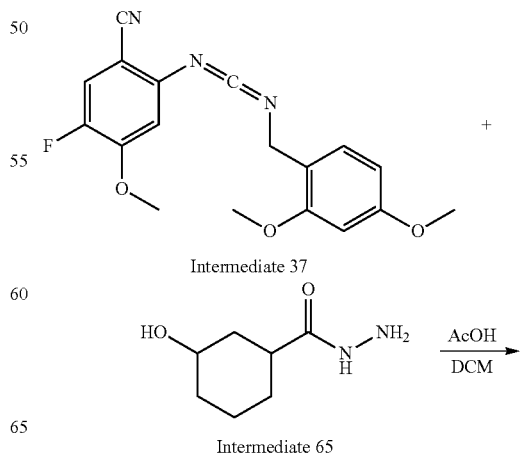

Intermediate 37

Intermediate 65

AcOH
DCM

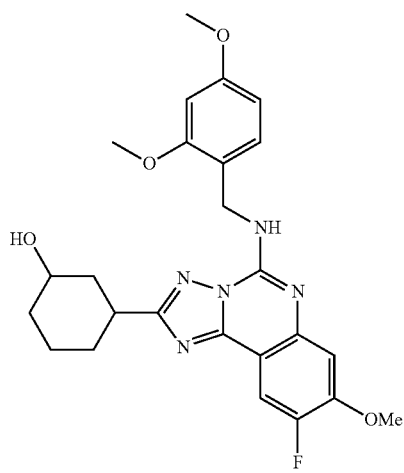

To a stirred mixture of 3-hydroxycyclohexanecarbohydrazide (Intermediate 65) (0.556 g, 3.52 mmol) in DCM (30 mL) was added AcOH (0.084 mL, 1.5 mmol). To the solution was added 2-((((2,4-dimethoxybenzyl)imino)methylene)amino)-5-fluoro-4-methoxybenzonitrile (Intermediate 37) (1.00 g, 2.93 mmol). The mixture was stirred and heated at 35° C. for 10 h. The mixture was concentrated. The resulting residue was purified by silica gel chromatography with 10-50% EtOAc in petroleum ether as eluent to afford 3-(5-((2,4-dimethoxybenzyl)amino)-9-fluoro-8-methoxy-[1,2,4]triazolo[1,5-c]quinazolin-2-yl)cyclohexanol. LCMS ($C_{25}H_{28}FN_5O_4$) (ES, m/z) [M+H]$^+$: 482.

Step 2: 3-(5-((2,4-Dimethoxybenzyl)amino)-9-fluoro-8-methoxy-[1,2,4]triazolo[1,5-c]quinazolin-2-yl)cyclohexan-1-one

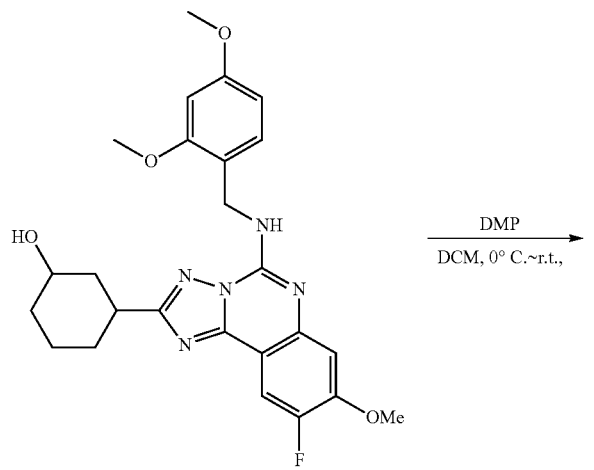

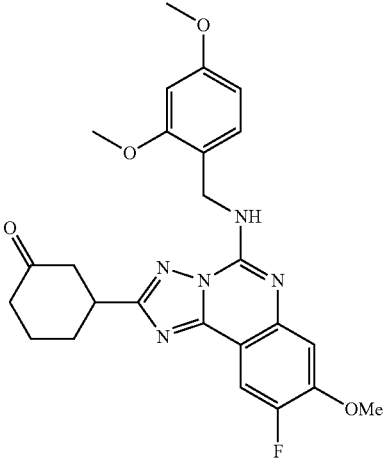

To a stirred solution of 3-(5-((2,4-dimethoxybenzyl)amino)-9-fluoro-8-methoxy-[1,2,4]triazolo[1,5-c]quinazolin-2-yl)cyclohexanol (780 mg, 1.62 mmol) in DCM (10 mL) was added DMP (1.37 g, 3.24 mmol) at 0° C. The mixture was warmed to room temperature and stirred for 3 h. The mixture was quenched with saturated aqueous sodium bicarbonate (5 mL), and the mixture was filtered. The filtrate was extracted with EtOAc (3×10 mL). The combined organic layers were washed with brine (30 mL), dried over anhydrous $Na_2SO_4$, filtered, and the solvents of the filtrate were evaporated. The residue was purified by silica gel chromatography with 10-50% EtOAc in petroleum ether to afford 3-(5-((2,4-dimethoxybenzyl)amino)-9-fluoro-8-methoxy-[1,2,4]triazolo[1,5-c]quinazolin-2-yl)cyclohexanone. LCMS ($C_{25}H_{26}FN_5O_4$) (ES, m/z) [M+H]$^+$: 480.

Step 3: 3-(5-((2,4-dimethoxybenzyl)amino)-9-fluoro-8-methoxy-[1,2,4]triazolo[1,5-c]quinazolin-2-yl)-1-(1-ethyl-1H-pyrazol-4-yl)cyclohexan-1-ol

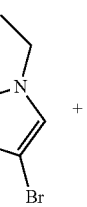

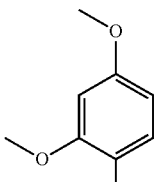

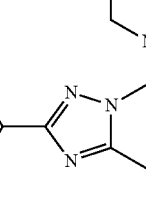

-continued

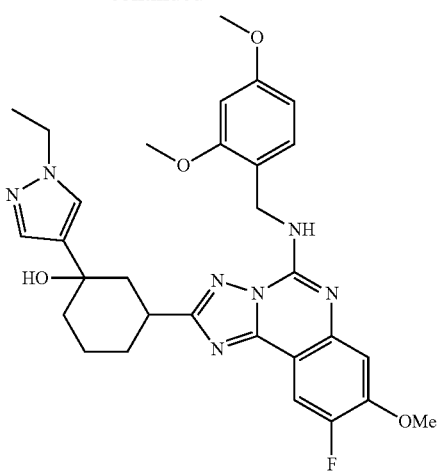

To a stirred solution of 4-bromo-1-ethyl-1H-pyrazole (621 mg, 3.55 mmol) in THF (3 mL) was added n-butyllithium (1.42 mL, 3.55 mmol, 2.5 M in hexane) at −78° C. The mixture was stirred at −78° C. for 20 min. To the mixture was added a solution of 3-(5-((2,4-dimethoxybenzyl)amino)-9-fluoro-8-methoxy-[1,2,4]triazolo[1,5-c]quinazolin-2-yl)cyclohexanone (340 mg, 0.709 mmol) in THF (3 mL) at −78° C., and the mixture was stirred at this temperature for 1 h. The mixture was quenched with saturated aqueous NH$_4$Cl (5 mL) and extracted with EtOAc (3×10 mL). The combined organic phases were washed with brine (20 mL), dried over anhydrous Na$_2$SO$_4$, filtered, and the solvents of the filtrate were evaporated. The residue was purified by silica gel chromatography with 10-50% EtOAc in petroleum ether as eluent to afford 3-(5-((2,4-dimethoxybenzyl)amino)-9-fluoro-8-methoxy-[1,2,4]triazolo[1,5-c]quinazolin-2-yl)-1-(1-ethyl-1H-pyrazol-4-yl). LCMS (C$_{34}$H$_{34}$FN$_7$O$_4$) (ES, m/z) [M+H]$^+$: 576.

Step 4: rac-(1R or 1S,3R or 3S)-3-(5-amino-9-fluoro-8-methoxy-[1,2,4]triazolo[1,5-c]quinazolin-2-yl)-1-(1-ethyl-1H-pyrazol-4-yl)cyclohexan-1-ol and rac-(1S or 1R,3S or 3R)-3-(5-amino-9-fluoro-8-methoxy-[1,2,4]triazolo[1,5-c]quinazolin-2-yl)-1-(1-ethyl-1H-pyrazol-4-yl)cyclohexan-1-ol

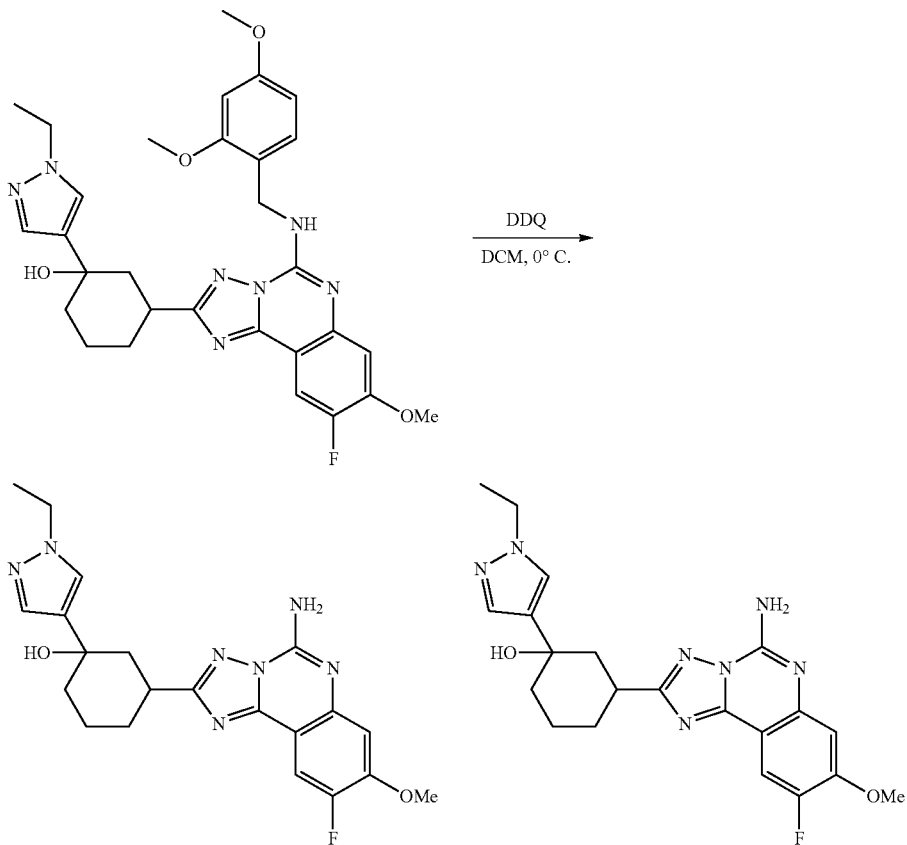

Intermediate 126      Intermediate 127

To a solution of 3-(5-((2,4-dimethoxybenzyl)amino)-9-fluoro-8-methoxy-[1,2,4]triazolo[1,5-c]quinazolin-2-yl)-1-(1-ethyl-1H-pyrazol-4-yl)cyclohexanol (180 mg, 0.313 mmol) in DCM (4 mL) and water (2 mL) was added DDQ (106 mg, 0.469 mmol) portionwise at 0° C. The mixture was stirred at 0° C. for 30 min. The mixture was diluted with DCM (10 mL) and was washed with Na$_2$SO$_3$ (2 M aqueous solution, 5 mL) and brine (2×10 mL). The organic layer was dried over anhydrous Na$_2$SO$_4$, filtered, and the solvents of the filtrate were evaporated. The residue was purified by reversed-phase HPLC (Waters XBridge C18 OBD Prep Column, 19 mm×100 mm with MeCN/water (w/10 mM NH$_4$HCO$_3$ modifier) as eluent) to afford two diastereomers rac-(1R or 1S,3R or 3S)-3-(5-amino-9-fluoro-8-methoxy-[1,2,4]triazolo[1,5-c]quinazolin-2-yl)-1-(1-ethyl-1H-pyrazol-4-yl)cyclohexan-1-ol and rac-(1S or 1R,3S or 3R)-3-(5-amino-9-fluoro-8-methoxy-[1,2,4]triazolo[1,5-c]quinazolin-2-yl)-1-(1-ethyl-1H-pyrazol-4-yl)cyclohexan-1-ol, corresponding to Intermediate 126 and Intermediate 127, respectively. For Intermediate 126: LCMS (C$_{21}$H$_{24}$FN$_7$O$_2$) (ES, m/z) [M+H]$^+$: 426. For Intermediate 127: LCMS (C$_{21}$H$_{24}$FN$_7$O$_2$) (ES, m/z) [M+H]$^+$: 426.

Intermediate 128: (2S,3S and 2R,3R)-3-(4-bromo-1H-pyrazol-1-yl)butan-2-ol

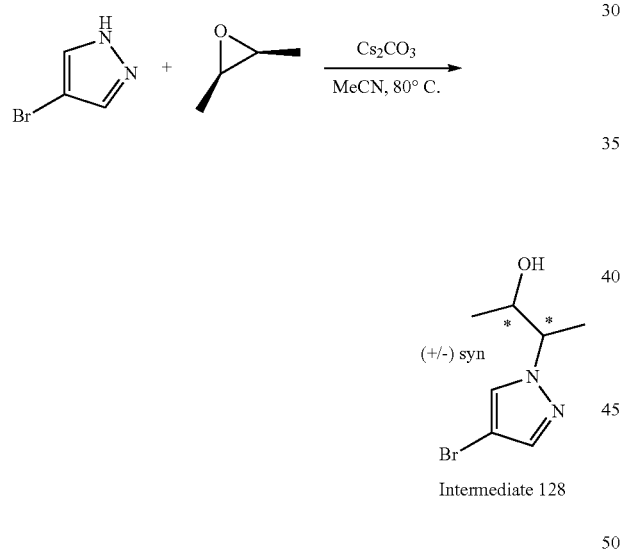

Intermediate 128

To a mixture of 4-bromo-1H-pyrazole (2.00 g, 13.6 mmol) and cesium carbonate (13.3 g, 40.8 mmol) in MeCN (20 mL) was added cis-2,3-dimethyloxirane (2.38 ml, 27.2 mmol). The mixture was stirred and heated at 80° C. for 16 h. The mixture was cooled to room temperature and the solids were removed by filtration. The filtrate was concentrated, and the residue was diluted with DCM and washed with water and brine solution. The organic layer was dried over anhydrous sodium sulfate. The residue was purified by silica gel chromatography with 0-100% EtOAc in hexanes as eluent to afford (2S,3S and 2R,3R)-3-(4-bromo-1H-pyrazol-1-yl)butan-2-ol. LCMS (C$_7$H$_{11}$BrN$_2$O) (ES, m/z) [M+H]$^+$: 219, 221.

The intermediates in the following Table 15 were prepared from the appropriate starting materials in a manner similar to Intermediate 128.

TABLE 15

| Intermediate | Structure Name | Observed m/z [M + H]$^+$ |
|---|---|---|
| 129 | racemic, anti-3-(4-bromo-1H-pyrazol-1-yl)butan-2-ol | 219, 221 |
| 130 | racemic, syn-3-(4-bromo-3-methyl-1H-pyrazol-1-yl)butan-2-ol | 233, 235 |
| 131 | racemic-syn-3-(4-bromo-5-methyl-1H-pyrazol-1-yl)butan-2-ol | 233, 235 |
| 132 | racemic-syn-3-(4-nitro-1H-pyrazol-1-yl)butan-2-ol | 186 |
| 133 | rac-2-methyl-3-(4-nitro-1H-pyrazol-1-yl)propane-1,2-diol | 202 |

TABLE 15-continued

| Intermediate | Structure Name | Observed m/z [M + H]+ |
|---|---|---|
| 134 | 2-methyl-1-(5-methyl-4-nitro-1H-pyrazol-1-yl)propan-2-ol | 200 |
| 135 | 2-methyl-1-(3-methyl-4-nitro-1H-pyrazol-1-yl)propan-2-ol | 200 |

Intermediate 136: ethyl 3-(4-bromo-1H-pyrazol-1-yl)propanoate

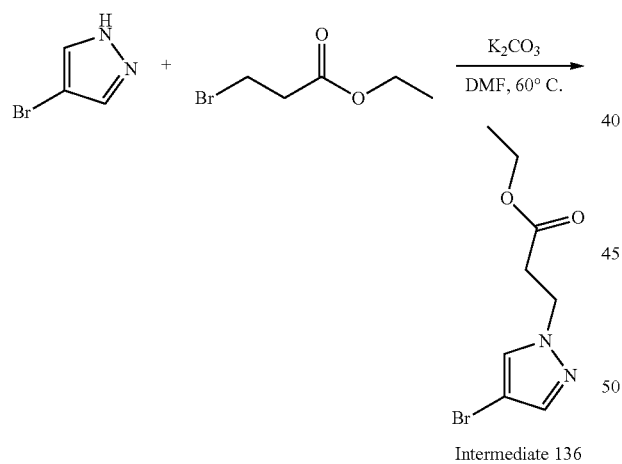

Intermediate 136

To a stirred mixture of 4-bromo-1H-pyrazole (0.500 g, 3.40 mmol) in DMF (10 mL) was added $K_2CO_3$ (1.18 g, 8.50 mmol) and ethyl 3-bromopropanoate (0.924 g, 5.10 mmol). The mixture was stirred and heated at 60° C. for 8 h. The mixture was diluted with water (30 mL), filtered, and the filtrate was extracted with EtOAc (2×30 mL). The organic layers were dried over anhydrous sodium sulfate, filtered, and the solvents of the filtrate were evaporated. The resulting residue was purified by silica gel column chromatography with 3-25% EtOAc in petroleum ether as eluent to afford ethyl 3-(4-bromo-1H-pyrazol-1-yl)propanoate. LCMS ($C_8H_{11}BrN_2O_2$) (ES, m/z) [M+H]+: 247, 249.

The intermediates in the following Table 16 were prepared from the appropriate pyrazole and alkyl halide or mesylate in a manner similar to that used in the preparation of Intermediate 136.

TABLE 16

| Intermediate | Structure Name | Observed m/z [M + H]+ |
|---|---|---|
| 137 | 3-(4-bromo-1H-pyrazol-1-yl)-3-methylbutan-2-one | 231, 233 |
| 138 | 3-(4-bromo-3-methyl-1H-pyrazol-1-yl)-3-methylbutan-2-one | 245, 247 |
| 139 | methyl 2-(4-bromo-3-methyl-1H-pyrazol-1-yl)-2-methylpropanoate | 261, 263 |
| 140 | methyl 2-(4-bromo-5-methyl-1H-pyrazol-1-yl)-2-methylpropanoate | 261, 263 |
| 141 | methyl 2-(4-bromo-5-methyl-1H-pyrazol-1-yl)-2-methylpropanoate | 203, 205 |

TABLE 16-continued

| Intermediate | Structure Name | Observed m/z [M + H]⁺ |
|---|---|---|
| 142 | tert-butyl (2-methyl-1-(4-nitro-1H-pyrazol-1-yl)propan-2-yl)carbamate | 307 [M + Na]⁺ |
| 143 | 3-methyl-3-(4-nitro-1H-pyrazol-1-yl)butan-2-one | 198 |
| 144 | diethyl 2-methyl-2-(4-nitro-1H-pyrazol-1-yl)malonate | — |

Intermediate 145: rac-1-(4-bromo-1H-pyrazol-1-yl)-2-methylbutan-2-ol

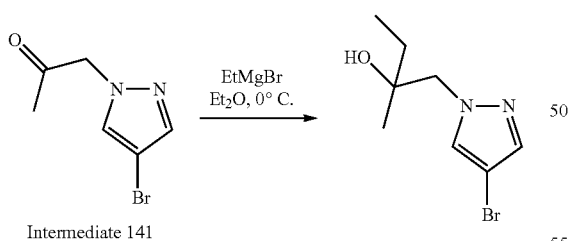

To a solution of 1-(4-bromo-1H-pyrazol-1-yl)propan-2-one (Intermediate 141) (2.00 g, 9.85 mmol) in Et₂O (22 mL) was added a 3 M solution of ethylmagnesium bromide (9.85 mL, 29.6 mmol) dropwise at 0° C. under a nitrogen atmosphere. The solution was stirred at 0° C. for 1 h, then warmed to room temperature and stirred for 15 h. The mixture was quenched with saturated aqueous ammonium chloride (50 mL), diluted with EtOAc (50 mL) and water (50 mL). The aqueous layer was extracted with EtOAc (3×100 mL). The combined organic layers were washed with brine (2×100 mL), dried over anhydrous Na₂SO₄, filtered and the solvents were evaporated. The resulting residue was purified by reversed phase HPLC (MeCN/water with 0.05% TFA) to afford rac-1-(4-bromo-1H-pyrazol-1-yl)-2-methylbutan-2-ol. LCMS ($C_8H_{13}BrN_2O$) (ES, m/z) [M+H]⁺: 233, 235.

Intermediate 146: 1-((5-methyl-2-phenyl-1,3-dioxan-5-yl)methyl)-4-nitro-1H-pyrazole

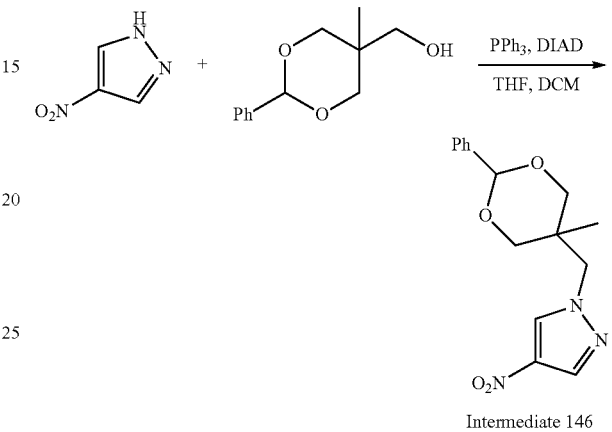

To a solution of (5-methyl-2-phenyl-1,3-dioxan-5-yl)methanol (4.00 g, 19.2 mmol) in THF (20 mL) was added 4-nitro-1H-pyrazole (2.61 g, 23.1 mmol), triphenylphosphine (10.1 g, 38.4 mmol). To the mixture was slowly added DIAD (5.83 g, 28.8 mmol) in DCM (20 mL). The mixture was stirred at room temperature for 15 h. The solvents were evaporated. The residue was purified by silica gel chromatography with 0-30% EtOAc in petroleum ether to afford 1-((5-methyl-2-phenyl-1,3-dioxan-5-yl)methyl)-4-nitro-1H-pyrazole. LCMS ($C_{15}H_{17}N_3O_4$) (ES, m/z) [M+H]⁺: 304.

The intermediate in the following Table 17 was prepared from the appropriate pyrazole and alcohol in a manner similar to that described for the synthesis of Intermediate 146.

TABLE 17

| Intermediate | Structure Name | Observed m/z [M + H]⁺ |
|---|---|---|
| 147 | 4-nitro-1-((1-((tetrahydro-2H-pyran-2-yl)oxy)cyclopropyl)methyl)-1H-pyrazole | 558 [2M + Na]⁺ |

Intermediate 148: rac-3-(4-bromo-3-methyl-1H-pyrazol-1-yl)-3-methylbutan-2-ol

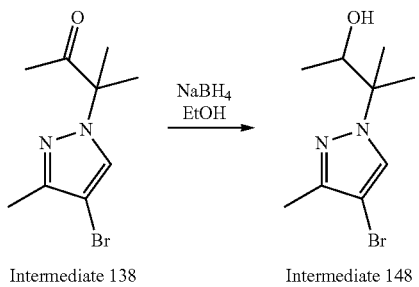

Intermediate 138 → Intermediate 148

To a suspension of 3-(4-bromo-3-methyl-1H-pyrazol-1-yl)-3-methylbutan-2-one (Intermediate 138) (1.27 g, 5.18 mmol) in EtOH (25.9 ml) was added sodium borohydride (0.588 g, 15.5 mmol). The mixture was stirred for 16 h. The mixture was diluted with EtOAc (50 mL), washed with water (50 mL) and aqueous potassium hydroxide (1 M, 20 mL). The organic layer was dried over anhydrous $MgSO_4$, filtered, and the solvent of the filtrate was evaporated to afford 3-(4-bromo-3-methyl-1H-pyrazol-1-yl)-3-methylbutan-2-ol, which was taken forward without further purification. LCMS ($C_9H_{15}BrN_2O$) (ES, m/z) $[M+H]^+$: 247, 249.

The intermediates in the following Table 18 were prepared from the appropriate ketone or ester containing pyrazole in a manner similar to that described in the preparation of Intermediate 148.

TABLE 18

| Intermediate | Structure Name | Observed m/z [M + H]+ |
|---|---|---|
| 149 | 2-(4-bromo-3-methyl-1H-pyrazol-1-yl)-2-methylpropan-1-ol | 233, 235 |
| 150 | 2-(4-bromo-5-methyl-1H-pyrazol-1-yl)-2-methylpropan-1-ol | 233, 235 |
| 151 | rac-3-methyl-3-(4-nitro-1H-pyrazol-1-yl)butan-2-ol | 200 |
| 152 | 4-nitro-1-((1-((tetrahydro-2H-pyran-2-yl)oxy)cyclopropyl)methyl)-1H-pyrazole | 202 |

Intermediate 153: 4-(4-bromo-1H-pyrazol-1-yl)-2-methylbutan-2-ol

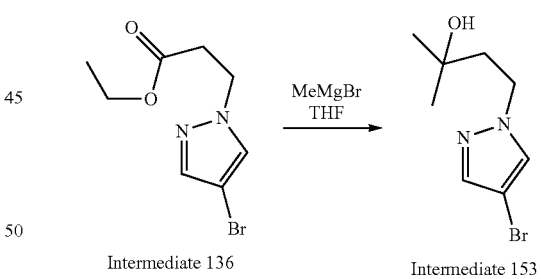

Intermediate 136 → Intermediate 153

To a solution of ethyl 3-(4-bromo-1H-pyrazol-1-yl)propanoate (100 mg, 0.405 mmol) (Intermediate 136) in THF (4 mL) was added a 3 M solution of MeMgBr in diethyl ether (1.35 mL, 4.05 mmol) at 15° C. under a nitrogen atmosphere. The mixture was stirred at 15° C. for 1 h. The mixture was cooled at 0° C., diluted with water (5 mL), extracted with EtOAc (2×5 mL). The organic layer was dried over anhydrous sodium sulfate, filtered, and the solvents of the filtrate were evaporated. The resulting residue was purified by preparative silica gel TLC with 25% EtOAc in petroleum ether as eluent to afford 4-(4-bromo-1H-pyrazol-1-yl)-2-methylbutan-2-ol. LCMS ($C_8H_{13}BrN_2O$) (ES, m/z) $[M+H]^+$: 233, 235.

Intermediate 154: 4-bromo-1-((racemic, anti)-3-((rac-tetrahydro-2H-pyran-2-yl)oxy)butan-2-yl)-1H-pyrazole

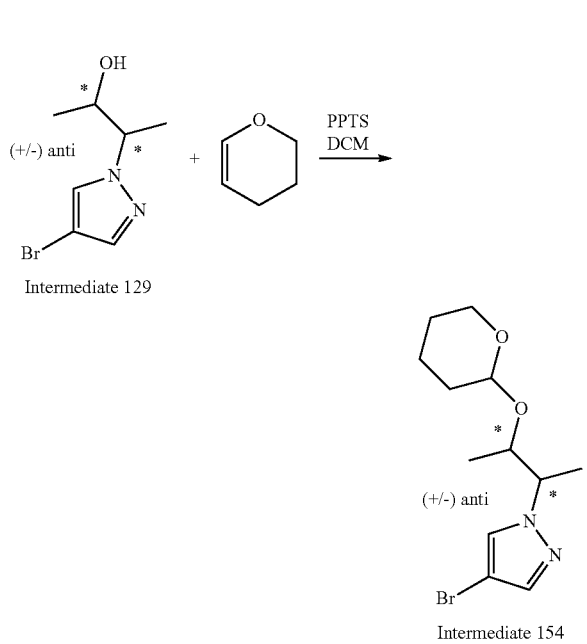

Intermediate 129

Intermediate 154

To a solution of Intermediate 129 (9.40 g, 42.9 mmol) in DCM (100 mL) was added 3,4-dihydro-2H-pyran (19.6 mL, 215 mmol) and PPTS (10.8 g, 42.9 mmol). The mixture was stirred at room temperature for 4 h. The mixture was diluted with DCM (15 mL), washed with saturated aqueous NaHCO$_3$ and brine solution. The organic layer was dried over anhydrous sodium sulfate, filtered, and the solvents of the filtrate were evaporated. The resulting residue was purified by silica gel chromatography with 0-100% EtOAc in hexanes as eluent to afford rac-4-bromo-1-((2S,3R)-3-((tetrahydro-2H-pyran-2-yl)oxy)butan-2-yl)-1H-pyrazole. LCMS (C$_{12}$H$_{19}$BrN$_2$O$_2$) (ES, m/z) [M+H]$^+$: 303, 305.

The intermediate in the following Table 19 was prepared from the appropriate starting materials in a manner similar to that described for the synthesis of Intermediate 154.

TABLE 19

| Intermediate | Structure Name | Observed m/z [M + H]$^+$ |
|---|---|---|
| 155 | ![structure] rac-4-bromo-1-(2-methyl-1-((tetrahydro-2H-pyran-2-yl)oxy)propan-2-yl)-1H-pyrazole | 303, 305 |

Intermediate 156: rac-3-(4-amino-1H-pyrazol-1-yl)-3-methylbutan-2-ol

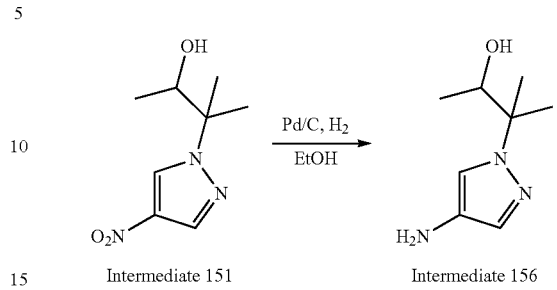

Intermediate 151      Intermediate 156

A 100 mL round-bottom flask was charged with 10% Pd/C (200 mg, 0.188 mmol), 3-methyl-3-(4-nitro-1H-pyrazol-1-yl)butan-2-ol (Intermediate 151) (750 mg, 3.76 mmol), and EtOH (31.4 mL). The mixture was degassed by evacuating and backfilling with nitrogen three times. The mixture was then evacuated and refilled with hydrogen from a balloon. The mixture was stirred for 3 h. The mixture was filtered through Celite, and the solvents of the filtrate were evaporated to afford 3-(4-amino-1H-pyrazol-1-yl)-3-methylbutan-2-ol. LCMS (C$_8$H$_{15}$N$_3$O) (ES, m/z) [M+H]$^+$: 170.

The intermediates in the following Table 20 were prepared from the appropriate nitro-pyrazole in a manner similar to that described for the preparation of Intermediate 156.

TABLE 20

| Intermediate | Structure Name | Observed m/z [M + H]$^+$ |
|---|---|---|
| 157 | ![structure] tert-butyl (1-(4-amino-1H-pyrazol-1-yl)-2-methylpropan-2-yl)carbamate | 255 |
| 158 | ![structure] 2-(4-amino-1H-pyrazol-1-yl)-2-methylpropane-1,3-diol | — |

TABLE 20-continued

| Intermediate | Structure Name | Observed m/z [M + H]+ |
|---|---|---|
| 159 | rac-3-(4-amino-1H-pyrazol-1-yl)-2-methylpropane-1,2-diol | 172 |
| 160 | racemic, syn--3-(4-amino-1H-pyrazol-1-yl)butan-2-ol | 156 |
| 161 | rac-1-((1-((tetrahydro-2H-pyran-2-yl)oxy)cyclopropyl)methyl)-1H-pyrazol-4-amine | 238 |
| 162 | 1-((5-methyl-2-phenyl-1,3-dioxan-5-yl)methyl)-1H-pyrazol-4-amine | 274 |
| 163 | 1-(4-amino-5-methyl-1H-pyrazol-1-yl)-2-methylpropan-2-ol | 170 |
| 164 | 1-(4-amino-3-methyl-1H-pyrazol-1-yl)-2-methylpropan-2-ol | 170 |

Intermediate 165: tert-butyl (1-(4-((2S,5R and 2R,5S)-5-(hydrazinecarbonyl)-2-methylpiperidin-1-yl)-1H-pyrazol-1-yl)-2-methylpropan-2-yl)carbamate

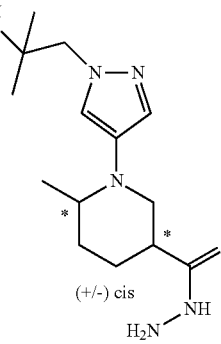

Intermediate 165

Step 1: methyl (3R,6S and 3S,6R)-1-(1-(2-((tert-butoxycarbonyl)amino)-2-methylpropyl)-1H-pyrazol-4-yl)-6-methylpiperidine-3-carboxylate To a 20 mL vial was added tert-butyl (1-(4-amino-1H-pyrazol-1-yl)-2-methylpropan-2-yl)carbamate (Intermediate 157) (85.0 mg, 0.334 mmol), sodium triacetoxyborohydride (106 mg, 0.501 mmol), and DCE (1.5 mL). The mixture was stirred. To the mixture was added methyl 2-methylene-5-oxohexanoate (0.063 ml, 0.40 mmol). After 20 minutes, to the mixture was added 1 M aqueous KOH (3 mL), water (3 mL), and DCM (3 mL). The organic layer was collected with a phase separator. The solvents were evaporated. To the resulting residue was dissolved in MeOH (1 mL), and water (0.4 mL). The mixture was stirred at room temperature for 72 h. To the mixture was added water (20 mL). The mixture was extracted with DCM (2×20 mL). The combined organic layers were dried over anhydrous sodium sulfate, filtered, and the solvents were evaporated. The resulting residue was purified by silica gel chromatography with 0-100% EtOAc in hexanes as eluent to afford methyl (3R,6S and 3S,6R)-1-(1-(2-((tert-butoxycarbonyl)amino)-2-methylpropyl)-1H-pyrazol-4-yl)-6-methylpiperidine-3-carboxylate. LCMS ($C_{24}H_{34}N_4O_4$) (ES, m/z) [M+H]$^+$: 395.

Step 2: tert-butyl (1-(4-((2S,5R and 2R,5S)-5-(hydrazinecarbonyl)-2-methylpiperidin-1-yl)-1H-pyrazol-1-yl)-2-methylpropan-2-yl)carbamate To a 20 mL vial was added methyl (3R,6S and 3S,6R)-1-(1-(2-((tert-butoxycarbonyl)amino)-2-methylpropyl)-1H-pyrazol-4-yl)-6-methylpiperidine-3-carboxylate (99.1 mg, 0.251 mmol), EtOH (1 mL), and hydrazine hydrate (0.175 ml, 3.77 mmol). The mixture was heated at 90° C. for 16 h. The solvents were evaporated to afford tert-butyl (1-(4-((2S, 5R and 2R,5S)-5-(hydrazinecarbonyl)-2-methylpiperidin-1-yl)-1H-pyrazol-1-yl)-2-methylpropan-2-yl)carbamate. LCMS ($C_{19}H34N_6O_3$) (ES, m/z) [M+H]$^+$: 395.

The intermediates in the following Table 21 were prepared from the appropriate amino-pyrazole in a manner similar to that described for the preparation of Intermediate 165.

TABLE 21

| Intermediate | Structure Name | Observed m/z [M + H]$^+$ |
|---|---|---|
| 166 | 1-(1-(1,3-dihydroxy-2-methylpropan-2-yl)-1H-pyrazol-4-yl)-6-methylpiperidine-3-carbohydrazide | 312 |
| 167 | 1-(1-(2,3-dihydroxy-2-methylpropyl)-1H-pyrazol-4-yl)-6-methylpiperidine-3-carbohydrazide | 312 |
| 168 | 6-methyl-1-(1-((5-methyl-2-phenyl-1,3-dioxan-5-yl)methyl)-1H-pyrazol-4-yl)piperidine-3-carbohydrazide | 414 |

TABLE 21-continued

| Intermediate | Structure Name | Observed m/z [M + H]+ |
|---|---|---|
| 169 | 6-methyl-1-(1-((1-((tetrahydro-2H-pyran-2-yl)oxy)cyclopropyl)methyl)-1H-pyrazol-4-yl)piperidine-3-carbohydrazide | 378 |
| 170 | (3R,6S and 3S,6R)-6-methyl-1-(1H-pyrazol-4-yl)piperidine-3-carbohydrazide | 224 |

Intermediate 171: 1-(1-(2-hydroxy-2-methylpropyl)-5-methyl-1H-pyrazol-4-yl)-5-methylpiperidine-3-carbohydrazide

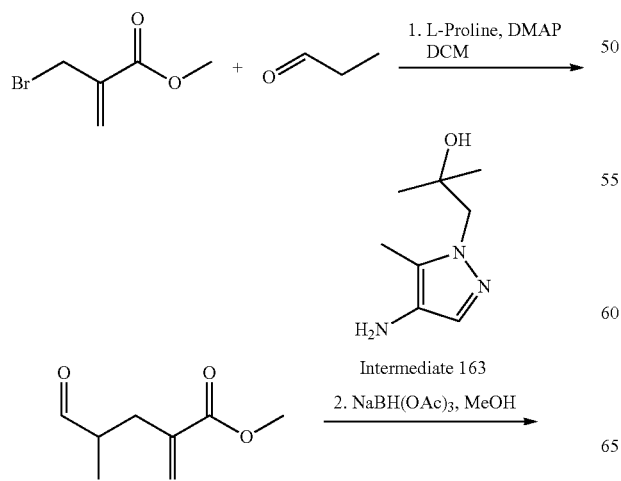

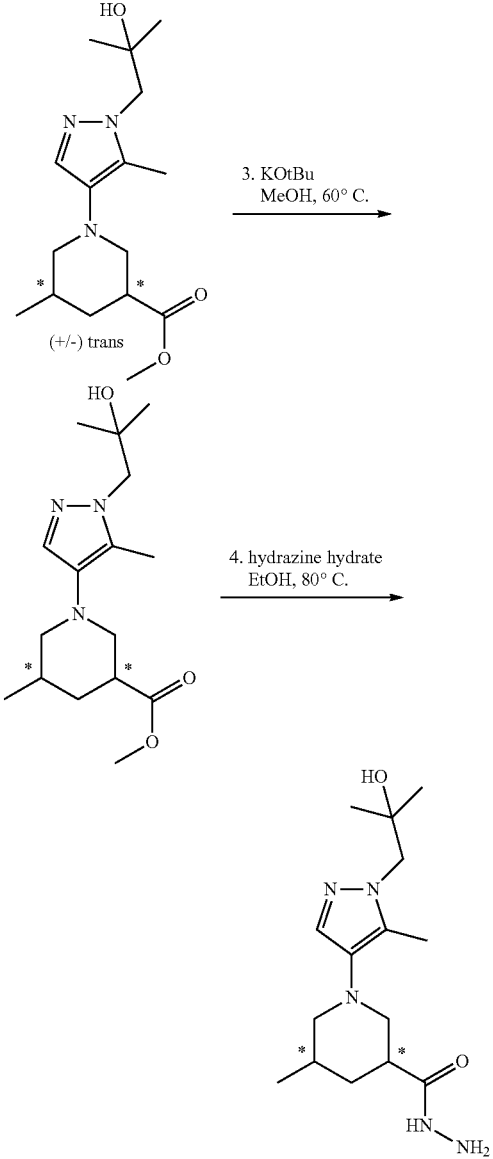

Step 1: methyl 4-methyl-2-methylene-5-oxopentanoate

A solution of methyl 2-(bromomethyl)acrylate (6.04 ml, 50.3 mmol) and DMAP (6.76 g, 55.3 mmol) in DCM (201 mL) was stirred at room temperature for 30 minutes. To the mixture were added propionaldehyde (5.41 ml, 75 mmol) and L-proline (5.79 g, 50.3 mmol). The mixture was stirred at 23° C. for 48 hours. The mixture was washed with water (200 mL), 1 M aqueous HCl (100 mL), and brine (100 mL). The organic layer was dried over anhydrous MgSO₄, filtered, and the solvents were evaporated. The resulting residue was purified by silica gel chromatography with 0-2.5% MeOH in DCM as eluent to afford methyl 4-methyl-2-methylene-5-oxopentanoate.

Step 2: methyl (3R,5R and 3S,5S)-1-(1-(2-hydroxy-2-methylpropyl)-5-methyl-1H-pyrazol-4-yl)-5-methylpiperidine-3-carboxylate 1-(4-amino-5-methyl-1H-pyrazol-1-yl)-2-methylpropan-2-ol (Intermediate 163) (1.43 g, 8.45 mmol) was dissolved in MeOH (25.6 mL). To the mixture was added sodium triacetoxyborohydride (6.51 g, 30.7 mmol), followed by methyl 4-methyl-2-methylene-5-oxopentanoate (1.20 mL, 7.68 mmol). The mixture was stirred for 5 min (until the sodium triacetoxyborohydride went into solution). The mixture was quenched with 1 M aqueous sodium hydroxide (30.7 mL, 30.7 mmol) and allowed to stir for 48 h. The MeOH was evaporated, and to the mixture was added DCM (30 mL). The layers were separated and the DCM layer was dried with anhydrous MgSO$_4$, filtered, and the solvents of the filtrate were evaporated. The residue was purified by silica gel chromatography with 0-10% MeOH in DCM to afford methyl (3R,5R and 3S,5S)-1-(1-(2-hydroxy-2-methylpropyl)-5-methyl-1H-pyrazol-4-yl)-5-methylpiperidine-3-carboxylate. LCMS (C$_{16}$H$_{27}$N$_3$O$_3$) (ES, m/z) [M+H]$^+$: 310.

Step 3: Mixture of methyl (3S,5R and 3R,5S)-1-(1-(2-hydroxy-2-methylpropyl)-5-methyl-1H-pyrazol-4-yl)-5-methylpiperidine-3-carboxylate and methyl (3R,5R and 3S,5S)-1-(1-(2-hydroxy-2-methylpropyl)-5-methyl-1H-pyrazol-4-yl)-5-methylpiperidine-3-carboxylate Methyl (3R,5R and 3S,5S)-1-(1-(2-hydroxy-2-methylpropyl)-5-methyl-1H-pyrazol-4-yl)-5-methylpiperidine-3-carboxylate (1.39 g, 4.49 mmol) was stirred in MeOH (35.9 ml) with potassium tert-butoxide (1.01 g, 8.98 mmol) for 18 h at 60° C. The mixture was cooled to room temperature, and the solvents were evaporated. The resulting residue was dissolved in DCM and quenched with saturated aqueous NH$_4$Cl. The layers were separated using a Biotage Isolute® phase separator and the DCM layer was concentrated. The resulting residue was purified by silica gel chromatography with 0-10% MeOH in DCM to afford a mixture of methyl (3S,5R and 3R,5S)-1-(1-(2-hydroxy-2-methylpropyl)-5-methyl-1H-pyrazol-4-yl)-5-methylpiperidine-3-carboxylate and methyl (3R,5R and 3S,5S)-1-(1-(2-hydroxy-2-methylpropyl)-5-methyl-1H-pyrazol-4-yl)-5-methylpiperidine-3-carboxylate. LCMS (C$_{16}$H$_{27}$N$_3$O$_3$) (ES, m/z) [M+H]$^+$: 310.

Step 4: (3R,5S and 3S,5R)-1-(1-(2-hydroxy-2-methylpropyl)-5-methyl-1H-pyrazol-4-yl)-5-methylpiperidine-3-carbohydrazide and (3R,5R and 3S,5S)-1-(1-(2-hydroxy-2-methylpropyl)-5-methyl-1H-pyrazol-4-yl)-5-methylpiperidine-3-carbohydrazide To a solution of the product from step 3 (1.18 g, 3.81 mmol) in ethanol (15.3 mL) was added hydrazine hydrate (1.87 mL, 38.1 mmol). The mixture was stirred and heated at 80° C. for 16 h. The mixture was cooled to room temperature and the solvents were evaporated to afford (3R,5S and 3S,5R)-1-(1-(2-hydroxy-2-methylpropyl)-5-methyl-1H-pyrazol-4-yl)-5-methylpiperidine-3-carbohydrazide and (3R,5R and 3S,5S)-1-(1-(2-hydroxy-2-methylpropyl)-5-methyl-1H-pyrazol-4-yl)-5-methylpiperidine-3-carbohydrazide LCMS (C$_{15}$H$_{27}$N$_5$O$_2$) (ES, m/z) [M+H]$^+$: 310.

Intermediate 172 and Intermediate 173: N-(2,4-dimethoxybenzyl)-9-fluoro-8-methoxy-2-((3R,5S and 3S,5R)-5-methylpiperidin-3-yl)-[1,2,4]triazolo[1,5-c]quinazolin-5-amine and N-(2,4-dimethoxybenzyl)-9-fluoro-8-methoxy-2-((3S,5S and 3R,5R)-5-methylpiperidin-3-yl)-[1,2,4]triazolo[1,5-c]quinazolin-5-amine N-(2,4-dimethoxybenzyl)-9-fluoro-8-methoxy-2-(5-methylpiperidin-3-yl)-[1,2,4]triazolo[1,5-c]quinazolin-5-amine (Intermediate 85) (2.52 g, 5.24 mmol) was subjected to chiral SFC separation (Phenomenex Lux-3 21×250 mm column with 20% MeOH (w/0.1% NH$_4$OH) as cosolvent) to afford rac-N-(2,4-dimethoxybenzyl)-9-fluoro-8-methoxy-2-((3R,5S)-5-methylpiperidin-3-yl)-[1,2,4]triazolo[1,5-c]quinazolin-5-amine (combination of peaks 2 and 3) and rac-N-(2,4-dimethoxybenzyl)-9-fluoro-8-methoxy-2-((3S,5S)-5-methylpiperidin-3-yl)-[1,2,4]triazolo[1,5-c]quinazolin-5-amine (combination of peaks 1 and 4). LCMS (C$_{25}$H$_{29}$FN$_6$O$_3$) (ES, m/z) [M+H]$^+$: 481.

Intermediate 174 and Intermediate 175: N-(2,4-dimethoxybenzyl)-7,9-difluoro-2-((3R,5S and 3S,5R)-5-methylpiperidin-3-yl)-[1,2,4]triazolo[1,5-c]quinazolin-5-amine and N-(2,4-dimethoxybenzyl)-7,9-difluoro-2-((3S,5S and 3R,5R)-5-methylpiperidin-3-yl)-[1,2,4]triazolo[1,5-c]quinazolin-5-amine

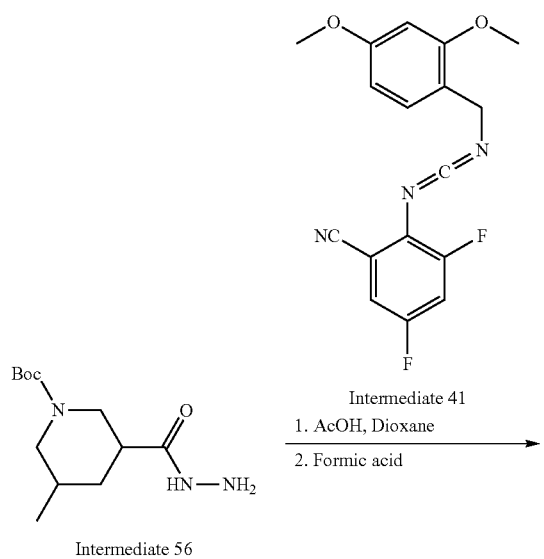

Intermediate 56

Intermediate 41
1. AcOH, Dioxane
2. Formic acid

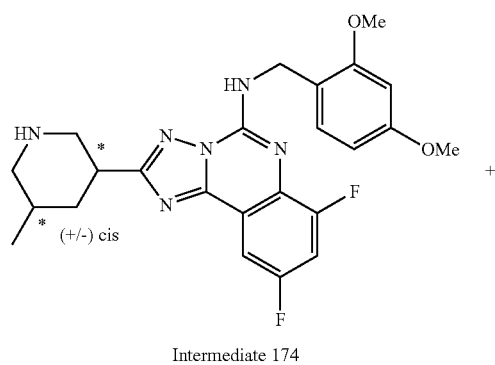

Intermediate 174

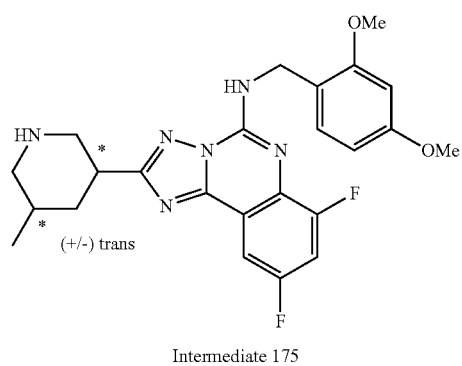

Intermediate 175

Step 1: tert-butyl (3R,5S and 3S,5R)-3-(5-((2,4-dimethoxybenzyl)amino)-7,9-difluoro-[1,2,4]triazolo[1,5-c]quinazolin-2-yl)-5-methylpiperidine-1-carboxylate and tert-butyl (3S,5S and 3R,5R)-3-(5-((2,4-dimethoxybenzyl)amino)-7,9-difluoro-[1,2,4]triazolo[1,5-c]quinazolin-2-yl)-5-methylpiperidine-1-carboxylate To a 100 mL round bottom flask was added tert-butyl 3-(hydrazinecarbonyl)-5-methylpiperidine-1-carboxylate (Intermediate 56) (1.56 g, 6.07 mmol), 1,4-dioxane (20 mL), and acetic acid (0.174 mL, 3.04 mmol). The mixture was stirred. To this stirring mixture was added 2-((((2,4-dimethoxybenzyl)imino)methylene)amino)-3,5-difluorobenzonitrile (Intermediate 41) (2.00 g, 6.07 mmol). The mixture was stirred at 75° C. for 16 h. The mixture was purified by silica gel chromatography with 0-50% EtOAc in hexanes as eluent to afford tert-butyl (3R,5S and 3S,5R)-3-(5-((2,4-dimethoxybenzyl)amino)-7,9-difluoro-[1,2,4]triazolo[1,5-c]quinazolin-2-yl)-5-methylpiperidine-1-carboxylate (first eluting) and tert-butyl (3S,5S and 3R,5R)-3-(5-((2,4-dimethoxybenzyl)amino)-7,9-difluoro-[1,2,4]triazolo[1,5-c]quinazolin-2-yl)-5-methylpiperidine-1-carboxylate (second eluting). LCMS ($C_{29}H_{34}F_2N_6O_4$) (ES, m/z) [M+H]$^+$: 569.

Step 2: N-(2,4-dimethoxybenzyl)-7,9-difluoro-2-((3R,5S and 3S,5R)-5-methylpiperidin-3-yl)-[1,2,4]triazolo[1,5-c]quinazolin-5-amine and N-(2,4-dimethoxybenzyl)-7,9-difluoro-2-((3S,5S and 3R,5R)-5-methylpiperidin-3-yl)-[1,2,4]triazolo[1,5-c]quinazolin-5-amine tert-butyl (3R,5S and 3S,5R)-3-(5-((2,4-dimethoxybenzyl)amino)-7,9-difluoro-[1,2,4]triazolo[1,5-c]quinazolin-2-yl)-5-methylpiperidine-1-carboxylate and tert-butyl (3S,5S and 3R,5R)-3-(5-((2,4-dimethoxybenzyl)amino)-7,9-difluoro-[1,2,4]triazolo[1,5-c]quinazolin-2-yl)-5-methylpiperidine-1-carboxylate from Step 1 were converted to N-(2,4-dimethoxybenzyl)-7,9-difluoro-2-((3R,5S and 3S,5R)-5-methylpiperidin-3-yl)-[1,2,4]triazolo[1,5-c]quinazolin-5-amine (Intermediate 174) and N-(2,4-dimethoxybenzyl)-7,9-difluoro-2-((3S,5S and 3R,5R)-5-methylpiperidin-3-yl)-[1,2,4]triazolo[1,5-c]quinazolin-5-amine (Intermediate 175) (LCMS ($C_{24}H_{26}F_2N_6O_2$) (ES, m/z) [M+H]$^+$: 469) with formic acid in a manner similar to the synthesis of Intermediate 82.

The intermediates in the following Table 22 were prepared in a similar manner to that described for the synthesis of Intermediate 174 from the appropriate hydrazide and carbodiimide.

TABLE 22

| Intermediate | Structure Name | Observed m/z [M + H]+ |
|---|---|---|
| 176 | 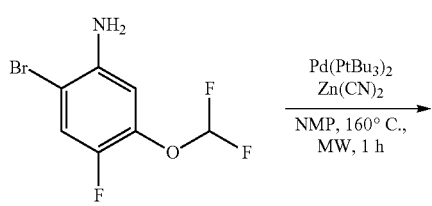<br>N-(2,4-dimethoxybenzyl)-9-fluoro-7-methoxy-2-((3R,5S and 3S,5R)-5-methylpiperidin-3-yl)-[1,2,4]triazolo[1,5-c]quinazolin-5-amine | 481 |
| 177 | 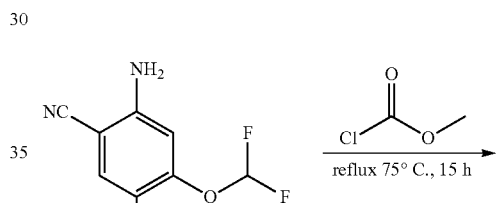<br>N-(2,4-dimethoxybenzyl)-9-fluoro-8-methoxy-2-((3R,6S and 3S,6R)-6-methyl-1-(1H-pyrazol-4-yl)piperidin-3-yl)-[1,2,4]triazolo[1,5-c]quinazolin-5-amine | 547 |

Intermediate 178: (R)-8-(difluoromethoxy)-N-(2,4-dimethoxybenzyl)-9-fluoro-2-(piperidin-3-yl)-[1,2,4]triazolo[1,5-c]quinazolin-5-amine Step 1:
2-amino-4-(difluoromethoxy)-5-fluorobenzonitrile

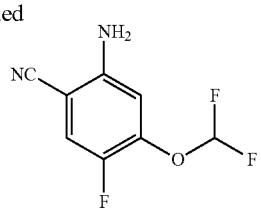

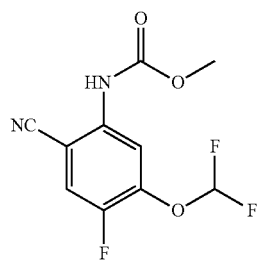

To a mixture of 2-bromo-5-(difluoromethoxy)-4-fluoroaniline (1.40 g, 5.47 mmol) and zinc cyanide (1.28 g, 10.9 mmol) in NMP (4 mL) was added bis(tri-tert-butylphosphine)palladium(0) (0.699 g, 1.37 mmol). The mixture was stirred and heated at 160° C. under nitrogen for 1 h in a microwave reactor. The mixture was cooled to room temperature. To the mixture was added brine (60 mL), and the mixture was extracted with petroleum ether:ethyl acetate (3:1) (3×25 mL), the combined organic layers were dried over anhydrous $Na_2SO_4$, filtered, and the solvents of the filtrate were evaporated. The resulting residue was purified by silica gel chromatography with 25% EtOAc in petroleum ether to afford 2-amino-4-(difluoromethoxy)-5-fluorobenzonitrile.

Step 2: methyl (2-cyano-5-(difluoromethoxy)-4-fluorophenyl)carbamate

A solution of 2-amino-4-(difluoromethoxy)-5-fluorobenzonitrile (500 mg, 2.47 mmol) in methyl carbonochloridate (3.04 g, 32.2 mmol) was stirred and heated at 75° C. under a nitrogen atmosphere for 15 h. The mixture was cooled, diluted with water (10 mL), extracted with EtOAc (3×20 mL), dried over anhydrous $Na_2SO_4$, filtered, and the solvents of the filtrate were evaporated. The residue was purified by silica gel chromatography to afford methyl (2-cyano-5-(difluoromethoxy)-4-fluorophenyl)carbamate.

Step 3: (R)-tert-butyl-3-(8-(difluoromethoxy)-9-fluoro-5-hydroxy-[1,2,4]triazolo[1,5-c]quinazolin-2-yl)piperidine-1-carboxylate

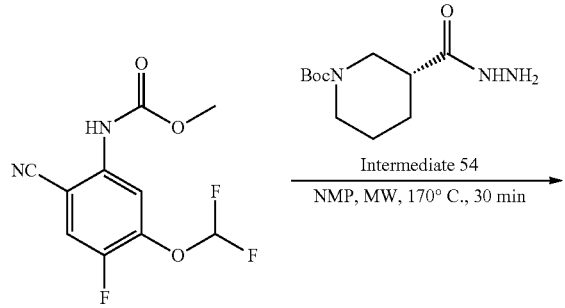

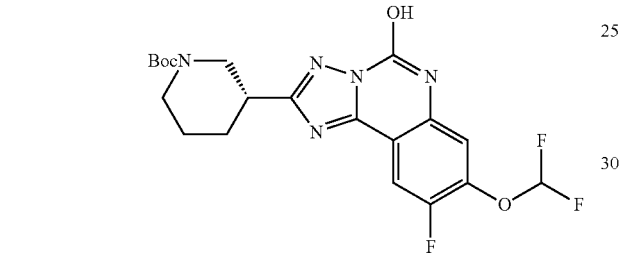

To a solution of methyl (2-cyano-5-(difluoromethoxy)-4-fluorophenyl)carbamate (400 mg, 1.537 mmol) in NMP (4 mL) was added (R)-tert-butyl 3-(hydrazinecarbonyl)piperidine-1-carboxylate (411 mg, 1.691 mmol) (Intermediate 54). The mixture was stirred and heated at 170° C. for 30 min. The mixture was cooled, diluted with water (30 mL) and extracted with EtOAc (3×30 mL). The combined organic extracts were dried over anhydrous Na$_2$SO$_4$, filtered, and the solvents of the filtrate were evaporated. The resulting residue was purified by silica gel chromatography with 0-30% EtOAc in hexanes as eluent to afford (R)-tert-butyl-3-(8-(difluoromethoxy)-9-fluoro-5-hydroxy-[1,2,4]triazolo[1,5-c]quinazolin-2-yl)piperidine-1-carboxylate. LCMS (C$_{24}$H$_{22}$F$_3$N$_5$O$_4$) (ES, m/z) [M+H]$^+$: 454.

Step 4: tert-butyl-3-(8-(difluoromethoxy)-5-((2,4-dimethoxybenzyl)amino)-9-fluoro-[1,2,4]triazolo[1,5-c]quinazolin-2-yl)piperidine-1-carboxylate

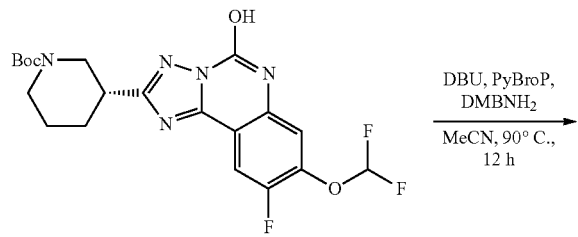

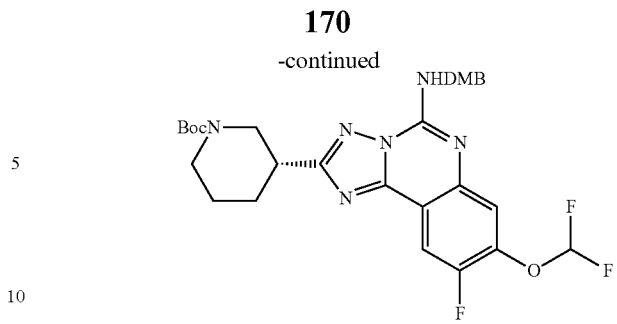

To a solution of tert-butyl-3-(8-(difluoromethoxy)-9-fluoro-5-hydroxy-[1,2,4]triazolo[1,5-c]quinazolin-2-yl)piperidine-1-carboxylate (1.00 g, 2.21 mmol) in MeCN (10 mL) was added DBU (0.831 mL, 5.51 mmol), PyBroP (1.34 g, 2.87 mmol) and (2,4-dimethoxyphenyl)methanamine (0.553 g, 3.31 mmol) at 90° C. under a nitrogen atmosphere. The mixture was stirred at 90° C. for 12 h. The solvents were evaporated. The resulting residue was purified by silica gel chromatography with 0-50% EtOAc in hexanes as eluent to afford tert-butyl-3-(8-(difluoromethoxy)-5-((2,4-dimethoxybenzyl)amino)-9-fluoro-[1,2,4]triazolo[1,5-c]quinazolin-2-yl)piperidine-1-carboxylate. LCMS (C$_{29}$H$_{33}$F$_3$N$_6$O$_5$) (ES, m/z) [M+H]$^+$: 603.

Step 5: (R)-8-(difluoromethoxy)-N-(2,4-dimethoxybenzyl)-9-fluoro-2-(piperidin-3-yl)-[1,2,4]triazolo[1,5-c]quinazolin-5-amine

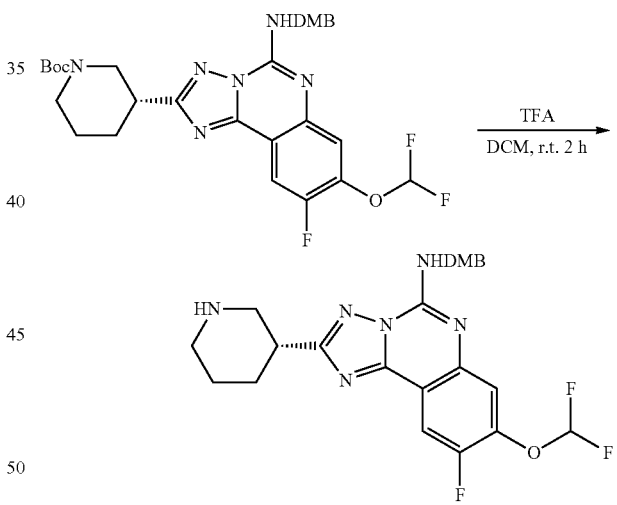

Intermediate 178

To a solution of tert-butyl-3-(8-(difluoromethoxy)-5-((2,4-dimethoxybenzyl)amino)-9-fluoro-[1,2,4]triazolo[1,5-c]quinazolin-2-yl)piperidine-1-carboxylate (700 mg, 1.16 mmol) in DCM (7 mL) was added TFA (0.7 mL) at 15° C. under a nitrogen atmosphere. The mixture was stirred at 15° C. for 2 h. The mixture was cooled, diluted with NaHCO$_3$ (15 mL), extracted with DCM (3×20 mL), dried over anhydrous Na$_2$SO$_4$, and the solvents were evaporated. The resulting residue was purified by silica gel chromatography with 0-50% EtOAc in petroleum ether as eluent to afford (R)-8-(difluoromethoxy)-N-(2,4-dimethoxybenzyl)-9-fluoro-2-(piperidin-3-yl)-[1,2,4]triazolo[1,5-c]quinazolin-5-amine. LCMS (C$_{24}$H$_{25}$F$_3$N$_6$O$_3$) (ES, m/z) [M+H]$^+$: 503.

Example 1: (R)-1-(3-(3-(5-amino-9-fluoro-8-methoxy-[1,2,4]triazolo[1,5-c]quinazolin-2-yl)piperidin-1-yl)-1H-1,2,4-triazol-1-yl)-2-methylpropan-2-ol

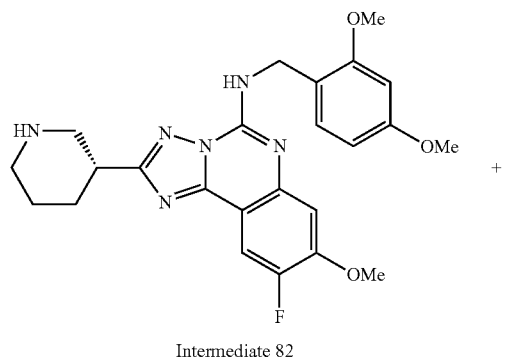

Intermediate 82

+

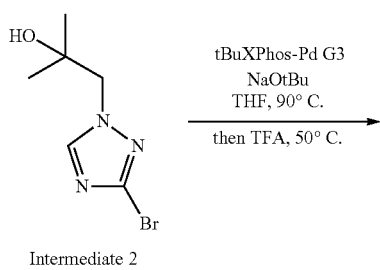

Intermediate 2 tBuXPhos-Pd G3
NaOtBu
THF, 90° C.
then TFA, 50° C.
⟶

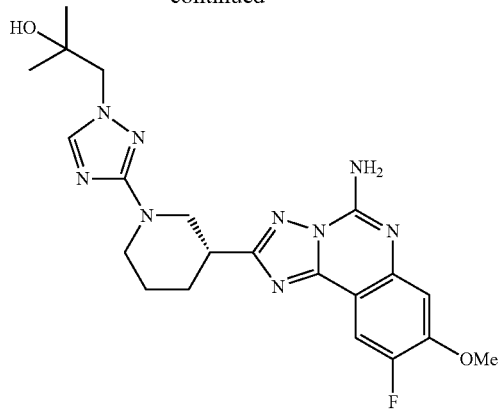

Example 1

A 5 mL microwave vial was charged with (R)—N-(2,4-dimethoxybenzyl)-9-fluoro-8-methoxy-2-(piperidin-3-yl)-[1,2,4]triazolo[1,5-c]quinazolin-5-amine (Intermediate 82) (100 mg, 0.214 mmol), tBuXPhos-Pd G3 (68.1 mg, 0.086 mmol) and sodium tert-butoxide (82 mg, 0.86 mmol). To the mixture was added 1-(3-bromo-1H-1,2,4-triazol-1-yl)-2-methylpropan-2-ol (Intermediate 2) (94 mg, 0.429 mmol) in THF (1.4 mL). The mixture was sparged with nitrogen for 10 min. The mixture was stirred and heated at 90° C. for 16 h. The mixture was cooled to room temperature, and the solids were removed by filtration and washed with DCM. The solvents of the filtrate were evaporated. To the resulting residue was added TFA (0.5 mL). The mixture was stirred and heated at 50° C. for 3 h. The mixture was cooled to room temperature, and the solvents were evaporated. The residue was purified by preparative reversed-phase HPLC (Waters SunFire C18 OBD Prep Column, 19 mm×100 mm MeCN/$H_2O$ with 0.1% TFA as eluent) to afford (R)-1-(3-(3-(5-amino-9-fluoro-8-methoxy-[1,2,4]triazolo[1,5-c]quinazolin-2-yl)piperidin-1-yl)-1H-1,2,4-triazol-1-yl)-2-methylpropan-2-ol. LCMS ($C_{21}H_{26}FN_9O_2$) (ES, m/z): 458 $[M+H]^+$. $^1H$ NMR (499 MHz, DMSO-$d_6$) δ 8.17 (s, 1H), 7.89 (d, J=10.9 Hz, 1H), 7.81 (s, 2H), 7.19 (d, J=7.9 Hz, 1H), 4.31 (d, J=12.8 Hz, 1H), 3.97 (s, 4H), 3.91 (s, 2H), 3.15 (ddt, J=10.9, 6.7, 3.4 Hz, 1H), 3.11-3.04 (m, 1H), 2.86 (td, J=12.5, 2.7 Hz, 1H), 2.23 (d, J=12.1 Hz, 1H), 1.92-1.77 (m, 2H), 1.75-1.63 (m, 1H), 1.10 (d, J=2.4 Hz, 6H).

The example compounds of the invention in the following Table 15 were prepared in a manner similar to that described in Example 1, from the appropriate starting aryl halide and amine intermediates.

TABLE 15

| Example | Structure Name | Observed m/z [M + H]+ |
|---|---|---|
| 2 | (R)-9-fluoro-8-methoxy-2-(1-(1-methyl-1H-pyrazol-4-yl)piperidin-3-yl)-[1,2,4]triazolo[1,5-c]quinazolin-5-amine | 397 |

TABLE 15-continued

| Example | Structure Name | Observed m/z [M + H]+ |
|---|---|---|
| 3 | (R)-2-(1-(1-(tert-butyl)-1H-pyrazol-4-yl)piperidin-3-yl)-9-fluoro-8-methoxy-[1,2,4]triazolo[1,5-c]quinazolin-5-amine | 439 |
| 4 | (R)-9-fluoro-2-(1-(1-isopropyl-1H-pyrazol-4-yl)piperidin-3-yl)-8-methoxy-[1,2,4]triazolo[1,5-c]quinazolin-5-amine | 425 |
| 5 | (R)-9-fluoro-8-methoxy-2-(1-(1-(2,2,2-trifluoroethyl)-1H-pyrazol-4-yl)piperidin-3-yl)-[1,2,4]triazolo[1,5-c]quinazolin-5-amine | 465 |
| 6 | (R)-9-fluoro-8-methoxy-2-(1-(1-methyl-1H-1,2,3-triazol-4-yl)piperidin-3-yl)-[1,2,4]triazolo[1,5-c]quinazolin-5-amine | 398 |

TABLE 15-continued

| Example | Structure Name | Observed m/z [M + H]+ |
|---|---|---|
| 7 | (R)-1-(4-(3-(5-amino-9-fluoro-8-methoxy-[1,2,4]triazolo[1,5-c]quinazolin-2-yl)piperidin-1-yl)-1H-pyrazol-1-yl)-2-methylpropan-2-ol | 455 |
| 8 | (R)-1-(4-(3-(5-amino-9-fluoro-8-methoxy-[1,2,4]triazolo[1,5-c]quinazolin-2-yl)piperidin-1-yl)-5-methyl-1H-pyrazol-1-yl)-2-methylpropan-2-ol | 469 |
| 9 | (R)-1-(4-(3-(5-amino-9-fluoro-8-methoxy-[1,2,4]triazolo[1,5-c]quinazolin-2-yl)piperidin-1-yl)-3-methyl-1H-pyrazol-1-yl)-2-methylpropan-2-ol | 469 |

TABLE 15-continued

| Example | Structure Name | Observed m/z [M + H]+ |
|---|---|---|
| 10 | 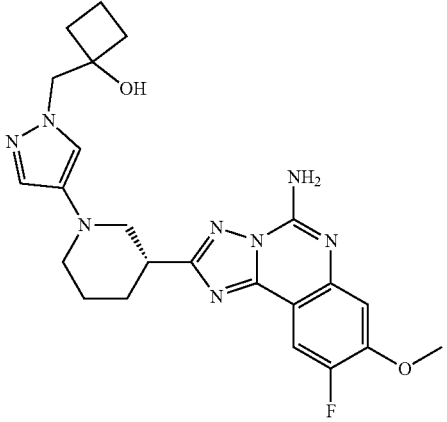 [SMILES: COc1cc2nc(N)n3nc([C@@H]4CCCN(c5cnn(CC6(O)CCC6)c5)C4)nc3c2cc1F]<br>(R)-1-((4-(3-(5-amino-9-fluoro-8-methoxy-[1,2,4]triazolo[1,5-c]quinazolin-2-yl)piperidin-1-yl)-1H-pyrazol-1-yl)methyl)cyclobutan-1-ol | 467 |
| 11 | 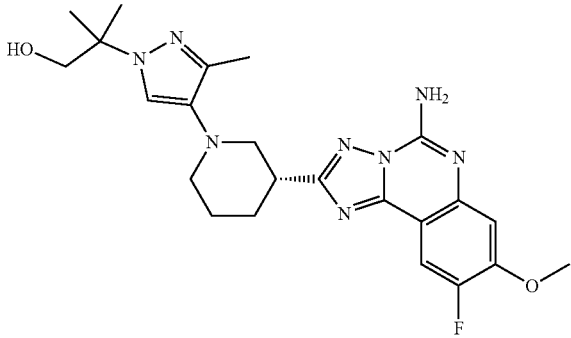 [SMILES: COc1cc2nc(N)n3nc([C@@H]4CCCN(c5cn(C(C)(C)CO)nc5C)C4)nc3c2cc1F]<br>(R)-2-(4-(3-(5-amino-9-fluoro-8-methoxy-[1,2,4]triazolo[1,5-c]quinazolin-2-yl)piperidin-1-yl)-3-methyl-1H-pyrazol-1-yl)-2-methylpropan-1-ol | 469 |
| 12 | 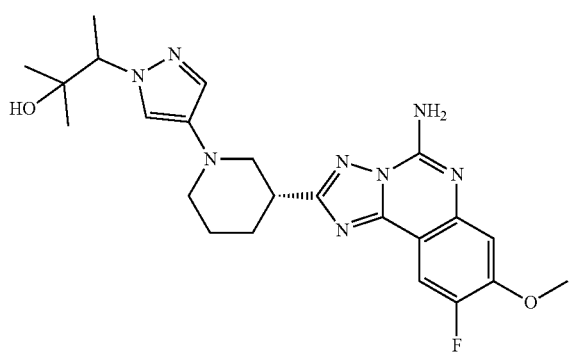 [SMILES: COc1cc2nc(N)n3nc([C@@H]4CCCN(c5cnn(C(C)C(C)(C)O)c5)C4)nc3c2cc1F]<br>(from Intermediate 26)<br>(S or R)-3-(4-((R)-3-(5-amino-9-fluoro-8-methoxy-[1,2,4]triazolo[1,5-c]quinazolin-2-yl)piperidin-1-yl)-1H-pyrazol-1-yl)-2-methylbutan-2-ol | 469 |

TABLE 15-continued

| Example | Structure Name | Observed m/z [M + H]⁺ |
|---|---|---|
| 13 | (from Intermediate 27) (R or S)-3-(4-((R)-3-(5-amino-9-fluoro-8-methoxy-[1,2,4]triazolo[1,5-c]quinazolin-2-yl)piperidin-1-yl)-1H-pyrazol-1-yl)-2-methylbutan-2-ol | 469 |
| 14 | (1s,3s)-3-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclobutan-1-ol | 467 |
| 15 | (R)-9-fluoro-8-methoxy-2-(1-(1-((3-methyloxetan-3-yl)methyl)-1H-pyrazol-4-yl)piperidin-3-yl)-[1,2,4]triazolo[1,5-c]quinazolin-5-amine | 467 |

TABLE 15-continued

| Example | Structure Name | Observed m/z [M + H]+ |
|---|---|---|
| 16 | 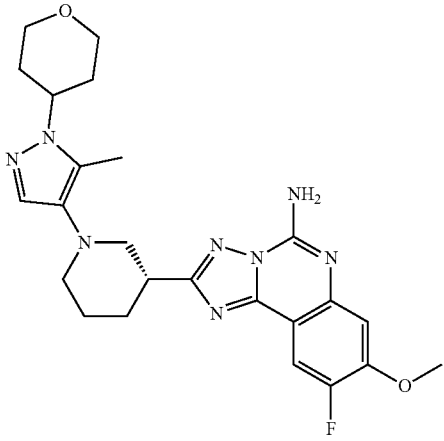 [SMILES: COc1cc2nc(N)n3nc([C@@H]4CCCN(c5cnn(C6CCOCC6)c5C)C4)nc3c2cc1F]<br>(R)-9-fluoro-8-methoxy-2-(1-(5-methyl-1-(tetrahydro-2H-pyran-4-yl)-1H-pyrazol-4-yl)piperidin-3-yl)-[1,2,4]triazolo[1,5-c]quinazolin-5-amine | 481 |
| 17 | 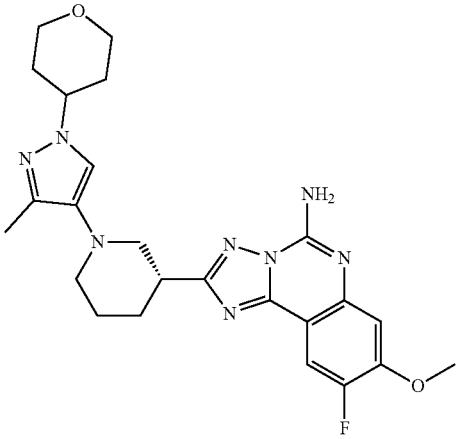<br>(R)-9-fluoro-8-methoxy-2-(1-(3-methyl-1-(tetrahydro-2H-pyran-4-yl)-1H-pyrazol-4-yl)piperidin-3-yl)-[1,2,4]triazolo[1,5-c]quinazolin-5-amine | 481 |
| 18 | 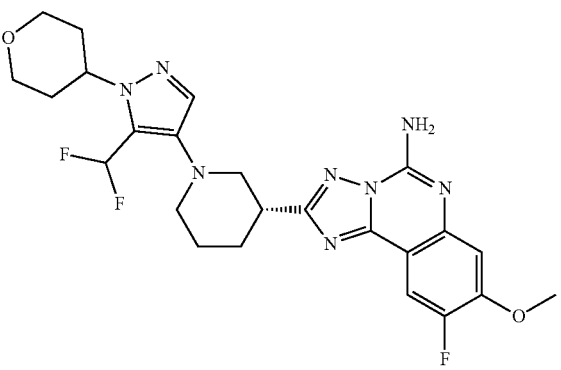 [SMILES: COc1cc2nc(N)n3nc([C@@H]4CCCN(c5cnn(C6CCOCC6)c5C(F)F)C4)nc3c2cc1F]<br>(R)-2-(1-(5-(difluoromethyl)-1-(tetrahydro-2H-pyran-4-yl)-1H-pyrazol-4-yl)piperidin-3-yl)-9-fluoro-8-methoxy-[1,2,4]triazolo[1,5-c]quinazolin-5-amine | 517 |

TABLE 15-continued

| Example | Structure Name | Observed m/z [M + H]+ |
|---|---|---|
| 19 | 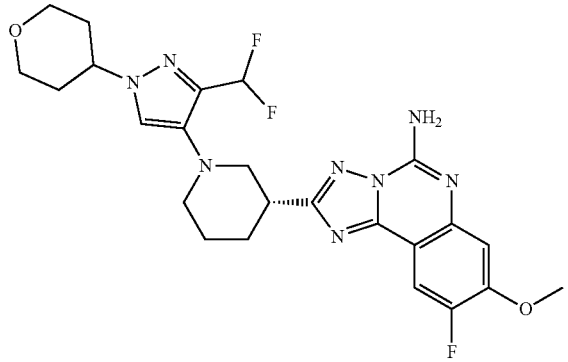 [SMILES: COc1cc2nc(N)n3nc([C@@H]4CCCN(c5cn(C6CCOCC6)nc5C(F)F)C4)nc3c2cc1F]<br>(R)-2-(1-(3-(difluoromethyl)-1-(tetrahydro-2H-pyran-4-yl)-1H-pyrazol-4-yl)piperidin-3-yl)-9-fluoro-8-methoxy-[1,2,4]triazolo[1,5-c]quinazolin-5-amine | 517 |
| 20 | 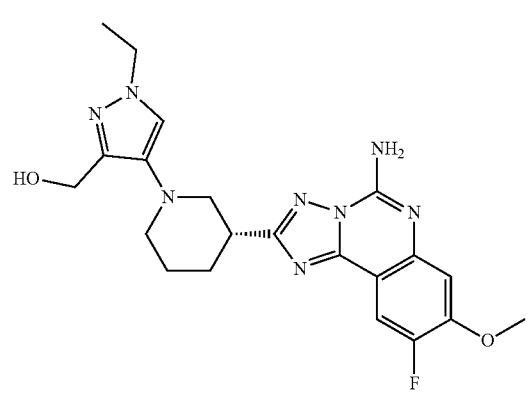 [SMILES: CCn1cc(N2CCC[C@@H](c3nc4c5cc(F)c(OC)cc5nc(N)n4n3)C2)c(CO)n1]<br>(R)-(4-(3-(5-amino-9-fluoro-8-methoxy-[1,2,4]triazolo[1,5-c]quinazolin-2-yl)piperidin-1-yl)-1-ethyl-1H-pyrazol-3-yl)methanol | 441 |
| 21 | 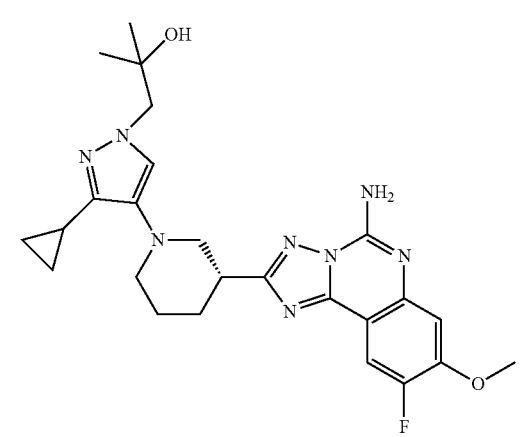 [SMILES: COc1cc2nc(N)n3nc([C@@H]4CCCN(c5cn(CC(C)(C)O)nc5C5CC5)C4)nc3c2cc1F]<br>(R)-1-(4-(3-(5-amino-9-fluoro-8-methoxy-[1,2,4]triazolo[1,5-c]quinazolin-2-yl)piperidin-1-yl)-3-cyclopropyl-1H-pyrazol-1-yl)-2-methylpropan-2-ol | 495 |

TABLE 15-continued
| Example | Structure Name | Observed m/z [M + H]+ |
|---|---|---|
| 22 | 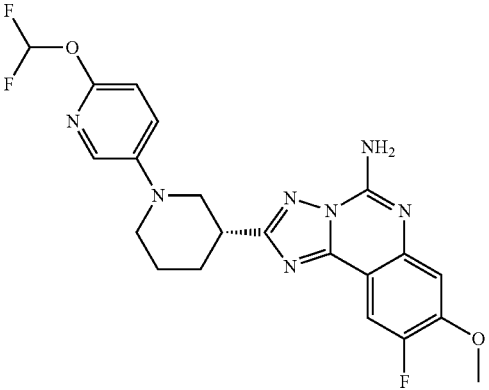 [SMILES: COc1cc2nc(N)n3nc([C@@H]4CCCN(c5ccc(OC(F)F)nc5)C4)nc3c2cc1F]<br>(R)-2-(1-(6-(difluoromethoxy)pyridin-3-yl)piperidin-3-yl)-9-fluoro-8-methoxy-[1,2,4]triazolo[1,5-c]quinazolin-5-amine | 460 |
| 23 | 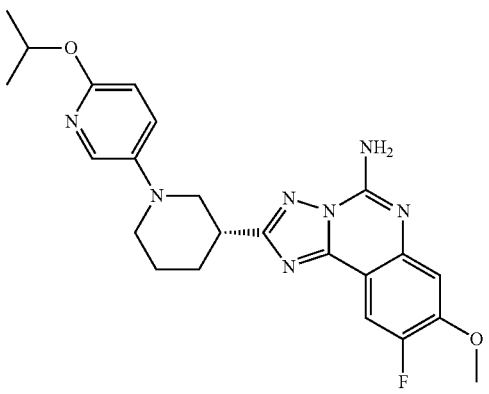 [SMILES: COc1cc2nc(N)n3nc([C@@H]4CCCN(c5ccc(OC(C)C)nc5)C4)nc3c2cc1F]<br>(R)-9-fluoro-2-(1-(6-isopropoxypyridin-3-yl)piperidin-3-yl)-8-methoxy-[1,2,4]triazolo[1,5-c]quinazolin-5-amine | 452 |
| 24 | 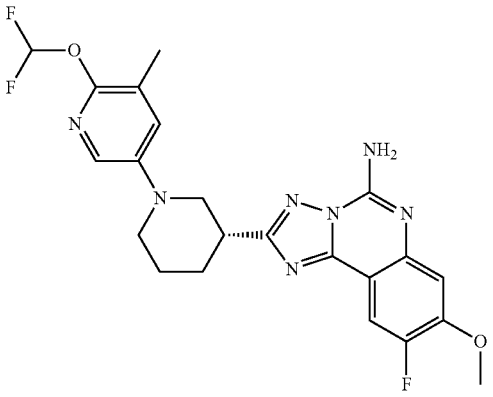 [SMILES: COc1cc2nc(N)n3nc([C@@H]4CCCN(c5cnc(OC(F)F)c(C)c5)C4)nc3c2cc1F]<br>(R)-2-(1-(6-(difluoromethoxy)-5-methylpyridin-3-yl)piperidin-3-yl)-9-fluoro-8-methoxy-[1,2,4]triazolo[1,5-c]quinazolin-5-amine | 474 |

TABLE 15-continued
| Example | Structure Name | Observed m/z [M + H]+ |
|---|---|---|
| 25 | 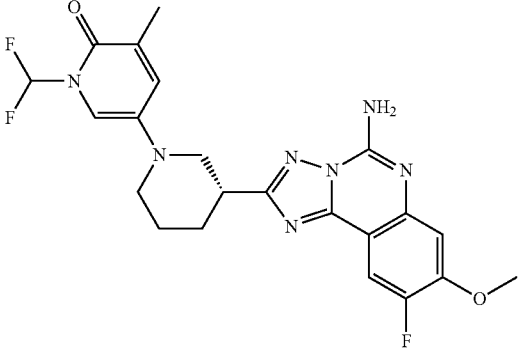 [SMILES: COc1cc2nc(N)n3nc([C@@H]4CCCN(c5cc(C)c(=O)n(C(F)F)c5)C4)nc3c2cc1F]<br>(R)-5-(3-(5-amino-9-fluoro-8-methoxy-[1,2,4]triazolo[1,5-c]quinazolin-2-yl)piperidin-1-yl)-1-(difluoromethyl)-3-methylpyridin-2(1H)-one | 474 |
| 26 | 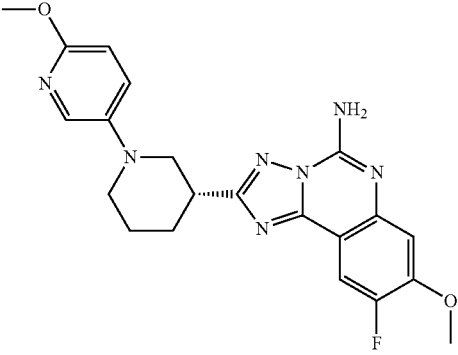<br>(R)-9-fluoro-8-methoxy-2-(1-(6-methoxypyridin-3-yl)piperidin-3-yl)-[1,2,4]triazolo[1,5-c]quinazolin-5-amine | 424 |
| 27 | 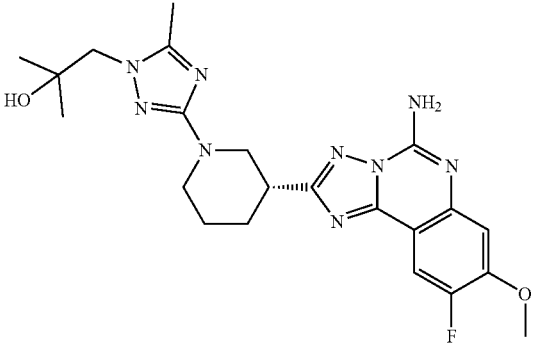 [SMILES: COc1cc2nc(N)n3nc([C@@H]4CCCN(c5nc(C)n(CC(C)(C)O)n5)C4)nc3c2cc1F]<br>(R)-1-(3-(3-(5-amino-9-fluoro-8-methoxy-[1,2,4]triazolo[1,5-c]quinazolin-2-yl)piperidin-1-yl)-5-methyl-1H-1,2,4-triazol-1-yl)-2-methylpropan-2-ol | 470 |

TABLE 15-continued

| Example | Structure Name | Observed m/z [M + H]+ |
|---|---|---|
| 28 | (R)-1-(4-(3-(5-amino-9-fluoro-7-methoxy-[1,2,4]triazolo[1,5-c]quinazolin-2-yl)piperidin-1-yl)-1H-pyrazol-1-yl)-2-methylpropan-2-ol | 455 |
| 29 | (R)-1-(4-(3-(5-amino-9-fluoro-7-methoxy-[1,2,4]triazolo[1,5-c]quinazolin-2-yl)piperidin-1-yl)-5-methyl-1H-pyrazol-1-yl)-2-methylpropan-2-ol | 469 |
| 30 | (R)-1-(4-(3-(5-amino-9-fluoro-7-methoxy-[1,2,4]triazolo[1,5-c]quinazolin-2-yl)piperidin-1-yl)-3-methyl-1H-pyrazol-1-yl)-2-methylpropan-2-ol | 469 |

TABLE 15-continued

| Example | Structure Name | Observed m/z [M + H]+ |
|---|---|---|
| 31 | (R)-1-((4-(3-(5-amino-9-fluoro-7-methoxy-[1,2,4]triazolo[1,5-c]quinazolin-2-yl)piperidin-1-yl)-1H-pyrazol-1-yl)methyl)cyclobutan-1-ol | 467 |
| 32 | (R)-2-(4-(3-(5-amino-9-fluoro-7-methoxy-[1,2,4]triazolo[1,5-c]quinazolin-2-yl)piperidin-1-yl)-1H-pyrazol-1-yl)-2-methylpropan-1-ol | 455 |
| 33 | (R)-2-(1-(6-(difluoromethoxy)pyridin-3-yl)piperidin-3-yl)-9-fluoro-7-methoxy-[1,2,4]triazolo[1,5-c]quinazolin-5-amine | 460 |

TABLE 15-continued
| Example | Structure Name | Observed m/z [M + H]+ |
|---|---|---|
| 34 | 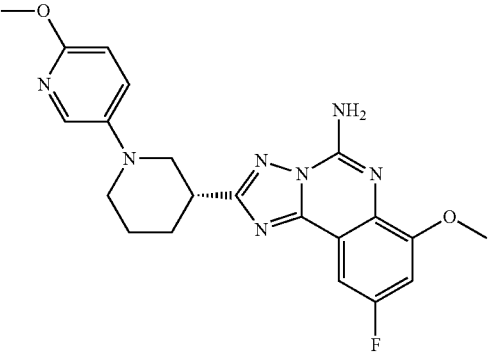<br>(R)-9-fluoro-7-methoxy-2-(1-(6-methoxypyridin-3-yl)piperidin-3-yl)-[1,2,4]triazolo[1,5-c]quinazolin-5-amine | 424 |
| 35 | 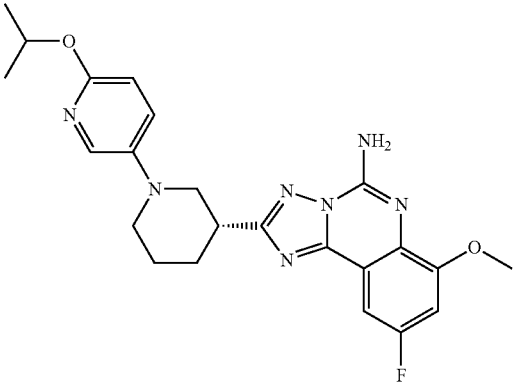 [SMILES: COc1cc(F)cc2c1nc(N)n1nc([C@@H]3CCCN(c4ccc(OC(C)C)nc4)C3)nc21]<br>(R)-9-fluoro-2-(1-(6-isopropoxypyridin-3-yl)piperidin-3-yl)-7-methoxy-[1,2,4]triazolo[1,5-c]quinazolin-5-amine | 452 |
| 36 | 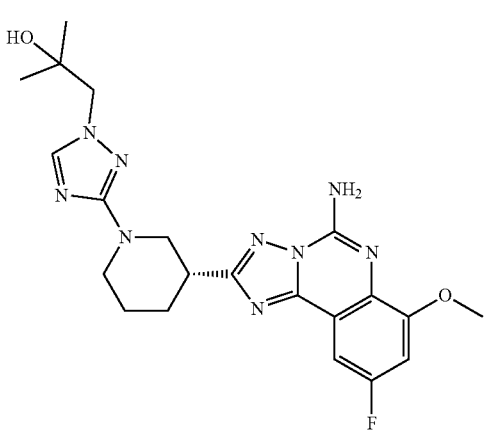 [SMILES: COc1cc(F)cc2c1nc(N)n1nc([C@@H]3CCCN(c4ncn(CC(C)(C)O)n4)C3)nc21]<br>(R)-1-(3-(3-(5-amino-9-fluoro-7-methoxy-[1,2,4]triazolo[1,5-c]quinazolin-2-yl)piperidin-1-yl)-1H-1,2,4-triazol-1-yl)-2-methylpropan-2-ol | 456 |

TABLE 15-continued

| Example | Structure Name | Observed m/z [M + H]+ |
|---|---|---|
| 37 | (R)-1-(3-(3-(5-amino-9-fluoro-7-methoxy-[1,2,4]triazolo[1,5-c]quinazolin-2-yl)piperidin-1-yl)-5-methyl-1H-1,2,4-triazol-1-yl)-2-methylpropan-2-ol | 470 |
| 38 | (R)-1-((4-(3-(5-amino-9-fluoro-8-methoxy-[1,2,4]triazolo[1,5-c]quinazolin-2-yl)pyrrolidin-1-yl)-1H-pyrazol-1-yl)methyl)cyclobutan-1-ol | 453 |
| 39 | rac-1-(4-(3-(5-amino-9-fluoro-7-methoxy-[1,2,4]triazolo[1,5-c]quinazolin-2-yl)azepan-1-yl)-1H-pyrazol-1-yl)-2-methylpropan-2-ol | 469 |

Example 40: 1-((4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)methyl)cyclobutan-1-ol Step 1: N-(2,4-dimethoxybenzyl)-9-fluoro-8-methoxy-2-((3R,6S or 3S,6R)-6-methyl-1-(1-(((RS)-tetrahydro-2H-pyran-2-yl)oxy)cyclobutyl)methyl)-1H-pyrazol-4-yl)piperidin-3-yl)-[1,2,4]triazolo[1,5-c]quinazolin-5-amine

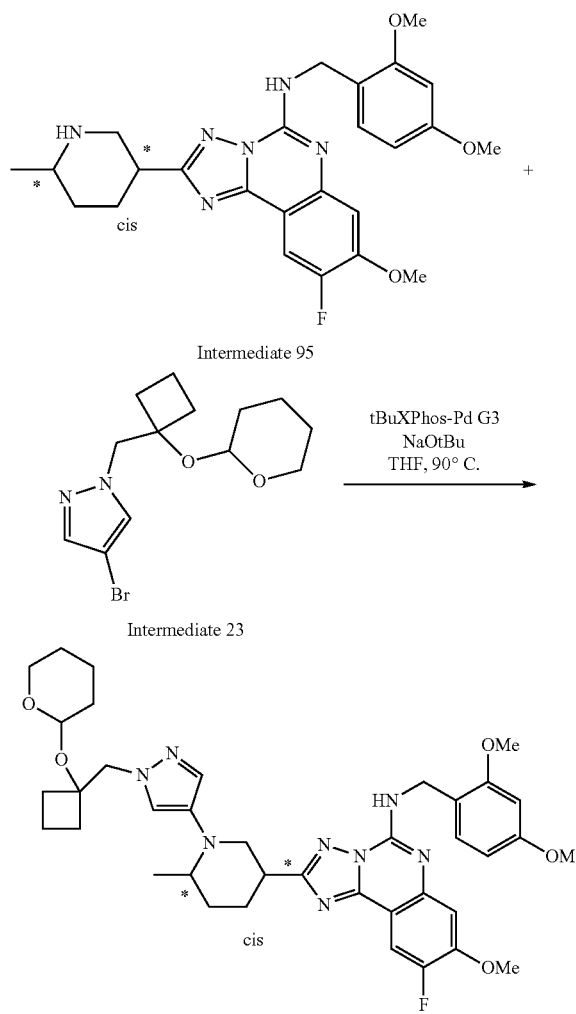

To a reaction vial containing of solution of N-(2,4-dimethoxybenzyl)-9-fluoro-8-methoxy-2-((3R,6S or 3S,6R)-6-methylpiperidin-3-yl)-[1,2,4]triazolo[1,5-c]quinazolin-5-amine (Intermediate 95) (600 mg, 1.25 mmol) in THF (12 ml) was added rac-4-bromo-1-((1-((tetrahydro-2H-pyran-2-yl)oxy)cyclobutyl)methyl)-1H-pyrazole (Intermediate 23) (590 mg, 1.87 mmol) followed by tBuXPhos-Pd G3 (298 mg, 0.375 mmol) and sodium tert-butoxide (420 mg, 4.37 mmol). Nitrogen was bubbled through the mixture for 10 min. The mixture was stirred and heated at 90° C. for 4 h. The mixture was cooled to room temperature. To the mixture was added additional tBuXPhos-Pd G3 (149 mg, 0.188 mmol) followed by sodium tert-butoxide (210 mg, 2.19 mmol). Nitrogen was bubbled through the mixture for an additional 10 min. The mixture was stirred and heated at 90° C. for 18 h. The mixture was cooled to room temperature, and then the solvents were evaporated. The residue was partitioned between DCM and water. The organic layer was washed with brine, dried over anhydrous MgSO$_4$, and the solids were removed by filtration. The filtrate was concentrated. The resulting residue was purified by silica gel chromatography with 0-40% EtOAc:EtOH (3:1) in hexane as eluent. The obtained residue was further purified by preparative silica gel TLC with 4% MeOH in DCM as eluent to afford N-(2,4-dimethoxybenzyl)-9-fluoro-8-methoxy-2-((3R,6S or 3S,6R)-6-methyl-1-(1-((1-(((RS)-tetrahydro-2H-pyran-2-yl)oxy)cyclobutyl)methyl)-1H-pyrazol-4-yl)piperidin-3-yl)-[1,2,4]triazolo[1,5-c]quinazolin-5-amine. LCMS (C$_{38}$H$_{47}$FN$_8$O$_5$) (ES, m/z): 715 [M+H]$^+$.

Step 2: 1-((4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)methyl)cyclobutan-1-ol

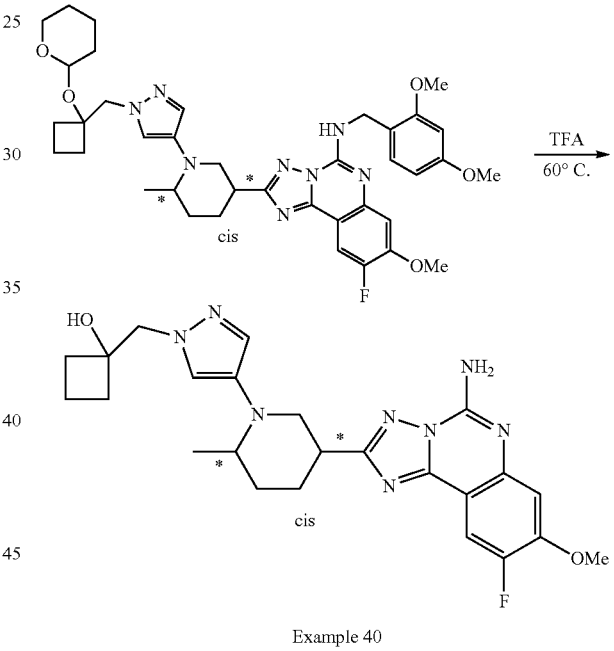

Example 40

To a reaction vial was added N-(2,4-dimethoxybenzyl)-9-fluoro-8-methoxy-2-((3R,6S or 3S,6R)-6-methyl-1-(1-((1-(((RS)-tetrahydro-2H-pyran-2-yl)oxy)cyclobutyl)methyl)-1H-pyrazol-4-yl)piperidin-3-yl)-[1,2,4]triazolo[1,5-c]quinazolin-5-amine (1.40 g, 2.22 mmol) and TFA (1.65 mL, 22.2 mmol). The mixture was stirred and heated at 60° C. for 1 h. The mixture was cooled to room temperature, and then the solvents were evaporated. The residue was purified by silica gel chromatography with 6% (7 M ammonia solution in MeOH) in DCM as eluent to afford 1-((4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)methyl)cyclobutan-1-ol (Example 40). LCMS (C$_{24}$H$_{29}$FN$_8$O$_2$) (ES, m/z): 481 [M+H]$^+$. $^1$H NMR (500 MHz, Methanol-d$_4$) δ 7.87 (d, J=10.9 Hz, 1H), 7.35 (s, 1H), 7.27 (s, 1H), 7.15 (d, J=7.6 Hz, 1H), 4.14 (s, 2H), 3.99 (s, 3H), 3.73 (d, J=4.9 Hz, 1H), 3.47 (d, J=9.2 Hz, 1H), 3.36-3.20 (m, 3H), 2.11 (d, J=7.9 Hz, 3H), 2.02 (p, J=10.7, 9.6 Hz, 2H), 1.89-1.69 (m, 2H), 1.55 (dq, J=19.0, 9.6 Hz, 1H), 1.37-1.20 (m, 2H), 1.12 (d, J=6.6 Hz, 3H), 0.96-0.82 (m, 2H).

The example compounds of the invention in the following Table 16 were prepared in a manner similar to that described for the preparation of Example 40 from the appropriate starting aryl halide and Intermediate 95.

TABLE 16

| Example | Structure Name | Observed m/z [M + H]+ |
|---|---|---|
| 41 | 1-(4-((2S,5R or 2R,5S)-5-(5-amino-9-fluoro-8-methoxy-[1,2,4]triazolo[1,5-c]quinazolin-2-yl)-2-methylpiperidin-1-yl)-5-methyl-1H-pyrazol-1-yl)-2-methylpropan-2-ol | 483 |
| 42 | 1-(4-((2S,5R or 2R,5S)-5-(5-amino-9-fluoro-8-methoxy-[1,2,4]triazolo[1,5-c]quinazolin-2-yl)-2-methylpiperidin-1-yl)-3-methyl-1H-pyrazol-1-yl)-2-methylpropan-2-ol | 483 |
| 43 | 3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2,3-dimethylbutan-2-ol | 497 |

TABLE 16-continued

| Example | Structure<br>Name | Observed m/z<br>[M + H]⁺ |
|---|---|---|
| 44 | 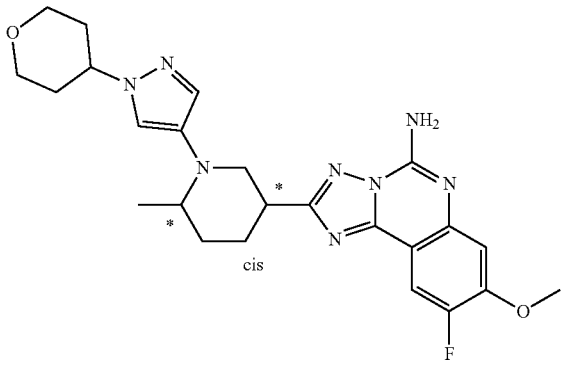 [SMILES: COc1cc2nc(N)n3nc(C4CCC(C)N(c5cnn(C6CCOCC6)c5)C4)nc3c2cc1F]<br>9-fluoro-8-methoxy-2-((3R,6S or 3S,6R)-6-methyl-1-(1-(tetrahydro-2H-pyran-4-yl)-1H-pyrazol-4-yl)piperidin-3-yl)-[1,2,4]triazolo[1,5-c]quinazolin-5-amine | 481 |
| 45 | 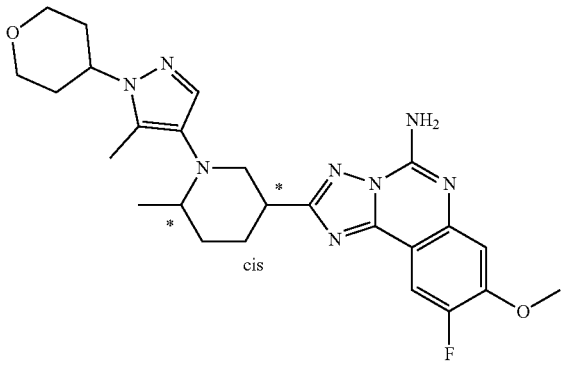 [SMILES: COc1cc2nc(N)n3nc(C4CCC(C)N(c5cnn(C6CCOCC6)c5C)C4)nc3c2cc1F]<br>9-fluoro-8-methoxy-2-((3R,6S or 3S,6R)-6-methyl-1-(5-methyl-1-(tetrahydro-2H-pyran-4-yl)-1H-pyrazol-4-yl)piperidin-3-yl)-[1,2,4]triazolo[1,5-c]quinazolin-5-amine | 495 |
| 46 | 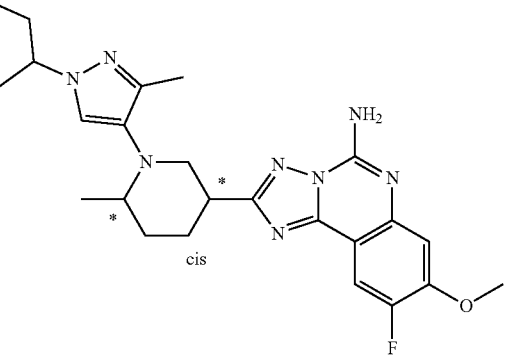<br>9-fluoro-8-methoxy-2-((3R,6S or 3S,6R)-6-methyl-1-(3-methyl-1-(tetrahydro-2H-pyran-4-yl)-1H-pyrazol-4-yl)piperidin-3-yl)-[1,2,4]triazolo[1,5-c]quinazolin-5-amine | 495 |

TABLE 16-continued

| Example | Structure Name | Observed m/z [M + H]+ |
|---|---|---|
| 47 | 9-fluoro-2-((3R,6S or 3S,6R)-1-(1-((3-(fluoromethyl)oxetan-3-yl)methyl)-1H-pyrazol-4-yl)-6-methylpiperidin-3-yl)-8-methoxy-[1,2,4]triazolo[1,5-c]quinazolin-5-amine | 499 |

Example 48 and Example 49: (R or S)-3-(4-((2S, 5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylbutan-2-ol and (S or R)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylbutan-2-ol Step 1: (R or S)-3-(4-((2S,5R or 2R,5S)-5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)-2-methylbutan-2-ol and (S or R)-3-(4-((2S,5R or 2R,5S)-5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)-2-methylbutan-2-ol

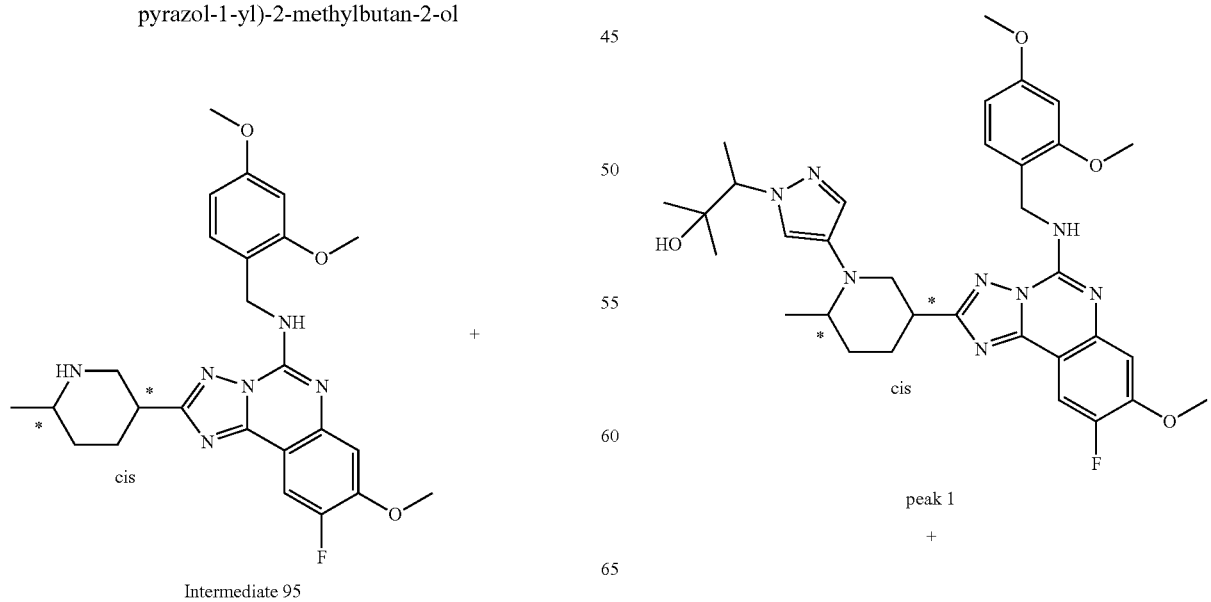

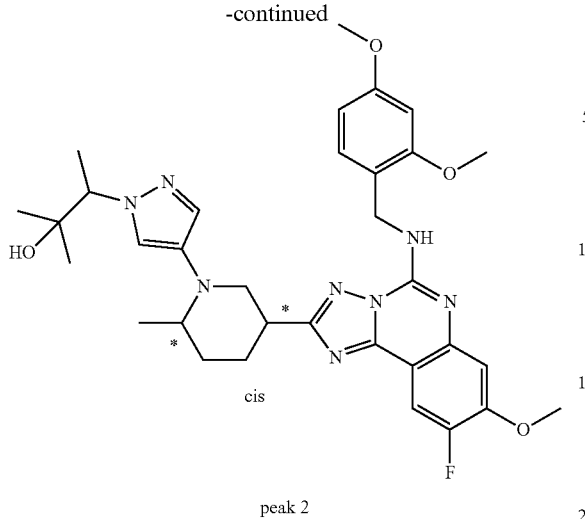

peak 2

Step 1 of the synthesis of Example 48 and Example 49 was conducted with Intermediate 95 and Intermediate 1 in a manner similar to that described in step 1 of the synthesis of Example 40. The resulting diastereomeric mixture was purified by SFC (Chiral Technologies AD-H 21×250 mm column with 55% (IPA+0.2% DIPA) as co-solvent), to afford peak 1 and peak 2 corresponding to (R or S)-3-(4-((2S,5R or 2R,5S)-5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)-2-methylbutan-2-ol and (S or R)-3-(4-((2S,5R or 2R,5S)-5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)-2-methylbutan-2-ol. For peak 1, LCMS ($C_{33}H_{41}FN_8O_4$) (ES, m/z): 633 [M+H]$^+$. For peak 2, LCMS ($C_{33}H_{41}FN_8O_4$) (ES, m/z): 633 [M+H]$^+$.

Step 2: (R or S)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylbutan-2-ol and (S or R)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylbutan-2-ol

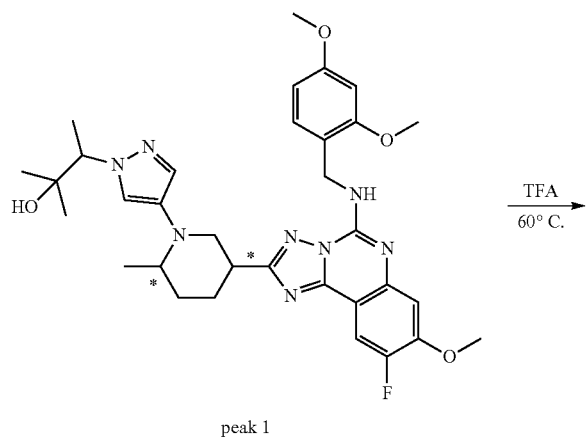

peak 1

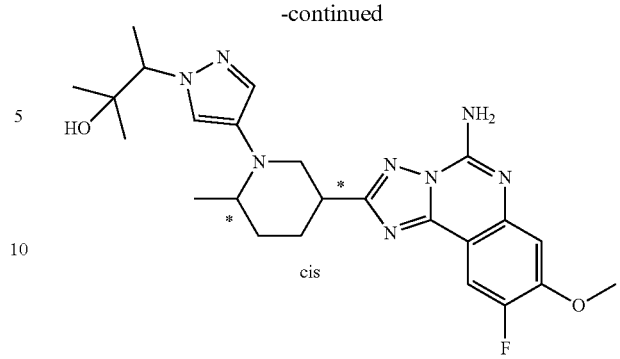

Example 48

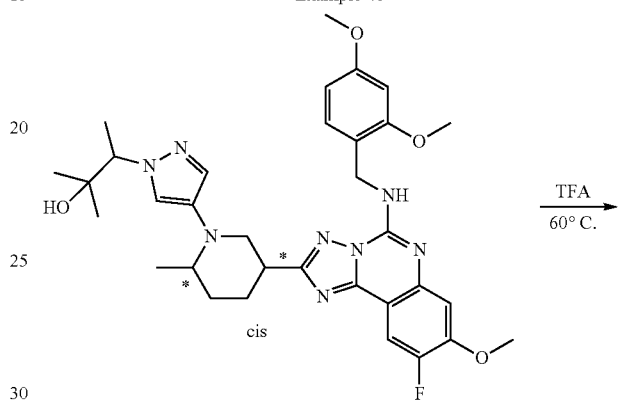

peak 2

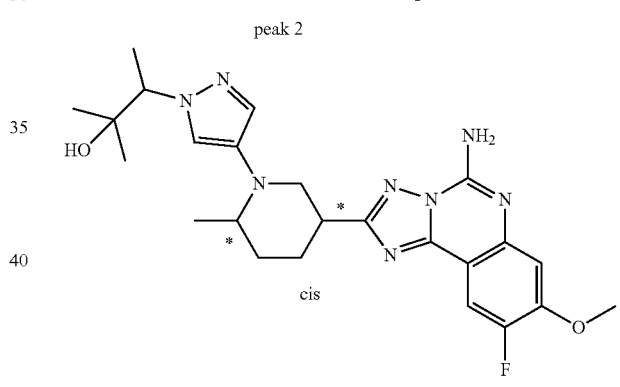

Example 49

Step 2 of the synthesis of Example 48 and Example 49 was conducted in a manner similar to that described in step 2 of Example 40, where peak 1 was converted to (R or S)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylbutan-2-ol (Example 48) and peak 2 was converted to (S or R)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylbutan-2-ol (Example 49).

For Example 48: LCMS ($C_{24}H_{31}FN_8O_2$) (ES, m/z): 483 [M+H]$^+$. $^1$H NMR (400 MHz, Chloroform-d) δ 7.99 (d, J=10.7 Hz, 1H), 7.26 (s, 1H), 7.15 (d, J=7.6 Hz, 1H), 7.01 (s, 1H), 5.74 (s, 2H), 4.14 (s, 1H), 4.02 (m, 1H), 4.00 (s, 3H), 3.74 (m, 1H), 3.49 (s, 1H), 3.45 (dd, J=11.6, 3.8 Hz, 1H), 3.32 (dd, J=11.3, 4.0 Hz, 1H), 3.20 (t, J=11.3 Hz, 1H), 2.18-2.00 (m, 3H), 1.78 (d, J=9.9 Hz, 1H), 1.52 (d, J=6.9 Hz, 3H), 1.14 (s, 3H), 1.11 (d, J=6.7 Hz, 2H), 1.01 (s, 3H).

For Example 49: LCMS ($C_{24}H_{31}FN_8O_2$) (ES, m/z): 483 [M+H]$^+$. $^1$H NMR (400 MHz, Chloroform-d) δ 7.99 (d, J=10.8 Hz, 1H), 7.26 (s, 1H), 7.15 (d, J=7.6 Hz, 1H), 7.01 (s, 1H), 5.78 (s, 2H), 4.18 (s, 1H), 4.03 (m, 1H), 4.00 (s, 4H), 3.74 (m, 1H), 3.49 (s, 1H), 3.44 (dd, J=11.6, 3.9 Hz, 1H), 3.33 (dd, J=11.0, 4.2 Hz, 1H), 3.21 (t, J=11.3 Hz, 1H), 2.18-2.00 (m, 3H), 1.78 (d, J=9.7 Hz, 1H), 1.52 (d, J=6.9 Hz, 3H), 1.14 (s, 3H), 1.11 (m, J=6.9 Hz, 3H), 1.02 (s, 3H).

Example 50 and Example 51: 1-((4-((2R,5S or 2S,5R)-5-(5-amino-9-fluoro-8-methoxy-[1,2,4]triazolo[1,5-c]quinazolin-2-yl)-2-methylpiperidin-1-yl)-3-methyl-1H-pyrazol-1-yl)methyl)cyclobutan-1-ol and 1-((4-((2R,5S or 2S,5R)-5-(5-amino-9-fluoro-8-methoxy-[1,2,4]triazolo[1,5-c]quinazolin-2-yl)-2-methylpiperidin-1-yl)-5-methyl-1H-pyrazol-1-yl)methyl)cyclobutan-1-ol Step 1: N-(2,4-dimethoxybenzyl)-9-fluoro-8-methoxy-2-((3S,6R or 3R,6S)-6-methyl-1-(3-methyl-1-((1-(((RS)-tetrahydro-2H-pyran-2-yl)oxy)cyclobutyl)methyl)-1H-pyrazol-4-yl)piperidin-3-yl)-[1,2,4]triazolo[1,5-c]quinazolin-5-amine and N-(2,4-dimethoxybenzyl)-9-fluoro-8-methoxy-2-((3S,6R, or 3R,6S)-6-methyl-1-(5-methyl-1-((1-(((RS)-tetrahydro-2H-pyran-2-yl)oxy)cyclobutyl)methyl)-1H-pyrazol-4-yl)piperidin-3-yl)-[1,2,4]triazolo[1,5-c]quinazolin-5-amine

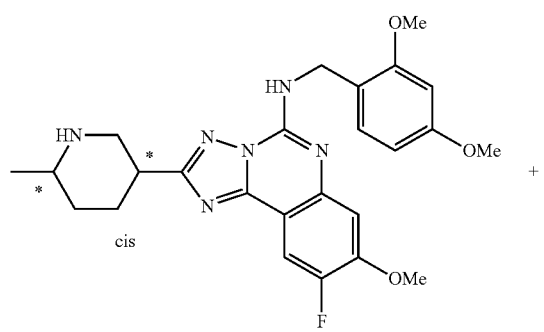

Intermediate 96

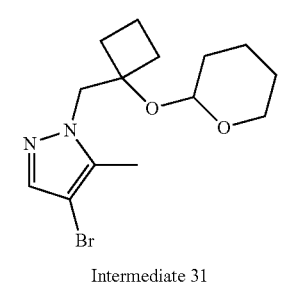

Intermediate 31

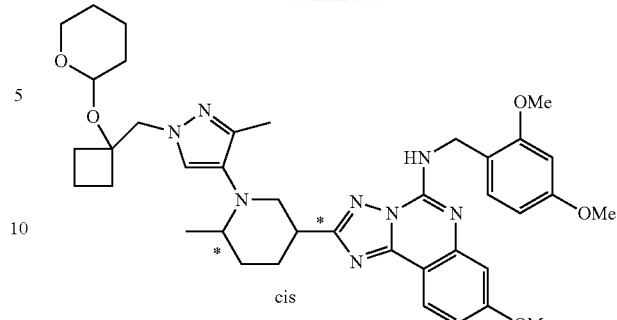

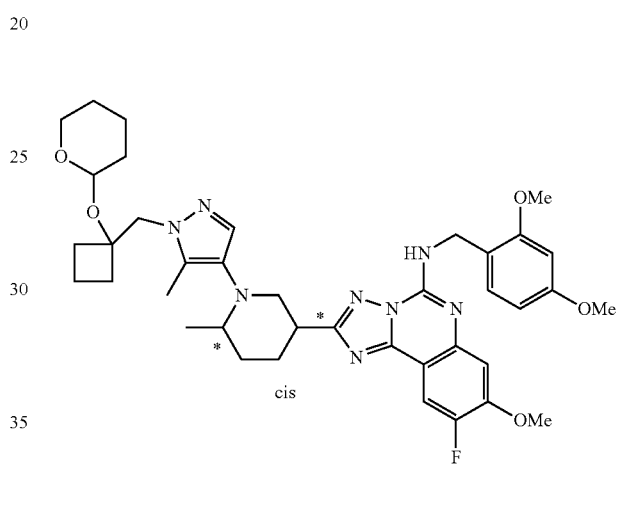

To a reaction vial was added N-(2,4-dimethoxybenzyl)-9-fluoro-8-methoxy-2-((3S,6R, or 3R,6S)-6-methylpiperidin-3-yl)-[1,2,4]triazolo[1,5-c]quinazolin-5-amine (Intermediate 96) (240 mg, 0.499 mmol, tBuXPhos-Pd G3 (119 mg, 0.150 mmol), rac-4-bromo-3-methyl-1-((1-((tetrahydro-2H-pyran-2-yl)oxy)cyclobutyl)methyl)-1H-pyrazole (Intermediate 31) (329 mg, 0.999 mmol), sodium tert-butoxide (288 mg, 3.00 mmol) and THF (5 mL). The mixture was sparged with nitrogen for 5 min. The mixture was stirred and heated at 100° C. for 19 h. The solvents were evaporated and the residue was purified by preparative silica gel TLC with 4% (7 M ammonia in MeOH) in DCM as eluent to afford a mixture of N-(2,4-dimethoxybenzyl)-9-fluoro-8-methoxy-2-((3S,6R or 3R,6S)-6-methyl-1-(3-methyl-1-((1-(((RS)-tetrahydro-2H-pyran-2-yl)oxy)cyclobutyl)methyl)-1H-pyrazol-4-yl)piperidin-3-yl)-[1,2,4]triazolo[1,5-c]quinazolin-5-amine and N-(2,4-dimethoxybenzyl)-9-fluoro-8-methoxy-2-((3S,6R or 3R,6S)-6-methyl-1-(5-methyl-1-((1-(((RS)-tetrahydro-2H-pyran-2-yl)oxy)cyclobutyl)methyl)-1H-pyrazol-4-yl)piperidin-3-yl)-[1,2,4]triazolo[1,5-c]quinazolin-5-amine.

Step 2: 1-((4-((2R,5S or 2S,5R)-5-(5-amino-9-fluoro-8-methoxy-[1,2,4]triazolo[1,5-c]quinazolin-2-yl)-2-methylpiperidin-1-yl)-3-methyl-1H-pyrazol-1-yl)methyl)cyclobutan-1-ol and 1-((4-((2R,5S or 2S,5R)-5-(5-amino-9-fluoro-8-methoxy-[1,2,4]triazolo[1,5-c]quinazolin-2-yl)-2-methylpiperidin-1-yl)-5-methyl-1H-pyrazol-1-yl)methyl)cyclobutan-1-ol

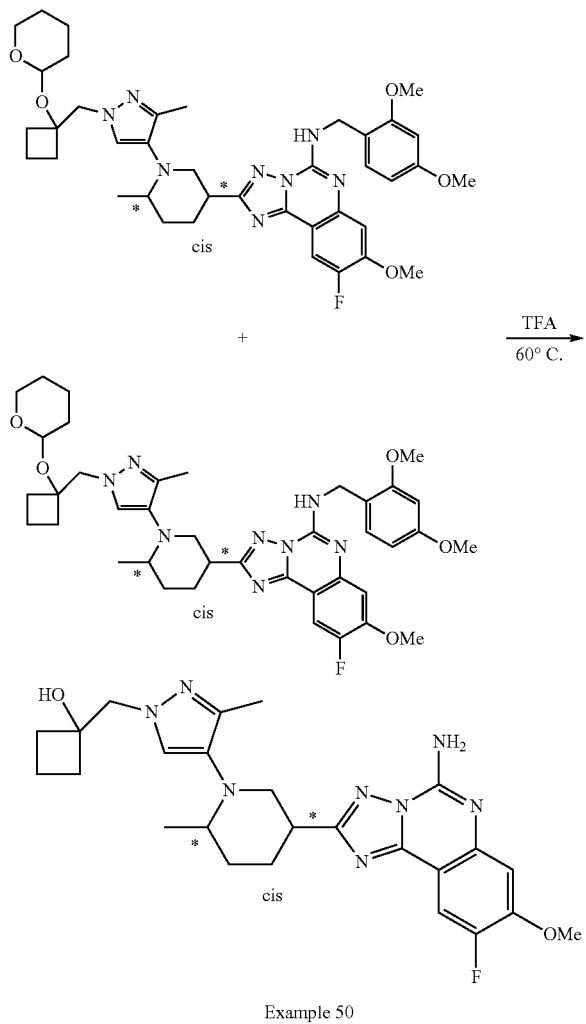

Example 50

Example 51

To the mixture of N-(2,4-dimethoxybenzyl)-9-fluoro-8-methoxy-2-((3S,6R or 3R,6S)-6-methyl-1-(3-methyl-1-((1-(((RS)-tetrahydro-2H-pyran-2-yl)oxy)cyclobutyl)methyl)-1H-pyrazol-4-yl)piperidin-3-yl)-[1,2,4]triazolo[1,5-c]quinazolin-5-amine and N-(2,4-dimethoxybenzyl)-9-fluoro-8-methoxy-2-((3S,6R or 3R,6S)-6-methyl-1-(5-methyl-1-((1-(((RS)-tetrahydro-2H-pyran-2-yl)oxy)cyclobutyl)methyl)-1H-pyrazol-4-yl)piperidin-3-yl)-[1,2,4]triazolo[1,5-c]quinazolin-5-amine (12.0 mg, 0.0186 mmol) was added TFA (2 mL). The mixture was stirred and heated at 60° C. for 1 h. The mixture was cooled to room temperature. The mixture was concentrated and the residue was purified by preparative silica gel TLC with 4% (7 M ammonia in MeOH) in DCM as eluent followed by reversed-phase HPLC (Waters SunFire C18 OBD Prep Column, 19 mm×100 mm MeCN/water w/0.1% TFA modifier as eluent) to afford 1-((4-((2R,5S or 2S,5R)-5-(5-amino-9-fluoro-8-methoxy-[1,2,4]triazolo[1,5-c]quinazolin-2-yl)-2-methylpiperidin-1-yl)-3-methyl-1H-pyrazol-1-yl)methyl)cyclobutan-1-ol (Example 50) and 1-((4-((2R,5S or 2S,5R)-5-(5-amino-9-fluoro-8-methoxy-[1,2,4]triazolo[1,5-c]quinazolin-2-yl)-2-methylpiperidin-1-yl)-5-methyl-1H-pyrazol-1-yl)methyl)cyclobutan-1-ol (Example 51).

For Example 50: LCMS ($C_{25}H_{31}FN_8O_2$) (ES, m/z): 495 [M+H]$^+$. $^1$H NMR (500 MHz, Methanol-$d_4$) δ 8.02 (s, 1H), 7.95 (d, J=10.8 Hz, 1H), 7.26 (d, J=7.7 Hz, 1H), 4.22 (s, 2H), 4.18 (d, J=12.9 Hz, 1H), 4.03 (s, 3H), 3.91 (s, 3H), 3.74 (s, 1H), 3.57-3.43 (m, 1H), 2.46 (s, 3H), 2.36-2.26 (m, 1H), 2.22-2.12 (m, 3H), 2.04 (q, J=9.7 Hz, 3H), 1.84-1.73 (m, 1H), 1.68-1.58 (m, 1H), 1.27 (d, J=6.5 Hz, 3H).

For Example 51: LCMS ($C_{25}H_{31}FN_8O_2$) (ES, m/z): 495 [M+H]$^+$. $^1$H NMR (500 MHz, Methanol-$d_4$) δ 7.98-7.91 (m, 1H), 7.82 (s, 1H), 7.26 (d, J=7.7 Hz, 1H), 4.27 (s, 2H), 4.03 (s, 3H), 3.96 (d, J=11.8 Hz, 2H), 3.76 (d, J=20.2 Hz, 1H), 2.61 (s, 2H), 2.45 (d, J=15.4 Hz, 2H), 2.40-2.29 (m, 2H), 2.26 (s, 1H), 2.15 (d, J=10.4 Hz, 3H), 2.11-1.97 (m, 3H), 1.89-1.74 (m, 1H), 1.75-1.58 (m, 1H), 1.28 (d, J=6.6 Hz, 3H).

The example compounds of the invention in the following Table 17 were prepared in a manner similar to that described for Example 50 and Example 51 from the appropriate starting aryl halide and Intermediate 96.

TABLE 17

| Example | Structure Name | Observed m/z [M + H]$^+$ |
|---|---|---|
| 52 | ![structure] 1-(4-((2R,5S, or 2S,5R)-5-(5-amino-9-fluoro-8-methoxy-[1,2,4]triazolo[1,5-c]quinazolin-2-yl)-2-methylpiperidin-1-yl)-5-methyl-1H-pyrazol-1-yl)-2-methylpropan-2-ol | 483 |

TABLE 17-continued

| Example | Structure Name | Observed m/z [M + H]⁺ |
|---|---|---|
| 53 | 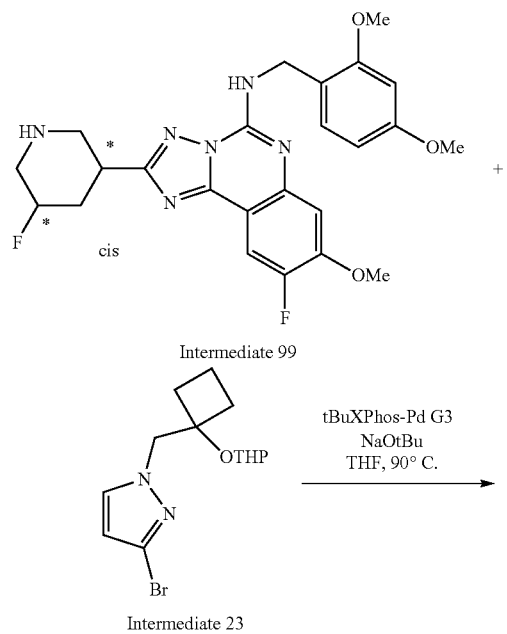<br>1-(4-((2R,5S, or 2S,5R)-5-(5-amino-9-fluoro-8-methoxy-[1,2,4]triazolo[1,5-c]quinazolin-2-yl)-2-methylpiperidin-1-yl)-3-methyl-1H-pyrazol-1-yl)-2-methylpropan-2-ol | 483 |

Example 54: 1-((4-((3R,5S or 3S,5R)-3-(5-amino-9-fluoro-8-methoxy-[1,2,4]triazolo[1,5-c]quinazolin-2-yl)-5-fluoropiperidin-1-yl)-1H-pyrazol-1-yl)methyl)cyclobutan-1-ol Step 1: N-(2,4-dimethoxybenzyl)-9-fluoro-2-((3R,5S or 3S,5R)-5-fluoro-1-(1-((1-((tetrahydro-2H-pyran-2-yl)oxy)cyclobutyl)methyl)-1H-pyrazol-4-yl)piperidin-3-yl)-8-methoxy-[1,2,4]triazolo[1,5-c]quinazolin-5-amine

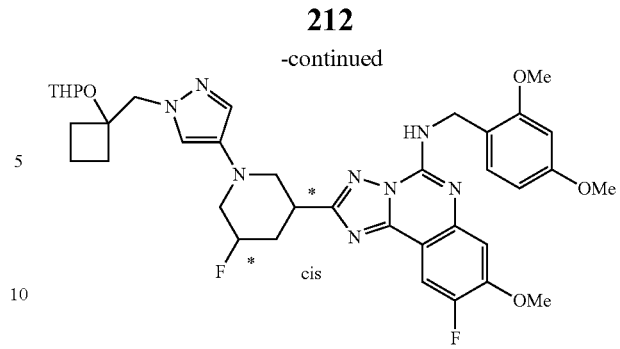

To a reaction vial containing of solution of N-(2,4-dimethoxybenzyl)-9-fluoro-2-((3R,5S or 3S,5R)-5-fluoropiperidin-3-yl)-8-methoxy-[1,2,4]triazolo[1,5-c]quinazolin-5-amine (Intermediate 99) (80.0 mg, 0.165 mmol) in THF (1.5 mL) was added 4-bromo-1-((1-(((tetrahydro-2H-pyran-2-yl)oxy)cyclobutyl)methyl)-1H-pyrazole (Intermediate 23) (83.0 mg, 0.260 mmol) followed by tBuXPhos-Pd G3 (39.3 mg, 0.0500 mmol) and sodium tert-butoxide (47.6 mg, 0.495 mmol). The mixture was flushed with nitrogen for 10 min. The mixture was stirred and heated at 90° C. for 2 h. The solvents were evaporated. The resulting residue was purified by silica gel chromatography with 0-40% EtOAc:EtOH (3:1) in hexanes as eluent to afford N-(2,4-dimethoxybenzyl)-9-fluoro-2-((3R,5S or 3S,5R)-5-fluoro-1-(1-((1-((tetrahydro-2H-pyran-2-yl)oxy)cyclobutyl)methyl)-1H-pyrazol-4-yl)piperidin-3-yl)-8-methoxy-[1,2,4]triazolo[1,5-c]quinazolin-5-amine. LCMS ($C_{37}H_{44}F_2N_8O_5$) (ES, m/z): 719 [M+H]⁺.

Step 2: 1-((4-((3R,5S or 3S,5R)-3-(5-amino-9-fluoro-8-methoxy-[1,2,4]triazolo[1,5-c]quinazolin-2-yl)-5-fluoropiperidin-1-yl)-1H-pyrazol-1-yl)methyl)cyclobutan-1-ol

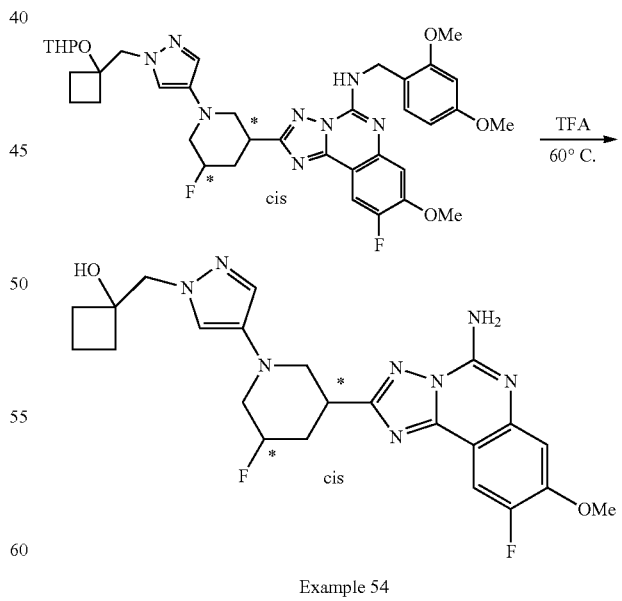

A mixture of N-(2,4-dimethoxybenzyl)-9-fluoro-2-((3R,5S or 3S,5R)-5-fluoro-1-(1-((1-(((tetrahydro-2H-pyran-2-yl)oxy)cyclobutyl)methyl)-1H-pyrazol-4-yl)piperidin-3-yl)-8-methoxy-[1,2,4]triazolo[1,5-c]quinazolin-5-amine (105 mg, 0.146 mmol) in TFA (1.2 mL) was stirred and heated at 60° C. for 1 h. The mixture was concentrated. The residue was purified by preparative silica gel TLC with 5% (7 M ammonia in MeOH) in DCM as eluent to afford 1-((4-((3R,5S or 3S,5R)-3-(5-amino-9-fluoro-8-methoxy-[1,2,4]triazolo[1,5-c]quinazolin-2-yl)-5-fluoropiperidin-1-yl)-1H-pyrazol-1-yl)methyl)cyclobutan-1-ol. LCMS ($C_{23}H_{26}F_2N_8O_2$) (ES, m/z): 485 [M+H]$^+$. $^1$H NMR (400 MHz, Chloroform-d) δ 7.96 (d, J=10.7 Hz, 1H), 7.26 (s, 1H), 7.15 (t, J=3.8 Hz, 2H), 5.91 (s, 2H), 4.90 (dtt, J=48.1, 9.9, 4.7 Hz, 1H), 4.13 (s, 2H), 4.00 (s, 3H), 3.74-3.64 (m, 2H), 3.42 (d, J=12.6 Hz, 1H), 2.86 (t, J=11.4 Hz, 1H), 2.71 (dq, J=10.3, 7.2, 5.2 Hz, 2H), 2.17-1.92 (m, 3H), 1.88-1.73 (m, 2H), 1.57 (dq, J=18.2, 9.1 Hz, 2H).

The example compounds of the invention in the following Table 18 were prepared in a manner similar to that described for the preparation of Example 54 from the appropriate starting aryl halide and Intermediate 99.

TABLE 18

| Example | Structure Name | Observed m/z [M + H]$^+$ |
|---|---|---|
| 55 | *[Structure]* 1-(4-((3R,5S or 3S,5R)-3-(5-amino-9-fluoro-8-methoxy-[1,2,4]triazolo[1,5-c]quinazolin-2-yl)-5-fluoropiperidin-1-yl)-1H-pyrazol-1-yl)-2-methylpropan-2-ol | 473 |
| 56 | *[Structure]* 9-fluoro-2-((3R,5S or 3S,5R)-5-fluoro-1-(1-(tetrahydro-2H-pyran-4-yl)-1H-pyrazol-4-yl)piperidin-3-yl)-8-methoxy-[1,2,4]triazolo[1,5-c]quinazolin-5-amine | 485 |

215

Example 57: 1-((4-((1R,5R or 1S,5S)-1-(5-amino-9-fluoro-8-methoxy-[1,2,4]triazolo[1,5-c]quinazolin-2-yl)-3-azabicyclo[3.1.0]hexan-3-yl)-1H-pyrazol-1-yl)methyl)cyclobutan-1-ol Step 1: N-(2,4-dimethoxybenzyl)-9-fluoro-8-methoxy-2-((1R,5R or 1S,5S)-3-(1-((1-((tetrahydro-2H-pyran-2-yl)oxy)cyclobutyl)methyl)-1H-pyrazol-4-yl)-3-azabicyclo[3.1.0]hexan-1-yl)-[1,2,4]triazolo[1,5-c]quinazolin-5-amine

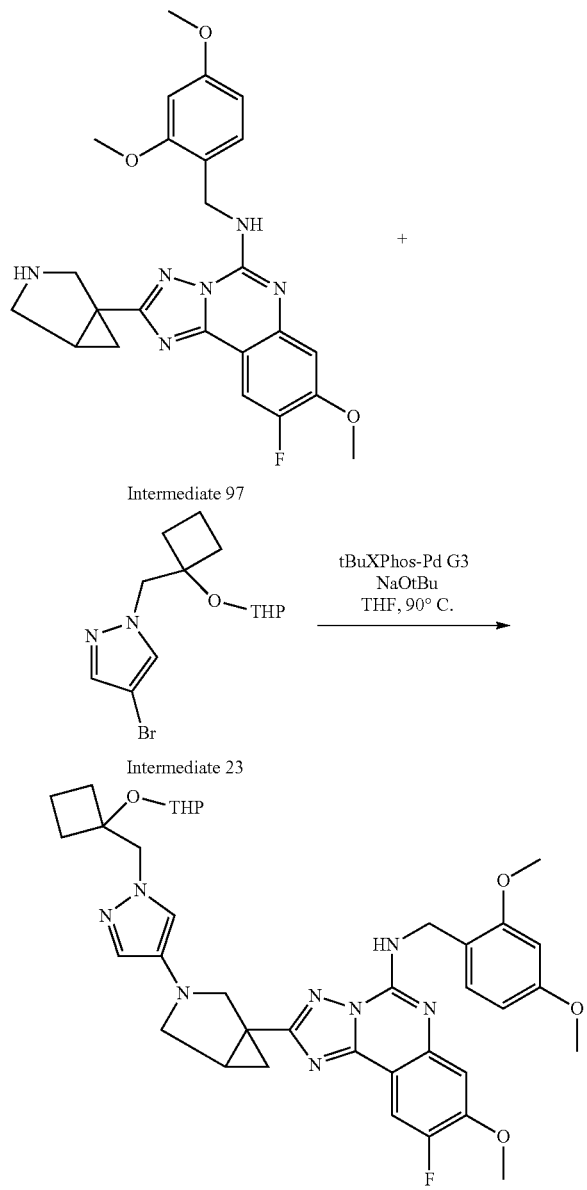

To a reaction vial containing of solution of 2-((1R,5R or 1S,5S)-3-azabicyclo[3.1.0]hexan-1-yl)-N-(2,4-dimethoxybenzyl)-9-fluoro-8-methoxy-[1,2,4]triazolo[1,5-c]quinazolin-5-amine (Intermediate 97) (60.0 mg, 0.129 mmol) in THF (1.5 mL) was added 4-bromo-1-((1-((tetrahydro-2H-pyran-2-yl)oxy)cyclobutyl)methyl)-1H-pyrazole (Intermediate 23) (61.1 mg, 0.194 mmol) followed by tBuXPhos-Pd G3 (30.8 mg, 0.039 mmol) and sodium tert-butoxide (43.4 mg, 0.452 mmol). Nitrogen was bubbled through the mix-

216 ture for 10 min. The mixture was stirred and heated at 90° C. for 18 h. The mixture was cooled to room temperature. The solvents were evaporated, and the resulting residue was purified by preparative silica gel TLC with 5% MeOH in DCM as eluent to afford N-(2,4-dimethoxybenzyl)-9-fluoro-8-methoxy-2-((1R,5R or 1S,5S)-3-(1-((1-((tetrahydro-2H-pyran-2-yl)oxy)cyclobutyl)methyl)-1H-pyrazol-4-yl)-3-azabicyclo[3.1.0]hexan-1-yl)-[1,2,4]triazolo[1,5-c]quinazolin-5-amine. LCMS ($C_{37}H_{43}FN_8O_5$) (ES, m/z): 699 [M+H]$^+$.

Step 2: 1-((4-((1R,5R or 1S,5S)-1-(5-amino-9-fluoro-8-methoxy-[1,2,4]triazolo[1,5-c]quinazolin-2-yl)-3-azabicyclo[3.1.0]hexan-3-yl)-1H-pyrazol-1-yl)methyl)cyclobutan-1-ol 2,2,2-trifluoroacetate

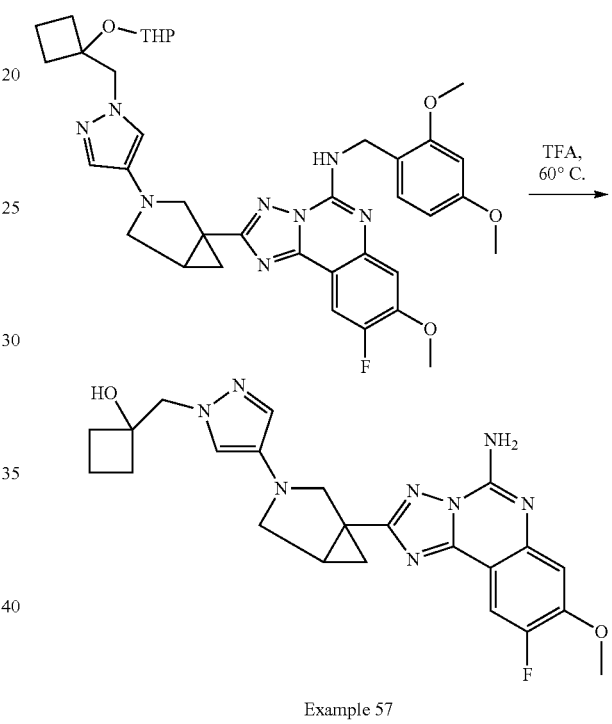

Example 57

A mixture of N-(2,4-dimethoxybenzyl)-9-fluoro-8-methoxy-2-((1R,5R or 1S,5S)-3-(1-((1-((tetrahydro-2H-pyran-2-yl)oxy)cyclobutyl)methyl)-1H-pyrazol-4-yl)-3-azabicyclo[3.1.0]hexan-1-yl)-[1,2,4]triazolo[1,5-c]quinazolin-5-amine (59 mg, 0.084 mmol) and TFA (1.0 mL) was stirred and heated at 60° C. for 1 h. The mixture was cooled to room temperature. The solvents were evaporated. The resulting residue was purified by preparative silica gel TLC with 8% (7 M ammonia in MeOH) in DCM as eluent. The obtained residue was further purified by preparative reversed-phase HPLC (Waters SunFire C18 OBD Prep Column, 19 mm×100 mm MeCN/H$_2$O with 0.1% TFA modifier as eluent) to afford 1-((4-((1R,5R or 1S,5S)-1-(5-amino-9-fluoro-8-methoxy-[1,2,4]triazolo[1,5-c]quinazolin-2-yl)-3-azabicyclo[3.1.0]hexan-3-yl)-1H-pyrazol-1-yl)methyl)cyclobutan-1-ol 2,2,2-trifluoroacetate). LCMS ($C_{23}H_{25}FN_8O_2$) (ES, m/z): 465 [M+H]$^+$. $^1$H NMR (400 MHz, Chloroform-d) δ 7.96 (d, J=10.0 Hz, 1H), 7.27 (s, 1H), 7.21 (s, 1H), 7.06 (s, 1H), 4.18 (s, 2H), 4.08 (s, 3H), 3.79 (d, J=8.6 Hz, 1H), 3.69 (d, J=8.7 Hz, 1H), 3.54 (d, J=8.6 Hz, 2H), 3.35 (s, 2H), 3.20 (dd, J=8.8, 3.8 Hz, 2H), 2.32 (s, 1H), 2.13-2.04 (m, 3H), 1.75 (d, J=3.8 Hz, 2H), 1.58 (d, J=4.9 Hz, 1H).

Example 58 in the following Table 19 was prepared in a manner similar to that described for the preparation of Example 57 from Intermediate 97 and the appropriate starting aryl halide.

TABLE 19

| Example | Structure Name | Observed m/z [M + H]+ |
|---|---|---|
| 58 | 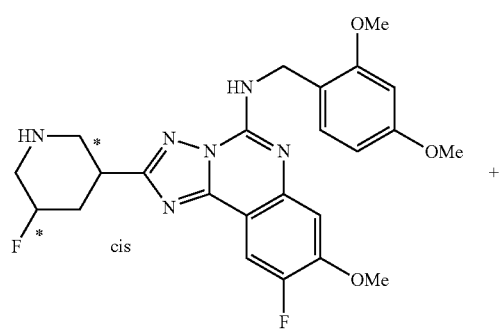<br>1-(4-((1R,5R or 1S,5S)-1-(5-amino-9-fluoro-8-methoxy-[1,2,4]triazolo[1,5-c]quinazolin-2-yl)-3-azabicyclo[3.1.0]hexan-3-yl)-1H-pyrazol-1-yl)-2-methylpropan-2-ol | 453 |

Example 59: 9-fluoro-2-((3S,5R or 3R,5S)-5-fluoro-1-(1-(tetrahydro-2H-pyran-4-yl)-1H-pyrazol-4-yl)piperidin-3-yl)-8-methoxy-[1,2,4]triazolo[1,5-c]quinazolin-5-amine

Step 1: N-(2,4-dimethoxybenzyl)-9-fluoro-2-((3S,5R or 3R,5S)-5-fluoro-1-(1-(tetrahydro-2H-pyran-4-yl)-1H-pyrazol-4-yl)piperidin-3-yl)-8-methoxy-[1,2,4]triazolo[1,5-c]quinazolin-5-amine

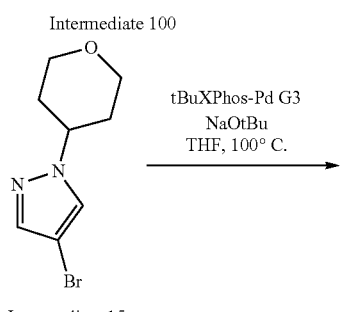

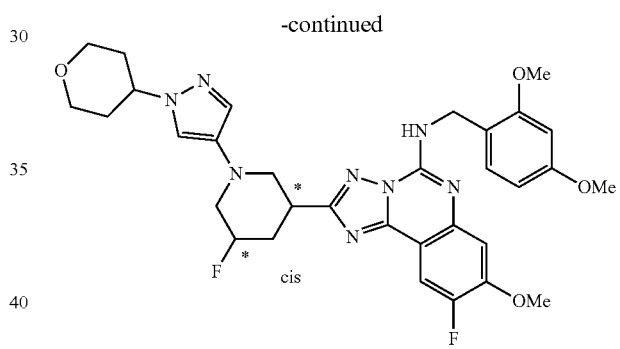

To a reaction vial was added N-(2,4-dimethoxybenzyl)-9-fluoro-2-((3S,5R or 3R,5S)-5-fluoropiperidin-3-yl)-8-methoxy-[1,2,4]triazolo[1,5-c]quinazolin-5-amine (Intermediate 100) (50.0 mg, 0.103 mmol), tBuXPhos-Pd G3 (24.6 mg, 0.0310 mmol), 4-bromo-1-(tetrahydro-2H-pyran-4-yl)-1H-pyrazole (Intermediate 15) (23.9 mg, 0.103 mmol), sodium tert-butoxide (59.5 mg, 0.619 mmol) and THF (1 mL). The mixture was flushed with nitrogen for 5 min. The mixture was stirred and heated at 100° C. for 4 h. The solvents were evaporated, and the resulting residue was purified by silica gel chromatography with 0-100% (30% MeOH in EtOAc) in hexanes, yielding N-(2,4-dimethoxybenzyl)-9-fluoro-2-((3S,5R or 3R,5S)-5-fluoro-1-(1-(tetrahydro-2H-pyran-4-yl)-1H-pyrazol-4-yl)piperidin-3-yl)-8-methoxy-[1,2,4]triazolo[1,5-c]quinazolin-5-amine.

Step 2: 9-fluoro-2-((3S,5R or 3R,5S)-5-fluoro-1-(1-(tetrahydro-2H-pyran-4-yl)-1H-pyrazol-4-yl)piperidin-3-yl)-8-methoxy-[1,2,4]triazolo[1,5-c]quinazolin-5-amine

Example 60 and Example 61: (R or S)-1-(4-(3-(5-amino-9-fluoro-8-methoxy-[1,2,4]triazolo[1,5-c]quinazolin-2-yl)azepan-1-yl)-1H-pyrazol-1-yl)-2-methylpropan-2-ol and (S or R)-1-(4-(3-(5-amino-9-fluoro-8-methoxy-[1,2,4]triazolo[1,5-c]quinazolin-2-yl)azepan-1-yl)-1H-pyrazol-1-yl)-2-methylpropan-2-ol

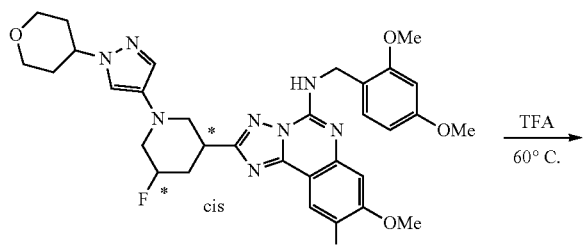

TFA
60° C.

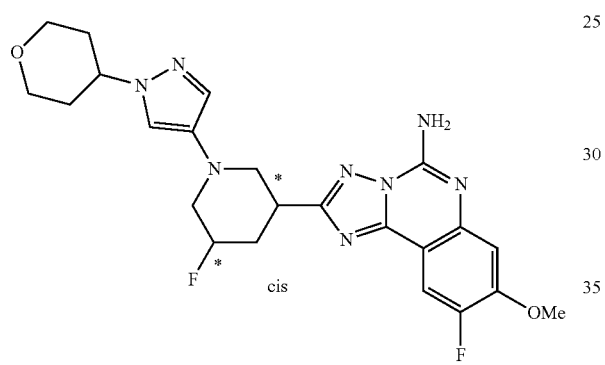

Intermediate 83

Example 59

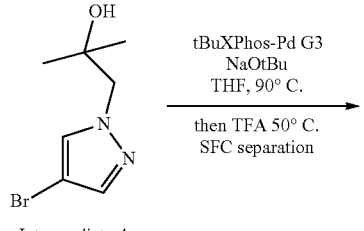

Intermediate 4 tBuXPhos-Pd G3
NaOtBu
THF, 90° C.

then TFA 50° C.
SFC separation

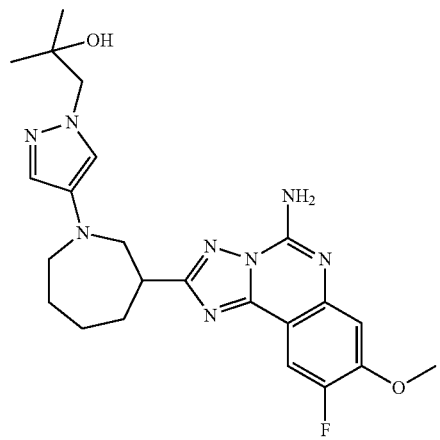

Example 60
+

To a reaction vial was added N-(2,4-dimethoxybenzyl)-9-fluoro-2-((3S,5R or 3R,5S)-5-fluoro-1-(1-(tetrahydro-2H-pyran-4-yl)-1H-pyrazol-4-yl)piperidin-3-yl)-8-methoxy-[1,2,4]triazolo[1,5-c]quinazolin-5-amine (85.0 mg, 0.130 mmol) was added TFA (2 mL). The mixture was stirred and heated at 60° C. for 1 h. The solvents were evaporated, and the residue was purified by preparative reversed-phase HPLC (Waters SunFire C18 OBD Prep Column, 19 mm×100 mm MeCN/H$_2$O with 0.1% TFA modifier as eluent), to afford 9-fluoro-2-((3S,5R or 3R,5S)-5-fluoro-1-(1-(tetrahydro-2H-pyran-4-yl)-1H-pyrazol-4-yl)piperidin-3-yl)-8-methoxy-[1,2,4]triazolo[1,5-c]quinazolin-5-amine. LCMS (C$_{23}$H$_{26}$F$_2$N$_8$O$_2$) (ES, m/z): 485 [M+H]$^+$. $^1$H NMR (500 MHz, Methanol-d$_4$) δ 7.93 (d, J=10.7 Hz, 1H), 7.51 (s, 1H), 7.38 (s, 1H), 7.23 (d, J=7.5 Hz, 1H), 4.95 (dt, J=10.3, 5.4 Hz, 1H), 4.32 (dq, J=11.0, 6.1, 5.6 Hz, 1H), 4.13-3.95 (m, 4H), 3.78 (d, J=11.1 Hz, 2H), 3.65-3.52 (m, 2H), 3.46 (t, J=11.2 Hz, 1H), 2.89 (t, J=11.4 Hz, 1H), 2.82-2.59 (m, 2H), 2.12-1.92 (m, 4H).

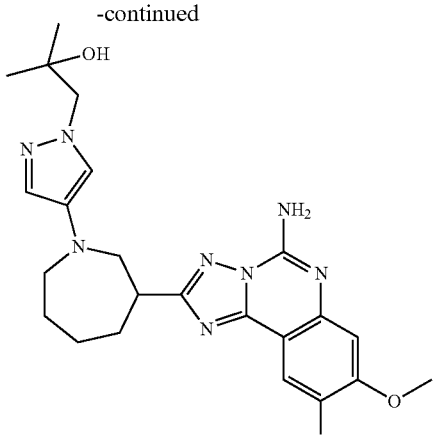

Example 61

A 5 mL microwave vial was charged with rac-2-(azepan-3-yl)-N-(2,4-dimethoxybenzyl)-9-fluoro-8-methoxy-[1,2,4]triazolo[1,5-c]quinazolin-5-amine (Intermediate 83) (100 mg, 0.208 mmol) and THF (1.3 mL). To the mixture was added 1-(4-bromo-1H-pyrazol-1-yl)-2-methylpropan-2-ol (Intermediate 4) (91.0 mg, 0.420 mmol), followed by tBuXPhos-Pd G3 (66.1 mg, 0.0830 mmol) and sodium tert-butoxide (80.0 mg, 0.832 mmol). Nitrogen was bubbled through the mixture for 10 min. The mixture was stirred and heated at 90° C. for 12 h. The mixture was cooled to room temperature, and then the solids were removed by filtration and washed with DCM. The solvents of the filtrate were evaporated. The resulting residue was dissolved in TFA (802 µL, 10.4 mmol) and heated at 50° C. for 3 h. The mixture was cooled to room temperature, and the solvents were evaporated. The resulting residue was purified by preparative reversed-phase HPLC (Waters SunFire C18 OBD Prep Column, 19 mm×100 mm MeCN/H$_2$O with 0.1% TFA modifier as eluent) to yield the racemic product. The racemic mixture was resolved by chiral SFC separation (Chiral Technologies OJ-H 21×250 mm column with 25% (isopropanol w/0.1% NH$_4$OH modifier) as co-solvent), to afford (R or S)-1-(4-(3-(5-amino-9-fluoro-8-methoxy-[1,2,4]triazolo[1,5-c]quinazolin-2-yl)azepan-1-yl)-1H-pyrazol-1-yl)-2-methylpropan-2-ol (Example 60, first eluting peak) and (S or R)-1-(4-(3-(5-amino-9-fluoro-8-methoxy-[1,2,4]triazolo[1,5-c]quinazolin-2-yl)azepan-1-yl)-1H-pyrazol-1-yl)-2-methylpropan-2-ol (Example 61, second eluting peak).

For Example 60: LCMS (C$_{23}$H$_{29}$FN$_8$O$_2$) (ES, m/z): 469 [M+H]$^+$. 1H NMR (499 MHz, DMSO-d6) δ 7.88 (d, J=11.0 Hz, 1H), 7.72 (d, J=26.0 Hz, 2H), 7.18 (d, J=7.9 Hz, 1H), 7.12 (s, 1H), 7.07 (s, 1H), 4.63 (s, 1H), 3.97 (s, 3H), 3.87 (s, 2H), 3.75 (dd, J=14.3, 3.9 Hz, 1H), 3.53 (dd, J=14.3, 10.0 Hz, 1H), 3.45 (dq, J=9.7, 5.0, 4.6 Hz, 1H), 3.37 (dd, J=14.0, 6.1 Hz, 1H), 3.23 (ddd, J=13.3, 7.6, 5.1 Hz, 1H), 2.07-1.82 (m, 3H), 1.71 (s, 1H), 1.58-1.45 (m, 2H), 1.03 (d, J=3.5 Hz, 6H).

For Example 61: LCMS (C$_{23}$H$_{29}$FN$_8$O$_2$) (ES, m/z): 469 [M+H]$^+$. 1H NMR (499 MHz, DMSO-d6) δ 7.88 (d, J=11.0 Hz, 1H), 7.70 (s, 2H), 7.18 (d, J=7.7 Hz, 1H), 7.13 (s, 1H), 7.07 (s, 1H), 4.62 (s, 1H), 3.97 (s, 3H), 3.87 (s, 2H), 3.75 (dd, J=14.4, 3.8 Hz, 1H), 3.53 (dd, J=14.2, 10.2 Hz, 1H), 3.45 (dt, J=9.5, 4.9 Hz, 1H), 3.38 (s, 1H), 3.24 (dd, J=13.6, 5.5 Hz, 2H), 2.08-1.84 (m, 3H), 1.71 (s, 1H), 1.50 (d, J=12.7 Hz, 2H), 1.03 (d, J=3.4 Hz, 6H).

The example compounds of the invention in the following Table 20 were prepared in a manner similar to that described for the preparation of Example 60 and Example 61 from the appropriate starting amine and aryl halide, where the resulting isomeric mixture of the corresponding final compounds were separated by SFC.

TABLE 20

| Example | Structure Name | SFC Conditions | Observed m/z [M + H]$^+$ |
|---|---|---|---|
| 62 | (R or S)-1-(4-(3-(5-amino-9-fluoro-8-methoxy-[1,2,4]triazolo[1,5-c]quinazolin-2-yl)-3-fluoropyrrolidin-1-yl)-1H-pyrazol-1-yl)-2-methylpropan-2-ol | Peak 1; Chiral Technologies AD-H 21 × 250 mm column with 50% (IPA w/ 0.2% DIPA modifier) as co-solvent | 459 |

TABLE 20-continued

| Example | Structure Name | SFC Conditions | Observed m/z [M + H]+ |
|---|---|---|---|
| 63 | 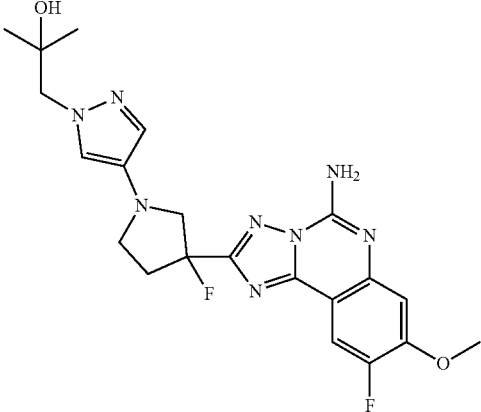 [SMILES: COc1cc2nc(N)n3nc(C4(F)CCN(c5cnn(CC(C)(C)O)c5)C4)nc3c2cc1F]<br>(S or R)-1-(4-(3-(5-amino-9-fluoro-8-methoxy-[1,2,4]triazolo[1,5-c]quinazolin-2-yl)-3-fluoropyrrolidin-1-yl)-1H-pyrazol-1-yl)-2-methylpropan-2-ol | Peak 2; Chiral Technologies AD-H 21 × 250 mm column with 50% (IPA w/ 0.2% DIPA modifier) as co-solvent | 459 |
| 64 | 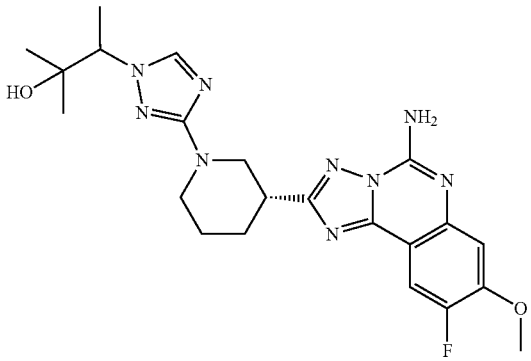 [SMILES: COc1cc2nc(N)n3nc([C@@H]4CCCN(c5ncn(C(C)C(C)(C)O)n5)C4)nc3c2cc1F]<br>(R or S)-3-(3-((R)-3-(5-amino-9-fluoro-8-methoxy-[1,2,4]triazolo[1,5-c]quinazolin-2-yl)piperidin-1-yl)-1H-1,2,4-triazol-1-yl)-2-methylbutan-2-ol | Peak 1; Chiral Technologies IC 21 × 250 mm column with 35% (MeOH w/ 0.1% NH4OH modifier) as co-solvent | 470 |
| 65 | 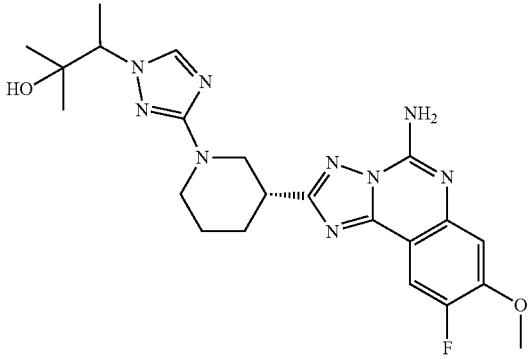 [SMILES: COc1cc2nc(N)n3nc([C@@H]4CCCN(c5ncn(C(C)C(C)(C)O)n5)C4)nc3c2cc1F]<br>(S or R)-3-(3-((R)-3-(5-amino-9-fluoro-8-methoxy-[1,2,4]triazolo[1,5-c]quinazolin-2-yl)piperidin-1-yl)-1H-1,2,4-triazol-1-yl)-2-methylbutan-2-ol | Peak 2; Chiral Technologies IC 21 × 250 mm column with 35% (MeOH w/ 0.1% NH4OH modifier) as co-solvent | 470 |

TABLE 20-continued

| Example | Structure Name | SFC Conditions | Observed m/z [M + H]+ |
|---|---|---|---|
| 66 | 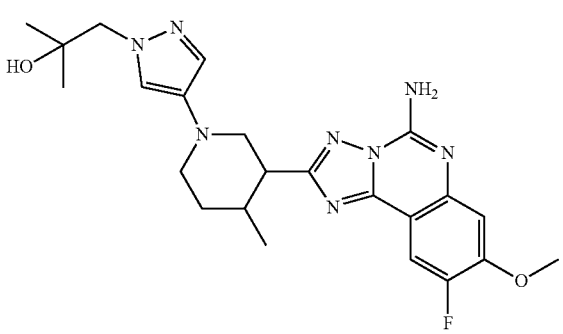 [SMILES: COc1cc2nc(N)n3nc(C4CN(c5cnn(CC(C)(C)O)c5)CCC4C)nc3c2cc1F]<br>1-(4-((3S or 3R, 4S or 4R)-3-(5-amino-9-fluoro-8-methoxy-[1,2,4]triazolo[1,5-c]quinazolin-2-yl)-4-methylpiperidin-1-yl)-1H-pyrazol-1-yl)-2-methylpropan-2-ol | Peak 1; Chiralcel OJ-H 4.6 × 150 mm column with 40% (MeOH w/ 0.05% DEA modifier) as co-solvent | 469 |
| 67 | 1-(4-((3R or 3S,4R or 4S)-3-(5-amino-9-fluoro-8-methoxy-[1,2,4]triazolo[1,5-c]quinazolin-2-yl)-4-methylpiperidin-1-yl)-1H-pyrazol-1-yl)-2-methylpropan-2-ol | Peak 2; Chiralcel OJ-H 4.6 × 150 mm column with 40% (MeOH w/ 0.05% DEA modifier) as co-solvent | 469 |

Example 68 and Example 69: 1-(4-((3R,5S or 3S,5R)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol and 1-(4-((3S,5R or 3R,5S)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol Step 1: rac-1-(4-((3R,5S or 3S,5R)-3-(5-((2,4-dimethoxybenzyl)amino)-9-fluoro-7-methoxy-[1,2,4]triazolo[1,5-c]quinazolin-2-yl)-5-fluoropiperidin-1-yl)-1H-pyrazol-1-yl)-2-methylpropan-2-ol

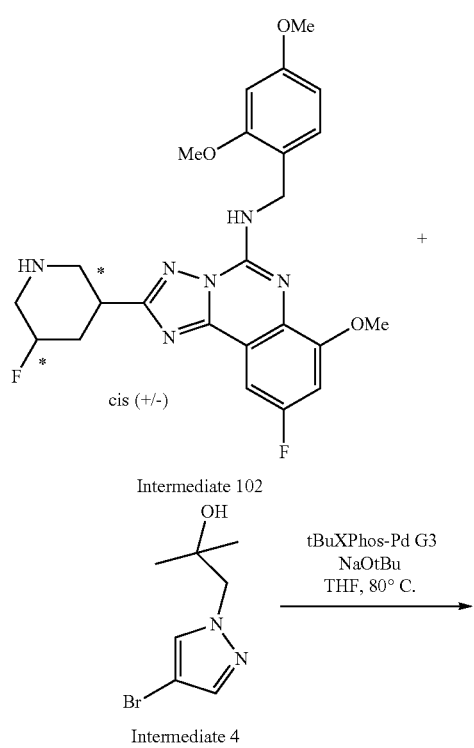

To a 40 mL vial was added rac-N-(2,4-dimethoxybenzyl)-9-fluoro-2-((3R,5S or 3S,5R)-5-fluoropiperidin-3-yl)-7-methoxy-[1,2,4]triazolo[1,5-c]quinazolin-5-amine (Intermediate 102) (736 mg, 1.52 mmol), 1-(4-bromo-1H-pyrazol-1-yl)-2-methylpropan-2-ol (Intermediate 4) (998 mg, 4.56 mmol), tBuXPhos-Pd G3 (965 mg, 1.22 mmol), sodium tert-butoxide (876 mg, 9.11 mmol), and THF (15.0 mL). The mixture was purged with nitrogen for 5 min. The mixture was stirred and heated at 80° C. for 6 h. The mixture was cooled to room temperature. The solvents were evaporated, and the resulting residue was purified by silica gel chromatography with 0-100% EtOAc:EtOH (3:1) in hexanes as eluent to afford rac-1-(4-((3R,5S or 3S,5R)-3-(5-((2,4-dimethoxybenzyl)amino)-9-fluoro-7-methoxy-[1,2,4]triazolo[1,5-c]quinazolin-2-yl)-5-fluoropiperidin-1-yl)-1H-pyrazol-1-yl)-2-methylpropan-2-ol. LCMS ($C_{31}H_{36}F_2N_8O_4$) (ES, m/z): 623 [M+H]$^+$.

Step 2: 1-(4-((3R,5S or 3S,5R)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol and 1-(4-((3S,5R or 3R,5S)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol

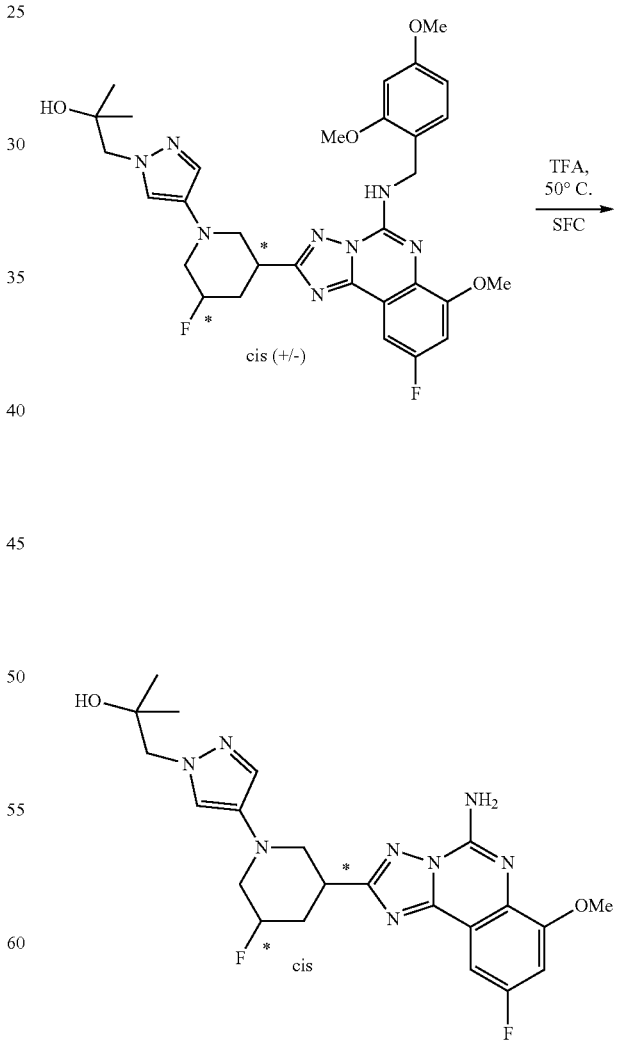

Example 68

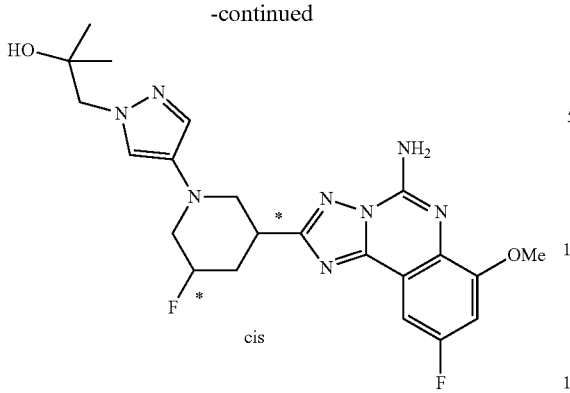

Example 69

To a 20 mL vial was added rac-1-(4-((3R,5S or 3S,5R)-3-(5-((2,4-dimethoxybenzyl)amino)-9-fluoro-7-methoxy-[1,2,4]triazolo[1,5-c]quinazolin-2-yl)-5-fluoropiperidin-1-yl)-1H-pyrazol-1-yl)-2-methylpropan-2-ol (550 mg, 0.883 mmol), and TFA (8.83 mL, 115 mmol). The mixture was stirred and heated at 50° C. for 2 h. The solvents were evaporated. To the resulting residue was added MeOH and the mixture was filtered. The solvents of the filtrate were evaporated. The racemic mixture was resolved by chiral SFC separation (Chiral Technologies AS-H 21×250 mm column with 15% (MeOH w/0.1% NH$_4$OH modifier) as co-solvent) to afford 1-(4-((3R,5S or 3S,5R)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol (Example 68, first eluting peak) and 1-(4-((3S,5R or 3R,5S)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol (Example 69, second eluting peak).

For Example 68: LCMS ($C_{22}H_{26}F_2N_8O_2$) (ES, m/z): 473 [M+H]$^+$. 1H NMR (600 MHz, DMSO-d6) δ 7.82 (s, 2H), 7.43 (dd, J=8.3, 2.6 Hz, 1H), 7.37 (s, 1H), 7.28 (s, 1H), 7.18 (dd, J=11.0, 2.6 Hz, 1H), 4.94 (dtt, J=48.3, 10.3, 4.8 Hz, 1H), 4.65 (s, 1H), 3.93 (s, 3H), 3.89 (s, 2H), 3.78-3.71 (m, 1H), 3.66 (d, J=11.5 Hz, 1H), 3.40 (t, J=11.8 Hz, 1H), 2.75 (t, J=11.5 Hz, 1H), 2.66 (d, J=6.1 Hz, 1H), 2.58 (td, J=10.4, 5.2 Hz, 1H), 1.92 (p, J=11.3 Hz, 1H), 1.04 (s, 6H).

For Example 69: LCMS ($C_{22}H_{26}F_2N_8O_2$) (ES, m/z): 473 [M+H]$^+$. 1H NMR (600 MHz, DMSO-d6) δ 7.82 (s, 1H), 7.44 (dd, J=8.3, 2.7 Hz, 1H), 7.37 (s, 1H), 7.28 (s, 1H), 7.19 (dd, J=11.1, 2.7 Hz, 1H), 4.95 (ddt, J=48.3, 10.4, 5.2 Hz, 1H), 4.64 (s, 1H), 3.94 (s, 2H), 3.89 (s, 1H), 3.74 (d, J=10.6 Hz, 1H), 3.66 (d, J=11.9 Hz, 1H), 3.40 (t, J=11.8 Hz, 1H), 2.74 (d, J=11.5 Hz, 1H), 2.65 (s, 1H), 2.58 (dt, J=10.3, 5.2 Hz, 1H), 1.97-1.89 (m, 1H), 1.04 (s, 6H).

The example compounds of the invention in the following Table 21 were prepared in a manner similar to that described for the preparation of Example 68 and Example 69 from Intermediate 102 and the appropriate starting aryl halide, where the resulting isomeric mixture of the corresponding final compounds were separated by SFC.

TABLE 21

| Example | Structure Name | SFC Conditions | Observed m/z [M + H]$^+$ |
|---|---|---|---|
| 70 | ![structure] 1-(4-((3R,5S or 3S,5R)-3-(5-amino-9-fluoro-7-methoxy-[1,2,4]triazolo[1,5-c]quinazolin-2-yl)-5-fluoropiperidin-1-yl)-3-methyl-1H-pyrazol-1-yl)-2-methylpropan-2-ol | Peak 1; Phenomenex Lux-2 21 × 250 mm column with 40% (MeOH w/ 0.1% NH$_4$OH modifier) as co-solvent | 487 |

TABLE 21-continued

| Example | Structure Name | SFC Conditions | Observed m/z [M + H]+ |
|---|---|---|---|
| 71 | 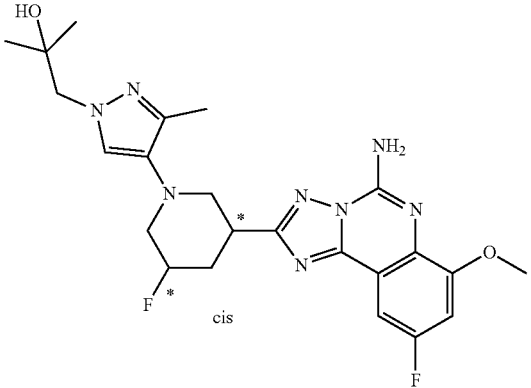 [SMILES: COc1cc(F)cc2c1nc(N)n1nc(C3CC(F)CN(c4cn(CC(C)(C)O)nc4C)C3)nc21]<br>1-(4-((3S,5R or 3R,5S)-3-(5-amino-9-fluoro-7-methoxy-[1,2,4]triazolo[1,5-c]quinazolin-2-yl)-5-fluoropiperidin-1-yl)-3-methyl-1H-pyrazol-1-yl)-2-methylpropan-2-ol | Peak 2; Phenomenex Lux-2 21 × 250 mm column with 40% (MeOH w/ 0.1% NH4OH modifier) as co-solvent | 487 |
| 72 | 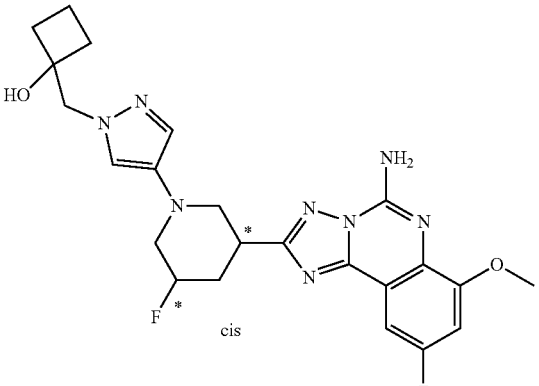<br>1-((4-((3R,5S or 3S,5R)-3-(5-amino-9-fluoro-7-methoxy-[1,2,4]triazolo[1,5-c]quinazolin-2-yl)-5-fluoropiperidin-1-yl)-1H-pyrazol-1-yl)methyl)cyclobutan-1-ol | Peak 1; ES Industries CCA 21 × 250 mm column with 20% (MeOH w/ 0.1% NH4OH modifier) as co-solvent | 485 |
| 73 | 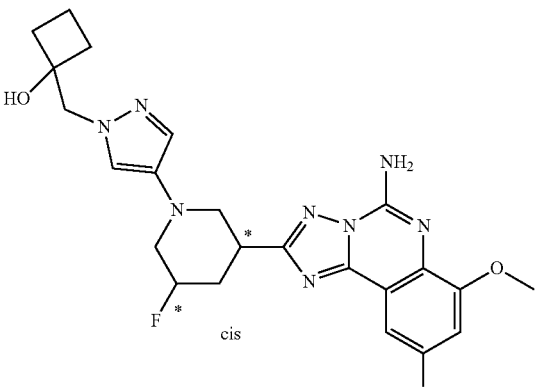<br>1-((4-((3S,5R or 3R,5S)-3-(5-amino-9-fluoro-7-methoxy-[1,2,4]triazolo[1,5-c]quinazolin-2-yl)-5-fluoropiperidin-1-yl)-1H-pyrazol-1-yl)methyl)cyclobutan-1-ol | Peak 2; ES Industries CCA 21 × 250 mm column with 20% (MeOH w/ 0.1% NH4OH modifier) as co-solvent | 485 |

Example 74 and Example 75: 1-(4-((3R,5R or 3S,5S)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol and 1-(4-((3S,5S or 3R,5R)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol Step 1: rac-1-(4-((3R,5R or 3S,5S)-3-(5-((2,4-dimethoxybenzyl)amino)-9-fluoro-7-methoxy-[1,2,4]triazolo[1,5-c]quinazolin-2-yl)-5-fluoropiperidin-1-yl)-1H-pyrazol-1-yl)-2-methylpropan-2-ol

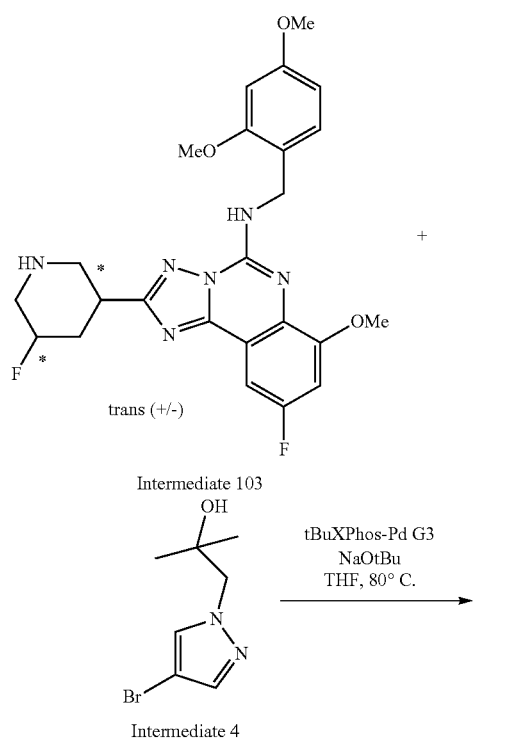

To a 20 mL vial was added rac-N-(2,4-dimethoxybenzyl)-9-fluoro-2-((3R,5R or 3S,5S)-5-fluoropiperidin-3-yl)-7-methoxy-[1,2,4]triazolo[1,5-c]quinazolin-5-amine (Intermediate 102) (434 mg, 0.896 mmol), 1-(4-bromo-1H-pyrazol-1-yl)-2-methylpropan-2-ol (Intermediate 4) (589 mg, 2.69 mmol), tBuXPhos-Pd G3 (569 mg, 0.717 mmol), sodium tert-butoxide (517 mg, 5.37 mmol) and THF (9.0 mL). The mixture was purged with nitrogen for 5 min. The mixture was stirred and heated at 80° C. for 6 h. The mixture was cooled to room temperature. The solvents were evaporated. The resulting residue was purified by silica gel chromatography with 30-50% EtOAc:EtOH (3:1) in hexane as eluent, yielding rac-1-(4-((3R,5R or 3S,5S)-3-(5-((2,4-dimethoxybenzyl)amino)-9-fluoro-7-methoxy-[1,2,4]triazolo[1,5-c]quinazolin-2-yl)-5-fluoropiperidin-1-yl)-1H-pyrazol-1-yl)-2-methylpropan-2-ol. LCMS ($C_{31}H_{36}F_2N_8O_4$) (ES, m/z): 623 [M+H]$^+$.

Step 2: 1-(4-((3R,5R or 3S,5S)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol and 1-(4-((3S,5S or 3R,5R)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol

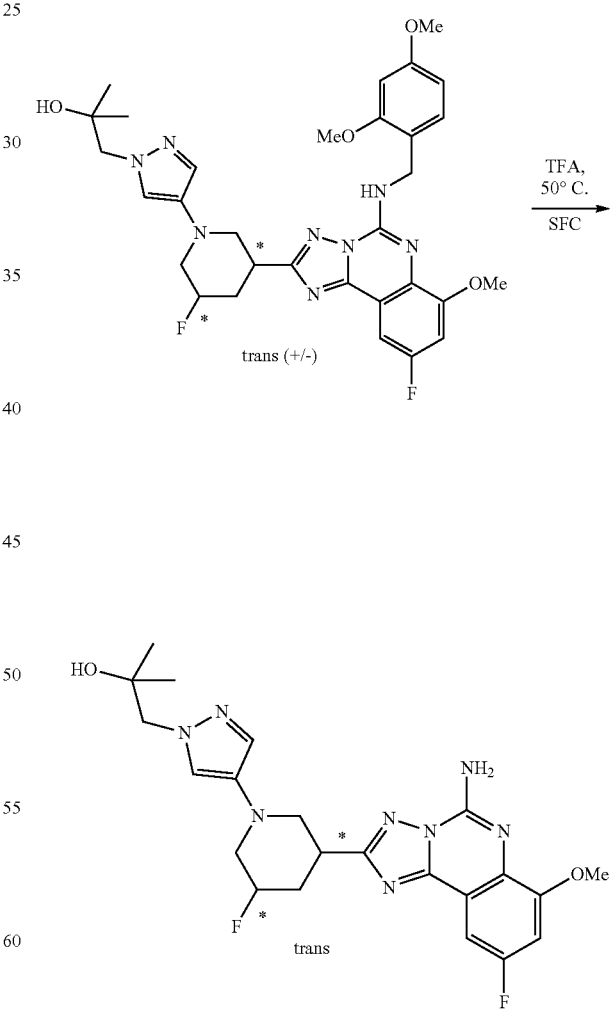

Example 74

-continued

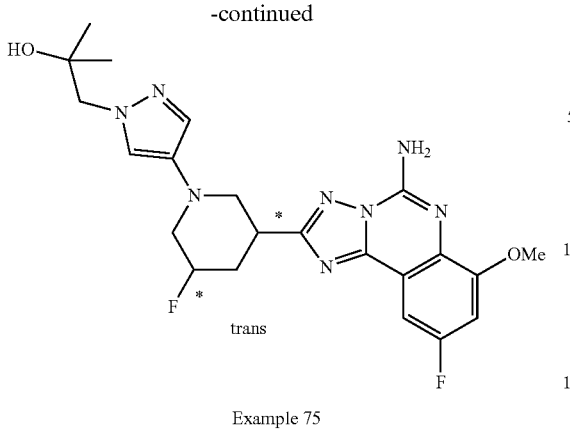

Example 75

To a 20 mL vial containing rac-1-(4-((3R,5R or 3S,5S)-3-(5-((2,4-dimethoxybenzyl)amino)-9-fluoro-7-methoxy-[1,2,4]triazolo[1,5-c]quinazolin-2-yl)-5-fluoropiperidin-1-yl)-1H-pyrazol-1-yl)-2-methylpropan-2-ol (439 mg, 0.705 mmol) was added TFA (7.05 mL, 92.0 mmol). The mixture was stirred and heated at 50° C. for 2 h. The solvents were evaporated. To the residue was added MeOH. The mixture was filtered, and then the solvents of the filtrate were evaporated. The racemic mixture was resolved by chiral SFC separation (Chiral Technologies AS-H 21×250 mm column with 15% (MeOH w/0.1% NH$_4$OH modifier) as co-solvent), yielding 1-(4-((3R,5R or 3S,5S)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol (Example 74, first eluting peak) and 1-(4-((3R,5R or 3S,5S)-3-(5-amino-9-fluoro-7-methoxy-[1,2,4]triazolo[1,5-c]quinazolin-2-yl)-5-fluoropiperidin-1-yl)-1H-pyrazol-1-yl)-2-methylpropan-2-ol (Example 75, second eluting peak).

For Example 74: LCMS (C$_{22}$H$_{26}$F$_2$N$_8$O$_2$) (ES, m/z): 473 [M+H]$^+$. 1H NMR (499 MHz, DMSO-d6) δ 7.83 (s, 2H), 7.43 (dd, J=8.4, 2.7 Hz, 1H), 7.32 (s, 1H), 7.24 (s, 1H), 7.19 (d, J=10.0 Hz, 1H), 5.11 (d, J=46.5 Hz, 1H), 4.64 (s, 1H), 3.94 (s, 3H), 3.89 (s, 2H), 3.69-3.48 (m, 3H), 2.97-2.89 (m, 1H), 2.90-2.79 (m, 1H), 2.40 (s, 1H), 2.14 (dt, J=40.9, 11.8 Hz, 1H), 1.04 (s, 6H).

For Example 75: LCMS (C$_{22}$H$_{26}$F$_2$N$_8$O$_2$) (ES, m/z): 473 [M+H]$^+$. 1H NMR (499 MHz, DMSO-d6) δ 7.83 (s, 2H), 7.43 (dd, J=8.4, 2.7 Hz, 1H), 7.32 (s, 1H), 7.24 (s, 1H), 7.19 (d, J=8.9 Hz, 1H), 5.11 (d, J=47.5 Hz, 1H), 3.94 (s, 3H), 3.89 (s, 2H), 3.67-3.50 (m, 3H), 2.97-2.90 (m, 1H), 2.90-2.79 (m, 1H), 2.41 (s, 1H), 2.14 (dt, J=40.8, 12.8 Hz, 1H), 1.04 (s, 6H).

The example compounds of the invention in the following Table 22 were prepared in a manner similar to that described for the preparation of Example 74 and Example 75 from Intermediate 103 and the appropriate starting aryl halide, where the resulting isomeric mixture of the corresponding final compounds were separated by SFC.

TABLE 22

| Example | Structure Name | SFC Conditions | Observed m/z [M + H]$^+$ |
|---|---|---|---|
| 76 | 1-(4-((3R,5R or 3S,5S)-3-(5-amino-9-fluoro-7-methoxy-[1,2,4]triazolo[1,5-c]quinazolin-2-yl)-5-fluoropiperidin-1-yl)-3-methyl-1H-pyrazol-1-yl)-2-methylpropan-2-ol | Peak 1; Phenomenex Lux-3 21 × 250 mm column with 15% (MeOH w/ 0.1% NH$_4$OH modifier) as co-solvent | 487 |

TABLE 22-continued

| Example | Structure Name | SFC Conditions | Observed m/z [M + H]+ |
|---|---|---|---|
| 77 | 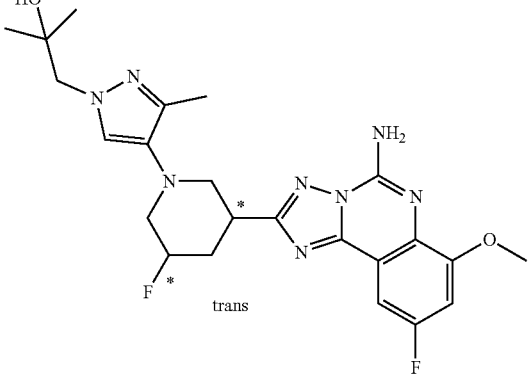<br>1-(4-((3S,5S or 3R,5R)-3-(5-amino-9-fluoro-7-methoxy-[1,2,4]triazolo[1,5-c]quinazolin-2-yl)-5-fluoropiperidin-1-yl)-3-methyl-1H-pyrazol-1-yl)-2-methylpropan-2-ol | Peak 2; Phenomenex Lux-2 21 × 250 mm column with 15% (MeOH w/ 0.1% NH₄OH modifier) as co-solvent | 487 |
| 78 | 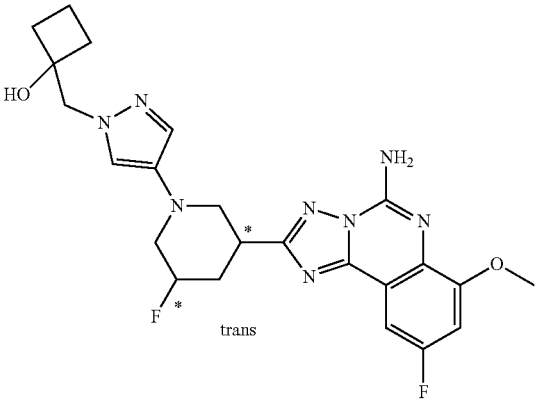 [SMILES: COc1cc(F)cc2c1nc(N)n1nc(C3CC(F)CN(c4cnn(CC5(O)CCC5)c4)C3)nc21]<br>1-((4-((3R,5R or 3S,5S)-3-(5-amino-9-fluoro-7-methoxy-[1,2,4]triazolo[1,5-c]quinazolin-2-yl)-5-fluoropiperidin-1-yl)-1H-pyrazol-1-yl)methyl)cyclobutan-1-ol | Peak 1; Chiral Technologies OJ-H 21 × 250 mm column with 20% (MeOH w/ 0.1% NH₄OH modifier) as co-solvent | 485 |
| 79 | 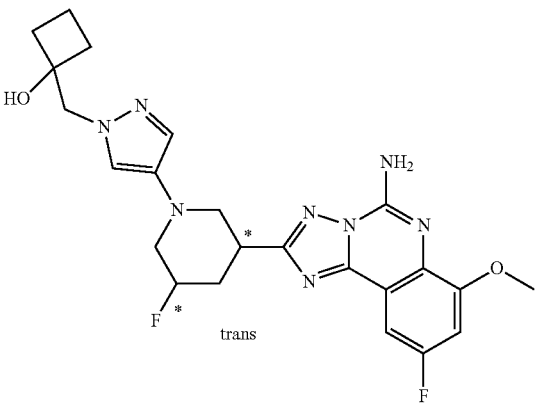 [SMILES: COc1cc(F)cc2c1nc(N)n1nc(C3CC(F)CN(c4cnn(CC5(O)CCC5)c4)C3)nc21]<br>1-((4-((3S,5S or 3R,5R)-3-(5-amino-9-fluoro-7-methoxy-[1,2,4]triazolo[1,5-c]quinazolin-2-yl)-5-fluoropiperidin-1-yl)-1H-pyrazol-1-yl)methyl)cyclobutan-1-ol | Peak 2; Chiral Technologies OJ-H 21 × 250 mm column with 20% (MeOH w/ 0.1% NH₄OH modifier) as co-solvent | 485 |

Example 80 and Example 81: 1-(4-((3R,5R or 3S,5S)-3-(5-amino-9-fluoro-8-methoxy-[1,2,4]triazolo[1,5-c]quinazolin-2-yl)-5-fluoropiperidin-1-yl)-1H-pyrazol-1-yl)-2-methylpropan-2-ol and 1-(4-((3S,5S or 3R,5R)-3-(5-amino-9-fluoro-8-methoxy-[1,2,4]triazolo[1,5-c]quinazolin-2-yl)-5-fluoropiperidin-1-yl)-1H-pyrazol-1-yl)-2-methylpropan-2-ol Step 1: rac-1-(4-((3R,5R or 3S,5S)-3-(5-((2,4-dimethoxybenzyl)amino)-9-fluoro-8-methoxy-[1,2,4]triazolo[1,5-c]quinazolin-2-yl)-5-fluoropiperidin-1-yl)-1H-pyrazol-1-yl)-2-methylpropan-2-ol

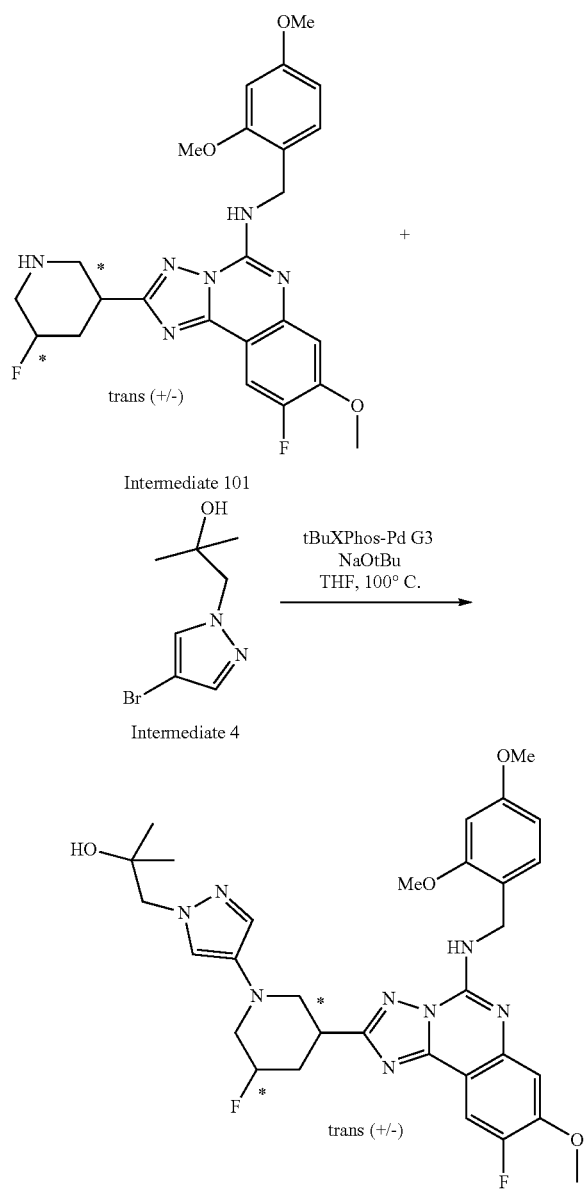

Step 1 of Example 80 and Example 81 was conducted in a manner similar to step 1 of Example 74 and Example 75, with Intermediate 101 and Intermediate 4 to afford rac-1-(4-((3R,5R or 3S,5S)-3-(5 #2,4-dimethoxybenzyl)amino)-9-fluoro-8-methoxy-[1,2,4]triazolo[1,5-c]quinazolin-2-yl)-5-fluoropiperidin-1-yl)-1H-pyrazol-1-yl)-2-methylpropan-2-ol. LCMS ($C_{31}H_{36}F_2N_8O_4$) (ES, m/z): 623 [M+H]$^+$.

Step 2: 1-(4-((3R,5R or 3S,5S)-3-(5-amino-9-fluoro-8-methoxy-[1,2,4]triazolo[1,5-c]quinazolin-2-yl)-5-fluoropiperidin-1-yl)-1H-pyrazol-1-yl)-2-methylpropan-2-ol and 1-(4-((3S,5S or 3R,5R)-3-(5-amino-9-fluoro-8-methoxy-[1,2,4]triazolo[1,5-c]quinazolin-2-yl)-5-fluoropiperidin-1-yl)-1H-pyrazol-1-yl)-2-methylpropan-2-ol

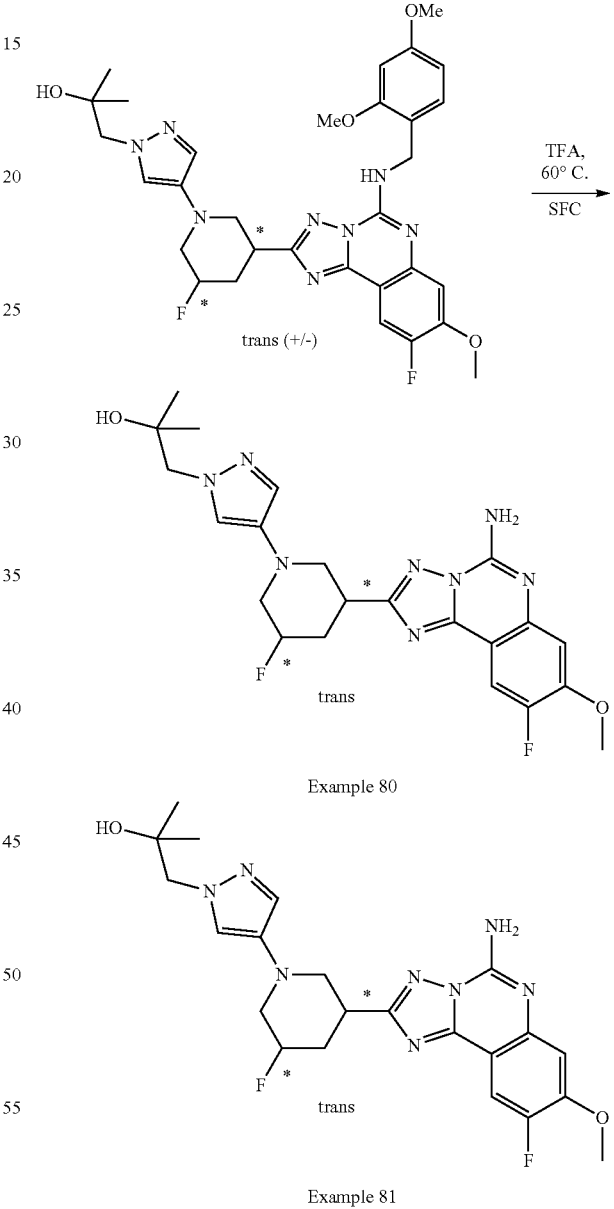

Step 2 of Example 80 and Example 81 was conducted in a manner similar to step 2 of Example 74 and Example 75, where rac-1-(4-((3R,5R or 3S,5S)-3-(5-((2,4-dimethoxybenzyl)amino)-9-fluoro-8-methoxy-[1,2,4]triazolo[1,5-c]quinazolin-2-yl)-5-fluoropiperidin-1-yl)-1H-pyrazol-1-yl)-2-methylpropan-2-ol is converted to the racemic mixture of the corresponding final compounds. The racemic mixture was resolved by chiral SFC separation (Chiral Technologies OJ-H 21×250 mm column with 25% (MeOH w/0.2% DIPA modifier) as co-solvent), to afford 1-(4-((3R,5R or 3S,5S)-3-(5-amino-9-fluoro-8-methoxy-[1,2,4]triazolo[1,5-c]quinazolin-2-yl)-5-fluoropiperidin-1-yl)-1H-pyrazol-1-yl)-2-methylpropan-2-ol (Example 80, first eluting peak) and 1-(4-((3S,5S or 3R,5R)-3-(5-amino-9-fluoro-8-methoxy-[1,2,4]triazolo[1,5-c]quinazolin-2-yl)-5-fluoropiperidin-1-yl)-1H-pyrazol-1-yl)-2-methylpropan-2-ol (Example 81, second eluting peak).

For Example 80: LCMS ($C_{22}H_{26}F_2N_8O_2$) (ES, m/z): 473 [M+H]$^+$. $^1$H NMR (500 MHz, Methanol-$d_4$) δ 7.94 (d, J=10.8 Hz, 1H), 7.48 (s, 1H), 7.42 (s, 1H), 7.24 (d, J=7.5 Hz, 1H), 5.12 (d, J=46.8 Hz, 1H), 4.02 (d, J=3.8 Hz, 3H), 3.84 (d, J=12.4 Hz, 1H), 3.82-3.74 (m, 1H), 3.74-3.62 (m, 1H), 3.11 (t, J=11.0 Hz, 1H), 3.08-2.95 (m, 1H), 2.67 (s, 1H), 2.59 (s, 1H), 2.31-2.12 (m, 1H), 1.16 (s, 6H).

For Example 81: LCMS ($C_{22}H_{26}F_2N_8O_2$) (ES, m/z): 473 [M+H]$^+$. $^1$H NMR (500 MHz, Methanol-$d_4$) δ 7.94 (d, J=10.8 Hz, 1H), 7.50 (s, 1H), 7.43 (s, 1H), 7.24 (d, J=7.5 Hz, 1H), 5.13 (d, J=47.0 Hz, 1H), 4.02 (d, J=4.8 Hz, 3H), 3.85 (d, J=11.0 Hz, 1H), 3.82-3.73 (m, 1H), 3.73-3.60 (m, 1H), 3.11 (t, J=11.0 Hz, 1H), 3.04 (dd, J=36.0, 12.9 Hz, 1H), 2.59 (s, 1H), 2.30-2.12 (m, 1H), 1.16 (s, 6H).

Example 82 and Example 83: (1R or 1S,2R or 2S)-2-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclopentan-1-ol and (1S or 1R,2S or 2R)-2-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclopentan-1-ol Step 1: (1R or 1S,2R or 2S)-2-(4-((R)-3-(5-((2,4-dimethoxybenzyl)amino)-9-fluoro-8-methoxy-[1,2,4]triazolo[1,5-c]quinazolin-2-yl)piperidin-1-yl)-1H-pyrazol-1-yl)-1-methylcyclopentan-1-ol and (1S or 1R,2S or 2R)-2-(4-((R)-3-(5-((2,4-dimethoxybenzyl)amino)-9-fluoro-8-methoxy-[1,2,4]triazolo[1,5-c]quinazolin-2-yl)piperidin-1-yl)-1H-pyrazol-1-yl)-1-methylcyclopentan-1-ol

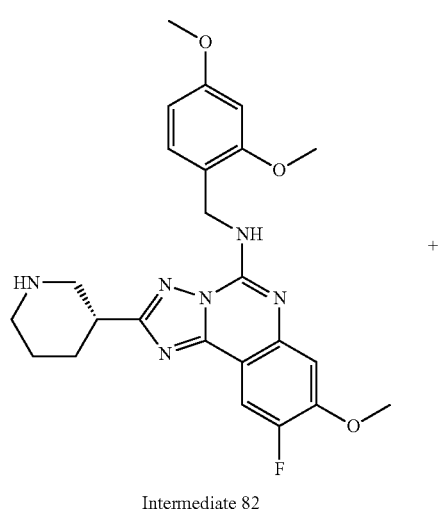

Intermediate 82

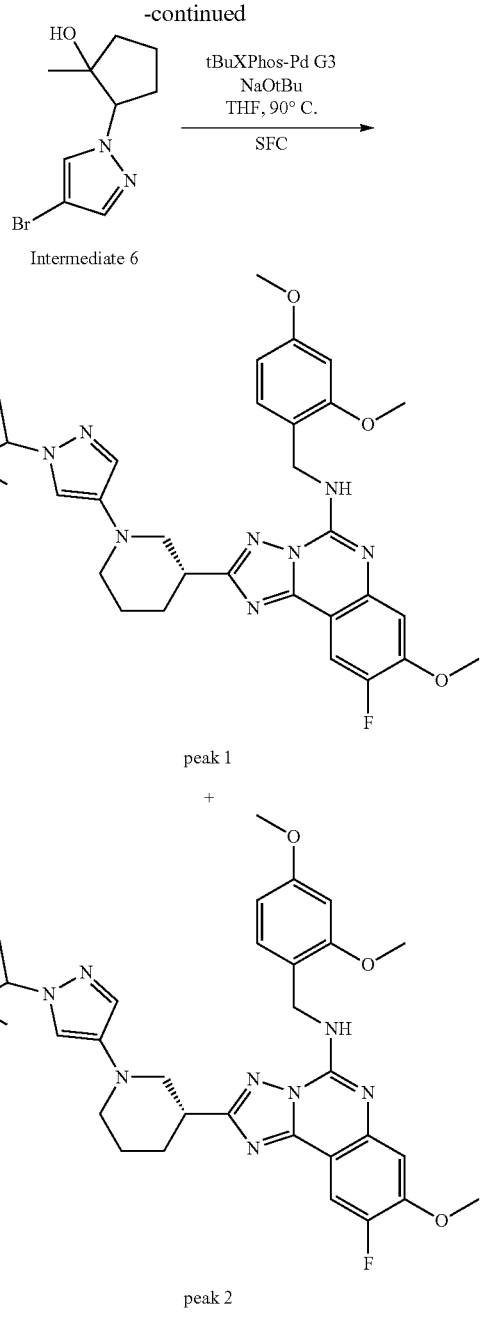

To a reaction vial containing a solution of (R)—N-(2,4-dimethoxybenzyl)-9-fluoro-8-methoxy-2-(piperidin-3-yl)-[1,2,4]triazolo[1,5-c]quinazolin-5-amine (Intermediate 82) (150 mg, 0.322 mmol) in THF (3.0 mL) was added 2-(4-bromo-1H-pyrazol-1-yl)-1-methylcyclopentanol 2,2,2-trifluoroacetate (Intermediate 6) (184 mg, 0.514 mmol) followed by tBuXPhos-Pd G3 (77.0 mg, 0.0960 mmol) and sodium tert-butoxide (93.0 mg, 0.965 mmol). Nitrogen was bubbled through the mixture for 10 min. The mixture was stirred and heated at 90° C. for 4 h. The mixture was cooled to room temperature, and then the resulting residue was purified by silica gel chromatography with 0-40% EtOAc:EtOH (3:1) in hexane as eluent, yielding a diastereomeric mixture of products. The mixture was purified by SFC separation (Chiral Technologies OJ-H 21×250 mm column with 30% MeOH as co-solvent), yielding peak 1 and peak 2 corresponding to (1R or 1S,2R or 2S)-2-(4-((R)-3-(5-((2,4-dimethoxybenzyl)amino)-9-fluoro-8-methoxy-[1,2,4]triazolo[1,5-c]quinazolin-2-yl)piperidin-1-yl)-1H-pyrazol-1-yl)-1-methylcyclopentan-1-ol and (1S or 1R,2S or 2R)-2-(4-((R)-3-(5-((2,4-dimethoxybenzyl)amino)-9-fluoro-8-methoxy-[1,2,4]triazolo[1,5-c]quinazolin-2-yl)piperidin-1-yl)-1H-pyrazol-1-yl)-1-methylcyclopentan-1-ol. For peak 1, LCMS ($C_{33}H_{39}FN_8O_4$) (ES, m/z): 631 [M+H]$^+$. For peak 2, LCMS ($C_{33}H_{39}FN_8O_4$) (ES, m/z): 631 [M+H]$^+$.

Step 2: (1R or 1S,2R or 2S)-2-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclopentan-1-ol and (1S or 1R,2S or 2R)-2-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclopentan-1-ol

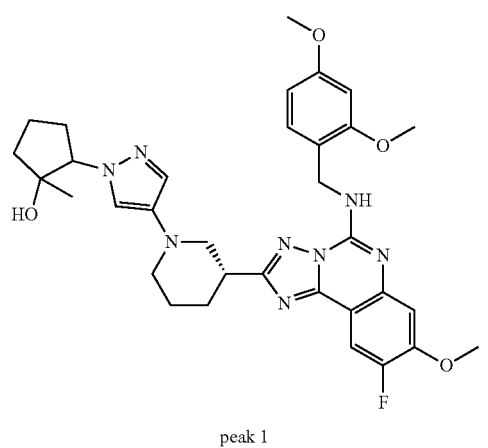

peak 1

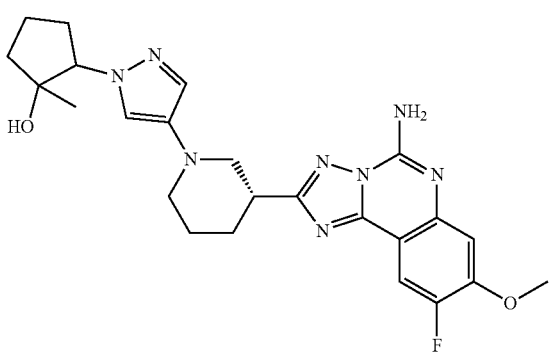

Example 82

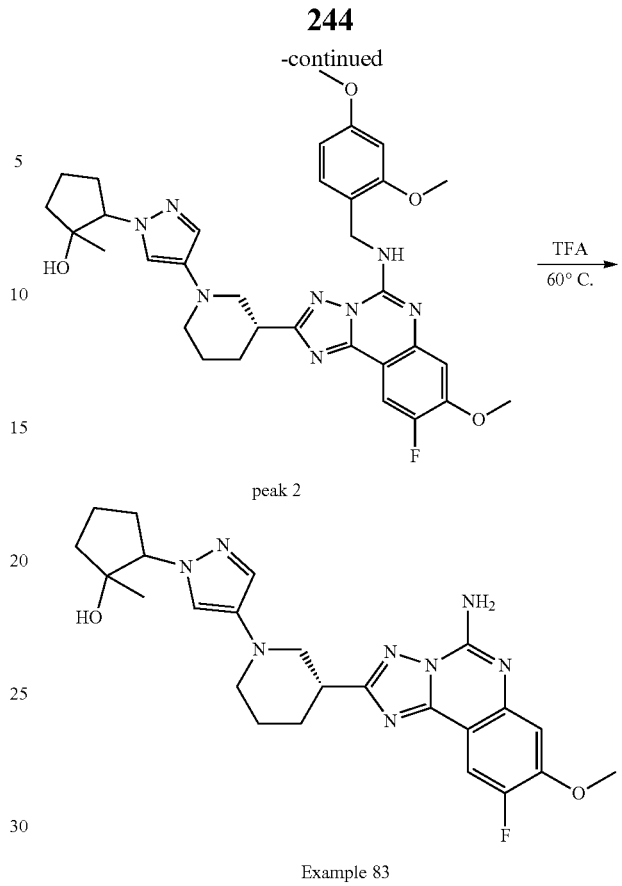

Step 2 of Example 82 and Example 83 was conducted in a manner similar to step 2 of Example 40, where peak 1 and peak 2 obtained from step 1 were converted to (1R or 1S,2R or 2S)-2-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclopentan-1-ol and (1S or 1R,2S or 2R)-2-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclopentan-1-ol, which are the final compounds of Example 82 and Example 83, respectively.

For Example 82: LCMS ($C_{24}H_{29}FN_8O_2$) (ES, m/z): 481 [M+H]$^+$. $^1$H NMR (400 MHz, Chloroform-d) δ 7.97 (d, J=10.7 Hz, 1H), 7.31 (s, 1H), 7.13 (d, J=7.6 Hz, 1H), 7.07 (s, 1H), 5.89 (s, 2H), 4.36 (t, J=8.8 Hz, 1H), 3.99 (s, 3H), 3.68 (dd, J=11.5, 3.6 Hz, 1H), 3.38 (tt, J=7.5, 3.8 Hz, 2H), 2.95 (t, J=11.1 Hz, 1H), 2.67 (td, J=11.3, 4.4 Hz, 1H), 2.40-2.07 (m, 3H), 1.99-1.73 (m, 7H), 0.88 (s, 3H).

For Example 83: LCMS ($C_{24}H_{29}FN_8O_2$) (ES, m/z): 481 [M+H]$^+$. $^1$H NMR (400 MHz, Chloroform-d) δ 7.97 (d, J=10.7 Hz, 1H), 7.31 (s, 1H), 7.13 (d, J=7.6 Hz, 1H), 7.07 (s, 1H), 5.88 (s, 2H), 4.35 (t, J=8.7 Hz, 1H), 3.99 (s, 3H), 3.74-3.64 (m, 1H), 3.43-3.31 (m, 2H), 2.95 (t, J=11.1 Hz, 1H), 2.67 (td, J=11.2, 4.5 Hz, 1H), 2.39-2.10 (m, 3H), 2.00-1.74 (m, 7H), 0.88 (s, 3H).

The example compounds of the invention in the following Table 23 were prepared in a manner similar to that described for the preparation of Example 82 and Example 83 from the appropriate intermediates and starting materials. In each case, an SFC separation was conducted on the intermediate mixture formed from the first step. The SFC conditions to isolate these intermediates are shown with the corresponding final products formed from the second step.

TABLE 23

| Example | Structure Name | SFC Conditions for intermediate from step 1 | Observed m/z [M + H]+ |
|---|---|---|---|
| 84 | (1R or 1S,2R or 2S)-2-(4-((R)-3-(5-amino-9-fluoro-8-methoxy-[1,2,4]triazolo[1,5-c]quinazolin-2-yl)piperidin-1-yl)-1H-pyrazol-1-yl)cyclopentan-1-ol | Peak 1; Whelko-1 21 × 250 mm column with 50% (MeOH w/ 0.2% DIPA modifier) as co-solvent | 467 |
| 85 | (1S or 1R,2S or 2R)-2-(4-((R)-3-(5-amino-9-fluoro-8-methoxy-[1,2,4]triazolo[1,5-c]quinazolin-2-yl)piperidin-1-yl)-1H-pyrazol-1-yl)cyclopentan-1-ol | Peak 2; Whelko-1 21 × 250 mm column with 50% (MeOH w/ 0.2% DIPA modifier) as co-solvent | 467 |
| 86 | (S or R)-3-(4-((R)-3-(5-amino-9-fluoro-7-methoxy-[1,2,4]triazolo[1,5-c]quinazolin-2-yl)piperidin-1-yl)-3-methyl-1H-pyrazol-1-yl)-2-methylbutan-2-ol | Peak 1; Chiral Technologies AD-H 21 × 250 mm column with 45% (IPA 1:1 w/ 0.2% DIPA modifier) as co-solvent | 483 |

TABLE 23-continued

| Example | Structure Name | SFC Conditions for intermediate from step 1 | Observed m/z [M + H]+ |
|---|---|---|---|
| 87 | 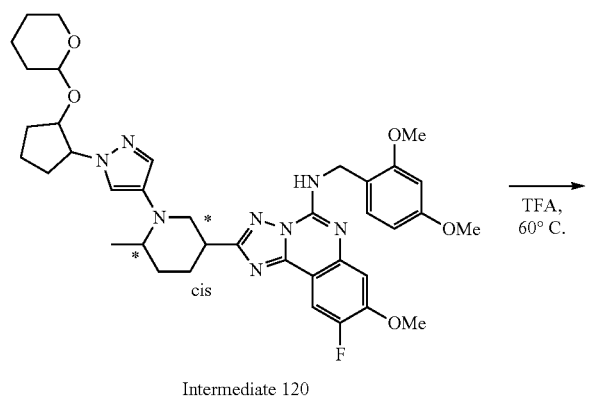<br>(R or S)-3-(4-((R)-3-(5-amino-9-fluoro-7-methoxy-[1,2,4]triazolo[1,5-c]quinazolin-2-yl)piperidin-1-yl)-3-methyl-1H-pyrazol-1-yl)-2-methylbutan-2-ol | Peak 2; Chiral Technologies AD-H 21 × 250 mm column with 45% (IPA 1:1 w/ 0.2% DIPA modifier) as co-solvent | 483 |

Example 88: (1R or 1S,2R or 2S)-2-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)cyclopentan-1-ol

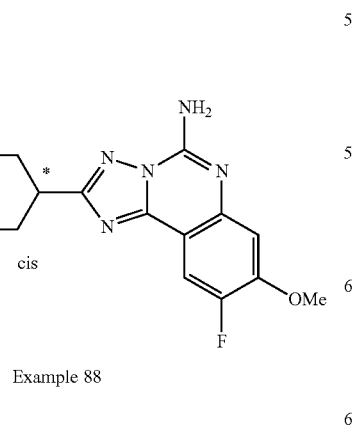

Example 88

The mixture of N-(2,4-dimethoxybenzyl)-9-fluoro-8-methoxy-2-((3R,6S or 3S,6R)-6-methyl-1-(14(1R or 1S,2R or 2S)-2-((tetrahydro-2H-pyran-2-yl)oxy)cyclopentyl)-1H-pyrazol-4-yl)piperidin-3-yl)-[1,2,4]triazolo[1,5-c]quinazolin-5-amine (Intermediate 120) (5.0 mg, 7.0 μmol) in TFA (0.3 mL) was heated at 60° C. for 25 min. The mixture was concentrated. The residue was purified by preparative silica gel TLC eluting with 5% (7 M ammonia in MeOH) in DCM to afford (1R or 1S,2R or 2S)-2-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)cyclopentan-1-ol. LCMS ($C_{24}H_{29}FN_8O_2$) (ES, m/z): 481 [M+H]+. $^1$H NMR (400 MHz, Chloroform-d) δ 7.99 (d, J=10.7 Hz, 1H), 7.25 (s, 1H), 7.15 (d, J=7.6 Hz, 1H), 7.02 (s, 1H), 5.87 (s, 2H), 4.35 (d, J=7.5 Hz, 1H), 4.21 (d, J=8.7 Hz, 1H), 4.01 (s, 3H), 3.74 (d, J=6.5 Hz, 1H), 3.47-3.41 (m, 1H), 3.32 (d, J=11.0 Hz, 1H), 3.23 (d, J=11.3 Hz, 1H), 2.26 (m, 1H), 2.16-2.08 (m, 3H), 2.08-2.00 (m, 2H), 1.90-1.71 (m, 4H), 1.13 (d, J=6.7 Hz, 3H).

Example 89: (1S or 1R,2S or 2R)-2-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)cyclopentan-1-ol

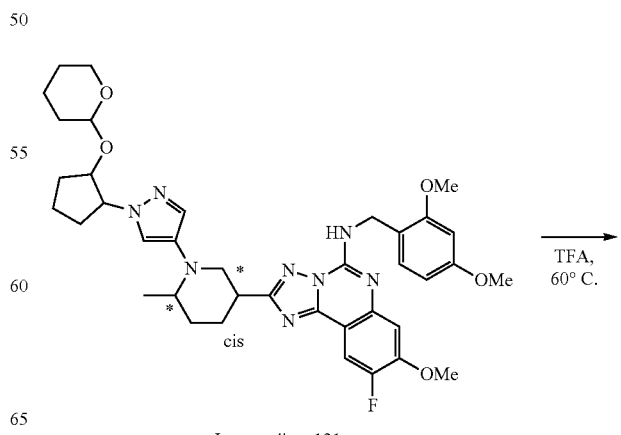

Intermediate 121

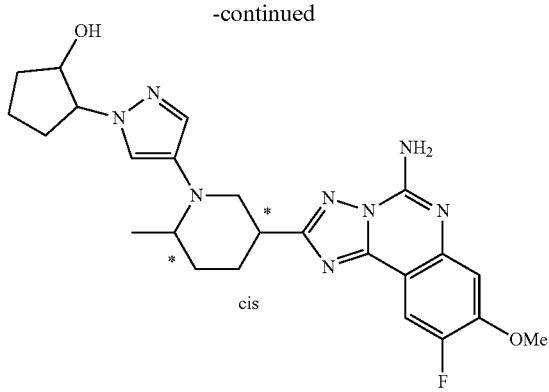

Example 89

Example 89 was prepared from Intermediate 121 in a manner similar to Example 88 to afford (1S or 1R,2S or 2R)-2-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)cyclopentan-1-ol. LCMS ($C_{24}H_{29}FN_8O_2$) (ES, m/z): 481 [M+H]+. ¹H NMR (400 MHz, Chloroform-d) δ 7.99 (d, J=10.7 Hz, 1H), 7.25 (s, 1H), 7.15 (d, J=7.6 Hz, 1H), 7.01 (s, 1H), 5.81 (s, 2H), 4.36 (q, J=7.1 Hz, 1H), 4.27-4.15 (m, 1H), 4.00 (s, 3H), 3.79-3.67 (m, 1H), 3.44 (dd, J=11.5, 4.2 Hz, 1H), 3.37-3.28 (m, 1H), 3.22 (t, J=11.1 Hz, 1H), 2.34-2.21 (m, 1H), 2.19-1.96 (m, 4H), 1.94-1.62 (m, 6H), 1.12 (d, J=6.7 Hz, 3H).

Example 90 and 91: 1-(4-((3R,5S or 3S,5R)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol and 1-(4-((3S,5R or 3R,5S)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol

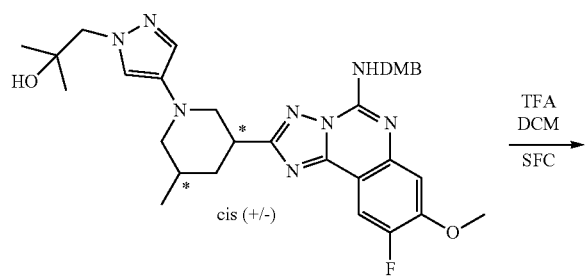

Intermediate 122

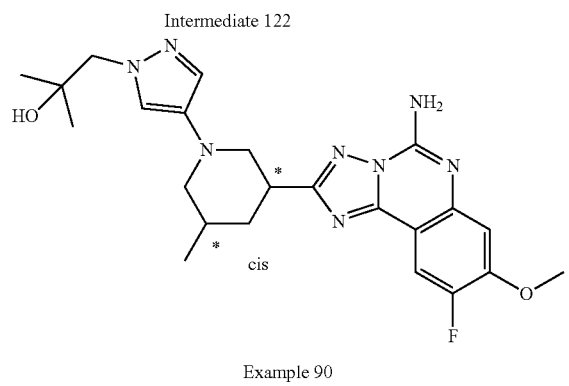

Example 90

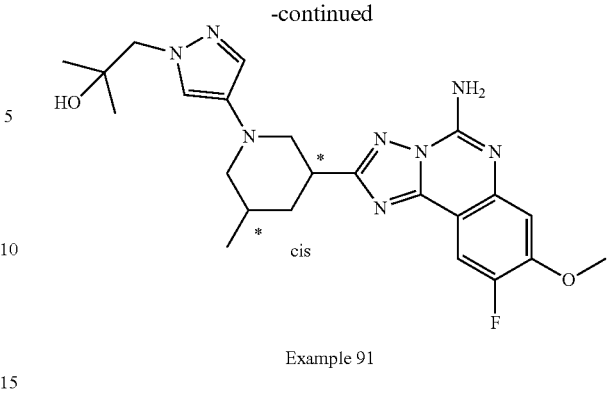

Example 91

To a solution of rac-1-(4-((3S,5R or 3R,5S)-3-(5-((2,4-dimethoxybenzyl)amino)-9-fluoro-8-methoxy-[1,2,4]triazolo[1,5-c]quinazolin-2-yl)-5-methylpiperidin-1-yl)-1H-pyrazol-1-yl)-2-methylpropan-2-ol (Intermediate 122) (150 mg, 0.242 mmol) in DCM (2 mL) was added TFA (2 mL). The mixture was stirred at 50° C. for 10 h. The mixture was concentrated. The racemic mixture was purified and resolved by chiral SFC (Phenomenex Lux-2 4.6×150 mm column with 0-40% (EtOH w/0.05% DEA) as cosolvent), to yield 1-(4-((3R,5S or 3S,5R)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol (first eluting peak) and 1-(4-((3S,5R or 3R,5S)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol (second eluting peak), corresponding to Example 90 and Example 91, respectively For Example 90: LCMS ($C_{23}H_{29}FN_8O_2$) (ES, m/z) [M+H]+: 469. ¹H NMR (400 MHz, METHANOL-$d_4$) δ=7.66 (d, J=10.8 Hz, 1H), 7.32 (d, J=10.0 Hz, 2H), 6.94 (d, J=7.8 Hz, 1H), 3.98 (s, 2H), 3.91 (s, 3H), 3.81-3.71 (m, 1H), 3.38 (br d, J=9.0 Hz, 1H), 3.32-3.22 (m, 2H), 2.69 (t, J=11.6 Hz, 1H), 2.32-2.13 (m, 2H), 2.02-1.89 (m, 1H), 1.36 (q, J=12.5 Hz, 1H), 1.14 (s, 6H), 1.00 (d, J=6.6 Hz, 3H).

For Example 91: LCMS ($C_{23}H_{29}FN_8O_2$) (ES, m/z) [M+H]+: 469. ¹H NMR (400 MHz, METHANOL-$d_4$) δ=7.68 (d, J=10.8 Hz, 1H), 7.37 (d, J=19.1 Hz, 2H), 6.98 (d, J=7.8 Hz, 1H), 3.99 (s, 2H), 3.93 (s, 3H), 3.84-3.76 (m, 1H), 3.42 (br d, J=10.3 Hz, 1H), 3.34-3.26 (m, 2H), 2.77 (t, J=11.6 Hz, 1H), 2.32-2.20 (m, 2H), 1.99 (br d, J=6.6 Hz, 1H), 1.40 (q, J=12.5 Hz, 1H), 1.19-1.09 (m, 7H), 1.02 (d, J=6.6 Hz, 3H).

Example 92: rac-1-(4-((3R,5R or 3S,5S)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol

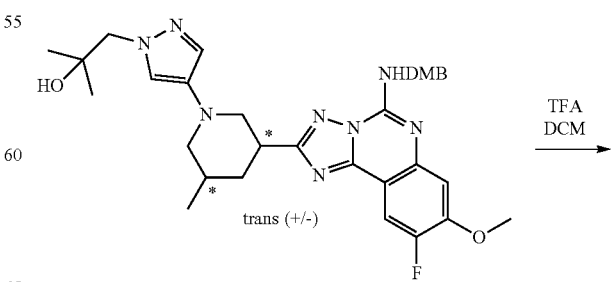

Intermediate 123

251

-continued

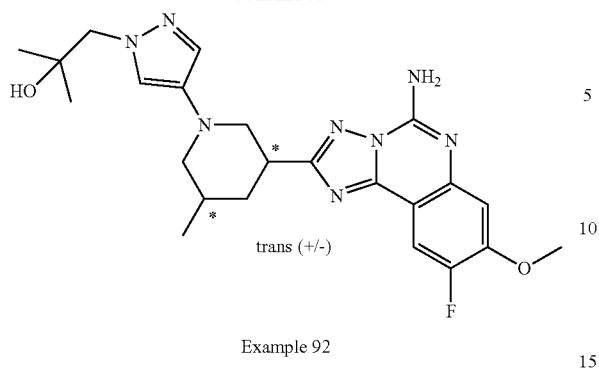

trans (+/−)

Example 92

To a solution of 1-(4-((3R,5R and 3S,5S)-3-(5-((2,4-dimethoxybenzyl)amino)-9-fluoro-8-methoxy-[1,2,4]triazolo[1,5-c]quinazolin-2-yl)-5-methylpiperidin-1-yl)-1H-pyrazol-1-yl)-2-methylpropan-2-ol (Intermediate 123) (20 mg, 0.032 mmol) in DCM (2 mL) was added TFA (2 mL). The mixture was stirred and heated at 45° C. for 5 h. The mixture was concentrated. The residue was purified by reversed-phase HPLC (Waters SunFire C18 OBD Prep Column, 19 mm×100 mm with MeCN/water (w/0.1% TFA as modifier) as eluent), to yield 1-(4-((3R,5R and 3S,5S)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol. LCMS ($C_{23}H_{29}FN_8O_2$) (ES, m/z) [M+H]$^+$: 469. $^1$H NMR (400 MHz, METHANOL-$d_4$) δ=8.02-7.90 (m, 2H), 7.73 (s, 1H), 7.27-7.15 (m, 1H), 4.22 (br d, J=11.2 Hz, 1H), 4.13-4.07 (m, 2H), 4.00 (s, 4H), 3.78-3.65 (m, 2H), 3.57-3.47 (m, 1H), 3.11 (t, J=11.0 Hz, 1H), 2.54 (br d, J=13.7 Hz, 1H), 2.27-2.14 (m, 1H), 1.90-1.80 (m, 1H), 1.17 (s, 6H), 1.11 (d, J=6.8 Hz, 3H).

Example 93: (R)-5-(4-(3-(5-amino-9-fluoro-8-methoxy-[1,2,4]triazolo[1,5-c]quinazolin-2-yl)piperidin-1-yl)-1H-pyrazol-1-yl)pentan-2-one

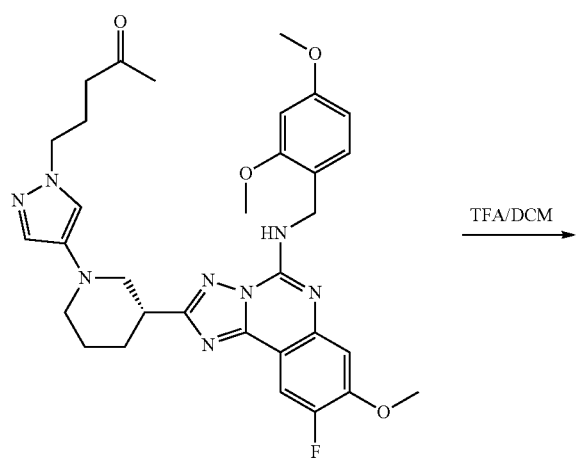

Intermediate 124

→ TFA/DCM

252

-continued

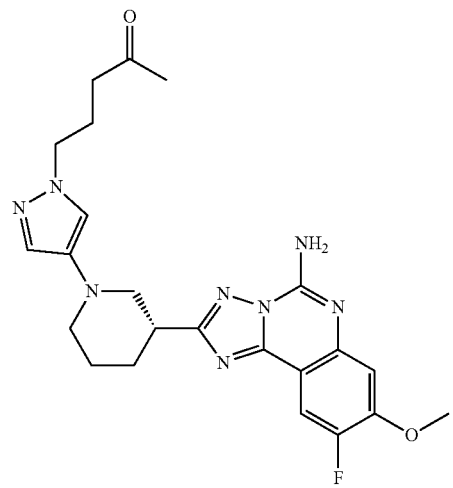

Example 93

To a stirred mixture of TFA (0.5 mL) in DCM (0.5 mL) was added (R)-5-(4-(3-(5-((2,4-dimethoxybenzyl)amino)-9-fluoro-8-methoxy-[1,2,4]triazolo[1,5-c]quinazolin-2-yl)piperidin-1-yl)-1H-pyrazol-1-yl)pentan-2-one (Intermediate 124) (28.0 mg, 0.0450 mmol). The mixture was stirred and heated at 50° C. for 15 h. The mixture was cooled, and the solvents were evaporated. The resulting residue was purified by preparative reversed-phase HPLC (Waters SunFire C18 OBD Prep Column, 19 mm×100 mm with MeCN/water (w/0.1% TFA as modifier) as eluent), to yield (R)-5-(4-(3-(5-amino-9-fluoro-8-methoxy-[1,2,4]triazolo[1,5-c]quinazolin-2-yl)piperidin-1-yl)-1H-pyrazol-1-yl)pentan-2-one. LCMS ($C_{23}H_{27}FN_8O_2$) (ES, m/z) [M+H]$^+$: 467. $^1$H NMR (400 MHz, CD$_3$OD) δ: 7.90 (d, J=10.96 Hz, 1H), 7.36 (s, 1H), 7.31 (s, 1H), 7.19 (d, J=7.45 Hz, 1H), 4.62 (br s, 1H), 4.05 (t, J=6.80 Hz, 2H), 3.99 (s, 3H), 3.67-3.78 (m, 1H), 3.39 (br d, J=11.84 Hz, 1H), 2.95 (t, J=11.18 Hz, 1H), 2.60-2.74 (m, 1H), 2.44 (t, J=7.02 Hz, 2H), 2.28 (br d, J=9.21 Hz, 1H), 2.10 (s, 3H), 2.02 (quin, J=7.02 Hz, 2H), 1.81-1.95 (m, 3H).

Example 94 and 95: (S or R)-5-(4-((R)-3-(5-amino-9-fluoro-8-methoxy-[1,2,4]triazolo[1,5-c]quinazolin-2-yl)piperidin-1-yl)-1H-pyrazol-1-yl)pentan-2-ol and (R or S)-5-(4-((R)-3-(5-amino-9-fluoro-8-methoxy-[1,2,4]triazolo[1,5-c]quinazolin-2-yl)piperidin-1-yl)-1H-pyrazol-1-yl)pentan-2-ol

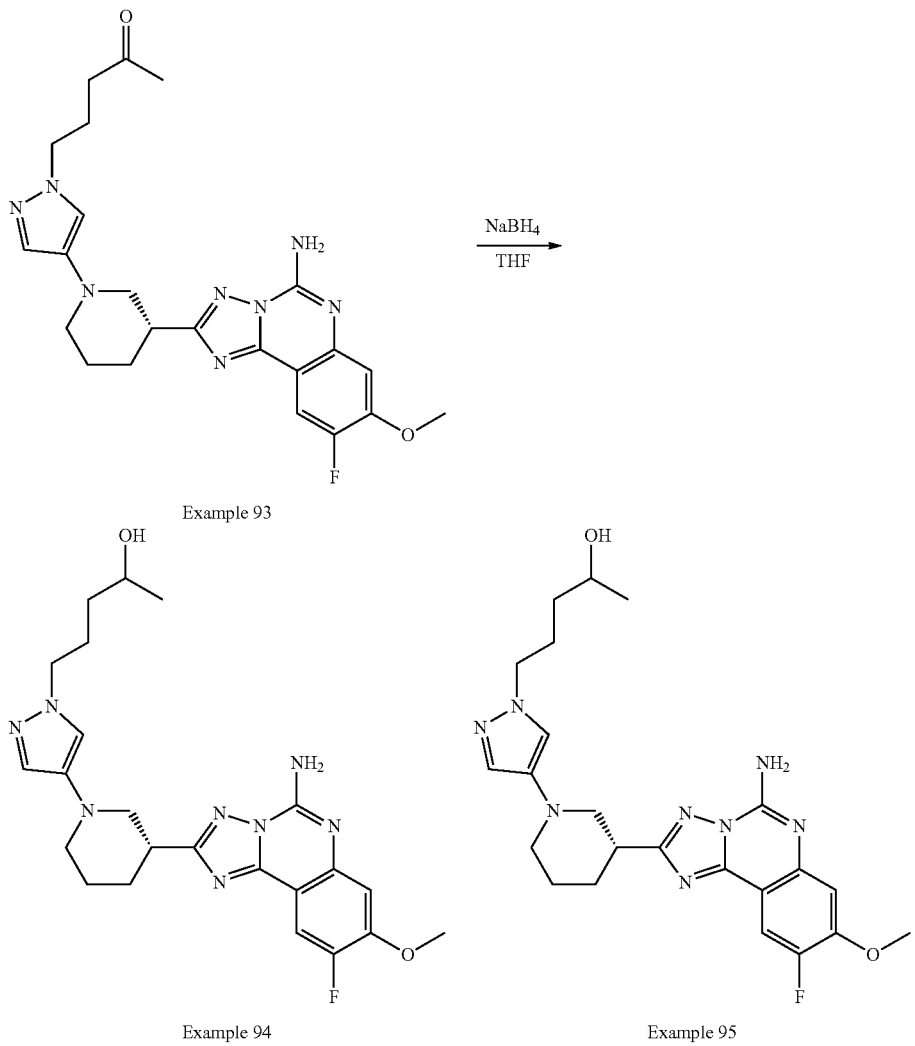

To a stirred mixture of (R)-5-(4-(3-(5-amino-9-fluoro-8-methoxy-[1,2,4]triazolo[1,5-c]quinazolin-2-yl)piperidin-1-yl)-1H-pyrazol-1-yl)pentan-2-one (Example 93) (15.0 mg, 0.0320 mmol) in THF (2 mL) was added NaBH$_4$ (2.4 mg, 0.064 mmol). The mixture was stirred at 25° C. for 3 h. The reaction mixture was quenched with 1 M aqueous HCl (2 mL). The mixture was extracted with EtOAc (2×30 mL), and the organic layer was dried over sodium sulfate, filtered and then the solvents of the filtrate were evaporated. The residue was purified by reversed-phase HPLC (Waters SunFire C18 OBD Prep Column, 19 mm×100 mm with MeCN/water (w/0.1% TFA as modifier) as eluent), to afford (S or R)-5-(4-((R)-3-(5-amino-9-fluoro-8-methoxy-[1,2,4]triazolo[1,5-c]quinazolin-2-yl)piperidin-1-yl)-1H-pyrazol-1-yl)pentan-2-ol and (R or S)-5-(4-((R)-3-(5-amino-9-fluoro-8-methoxy-[1,2,4]triazolo[1,5-c]quinazolin-2-yl)piperidin-1-yl)-1H-pyrazol-1-yl)pentan-2-ol, corresponding to Example 94 and Example 95, respectively.

For Example 94: LCMS ($C_{23}H_{29}FN_8O_2$) (ES, m/z) [M+H]$^+$: 469. $^1$H NMR (400 MHz, CD$_3$OD) δ: 7.94 (d, J=10.83 Hz, 1H), 7.89 (s, 1H), 7.67 (s, 1H), 7.25 (d, J=7.63 Hz, 1H), 4.19 (br t, J=7.10 Hz, 2H), 4.08-4.00 (m, 4H), 3.78-3.66 (m, 2H), 3.57 (br s, 2H), 3.36 (t, J=1.68 Hz, 1H), 2.40 (br s, 1H), 2.16-1.85 (m, 5H), 1.48-1.36 (m, 2H), 1.17 (d, J=6.26 Hz, 3H).

For Example 95: LCMS ($C_{23}H_{29}FN_8O_2$) (ES, m/z) [M+H]$^+$: 469. $^1$H NMR (400 MHz, CD$_3$OD) δ: 7.95 (d, J=10.68 Hz, 1H), 7.46 (s, 1H), 7.37 (s, 1H), 7.24 (d, J=7.78 Hz, 1H), 4.11 (t, J=6.87 Hz, 3H), 4.03 (s, 4H), 3.84-3.62 (m, 3H), 3.48-3.37 (m, 5H), 3.31 (br s, 1H), 3.19 (s, 1H), 2.33 (s, 1H), 2.02-1.77 (m, 5H), 1.41 (br d, J=5.80 Hz, 2H), 1.16 (d, J=6.10 Hz, 3H).

Example 96 and Example 97: rac-(1r,4s or 1r,4r)-4-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-1-methylcyclohexan-1-ol and rac-(1r,4r or 1r,4s)-4-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-1-methylcyclohexan-1-ol

Step 1: 4-nitro-1-(1,4-dioxaspiro[4.5]decan-8-yl)-1H-pyrazole

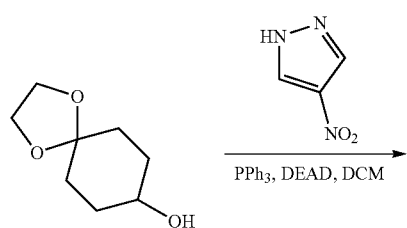

To a stirred mixture of 1,4-dioxaspiro[4.5]decan-8-ol (5.00 g, 31.6 mmol), PPh₃ (12.4 g, 47.4 mmol), and 4-nitro-1H-pyrazole (4.29 g, 37.9 mmol) in DCM (80 mL) was added di-tert-butyl diazene-1,2-dicarboxylate (18.2 g, 79.0 mmol) under a nitrogen atmosphere, and the mixture was stirred at 25° C. for 10 h. The mixture was concentrated and purified by silica gel chromatography with 10-25% EtOAc in petroleum ether as eluent to afford 4-nitro-1-(1,4-dioxaspiro[4.5]decan-8-yl)-1H-pyrazole. LCMS (C₁₁H₁₅N₃O₄) (ES, m/z) [M+H]⁺: 254.

Step 2: 1-(1,4-dioxaspiro[4.5]decan-8-yl)-1H-pyrazol-4-amine

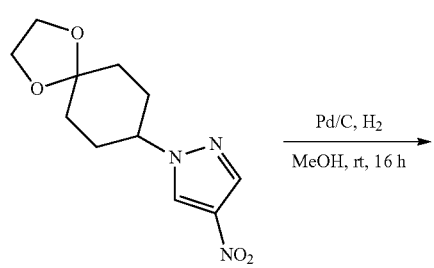

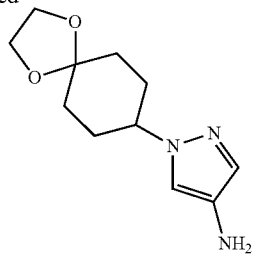

To a stirred mixture of 4-nitro-1-(1,4-dioxaspiro[4.5]decan-8-yl)-1H-pyrazole (5.50 g, 21.7 mmol) in MeOH (50 mL) and EtOAc (50 mL) was added 10% Pd/C (0.462 g, 4.34 mmol). The mixture was purged with nitrogen twice and was stirred under an atmosphere of hydrogen for 6 h. The mixture was filtered and the solvents were evaporated. The resulting residue was purified by silica gel chromatography with 20-50% EtOAc in petroleum ether as eluent to afford 1-(1,4-dioxaspiro[4.5]decan-8-yl)-1H-pyrazol-4-amine. LCMS (C₁₁H₁₇N₃O₂) (ES, m/z) [M+H]⁺: 224.

Step 3: methyl 1-(1-(1,4-dioxaspiro[4.5]decan-8-yl)-1H-pyrazol-4-yl)-6-methylpiperidine-3-carboxylate

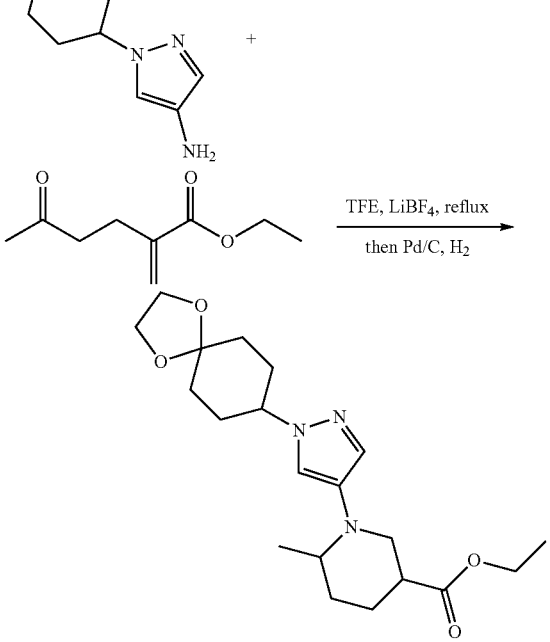

To a stirred mixture of 1-(1,4-dioxaspiro[4.5]decan-8-yl)-1H-pyrazol-4-amine (2.14 g, 9.60 mmol) and lithium tetrafluoroborate (0.600 g, 6.40 mmol) in TFE (15 mL) was added ethyl 2-methylene-5-oxohexanoate (1.00 g, 5.88 mmol). The mixture was stirred and heated at 80° C. for 10 h. The mixture was cooled, diluted with water (15 mL), and extracted with EtOAc (2×30 mL). The organic layer was dried (anhydrous Na₂SO₄), filtered, and the solvents of the filtrate were evaporated. To the resulting residue was added MeOH (15 mL) and 10% Pd/C (0.068 g, 0.64 mmol). The mixture was degassed and purged with nitrogen twice and was stirred under an atmosphere of hydrogen for 10 h. The mixture was filtered, and then the filtrate was concentrated. The residue was purified by silica gel chromatography with 10-50% EtOAc in petroleum ether as eluent to afford ethyl 1-(1-(1,4-dioxaspiro[4.5]decan-8-yl)-1H-pyrazol-4-yl)-6-methylpiperidine-3-carboxylate. LCMS ($C_{20}H_{31}N_3O_4$) (ES, m/z) [M+H]$^+$: 378.

Step 4: 1-(1-(1,4-dioxaspiro[4.5]decan-8-yl)-1H-pyrazol-4-yl)-6-methylpiperidine-3-carbohydrazide

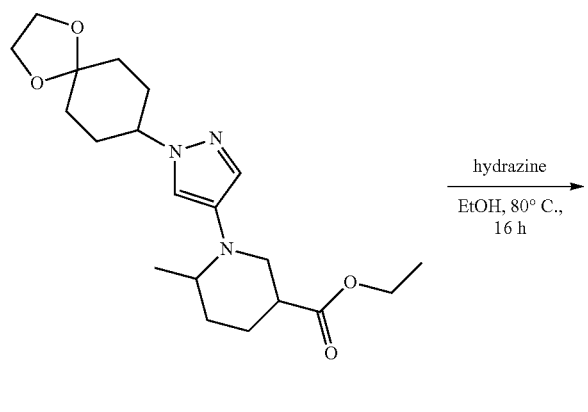

Step 5: rac-2-((3R,6S or 3S,6R)-1-(1-(1,4-dioxaspiro[4.5]decan-8-yl)-1H-pyrazol-4-yl)-6-methylpiperidin-3-yl)-N-(2,4-dimethoxybenzyl)-9-fluoro-8-methoxy-[1,2,4]triazolo[1,5-c]quinazolin-5-amine

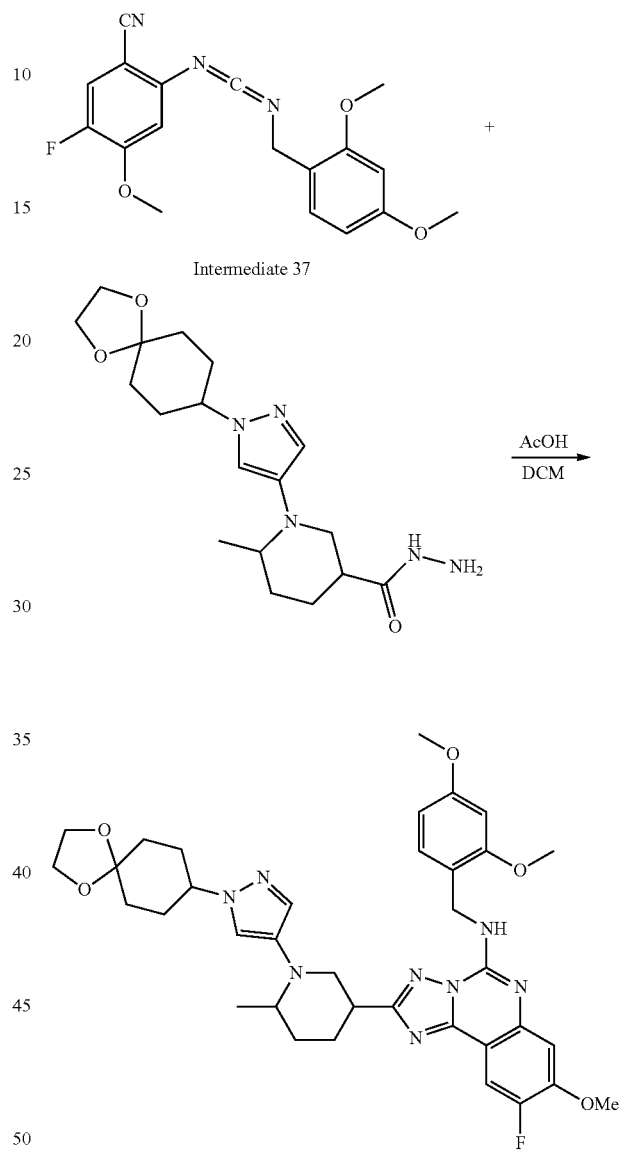

To a stirred mixture of 1-(1-(1,4-dioxaspiro[4.5]decan-8-yl)-1H-pyrazol-4-yl)-6-methylpiperidine-3-carboxylate (450 mg, 1.192 mmol) in EtOH (10 mL) was added hydrazine hydrate (382 mg, 11.92 mmol). The mixture was stirred and heated at 80° C. for 10 h. The mixture was concentrated to afford 1-(1-(1,4-dioxaspiro[4.5]decan-8-yl)-1H-pyrazol-4-yl)-6-methylpiperidine-3-carbohydrazide, which was used without further purification. LCMS ($C_{18}H_{29}N_5O_3$) (ES, m/z) [M+H]$^+$ 364.

A 40 mL vial was charged with 1-(1-(1,4-dioxaspiro[4.5] decan-8-yl)-1H-pyrazol-4-yl)-6-methylpiperidine-3-carbohydrazide (351 mg, 0.967 mmol) and DCM (2 mL). To this mixture was added AcOH (0.025 mL, 0.44 mmol) followed by 2-((((2,4-dimethoxybenzyl)imino)methylene)amino)-5-fluoro-4-methoxybenzonitrile (Intermediate 37) (300 mg, 0.879 mmol). The mixture was stirred and heated at 35° C. for 16 h. The mixture was then concentrated. The resulting residue was purified by silica gel chromatography with 10-50% EtOAc in petroleum ether as eluent to afford the cis diastereomer, 2-((3R,6S and 3S,6R)-1-(1-(1,4-dioxaspiro[4.5]decan-8-yl)-1H-pyrazol-4-yl)-6-methylpiperidin-3-yl)-N-(2,4-dimethoxybenzyl)-9-fluoro-8-methoxy-[1,2,4]triazolo[1,5-c]quinazolin-5-amine. LCMS ($C_{36}H_{43}FN_8O_5$) (ES, m/z) [M+H]$^+$ 687.

Step 6: 4-(4-((2S,5R and 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)cyclohexanone

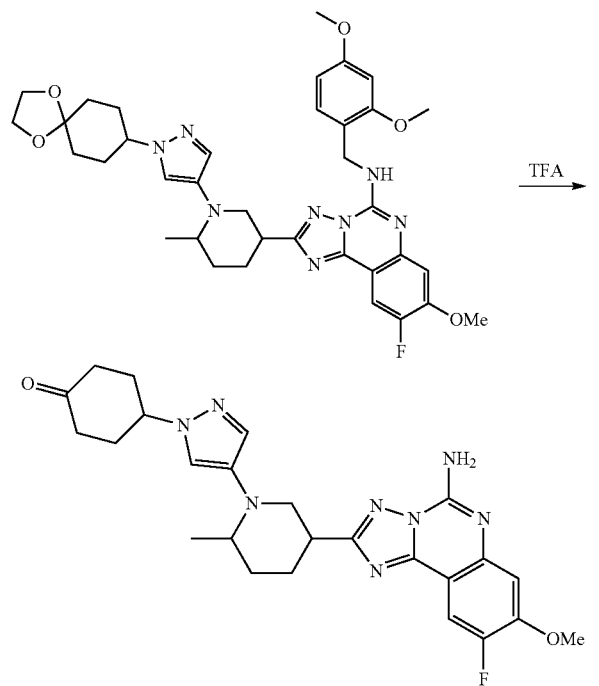

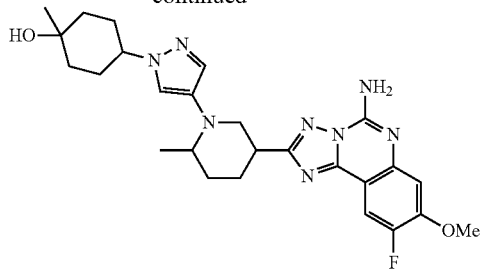

Example 96

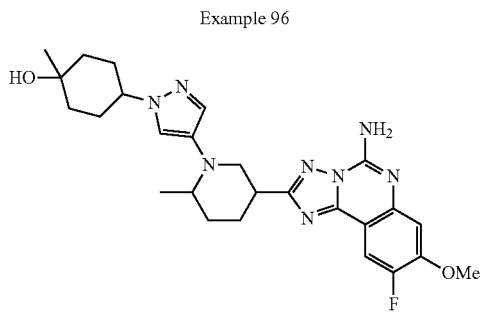

Example 97

To a stirred mixture of 2-((3R,6S and 3S,6R)-1-(1-(1,4-dioxaspiro[4.5]decan-8-yl)-1H-pyrazol-4-yl)-6-methylpiperidin-3-yl)-N-(2,4-dimethoxybenzyl)-9-fluoro-8-methoxy-[1,2,4]triazolo[1,5-c]quinazolin-5-amine (40.0 mg, 0.0580 mmol) in DCM (2 mL) was added TFA (2 mL). The mixture was stirred for 10 h. The mixture was concentrated. To the residue was added saturated aqueous sodium bicarbonate. The mixture was extracted with EtOAc (2×5 mL). The combined organic layer was dried over anhydrous Na$_2$SO$_4$, filtered, and the solvents of the filtrate were evaporated. The resulting residue was purified by preparative silica gel TLC with EtOAc as eluent to afford rac-4-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)cyclohexanone. LCMS (C$_{25}$H$_{29}$FN$_8$O$_2$) (ES, m/z) [M+H]$^+$ 493.

Step 7: (1r,4s or 1r,4r)-4-(4-((2S,5R and 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-1-methylcyclohexan-1-ol and (1r,4r or 1r,4s)-4-(4-((2S,5R and 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-1-methylcyclohexan-1-ol

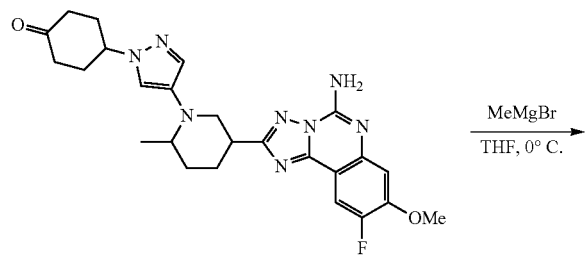

To a stirred mixture of rac-4-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)cyclohexanone (18 mg, 0.037 mmol) in THF (5 mL) was added methylmagnesium bromide (0.122 mL, 0.365 mmol). The mixture was stirred at 0° C. for 12 h. The reaction mixture was quenched with aqueous NH$_4$Cl (5 mL) and extracted with EtOAc (2×5 mL). The combined organic layer was dried over anhydrous Na$_2$SO$_4$, filtered, and the solvents of the filtrate were evaporated. The resulting residue was purified by preparative reversed-phase HPLC (Waters SunFire C18 OBD Prep Column, 19 mm×100 mm with MeCN/water (w/0.1% TFA modifier) as eluent) to afford (1r,4s or 1r,4r)-4-(4-((2S,5R and 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-1-methylcyclohexan-1-ol and (1r,4r or 1r,4s)-4-(4-((2S,5R and 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-1-methylcyclohexan-1-ol, corresponding to Example 96 and Example 97.

For Example 96: $^1$H NMR (400 MHz, MeOD) δ 7.98 (s, 1H), 7.92 (d, J=11.2 Hz, 1H), 7.68 (s, 1H), 7.22 (d, J=7.6 Hz, 1H), 4.18-4.29 (m, 1H), 4.01 (s, 4H), 3.85-3.97 (m, 2H), 3.63-3.65 (m, 1H), 2.46-2.48 (m, 1H), 2.15-2.30 (m, 2H), 1.90-2.13 (m, 5H), 1.73-1.84 (m, 2H), 1.60-1.72 (m, 2H), 1.31 (s, 3H), 1.20 (d, J=6.8 Hz, 3H). LCMS (C$_{26}$H$_{33}$FN$_8$O$_2$) (ES, m/z) [M+H]$^+$ 509.

For Example 97: $^1$H NMR (400 MHz, MeOD) δ 8.01 (s, 1H), 7.91 (d, J=11.2 Hz, 1H), 7.70 (s, 1H), 7.21 (d, J=8.0 Hz, 1H), 4.06-4.25 (m, 2H), 4.00 (s, 3H), 3.84-3.98 (m, 2H), 3.65-3.68 (m, 1H), 2.48-2.50 (m, 1H), 2.10-2.32 (m, 3H), 2.02-2.08 (m, 2H), 1.87-1.96 (m, 2H), 1.80-1.82 (m, 2H), 1.56-1.67 (m, 2H), 1.25 (s, 3H), 1.21 (d, J=6.8 Hz, 3H). LCMS (C$_{26}$H$_{33}$FN$_8$O$_2$) (ES, m/z) [M+H]$^+$ 509.

Example 98 and 99: (1S or 1R,2S or 2R)-2-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclobutan-1-ol and (1R or 1S,2R or 2S)-2-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclobutan-1-ol

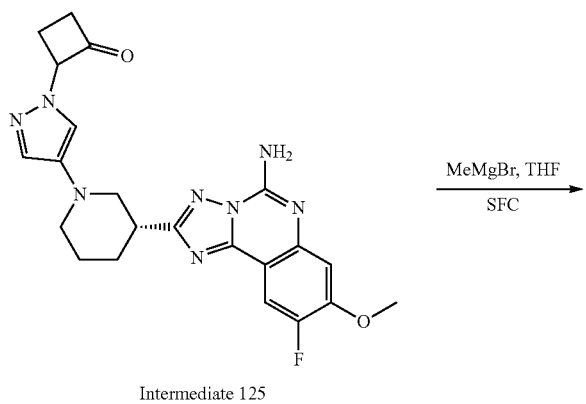

lin-2-yl)piperidin-1-yl)-1H-pyrazol-1-yl)-1-methylcyclobutan-1-ol (first eluting peak) and (1R or 1S,2R or 2S)-2-(4-((R)-3-(5-amino-9-fluoro-8-methoxy-[1,2,4]triazolo[1,5-c]quinazolin-2-yl)piperidin-1-yl)-1H-pyrazol-1-yl)-1-methylcyclobutan-1-ol (second eluting peak) corresponding to Example 98 and Example 99, respectively.

For Example 98: LCMS ($C_{23}H_{27}FN_8O_2$) (ES, m/z) [M+H]$^+$: 467. $^1$H NMR (400 MHz, CD$_3$OD) δ=7.98 (d, J=10.68 Hz, 1H), 7.37 (s, 1H), 7.15 (d, J=7.48 Hz, 1H), 7.09 (s, 1H), 5.78 (br s, 2H), 4.48-4.34 (m, 1H), 4.05-3.96 (m, 3H), 3.81-3.73 (m, 1H), 3.72-3.62 (m, 1H), 3.42-3.31 (m, 2H), 2.98 (t, J=11.06 Hz, 1H), 2.76-2.59 (m, 1H), 2.52-2.38 (m, 1H), 2.33-2.15 (m, 3H), 2.06-1.77 (m, 5H), 1.42 (s, 3H).

For Example 99: LCMS ($C_{23}H_{27}FN_8O_2$) (ES, m/z) [M+H]$^+$: 467. $^1$H NMR (400 MHz, CD$_3$OD) δ=7.98 (d, J=10.68 Hz, 1H), 7.37 (s, 1H), 7.15 (d, J=7.48 Hz, 1H), 7.09 (s, 1H), 5.78 (br s, 2H), 4.48-4.34 (m, 1H), 4.05-3.96 (m, 3H), 3.81-3.73 (m, 1H), 3.72-3.62 (m, 1H), 3.42-3.31 (m, 2H), 2.98 (t, J=11.06 Hz, 1H), 2.76-2.59 (m, 1H), 2.52-2.38 (m, 1H), 2.33-2.15 (m, 3H), 2.06-1.77 (m, 5H), 1.42 (s, 3H).

Example 100: (R)-9-fluoro-7-methoxy-2-(1-(1-methyl-1H-pyrazol-4-yl)piperidin-3-yl)-[1,2,4]triazolo[1,5-c]quinazolin-5-amine

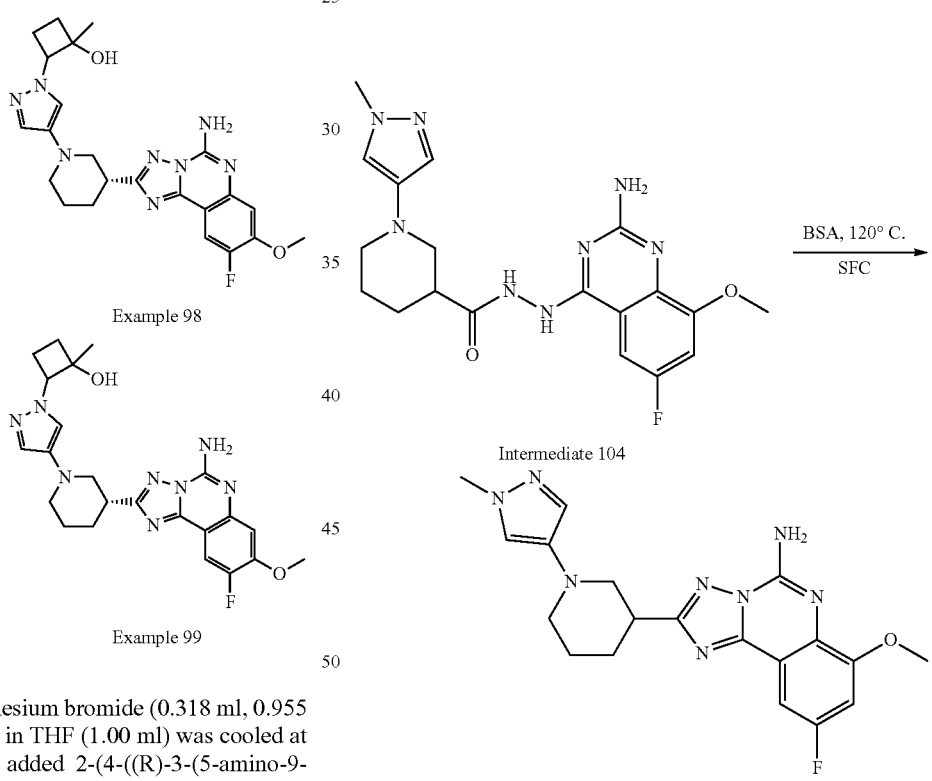

A mixture of methylmagnesium bromide (0.318 ml, 0.955 mmol, 3 M in diethyl ether) in THF (1.00 ml) was cooled at 0° C. To the mixture was added 2-(4-((R)-3-(5-amino-9-fluoro-8-methoxy-[1,2,4]triazolo[1,5-c]quinazolin-2-yl)piperidin-1-yl)-1H-pyrazol-1-yl)cyclobutanone (Intermediate 125) (86.0 mg, 0.191 mmol) in THF (1.0 mL) The mixture was stirred at 0° C. for 5 h. To the mixture was added water (3 mL), and then the mixture was extracted with EtOAc (3×20 mL). The combined organic layers were dried over anhydrous Na$_2$SO$_4$, filtered, and the solvents of the filtrate were evaporated. The resulting residue was purified by preparative silica gel TLC with 10% MeOH in DCM as eluent. The isomeric mixture was purified by SFC (OJ-3 100×4.6 mm column with 5-40% (MeOH w/0.05% DEA) as co-solvent) to afford (1S or 1R,2S or 2R)-2-(4-((R)-3-(5-amino-9-fluoro-8-methoxy-[1,2,4]triazolo[1,5-c]quinazo- BSA (2 mL, 8.18 mmol) was added to N'-(2-amino-6-fluoro-8-methoxyquinazolin-4-yl)-1-(1-methyl-1H-pyrazol-4-yl)piperidine-3-carbohydrazide (Intermediate 104) (25.0 mg, 0.0600 mmol), and the mixture was stirred at 120° C. for 2 h. The solvents were then evaporated. The resulting residue was diluted with chloroform/isopropanol—3:1 (5 mL), washed with aqueous sodium bicarbonate (saturated, 5 mL), and the organic layer collected using a phase separator column (25 mL) and concentrated. The residue was purified by preparative reversed-phase HPLC (Waters SunFire C18

OBD Prep Column, 19 mm×100 mm MeCN/water (with 0.1% TFA modifier) as eluent). The racemic mixture was resolved by chiral SFC separation (OJ-H column 21×250 mm column with 20% (MeOH w/0.25% DMEA modifier) as co-solvent) to afford (R or S)-9-fluoro-7-methoxy-2-(1-(1-methyl-1H-pyrazol-4-yl)piperidin-3-yl)-[1,2,4]triazolo[1,5-c]quinazolin-5-amine (Example 100, first eluting peak). LCMS ($C_{19}H_{21}FN_8O$) (ES, m/z): 397 [M+H]$^+$. $^1$H NMR (600 MHz, DMSO-$d_6$) δ 7.79 (s, 2H), 7.42 (dd, J=8.4, 2.7 Hz, 1H), 7.30 (s, 1H), 7.21-7.16 (m, 2H), 3.93 (s, 3H), 3.72 (s, 3H), 3.60 (dd, J=11.5, 3.7 Hz, 1H), 3.32-3.30 (m, 1H), 3.29-3.23 (m, 1H), 2.83 (t, J=11.1 Hz, 1H), 2.58-2.52 (m, 2H), 2.20-2.12 (m, 1H), 1.88-1.81 (m, 1H), 1.80-1.74 (m, 2H).

The example compounds of the invention in following Table 24 were prepared from the appropriate intermediates in a manner similar to Example 100, with the exception that the starting materials were enantiopure, thus no SFC separation was conducted for these examples.

TABLE 24

| Example | Structure Name | Observed m/z [M + H]$^+$ |
|---|---|---|
| 101 | (R or S)-8,9-difluoro-2-(1-(1-methyl-1H-pyrazol-4-yl)piperidin-3-yl)-[1,2,4]triazolo[1,5-c]quinazolin-5-amine | 385 |
| 102 | (R or S)-9-fluoro-2-(1-(1-methyl-1H-pyrazol-4-yl)piperidin-3-yl)-[1,2,4]triazolo[1,5-c]quinazolin-5-amine | 367 |
| 103 | (R or S)-7,9-difluoro-2-(1-(1-methyl-1H-pyrazol-4-yl)piperidin-3-yl)-[1,2,4]triazolo[1,5-c]quinazolin-5-amine | 385 |
| 104 | (R or S)-9-chloro-7-methoxy-2-(1-(1-methyl-1H-pyrazol-4-yl)piperidin-3-yl)-[1,2,4]triazolo[1,5-c]quinazolin-5-amine | 413 |
| 105 | (R or S)-9-chloro-7-methyl-2-(1-(1-methyl-1H-pyrazol-4-yl)piperidin-3-yl)-[1,2,4]triazolo[1,5-c]quinazolin-5-amine | 397 |
| 106 | (R or S)-9-chloro-2-(1-(1-methyl-1H-pyrazol-4-yl)piperidin-3-yl)-[1,2,4]triazolo[1,5-c]quinazolin-5-amine | 383 |

TABLE 24-continued

| Example | Structure Name | Observed m/z [M + H]+ |
|---|---|---|
| 107 | (R or S)-9,10-difluoro-2-(1-(1-methyl-1H-pyrazol-4-yl)piperidin-3-yl)-[1,2,4]triazolo[1,5-c]quinazolin-5-amine | 385 |
| 108 | (R or S)-9-methoxy-2-(1-(1-methyl-1H-pyrazol-4-yl)piperidin-3-yl)-[1,2,4]triazolo[1,5-c]quinazolin-5-amine | 379 |

Example 109: 1-(4-((2S,5R)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropan-2-ol Step 1: 1-(4-((2S,5R)-5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)-2-methylpropan-2-ol

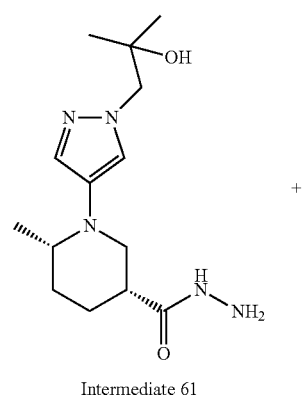

Intermediate 61

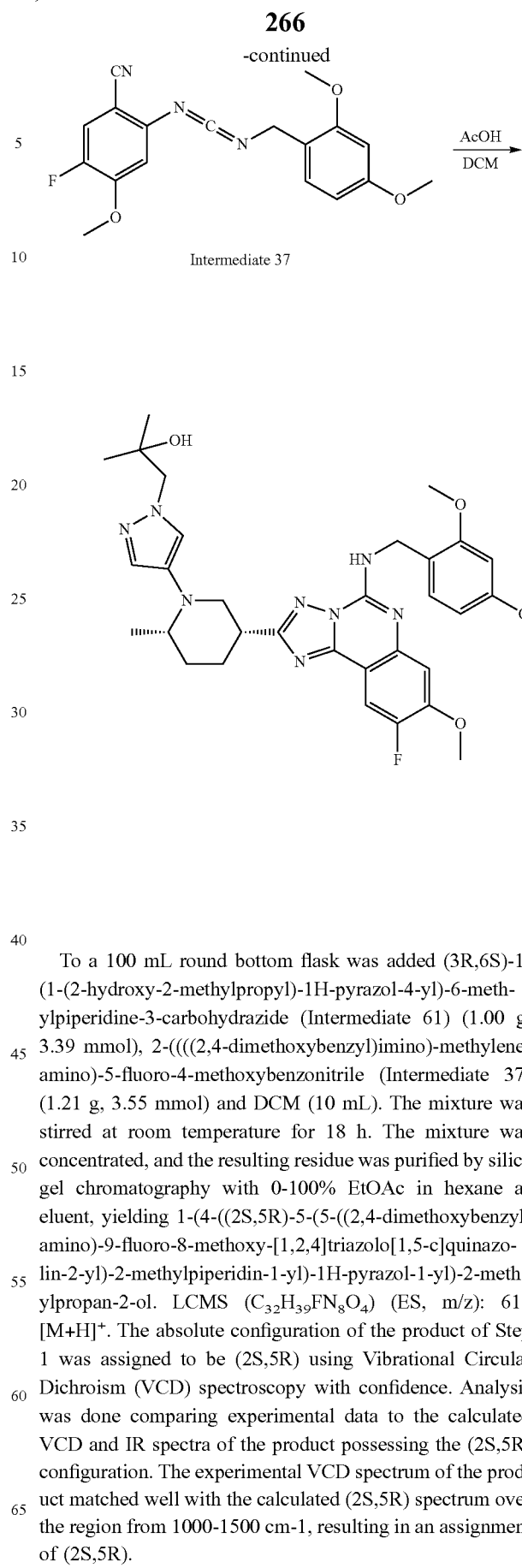

To a 100 mL round bottom flask was added (3R,6S)-1-(1-(2-hydroxy-2-methylpropyl)-1H-pyrazol-4-yl)-6-methylpiperidine-3-carbohydrazide (Intermediate 61) (1.00 g, 3.39 mmol), 2-((((2,4-dimethoxybenzyl)imino)-methylene)amino)-5-fluoro-4-methoxybenzonitrile (Intermediate 37) (1.21 g, 3.55 mmol) and DCM (10 mL). The mixture was stirred at room temperature for 18 h. The mixture was concentrated, and the resulting residue was purified by silica gel chromatography with 0-100% EtOAc in hexane as eluent, yielding 1-(4-((2S,5R)-5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)-2-methylpropan-2-ol. LCMS ($C_{32}H_{39}FN_8O_4$) (ES, m/z): 619 [M+H]+. The absolute configuration of the product of Step 1 was assigned to be (2S,5R) using Vibrational Circular Dichroism (VCD) spectroscopy with confidence. Analysis was done comparing experimental data to the calculated VCD and IR spectra of the product possessing the (2S,5R) configuration. The experimental VCD spectrum of the product matched well with the calculated (2S,5R) spectrum over the region from 1000-1500 cm-1, resulting in an assignment of (2S,5R).

Step 2: 1-(4-((2S,5R)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropan-2-ol

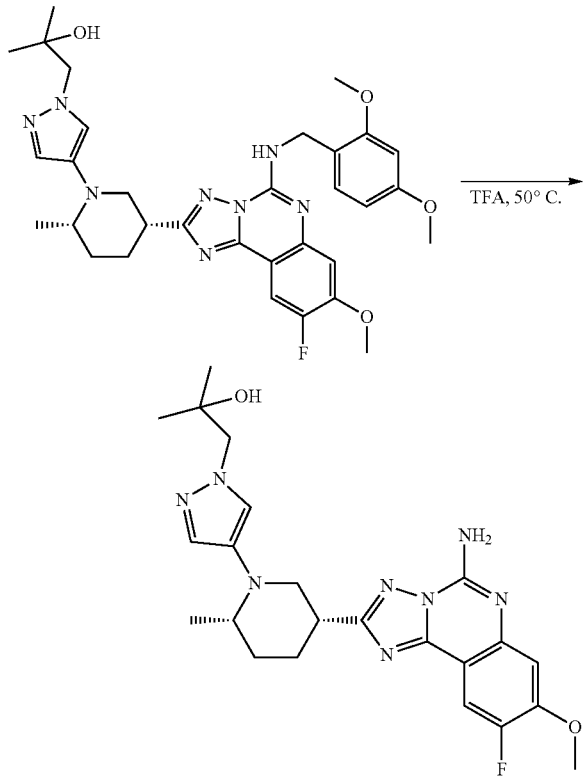

Example 109

To a 20 mL vial was added 1-(4-((2S,5R)-5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)-2-methylpropan-2-ol (962 mg, 1.56 mmol) and TFA (7 mL). The mixture was stirred and heated at 50° C. for 1 h. The mixture was then concentrated. To the resulting residue was added 1 M aqueous HCl (50 mL) and DCM (50 mL). The aqueous layer was washed with DCM (2×50 mL), then filtered. The pH of the aqueous layer was then adjusted to ~pH 10 with 10 M aqueous NaOH. The aqueous layer was extracted with 10% MeOH in DCM (2×100 mL). The organic layers were combined, dried over anhydrous sodium sulfate, filtered, and the solvents of the filtrate were evaporated. The resulting residue was purified by silica gel chromatography with 0-10% MeOH in DCM, yielding 1-(4-((2S,5R)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropan-2-ol (Example 109). LCMS ($C_{23}H_{29}FN_8O_2$) (ES, m/z): 469 [M+H]$^+$. $^1$H NMR (499 MHz, DMSO-$d_6$) δ 7.90 (d, J=11.0 Hz, 1H), 7.72 (s, 2H), 7.20 (s, 1H), 7.19 (d, J=7.9 Hz, 1H), 7.15 (s, 1H), 3.69 (d, J=6.7 Hz, 1H), 3.35 (d, J=3.9 Hz, 1H), 3.20 (dt, J=11.1, 5.8 Hz, 1H), 3.10 (t, J=11.5 Hz, 1H), 2.00 (d, J=6.1 Hz, 3H), 1.70 (d, J=9.3 Hz, 1H), 1.03 (d, J=4.4 Hz, 9H).

The example compounds of the invention in the following Table 25 were prepared in a manner similar to that described for the preparation of Example 109 from the appropriate hydrazide and carbodiimide intermediates.

TABLE 25

| Example | Structure Name | Observed m/z [M + H]$^+$ |
|---|---|---|
| 110 | 1-(4-((2S,5R)-5-(5-amino-8-chloro-9-fluoro-[1,2,4]triazolo[1,5-c[quinazolin-2-yl)-2-methylpiperidin-1-yl)-1H-pyrazol-1-yl)-2-methylpropan-2-ol | 473 |

TABLE 25-continued

| Example | Structure Name | Observed m/z [M + H]+ |
|---|---|---|
| 111 | 1-(4-((2S,5R)-5-(5-amino-7,9-difluoro-[1,2,4]triazolo[1,5-c]quinazolin-2-yl)-2-methylpiperidin-1-yl)-1H-pyrazol-1-yl)-2-methylpropan-2-ol | 457 |
| 112 | 1-(4-((2S,5R)-5-(5-amino-9-fluoro-8-methyl-[1,2,4]triazolo[1,5-c]quinazolin-2-yl)-2-methylpiperidin-1-yl)-1H-pyrazol-1-yl)-2-methylpropan-2-ol | 453 |
| 113 | (R)-7,9-dichloro-2-(1-(1-methyl-1H-pyrazol-4-yl)piperidin-3-yl)-[1,2,4]triazolo[1,5-c]quinazolin-5-amine | 417 |

Examples 114-117: 1-(4-((2R or 2S,5R or 5S)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol and 1-(4-((2S or 2R,5R or 5S)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol and 1-(4-((2S or 2R,5S or 5R)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol and 1-(4-((2R or 2S,5S or 5R)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol

Step 1: 1-(4-(5-(5-((2,4-dimethoxybenzyl)amino)-9-fluoro-7-methoxy-[1,2,4]triazolo[1,5-c]quinazolin-2-yl) 2-methylpiperidin-1-yl)-3-methyl-1H-pyrazol-1-yl)-2-methylpropan-2-ol

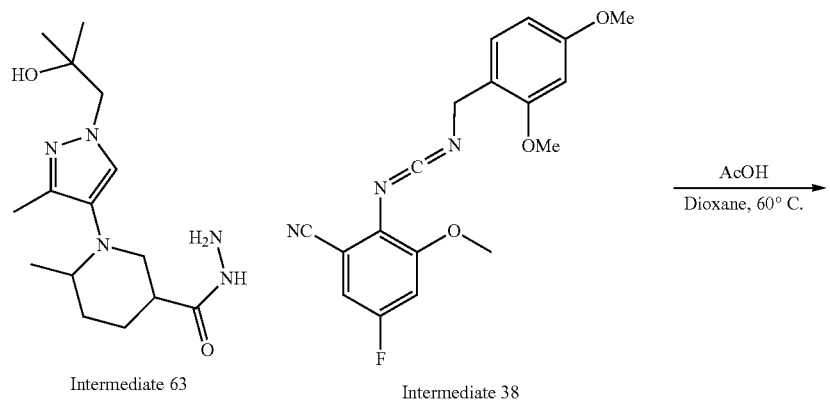

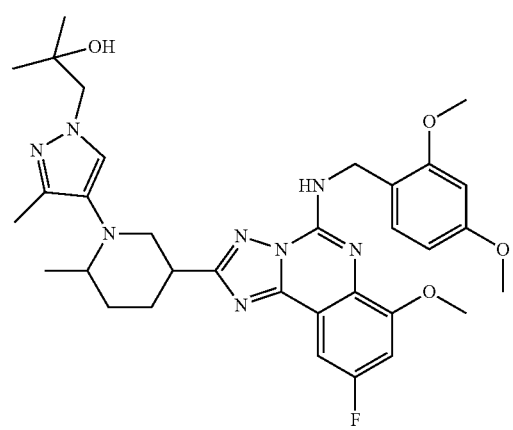

To a 2 dram vial was added 1-(1-(2-hydroxy-2-methylpropyl)-3-methyl-1H-pyrazol-4-yl)-6-methylpiperidine-3-carbohydrazide (Intermediate 63) (133 mg, 0.431 mmol) and 2-((((2,4-dimethoxybenzyl)imino)methylene)amino)-5-fluoro-3-methoxybenzonitrile (Intermediate 38) (140 mg, 0.410 mmol). To the mixture was added dioxane (1.6 mL) and acetic acid (24 µL, 0.41 mmol), and then the mixture was stirred and then heated at 60° C. for 2 h. The mixture was then allowed to slowly cool to room temperature. The mixture was diluted with DCM (10 mL) and washed with saturated aqueous sodium bicarbonate (2×10 mL) and brine. The combined organic layers were dried over anhydrous $MgSO_4$, filtered, and the solvents of the filtrate were evaporated. The residue was purified by silica gel chromatography with 10-100% EtOAc in hexanes to afford 1-(4-(5-(5-((2,4-dimethoxybenzyl)amino)-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol as a mixture of racemic diastereomers. LCMS ($C_{33}H_{42}FN_8O_4$) (ES, m/z): 633 [M+H]$^+$ Step 2: 1-(4-((2R or 2S,5R or 5S)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol and 1-(4-((2S or 2R,5R or 5S)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol and 1-(4-((2S or 2R,5S or 5R)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol and 1-(4-((2R or 2S,5S or 5R)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol

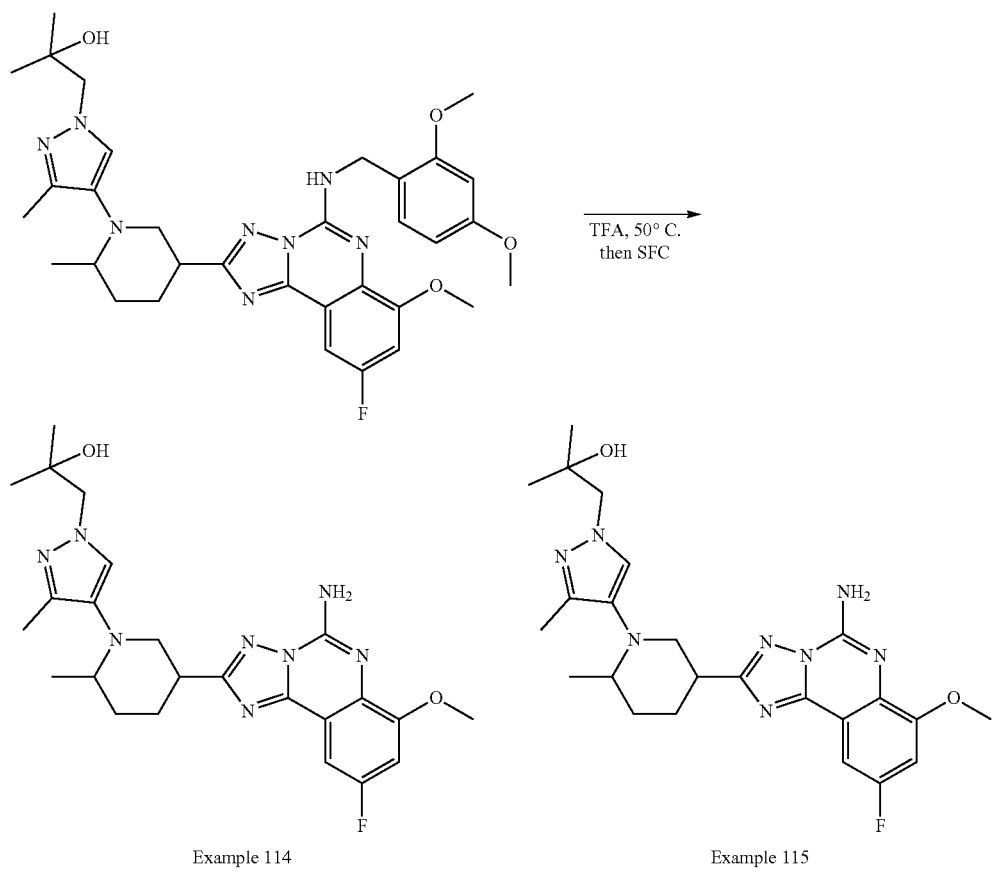

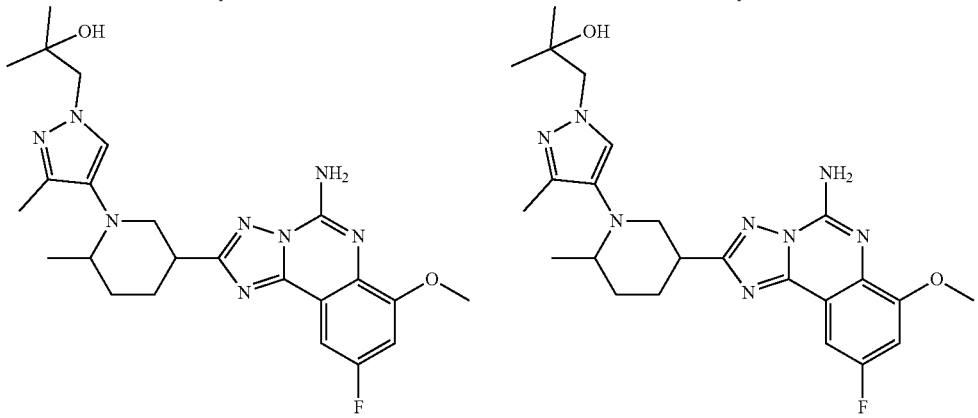

Example 114

Example 115

Example 116

Example 117

To a 20 mL vial was added 1-(4-(5-(5-(((2,4-dimethoxybenzyl)amino)-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol (80 mg, 0.126 mmol) followed by TFA (0.13 mL). The mixture was stirred and heated at 50° C. for 2 h. The mixture was then concentrated. The resulting residue was purified by preparative reversed-phase HPLC (Waters SunFire C18 OBD Prep Column, 19 mm×100 mm with MeCN/water w/0.1% TFA as eluent) to afford the product as a mixture of diastereomers. The four isomers were resolved by chiral SFC separation (IC, 21×250 mm column with 35% (2-Propanol w/0.1% NH$_4$OH modifier) as cosolvent) to afford 1-(4-((2R or 2S,5R or 5S)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol (Example 114, first eluting peak) and 1-(4-((2S or 2R,5R or 5S)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol (Example 115, second eluting peak) and 1-(4-((2S or 2R,5S or 5R)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol (Example 116, third eluting peak) and 1-(4-((2R or 2S,5S or 5R)-5-(5-amino-9-fluoro-7-methoxy-[1,2,4]triazolo[1,5-c]quinazolin-2-yl)-2-methylpiperidin-1-yl)-3-methyl-1H-pyrazol-1-yl)-2-methylpropan-2-ol (Example 117, fourth eluting peak).

For Example 114: LCMS ($C_{24}H_{32}FN_8O_2$) (ES, m/z): 483 [M+H]$^+$. $^1$H NMR (499 MHz, DMSO-d$_6$) δ 7.70 (br s, 2H), 7.42 (dd, J=8.4, 2.7 Hz, 1H), 7.30 (s, 1H), 7.18 (dd, J=11.1, 2.7 Hz, 1H), 4.75 (br s, 1H), 3.93 (s, 3H), 3.80 (s, 2H), 3.37-3.31 (m, 1H), 3.23-3.16 (m, 1H), 2.18-2.15 (m, 1H), 2.01 (s, 3H), 2.09-1.94 (m, 2H), 1.70-1.59 (m, 1H), 1.25-1.10 (m, 2H), 1.04 (s, 3H), 1.03 (s, 3H), 0.95 (d, J=12.0 Hz, 3H).

For Example 115: LCMS ($C_{24}H_{32}FN_8O_2$) (ES, m/z): 483 [M+H]$^+$. $^1$H NMR (499 MHz, DMSO-d$_6$) δ 7.61 (br s, 2H), 7.40 (dd, J=8.2, 2.4 Hz, 1H), 7.30 (s, 1H), 7.18 (dd, J=11.0, 2.1 Hz, 1H), 4.75 (br s, 1H), 3.93 (s, 3H), 3.80 (s, 2H), 3.38-3.30 (m, 1H), 3.19-3.12 (m, 1H), 2.15-2.10 (m, 1H), 2.07 (s, 3H), 2.09-1.94 (m, 2H), 1.72-1.65 (m, 1H), 1.25-1.10 (m, 2H), 1.07 (s, 3H), 1.06 (s, 3H), 0.93 (d, J=11.8 Hz, 3H).

For Example 116: LCMS ($C_{24}H_{32}FN_8O_2$) (ES, m/z): 483 [M+H]$^+$. $^1$H NMR (499 MHz, DMSO-d$_6$) δ 7.52 (br s, 2H), 7.41 (dd, J=8.4, 2.7 Hz, 1H), 7.39 (s, 1H), 7.15-7.11 (m, 1H), 4.41 (br s, 1H), 3.90 (s, 3H), 3.85 (s, 2H), 3.30-3.20 (m, 1H), 3.13-3.09 (m, 1H), 2.18-2.11 (m, 1H), 2.00 (s, 3H), 2.00-1.84 (m, 2H), 1.75-1.66 (m, 1H), 1.24-1.10 (m, 2H), 1.04 (m, 6H), 0.91 (d, J=6.5 Hz, 3H).

For Example 117: LCMS ($C_{24}H_{32}FN_8O_2$) (ES, m/z): 483 [M+H]$^+$. $^1$H NMR (499 MHz, DMSO-d$_6$) δ 7.77 (br s, 2H), 7.43 (dd, J=8.4, 2.7 Hz, 1H), 7.33 (s, 1H), 7.18 (dd, J=11.1, 2.7 Hz, 1H), 4.60 (br s, 1H), 3.94 (s, 3H), 3.83 (s, 2H), 3.26-3.22 (m, 1H), 3.10-3.06 (m, 1H), 2.18-2.16 (m, 1H), 2.04 (s, 3H), 2.01-1.87 (m, 2H), 1.75-1.69 (m, 1H), 1.24-1.10 (m, 2H), 1.03 (s, 3H), 1.02 (s, 3H), 0.93 (d, J=6.5 Hz, 3H).

The example compounds of the invention in the following Table 26 were prepared in a manner similar to that described for the preparation of Examples 114-117 from the appropriate hydrazide and carbodiimide intermediates. The resulting isomeric mixtures were resolved by SFC separation.

TABLE 26

| Example | Structure Name | SFC Conditions | Observed m/z [M + H]$^+$ |
| --- | --- | --- | --- |
| 118 | 1-(4-((2R or 2S,5R or 5S)-5-(5-amino-9-fluoro-7-methoxy-[1,2,4]triazolo[1,5-c]quinazolin-2-yl)-2-methylpiperidin-1-yl)-1H-pyrazol-1-yl)-2-methylpropan-2-ol | Peak 1; Lux-4 21 × 250 mm column with 35% (MeOH w/0.1% NH$_4$OH modifier) as co-solvent | 469 |

TABLE 26-continued

| Example | Structure Name | SFC Conditions | Observed m/z [M + H]+ |
|---|---|---|---|
| 119 | 1-(4-((2S or 2R,5S or 5R)-5-(5-amino-9-fluoro-7-methoxy-[1,2,4]triazolo[1,5-c]quinazolin-2-yl)-2-methylpiperidin-1-yl)-1H-pyrazol-1-yl)-2-methylpropan-2-ol | Peak 2; Lux-4 21 × 250 mm column with 35% (MeOH w/0.1% NH4OH modifier) as co-solvent | 469 |
| 120 | 1-(4-((2R or 2S,5S or 5R)-5-(5-amino-9-fluoro-7-methoxy-[1,2,4]triazolo[1,5-c]quinazolin-2-yl)-2-methylpiperidin-1-yl)-1H-pyrazol-1-yl)-2-methylpropan-2-ol | Peak 3; Lux-4 21 × 250 mm column with 35% (MeOH w/0.1% NH4OH modifier) as co-solvent | 469 |
| 121 | 1-(4-((2S or 2R,5R or 5S)-5-(5-amino-9-fluoro-7-methoxy-[1,2,4]triazolo[1,5-c]quinazolin-2-yl)-2-methylpiperidin-1-yl)-1H-pyrazol-1-yl)-2-methylpropan-2-ol | Peak 4; Lux-4 21 × 250 mm column with 35% (MeOH w/0.1% NH4OH modifier) as co-solvent | 469 |

TABLE 26-continued

| Example | Structure Name | SFC Conditions | Observed m/z [M + H]+ |
|---|---|---|---|
| 122 | 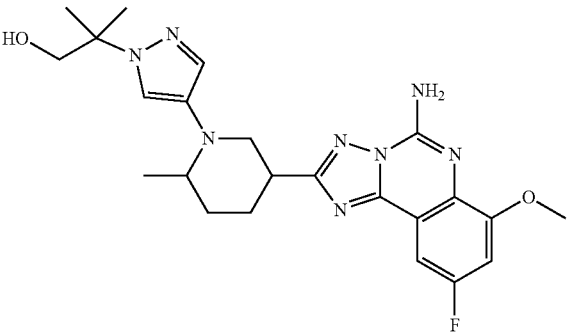 [SMILES: COc1cc(F)cc2c1nc(N)n1nc(C3CCC(C)N(c4cnn(C(C)(C)CO)c4)C3)nc21]<br>2-(4-((2R or 2S,5R or 5S)-5-(5-amino-9-fluoro-7-methoxy-[1,2,4]triazolo[1,5-c]quinazolin-2-yl)-2-methylpiperidin-1-yl)-1H-pyrazol-1-yl)-2-methylpropan-1-ol | Peak 1; IC-3 4.6 × 100 mm column with 40% (IPA w/ 0.05% DEA modifier) as cosolvent | 469 |
| 123 | 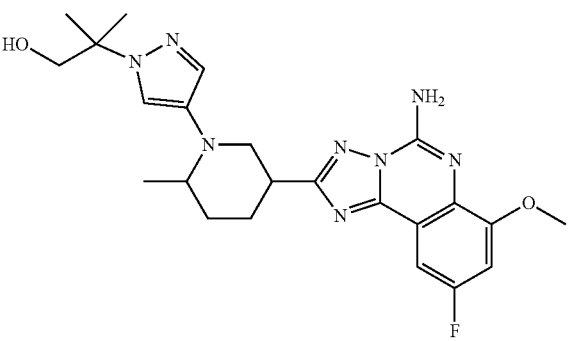 [SMILES: COc1cc(F)cc2c1nc(N)n1nc(C3CCC(C)N(c4cnn(C(C)(C)CO)c4)C3)nc21]<br>2-(4-((2S or 2R,5S or 5R)-5-(5-amino-9-fluoro-7-methoxy-[1,2,4]triazolo[1,5-c]quinazolin-2-yl)-2-methylpiperidin-1-yl)-1H-pyrazol-1-yl)-2-methylpropan-1-ol | Peak 2; IC-3 4.6 × 100 mm column with 40% (IPA w/ 0.05% DEA modifier) as cosolvent | 469 |
| 124 | 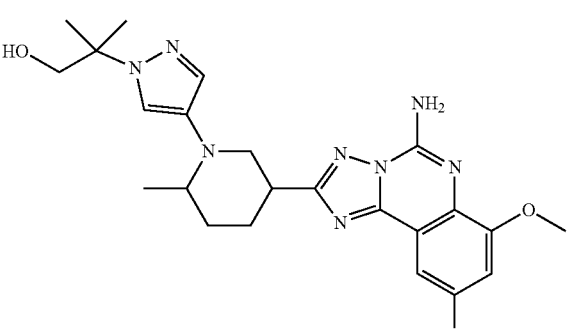<br>2-(4-((2R or 2S,5S or 5R)-5-(5-amino-9-fluoro-7-methoxy-[1,2,4]triazolo[1,5-c]quinazolin-2-yl)-2-methylpiperidin-1-yl)-1H-pyrazol-1-yl)-2-methylpropan-1-ol | Peak 3; IC-3 4.6 × 100 mm column with 40% (IPA w/ 0.05% DEA modifier) as cosolvent | 469 |

TABLE 26-continued

| Example | Structure Name | SFC Conditions | Observed m/z [M + H]+ |
|---|---|---|---|
| 125 | 2-(4-((2S or 2R,5R or 5S)-5-(5-amino-9-fluoro-7-methoxy-[1,2,4]triazolo[1,5-c]quinazolin-2-yl)-2-methylpiperidin-1-yl)-1H-pyrazol-1-yl)-2-methylpropan-1-ol | Peak 4; IC-3 4.6 × 100 mm column with 40% (IPA w/ 0.05% DEA modifier) as cosolvent | 469 |
| 126 | rac-2-(4-((2R or 2S,5R or 5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropan-1-ol | Peak 1 and 2 overlapping; Chiralcel OJ-3 4.6 × 100 mm column with 5-40% (MeOH w/ 0.05% DEA modifier) as cosolvent | 469 |
| 127 | 2-(4-((2R or 2S,5S or 5R)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropan-1-ol | Peak 3; Chiralcel OJ-3 4.6 × 100 mm column with 5-40% (MeOH w/ 0.05% DEA modifier) as cosolvent | 469 |

TABLE 26-continued

| Example | Structure Name | SFC Conditions | Observed m/z [M + H]+ |
|---|---|---|---|
| 128 | 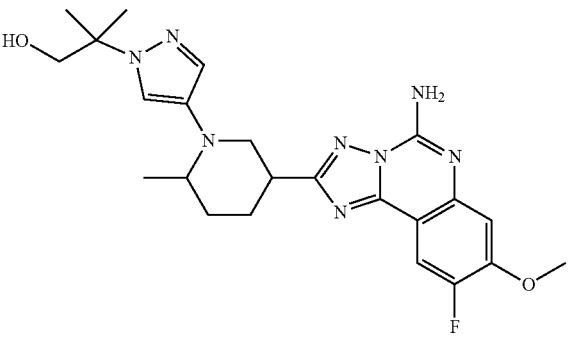 [SMILES: COc1cc2nc(N)n3nc(C4CCC(C)N(c5cnn(C(C)(C)CO)c5)C4)nc3c2cc1F]  1-(4-((2S or 2R,5R or 5S)-3-(5-amino-9-fluoro-8-methoxy-[1,2,4]triazolo[1,5-c]quinazolin-2-yl)-4-methylpiperidin-1-yl)-1H-pyrazol-1-yl)-2-methylpropan-2-ol | Peak 4; Chiralcel OJ-3 4.6 × 100 mm column with 5-40% (MeOH w/ 0.05% DEA modifier) as cosolvent | 469 |

Example 129 and Example 130: (R)-9-fluoro-8-methoxy-2-(1-(3-methyl-1-((methylsulfonyl)methyl)-1H-pyrazol-4-yl)piperidin-3-yl)-[1,2,4]triazolo[1,5-c]quinazolin-5-amine and (R)-9-fluoro-8-methoxy-2-(1-(5-methyl-1-((methylsulfonyl)methyl)-1H-pyrazol-4-yl)piperidin-3-yl)-[1,2,4]triazolo[1,5-c]quinazolin-5-amine Step 1: mixture of (R)—N-(2,4-dimethoxybenzyl)-9-fluoro-8-methoxy-2-(1-(3-methyl-1-((methylthio)methyl)-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(5-methyl-1-((methylthio)methyl)-1H-pyrazol-4-yl)piperidin-3-yl)-[1,2,4]triazolo[1,5-c]quinazolin-5-amine

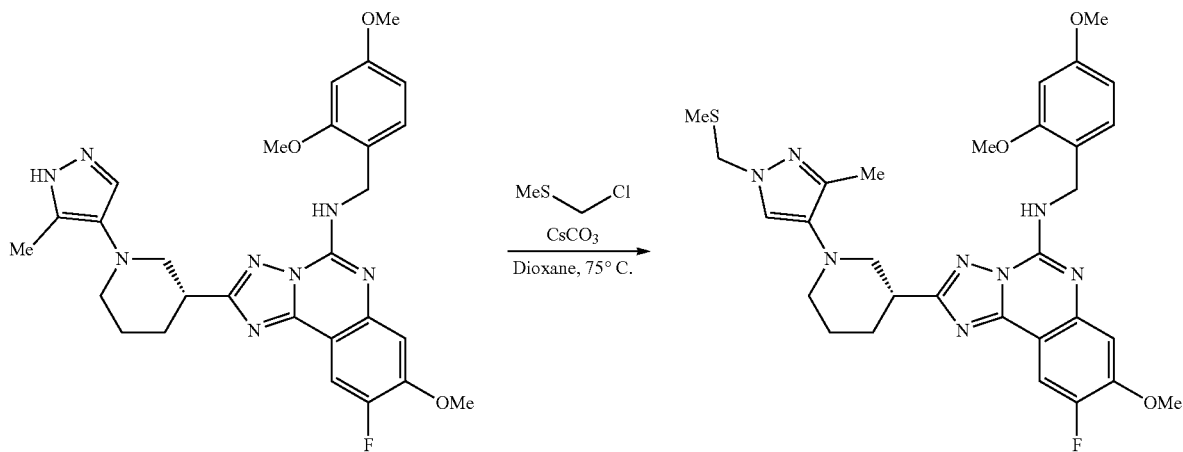

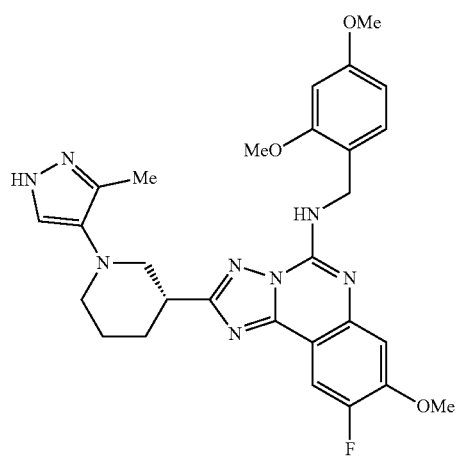

Intermediate 117

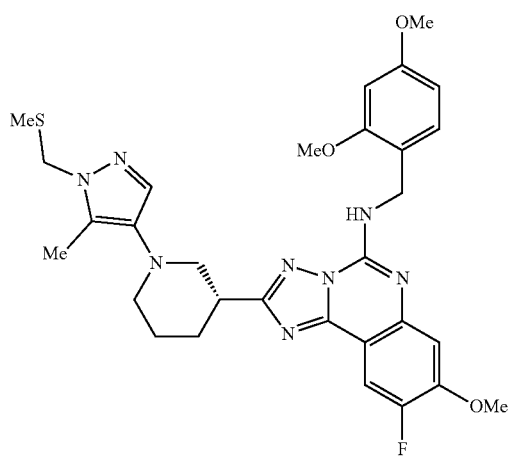

A 1-dram vial was charged with the mixture of (R)—N-(2,4-dimethoxybenzyl)-9-fluoro-8-methoxy-2-(1-(3-methyl-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(5-methyl-1H-pyrazol-4-yl)piperidin-3-yl)-[1,2,4]triazolo[1,5-c]quinazolin-5-amine (Intermediate 117) (391 mg, 0.715 mmol) and (chloromethyl)(methyl)sulfane (359 μL, 4.29 mmol) in dioxane (7.0 mL). To the mixture was added cesium carbonate (466 mg, 1.43 mmol), and then the mixture was stirred and heated at 75° C. for 60 h. The mixture was cooled to room temperature. The mixture was diluted with water and DCM. The mixture was poured into a phase separator. The DCM layer was collected and concentrated. The resulting residue was purified by silica gel column chromatography with 0-10% MeOH in DCM as eluent to afford the mixture of (R)—N-(2,4-dimethoxybenzyl)-9-fluoro-8-methoxy-2-(1-(3-methyl-1-((methylthio)methyl)-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(5-methyl-1-((methylthio)methyl)-1H-pyrazol-4-yl)piperidin-3-yl)-[1,2,4]triazolo[1,5-c]quinazolin-5-amine. LCMS ($C_{30}H_{35}FN_8O_3S$) (ES, m/z): 607 [M+H]$^+$.

Step 2: (R)-9-fluoro-8-methoxy-2-(1-(3-methyl-1-((methylsulfonyl)methyl)-1H-pyrazol-4-yl)piperidin-3-yl)-[1,2,4]triazolo[1,5-c]quinazolin-5-amine and (R)-9-fluoro-8-methoxy-2-(1-(5-methyl-1-((methylsulfonyl)methyl)-1H-pyrazol-4-yl)piperidin-3-yl)-[1,2,4]triazolo[1,5-c]quinazolin-5-amine

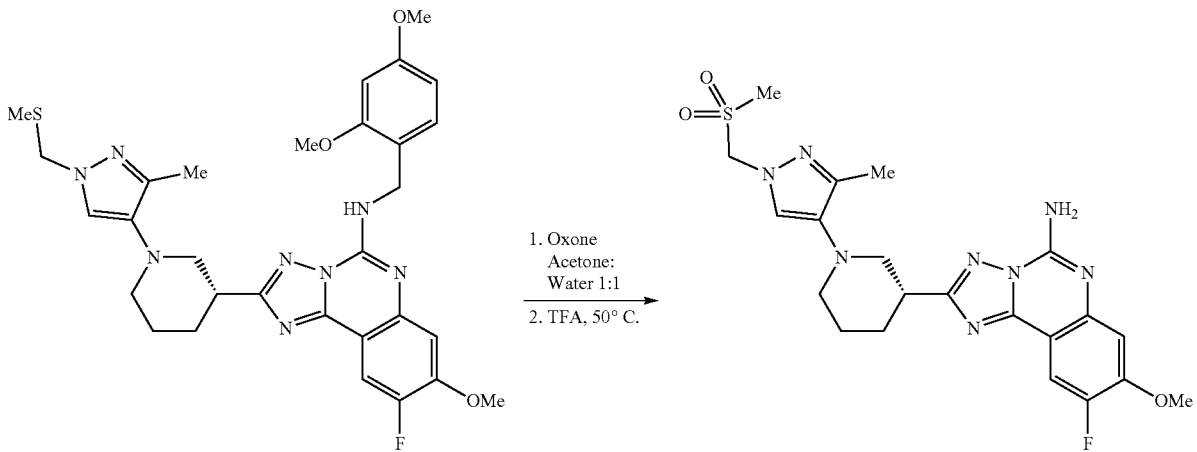

Example 129

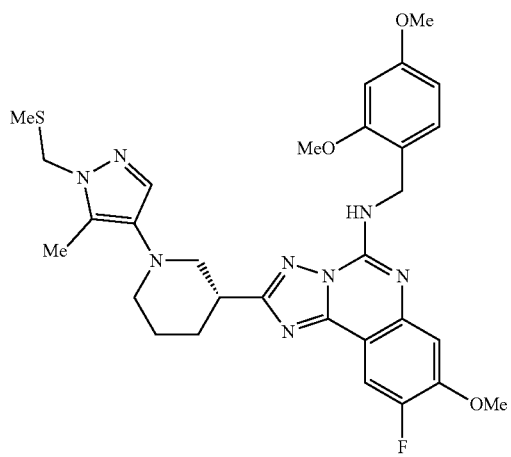

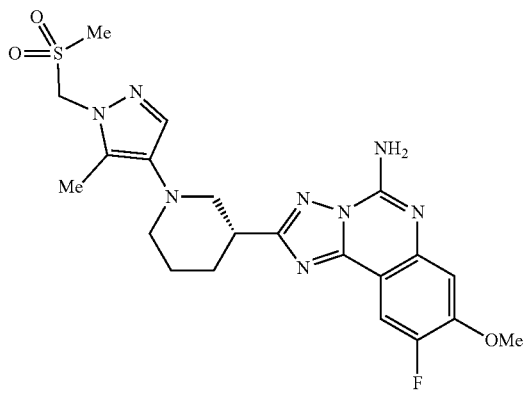

Example 130

The mixture of (R)—N-(2,4-dimethoxybenzyl)-9-fluoro-8-methoxy-2-(1-(3-methyl-1-((methylthio)methyl)-1H-pyrazol-4-yl)piperidin-3-yl)-[1,2,4]triazolo[1,5-c]quinazolin-5-amine and (R)—N-(2,4-dimethoxybenzyl)-9-fluoro-8-methoxy-2-(1-(5-methyl-1-((methylthio)methyl)-1H-pyrazol-4-yl)piperidin-3-yl)-[1,2,4]triazolo[1,5-c]quinazolin-5-amine (328 mg, 0.541 mmol) was dissolved in acetone (4 mL) and water (1.35 mL). To the mixture was added Oxone® (potassium peroxymonosulfate, 665 mg, 1.08 mmol). The mixture was stirred for 10 min at room temperature. The mixture was concentrated to remove the acetone, diluted with water and DCM, and the organic layer was collected via a phase separator. The organic layer was concentrated. To the resulting residue was added and TFA (2.08 mL, 27.0 mmol), and the mixture was stirred and heated at 50° C. for 16 h. The mixture was then diluted with water and DCM, and the DCM layer was collected via a phase separator and concentrated. The resulting residue was purified by preparative reversed-phase HPLC (Waters SunFire C18 OBD Prep Column, 19 mm×100 mm, MeCN/water (w/0.1% TFA modifier) as eluent) to afford (R)-9-fluoro-8-methoxy-2-(1-(3-methyl-1-((methylsulfonyl)methyl)-1H-pyrazol-4-yl)piperidin-3-yl)-[1,2,4]triazolo[1,5-c]quinazolin-5-amine, TFA (Example 129, first eluting peak) and (R)-9-fluoro-8-methoxy-2-(1-(5-methyl-1-((methylsulfonyl)methyl)-1H-pyrazol-4-yl)piperidin-3-yl)-[1,2,4]triazolo[1,5-c]quinazolin-5-amine, TFA, (Example 130, second eluting peak).

For Example 129: LCMS ($C_{21}H_{25}FN_8O_3S$) (ES, m/z): 489 [M+H]$^+$. $^1$H NMR (500 MHz, DMSO-$d_6$) δ 7.87 (d, J=10.9 Hz, 1H), 7.77 (s, 1H), 7.61 (s, 1H), 7.19 (d, J=7.9 Hz, 1H), 5.67 (s, 2H), 3.97 (s, 3H), 3.44 (m, 1H), 3.17 (s, 1H), 2.99 (s, 3H), 2.31 (s, 3H), 2.20 (m, 1H), 1.87 (m, 3H).

For Example 130: LCMS ($C_{21}H_{25}FN_8O_3S$) (ES, m/z): 489 [M+H]$^+$. $^1$H NMR (500 MHz, DMSO-$d_6$) δ 7.87 (dd, J=10.9, 3.6 Hz, 1H), 7.78 (s, 2H), 7.58 (s, 1H), 7.19 (d, J=7.8 Hz, 1H), 5.52 (s, 2H), 3.97 (s, 3H), 3.48 (d, J=9.4 Hz, 1H), 3.32 (d, J=10.1 Hz, 1H), 3.21 (d, J=11.2 Hz, 1H), 2.98 (s, 3H), 2.65 (m, 1H), 2.18 (s, 3H), 1.97-1.71 (m, 3H).

The example compounds of the invention in the following Table 27 were prepared in a manner similar to that described for the preparation of Example 129 and Example 130 from the appropriate intermediates and commercially available starting materials.

TABLE 27

| Example | Structure Name | Observed m/z [M + H]$^+$ |
|---|---|---|
| 131 | ![structure] (R)-9-fluoro-8-methoxy-2-(1-(1-((methylsulfonyl)methyl)-1H-pyrazol-4-yl)piperidin-3-yl)-[1,2,4]triazolo[1,5-c]quinazolin-5-amine | 475 |

TABLE 27-continued

| Example | Structure Name | Observed m/z [M + H]+ |
|---|---|---|
| 132 | 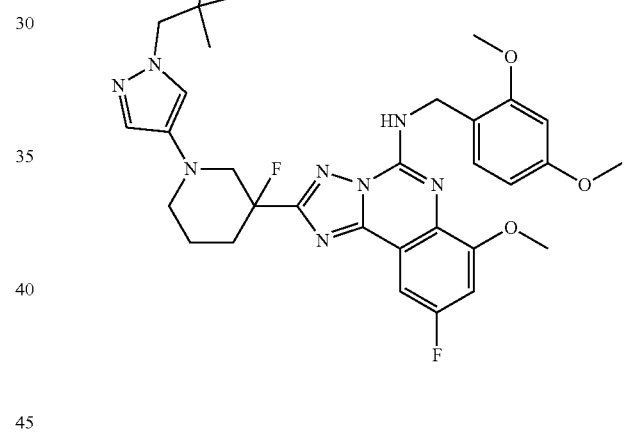 (R)-2-(1-(3-(difluoromethyl)-1-((methylsulfonyl)methyl)-1H-pyrazol-4-yl)piperidin-3-yl)-9-fluoro-8-methoxy-[1,2,4]triazolo[1,5-c]quinazolin-5-amine | 525 |

Example 133: (S or R)-1-(4-(3-(5-amino-9-fluoro-7-methoxy-[1,2,4]triazolo[1,5-c]quinazolin-2-yl)-3-fluoropiperidin-1-yl)-1H-pyrazol-1-yl)-2-methylpropan-2-ol Step 1: (S or R)-1-(4-(3-(5-((2,4-dimethoxybenzyl)amino)-9-fluoro-7-methoxy-[1,2,4]triazolo[1,5-c]quinazolin-2-yl)-3-fluoropiperidin-1-yl)-1H-pyrazol-1-yl)-2-methylpropan-2-ol

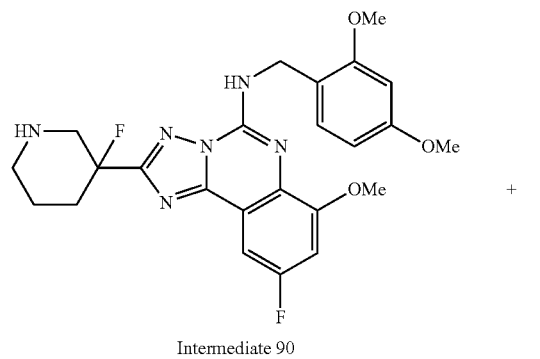

Intermediate 90

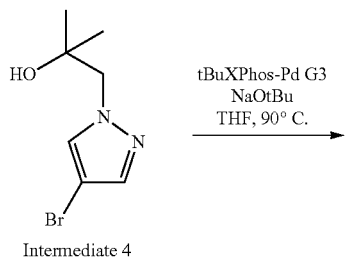

Intermediate 4

To a reaction vial was added (S or R)—N-(2,4-dimethoxybenzyl)-9-fluoro-2-(3-fluoropiperidin-3-yl)-7-methoxy-[1,2,4]triazolo[1,5-c]quinazolin-5-amine (Intermediate 90) (78 mg, 0.161 mmol), 1-(4-bromo-1H-pyrazol-1-yl)-2-methylpropan-2-ol (Intermediate 4) (52.9 mg, 0.241 mmol), tBuXPhos-Pd G3 (38.4 mg, 0.048 mmol), and sodium tert-butoxide (93 mg, 0.97 mmol) in THF (3 mL). The mixture was flushed with nitrogen for 10 min. The mixture was stirred and heated at 90° C. for 16 h. The mixture was cooled to room temperature, filtered, and the solvents of the filtrate were evaporated. The residue was purified by silica gel chromatography with 0-8% MeOH in DCM (with 0.2% NH$_4$OH) as eluent to afford (S or R)-1-(4-(3-(5-((2,4-dimethoxybenzyl)amino)-9-fluoro-7-methoxy-[1,2,4]triazolo[1,5-c]quinazolin-2-yl)-3-fluoropiperidin-1-yl)-1H-pyrazol-1-yl)-2-methylpropan-2-ol. LCMS (C$_{31}$H$_{36}$F$_2$N$_8$O$_4$) (ES, m/z): 623 [M+H]+.

Step 2: (S or R)-1-(4-(3-(5-amino-9-fluoro-7-methoxy-[1,2,4]triazolo[1,5-c]quinazolin-2-yl)-3-fluoropiperidin-1-yl)-1H-pyrazol-1-yl)-2-methylpropan-2-ol

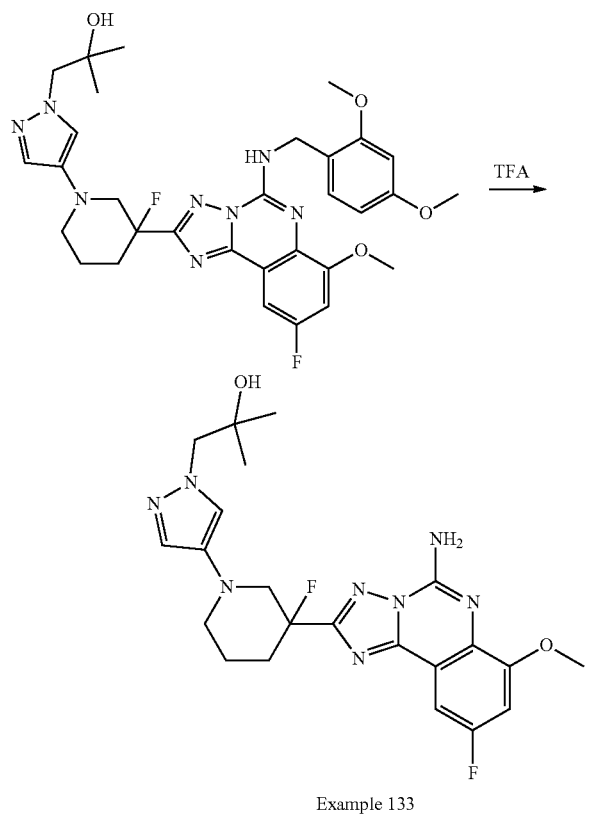

Example 133

An 8 mL scintillation vial was charged with (S or R)-1-(4-(3-(5-((2,4-dimethoxybenzyl)amino)-9-fluoro-7-methoxy-[1,2,4]triazolo[1,5-c]quinazolin-2-yl)-3-fluoropiperidin-1-yl)-1H-pyrazol-1-yl)-2-methylpropan-2-ol (70.0 mg, 0.112 mmol) and TFA (750 μL, 9.73 mmol). The mixture was stirred and heated at 40° C. for 2 h. The mixture was then cooled, and the solvents were evaporated. The resulting residue was purified by preparative reversed-phase HPLC (Waters SunFire C18 OBD Prep Column, 19 mm×100 mm MeCN/H$_2$O with 0.05% TFA as eluent) to afford (S or R)-1-(4-(3-(5-amino-9-fluoro-7-methoxy-[1,2,4]triazolo[1,5-c]quinazolin-2-yl)-3-fluoropiperidin-1-yl)-1H-pyrazol-1-yl)-2 methylpropan-2-ol 2,2,2-trifluoroacetate. LCMS (C$_{22}$H$_{26}$F$_2$N$_8$O$_2$) (ES, m/z): 473 [M+H]$^+$. $^1$H NMR (500 MHz, DMSO-d$_6$) δ 7.89 (s, 2H), 7.48 (dd, J=8.3, 2.7 Hz, 1H), 7.30 (s, 1H), 7.24 (d, J=0.7 Hz, 1H), 7.21 (dd, J=11.1, 2.8 Hz, 1H), 3.93 (s, 3H), 3.88 (s, 2H), 3.68-3.47 (m, −1H), 3.45-3.42 (m, 1H), 3.22-3.08 (m, 1H), 2.84-2.65 (m, 1H), 2.45-2.18 (m, 2H), 1.99 (d, J=9.7 Hz, 1H), 1.80 (dd, J=9.0, 4.0 Hz, 1H), 1.03 (d, J=2.7 Hz, 6H).

Example 134 in the following Table 28 was prepared from Intermediate 91 and the appropriate starting materials in a manner similar to that described for the preparation of Example 133.

TABLE 28

| Example | Structure Name | Observed m/z [M +H]$^+$ |
|---|---|---|
| 134 | (R or S)-1-(4-(3-(5-amino-9-fluoro-7-methoxy-[1,2,4]triazolo[1,5-c[quinazolin-2-yl)-3-fluoropiperidin-1-yl)-1H-pyrazol-1-yl)-2-methylpropan-2-ol | 473 |

Example 135: 1-(4-((2R or 2S,5S or 5R)-5-(5-amino-9-fluoro-8-methoxy-[1,2,4]triazolo[1,5-c]quinazolin-2-yl)-2-ethylpiperidin-1-yl)-1H-pyrazol-1-yl)-2-methylpropan-2-ol Intermediate 113

Example 135

A mixture of 1-(4-((2R or 2S,5S or 5R)-5-(5-((2,4-dimethoxybenzyl)amino)-9-fluoro-8-methoxy-[1,2,4]triazolo[1, 5-c]quinazolin-2-yl)-2-ethylpiperidin-1-yl)-1H-pyrazol-1-yl)-2-methylpropan-2-ol (Intermediate 113) (28.0 mg, 0.0440 mmol) in TFA (50.5 mg, 0.443 mmol) was heated at 60° C. for 1 h. The solvents were evaporated, and the resulting residue was purified by preparative reversed-phase HPLC (Waters SunFire C18 OBD Prep Column, 19 mm×100 mm MeCN/H$_2$O with 0.1% TFA as eluent) to afford 1-(4-((2R or 2S,5S or 5R)-5-(5-amino-9-fluoro-8-methoxy-[1,2,4]triazolo[1,5-c]quinazolin-2-yl)-2-ethylpiperidin-1-yl)-1H-pyrazol-1-yl)-2-methylpropan-2-ol.: LCMS (C$_{24}$H$_{31}$FN$_8$O$_2$) (ES, m/z): 483 [M+H]$^+$. $^1$H NMR (500 MHz, Methanol-d$_4$) δ 7.97-7.89 (m, 2H), 7.70 (s, 1H), 7.24 (d, J=7.5 Hz, 1H), 4.12 (s, 2H), 4.08-3.92 (m, 5H), 3.72-3.57 (m, 2H), 2.52-2.38 (m, 1H), 2.31-2.14 (m, 2H), 2.09-1.98 (m, 1H), 1.75-1.56 (m, 2H), 1.18 (s, 6H), 0.94 (t, J=7.4 Hz, 3H).

Example 136: 1-(4-((2S or 2R,5S or 5R)-5-(5-amino-9-fluoro-8-methoxy-[1,2,4]triazolo[1,5-c]quinazolin-2-yl)-2-ethylpiperidin-1-yl)-1H-pyrazol-1-yl)-2-methylpropan-2-ol

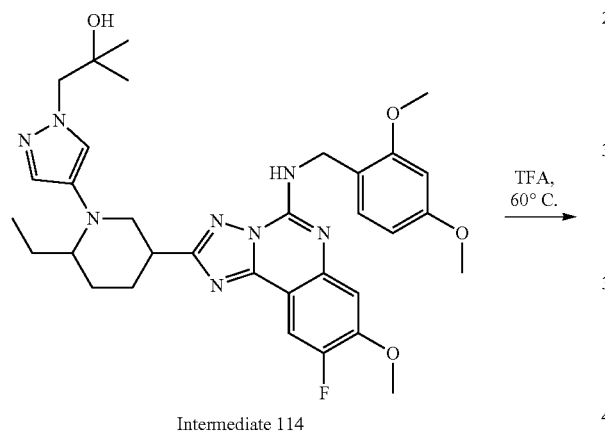

Intermediate 114

TFA, 60° C.

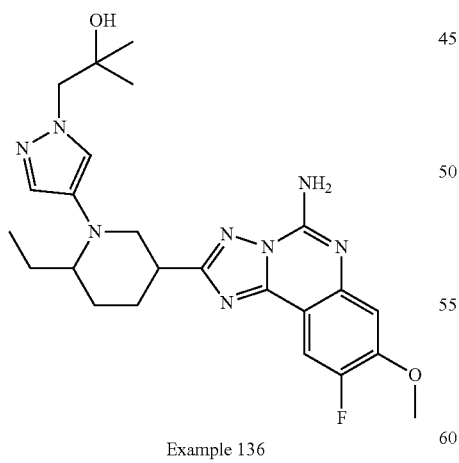

Example 136

Example 136 was prepared from Intermediate 114 in a manner similar to that described for the preparation of Example 135. LCMS (C$_{24}$H$_{31}$FN$_8$O$_2$) (ES, m/z): 483 [M+H]$^+$. $^1$H NMR (500 MHz, Methanol-d$_4$) δ 7.93 (d, J=11.9 Hz, 2H), 7.70 (s, 1H), 7.24 (d, J=7.5 Hz, 1H), 4.12 (s, 2H), 4.07-3.93 (m, 5H), 3.69-3.58 (m, 2H), 2.51-2.37 (m, 1H), 2.32-2.15 (m, 2H), 2.10-1.99 (m, 1H), 1.74-1.58 (m, 2H), 1.17 (s, 6H), 0.94 (t, J=7.3 Hz, 3H).

Example 137: 1-(4-((2S or 2R,5S or 5R)-5-(5-amino-9-fluoro-8-methoxy-[1,2,4]triazolo[1,5-c]quinazolin-2-yl)-2-ethylpiperidin-1-yl)-1H-pyrazol-1-yl)-2-methylpropan-2-ol

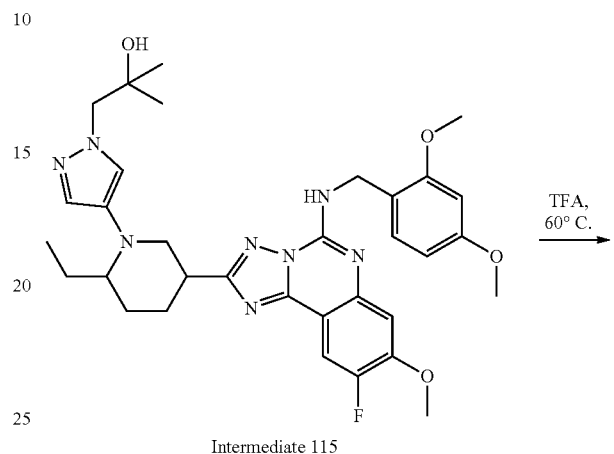

Intermediate 115

TFA, 60° C.

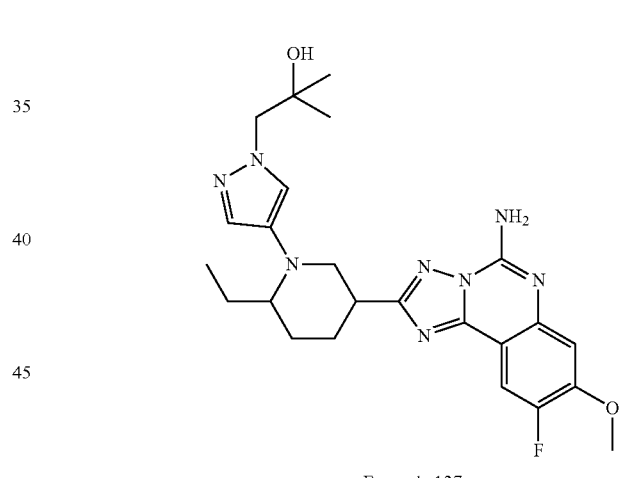

Example 137

Example 137 was prepared from Intermediate 115 in a manner similar to that described for the preparation of Example 135. LCMS (C$_{24}$H$_{31}$FN$_8$O$_2$) (ES, m/z): 483 [M+H]$^+$. $^1$H NMR (500 MHz, Methanol-d$_4$) δ 8.11 (s, 1H), 7.90-7.81 (m, 2H), 7.21 (d, J=7.5 Hz, 1H), 4.14 (d, J=20.7 Hz, 3H), 3.98 (d, J=12.7 Hz, 4H), 3.72-3.54 (m, 2H), 2.56 (d, J=16.8 Hz, 1H), 2.45 (d, J=20.5 Hz, 1H), 2.21-2.07 (m, 1H), 1.98-1.82 (m, 1H), 1.81-1.69 (m, 1H), 1.56-1.43 (m, 1H), 1.19 (s, 6H), 0.97 (t, J=7.3 Hz, 3H).

Example 138: 1-(4-((2S or 2R,5S or 5R)-5-(5-amino-9-fluoro-8-methoxy-[1,2,4]triazolo[1,5-c]quinazolin-2-yl)-2-ethylpiperidin-1-yl)-1H-pyrazol-1-yl)-2-methylpropan-2-ol

Example 139: rac-3-(5-amino-9-fluoro-8-methoxy-[1,2,4]triazolo[1,5-c]quinazolin-2-yl)-1-(1-(2-hydroxy-2-methylpropyl)-1H-pyrazol-4-yl)piperidin-2-one

Step 1: rac-3-(5-((2,4-dimethoxybenzyl)amino)-9-fluoro-8-methoxy-[1,2,4]triazolo[1,5-c]quinazolin-2-yl)-1-(1-(2-hydroxy-2-methylpropyl)-1H-pyrazol-4-yl)piperidin-2-one

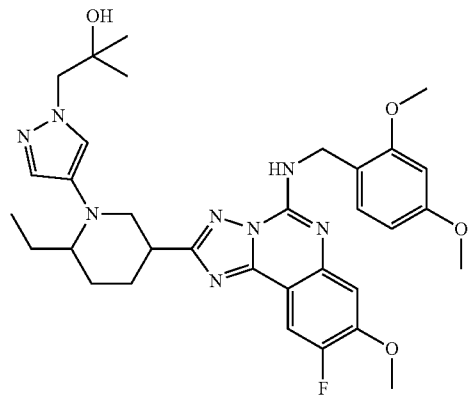

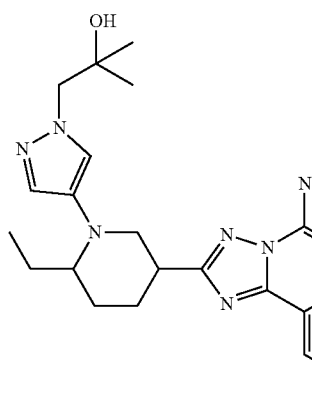

Example 138 was prepared from Intermediate 116 in a manner similar to that described for the preparation of Example 135. LCMS ($C_{24}H_{31}FN_8O_2$) (ES, m/z): 483 [M+H]$^+$. $^1$H NMR (500 MHz, Methanol-$d_4$) δ 8.13 (s, 1H), 7.86 (d, J=13.4 Hz, 2H), 7.21 (d, J=7.6 Hz, 1H), 4.15 (d, J=13.4 Hz, 3H), 3.99 (d, J=8.8 Hz, 4H), 3.74-3.54 (m, 2H), 2.57 (d, J=11.0 Hz, 1H), 2.50-2.39 (m, 1H), 2.24-2.05 (m, 1H), 1.96-1.83 (m, 1H), 1.82-1.67 (m, 1H), 1.59-1.42 (m, 1H), 1.18 (s, 6H), 0.97 (t, J=7.5 Hz, 3H).

To a 20 mL vial was added rac-3-(5-((2,4-dimethoxybenzyl)amino)-9-fluoro-8-methoxy-[1,2,4]triazolo[1,5-c]quinazolin-2-yl)piperidin-2-one (Intermediate 89) (0.102 g, 0.212 mmol), 1-(4-iodo-1H-pyrazol-1-yl)-2-methylpropan-2-ol (0.172 g, 0.646 mmol), copper(I) iodide (42.7 mg, 0.224 mmol), potassium phosphate (267 mg, 1.26 mmol), and anhydrous DMF (2.1 mL).

The mixture was sparged with nitrogen for 5 min. To the mixture was added $N^1,N^2$-dimethylethane-1,2-diamine (0.046 mL, 0.43 mmol). The mixture was stirred and heated at 100° C. for 2 h. The mixture was purified by reversed-phase HPLC (Waters SunFire C18 OBD Prep Column, 19 mm×100 mm with MeCN/H₂O (with 0.1% TFA) as eluent), to afford rac-3-(5-((2,4-dimethoxybenzyl)amino)-9-fluoro-8-methoxy-[1,2,4]triazolo[1,5-c]quinazolin-2-yl)-1-(1-(2-hydroxy-2-methylpropyl)-1H-pyrazol-4-yl)piperidin-2-one. LCMS ($C_{31}H_{35}FN_8O_5$) (ES, m/z): 619 [M+H]⁺.

Step 2: rac-3-(5-amino-9-fluoro-8-methoxy-[1,2,4]triazolo[1,5-c]quinazolin-2-yl)-1-(1-(2-hydroxy-2-methylpropyl)-1H-pyrazol-4-yl)piperidin-2-one

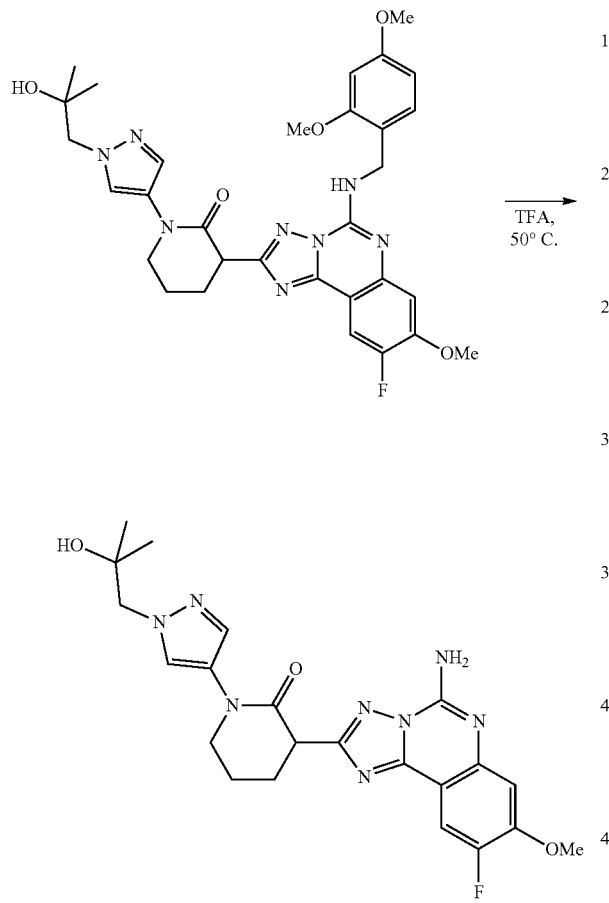

Example 139

To a 20 mL vial was added rac-3-(5-((2,4-dimethoxybenzyl)amino)-9-fluoro-8-methoxy-[1,2,4]triazolo[1,5-c]quinazolin-2-yl)-1-(1-(2-hydroxy-2-methylpropyl)-1H-pyrazol-4-yl)piperidin-2-one (11.9 mg, 0.0192 mmol) and TFA (0.26 mL). The mixture was stirred and heated at 50° C. for 1 h. The mixture was concentrated. The residue was purified by preparative reversed-phase HPLC (Waters SunFire C18 OBD Prep Column, 19 mm×100 mm with MeCN/H₂O (with 0.1% TFA) as eluent) to afford rac-3-(5-amino-9-fluoro-8-methoxy-[1,2,4]triazolo[1,5-c]quinazolin-2-yl)-1-(1-(2-hydroxy-2-methylpropyl)-1H-pyrazol-4-yl)piperidin-2-one. LCMS ($C_{22}H_{25}FN_8O_3$) (ES, m/z): 469 [M+H]⁺. ¹H NMR (499 MHz, DMSO-$d_6$) δ 8.05 (s, 1H), 7.88 (d, J=11.0 Hz, 1H), 7.79 (br s, 2H), 7.66 (s, 1H), 7.18 (d, J=7.8 Hz, 1H), 4.18 (t, J=7.8 Hz, 1H), 3.99-3.93 (m, 5H), 3.86-3.76 (m, 2H), 2.28-2.16 (m, 3H), 2.10-2.00 (m, 1H), 1.03 (s, 3H), 1.03 (s, 3H).

Example 140 and Example 141: (R)-1-(4-(2-(5-((2,4-dimethoxybenzyl)amino)-9-fluoro-8-methoxy-[1,2,4]triazolo[1,5-c]quinazolin-2-yl)morpholino)-3-methyl-1H-pyrazol-1-yl)-2-methylpropan-2-ol and (R)-1-(4-(2-(5-((2,4-dimethoxybenzyl)amino)-9-fluoro-8-methoxy-[1,2,4]triazolo[1,5-c]quinazolin-2-yl)morpholino)-5-methyl-1H-pyrazol-1-yl)-2-methylpropan-2-ol Step 1: Mixture of (R)-1-(4-(2-(5-((2,4-dimethoxybenzyl)amino)-9-fluoro-8-methoxy-[1,2,4]triazolo[1,5-c]quinazolin-2-yl)morpholino)-3-methyl-1H-pyrazol-1-yl)-2-methylpropan-2-ol and (R)-1-(4-(2-(5-((2,4-dimethoxybenzyl)amino)-9-fluoro-8-methoxy-[1,2,4]triazolo[1,5-c]quinazolin-2-yl)morpholino)-5-methyl-1H-pyrazol-1-yl)-2-methylpropan-2-ol

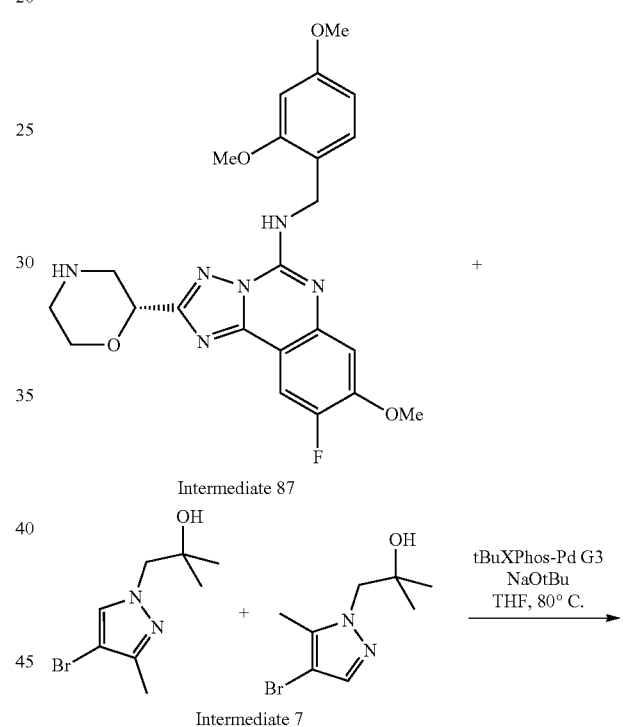

Intermediate 87

Intermediate 7

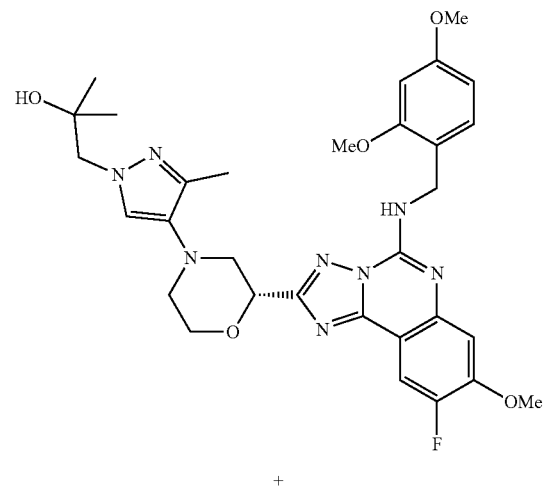

+

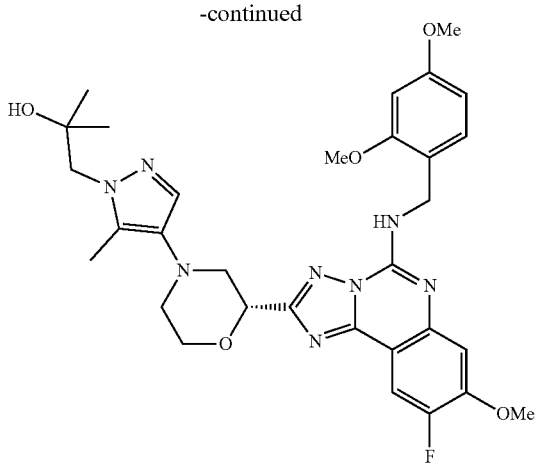

To a 20 mL vial was added (R)—N-(2,4-dimethoxybenzyl)-9-fluoro-8-methoxy-2-(morpholin-2-yl)-[1,2,4]triazolo[1,5-c]quinazolin-5-amine (Intermediate 87) (49.4 mg, 0.105 mmol), a mixture of 1-(4-bromo-3-methyl-1H-pyrazol-1-yl)-2-methylpropan-2-ol and 1-(4-bromo-5-methyl-1H-pyrazol-1-yl)-2-methylpropan-2-ol (Intermediate 7) (31.0 mg, 0.133 mmol), tBuXPhos-Pd G3 (33.5 mg, 0.0422 mmol), sodium tert-butoxide (60.8 mg, 0.633 mmol), and anhydrous THF (1.5 mL). The mixture was sparged with nitrogen. The mixture was then stirred and heated at 100° C. for several minutes, then cooled to 23° C., and additional THF (1 mL) was added. The mixture was stirred and heated at 80° C. for 14 h. Additional amounts of the mixture of 1-(4-bromo-3-methyl-1H-pyrazol-1-yl)-2-methylpropan-2-ol and 1-(4-bromo-5-methyl-1H-pyrazol-1-yl)-2-methylpropan-2-ol (Intermediate 7) (42.5 mg, 0.182 mmol) and tBuXPhos-Pd G3 (33.5 mg, 0.0422 mmol) were added. The mixture was stirred and heated at 80° C. for 8 h. The mixture was diluted with DCM and MeOH and filtered through Celite® (diatomaceous earth). The filtrate was concentrated. The resulting residue was purified by silica gel chromatography with 0-100% EtOAc:EtOH (3:1) in hexanes as eluent to afford a mixture of (R)-1-(4-(2-(5-((2,4-dimethoxybenzyl)amino)-9-fluoro-8-methoxy-[1,2,4]triazolo[1,5-c]quinazolin-2-yl)morpholino)-3-methyl-1H-pyrazol-1-yl)-2-methylpropan-2-ol and (R)-1-(4-(2-(5-((2,4-dimethoxybenzyl)amino)-9-fluoro-8-methoxy-[1,2,4]triazolo[1,5-c]quinazolin-2-yl)morpholino)-5-methyl-1H-pyrazol-1-yl)-2-methylpropan-2-ol. LCMS ($C_{31}H_{37}FN_8O_5$) (ES, m/z): 621 [M+H]$^+$.

Step 2: (R)-1-(4-(2-(5-amino-9-fluoro-8-methoxy-[1,2,4]triazolo[1,5-c]quinazolin-2-yl)morpholino)-3-methyl-1H-pyrazol-1-yl)-2-methylpropan-2-ol and (R)-1-(4-(2-(5-amino-9-fluoro-8-methoxy-[1,2,4]triazolo[1,5-c]quinazolin-2-yl)morpholino)-5-methyl-1H-pyrazol-1-yl)-2-methylpropan-2-ol

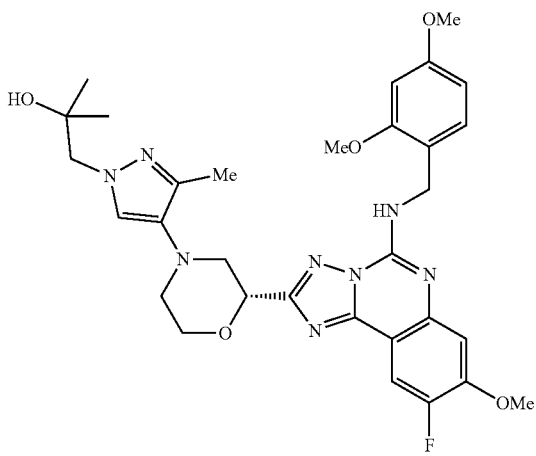

+

TFA, 50° C.
─────→
SFC

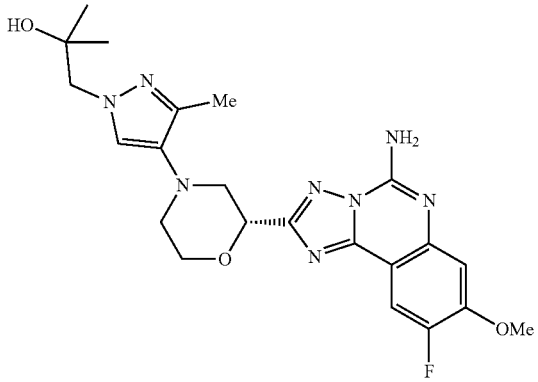

Example 140

+

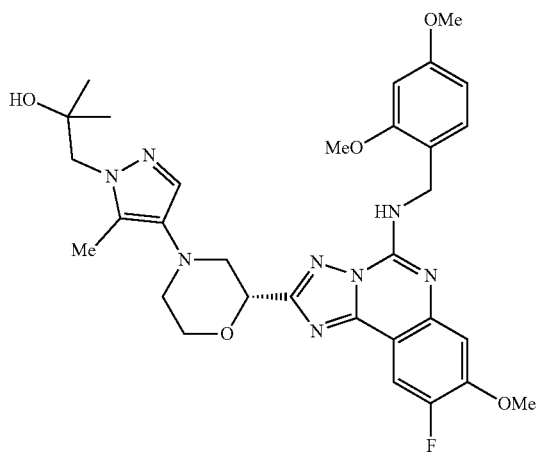

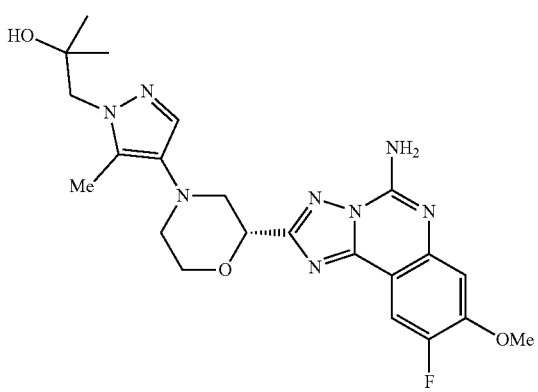

Example 141

To a 4 mL vial was added the mixture of (R)-1-(4-(2-(5-((2,4-dimethoxybenzyl)amino)-9-fluoro-8-methoxy-[1,2,4]triazolo[1,5-c]quinazolin-2-yl)morpholino)-3-methyl-1H-pyrazol-1-yl)-2-methylpropan-2-ol and (R)-1-(4-(2-(5-((2,4-dimethoxybenzyl)amino)-9-fluoro-8-methoxy-[1,2,4]triazolo[1,5-c]quinazolin-2-yl)morpholino)-5-methyl-1H-pyrazol-1-yl)-2-methylpropan-2-ol (4.6 mg, 0.0074 mmol) and TFA (0.10 mL). The mixture was stirred at 23° C. for 2 h. The mixture was then stirred and heated at 50° C. for 50 min. To a separate vial was added the mixture of (R)-1-(4-(2-(5-((2,4-dimethoxybenzyl)amino)-9-fluoro-8-methoxy-[1,2,4]triazolo[1,5-c]quinazolin-2-yl)morpholino)-3-methyl-1H-pyrazol-1-yl)-2-methylpropan-2-ol and (R)-1-(4-(2-(5-((2,4-dimethoxybenzyl)amino)-9-fluoro-8-methoxy-[1,2,4]triazolo[1,5-c]quinazolin-2-yl)morpholino)-5-methyl-1H-pyrazol-1-yl)-2-methylpropan-2-ol (35.6 mg, 0.0574 mmol) and TFA (0.78 mL), and this mixture was stirred and heated at 50° C. for 50 min. The contents of the two reaction vials were combined and concentrated to a residue. The residue was suspended in MeOH and filtered. The filtrate was concentrated to a residue. The resulting residue was subjected to chiral SFC separation (Chiral Technologies OJ-H 21×250 mm column with 15% (MeOH w/0.1% NH$_4$OH modifier) as co-solvent), to afford (R)-1-(4-(2-(5-((2,4-dimethoxybenzyl)amino)-9-fluoro-8-methoxy-[1,2,4]triazolo[1,5-c]quinazolin-2-yl)morpholino)-3-methyl-1H-pyrazol-1-yl)-2-methylpropan-2-ol (Example 140) as peak 1, and a second peak. The second peak contained an impurity, and therefore was purified by SFC (Chiral Technologies AS-H 21×250 mm column with 20% (MeOH w/0.1% NH$_4$OH modifier) as co-solvent), yielding (R)-1-(4-(2-(5-amino-9-fluoro-8-methoxy-[1,2,4]triazolo[1,5-c]quinazolin-2-yl)morpholino)-5-methyl-1H-pyrazol-1-yl)-2-methylpropan-2-ol (Example 141).

For Example 140: LCMS (C$_{22}$H$_{27}$FN$_8$O$_3$) (ES, m/z): 471 [M+H]$^+$. $^1$H NMR (499 MHz, DMSO-d$_6$) δ 7.90 (d, J=10.9 Hz, 1H), 7.80 (br s, 2H), 7.37 (s, 1H), 7.18 (d, J=7.9 Hz, 1H), 4.95 (dd, J=10.0, 2.5 Hz, 1H), 4.62 (s, 1H), 4.07-4.00 (m, 1H), 3.97 (s, 3H), 3.88 (td, J=11.1, 2.3 Hz, 1H), 3.83 (s, 2H), 3.07-2.97 (m, 2H), 2.72 (td, J=11.5, 3.1 Hz, 1H), 2.12 (s, 3H), 1.03 (s, 3H), 1.02 (s, 3H).

For Example 141: LCMS (C$_{22}$H$_{27}$FN$_8$O$_3$) (ES, m/z): 471 [M+H]$^+$. $^1$H NMR (499 MHz, DMSO-d$_6$) δ 7.89 (d, J=10.9 Hz, 1H), 7.79 (br s, 2H), 7.34 (s, 1H), 7.18 (d, J=7.9 Hz, 1H), 4.95 (dd, J=9.7, 2.6 Hz, 1H), 4.63 (s, 1H), 4.08-4.00 (m, 1H), 3.96 (s, 3H), 3.92-3.82 (m, 3H), 3.25-3.20 (m, 1H), 3.11 (dd, J=11.5, 10.0 Hz, 1H), 2.96-2.90 (m, 1H), 2.87 (td, J=11.3, 3.1 Hz, 1H), 2.22 (s, 3H), 1.07 (s, 3H), 1.06 (s, 3H).

Examples 142-145: (R or S)-2-(5-amino-9-fluoro-8-methoxy-[1,2,4]triazolo[1,5-c]quinazolin-2-yl)-4-(1-(2-hydroxy-2-methylpropyl)-3-methyl-1H-pyrazol-4-yl)thiomorpholine 1,1-dioxide and (S or R)-2-(5-amino-9-fluoro-8-methoxy-[1,2,4]triazolo[1,5-c]quinazolin-2-yl)-4-(1-(2-hydroxy-2-methylpropyl)-3-methyl-1H-pyrazol-4-yl)thiomorpholine 1,1-dioxide and (R or S)-2-(5-amino-9-fluoro-8-methoxy-[1,2,4]triazolo[1,5-c]quinazolin-2-yl)-4-(1-(2-hydroxy-2-methylpropyl)-5-methyl-1H-pyrazol-4-yl)thiomorpholine 1,1-dioxide and (S or R)-2-(5-amino-9-fluoro-8-methoxy-[1,2,4]triazolo[1,5-c]quinazolin-2-yl)-4-(1-(2-hydroxy-2-methylpropyl)-5-methyl-1H-pyrazol-4-yl)thiomorpholine 1,1-dioxide Step 1: mixture of 2-(5-((2,4-dimethoxybenzyl)amino)-9-fluoro-8-methoxy-[1,2,4]triazolo[1,5-c]quinazolin-2-yl)-4-(1-(2-hydroxy-2-methylpropyl)-3-methyl-1H-pyrazol-4-yl)thiomorpholine 1,1-dioxide and 2-(5-((2,4-dimethoxybenzyl)amino)-9-fluoro-8-methoxy-[1,2,4]triazolo[1,5-c]quinazolin-2-yl)-4-(1-(2-hydroxy-2-methylpropyl)-5-methyl-1H-pyrazol-4-yl)thiomorpholine 1,1-dioxide

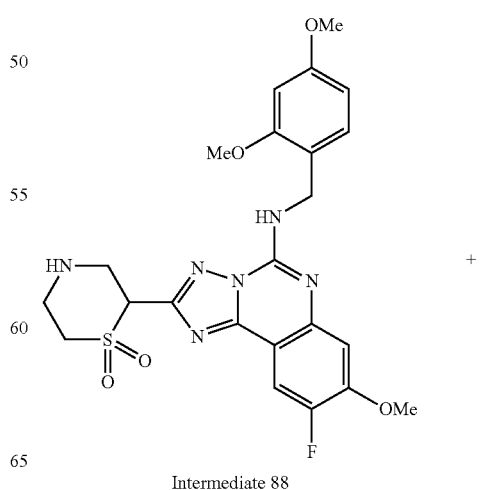

Intermediate 88

-continued

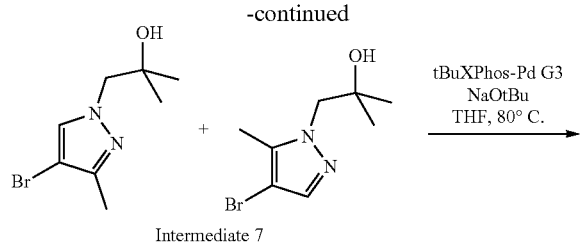

Intermediate 7

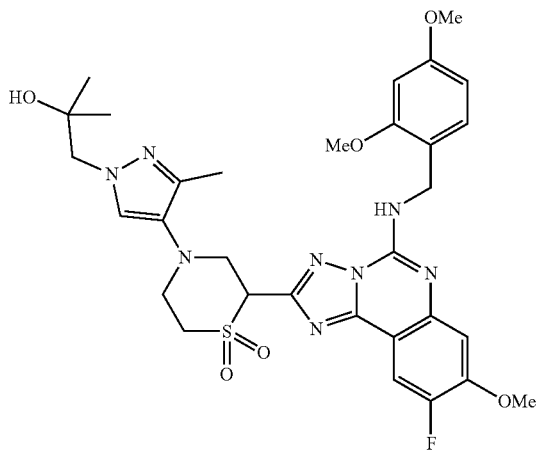

+

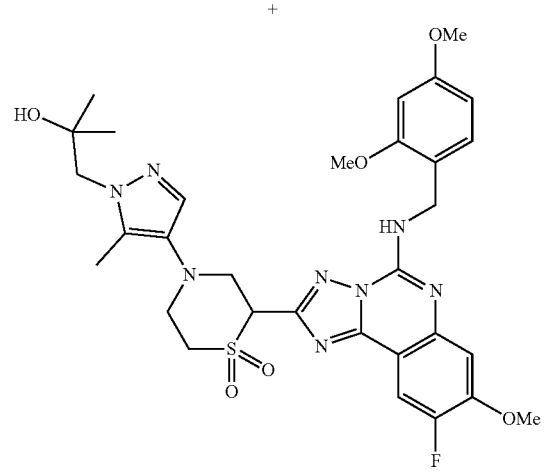

+

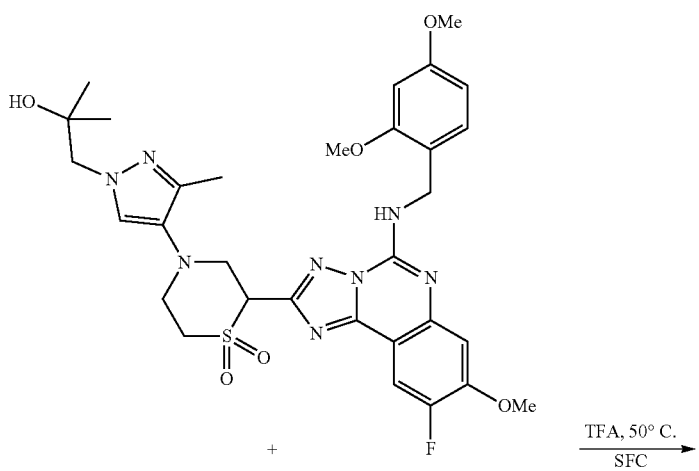

TFA, 50° C.
SFC

To a 20 mL vial was added rac-2-(5-((2,4-dimethoxybenzyl)amino)-9-fluoro-8-methoxy-[1,2,4]triazolo[1,5-c]quinazolin-2-yl)thiomorpholine 1,1-dioxide (Intermediate 88) (100 mg, 0.194 mmol), tBuXPhos-Pd G3 (154 mg, 0.194 mmol), a mixture of 1-(4-bromo-3-methyl-1H-pyrazol-1-yl)-2-methylpropan-2-ol and 1-(4-bromo-5-methyl-1H-pyrazol-1-yl)-2-methylpropan-2-ol (Intermediate 7) (140 mg, 0.598 mmol), and dry THF (3 mL). The mixture was sparged with nitrogen for 4 min. To the mixture was added sodium tert-butoxide (112 mg, 1.16 mmol). The mixture was stirred and heated at 80° C. for 18 h. The mixture was concentrated. The resulting residue was suspended in DCM, mixed with Celite® (diatomaceous earth), and filtered. The filtrate was concentrated. The resulting residue was purified by silica gel chromatography with 0-70% EtOAc:EtOH (3:1) in hexanes as eluent, yielding a mixture of rac-2-(5-((2,4-dimethoxybenzyl)amino)-9-fluoro-8-methoxy-[1,2,4]triazolo[1,5-c]quinazolin-2-yl)-4-(1-(2-hydroxy-2-methylpropyl)-3-methyl-1H-pyrazol-4-yl)thiomorpholine 1,1-dioxide and rac-2-(5-((2,4-dimethoxybenzyl)amino)-9-fluoro-8-methoxy-[1,2,4]triazolo[1,5-c]quinazolin-2-yl)-4-(1-(2-hydroxy-2-methylpropyl)-5-methyl-1H-pyrazol-4-yl)thiomorpholine 1,1-dioxide. LCMS ($C_{31}H_{37}FN_8O_6S$) (ES, m/z): 669 [M+H]$^+$.

Step 2: (R or S)-2-(5-amino-9-fluoro-8-methoxy-[1,2,4]triazolo[1,5-c]quinazolin-2-yl)-4-(1-(2-hydroxy-2-methylpropyl)-3-methyl-1H-pyrazol-4-yl)thiomorpholine 1,1-dioxide and (S or R)-2-(5-amino-9-fluoro-8-methoxy-[1,2,4]triazolo[1,5-c]quinazolin-2-yl)-4-(1-(2-hydroxy-2-methylpropyl)-3-methyl-1H-pyrazol-4-yl)thiomorpholine 1,1-dioxide and (R or S)-2-(5-amino-9-fluoro-8-methoxy-[1,2,4]triazolo[1,5-c]quinazolin-2-yl)-4-(1-(2-hydroxy-2-methylpropyl)-5-methyl-1H-pyrazol-4-yl)thiomorpholine 1,1-dioxide and (S or R)-2-(5-amino-9-fluoro-8-methoxy-[1,2,4]triazolo[1,5-c]quinazolin-2-yl)-4-(1-(2-hydroxy-2-methylpropyl)-5-methyl-1H-pyrazol-4-yl)thiomorpholine 1,1-dioxide -continued

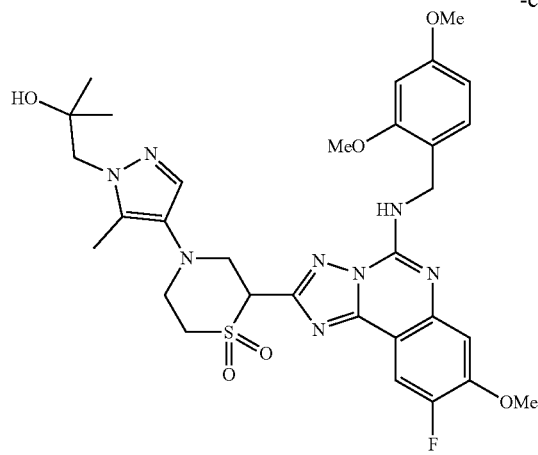

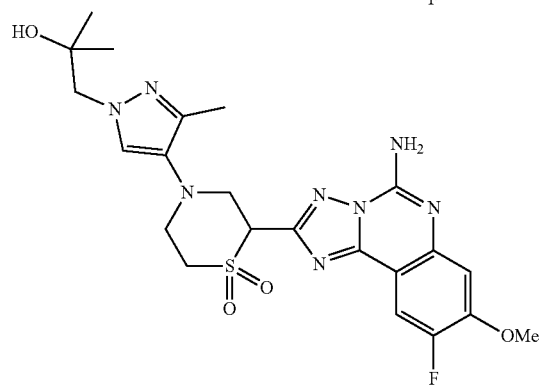

Example 142

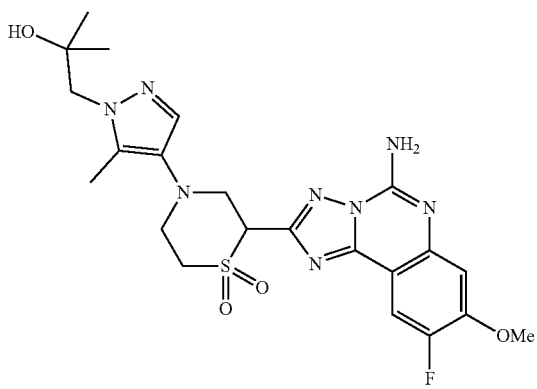

Example 144

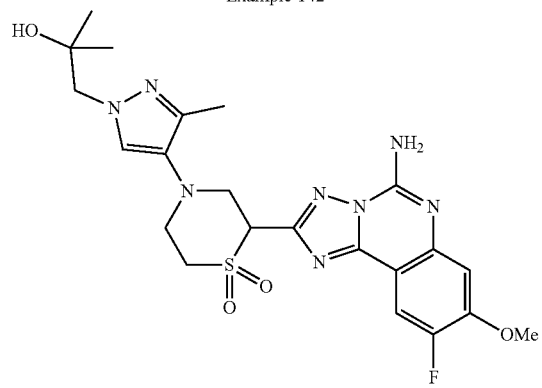

Example 143

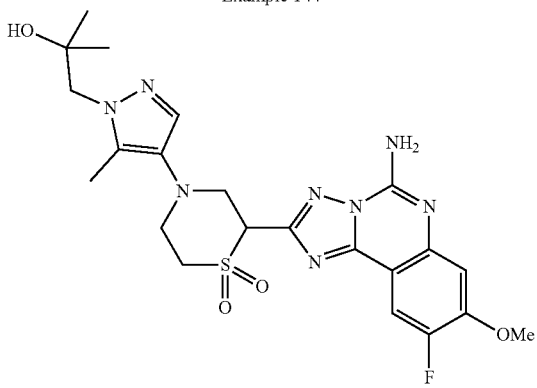

Example 145

To a 20 mL vial was added the mixture of rac-2-(5-((2,4-dimethoxybenzyl)amino)-9-fluoro-8-methoxy-[1,2,4]triazolo[1,5-c]quinazolin-2-yl)-4-(1-(2-hydroxy-2-methylpropyl)-3-methyl-1H-pyrazol-4-yl)thiomorpholine 1,1-dioxide and rac-2-(5-((2,4-dimethoxybenzyl)amino)-9-fluoro-8-methoxy-[1,2,4]triazolo[1,5-c]quinazolin-2-yl)-4-(1-(2-hydroxy-2-methylpropyl)-5-methyl-1H-pyrazol-4-yl)thiomorpholine 1,1-dioxide (48.1 mg, 0.0719 mmol) and TFA (0.96 mL). The mixture was stirred and heated at 50° C. for 1 h. The mixture was concentrated to a residue. The resulting residue was suspended in MeOH and filtered. The filtrate was concentrated to a residue that was purified by SFC (Chiral Technologies AS-H 21×250 mm column with 20% (MeOH w/0.1% NH$_4$OH modifier) as co-solvent) to afford four peaks that were concentrated. Each peak was subsequently purified individually by preparative reversed-phase HPLC (Waters SunFire C18 OBD Prep Column, 19 mm×100 mm with MeCN/H$_2$O (with 0.1% TFA) as eluent) to afford the final compounds, (R or S)-2-(5-amino-9-fluoro-8-methoxy-[1,2,4]triazolo[1,5-c]quinazolin-2-yl)-4-(1-(2-hydroxy-2-methylpropyl)-3-methyl-1H-pyrazol-4-yl)thiomorpholine 1,1-dioxide, and (S or R)-2-(5-amino-9-fluoro-8-methoxy-[1,2,4]triazolo[1,5-c]quinazolin-2-yl)-4-(1-(2-hydroxy-2-methylpropyl)-3-methyl-1H-pyrazol-4-yl) thiomorpholine 1,1-dioxide, and (R or S)-2-(5-amino-9-fluoro-8-methoxy-[1,2,4]triazolo[1,5-c]quinazolin-2-yl)-4-(1-(2-hydroxy-2-methylpropyl)-5-methyl-1H-pyrazol-4-yl) thiomorpholine 1,1-dioxide, and (S or R)-2-(5-amino-9-fluoro-8-methoxy-[1,2,4]triazolo[1,5-c]quinazolin-2-yl)-4-(1-(2-hydroxy-2-methylpropyl)-5-methyl-1H-pyrazol-4-yl)

thiomorpholine 1,1-dioxide, corresponding to Example 142 (SFC peak 1), Example 143 (SFC peak 2), Example 144 (SFC peak 3), and Example 145 (SFC peak 4), respectively.

For Example 142: LCMS (C₂₂H₂₇FN₈O₄S) (ES, m/z): 519 [M+H]⁺. ¹H NMR (499 MHz, DMSO-d₆) δ 7.91 (d, J=10.9 Hz, 1H), 7.88 (br s, 2H), 7.55 (s, 1H), 7.21 (d, J=7.8 Hz, 1H), 4.96 (dd, J=10.3, 3.5 Hz, 1H), 3.99 (s, 3H), 3.87-3.76 (m, 3H), 3.72-3.65 (m, 1H), 3.65-3.53 (m, 2H), 3.53-3.45 (m, 1H), 3.44-3.34 (m, 1H), 2.06 (s, 3H), 1.05 (s, 3H), 1.04 (s, 3H).

For Example 143: LCMS (C₂₂H₂₇FN₈O₄S) (ES, m/z): 519 [M+H]⁺. ¹H NMR (499 MHz, DMSO-d₆) δ 7.91 (d, J=10.9 Hz, 1H), 7.88 (br s, 2H), 7.55 (s, 1H), 7.21 (d, J=7.8 Hz, 1H), 4.96 (dd, J=10.3, 3.5 Hz, 1H), 3.99 (s, 3H), 3.87-3.76 (m, 3H), 3.72-3.65 (m, 1H), 3.65-3.53 (m, 2H), 3.53-3.45 (m, 1H), 3.44-3.34 (m, 1H), 2.06 (s, 3H), 1.05 (s, 3H), 1.04 (s, 3H).

For Example 144: LCMS (C₂₂H₂₇FN₈O₄S) (ES, m/z): 519 [M+H]⁺. ¹H NMR (499 MHz, DMSO-d₆) δ 7.89 (d, J=10.9 Hz, 1H), 7.86 (br s, 2H), 7.48 (s, 1H), 7.20 (d, J=7.8 Hz, 1H), 4.96 (dd, J=10.1, 3.4 Hz, 1H), 3.98 (s, 3H), 3.87-3.78 (m, 3H), 3.64-3.54 (m, 3H), 3.51-3.35 (m, 2H), 2.15 (s, 3H), 1.05 (s, 3H), 1.04 (s, 3H).

For Example 145: LCMS (C₂₂H₂₇FN₈O₄S) (ES, m/z): 519 [M+H]⁺. ¹H NMR (499 MHz, DMSO-d₆) δ 7.89 (d, J=10.9 Hz, 1H), 7.86 (br s, 2H), 7.48 (s, 1H), 7.20 (d, J=7.8 Hz, 1H), 4.96 (dd, J=10.1, 3.4 Hz, 1H), 3.98 (s, 3H), 3.87-3.78 (m, 3H), 3.64-3.54 (m, 3H), 3.51-3.35 (m, 2H), 2.15 (s, 3H), 1.05 (s, 3H), 1.04 (s, 3H).

Example 146 and Example 147: (1R or 1S,3R or 3S)-3-(5-amino-9-fluoro-8-methoxy-[1,2,4]triazolo[1,5-c]quinazolin-2-yl)-1-(1-ethyl-1H-pyrazol-4-yl)cyclohexan-1-ol and (1S or 1R,3S or 3R)-3-(5-amino-9-fluoro-8-methoxy-[1,2,4]triazolo[1,5-c]quinazolin-2-yl)-1-(1-ethyl-1H-pyrazol-4-yl)cyclohexan-1-ol

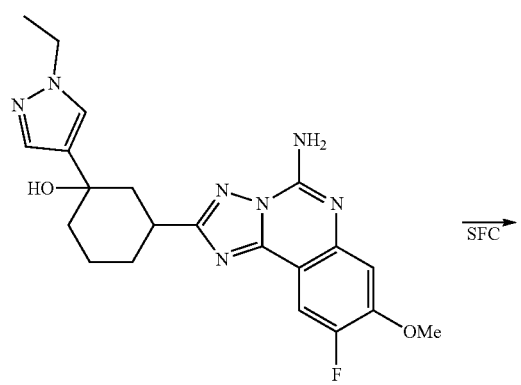

Intermediate 124

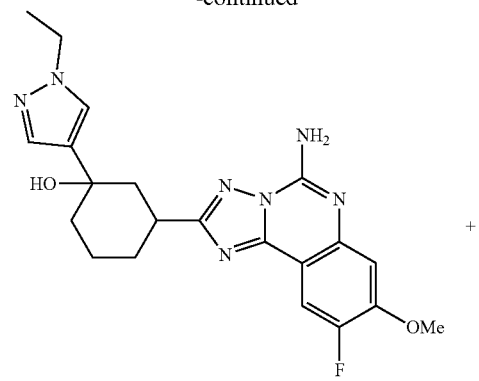

Example 146

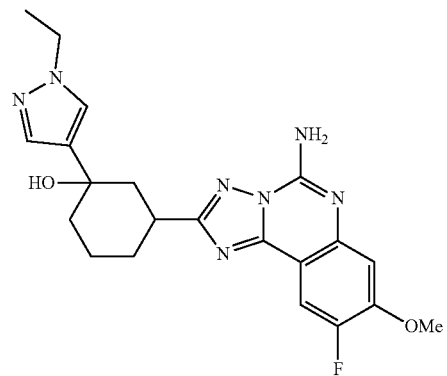

Example 147

Intermediate 124 (70.0 mg, 0.170 mmol) was resolved by chiral SFC (AD 250×30 mm column with MeOH (0.1% NH₄OH modifier) as cosolvent) to afford (1R or 1S,3R or 3S)-3-(5-amino-9-fluoro-8-methoxy-[1,2,4]triazolo[1,5-c]quinazolin-2-yl)-1-(1-ethyl-1H-pyrazol-4-yl)cyclohexan-1-ol (Example 146, first eluting peak) and (1S or 1R,3S or 3R)-3-(5-amino-9-fluoro-8-methoxy-[1,2,4]triazolo[1,5-c]quinazolin-2-yl)-1-(1-ethyl-1H-pyrazol-4-yl)cyclohexan-1-ol (Example 147, second eluting peak).

For Example 146: LCMS (C₂₁H₂₄FN₇O₂) (ES, m/z) [M+H]⁺: 426. ¹H NMR (400 MHz, MeOD-d₄) δ (ppm) 7.81 (s, 1H), 7.59-7.70 (m, 2H), 6.91 (br d, J=7.9 Hz, 1H), 4.20 (q, J=7.3 Hz, 2H), 3.88-3.99 (m, 3H), 2.89-3.01 (m, 1H), 2.75 (br d, J=13.2 Hz, 1H), 2.39 (br d, J=12.3 Hz, 1H), 1.97-2.13 (m, 2H), 1.88 (br dd, J=9.9, 3.3 Hz, 1H), 1.58-1.77 (m, 2H), 1.50-1.55 (m, 1H), 1.42-1.49 (m, 3H).

For Example 147: LCMS (C₂₁H₂₄FN₇O₂) (ES, m/z) [M+H]⁺: 426. ¹H NMR (400 MHz, MeOD-d₄) δ (ppm) 7.71-7.87 (m, 2H), 7.64 (d, J=2.6 Hz, 1H), 6.96-7.18 (m, 1H), 4.20 (q, J=7.3 Hz, 2H), 3.97 (br d, J=13.2 Hz, 3H), 2.89-3.05 (m, 1H), 2.73 (br d, J=12.7 Hz, 1H), 2.40 (br d, J=12.7 Hz, 1H), 1.99-2.13 (m, 2H), 1.91 (br d, J=13.2 Hz, 1H), 1.62-1.79 (m, 2H), 1.52-1.59 (m, 1H), 1.47 (t, J=7.5 Hz, 3H).

Example 148 and Example 149: (1S or 1R,3R or 3S)-3-(5-amino-9-fluoro-8-methoxy-[1,2,4]triazolo[1,5-c]quinazolin-2-yl)-1-(1-ethyl-1H-pyrazol-4-yl)cyclohexan-1-ol and (1S or 1R,3R or 3S)-3-(5-amino-9-fluoro-8-methoxy-[1,2,4]triazolo[1,5-c]quinazolin-2-yl)-1-(1-ethyl-1H-pyrazol-4-yl)cyclohexan-1-ol

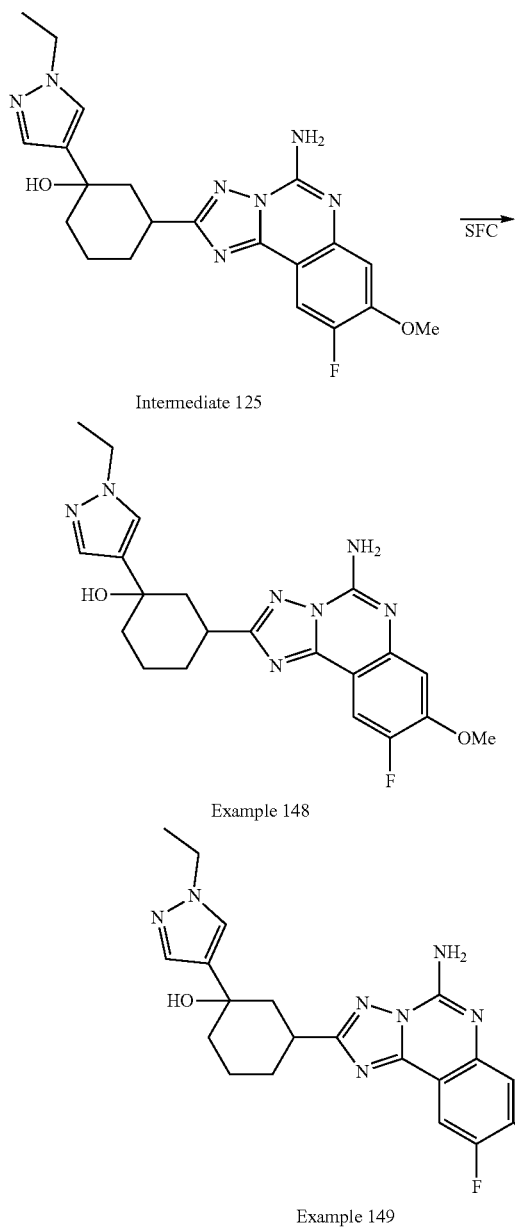

Intermediate 125 (50.0 mg, 0.120 mmol) was resolved by chiral SFC (AD 250×30 mm column with IPA (0.1% NH₄OH modifier) as cosolvent) to afford (1S or 1R,3R or 3S)-3-(5-amino-9-fluoro-8-methoxy-[1,2,4]triazolo[1,5-c]quinazolin-2-yl)-1-(1-ethyl-1H-pyrazol-4-yl)cyclohexan-1-ol (Example 148, first eluting peak) and (1S or 1R,3R or 3S)-3-(5-amino-9-fluoro-8-methoxy-[1,2,4]triazolo[1,5-c]quinazolin-2-yl)-1-(1-ethyl-1H-pyrazol-4-yl)cyclohexan-1-ol (Example 149, second eluting peak).

For Example 148: LCMS ($C_{21}H_{24}FN_7O_2$) (ES, m/z) [M+H]⁺: 426. ¹H NMR (400 MHz, MeOD-d₄) δ (ppm) 7.78-7.94 (m, 1H), 7.60 (s, 1H), 7.50 (s, 1H), 7.01-7.23 (m, 1H), 4.14 (q, J=7.2 Hz, 2H), 3.99 (br s, 3H), 3.46-3.56 (m, 1H), 2.38 (br d, J=14.0 Hz, 1H), 1.92-2.25 (m, 4H), 1.63-1.85 (m, 3H), 1.42 (t, J=7.2 Hz, 3H).

For Example 149: LCMS ($C_{21}H_{24}FN_7O_2$) (ES, m/z) [M+H]⁺: 426. ¹H NMR (400 MHz, MeOD-d₄) δ (ppm) 7.81 (br s, 1H), 7.60 (s, 1H), 7.50 (s, 1H), 7.11 (br s, 1H), 4.09-4.20 (m, 2H), 3.96 (br s, 3H), 3.51 (br s, 1H), 2.38 (br d, J=13.6 Hz, 1H), 1.96-2.24 (m, 4H), 1.59-1.85 (m, 3H), 1.42 (t, J=7.2 Hz, 3H).

Example 150: (1R,3R or 1S,3S)-3-(5-amino-7-methoxy-[1,2,4]triazolo[1,5-c]quinazolin-2-yl)-1-(1-(2-hydroxy-2-methylpropyl)-1H-pyrazol-4-yl)cyclohexan-1-ol Step 1: ethyl 3-(((trifluoromethyl)sulfonyl)oxy)cyclohex-3-ene-1-carboxylate

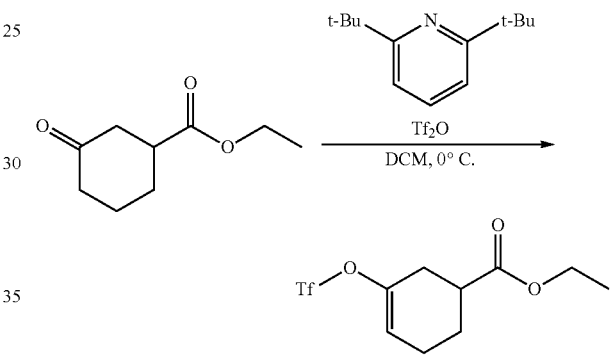

To a 100 mL round bottom flask was added 2,6-di-tert-butylpyridine (11.1 ml, 49.4 mmol), ethyl 3-oxocyclohexane-1-carboxylate (6.32 ml, 35.3 mmol), and DCE (70.5 mL). The mixture was stirred and cooled at 0° C. To the mixture was added a 1 M solution in THF of Tf₂O (45.8 mL, 45.8 mmol), dropwise over 5 min. The mixture was stirred for 30 min. The mixture was warmed to room temperature. After 2 h, the mixture was concentrated. To the resulting residue was added 1:1 DCM:hexanes (20 mL) and solids precipitated. The solids were removed by filtration. The filter cake was washed with 1:1 DCM:hexanes. The solvents of the filtrate were evaporated. The resulting residue was purified by silica gel chromatography with 0-100% EtOAc in hexanes as eluent, yielding ethyl 3-(((trifluoromethyl)sulfonyl)oxy)cyclohex-3-ene-1-carboxylate.

Step 2: ethyl 3-(4,4,5,5-tetramethyl-1,3,2-dioxaborolan-2-yl)cyclohex-3-ene-1-carboxylate

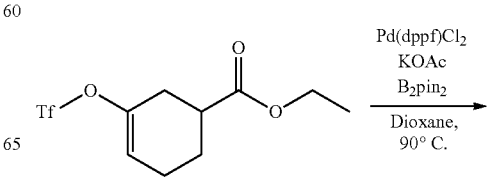

-continued

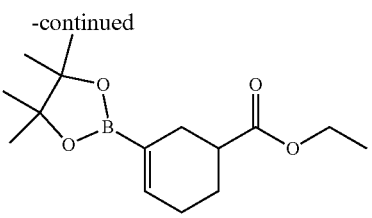

To a 100 mL round bottom flask was added potassium acetate (3.96 g, 40.4 mmol), Pd(dppf)Cl$_2$ (0.660 g, 0.808 mmol), bis(pinacolato)diboron (8.21 g, 32.3 mmol), and ethyl 3-(((trifluoromethyl)sulfonyl)oxy)cyclohex-3-ene-1-carboxylate (7.08 mL, 26.9 mmol). The flask was evacuated and refilled with nitrogen three times. To the flask was added DMA (40 mL). The mixture was stirred and heated at 90° C. for 16 h. The mixture was cooled to room temperature. The mixture was poured into a flask containing diethyl ether (150 mL). The mixture was stirred for 15 min. The solids were removed by filtration. The filtrate was washed with water (3×100 mL). The organic layer was dried over anhydrous magnesium sulfate, filtered, and the solvents were evaporated. The resulting residue was purified by silica gel chromatography with 0-30% EtOAc in hexanes as eluent to afford ethyl 3-(4,4,5,5-tetramethyl-1,3,2-dioxaborolan-2-yl)cyclohex-3-ene-1-carboxylate. LCMS (C$_{15}$H$_{25}$BO$_4$) (ES, m/z) [M+H]$^+$: 281.

Step 3: ethyl (R or S)-3-(1-(2-hydroxy-2-methylpropyl)-1H-pyrazol-4-yl)cyclohex-3-ene-1-carboxylate

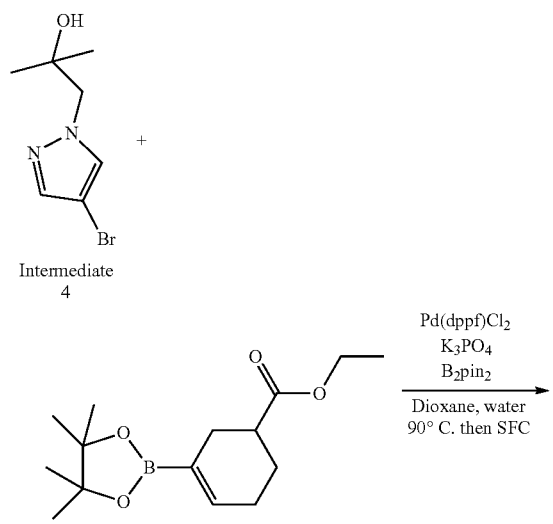

To a 100 mL flask was added Pd(dppf)Cl$_2$ (0.708 g, 0.968 mmol), K$_3$PO$_4$ (15.4 g, 72.6 mmol), ethyl 3-(4,4,5,5-tetramethyl-1,3,2-dioxaborolan-2-yl)cyclohex-3-ene-1-carboxylate (7.12 g, 25.4 mmol), and 1-(4-bromo-1H-pyrazol-1-yl)-2-methylpropan-2-ol (Intermediate 4) (5.30 g, 24.2 mmol). To the flask was added dioxane (60 mL) and water (12 mL). The mixture was sparged with nitrogen for 5 min. The mixture was stirred and heated at 90° C. for 2 h. The mixture was diluted in EtOAc (10 mL) and filtered through Celite® (diatomaceous earth) topped with anhydrous sodium sulfate. The solvents of the filtrate were evaporated. The resulting residue was purified by silica gel chromatography with 0-70% EtOAc in hexanes as eluent, to afford the racemate. The racemate was resolved by chiral SFC (ES Industries CCA 21×250 mm column, 15% (MeOH w/NH$_4$OH modifier) as cosolvent) to afford ethyl (R or S)-3-(1-(2-hydroxy-2-methylpropyl)-1H-pyrazol-4-yl)cyclohex-3-ene-1-carboxylate (first eluting peak). LCMS (C$_{16}$H$_{24}$N$_2$O$_3$) (ES, m/z) [M+H]$^+$: 293.

Step 4: ethyl (1R,3R or 1S,3S)-3-hydroxy-3-(1-(2-hydroxy-2-methylpropyl)-1H-pyrazol-4-yl)cyclohexane-1-carboxylate

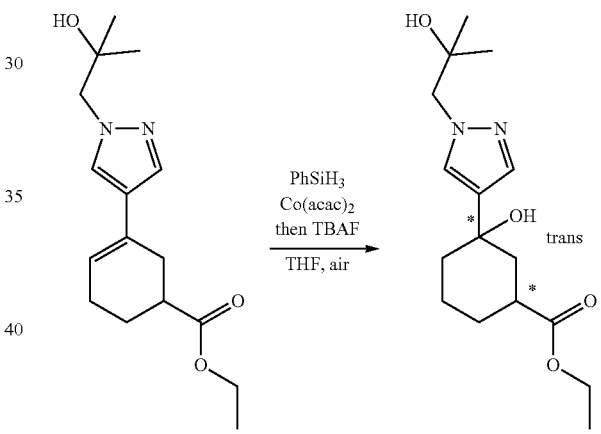

To a 250 mL round bottom flask was added (R or S)-3-(1-(2-hydroxy-2-methylpropyl)-1H-pyrazol-4-yl)cyclohex-3-ene-1-carboxylate (933 mg, 3.19 mmol), cobalt (II) acetylacetonate hydrate (220 mg, 0.798 mmol), and THF (50 mL). To the mixture was added phenylsilane (1.18 mL, 9.57 mmol), and the mixture was stirred, open to air, at room temperature for 5 days. To the mixture was added a 1 M solution of TBAF (6.38 mL, 6.38 mmol) in THF. The mixture was stirred for 15 min. The solvents were evaporated. The resulting residue was purified by silica gel chromatography with 0-10% MeOH in DCM as eluent, to afford the trans-diastereomer ethyl (1R,3R or 1S,3S)-3-hydroxy-3-(1-(2-hydroxy-2-methylpropyl)-1H-pyrazol-4-yl)cyclohexane-1-carboxylate. LCMS (C$_{16}$H$_{26}$N$_2$O$_4$) (ES, m/z) [M+H]$^+$: 311.

313

Step 5: (1R,3R or 1S,3S)-3-hydroxy-3-(1-(2-hydroxy-2-methylpropyl)-1H-pyrazol-4-yl)cyclohexane-1-carbohydrazide

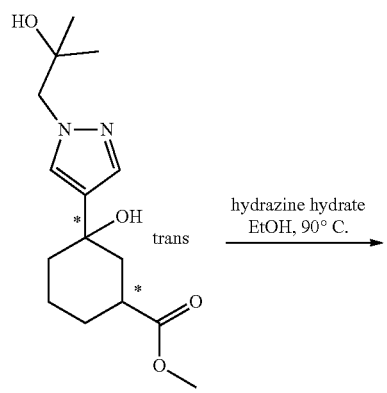

hydrazine hydrate
EtOH, 90° C.

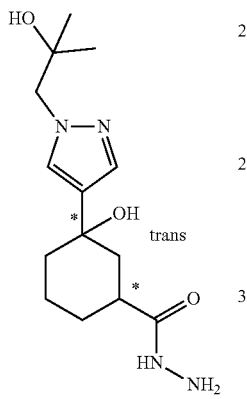

To a 20 mL vial was added ethyl (1R,3R or 1S,3S)-3-hydroxy-3-(1-(2-hydroxy-2-methylpropyl)-1H-pyrazol-4-yl)cyclohexane-1-carboxylate (190 mg, 0.612 mmol), EtOH (1.5 mL), and hydrazine hydrate (0.210 ml, 3.67 mmol). The mixture was heated at 90° C. for 24 h. The solvents were evaporated to afford (1R,3R or 1S,3S)-3-hydroxy-3-(1-(2-hydroxy-2-methylpropyl)-1H-pyrazol-4-yl)cyclohexane-1-carbohydrazide. LCMS ($C_{14}H_{24}N_2O_4$) (ES, m/z) [M+H]$^+$: 297.

Step 6: (1R,3R or 1S,3S)-3-(5-((2,4-dimethoxybenzyl)amino)-7-methoxy-[1,2,4]triazolo[1,5-c]quinazolin-2-yl)-1-(1-(2-hydroxy-2-methylpropyl)-1H-pyrazol-4-yl)cyclohexan-1-ol

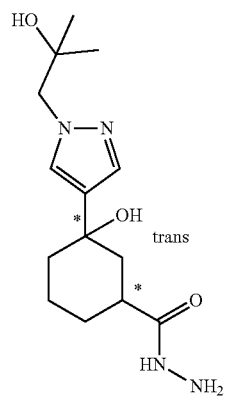
+

314

-continued

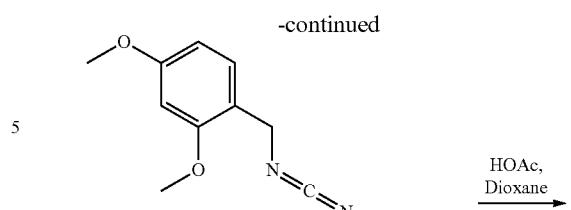

HOAc,
Dioxane
→

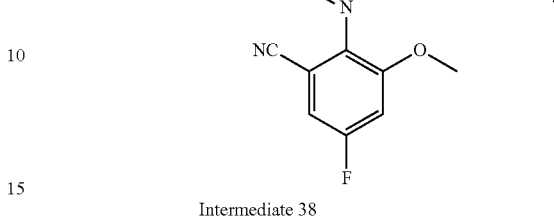

Intermediate 38

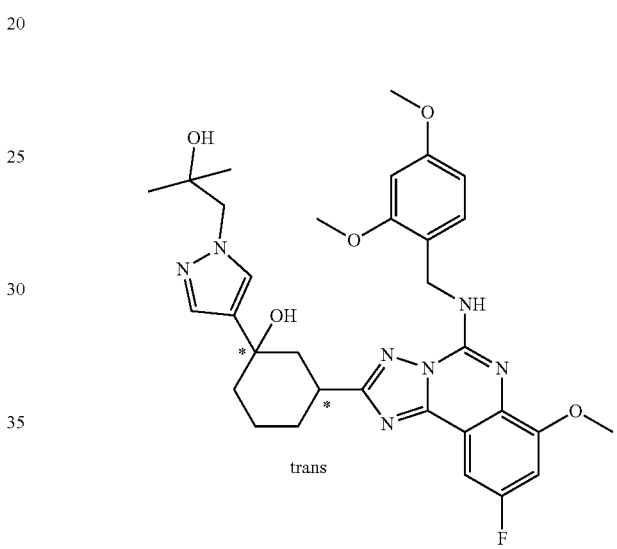

The asterisks (*) in the above scheme indicate chiral centers. To a 20 mL vial was added (1R,3R or 1S,3S)-3-hydroxy-3-(1-(2-hydroxy-2-methylpropyl)-1H-pyrazol-4-yl)cyclohexane-1-carbohydrazide (70.0 mg, 0.236 mmol), 2-((((2,4-dimethoxybenzyl)imino)methylene)amino)-5-fluoro-3-methoxybenzonitrile (105 mg, 0.307 mmol), dioxane (0.5 mL), and AcOH (7 µl, 0.12 mmol). The mixture was stirred and heated at 65° C. for 2 h. The solvents were evaporated. The residue was purified by silica gel chromatography with 0-100% EtOAc:EtOH (3:1) in hexanes as eluent to afford (1R,3R or 1S,3S)-3-(5-((2,4-dimethoxybenzyl)amino)-9-fluoro-7-methoxy-[1,2,4]triazolo[1,5-c]quinazolin-2-yl)-1-(1-(2-hydroxy-2-methylpropyl)-1H-pyrazol-4-yl)cyclohexan-1-ol. LCMS ($C_{32}H_{39}N_7O_5$) (ES, m/z) [M+H]$^+$: 602.

315

Step 7: (1R,3R or 1S,3S)-3-(5-amino-7-methoxy-[1,2,4]triazolo[1,5-c]quinazolin-2-yl)-1-(1-(2-hydroxy-2-methylpropyl)-1H-pyrazol-4-yl)cyclohexan-1-ol

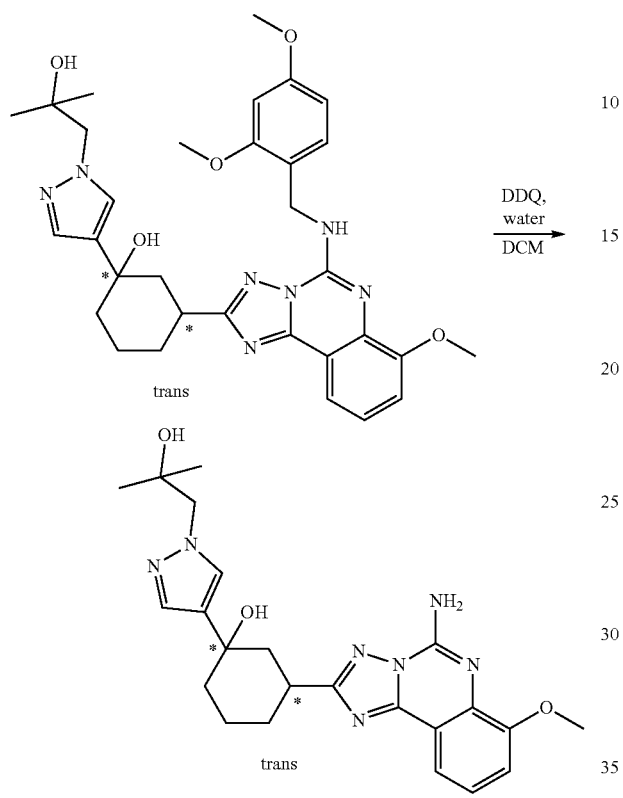

To a 20 mL vial was added DDQ (30.3 mg, 0.133 mmol) and DCM (1.0 mL). The mixture was cooled at 0° C. To the mixture was added water (0.05 mL). To the mixture was added (1R,3R or 1S,3S)-3-(5-((2,4-dimethoxybenzyl)amino)-7-methoxy-[1,2,4]triazolo[1,5-c]quinazolin-2-yl)-1-(1-(2-hydroxy-2-methylpropyl)-1H-pyrazol-4-yl)cyclohexan-1-ol (53.5 mg, 0.089 mmol) as a solution in DCM (1 mL). The mixture was stirred for 4 h. To the mixture was added 1 M aqueous KOH (20 mL), and then the mixture was extracted with DCM (2×20 mL). The organic layers were combined, dried over anhydrous sodium sulfate, filtered, and the solvents of the filtrate were evaporated. The resulting residue was purified by silica gel chromatography with 0-100% EtOAc:EtOH (3:1) in hexane as eluent. The product was further purified by chiral SFC (Chiral Technologies OJ-H 21×250 mm column, with 20% (MeOH with NH$_4$OH modifier) as cosolvent) to afford (1R,3R or 1S,3S)-3-(5-amino-7-methoxy-[1,2,4]triazolo[1,5-c]quinazolin-2-yl)-1-(1-(2-hydroxy-2-methylpropyl)-1H-pyrazol-4-yl)cyclohexan-1-ol (Example 150). LCMS (C$_{23}$H$_{29}$N$_7$O$_3$) (ES, m/z) [M+H]$^+$: 452. $^1$H NMR (499 MHz, DMSO-d$_6$) δ 7.73 (dd, J=8.0, 1.2 Hz, 3H), 7.56 (s, 1H), 7.39 (s, 1H), 7.29 (t, J=7.9 Hz, 1H), 7.24-7.10 (m, 1H), 4.81 (s, 1H), 4.65 (s, 1H), 3.95 (s, 2H), 3.90 (s, 3H), 3.48-3.40 (m, 1H), 2.22 (d, J=13.4 Hz, 1H), 2.09 (d, J=11.9 Hz, 1H), 1.98-1.84 (m, 3H), 1.73-1.58 (m, 3H), 1.16-0.89 (m, 9H).

316

Example 151: (R)-2-(4-(3-(5-amino-9-fluoro-8-methoxy-[1,2,4]triazolo[1,5-c]quinazolin-2-yl)piperidin-1-yl)-1H-pyrazol-1-yl)-2-methylpropan-1-ol

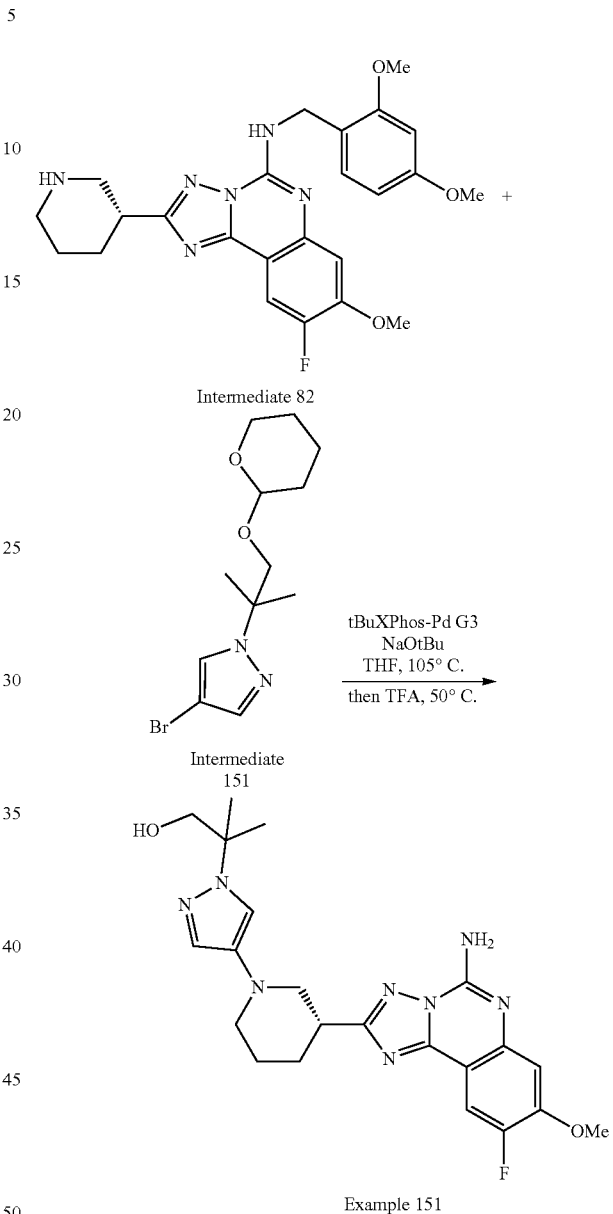

To a 20 mL vial was added (R)—N-(2,4-dimethoxybenzyl)-9-fluoro-8-methoxy-2-(piperidin-3-yl)-[1,2,4]triazolo[1,5-c]quinazolin-5-amine (Intermediate 82) (400 mg, 0.857 mmol), sodium tert-butoxide (330 mg, 3.43 mmol), 4-bromo-1-(2-methyl-1-((tetrahydro-2H-pyran-2-yl)oxy)propan-2-yl)-1H-pyrazole (Intermediate 151) (520 mg, 1.72 mmol), tBuXPhos-Pd G3 (272 mg, 0.343 mmol), and THF (5.7 mL). The mixture was purged with nitrogen for 5 min, sealed, and heated at 105° C. for 16 h. The reaction mixture was cooled to room temperature. To the mixture was added water (10 mL) and DCM (10 mL). The mixture was stirred for 10 min and filtered. The organic layer was collected with a phase separator. The solvents were evaporated. To the resulting residue was added TFA (3.8 mL, 49 mmol), and the mixture was heated at 50° C. for 3 h. The solvents were evaporated, and to the resulting residue was added DCM (10 mL), and a 7 M solution of ammonia in MeOH (1.07 mL, 7.52 mmol). The mixture was stirred for 1 h. The mixture was washed with water then brine. The organic layer was dried over anhydrous sodium sulfate, filtered, and the solvents of the filtrate were evaporated. The resulting residue was purified by silica gel chromatography column with 0-40% of MeOH in DCM as eluent to afford (R)-2-(4-(3-(5-amino-9-fluoro-8-methoxy-[1,2,4]triazolo[1,5-c]quinazolin-2-yl)piperidin-1-yl)-1H-pyrazol-1-yl)-2-methylpropan-1-ol (Example 151). LCMS ($C_{22}H_{27}FN_8O_2$) (ES, m/z): 455 [M+H]$^+$. $^1$H NMR (600 MHz, Methanol-$d_4$) δ 8.18 (s, 1H), 7.92 (d, J=10.7 Hz, 1H), 7.82 (s, 1H), 7.25 (d, J=7.6 Hz, 1H), 4.14 (dd, J=12.0, 3.5 Hz, 1H), 3.84 (dd, J=26.2, 11.7 Hz, 2H), 3.76 (s, 2H), 3.66 (dt, J=9.9, 5.9 Hz, 1H), 3.57-3.46 (m, 1H), 2.51-2.39 (m, 1H), 2.30-2.02 (m, 3H), 1.59 (s, 6H).

The example compounds of the invention in the following Table 29 were prepared from the appropriate starting aryl halide and amine intermediates in a manner similar to that described for the preparation of Example 151.

TABLE 29

| Example | Structure Name | Observed m/z [M + H]$^+$ |
|---|---|---|
| 152 | (R)-4-(4-(3-(5-amino-9-fluoro-8-methoxy-[1,2,4]triazolo[1,5-c]quinazolin-2-yl)piperidin-1-yl)-1H-pyrazol-1-yl)-2-methylbutan-2-ol | 469 |
| 153 | (R)-1-(4-(3-(5-amino-8-(difluoromethoxy)-9-fluoro-[1,2,4]triazolo[1,5-c]quinazolin-2-yl)piperidin-1-yl)-1H-pyrazol-1-yl)-2-methylpropan-2-ol | 491 |
| 154 | (R)-1-(4-(3-(5-amino-8-(difluoromethoxy)-9-fluoro-[1,2,4]triazolo[1,5-c]quinazolin-2-yl)piperidin-1-yl)-3-methyl-1H-pyrazol-1-yl)-2-methylpropan-2-ol | 505 |

TABLE 29-continued

| Example | Structure Name | Observed m/z [M + H]+ |
|---|---|---|
| 155 | racemic, trans-2-(4-(3-(5-amino-9-fluoro-8-methoxy-[1,2,4]triazolo[1,5-c]quinazolin-2-yl)-5-methylpiperidin-1-yl)-3-methyl-1H-pyrazol-1-yl)-2-methylpropan-1-ol | 483 |
| 156 | racemic, trans-2-(4-(3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-1-ol | 469 |

Example 157 and Example 158: 1-(4-((3R,5S or 3S,5R)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol and 1-(4-((3S,5R or 3R,5S)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol Intermediate 83

-continued

Intermediate 24 tBuXPhos-Pd G3
NaOtBu
THF, 90° C.
then TFA, 50° C.
SFC separation

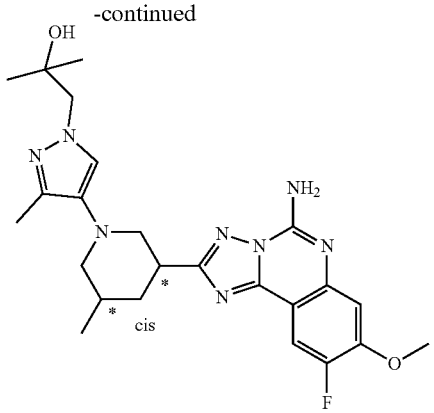

Example 157

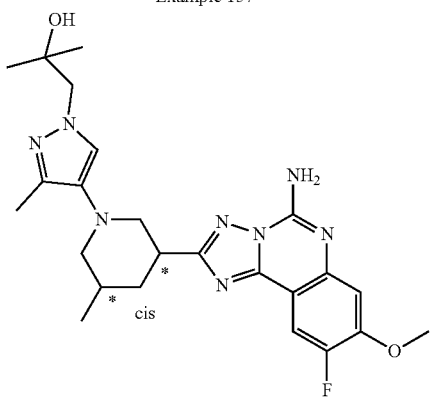

Example 158

A 20 mL microwave vial equipped with a stirbar was charged with rac, cis-N-(2,4-dimethoxybenzyl)-9-fluoro-8-methoxy-2-(5-methylpiperidin-3-yl)-[1,2,4]triazolo[1,5-c]quinazolin-5-amine (Intermediate 83) (400 mg, 0.832 mmol) and THF (5.20 mL). To the mixture was added 1-(4-bromo-3-methyl-1H-pyrazol-1-yl)-2-methylpropan-2-ol (Intermediate 24) (388 mg, 1.67 mmol), followed by tBuXPhos-Pd G3 (264 mg, 0.333 mmol) and sodium tert-butoxide (320 mg, 3.33 mmol). Nitrogen was bubbled through the mixture for 10 min. The vial was then sealed with a fresh cap and heated at 90° C. for 16 h. The reaction was cooled, quenched with saturated ammonium chloride (1 mL), and Celite was added. The biphasic mixture was filtered over Celite topped with anhydrous MgSO₄, and the solvents of the filtrate were concentrated. The resulting residue was dissolved in TFA (3.2 mL, 42 mmol) and heated at 50° C. for 3 h. The reaction mixture was cooled, diluted with DCM, and quenched with saturated aqueous NaHCO₃. The biphasic mixture was separated and the aqueous phase was further extracted with DCM. The organic layers were combined, dried over anhydrous MgSO₄, filtered, and the solvents of the filtrate were concentrated. The resulting residue was purified by silica gel chromatography with 0-20% MeOH in DCM as eluent. The purified product was then subjected to chiral SFC separation (Chiral Technologies AD-H 21×250 mm column with 30% (IPA w/0.1% NH₄OH modifier) as co-solvent), to afford 1-(4-((3R,5S or 3S,5R)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol (Example 157, first eluting peak) and 1-(4-((3S,5R or 3R,5S)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol (Example 158, second eluting peak).

For Example 157: LCMS ($C_{24}H_{31}FN_8O_2$) (ES, m/z): 483 [M+H]⁺. ¹H NMR (499 MHz, DMSO-$d_6$) δ 7.87 (d, J=11.0 Hz, 1H), 7.69 (s, 2H), 7.34 (s, 1H), 7.18 (d, J=7.9 Hz, 1H), 4.61 (s, 1H), 3.97 (s, 3H), 3.83 (s, 2H), 3.46 (d, J=10.9 Hz, 1H), 3.28 (d, J=11.8 Hz, 1H), 3.13 (d, J=8.6 Hz, 1H), 2.64 (t, J=11.3 Hz, 1H), 2.22 (d, J=13.4 Hz, 1H), 2.16 (t, J=11.1 Hz, 1H), 2.11 (s, 3H), 1.94 (s, 1H), 1.38 (q, J=12.3 Hz, 1H), 1.03 (d, J=3.1 Hz, 6H), 0.97 (d, J=6.6 Hz, 3H). For Example 158: LCMS ($C_{24}H_{31}FN_8O_2$) (ES, m/z): 483 [M+H]⁺. ¹H NMR (499 MHz, DMSO-$d_6$) δ 7.87 (d, J=11.0 Hz, 1H), 7.69 (s, 2H), 7.34 (s, 1H), 7.18 (d, J=7.8 Hz, 1H), 4.61 (s, 1H), 3.97 (s, 3H), 3.83 (s, 2H), 3.47 (d, J=8.4 Hz, 1H), 3.29 (s, 1H), 3.13 (d, J=8.0 Hz, 1H), 2.64 (t, J=11.3 Hz, 1H), 2.22 (d, J=12.5 Hz, 1H), 2.16 (t, J=11.0 Hz, 1H), 2.11 (s, 3H), 1.96 (s, 1H), 1.38 (q, J=12.4 Hz, 1H), 1.03 (d, J=3.1 Hz, 6H), 0.97 (d, J=6.6 Hz, 3H).

The example compounds of the invention in the following Table 30 were prepared from the appropriate starting amine and aryl halide in a manner similar to that described for the preparation of Example 157 and Example 158, where the resulting isomeric mixture of the corresponding final compounds were separated by SFC.

TABLE 30

| Example | Structure Name | SFC Conditions | Observed m/z [M + H]⁺ |
|---|---|---|---|
| 159 | | Peak 1; Cellulose-2 30 × 250 mm column with 5-15% (MeOH w/0.05% DEA modifier) as co-solvent | 469 |

TABLE 30-continued

| Example | Structure Name | SFC Conditions | Observed m/z [M + H]+ |
|---|---|---|---|
| 160 | 1-(4-(3R,5S or 3S,5R)-3-(5-amino-9-fluoro-7-methoxy-[1,2,4]triazolo[1,5-c]quinazolin-2-yl)-5-methylpiperidin-1-yl)-1H-pyrazol-1-yl)-2-methylpropan-2-ol | Peak 2; Cellulose-2 30 × 250 mm column with 5-15% (MeOH w/0.05% DEA modifier) as co-solvent | 469 |
| 161 | 1-(4-((3S,5R or 3R,5S)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)-2-methylpropan-2-ol | Peak 1; Cellulose-3 4.6 × 150 mm column with 5-15% (MeOH w/0.05% DEA modifier) as co-solvent | 483 |

TABLE 30-continued

| Example | Structure Name | SFC Conditions | Observed m/z [M + H]+ |
|---|---|---|---|
| 162 | 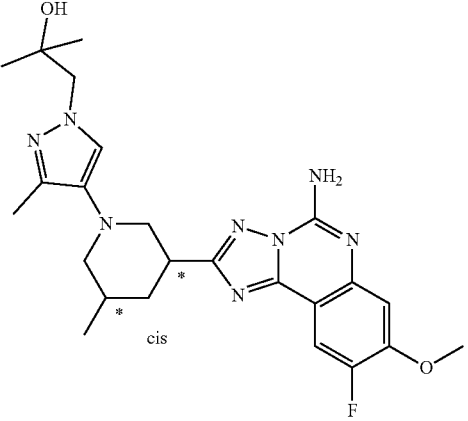 [SMILES: COc1cc2nc(N)n3nc(C4CC(C)CN(c5cn(CC(C)(C)O)nc5C)C4)nc3c2cc1F]<br>1-(4-((3S,5R or 3R,5S)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)-2-methylpropan-2-ol | Peak 2; Cellulose-3 4.6 × 150 mm column with 5-15% (MeOH w/0.05% DEA modifier) as co-solvent | 483 |
| 163 | 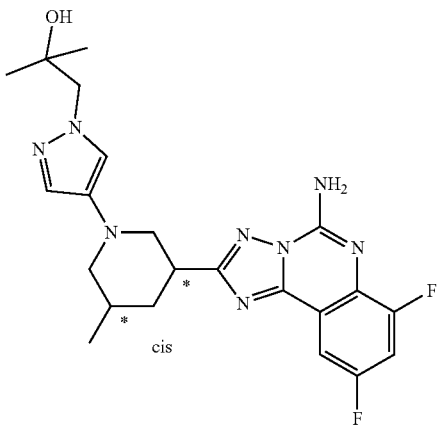 [SMILES: CC1CC(c2nc3c4cc(F)cc(F)c4nc(N)n3n2)CN(c2cnn(CC(C)(C)O)c2)C1]<br>1-(4-((3R,5S or 3S,5R)-3-(5-amino-7,9-difluoro-[1,2,4]triazolo[1,5-c]quinazolin-2-yl)-5-methylpiperidin-1-yl)-1H-pyrazol-1-yl)-2-methylpropan-2-ol | Peak 1; Chiral Technologies AS-H 21 × 250 mm column with 25% (MeOH w/ 0.1% NH4OH modifier) as co-solvent | 457 |

TABLE 30-continued

| Example | Structure Name | SFC Conditions | Observed m/z [M + H]+ |
|---|---|---|---|
| 164 | 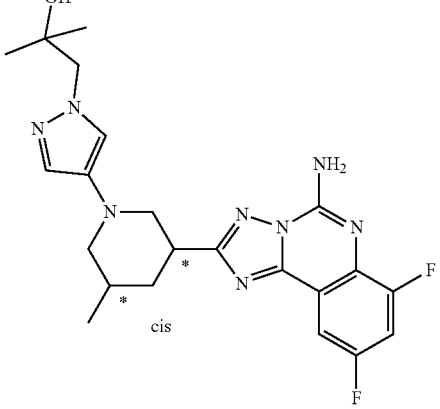<br>1-(4-((3S,5R or 3R,5S)-3-(5-amino-7,9-difluoro-[1,2,4]triazolo[1,5-c]quinazolin-2-yl)-5-methylpiperidin-1-yl)-1H-pyrazol-1-yl)-2-methylpropan-2-ol | Peak 2; Chiral Technologies AS-H 21 × 250 mm column with 25% (MeOH w/ 0.1% NH₄OH modifier) as co-solvent | 457 |
| 165 | 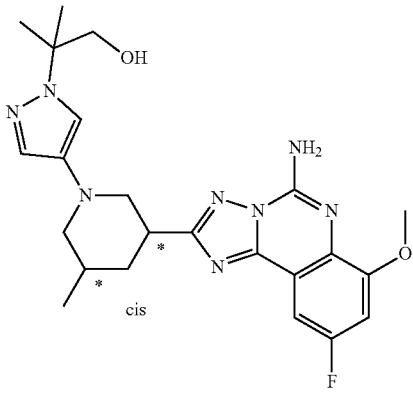 [SMILES: COc1cc(F)cc2c1nc(N)n1nc(C3CC(C)CN(c4cnn(C(C)(C)CO)c4)C3)nc21]<br>2-(4-((3R,5S or 3S,5R)-3-(5-amino-9-fluoro-7-methoxy-[1,2,4]triazolo[1,5-c]quinazolin-2-yl)-5-methylpiperidin-1-yl)-1H-pyrazol-1-yl)-2-methylpropan-1-ol | Peak 1; Lux-4 21 × 250 mm column with 40% (MeOH w/0.1% NH₄OH modifier) as co-solvent | 469 |
| 166 | 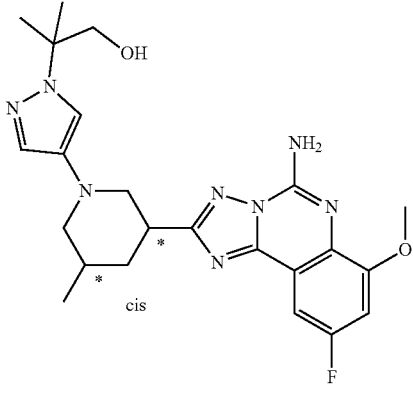 [SMILES: COc1cc(F)cc2c1nc(N)n1nc(C3CC(C)CN(c4cnn(C(C)(C)CO)c4)C3)nc21]<br>2-(4-((3S,5R or 3R,5S)-3-(5-amino-9-fluoro-7-methoxy-[1,2,4]triazolo[1,5-c]quinazolin-2-yl)-5-methylpiperidin-1-yl)-1H-pyrazol-1-yl)-2-methylpropan-1-ol | Peak 2; Lux-4 21 × 250 mm column with 40% (MeOH w/0.1% NH₄OH modifier) as co-solvent | 469 |

TABLE 30-continued

| Example | Structure Name | SFC Conditions | Observed m/z [M + H]+ |
|---|---|---|---|
| 167 | 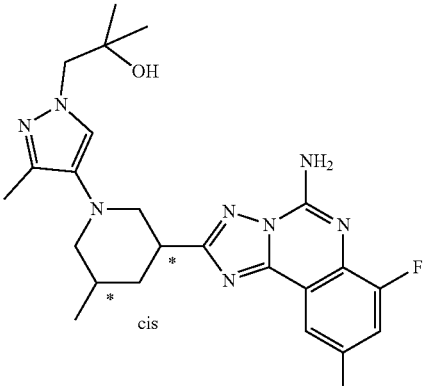<br>1-(4-((3R,5S or 3S,5R)-3-(5-amino-7,9-difluoro-[1,2,4]triazolo[1,5-c]quinazolin-2-yl)-5-methylpiperidin-1-yl)-3-methyl-1H-pyrazol-1-yl)-2-methylpropan-2-ol | Peak 1; Lux-4 21 × 250 mm column with 30% (MeOH w/0.1% NH4OH modifier) as co-solvent | 471 |
| 168 | 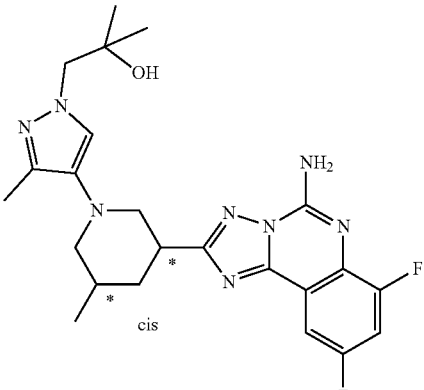<br>1-(4-((3S,5R or 3R,5S)-3-(5-amino-7,9-difluoro-[1,2,4]triazolo[1,5-c]quinazolin-2-yl)-5-methylpiperidin-1-yl)-3-methyl-1H-pyrazol-1-yl)-2-methylpropan-2-ol | Peak 2; Lux-4 21 × 250 mm column with 30% (MeOH w/0.1% NH4OH modifier) as co-solvent | 471 |
| 169 | 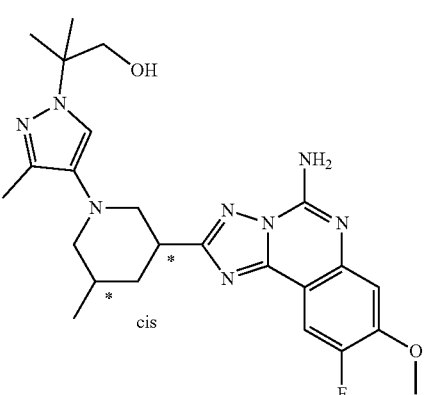<br>2-(4-((3R,5S or 3S,5R)-3-(5-amino-9-fluoro-8-methoxy-[1,2,4]triazolo[1,5-c]quinazolin-2-yl)-5-methylpiperidin-1-yl)-3-methyl-1H-pyrazol-1-yl)-2-methylpropan-1-ol | Peak 1; Chiralpak AD-3 4.6 × 150 mm column with 0-40% (IPA w/0.05% DEA modifier) as co-solvent | 483 |

TABLE 30-continued

| Example | Structure Name | SFC Conditions | Observed m/z [M + H]+ |
|---|---|---|---|
| 170 | 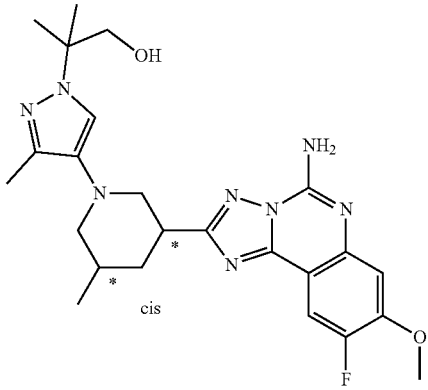<br>2-(4-((3S,5R or 3R,5S)-3-(5-amino-9-fluoro-8-methoxy-[1,2,4]triazolo[1,5-c]quinazolin-2-yl)-5-methylpiperidin-1-yl)-3-methyl-1H-pyrazol-1-yl)-2-methylpropan-1-ol | Peak 2; Chiralpak AD-3 4.6 × 150 mm column with 0-40% (IPA w/0.05% DEA modifier) as co-solvent | 483 |
| 171 | 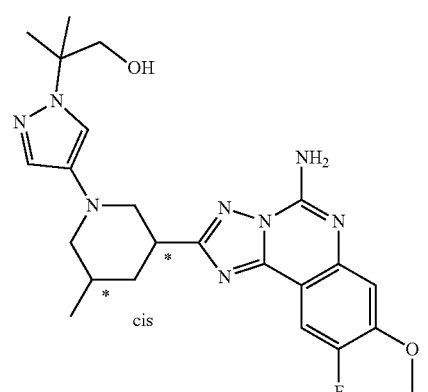<br>2-(4-((3R,5S or 3S,5R)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-1-ol | Peak 1; Chiralpak AD-3 4.6 × 150 mm column with 5-40% (EtOH w/0.05% DEA modifier) as co-solvent | 469 |
| 172 | 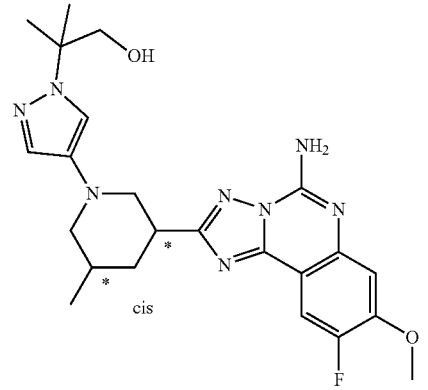 [SMILES: COc1cc2nc(N)n3nc(C4CC(C)CN(c5cnn(C(C)(C)CO)c5)C4)nc3c2cc1F]<br>2-(4-((3S,5R or 3R,5S)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-1-ol | Peak 2; Chiralpak AD-3 4.6 × 150 mm column with 5-40% (EtOH w/0.05% DEA modifier) as co-solvent | 469 |

TABLE 30-continued

| Example | Structure Name | SFC Conditions | Observed m/z [M + H]+ |
|---|---|---|---|
| 173 | 1-(4-((3R,5S or 3S,5R)-3-(5-amino-9-fluoro-7-methoxy-[1,2,4]triazolo[1,5-c]quinazolin-2-yl)-5-methylpiperidin-1-yl)-5-methyl-1H-pyrazol-1-yl)-2-methylpropan-2-ol | Peak 1; ES Industries CCA 21 × 250 mm column with 25% (MeOH w/0.1% NH4OH modifier) as co-solvent | 483 |
| 174 | 1-(4-((3S,5R or 3R,5S)-3-(5-amino-9-fluoro-7-methoxy-[1,2,4]triazolo[1,5-c]quinazolin-2-yl)-5-methylpiperidin-1-yl)-5-methyl-1H-pyrazol-1-yl)-2-methylpropan-2-ol | Peak 2; ES Industries CCA 21 × 250 mm column with 25% (MeOH w/0.1% NH4OH modifier) as co-solvent | 483 |
| 175 | 2-(4-((3R,5S or 3S,5R)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)-2-methylpropan-1-ol | Peak 1; Chiralpak AD-3 4.6 × 150 mm column with 5-40% (MeOH w/0.05% DEA modifier) as co-solvent | 483 |

TABLE 30-continued

| Example | Structure Name | SFC Conditions | Observed m/z [M + H]+ |
|---|---|---|---|
| 176 | 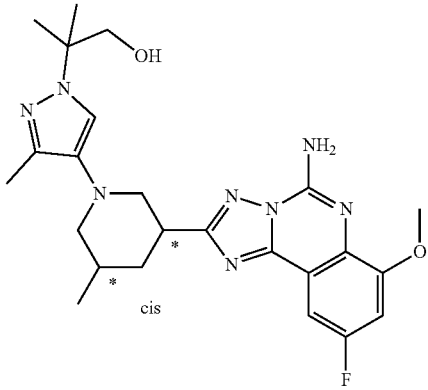<br>2-(4-((3S,5R or 3R,5S)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)-2-methylpropan-1-ol | Peak 2; Chiralpak AD-3 4.6 × 150 mm column with 5-40% (MeOH w/0.05% DEA modifier) as co-solvent | 483 |
| 177 | 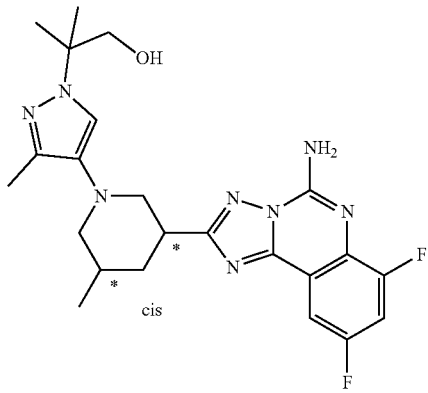 [SMILES: Cc1nn(C(C)(C)CO)cc1N1CC(C)CC(c2nc3c4cc(F)cc(F)c4nc(N)n3n2)C1]<br>2-(4-((3R,5S or 3S,5R)-3-(5-amino-7,9-difluoro-[1,2,4]triazolo[1,5-c]quinazolin-2-yl)-5-methylpiperidin-1-yl)-3-methyl-1H-pyrazol-1-yl)-2-methylpropan-1-ol | Peak 1; Chiralpak AD-3 4.6 × 150 mm column with 5-40% (IPA w/0.05% DEA modifier) as co-solvent | 471 |
| 178 | 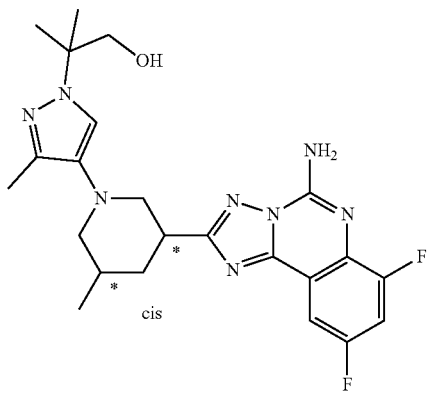 [SMILES: Cc1nn(C(C)(C)CO)cc1N1CC(C)CC(c2nc3c4cc(F)cc(F)c4nc(N)n3n2)C1]<br>2-(4-((3S,5R or 3R,5S)-3-(5-amino-7,9-difluoro-[1,2,4]triazolo[1,5-c]quinazolin-2-yl)-5-methylpiperidin-1-yl)-3-methyl-1H-pyrazol-1-yl)-2-methylpropan-1-ol | Peak 2; Chiralpak AD-3 4.6 × 150 mm column with 5-40% (IPA w/0.05% DEA modifier) as co-solvent | 471 |

TABLE 30-continued

| Example | Structure Name | SFC Conditions | Observed m/z [M + H]⁺ |
|---|---|---|---|
| 179 | 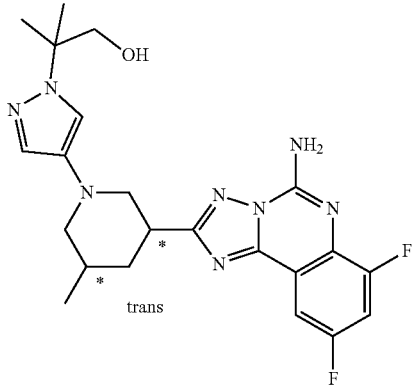 [SMILES: CC1CC(c2nc3c4cc(F)cc(F)c4nc(N)n3n2)CN(c2cnn(C(C)(C)CO)c2)C1]<br>2-(4-((3S,5S or 3R,5R)-3-(5-amino-7,9-difluoro-[1,2,4]triazolo[1,5-c]quinazolin-2-yl)-5-methylpiperidin-1-yl)-1H-pyrazol-1-yl)-2-methylpropan-1-ol | Peak 1; Chiral Technologies OJ-H 21 × 250 mm colum with 20% (MeOH w/0.1% NH₄OH modifier) as co-solvent | 457 |
| 180 | 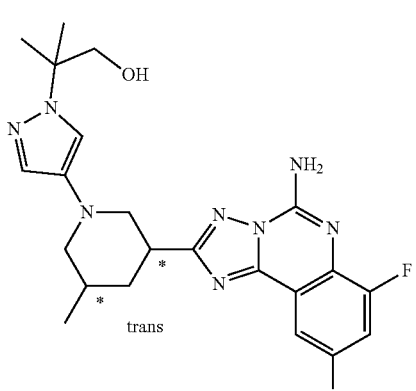<br>2-(4-((3R,5R or 3S,5S)-3-(5-amino-7,9-difluoro-[1,2,4]triazolo[1,5-c]quinazolin-2-yl)-5-methylpiperidin-1-yl)-1H-pyrazol-1-yl)-2-methylpropan-1-ol | Peak 2; Chiral Technologies OJ-H 21 × 250 mm column with 20% (MeOH w/0.1% NH₄OH modifier) as co-solvent | 457 |
| 181 | 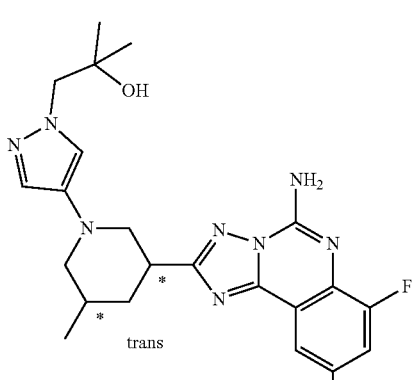<br>1-(4-((3S,5S or 3R,5R)-3-(5-amino-7,9-difluoro-[1,2,4]triazolo[1,5-c]quinazolin-2-yl)-5-methylpiperidin-1-yl)-1H-pyrazol-1-yl)-2-methylpropan-2-ol | Peak 1; Chiral Technologies OJ-H 21 × 250 mm column with 20% (MeOH w/0.1% NH₄OH modifier) as co-solvent | 457 |

TABLE 30-continued

| Example | Structure Name | SFC Conditions | Observed m/z [M + H]+ |
|---|---|---|---|
| 182 | 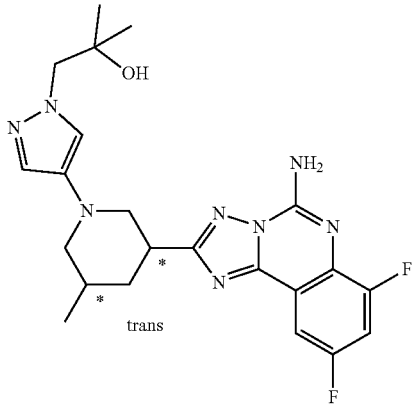 [SMILES: CC1CC(c2nc3c4cc(F)cc(F)c4nc(N)n3n2)CN(c2cnn(CC(C)(C)O)c2)C1]<br>1-(4-((3R,5R or 3S,5S)-3-(5-amino-7,9-difluoro-[1,2,4]triazolo[1,5-c]quinazolin-2-yl)-5-methylpiperidin-1-yl)-1H-pyrazol-1-yl)-2-methylpropan-2-ol | Peak 2; Chiral Technologies OJ-H 21 × 250 mm column with 20% (MeOH w/0.1% NH4OH modifier) as co-solvent | 457 |
| 183 | 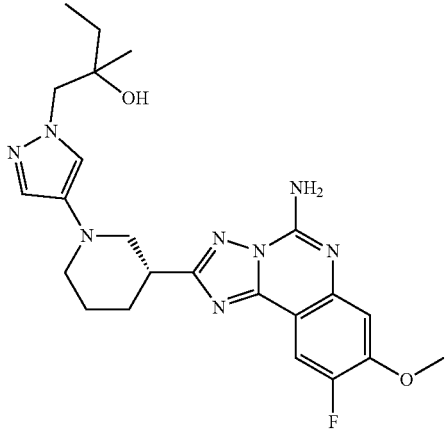 [SMILES: CCC(C)(O)Cn1cc(N2CCC[C@@H](c3nc4c5cc(F)c(OC)cc5nc(N)n4n3)C2)cn1]<br>(R or S)-1-(4-((R)-3-(5-amino-9-fluoro-8-methoxy-[1,2,4]triazolo[1,5-c]quinazolin-2-yl)piperidin-1-yl)-1H-pyrazol-1-yl)-2-methylbutan-2-ol | Peak 1; Chiralpak AD-3 4.6 × 150 mm column with 5-40% (IPA w/0.05% DEA modifier) as co-solvent | 469 |

TABLE 30-continued

| Example | Structure Name | SFC Conditions | Observed m/z [M + H]+ |
|---|---|---|---|
| 184 | (S or R)-1-(4-((R)-3-(5-amino-9-fluoro-8-methoxy-[1,2,4]triazolo[1,5-c]quinazolin-2-yl)piperidin-1-yl)-1H-pyrazol-1-yl)-2-methylbutan-2-ol | Peak 2; Chiralpak AD-3 4.6 × 150 mm column with 5-40% (IPA w/0.05% DEA modifier) as co-solvent | 469 |
| 185 | (2S,3S or 2R,3R)-3-(4-((R)-3-(5-amino-9-fluoro-7-methoxy-[1,2,4]triazolo[1,5-c]quinazolin-2-yl)piperidin-1-yl)-1H-pyrazol-1-yl)butan-2-ol | Peak 1; ES Industries CCA 21 × 250 mm column with 30% (MeOH w/0.1% NH4OH modifier) as co-solvent | 455 |
| 186 | (2R,3R or 2S,3S)-3-(4-((R)-3-(5-amino-9-fluoro-7-methoxy-[1,2,4]triazolo[1,5-c]quinazolin-2-yl)piperidin-1-yl)-1H-pyrazol-1-yl)butan-2-ol | Peak 2; ES Industries CCA 21 × 250 mm column with 30% (MeOH w/0.1% NH4OH modifier) as co-solvent | 455 |

TABLE 30-continued

| Example | Structure Name | SFC Conditions | Observed m/z [M + H]+ |
|---|---|---|---|
| 187 | 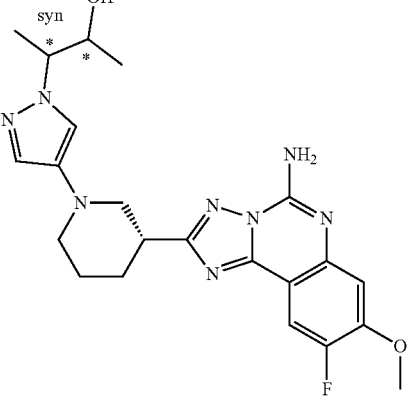<br>(2S,3S or 2R,3R)-3-(4-((R)-3-(5-amino-9-fluoro-8-methoxy-[1,2,4]triazolo[1,5-c]quinazolin-2-yl)piperidin-1-yl)-1H-pyrazol-1-yl)butan-2-ol | Peak 1; Chiral Technologies AS-H 21 × 250 mm column with 30% (MeOH w/ 0.1% NH$_4$OH modifier) as co-solvent | 455 |
| 188 | 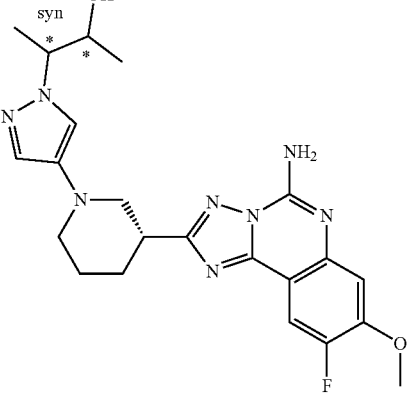<br>(2R,3R or 2S,3S)-3-(4-((R)-3-(5-amino-9-fluoro-8-methoxy-[1,2,4]triazolo[1,5-c]quinazolin-2-yl)piperidin-1-yl)-1H-pyrazol-1-yl)butan-2-ol | Peak 2; Chiral Technologies AS-H 21 × 250 mm column with 30% (MeOH w/ 0.1% NH$_4$OH modifier) as co-solvent | 455 |
| 189 | 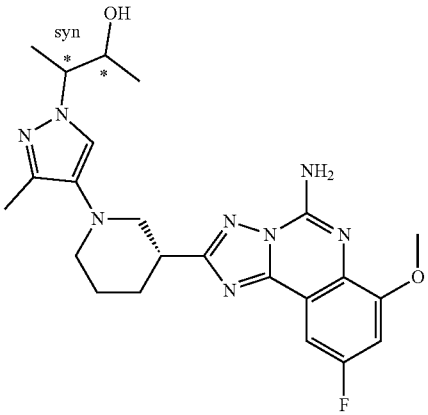<br>(2S,3S or 2R,3R)-3-(4-((R)-3-(5-amino-9-fluoro-7-methoxy-[1,2,4]triazolo[1,5-c]quinazolin-2-yl)piperidin-1-yl)-3-methyl-1H-pyrazol-1-yl)butan-2-ol | Peak 1; ES Industries CCA 21 × 250 mm column with 15% (MeOH w/0.1% NH$_4$OH modifier) as co-solvent | 469 |

TABLE 30-continued

| Example | Structure Name | SFC Conditions | Observed m/z [M + H]+ |
|---|---|---|---|
| 190 | 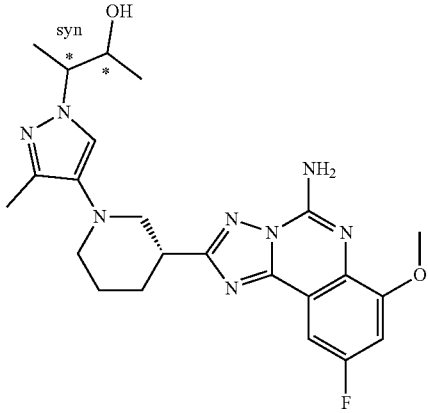<br>(2R,3R or 2S,3S)-3-(4-((R)-3-(5-amino-9-fluoro-7-methoxy-[1,2,4]triazolo[1,5-c]quinazolin-2-yl)piperidin-1-yl)-3-methyl-1H-pyrazol-1-yl)butan-2-ol | Peak 2; ES Industries CCA 21 × 250 mm column with 15% (MeOH w/0.1% NH4OH modifier) as co-solvent | 469 |
| 191 | 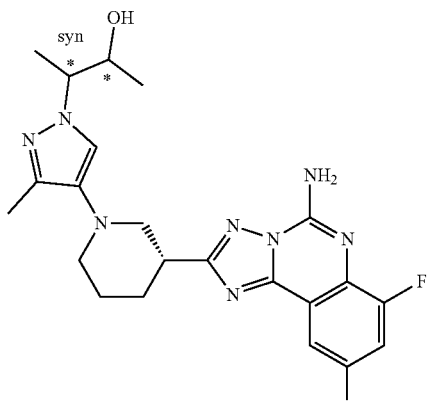<br>(2S,3S or 2R,3R)-3-(4-((R)-3-(5-amino-7,9-difluoro-[1,2,4]triazolo[1,5-c]quinazolin-2-yl)piperidin-1-yl)-3-methyl-1H-pyrazol-1-yl)butan-2-ol | Peak 1; Chiral Technologies AD-H 21 × 250 mm column with 30% (MeOH w/ 0.1% NH4OH modifier) as co-solvent | 457 |
| 192 | 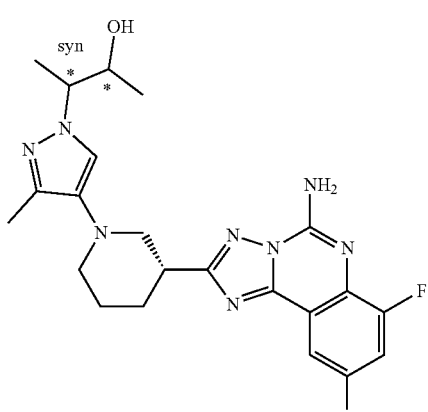<br>(2R,3R or 2S,3S)-3-(4-((R)-3-(5-amino-7,9-difluoro-[1,2,4]triazolo[1,5-c]quinazolin-2-yl)piperidin-1-yl)-3-methyl-1H-pyrazol-1-yl)butan-2-ol | Peak 2; Chiral Technologies AD-H 21 × 250 mm column with 30% (MeOH w/ 0.1% NH4OH modifier) as co-solvent | 457 |

TABLE 30-continued

| Example | Structure Name | SFC Conditions | Observed m/z [M + H]+ |
|---|---|---|---|
| 193 | (2S,3S or 2R,3R)-3-(4-((R)-3-(5-amino-9-fluoro-7-methoxy-[1,2,4]triazolo[1,5-c]quinazolin-2-yl)piperidin-1-yl)-5-methyl-1H-pyrazol-1-yl)butan-2-ol | Peak 1; Chiral Technologies AD-H 21 × 250 mm column with 25% (MeOH w/ 0.1% NH4OH modifier) as co-solvent | 469 |
| 194 | (2R,3R or 2S,3S)-3-(4-((R)-3-(5-amino-9-fluoro-7-methoxy-[1,2,4]triazolo[1,5-c]quinazolin-2-yl)piperidin-1-yl)-5-methyl-1H-pyrazol-1-yl)butan-2-ol | Peak 2; Chiral Technologies AD-H 21 × 250 mm column with 25% (MeOH w/ 0.1% NH4OH modifier) as co-solvent | 469 |
| 195 | (2S,3S or 2R,3R)-3-(4-((R)-3-(5-amino-9-fluoro-8-methoxy-[1,2,4]triazolo[1,5-c]quinazolin-2-yl)piperidin-1-yl)-5-methyl-1H-pyrazol-1-yl)butan-2-ol | Peak 1; Chiral Technologies IG 21 × 250 mm column with 35% (MeOH w/0.1% NH4OH modifier) as co-solvent | 469 |

TABLE 30-continued

| Example | Structure Name | SFC Conditions | Observed m/z [M + H]+ |
|---|---|---|---|
| 196 | (2R,3R or 2S,3S)-3-(4-((R)-3-(5-amino-9-fluoro-8-methoxy-[1,2,4]triazolo[1,5-c]quinazolin-2-yl)piperidin-1-yl)-5-methyl-1H-pyrazol-1-yl)butan-2-ol | Peak 2; Chiral Technologies IG 21 × 250 mm column with 35% (MeOH w/0.1% NH4OH modifier) as co-solvent | 469 |
| 197 | (2S,3S or 2R,3R)-3-(4-((R)-3-(5-amino-7,9-difluoro-[1,2,4]triazolo[1,5-c]quinazolin-2-yl)piperidin-1-yl)-1H-pyrazol-1-yl)butan-2-ol | Peak 1; Chiralpak AS-3 4.6 × 150 mm column with 5-40% (IPA w/0.05% DEA modifier) as co-solvent | 443 |
| 198 | (2R,3R or 2S,3S)-3-(4-((R)-3-(5-amino-7,9-difluoro-[1,2,4]triazolo[1,5-c]quinazolin-2-yl)piperidin-1-yl)-1H-pyrazol-1-yl)butan-2-ol | Peak 2; Chiralpak AS-3 4.6 × 150 mm column with 5-40% (IPA w/0.05% DEA modifier) as co-solvent | 443 |

TABLE 30-continued

| Example | Structure Name | SFC Conditions | Observed m/z [M + H]+ |
|---|---|---|---|
| 199 | (2R,3S or 2S,3R)-3-(4-((R)-3-(5-amino-9-fluoro-8-methoxy-[1,2,4]triazolo[1,5-c]quinazolin-2-yl)piperidin-1-yl)-1H-pyrazol-1-yl)butan-2-ol | Peak 1; Chiral Technologies OJ-H 21 × 250 mm column with 15% (MeOH w/0.1% NH₄OH modifier) as co-solvent | 455 |
| 200 | (2S,3R or 2R,3S)-3-(4-((R)-3-(5-amino-9-fluoro-8-methoxy-[1,2,4]triazolo[1,5-c]quinazolin-2-yl)piperidin-1-yl)-1H-pyrazol-1-yl)butan-2-ol | Peak 2; Chiral Technologies OJ-H 21 × 250 mm column with 15% (MeOH w/0.1% NH₄OH modifier) as co-solvent | 455 |
| 201 | (2R,3S or 2S,3R)-3-(4-((R)-3-(5-amino-9-fluoro-7-methoxy-[1,2,4]triazolo[1,5-c]quinazolin-2-yl)piperidin-1-yl)-1H-pyrazol-1-yl)butan-2-ol | Peak 1; Chiral Technologies AD-H 21 × 250 mm column with 35% (MeOH w/ 0.1% NH₄OH modifier) as co-solvent | 455 |

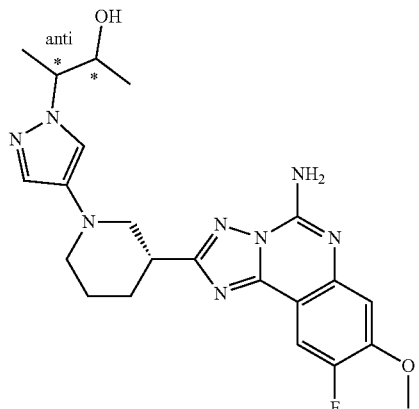

TABLE 30-continued

| Example | Structure Name | SFC Conditions | Observed m/z [M + H]+ |
|---|---|---|---|
| 202 | 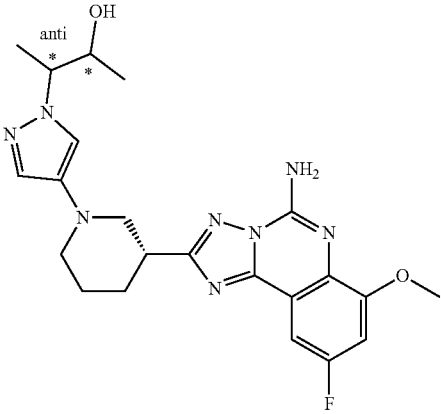 [SMILES: COc1cc(F)cc2c1nc(N)n1nc([C@@H]3CCCN(c4cnn(C(C)C(C)O)c4)C3)nc21]<br>(2S,3R or 2R,3S)-3-(4-((R)-3-(5-amino-9-fluoro-7-methoxy-[1,2,4]triazolo[1,5-c]quinazolin-2-yl)piperidin-1-yl)-1H-pyrazol-1-yl)butan-2-ol | Peak 2; Chiral Technologies AD-H 21 × 250 mm column with 35% (MeOH w/ 0.1% NH₄OH modifier) as co-solvent | 455 |
| 203 | 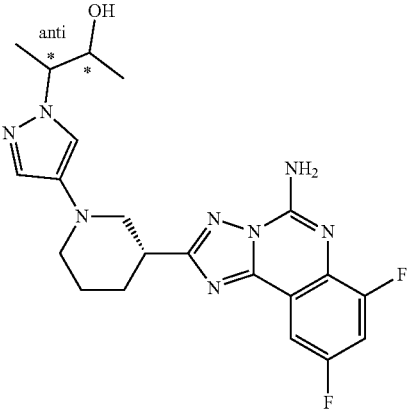 [SMILES: CC(O)C(C)n1cc(N2CCC[C@@H](c3nc4c5cc(F)cc(F)c5nc(N)n4n3)C2)cn1]<br>(2R,3S or 2S,3R)-3-(4-((R)-3-(5-amino-7,9-difluoro-[1,2,4]triazolo[1,5-c]quinazolin-2-yl)piperidin-1-yl)-1H-pyrazol-1-yl)butan-2-ol | Peak 1; Chiralpak AS-3 4.6 × 100 mm column with 0-40% (IPA w/0.05% DEA modifier) as co-solvent | 443 |
| 204 | 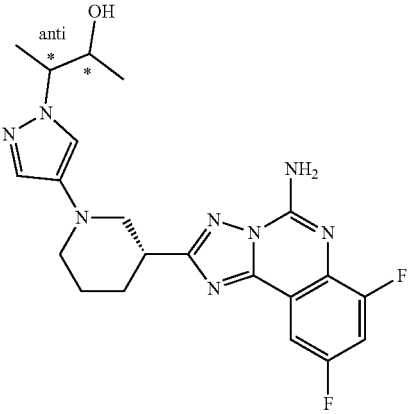 [SMILES: CC(O)C(C)n1cc(N2CCC[C@@H](c3nc4c5cc(F)cc(F)c5nc(N)n4n3)C2)cn1]<br>(2S,3R or 2R,3S)-3-(4-((R)-3-(5-amino-7,9-difluoro-[1,2,4]triazolo[1,5-c]quinazolin-2-yl)piperidin-1-yl)-1H-pyrazol-1-yl)butan-2-ol | Peak 2; Chiralpak AS-3 4.6 × 100 mm column with 0-40% (IPA w/0.05% DEA modifier) as co-solvent | 443 |

TABLE 30-continued

| Example | Structure Name | SFC Conditions | Observed m/z [M + H]+ |
|---|---|---|---|
| 205 | 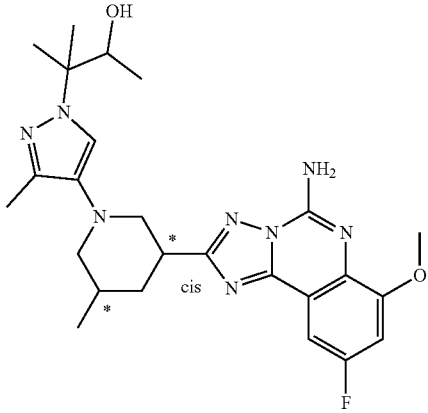<br>(R or S)-3-(4-((3R,5S or 3S,5R)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)-3-methylbutan-2-ol | Peak 1; Chiralpak AD-3 4.6 × 100 mm column with 5-40% (IPA w/0.05% DEA modifier) as co-solvent. Then Peak 1; Chiral Technologies AD-H 21 × 250 mm column with 20% (IPA w/0.1% NH4OH modifier) as co-solvent | 497 |
| 206 | 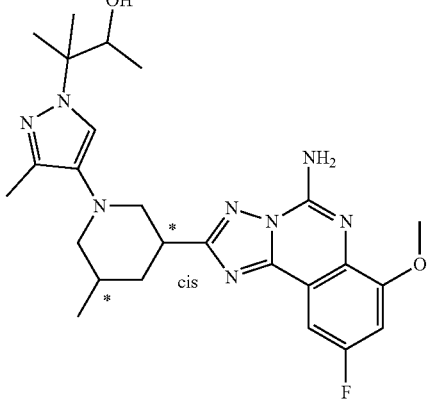<br>(S or R)-3-(4-((3R,5S or 3S,5R)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)-3-methylbutan-2-ol | Peak 1; Chiralpak AD-3 4.6 × 100 mm column with 5-40% (IPA w/0.05% DEA modifier) as co-solvent. Then Peak 2; Chiral Technologies AD-H 21 × 250 mm column with 20% (IPA w/0.1% NH4OH modifier) as co-solvent | 497 |
| 207 | 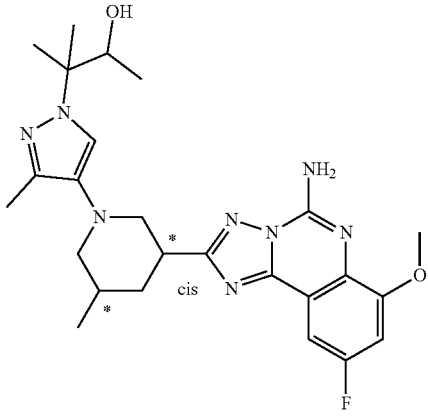<br>(R or S)-3-(4-((3S,5R or 3R,5S)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)-3-methylbutan-2-ol | Peak 2; Chiralpak AD-3 4.6 × 100 mm column with 5-40% (IPA w/0.05% DEA modifier) as co-solvent. | 497 |

TABLE 30-continued

| Example | Structure Name | SFC Conditions | Observed m/z [M + H]+ |
|---|---|---|---|
| 208 | (2S,3S or 2R,3R)-3-(4-((3R,5S or 3S,5R)-3-(5-amino-9-fluoro-8-methoxy-[1,2,4]triazolo[1,5-c]quinazolin-2-yl)-5-methylpiperidin-1-yl)-3-methyl-1H-pyrazol-1-yl)butan-2-ol | Peak 1; ES Industries CC4 21 × 250 mm column with 35% (MeOH w/0.1% NH4OH modifier) as co-solvent. Then Peak 1; ES Industries CCA 21 × 250 mm column with 15% (MeOH w/ 0.1% NH4OH modifier) as co-solvent | 483 |
| 209 | (2R,3R or 2S,3S)-3-(4-((3R,5S or 3S,5R)-3-(5-amino-9-fluoro-8-methoxy-[1,2,4]triazolo[1,5-c]quinazolin-2-yl)-5-methylpiperidin-1-yl)-3-methyl-1H-pyrazol-1-yl)butan-2-ol | Peak 1; ES Industries CC4 21 × 250 mm column with 35% (MeOH w/0.1% NH4OH modifier) as co-solvent. Then Peak 2; ES Industries CCA 21 × 250 mm column with 15% (MeOH w/ 0.1% NH4OH modifier) as co-solvent | 483 |
| 210 | (2R,3R or 2S,3S)-3-(4-((3S,5R or 3R,5S)-3-(5-amino-9-fluoro-8-methoxy-[1,2,4]triazolo[1,5-c]quinazolin-2-yl)-5-methylpiperidin-1-yl)-3-methyl-1H-pyrazol-1-yl)butan-2-ol | Peak 2; ES Industries CC4 21 × 250 mm column with 35% (MeOH w/0.1% NH4OH modifier) as co-solvent. | 483 |

TABLE 30-continued

| Example | Structure Name | SFC Conditions | Observed m/z [M + H]+ |
|---|---|---|---|
| 211 | 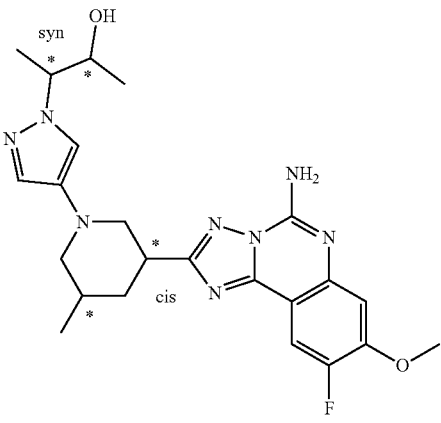 [SMILES: COc1cc2nc(N)n3nc(C4CC(C)CN(c5cnn(C(C)C(C)O)c5)C4)nc3c2cc1F]<br>(2S,3S or 2R,3R)-3-(4-((3S,5R or 3R,5S)-3-(5-amino-9-fluoro-8-methoxy-[1,2,4]triazolo[1,5-c]quinazolin-2-yl)-5-methylpiperidin-1-yl)-3-methyl-1H-pyrazol-1-yl)butan-2-ol | Peak 3; ES Industries CC4 21 × 250 mm column with 35% (MeOH w/0.1% NH₄OH modifier) as co-solvent. | 483 |
| 212 | 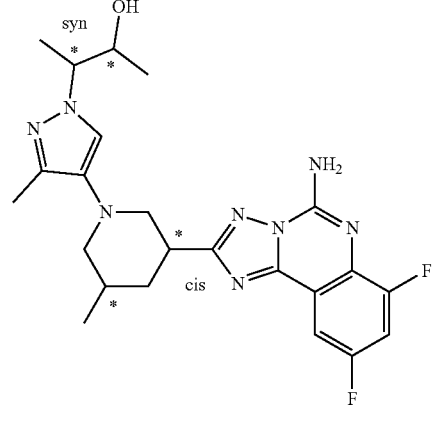 [SMILES: Cc1nn(C(C)C(C)O)cc1N1CC(C)CC(c2nc3c4cc(F)cc(F)c4nc(N)n3n2)C1]<br>(2S,3S or 2R,3R)-3-(4-((3R,5S or 3S,5R)-3-(5-amino-7,9-difluoro-[1,2,4]triazolo[1,5-c]quinazolin-2-yl)-5-methylpiperidin-1-yl)-3-methyl-1H-pyrazol-1-yl)butan-2-ol | Peak 1; Chiral Technologies AD-H 30 × 250 mm column with 5-40% (IPA w/ 0.05% DEA modifier) as co-solvent. | 471 |
| 213 | 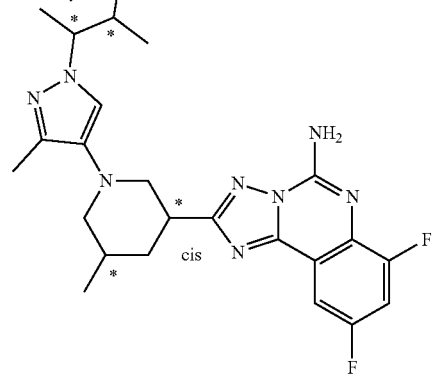<br>(2R,3R or 2S,3S)-3-(4-((3R,5S or 3S,5R)-3-(5-amino-7,9-difluoro-[1,2,4]triazolo[1,5-c]quinazolin-2-yl)-5-methylpiperidin-1-yl)-3-methyl-1H-pyrazol-1-yl)butan-2-ol | Peak 2; Chiral Technologies AD-H 30 × 250 mm column with 5-40% (IPA w/ 0.05% DEA modifier) as co-solvent. | 471 |

TABLE 30-continued

| Example | Structure Name | SFC Conditions | Observed m/z [M + H]+ |
|---|---|---|---|
| 214 | (2R,3R or 2S,3S)-3-(4-((3S,5R or 3R,5S)-3-(5-amino-7,9-difluoro-[1,2,4]triazolo[1,5-c]quinazolin-2-yl)-5-methylpiperidin-1-yl)-3-methyl-1H-pyrazol-1-yl)butan-2-ol | Peak 3; Chiral Technologies AD-H 30 × 250 mm column with 5-40% (IPA w/ 0.05% DEA modifier) as co-solvent. | 471 |
| 215 | (2S,3S or 2R,3R)-3-(4-((3S,5R or 3R,5S)-3-(5-amino-7,9-difluoro-[1,2,4]triazolo[1,5-c]quinazolin-2-yl)-5-methylpiperidin-1-yl)-3-methyl-1H-pyrazol-1-yl)butan-2-ol | Peak 4; Chiral Technologies AD-H 30 × 250 mm column with 5-40% (IPA w/ 0.05% DEA modifier) as co-solvent. | 471 |
| 216 | (2S,3S or 2R,3R)-3-(4-((3R,5S or 3S,5R)-3-(5-amino-7,9-difluoro-[1,2,4]triazolo[1,5-c]quinazolin-2-yl)-5-methylpiperidin-1-yl)-5-methyl-1H-pyrazol-1-yl)butan-2-ol | Peak 1; IG 50 × 250 mm column with 5-40% (EtOH w/0.05% DEA modifier) as co-solvent. | 471 |

TABLE 30-continued

| Example | Structure Name | SFC Conditions | Observed m/z [M + H]+ |
|---|---|---|---|
| 217 | (2R,3R or 2S,3S)-3-(4-((3R,5S or 3S,5R)-3-(5-amino-7,9-difluoro-[1,2,4]triazolo[1,5-c]quinazolin-2-yl)-5-methylpiperidin-1-yl)-5-methyl-1H-pyrazol-1-yl)butan-2-ol | Peak 2; IG 50 × 250 mm column with 5-40% (EtOH w/0.05% DEA modifier) as co-solvent. | 471 |
| 218 | (2R,3R or 2S,3S)-3-(4-((3S,5R or 3R,5S)-3-(5-amino-7,9-difluoro-[1,2,4]triazolo[1,5-c]quinazolin-2-yl)-5-methylpiperidin-1-yl)-5-methyl-1H-pyrazol-1-yl)butan-2-ol | Peak 3; IG 50 × 250 mm column with 5-40% (EtOH w/0.05% DEA modifier) as co-solvent. | 471 |
| 219 | (2S,3S or 2R,3R)-3-(4-((3S,5R or 3R,5S)-3-(5-amino-7,9-difluoro-[1,2,4]triazolo[1,5-c]quinazolin-2-yl)-5-methylpiperidin-1-yl)-5-methyl-1H-pyrazol-1-yl)butan-2-ol | Peak 4; IG 50 × 250 mm column with 5-40% (EtOH w/0.05% DEA modifier) as co-solvent. | 471 |

TABLE 30-continued

| Example | Structure Name | SFC Conditions | Observed m/z [M + H]+ |
|---|---|---|---|
| 220 | (2S,3S or 2R,3R)-3-(4-((3R,5S or 3S,5R)-3-(5-amino-9-fluoro-7-methoxy-[1,2,4]triazolo[1,5-c]quinazolin-2-yl)-5-methylpiperidin-1-yl)-5-methyl-1H-pyrazol-1-yl)butan-2-ol | Peak 1; Chiralpak AD-3 4.6 × 150 mm column with 5-40% (IPA w/0.05% DEA modifier) as co-solvent. | 483 |
| 221 | (2R,3R or 2S,3S)-3-(4-((3R,5S or 3S,5R)-3-(5-amino-9-fluoro-7-methoxy-[1,2,4]triazolo[1,5-c]quinazolin-2-yl)-5-methylpiperidin-1-yl)-5-methyl-1H-pyrazol-1-yl)butan-2-ol | Peak 2; Chiralpak AD-3 4.6 × 150 mm column with 5-40% (IPA w/0.05% DEA modifier) as co-solvent. | 483 |
| 222 | (2R,3R or 2S,3S)-3-(4-((3S,5R or 3R,5S)-3-(5-amino-9-fluoro-7-methoxy-[1,2,4]triazolo[1,5-c]quinazolin-2-yl)-5-methylpiperidin-1-yl)-5-methyl-1H-pyrazol-1-yl)butan-2-ol | Peak 3; Chiralpak AD-3 4.6 × 150 mm column with 5-40% (IPA w/0.05% DEA modifier) as co-solvent | 483 |

TABLE 30-continued

| Example | Structure Name | SFC Conditions | Observed m/z [M + H]+ |
|---|---|---|---|
| 223 | (2S,3S or 2R,3R)-3-(4-((3S,5R or 3R,5S)-3-(5-amino-9-fluoro-7-methoxy-[1,2,4]triazolo[1,5-c]quinazolin-2-yl)-5-methylpiperidin-1-yl)-5-methyl-1H-pyrazol-1-yl)butan-2-ol | Peak 4; Chiralpak AD-3 4.6 × 150 mm column with 5-40% (IPA w/0.05% DEA modifier) as co-solvent. | 483 |
| 224 | (2S,3S or 2R,3R)-3-(4-((3R,5S or 3S,5R)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)butan-2-ol | Peak 1; Chiral Technologies AD-H 30 × 250 mm column with 5-40% (EtOH w/ 0.05% DEA modifier) as co-solvent. Then Peak 1; Chiral Technologies AD-H 30 × 250 mm column with 5-40% (IPA w/ 0.05% DEA modifier) as co-solvent. | 483 |
| 225 | (2R,3R or 2S,3S)-3-(4-((3R,5S or 3S,5R)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)butan-2-ol | Peak 1; Chiral Technologies AD-H 30 × 250 mm column with 5-40% (EtOH w/ 0.05% DEA modifier) as co-solvent. Then Peak 2; Chiral Technologies AD-H 30 × 250 mm column with 5-40% (IPA w/ 0.05% DEA modifier) as co-solvent. | 483 |

TABLE 30-continued

| Example | Structure Name | SFC Conditions | Observed m/z [M + H]+ |
|---|---|---|---|
| 226 | (2R,3R or 2S,3S)-3-(4-((3S,5R or 3R,5S)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)butan-2-ol | Peak 2; Chiral Technologies AD-H 30 × 250 mm column with 5-40% (EtOH w/ 0.05% DEA modifier) as co-solvent. | 483 |
| 227 | (2S,3S or 2R,3R)-3-(4-((3S,5R or 3R,5S)-3-(5-amino-9-fluoro-7-methoxy-[1,2,4]triazolo[1,5-c]quinazolin-2-yl)-5-methylpiperidin-1-yl)-3-methyl-1H-pyrazol-1-yl)butan-2-ol | Peak 3; Chiral Technologies AD-H 30 × 250 mm column with 5-40% (EtOH w/ 0.05% DEA modifier) as co-solvent. | 483 |

Example 228-231: (2S,3S or 2R,3R)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol and (2S,3S or 2R,3R)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol and (2R,3R or 2S,3S)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol and (2R,3R or 2S,3S)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol

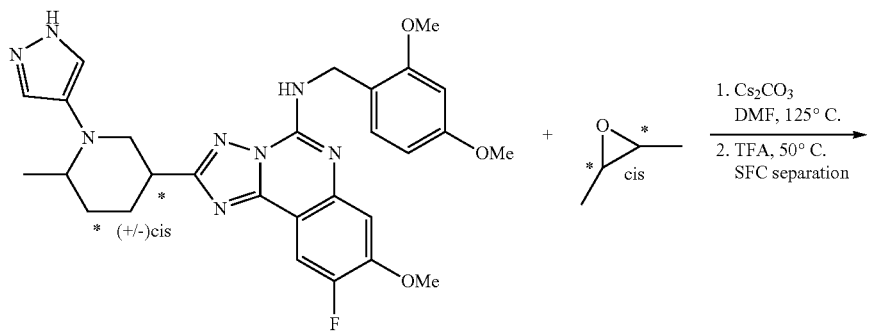

Intermediate 177

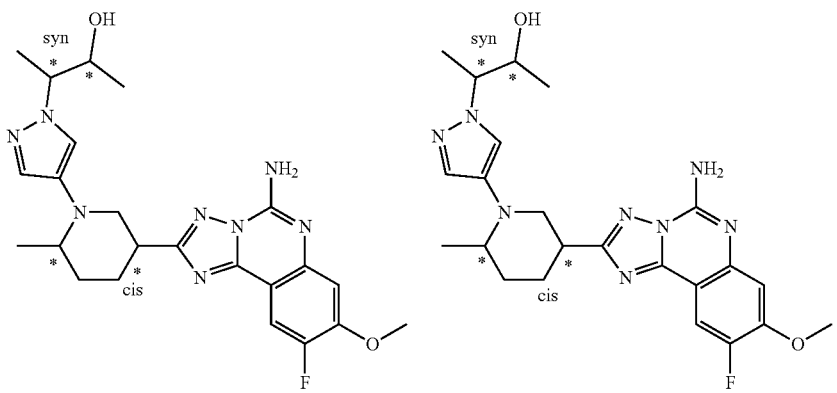

Example 228  Example 230

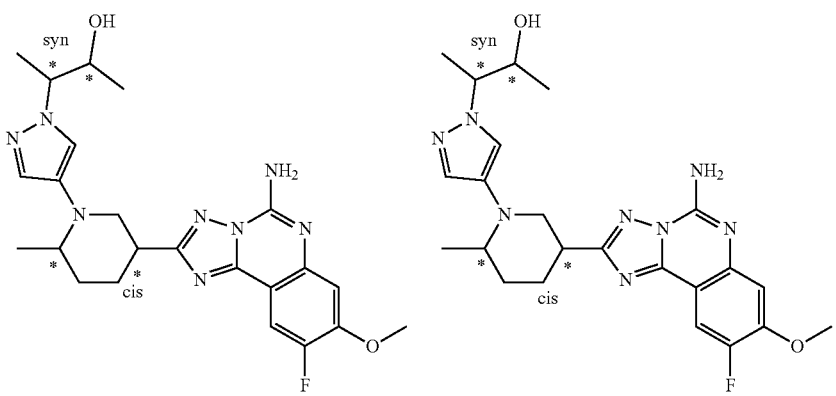

Example 229  Example 231

Step 1: Mixture of diastereomers of (2S,3S and 2R,3R)-3-(4-((2S,5R or 2R,5S)-5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)butan-2-ol To solution of N-(2,4-dimethoxybenzyl)-9-fluoro-8-methoxy-2-((3R,6S and 3S,6R)-6-methyl-1-(1H-pyrazol-4-yl)piperidin-3-yl)-[1,2,4]triazolo[1,5-c]quinazolin-5-amine (Intermediate 177) (530 mg, 0.970 mmol) in DMF (10 mL) was added cis-2,3-dimethyloxirane (846 µl, 9.70 mmol) and cesium carbonate (1.26 g, 3.88 mmol). The mixture was stirred and heated at 125° C. for 5 h. The mixture was cooled to room temperature, and the mixture was diluted with water (20 mL) and ethyl acetate (20 mL). The biphasic mixture was separated and the aqueous phase was further extracted with ethyl acetate (20 mL). The combined organic layers were then washed with water (2×20 mL) and brine (1×20 mL). The organic layer was dried over anhydrous $MgSO_4$, filtered, and the solvents were evaporated. The residue was purified by silica gel chromatography with 0-20% MeOH in DCM as eluent to afford the intermediate mixture of diastereomers of (2S,3S and 2R,3R)-3-(4-((2S,5R or 2R,5S)-5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)butan-2-ol.

Step 2: (2S,3S or 2R,3R)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol and (2S,3S or 2R,3R)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol and (2R,3R or 2S,3S)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol and (2R,3R or 2S,3S)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol To a 20 mL vial was added 3-(4-(5-(5-((2,4-dimethoxybenzyl)amino)-9-fluoro-8-methoxy-[1,2,4]triazolo[1,5-c]quinazolin-2-yl)-2-methylpiperidin-1-yl)-1H-pyrazol-1-yl)butan-2-ol (475 mg, 0.768 mmol) and TFA (1.77 mL 23.0 mmol). The mixture was stirred and heated at 50° C. for 3 h. The mixture was cooled at room temperature, and the solvents were evaporated. The residue was dissolved in MeOH (10 mL) and quenched with a 7 M solution of ammonia in MeOH (1.10 mL, 7.68 mmol). The mixture was stirred for 20 minutes. The mixture was filtered, rinsing the solids with MeOH, and the filtrate was concentrated. The residue was suspended in DCM and filtered to remove remaining ammonium salts. The filtrate was was loaded directly onto a silica gel column, eluting with 0-15% MeOH in DCM to afford a mixture of isomers. The mixture was submitted for chiral SFC separation (Phenomenex Lux-2 21×250 mm column with 45% (MeOH w/0.1% $NH_4OH$ modifier) as co-solvent), to afford a mixture of Example 228 and Example 229 (peak 1), (2R,3R or 2S,3S)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol (Example 230, peak 2) and (2R,3R or 2S,3S)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol (Example 231, peak 3). The mixture obtained in peak 1 was further purified by SFC separation (Chiral Technologies AS-H 21×250 mm column with 20% (MeOH w/0.1% $NH_4OH$ modifier) as co-solvent), to afford (2S,3S or 2R,3R)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol (Example 228, peak 1) and (2S,3S or 2R,3R)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol (Example 229, peak 2).

For Example 228: LCMS ($C_{23}H_{29}FN_8O_2$) (ES, m/z): 469 $[M+H]^+$. $^1H$ NMR (499 MHz, DMSO-$d_6$) δ 7.90 (d, J=10.6 Hz, 1H), 7.73 (s, 2H), 7.22 (s, 1H), 7.19 (d, J=7.4 Hz, 1H), 7.12 (s, 1H), 4.73 (d, J=5.0 Hz, 1H), 4.13-4.05 (m, 1H), 3.98 (s, 3H), 3.88-3.78 (m, 1H), 3.70 (s, 1H), 3.19 (s, 1H), 3.10 (t, J=11.5 Hz, 1H), 2.01 (d, J=21.4 Hz, 3H), 1.70 (d, J=9.1 Hz, 1H), 1.34 (d, J=6.9 Hz, 3H), 1.03 (d, J=6.6 Hz, 3H), 0.92 (d, J=6.1 Hz, 3H).

For Example 229: LCMS ($C_{23}H_{29}FN_8O_2$) (ES, m/z): 469 $[M+H]^+$. $^1H$ NMR (499 MHz, DMSO-$d_6$) δ 7.90 (d, J=8.2 Hz, 1H), 7.73 (s, 2H), 7.25-7.21 (m, 1H), 7.19 (d, J=4.8 Hz, 1H), 7.12 (d, J=2.9 Hz, 1H), 4.72 (s, 1H), 4.09 (s, 1H), 3.98 (d, J=2.7 Hz, 3H), 3.83 (s, 1H), 3.70 (s, 1H), 3.19 (s, 1H), 3.10 (t, J=10.5 Hz, 1H), 1.99 (s, 3H), 1.72 (s, 1H), 1.43-1.30 (m, 3H), 1.03 (d, J=3.4 Hz, 3H), 0.92 (d, J=3.0 Hz, 3H).

For Example 230: LCMS ($C_{23}H_{29}FN_8O_2$) (ES, m/z): 469 $[M+H]^+$. $^1H$ NMR (499 MHz, DMSO-$d_6$) δ 7.90 (d, J=11.0 Hz, 1H), 7.72 (s, 2H), 7.22 (s, 1H), 7.18 (d, J=7.8 Hz, 1H), 7.11 (s, 1H), 4.77-4.64 (m, 1H), 4.14-4.04 (m, 1H), 4.02-3.94 (m, 3H), 3.88-3.78 (m, 3H), 3.71 (d, J=9.9 Hz, 1H), 3.18 (dd, J=6.4, 4.4 Hz, 1H), 3.09 (t, J=11.4 Hz, 1H), 2.01 (d, J=22.2 Hz, 3H), 1.70 (d, J=10.4 Hz, 1H), 1.38-1.31 (m, 3H), 1.03 (d, J=6.4 Hz, 3H), 0.95-0.89 (m, 3H).

For Example 231: LCMS ($C_{23}H_{29}FN_8O_2$) (ES, m/z): 469 $[M+H]^+$. $^1H$ NMR (499 MHz, DMSO-$d_6$) δ 7.90 (d, J=9.6 Hz, 1H), 7.73 (s, 2H), 7.22 (s, 1H), 7.19 (d, J=6.7 Hz, 1H), 7.12 (s, 1H), 4.73 (d, J=3.3 Hz, 1H), 4.15-4.03 (m, 1H), 3.98 (s, 3H), 3.83 (d, J=5.2 Hz, 1H), 3.70 (s, 1H), 3.19 (s, 1H), 3.10 (t, J=11.0 Hz, 1H), 2.01 (d, J=21.8 Hz, 3H), 1.70 (d, J=9.6 Hz, 1H), 1.33 (d, J=5.7 Hz, 3H), 1.03 (d, J=5.4 Hz, 3H), 0.92 (d, J=5.0 Hz, 3H).

The example compounds of the invention in the following Table 31 were prepared in a manner similar to that described for the preparation of Example 228-231 from the appropriate starting materials and intermediates, where the resulting isomeric mixture of the corresponding final compounds were separated by SFC.

TABLE 31

| Example | Structure Name | SFC Conditions | Observed m/z [M + H]+ |
|---|---|---|---|
| 232 | (2S,3S or 2R,3R)-3-(4-((2S,5R or 2R,5S)-5-(5-amino-7,9-difluoro-[1,2,4]triazolo[1,5-c]quinazolin-2-yl)-2-methylpiperidin-1-yl)-1H-pyrazol-1-yl)butan-2-ol | Peak 1 (mixture of Example 232 and Example 233); Phenomenex Lux-2 21 × 250 mm column with 45% (MeOH w/0.1% NH4OH modifier) as co-solvent. Then Peak 1; Chiral Technologies AS-H 21 × 250 mm column with 20% (MeOH w/0.1% NH4OH modifier) as co-solvent. | 457 |
| 233 | (2R,3R or 2S,3S)-3-(4-((2S,5R or 2R,5S)-5-(5-amino-7,9-difluoro-[1,2,4]triazolo[1,5-c]quinazolin-2-yl)-2-methylpiperidin-1-yl)-1H-pyrazol-1-yl)butan-2-ol | Peak 1 (mixture of Example 232 and Example 233); Phenomenex Lux-2 21 × 250 mm column with 45% (MeOH w/0.1% NH4OH modifier) as co-solvent. Then Peak 2; Chiral Technologies AS-H 21 × 250 mm column with 20% (MeOH w/0.1% NH4OH modifier) as co-solvent. | 457 |
| 234 | (2R,3R or 2S,3S)-3-(4-((2R,5S or 2S,5R)-5-(5-amino-7,9-difluoro-[1,2,4]triazolo[1,5-c]quinazolin-2-yl)-2-methylpiperidin-1-yl)-1H-pyrazol-1-yl)butan-2-ol | Peak 2; Phenomenex Lux-2 21 × 250 mm column with 45% (MeOH w/0.1% NH4OH modifier) as co-solvent. | 457 |

TABLE 31-continued

| Example | Structure Name | SFC Conditions | Observed m/z [M + H]+ |
|---|---|---|---|
| 235 | (2S,3S or 2R,3R)-3-(4-((2R,5S or 2S,5R)-5-(5-amino-7,9-difluoro-[1,2,4]triazolo[1,5-c]quinazolin-2-yl)-2-methylpiperidin-1-yl)-1H-pyrazol-1-yl)butan-2-ol | Peak 3; Phenomenex Lux-2 21 × 250 mm column with 45% (MeOH w/0.1% NH4OH modifier) as co-solvent. | 457 |
| 236 | (2S,3R or 2R,3S)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol | Peak 1; Chiral Technologies AD-H 21 × 250 mm column with 40% (MeOH w/0.1% NH4OH modifier) as co-solvent. | 469 |
| 237 | (2R,3S or 2S,3R)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol | Peak 2; Chiral Technologies AD-H 21 × 250 mm column with 40% (MeOH w/0.1% NH4OH modifier) as co-solvent. | 469 |

TABLE 31-continued

| Example | Structure Name | SFC Conditions | Observed m/z [M + H]+ |
|---|---|---|---|
| 238 | 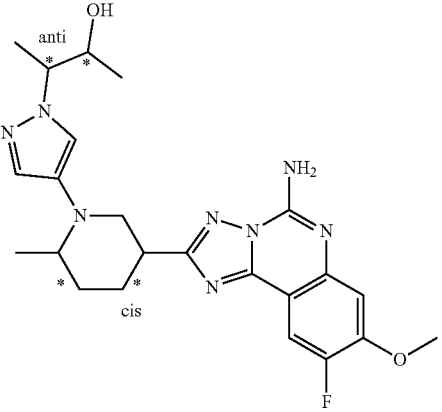 [SMILES: COc1cc2nc(N)n3nc(C4CCC(C)N(c5cnn(C(C)C(C)O)c5)C4)nc3c2cc1F]<br>(2S,3R or 2R,3S)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol | Peak 1; Phenomenex Lux-3 21 × 250 mm column with 15% (MeOH w/0.1% NH4OH modifier) as co-solvent. | 469 |
| 239 | 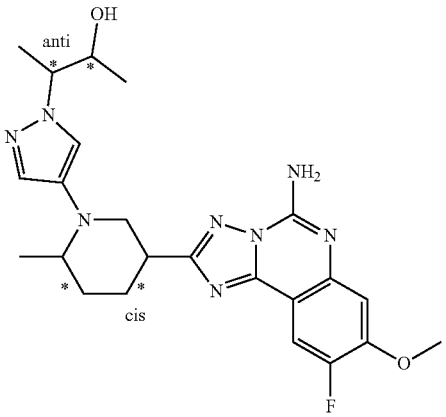 [SMILES: COc1cc2nc(N)n3nc(C4CCC(C)N(c5cnn(C(C)C(C)O)c5)C4)nc3c2cc1F]<br>(2R,3S or 2S,3R)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)butan-2-ol | Peak 2; Phenomenex Lux-3 21 × 250 mm column with 15% (MeOH w/0.1% NH4OH modifier) as co-solvent. | 469 |
| 240 | 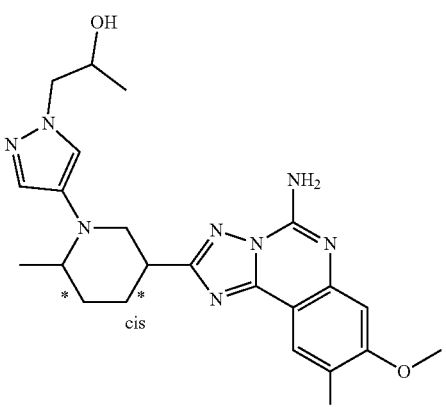<br>(R or S)-1-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)propan-2-ol | Peak 1; Chiral Technologies AS-H 21 × 250 mm column with 25% (MeOH w/0.1% NH4OH modifier) as co-solvent. | 469 |

TABLE 31-continued

| Example | Structure Name | SFC Conditions | Observed m/z [M + H]+ |
|---|---|---|---|
| 241 | 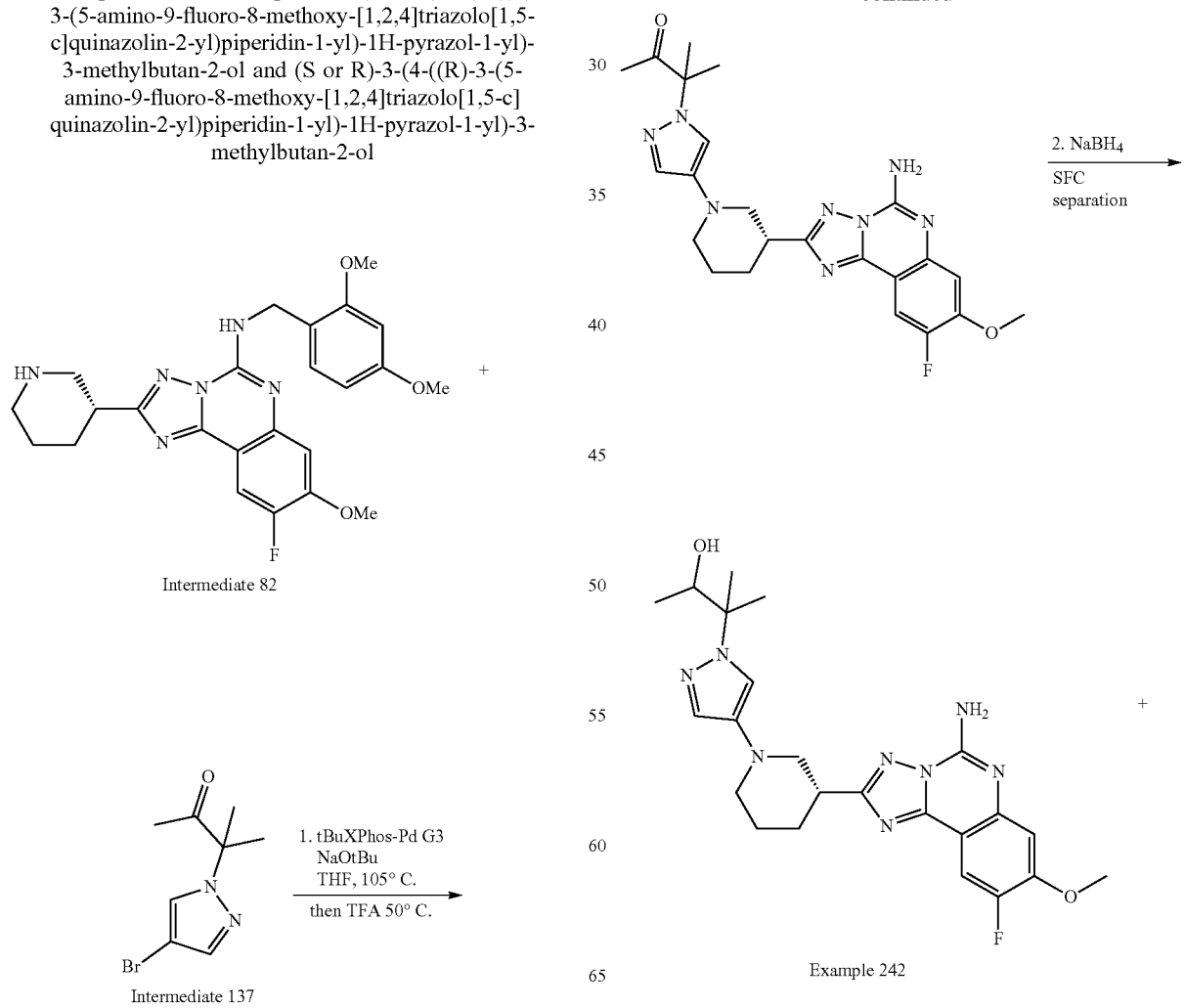 (S or R)-1-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)propan-2-ol | Peak 2; Chiral Technologies AS-H 21 × 250 mm column with 25% (MeOH w/0.1% NH4OH modifier) as co-solvent. | 469 |

Example 242 and Example 243: (R or S)-3-(4-((R)-3-(5-amino-9-fluoro-8-methoxy-[1,2,4]triazolo[1,5-c]quinazolin-2-yl)piperidin-1-yl)-1H-pyrazol-1-yl)-3-methylbutan-2-ol and (S or R)-3-(4-((R)-3-(5-amino-9-fluoro-8-methoxy-[1,2,4]triazolo[1,5-c]quinazolin-2-yl)piperidin-1-yl)-1H-pyrazol-1-yl)-3-methylbutan-2-ol

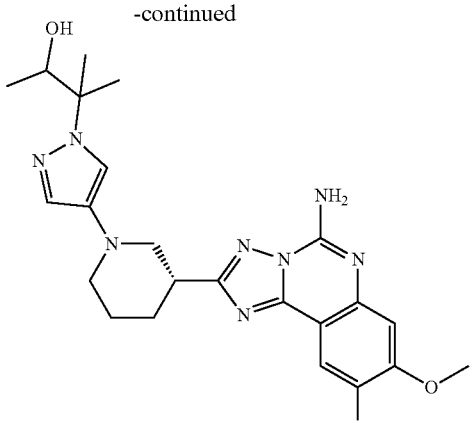

Example 243

Step 1: (R)-3-(4-(3-(5-amino-9-fluoro-8-methoxy-[1,2,4]triazolo[1,5-c]quinazolin-2-yl)piperidin-1-yl)-1H-pyrazol-1-yl)-3-methylbutan-2-one A 5 mL microwave vial equipped with a stirbar was charged with (R)—N-(2,4-dimethoxybenzyl)-9-fluoro-8-methoxy-2-(piperidin-3-yl)-[1,2,4]triazolo[1,5-c]quinazolin-5-amine (Intermediate 82) (100 mg, 0.214 mmol) and THF (1.3 mL). To the mixture was added 3-(4-bromo-1H-pyrazol-1-yl)-3-methylbutan-2-one (Intermediate 137) (99.0 mg, 0.429 mmol), followed by tBuXPhos-Pd G3 (85.0 mg, 0.107 mmol) and sodium tert-butoxide (82.0 mg, 0.857 mmol). Nitrogen was bubbled through the mixture for 10 min. The vial was then sealed with a fresh cap and heated at 105° C. for 16 h. The reaction mixture was cooled to room temperature, and to the mixture was added water (10 mL) and DCM (10 mL). The mixture was stirred for 10 min and filtered. The organic layer was collected and concentrated. To the resulting residue was added TFA (826 μL, 10.7 mmol), and the mixture was heated at 50° C. for 3 h. The solvents were evaporated. The resulting residue was dissolved in MeOH (5 mL), and to the mixture was added a 7 M solution of ammonia in MeOH (1.53 mL, 10.7 mmol). The mixture was stirred for 30 min and filtered. The solids were washed with methanol. The filtrate was concentrated. The residue was dissolved in DCM, and the resulting solution was washed with water. The organic layer was dried over anhydrous sodium sulfate, filtered, and the solvents were evaporated. The resulting residue was purified by silica gel chromatography with 5-30% MeOH in DCM as eluent to afford (R)-3-(4-(3-(5-amino-9-fluoro-8-methoxy-[1,2,4]triazolo[1,5-c]quinazolin-2-yl)piperidin-1-yl)-1H-pyrazol-1-yl)-3-methylbutan-2-one LCMS ($C_{23}H_{27}FN_8O_2$) (ES, m/z): 467 [M+H]$^+$. Step 2: (R or S)-3-(4-((R)-3-(5-amino-9-fluoro-8-methoxy-[1,2,4]triazolo[1,5-c]quinazolin-2-yl)piperidin-1-yl)-1H-pyrazol-1-yl)-3-methylbutan-2-ol and (S or R)-3-(4-((R)-3-(5-amino-9-fluoro-8-methoxy-[1,2,4]triazolo[1,5-c]quinazolin-2-yl)piperidin-1-yl)-1H-pyrazol-1-yl)-3-methylbutan-2-ol To a solution of (R)-3-(4-(3-(5-amino-9-fluoro-8-methoxy-[1,2,4]triazolo[1,5-c]quinazolin-2-yl)piperidin-1-yl)-1H-pyrazol-1-yl)-3-methylbutan-2-one (49.0 mg, 0.105 mmol) in EtOH (1 mL) was added NaBH$_4$ (11.9 mg, 0.315 mmol), and the mixture was stirred at room temperature for 1 h. The solvents were evaporated. To the resulting residue was added DCM, and the mixture was washed with water. The organic layer was dried over anhydrous sodium sulfate, filtered, and the solvents of the filtrate were evaporated to afford a mixture of isomers. The mixture was submitted for SFC chiral separation (Chiral Technologies IA 21×250 mm column with 45% (MeOH w/0.1% NH$_4$OH modifier) as co-solvent), to afford (R or S)-3-(4-((R)-3-(5-amino-9-fluoro-8-methoxy-[1,2,4]triazolo[1,5-c]quinazolin-2-yl)piperidin-1-yl)-1H-pyrazol-1-yl)-3-methylbutan-2-ol (Example 242, peak 1) and (S or R)-3-(4-((R)-3-(5-amino-9-fluoro-8-methoxy-[1,2,4]triazolo[1,5-c]quinazolin-2-yl)piperidin-1-yl)-1H-pyrazol-1-yl)-3-methylbutan-2-ol (Example 243, peak 2).

For Example 242: LCMS ($C_{23}H_{29}FN_8O_2$) (ES, m/z): 469 [M+H]$^+$. $^1$H NMR (499 MHz, DMSO-d$_6$) δ 7.88 (dd, J=10.9, 2.3 Hz, 1H), 7.71 (s, 2H), 7.42-7.34 (m, 1H), 7.24-7.07 (m, 2H), 4.80 (s, 1H), 3.97 (d, J=2.2 Hz, 3H), 3.82 (s, 1H), 3.62 (d, J=11.3 Hz, 1H), 3.36 (s, 1H), 3.24 (s, 1H), 2.82 (t, J=10.2 Hz, 1H), 2.15 (s, 1H), 1.80 (d, J=40.9 Hz, 3H), 1.48-1.42 (m, 3H), 1.42-1.34 (m, 3H), 0.73 (dd, J=6.1, 2.3 Hz, 3H).

For Example 243: LCMS ($C_{23}H_{29}FN_8O_2$) (ES, m/z): 469 [M+H]$^+$. $^1$H NMR (499 MHz, DMSO-d$_6$) δ 7.93-7.83 (m, 1H), 7.71 (s, 2H), 7.38 (s, 1H), 7.22-7.10 (m, 2H), 4.81 (s, 1H), 4.01-3.95 (m, 3H), 3.82 (s, 1H), 3.62 (d, J=10.8 Hz, 1H), 3.37 (s, 1H), 3.24 (s, 1H), 2.82 (t, J=11.3 Hz, 1H), 2.55 (d, J=9.7 Hz, 1H), 2.15 (s, 1H), 1.90-1.67 (m, 3H), 1.45 (s, 3H), 1.39 (s, 3H), 0.76-0.67 (m, 3H).

The example compounds of the invention in the following Table 32 were prepared in a manner similar to that described for the preparation of Example 242 and Example 243 from the appropriate starting amine and aryl halide, where the resulting isomeric mixture of the corresponding final compounds were separated by SFC.

TABLE 32

| Example | Structure | SFC Conditions | Observed m/z [M + H]+ |
|---|---|---|---|
| 244 | 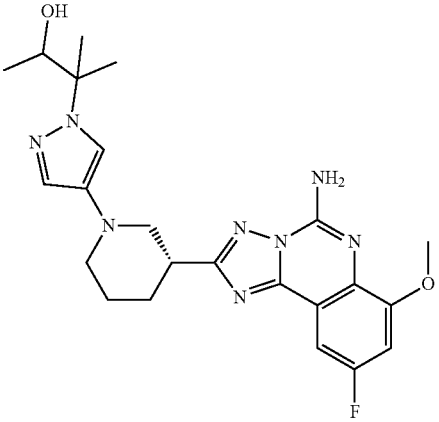 [SMILES: COc1cc(F)cc2c1nc(N)n1nc([C@@H]3CCCN(c4cnn(C(C)(C)C(C)O)c4)C3)nc21]<br>(R or S)-3-(4-((R)-3-(5-amino-9-fluoro-7-methoxy-[1,2,4]triazolo[1,5-c]quinazolin-2-yl)piperidin-1-yl)-1H-pyrazol-1-yl)-3-methylbutan-2-ol | Peak 1; Chiral Technologies IA 21 × 250 mm column with 40% (MeOH w/0.1% NH$_4$OH modifier) as co-solvent | 469 |
| 245 | 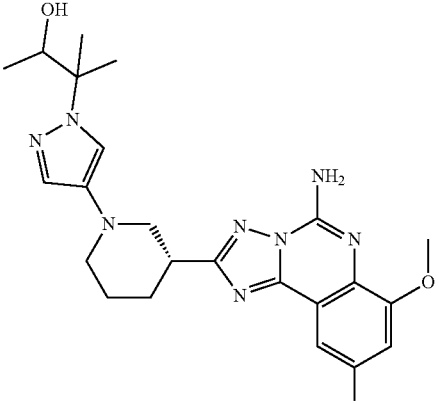<br>(S or R)-3-(4-((R)-3-(5-amino-9-fluoro-7-methoxy-[1,2,4]triazolo[1,5-c]quinazolin-2-yl)piperidin-1-yl)-1H-pyrazol-1-yl)-3-methylbutan-2-ol | Peak 2; Chiral Technologies IA 21 × 250 mm column with 40% (MeOH w/0.1% NH$_4$OH modifier) as co-solvent | 469 |
| 246 | 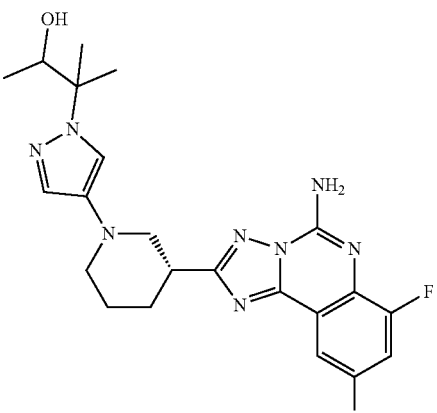<br>(R or S)-3-(4-((R)-3-(5-amino-7,9-difluoro-[1,2,4]triazolo[1,5-c]quinazolin-2-yl)piperidin-1-yl)-1H-pyrazol-1-yl)-3-methylbutan-2-ol | Peak 1; ES Industries CCA 21 × 250 mm column with 35% (MeOH w/0.1% NH$_4$OH modifier) as co-solvent | 457 |

TABLE 32-continued

| Example | Structure Name | SFC Conditions | Observed m/z [M + H]+ |
|---|---|---|---|
| 247 | 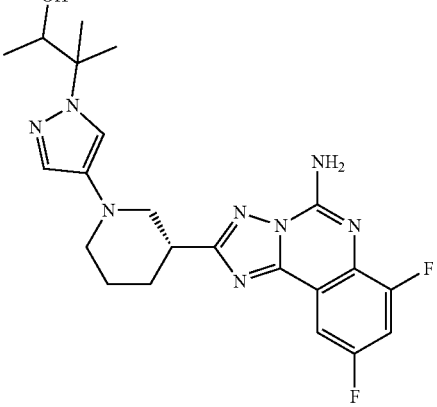<br>(S or R)-3-(4-((R)-3-(5-amino-7,9-difluoro-[1,2,4]triazolo[1,5-c]quinazolin-2-yl)piperidin-1-yl)-1H-pyrazol-1-yl)-3-methylbutan-2-ol | Peak 2; ES Industries CCA 21 × 250 mm column with 35% (MeOH w/0.1% NH4OH modifier) as co-solvent | 457 |

Example 248 and Example 249: 2-(4-((2S,5R or 2R,5S)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,3-diol and 2-(4-((2R, 5S or 2S,5R)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,3-diol

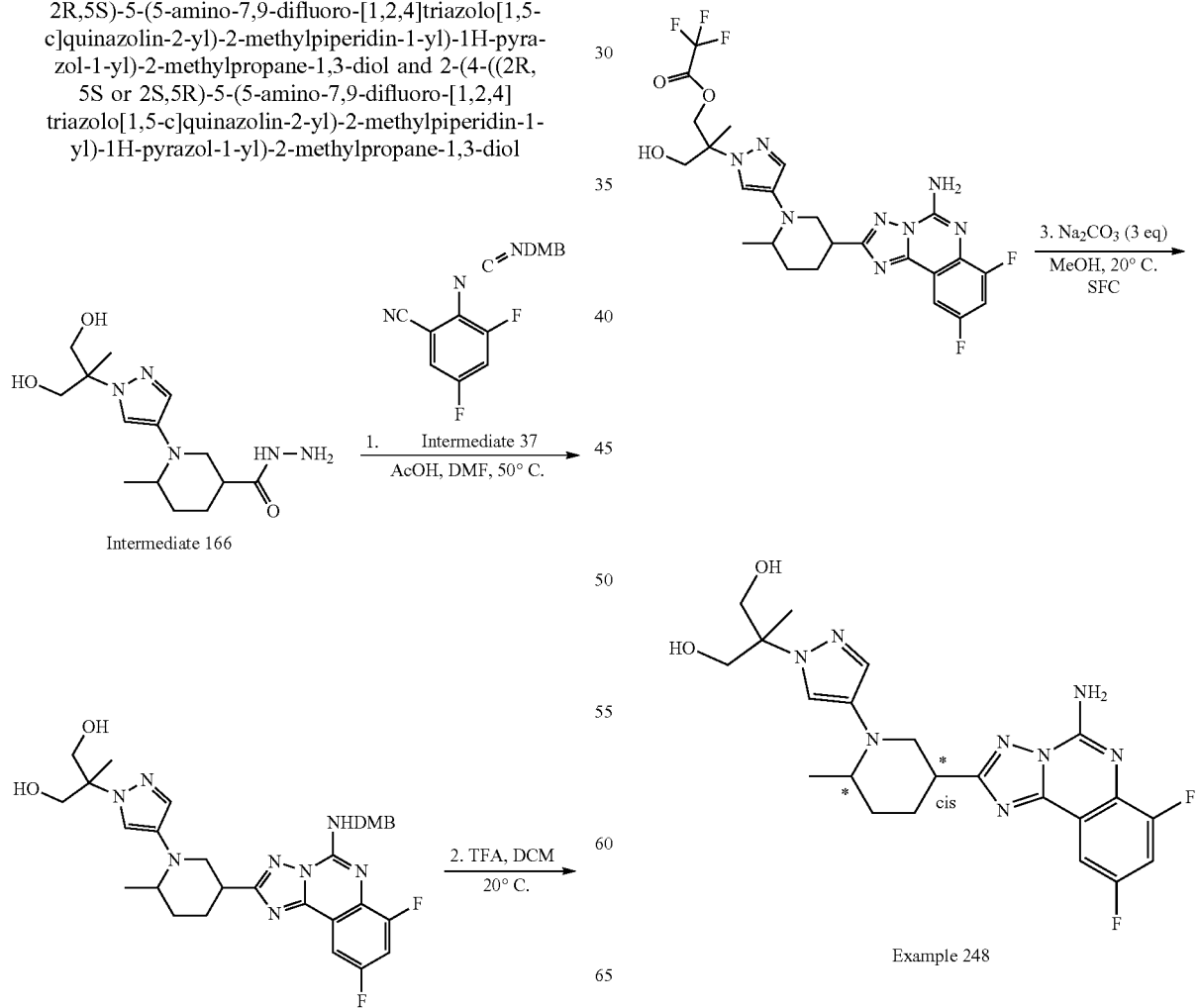

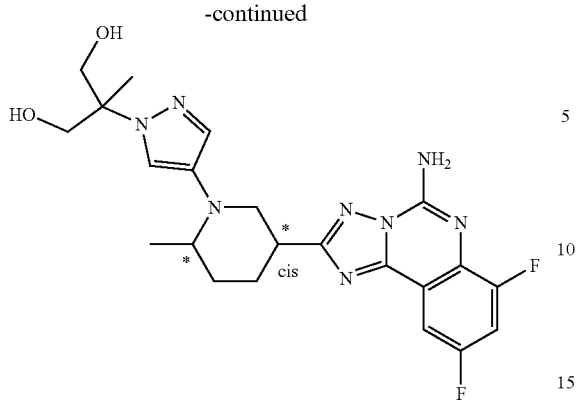

Example 249

Step 1: 2-(4-(5-(5-(((2,4-dimethoxybenzyl)amino)-7,9-difluoro-[1,2,4]triazolo[1,5-c]quinazolin-2-yl)-2-methylpiperidin-1-yl)-1H-pyrazol-1-yl)-2-methylpropane-1,3-diol To a solution of 1-(1-(1,3-dihydroxy-2-methylpropan-2-yl)-1H-pyrazol-4-yl)-6-methylpiperidine-3-carbohydrazide (105 mg, 0.336 mmol) (Intermediate 166) in DMF (1 mL) was added AcOH (9.63 μl, 0.168 mmol), 2-((((3,4-dimethylbenzyl)imino)methylene)amino)-3,5-difluorobenzonitrile (Intermediate 37) (100 mg, 0.336 mmol) at 50° C. under an atmosphere of nitrogen. The mixture was stirred and heated at 50° C. for 16 h. The mixture was cooled, diluted with water (20 mL), and extracted with EtOAc (2×20 mL). The organic layer was dried over anhydrous $Na_2SO_4$, filtered and the solvents were evaporated. The resulting residue was purified by preparative silica gel TLC with 10% MeOH in DCM as eluent to afford 2-(4-(5-(5-(((2,4-dimethoxybenzyl)amino)-7,9-difluoro-[1,2,4]triazolo[1,5-c]quinazolin-2-yl)-2-methylpiperidin-1-yl)-1H-pyrazol-1-yl)-2-methylpropane-1,3-diol. LCMS ($C_{31}H_{36}F_2N_8O_4$) (ES, m/z): 623 [M+H]$^+$.

Step 2: 2-(4-(5-(5-amino-7,9-difluoro-[1,2,4]triazolo[1,5-c]quinazolin-2-yl)-2-methylpiperidin-1-yl)-1H-pyrazol-1-yl)-3-hydroxy-2-methylpropyl 2,2,2-trifluoroacetate To a solution of 2-(4-(5-(5-(((2,4-dimethoxybenzyl)amino)-7,9-difluoro-[1,2,4]triazolo[1,5-c]quinazolin-2-yl)-2-methylpiperidin-1-yl)-1H-pyrazol-1-yl)-2-methylpropane-1,3-diol (60 mg, 0.096 mmol) in DCM (2 mL) was added TFA (2.0 mL, 26 mmol) at 10° C. under a nitrogen atmosphere. The mixture was stirred at 10° C. for 16 h. The solvents were evaporated to afford the crude product of 2-(4-(5-(5-amino-7,9-difluoro-[1,2,4]triazolo[1,5-c]quinazolin-2-yl)-2-methylpiperidin-1-yl)-1H-pyrazol-1-yl)-3-hydroxy-2-methylpropyl 2,2,2-trifluoroacetate, which was used in the next step without any further purification. LCMS ($C_{24}H_{25}F_5N_8O_3$) (ES, m/z): 569 [M+H]$^+$.

Step 3: 2-(4-((2S,5R or 2R,5S)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,3-diol and 2-(4-((2R,5S or 2S,5R)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,3-diol To a solution of 2-(4-(5-(5-amino-7,9-difluoro-[1,2,4]triazolo[1,5-c]quinazolin-2-yl)-2-methylpiperidin-1-yl)-1H-pyrazol-1-yl)-3-hydroxy-2-methylpropyl 2,2,2-trifluoroacetate (40 mg, 0.070 mmol) in MeOH (2 mL) was added $Na_2CO_3$ (7.5 mg, 0.070 mmol) at 10° C. under a nitrogen atmosphere. The mixture was stirred at 10° C. for 1 h. The solvents were evaporated to afford a mixture of isomers. The mixture was submitted for SFC chiral separation (Chiralpak AD-3 4.6×150 mm column with 5-40% (MeOH w/0.05% DEA modifier) as co-solvent), to afford 2-(4-((2S,5R or 2R,5S)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,3-diol (Example 248, peak 1) and 2-(4-((2R,5S or 2S,5R)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,3-diol (Example 249, peak 2).

For Example 248: LCMS ($C_{22}H_{26}F_2N_8O_2$) (ES, m/z): 473 [M+H]$^+$. $^1$H NMR (500 MHz, methanol-$d_4$) δ=7.71 (br dd, J=1.3, 6.8 Hz, 1H), 7.38-7.26 (m, 2H), 7.22 (s, 1H), 3.78-3.68 (m, 4H), 3.64 (br dd, J=3.8, 6.1 Hz, 1H), 3.41 (br d, J=8.2 Hz, 1H), 2.96 (s, 1H), 2.82 (s, 1H), 2.06-1.99 (m, 2H), 1.98 (s, 1H), 1.73 (br dd, J=3.1, 12.7 Hz, 1H), 1.42 (s, 3H), 1.03 (d, J=6.7 Hz, 3H).

For Example 249: LCMS ($C_{22}H_{26}F_2N_8O_2$) (ES, m/z): 473 [M+H]$^+$. $^1$H NMR (500 MHz, methanol-$d_4$) δ=7.84 (br s, 1H), 7.53-7.41 (m, 2H), 7.36 (br s, 1H), 3.93-3.79 (m, 4H), 3.78 (br s, 1H), 3.55 (br s, 1H), 2.22 (br s, 1H), 2.18-2.09 (m, 2H), 1.87 (br d, J=10.1 Hz, 1H), 1.54 (s, 3H), 1.31 (s, 2H), 1.16 (d, J=6.6 Hz, 3H).

The example compounds of the invention in the following Table 33 were prepared in a manner similar to that described for the preparation of Example 248 and Example 249 from the appropriate starting hydrazide, where the resulting isomeric mixture of the corresponding final compounds were separated by SFC.

TABLE 33

| Example | Structure Name | SFC Conditions | Observed m/z [M + H]+ |
|---|---|---|---|
| 250 | 2-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropane-1,3-diol | Peak 1; Chiralpak AD-3 4.6 × 150 mm column with 5-40% (MeOH w/0.05% DEA modifier) as co-solvent | 485 |
| 251 | 2-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropane-1,3-diol | Peak 2; Chiralpak AD-3 4.6 × 150 mm column with 5-40% (MeOH w/0.05% DEA modifier) as co-solvent. | 485 |
| 252 | (R or S)-2-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropane-1,2-diol | Peak 2; Chiralcel OJ-3 4.6 × 100 mm column with 5-40% (EtOH w/0.05% DEA modifier) as co-solvent. Then Peak 1; Chiralpak AD-3 4.6 × 150 mm column with 40% (MeOH w/0.05% DEA modifier) as co-solvent. | 485 |

TABLE 33-continued

| Example | Structure Name | SFC Conditions | Observed m/z [M + H]+ |
|---|---|---|---|
| 253 | (S or R)-2-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropane-1,2-diol | Peak 2; Chiralcel OJ-3 4.6 × 100 mm column with 5-40% (EtOH w/0.05% DEA modifier) as co-solvent. Then Peak 2; Chiralpak AD-3 4.6 × 150 mm column with 40% (MeOH w/0.05% DEA modifier) as co-solvent. | 485 |
| 254 | (R or S)-2-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropane-1,2-diol | Peak 3; Chiralcel OJ-3 4.6 × 100 mm column with 5-40% (EtOH w/0.05% DEA modifier) as co-solvent. | 485 |
| 255 | (S or R)-2-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)-2-methylpropane-1,2-diol | Peak 4; Chiralcel OJ-3 4.6 × 100 mm column with 5-40% (EtOH w/0.05% DEA modifier) as co-solvent. | 485 |

TABLE 33-continued

| Example | Structure Name | SFC Conditions | Observed m/z [M + H]+ |
|---|---|---|---|
| 256 | 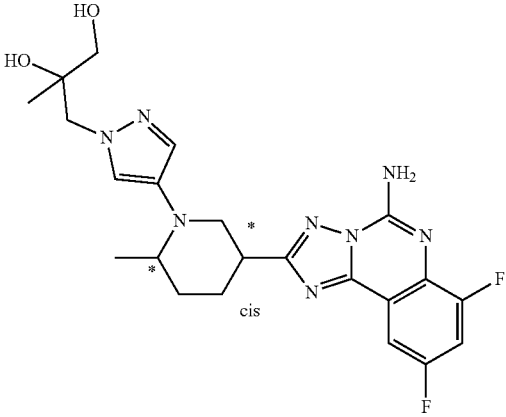 [SMILES: CC1CCC(c2nc3c4cc(F)cc(F)c4nc(N)n3n2)CN1c1cnn(CC(C)(O)CO)c1]<br>(R or S)-2-(4-((2S,5R or 2R,5S)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,2-diol | Peak 3; Cellulose 2 4.6 × 100 mm column with 40% (MeOH w/0.05% DEA modifier) as co-solvent. Then Peak 1; Chiralpak AS-3 4.6 × 150 mm column with 5-40% (IPA w/0.05% DEA modifier) as co-solvent. | 473 |
| 257 | 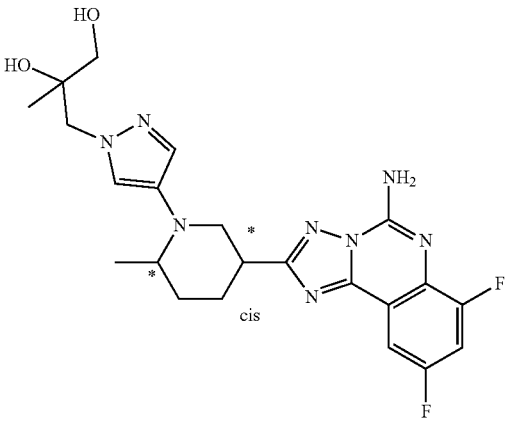 [SMILES: CC1CCC(c2nc3c4cc(F)cc(F)c4nc(N)n3n2)CN1c1cnn(CC(C)(O)CO)c1]<br>(S or R)-2-(4-((2S,5R or 2R,5S)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,2-diol | Peak 3; Cellulose 2 4.6 × 100 mm column with 40% (MeOH w/0.05% DEA modifier) as co-solvent. Then Peak 2; Chiralpak AS-3 4.6 × 150 mm column with 5-40% (IPA w/0.05% DEA modifier) as co-solvent. | 473 |
| 258 | 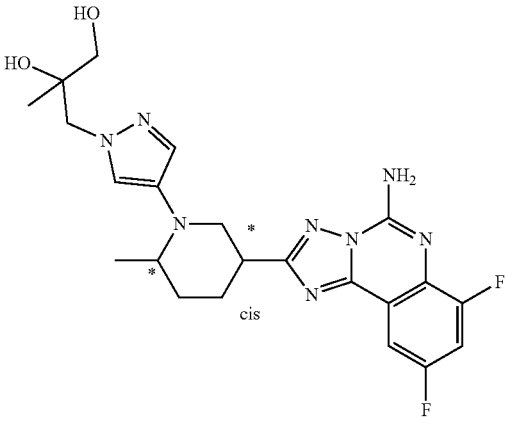 [SMILES: CC1CCC(c2nc3c4cc(F)cc(F)c4nc(N)n3n2)CN1c1cnn(CC(C)(O)CO)c1]<br>(R or S)-2-(4-((2R,5S or 2S,5R)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,2-diol | Peak 4; Cellulose 2 4.6 × 100 mm column with 40% (MeOH w/0.05% DEA modifier) as co-solvent. | 473 |

TABLE 33-continued

| Example | Structure Name | SFC Conditions | Observed m/z [M + H]+ |
|---|---|---|---|
| 259 | 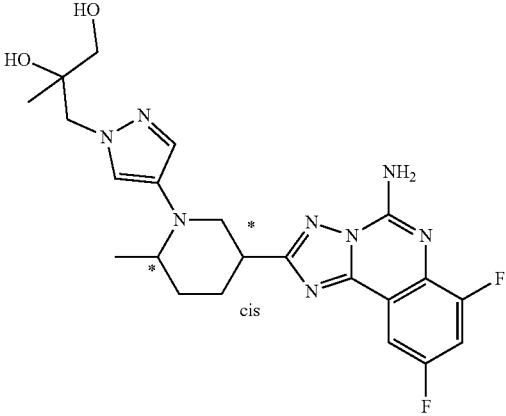 [SMILES: CC1CCC(c2nc3c4cc(F)cc(F)c4nc(N)n3n2)CN1c1cnn(CC(C)(O)CO)c1]<br>(S or R)-2-(4-((2R,5S or 2S,5R)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,2-diol | Peak 5; Cellulose 2 4.6 × 100 mm column with 40% (MeOH w/0.05% DEA modifier) as co-solvent. | 473 |
| 260 | 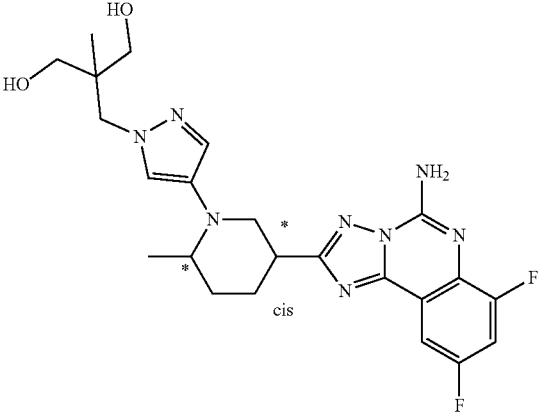 [SMILES: CC1CCC(c2nc3c4cc(F)cc(F)c4nc(N)n3n2)CN1c1cnn(CC(C)(CO)CO)c1]<br>(R or S)-2-(4-((2R,5S or 2S,5R)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,2-diol | Peak 1; Chiralpak AS-3 4.6 × 100 mm column with 5-40% (MeOH w/0.05% DEA modifier) as co-solvent. | 487 |
| 261 | 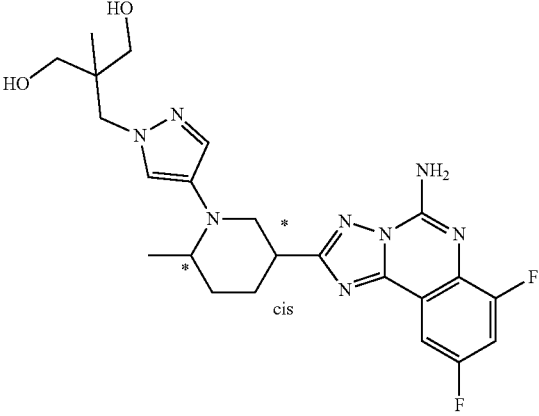 [SMILES: CC1CCC(c2nc3c4cc(F)cc(F)c4nc(N)n3n2)CN1c1cnn(CC(C)(CO)CO)c1]<br>(S or R)-2-(4-((2R,5S or 2S,5R)-5-(5-amino-7,9-difluoro-[1,2,4]triazolo[1,5-c]quinazolin-2-yl)-2-methylpiperidin-1-yl)-1H-pyrazol-1-yl)-2-methylpropane-1,2-diol | Peak 2; Chiralpak AS-3 4.6 × 100 mm column with 5-40% (MeOH w/0.05% DEA modifier) as co-solvent. | 487 |

TABLE 33-continued

| Example | Structure Name | SFC Conditions | Observed m/z [M + H]+ |
|---|---|---|---|
| 262 | 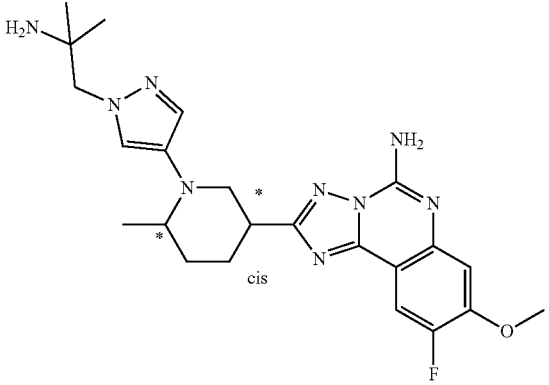 [SMILES: COc1cc2nc(N)n3nc(C4CCC(C)N(c5cnn(CC(C)(C)N)c5)C4)nc3c2cc1F]<br>2-((3R,6S or 3S,6R)-1-(1-(2-amino-2-methylpropyl)-1H-pyrazol-4-yl)-6-methylpiperidin-3-yl)-9-fluoro-8-methoxy-[1,2,4]triazolo[1,5-c]quinazolin-5-amine | Peak 1; ES Industries CC4 21 × 250 mm column with 40% (MeOH w/0.1% NH4OH modifier) as co-solvent. | 468 |
| 263 | 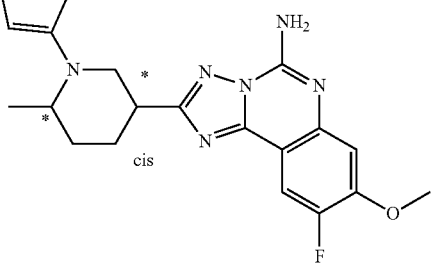<br>2-((3S,6R or 3R,6S)-1-(1-(2-amino-2-methylpropyl)-1H-pyrazol-4-yl)-6-methylpiperidin-3-yl)-9-fluoro-8-methoxy-[1,2,4]triazolo[1,5-c]quinazolin-5-amine | Peak 2; ES Industries CC4 21 × 250 mm column with 40% (MeOH w/0.1% NH4OH modifier) as co-solvent. | 468 |
| 264 | 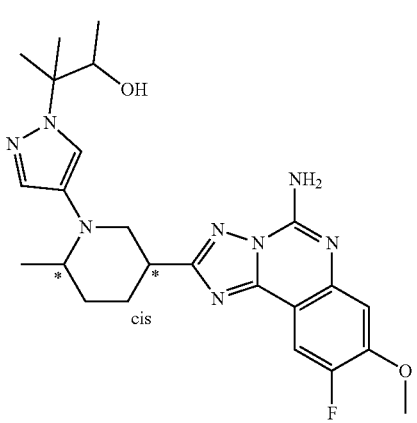 [SMILES: COc1cc2nc(N)n3nc(C4CCC(C)N(c5cnn(C(C)(C)C(C)O)c5)C4)nc3c2cc1F]<br>(R or S)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-3-methylbutan-2-ol | Peak 1; ES Industries CCA 21 × 250 mm column with 25% (MeOH w/0.1% NH4OH modifier) as co-solvent | 483 |

TABLE 33-continued

| Example | Structure Name | SFC Conditions | Observed m/z [M + H]+ |
|---|---|---|---|
| 265 | 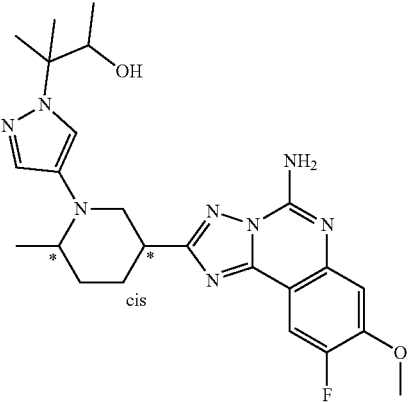 [SMILES: COc1cc2nc(N)n3nc(C4CCC(C)N(c5cnn(C(C)(C)C(C)O)c5)C4)nc3c2cc1F]<br>(S or R)-3-(4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)-3-methylbutan-2-ol | Peak 2 (mixture of Example 265 and Example 266); ES Industries CCA 21 × 250 mm column with 25% (MeOH w/0.1% NH4OH modifier) as co-solvent. Then Peak 1; Lux-4 21 × 250 mm column with 35% (MeOH w/0.1% NH4OH modifier) | 483 |
| 266 | 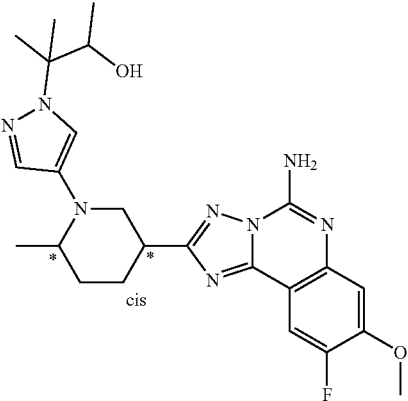 [SMILES: COc1cc2nc(N)n3nc(C4CCC(C)N(c5cnn(C(C)(C)C(C)O)c5)C4)nc3c2cc1F]<br>(R or S)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)-3-methylbutan-2-ol | Peak 2 (mixture of Example 265 and Example 266); ES Industries CCA 21 × 250 mm column with 25% (MeOH w/0.1% NH4OH modifier) as co-solvent. Then Peak 2; Lux-4 21 × 250 mm column with 35% (MeOH w/0.1% NH4OH modifier) | 483 |
| 267 | 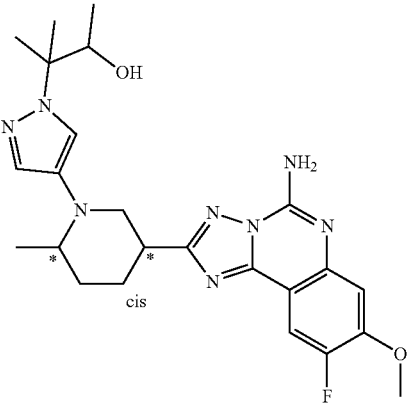 [SMILES: COc1cc2nc(N)n3nc(C4CCC(C)N(c5cnn(C(C)(C)C(C)O)c5)C4)nc3c2cc1F]<br>(S or R)-3-(4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)-3-methylbutan-2-ol | Peak 3; ES Industries CCA 21 × 250 mm column with 25% (MeOH w/0.1% NH4OH modifier) as co-solvent | 483 |

TABLE 33-continued

| Example | Structure Name | SFC Conditions | Observed m/z [M + H]+ |
|---|---|---|---|
| 268 | 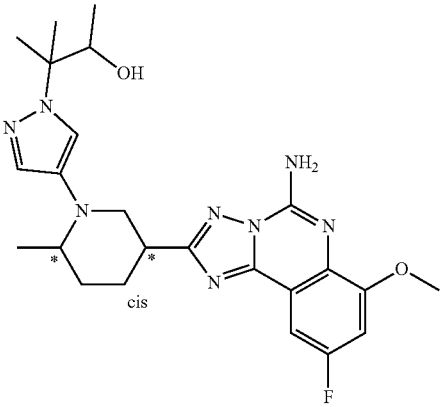 [SMILES: COc1cc(F)cc2c1nc(N)n1nc(C3CCC(C)N(c4cnn(C(C)(C)C(C)O)c4)C3)nc21]<br>(R or S)-3-(4-((2S,5R or 2R,5S)-5-(5-amino-9-fluoro-7-methoxy-[1,2,4]triazolo[1,5-c]quinazolin-2-yl)-2-methylpiperidin-1-yl)-1H-pyrazol-1-yl)-3-methylbutan-2-ol | Peak 1 (mixture of Example 268 and Example 269); Chiral Technologies OJ-H 21 × 250 mm column with 10% (MeOH w/0.1% NH4OH modifier) as co-solvent. Then peak 1; ID 21 × 250 mm column with 35% (MeOH w/0.1% NH4OH modifier) as co-solvent. | 483 |
| 269 | 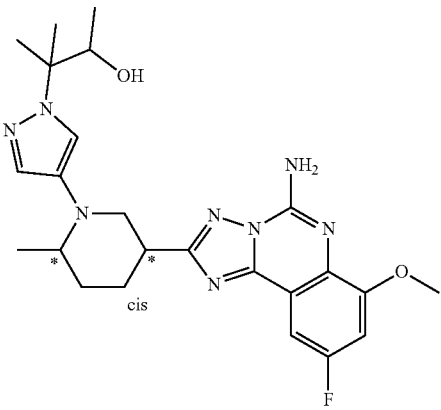 [SMILES: COc1cc(F)cc2c1nc(N)n1nc(C3CCC(C)N(c4cnn(C(C)(C)C(C)O)c4)C3)nc21]<br>(S or R)-3-(4-((2S,5R or 2R,5S)-5-(5-amino-9-fluoro-7-methoxy-[1,2,4]triazolo[1,5-c]quinazolin-2-yl)-2-methylpiperidin-1-yl)-1H-pyrazol-1-yl)-3-methylbutan-2-ol | Peak 1 (mixture of Example 268 and Example 269); Chiral Technologies OJ-H 21 × 250 mm column with 10% (MeOH w/0.1% NH4OH modifier) as co-solvent. Then peak 2; ID 21 × 250 mm column with 35% (MeOH w/0.1% NH4OH modifier) as co-solvent. | 483 |
| 270 | 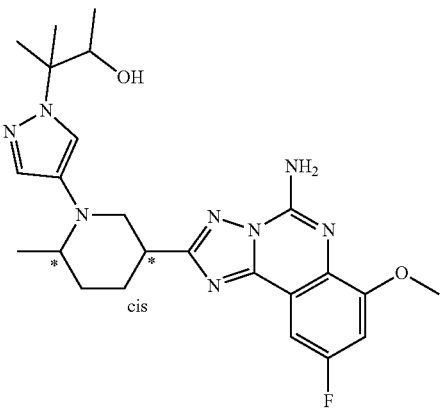 [SMILES: COc1cc(F)cc2c1nc(N)n1nc(C3CCC(C)N(c4cnn(C(C)(C)C(C)O)c4)C3)nc21]<br>(R or S)-3-(4-((2R,5S or 2S,5R)-5-(5-amino-9-fluoro-7-methoxy-[1,2,4]triazolo[1,5-c]quinazolin-2-yl)-2-methylpiperidin-1-yl)-1H-pyrazol-1-yl)-3-methylbutan-2-ol | Peak 2; Chiral Technologies OJ-H 21 × 250 mm column with 10% (MeOH w/0.1% NH4OH modifier) as co-solvent. | 483 |

TABLE 33-continued

| Example | Structure Name | SFC Conditions | Observed m/z [M + H]+ |
|---|---|---|---|
| 271 | (S or R)-3-(4-((2R,5S or 2S,5R)-5-(5-amino-9-fluoro-7-methoxy-[1,2,4]triazolo[1,5-c]quinazolin-2-yl)-2-methylpiperidin-1-yl)-1H-pyrazol-1-yl)-3-methylbutan-2-ol | Peak 3; Chiral Technologies OJ-H 21 × 250 mm column with 10% (MeOH w/0.1% NH4OH modifier) as co-solvent. | 483 |
| 272 | 1-((4-((2S,5R or 2R,5S)-5-(5-amino-9-fluoro-8-methoxy-[1,2,4]triazolo[1,5-c]quinazolin-2-yl)-2-methylpiperidin-1-yl)-1H-pyrazol-1-yl)methyl)cyclopropan-1-ol | Peak 1; Chiralpak AS-3 4.6 × 150 mm column with 5-40% (EtOH w/0.05% DEA modifier) as co-solvent. | 467 |
| 273 | 1-((4-((2R,5S or 2S,5R)-5-(5-amino-9-fluoro-8-methoxy-[1,2,4]triazolo[1,5-c]quinazolin-2-yl)-2-methylpiperidin-1-yl)-1H-pyrazol-1-yl)methyl)cyclopropan-1-ol | Peak 2; Chiralpak AS-3 4.6 × 150 mm column with 5-40% (EtOH w/0.05% DEA modifier) as co-solvent. | 467 |

TABLE 33-continued

| Example | Structure Name | SFC Conditions | Observed m/z [M + H]+ |
|---|---|---|---|
| 274 | 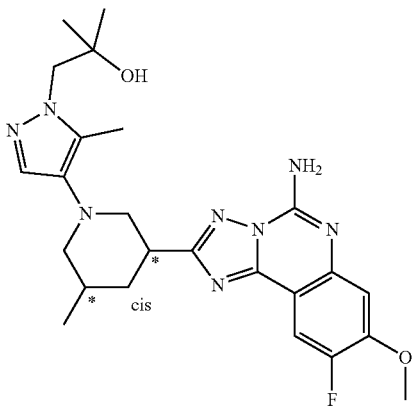 [SMILES: COc1cc2nc(N)n3nc(C4CC(C)CN(c5cnn(CC(C)(C)O)c5C)C4)nc3c2cc1F]<br>1-((4-((3R,5S or 3S,5R)-3-(5-amino-9-fluoro-8-methoxy-[1,2,4]triazolo[1,5-c]quinazolin-2-yl)-5-methylpiperidin-1-yl)-1H-pyrazol-1-yl)-2-methylpropan-2-ol | Peak 2; Chiral Technologies AD-H 21 × 250 mm column with 30% (MeOH w/ 0.1% NH$_4$OH modifier) as co-solvent. | 483 |
| 275 | 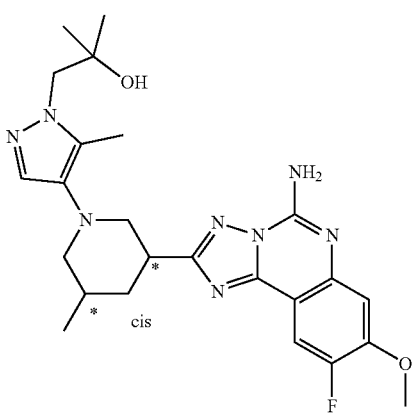 [SMILES: COc1cc2nc(N)n3nc(C4CC(C)CN(c5cnn(CC(C)(C)O)c5C)C4)nc3c2cc1F]<br>1-(4-((3S,5R or 3R,5S)-3-(5-amino-9-fluoro-8-methoxy-[1,2,4]triazolo[1,5-c]quinazolin-2-yl)-5-methylpiperidin-1-yl)-5-methyl-1H-pyrazol-1-yl)-2-methylpropan-2-ol | Peak 3; Chiral Technologies AD-H 21 × 250 mm column with 30% (MeOH w/ 0.1% NH$_4$OH modifier) as co-solvent. | 483 |

Biological Assays

The IC$_{50}$ values reported for each of the compounds of the invention shown in the table below were measured in accordance with the methods described below.

The A2a receptor affinity binding assay measured the amount of binding of a tritiated ligand with high affinity for the A2a adenosine receptor to membranes made from HEK293 or CHO cells recombinantly expressing the human A2a adenosine receptor, in the presence of varying concentrations of a compound of the invention. In each assay, the tested compounds of the invention were solubilized in 100% DMSO and further diluted in 100% DMSO to generate, typically, a 10-point titration at half-log intervals such that the final assay concentrations did not exceed 10 μM of compound or 1% DMSO.

Measurement of A2a Binding Affinity Using Radioligand Binding

148 μL (5 μg/mL) membranes (Perkin Elmer, Cat. No. RBHA2aM400UA) and 2 μL compounds of the invention to be tested (test compound) were transferred to individual wells of a 96-well polypropylene assay plate and incubated for 15 to 30 minutes at room temperature. [$^3$H] SCH58261 ((7-(2-phenylethyl)-5-amino-2-(2-furyl)-pyrazolo-[4,3-e]-1,2,4-triazolo[1,5-c]pyrimidine)) was diluted in assay buffer (50 mM Tris pH 7.4, 10 mM MgCl$_2$, 0.005% Tween20) to a concentration of 4 nM and 50 μL transferred to each well of the assay plate. To define total and non-specific binding, wells containing 1% DMSO and 1 μM ZM241385 (Tocris Bioscience, Cat. No. 1036) respectively, were also included. The assay plate was incubated at room temperature for 60 minutes with agitation. Using a FilterMate Harvester® (Perkin Elmer), the contents of the assay plate were filtered through a UniFilter-96® PEI coated plate (Perkin Elmer Cat. No. 6005274 or 6005277). Filtering was achieved by aspirating the contents of the assay plate for 5 seconds, then washing and aspirating the contents three times with ice-cooled wash buffer (50 mM Tris-HCl pH 7.4, 150 mM NaCl) and allowing the vacuum manifold to dry the plate for 30 seconds. The filter plate was incubated for at least 1 hour at 55° C. and allowed to dry. The bottom of the filter plate was sealed with backing tape. 40 µL Ultima Gold™ (Perkin Elmer, Cat. No. 6013329) was added to each well of the filter plate and the top of the plate was sealed with TopSeal-A PLUS® clear plate seal (Perkin Elmer, Cat. No. 6050185). The plate was incubated for at least 20 minutes, and then the amount of radioactivity remaining in each well was determined using a TopCount® (Perkin Elmer) scintillation counter. After normalization to total and non-specific binding, the percent effect at each compound concentration was calculated. The plot of percent effect versus the log of compound concentration was analyzed electronically using a 4-parameter logistic fit based on the Levenberg-Marquardt algorithm to generate $IC_{50}$ values.

Measurement of A2b Binding Affinity

The reported affinity of the compounds of the invention for the human A2b adenosine receptor was determined experimentally using a radioligand filtration binding assay. This assay measures the amount of binding of a tritiated proprietary A2b receptor antagonist, in the presence and absence of a compound of the invention, to membranes made from HEK293 cells recombinantly expressing the human A2b adenosine receptor (Perkin Elmer, Cat. No. ES-013-C).

To perform the assay, compounds of the invention to be tested were first solubilized in 100% DMSO and further diluted in 100% DMSO to generate, typically, a 10-point titration at half-log intervals such that the final assay concentrations did not exceed 10 µM of compound or 1% DMSO. 148 µL (135 µg/mL) membranes and 2 µL test compounds were transferred to individual wells of a 96-well polypropylene assay plate and incubated for 15 to 30 minutes at room temperature with agitation. Tritiated radioligand was diluted to a concentration of 14 nM in assay buffer (phosphate buffered saline without Magnesium and Calcium, pH 7.4; GE Healthcare Life Sciences, Cat. No. SH30256.01) and then 50 µL of the solution were transferred to each well of the assay plate. To define total and non-specific binding, wells containing 1% DMSO and 20 µM N-ethylcarboxamidoadenosine (Tocris Bioscience, Cat. No. 1691) respectively, were also included. The wells of the assay plate were incubated at room temperature for 60 minutes with agitation, then filtered using a FilterMate Harvester® (Perkin Elmer) or similar equipment through a UniFilter-96® PEI coated plate (Perkin Elmer Cat. No. 6005274 or 6005277). Filtering was achieved by aspirating the contents of the assay plate for 5 seconds, then washing and aspirating the contents three times with ice-cooled wash buffer (assay buffer supplemented with 0.0025% Brij58) and allowing the vacuum manifold to dry the plate for 30 seconds. The filter plate was incubated for at least 1 hour at 55° C. and allowed to dry. The bottom of the filter plate was then sealed with backing tape. 40 µL Ultima Gold™ (Perkin Elmer, Cat. No. 6013329) was added to each well of the filter plate and the top of the plate was sealed with TopSeal-A PLUS® clear plate seal (Perkin Elmer, Cat. No. 6050185). The plates were then incubated for at least 20 minutes, and then the amount of radioactivity remaining in each well was determined using a TopCount® (Perkin Elmer) scintillation counter. After normalization to total and non-specific binding, the percent effect at each compound concentration was calculated. The plot of percent effect versus the log of compound concentration was analyzed electronically using a 4-parameter logistic fit based on the Levenberg-Marquardt algorithm to generate $IC_{50}$ values.

| Example | $A_{2A}$ $IC_{50}$ binding (nM) | $A_{2B}$ $IC_{50}$ binding (nM) |
|---|---|---|
| 1 | 7.5 | 554.2 |
| 2 | 3.7 | 9.4 |
| 3 | 1.5 | 180.4 |
| 4 | 4.6 | 2.6 |
| 5 | 3.3 | 1.6 |
| 6 | 2.0 | 85.9 |
| 7 | 3.7 | 104.1 |
| 8 | 4.5 | 149.3 |
| 9 | 0.5 | 136.0 |
| 10 | 3.5 | 63.4 |
| 11 | 0.5 | 56.0 |
| 12 | 1.7 | 75.0 |
| 13 | 0.7 | 72.6 |
| 14 | 3.0 | 224.9 |
| 15 | 38.4 | 905.2 |
| 16 | 0.8 | 426.0 |
| 17 | 1.7 | 433.9 |
| 18 | 0.7 | 13.5 |
| 19 | 0.7 | 87.3 |
| 20 | 5.8 | 163 |
| 21 | 0.3 | 514.6 |
| 22 | 8.6 | 27.6 |
| 23 | 2.0 | 15.9 |
| 24 | 13.8 | 480.5 |
| 25 | 0.6 | 61.7 |
| 26 | 3.9 | 48.7 |
| 27 | 1.8 | 860.8 |
| 28 | 2.8 | 76.3 |
| 29 | 1.5 | 301.1 |
| 30 | 0.4 | 97.9 |
| 31 | 1.7 | 94.8 |
| 32 | 0.5 | 6.9 |
| 33 | 3.6 | 17.5 |
| 34 | 1.4 | 29.7 |
| 35 | 0.6 | 12.2 |
| 36 | 1.6 | 93.0 |
| 37 | 1.1 | 468.1 |
| 38 | 16.9 | 182.4 |
| 39 | 1.1 | 43.3 |
| 40 | 1.2 | 9.2 |
| 41 | 1.2 | 42.8 |
| 42 | 4.3 | 475.7 |
| 43 | 0.7 | 3.4 |
| 44 | 1.3 | 20.4 |
| 45 | 1.8 | 150.4 |
| 46 | 0.6 | 86.4 |
| 47 | 8.2 | 284.2 |
| 48 | 0.6 | 17.6 |
| 49 | 0.3 | 2.7 |
| 50 | 18.3 | 1889 |
| 51 | 21.0 | 2079 |
| 52 | 18.3 | 3006 |
| 53 | 44.1 | 4239 |
| 54 | 3.3 | 194.6 |
| 55 | 10.6 | 500.2 |
| 56 | 1.8 | 846.5 |
| 57 | 48.3 | 85.6 |
| 58 | 13.6 | 136.2 |
| 59 | 67.0 | 4744 |
| 60 | 31.4 | 5862 |
| 61 | 5.0 | 99.0 |
| 62 | 146.1 | 382.8 |
| 63 | 242.2 | 2431 |
| 64 | 1.0 | 555.3 |
| 65 | 1.2 | 227.9 |
| 66 | 0.6 | 957.1 |
| 67 | 44% Inh. @ 1000 nM | 31% Inh. @ 10000 nM |
| 68 | 181.4 | 31% Inh. @ 10000 nM |
| 69 | 2.6 | 561.4 |
| 70 | 0.6 | 786.5 |
| 71 | 35.6 | 43% Inh. @ 10000 nM |
| 72 | 2.0 | 484 |
| 73 | 436.0 | 5124 |
| 74 | 0.9 | 153.3 |
| 75 | 56.9 | 54% Inh. @ 10000 nM |

-continued

| Example | $A_{2A}$ IC$_{50}$ binding (nM) | $A_{2B}$ IC$_{50}$ binding (nM) |
|---|---|---|
| 76 | 256.4 | 34% Inh. @ 10000 nM |
| 77 | 0.4 | 107.9 |
| 78 | 0.9 | 233.7 |
| 79 | 16.0 | 3141 |
| 80 | 11.6 | 404.5 |
| 81 | 121.1 | 6582 |
| 82 | 4.9 | 63.0 |
| 83 | 2.7 | 113.0 |
| 84 | 2.3 | 116.6 |
| 85 | 5.2 | 192.1 |
| 86 | 0.3 | 164.7 |
| 87 | 0.4 | 133.8 |
| 88 | 0.1 | 1.8 |
| 89 | 0.2 | 3.4 |
| 90 | 1.2 | 29.0 |
| 91 | 44.7 | 4624 |
| 92 | 10.9 | 602.3 |
| 93 | 5.8 | 314.6 |
| 94 | 7.8 | 752.0 |
| 95 | 205 | 5041 |
| 96 | 0.7 | 24.6 |
| 97 | 0.6 | 33.3 |
| 98 | 0.9 | 116.4 |
| 99 | 4.4 | 230.9 |
| 100 | 1.4 | 4.8 |
| 101 | 32.7 | 390.0 |
| 102 | 103.5 | 538.7 |
| 103 | 0.5 | 136.7 |
| 104 | 17.7 | 766.1 |
| 105 | 328.6 | 743.0 |
| 106 | 316.4 | 429.6 |
| 107 | 126.9 | 1522 |
| 108 | 36% Inh. @ 1000 nM | 8474 |
| 109 | 0.7 | 7.8 |
| 110 | 0.2 | 1.8 |
| 111 | 0.7 | 16.5 |
| 112 | 0.4 | 7.9 |
| 113 | 58.1 | 470.5 |
| 114 | 50.6 | 2905 |
| 115 | 2.9 | 895.1 |
| 116 | 207.4 | 35% Inh. @ 10000 nM |
| 117 | 0.2 | 13.0 |
| 118 | 1.9 | 386.7 |
| 119 | 51.6 | 1302 |
| 120 | 0.6 | 7.8 |
| 121 | 55.4 | 5344 |
| 122 | 368.7 | 2058 |
| 123 | 0.3 | 422.2 |
| 124 | 0.3 | 1.7 |
| 125 | 86.4 | 2501 |
| 126 | 2.6 | 2158 |
| 127 | 120.5 | 1158 |
| 128 | 0.3 | 2.4 |
| 129 | 4.1 | 469.9 |
| 130 | 1.2 | 78.7 |
| 131 | 11.8 | 66.0 |
| 132 | 6.7 | 242.6 |
| 133 | 4.3 | 558.5 |
| 134 | 123.6 | 4288 |
| 135 | 14.1 | 583.3 |
| 136 | 1.0 | 7.9 |
| 137 | 79.3 | 924.5 |
| 138 | 13.2 | 2257 |
| 139 | 16.8 | 2824 |
| 140 | 0.8 | 2723 |
| 141 | 24.1 | 1756 |
| 142 | 32% Inh. @ 1000 nM | 7937 |
| 143 | 984.1 | 7557 |
| 144 | 30% Inh. @ 1000 nM | 7143 |
| 145 | 32% Inh. @ 1000 nM | 8046 |
| 146 | 2.1 | 137.1 |
| 147 | 870.2 | 6333 |
| 148 | 385.1 | 4429 |
| 149 | 1.8 | 96.6 |
| 150 | 1.4 | 180.6 |

Measurement of $A_{2A}$ and $A_{2B}$ Antagonism in cAMP Cell-Based Assay

The ability of compounds to antagonize human $A_{2A}$ and $A_{2B}$ adenosine receptors was determined using a kit to measure changes in intracellular cyclic AMP levels (LANCE cAMP 384 Kit, Perkin Elmer, Cat. No. AD0264). HEK293 cells recombinantly expressing either human $A_{2A}$ or $A_{2B}$ receptors, previously frozen in Recovery Medium (Life Technologies, Cat. No. 12648-010) were thawed and diluted into stimulation buffer (HBSS (Hyclone SH 30268.01), 5 mM HEPES (Gibco 15630-106), 200 nM rolipram (Tocris, Cat. No. 0905), and 1.5% (V/v) BSA stabilizer (kit component). The cell suspension was centrifuged at 200×g for 10 min and then resuspended in stimulation buffer, supplemented with a 1:10 000 dilution of Alexa Fluor 647 anti-cAMP antibody, to a density of $6.0 \times 10^5$ cells/mL. A Labcyte Echo 550 acoustic dispenser was used to transfer up to 25 nL of test compound dissolved in DMSO into the wells of a dry Optiplate-384 plate (Perkin Elmer, Cat. No. 6008289). All subsequent liquid additions were performed using a multichannel pipettor. Next, 5 μL of the cell suspension was added to the wells of the Optiplate-384 and incubated for 30 min. at 37° C. and 5% $CO_2$ in a humidified environment. After this time 5 μL of either 300 nM or 600 nM adenosine (Sigma Cat. No. A9251) for $A_{2A}$ and $A_{2B}$ respectively was added and incubated for 30 minutes at 37° C. and 5% $CO_2$ in a humidified environment. At this time detection mix was prepared by combining the LANCE Eu-W8044 labeled streptavidin and Biotin-cAMP in detection buffer according to the manufacturers protocol. 10 μL of the detection mix was added to each well of the Optiplate-384 which was covered with a plate seal and incubated under ambient conditions for 2 hours prior to reading the plate using an Envision (Perkin Elmer, Waltham, MA) multimode plate reader. Data was normalized by defining minimal effect as stimulation in the presence of 0.25% (v/v) DMSO and maximal effect as stimulation in the presence of 1 μM ZM241385 (Cayman, Cat. No. 1036). Curve fitting of the percent effect data versus the log of compound concentration used a 4-parameter concentration response curve fitting algorithm to calculate IC$_{50}$ values. Compound concentrations tested were 10,000, 3,333, 1,111, 370.4, 123.4, 41.2, 13.7, 4.6, 1.5 and 0.5 nM with 0.25% residual DMSO.

| Example | $A_{2A}$ IC$_{50}$ c AMP (nM) | $A_{2B}$ IC$_{50}$ c AMP (nM) |
|---|---|---|
| 151 | 3.8 | 56.9 |
| 152 | 5.9 | 371 |
| 153 | 7.4 | 719.8 |
| 154 | 1.2 | 974.1 |
| 155 | 23.9 | 1436 |
| 156 | 9.5 | 358.1 |
| 157 | 33.4 | 4481 |
| 158 | 1.1 | 32.9 |
| 159 | 1.0 | 29.3 |
| 160 | 8.7 | 647.8 |
| 161 | 38.9 | 3268 |
| 162 | 0.7 | 20.7 |

-continued

| Example | $A_{2A}$ IC$_{50}$ c AMP (nM) | $A_{2B}$ IC$_{50}$ c AMP (nM) |
|---|---|---|
| 163 | 36.0 | 5306 |
| 164 | 1.9 | 47.7 |
| 165 | 0.8 | 6.4 |
| 166 | 20.0 | 2769 |
| 167 | 0.6 | 46.0 |
| 168 | 23.9 | 4723 |
| 169 | 96.5 | 3382 |
| 170 | 0.8 | 14.1 |
| 171 | 1.2 | 11.3 |
| 172 | 60.5 | 14% Inh. @ 10000 nM |
| 173 | 20.7 | 2022 |
| 174 | 0.6 | 30.7 |
| 175 | 30.2 | 2004 |
| 176 | 0.9 | 10.2 |
| 177 | 154 | 3957 |
| 178 | 0.6 | 11.5 |
| 179 | 4.0 | 335.5 |
| 180 | 54.0 | 5342 |
| 181 | 16.0 | 5099 |
| 182 | 361.9 | >10000 |
| 183 | 2.0 | 90.6 |
| 184 | 4.9 | 345.5 |
| 185 | 1.1 | 49.8 |
| 186 | 1.0 | 25.8 |
| 187 | 2.6 | 95.8 |
| 188 | 1.5 | 53.1 |
| 189 | 0.5 | 53.4 |
| 190 | 0.8 | 55.9 |
| 191 | 0.9 | 92.4 |
| 192 | 0.8 | 72.4 |
| 193 | 1.3 | 250.7 |
| 194 | 1.7 | 318.4 |
| 195 | 3.4 | 389.5 |
| 196 | 3.7 | 474.9 |
| 197 | 6.4 | 93.0 |
| 198 | 4.3 | 52.4 |
| 199 | 2.5 | 97.5 |
| 200 | 2.5 | 102.5 |
| 201 | 1.9 | 38.4 |
| 202 | 1.4 | 62.4 |
| 203 | 7.7 | 53.2 |
| 204 | 7.8 | 87.7 |
| 205 | 7.0 | 1146 |
| 206 | 13.0 | 4314 |
| 207 | 0.9 | 10.37 |
| 208 | 0.7 | 2799 |
| 209 | 0.7 | 634.9 |
| 210 | 16.2 | 35% Inh. @ 10000 nM |
| 211 | 89.3 | >10000 |
| 212 | 121.7 | 27% Inh. @ 10000 nM |
| 213 | 330.8 | >10000 |
| 214 | 0.5 | 34.09 |
| 215 | 0.4 | 27.5 |
| 216 | 1.0 | 159.7 |
| 217 | 1.1 | 161.3 |
| 218 | 235.8 | 5775 |
| 219 | 246.7 | 27% Inh. @ 10000 nM |
| 220 | 20.4 | 30% Inh. @ 10000 nM |
| 221 | 0.5 | 63 |
| 222 | 34.6 | 3277 |
| 223 | 0.7 | 46 |
| 224 | 0.4 | 13.1 |
| 225 | 0.4 | 12.1 |
| 226 | 17.6 | 1611 |
| 227 | 40.2 | 5071 |
| 228 | 0.8 | 16.1 |
| 229 | 1.0 | 6.6 |
| 230 | 32.9 | 723.7 |
| 231 | 121.5 | 3845 |
| 232 | 1.3 | 12.7 |
| 233 | 0.7 | 5.6 |
| 234 | 46.8 | 1195 |

-continued

| Example | $A_{2A}$ IC$_{50}$ c AMP (nM) | $A_{2B}$ IC$_{50}$ c AMP (nM) |
|---|---|---|
| 235 | 438.8 | 4450 |
| 236 | 1.0 | 5.1 |
| 237 | 0.8 | 8.7 |
| 238 | 21.8 | 2438 |
| 239 | 75.1 | 10% Inh. @ 10000 nM |
| 240 | 1.2 | 22.6 |
| 241 | 1.3 | 21.7 |
| 242 | 2.0 | 34.9 |
| 243 | 2.6 | 50.7 |
| 244 | 0.9 | 18.8 |
| 245 | 2.0 | 25.8 |
| 246 | 3.2 | 21.3 |
| 247 | 4.5 | 21.8 |
| 248 | 1.4 | 8.4 |
| 249 | 26.9 | 197.1 |
| 250 | 0.7 | 4.9 |
| 251 | 39.5 | 387.1 |
| 252 | 95.0 | 8157 |
| 253 | 123.1 | >10000 |
| 254 | 1.5 | 10. |
| 255 | 2.6 | 28.8 |
| 256 | 240.7 | 3892 |
| 257 | 540.6 | 25% Inh. @ 10000 nM |
| 258 | 2.3 | 8.1 |
| 259 | 2.3 | 11.8 |
| 260 | 1.7 | 10.0 |
| 261 | 86.6 | 1473 |
| 262 | 2.2 | 23.9 |
| 263 | 26.0 | 510.8 |
| 264 | 3.0 | 14.3 |
| 265 | 1.3 | 4.5 |
| 266 | 64.2 | 579.6 |
| 267 | 175.1 | 1215 |
| 268 | 0.7 | 4.7 |
| 269 | 1.2 | 6.4 |
| 270 | 5.2 | 30.3 |
| 271 | 21.4 | 241.8 |
| 272 | 43.6 | 5800 |
| 273 | 1.2 | 26.7 |
| 274 | 0.7 | 70.5 |
| 275 | 15.6 | 2468 |

What is claimed is:

1. A method of treating cancer comprising administering an effective amount of a compound having a structural Formula (I.1)

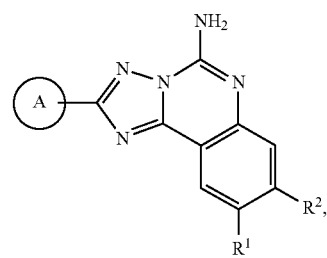

or a pharmaceutically acceptable salt thereof, wherein:

$R^1$ is selected from F, Cl, and OCH$_3$;

$R^2$ is O(C$_1$-C$_6$)alkyl;

ring A is

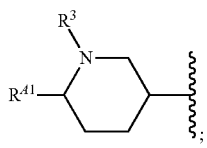

-continued $R^{41}$ is selected from H, and $(C_1-C_4)$alkyl.

2. The method of claim 1, wherein said cancer is selected from the group consisting of melanoma, head & neck cancer, classical Hodgkin lymphoma, urothelial carcinoma, gastric cancer, cervical cancer, primary mediastinal large-B-cell lymphoma, microsatellite instability-high cancer, non-small cell lung cancer, hepatocellular carcinoma, clear cell kidney cancer, colorectal cancer, breast cancer, squamous cell lung cancer, basal carcinoma, sarcoma, bladder cancer, endometrial cancer, pancreatic cancer, liver cancer, gastrointestinal cancer, multiple myeloma, renal cancer, mesothelioma, ovarian cancer, anal cancer, biliary tract cancer, esophageal cancer, salivary cancer, and prostate cancer, and metastatic castration resistant prostate cancer.

3. The method of claim 2, wherein the cancer is selected from the group consisting of non-small cell lung cancer, colorectal cancer, pancreatic cancer, head & neck cancer, and cervical cancer.

4. The method of claim 2, wherein said compound, or pharmaceutically acceptable salt thereof, is administered in combination with an additional therapeutic agent.

5. The method of claim 4, wherein said additional therapeutic agent is a PD-1 antagonist.

6. The method of claim 5, wherein said PD-1 antagonist is selected from the group consisting of pembrolizumab, nivolumab, atezolizumab, durvalumab, and avelumab.

7. The method of claim 6, wherein said PD-1 antagonist is pembrolizumab.

8. A method of treating cancer comprising administering an effective amount of a compound to a person in need thereof, wherein the compound is

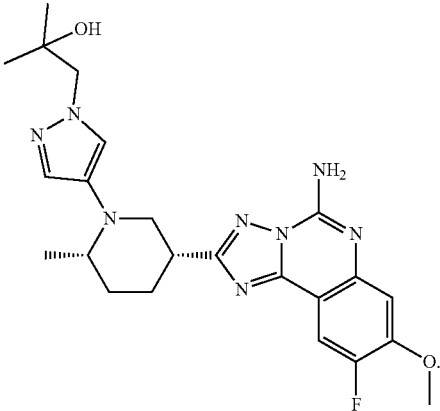 [SMILES: COc1cc2nc(N)n3nc([C@@H]4CC[C@H](C)N(c5cnn(CC(C)(C)O)c5)C4)nc3c2cc1F]

$R^3$ is selected from pyrazolyl, triazolyl, and pyridinyl, wherein said pyrazolyl and said triazolyl, are substituted with 1 or 2 $R^{3A}$ groups, and wherein said pyridinyl is substituted with 1, 2, or 3 $R^{3A}$ groups, wherein:
each $R^{3A}$ is independently selected from $CH_3$,

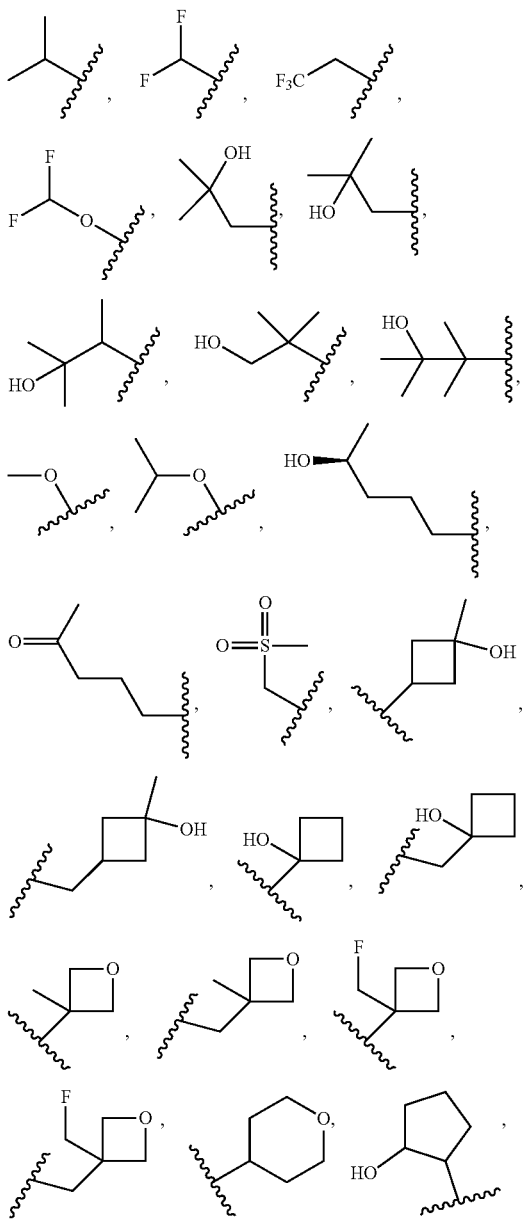

9. The method of claim 8, wherein said cancer is selected from the group consisting of melanoma, head & neck cancer, classical Hodgkin lymphoma, urothelial carcinoma, gastric cancer, cervical cancer, primary mediastinal large-B-cell lymphoma, microsatellite instability-high cancer, non-small cell lung cancer, hepatocellular carcinoma, clear cell kidney cancer, colorectal cancer, breast cancer, squamous cell lung cancer, basal carcinoma, sarcoma, bladder cancer, endometrial cancer, pancreatic cancer, liver cancer, gastrointestinal cancer, multiple myeloma, renal cancer, mesothelioma, ovarian cancer, anal cancer, biliary tract cancer, esophageal cancer, salivary cancer, and prostate cancer, and metastatic castration resistant prostate cancer.

10. The method of claim 9, wherein the cancer is selected from the group consisting of non-small cell lung cancer, colorectal cancer, pancreatic cancer, head & neck cancer, and cervical cancer.

11. The method of claim 9, wherein said compound is administered in combination with an additional therapeutic agent.

12. The method of claim 11, wherein said additional therapeutic agent is a PD-1 antagonist.

13. The method of claim 12, wherein said PD-1 antagonist is selected from the group consisting of pembrolizumab, nivolumab, atezolizumab, durvalumab, and avelumab.

14. The method of claim 13, wherein said PD-1 antagonist is pembrolizumab.

15. A method of treating cancer comprising administering an effective amount of a pharmaceutically acceptable salt of a compound to a person in need thereof, wherein the compound is

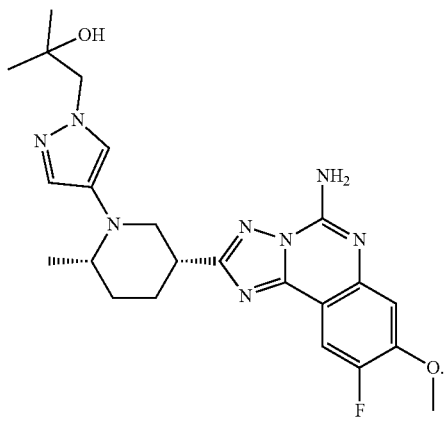 [SMILES: COc1cc2nc(N)n3nc([C@@H]4CC[C@H](C)N(c5cnn(CC(C)(C)O)c5)C4)nc3c2cc1F]

16. The method of claim 15, wherein said cancer is selected from the group consisting of melanoma, head & neck cancer, classical Hodgkin lymphoma, urothelial carcinoma, gastric cancer, cervical cancer, primary mediastinal large-B-cell lymphoma, microsatellite instability-high cancer, non-small cell lung cancer, hepatocellular carcinoma, clear cell kidney cancer, colorectal cancer, breast cancer, squamous cell lung cancer, basal carcinoma, sarcoma, bladder cancer, endometrial cancer, pancreatic cancer, liver cancer, gastrointestinal cancer, multiple myeloma, renal cancer, mesothelioma, ovarian cancer, anal cancer, biliary tract cancer, esophageal cancer, salivary cancer, and prostate cancer, and metastatic castration resistant prostate cancer.

17. The method of claim 16, wherein the cancer is selected from the group consisting of non-small cell lung cancer, colorectal cancer, pancreatic cancer, head & neck cancer, and cervical cancer.

18. The method of claim 16, wherein said pharmaceutically acceptable salt of said compound is administered in combination with an additional therapeutic agent.

19. The method of claim 18, wherein said additional therapeutic agent is a PD-1 antagonist.

20. The method of claim 19, wherein said PD-1 antagonist is selected from the group consisting of pembrolizumab, nivolumab, atezolizumab, durvalumab, and avelumab.

21. The method of claim 20, wherein said PD-1 antagonist is pembrolizumab.

22. A method of treating cancer comprising administering an effective amount of a compound, or pharmaceutically acceptable salt thereof to a person in need thereof, wherein the compound is selected from the group consisting of:

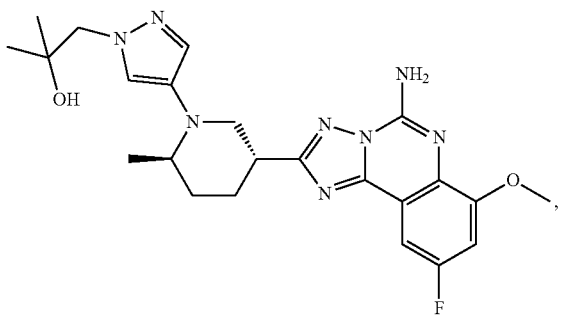

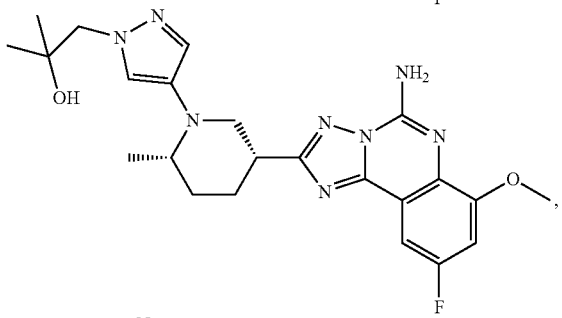

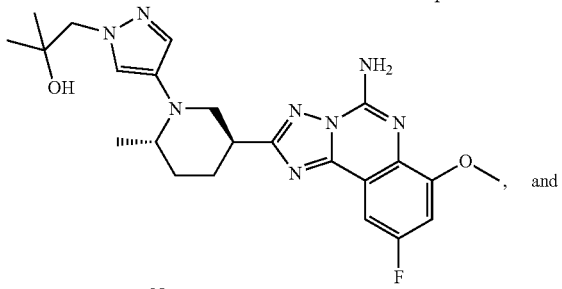

, and

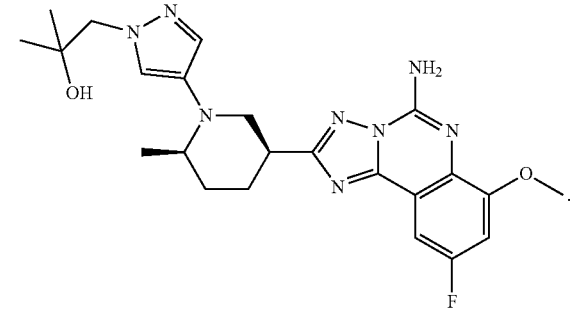

23. The method of claim 22, wherein said cancer is selected from the group consisting of melanoma, head & neck cancer, classical Hodgkin lymphoma, urothelial carcinoma, gastric cancer, cervical cancer, primary mediastinal large-B-cell lymphoma, microsatellite instability-high cancer, non-small cell lung cancer, hepatocellular carcinoma, clear cell kidney cancer, colorectal cancer, breast cancer, squamous cell lung cancer, basal carcinoma, sarcoma, bladder cancer, endometrial cancer, pancreatic cancer, liver cancer, gastrointestinal cancer, multiple myeloma, renal cancer, mesothelioma, ovarian cancer, anal cancer, biliary tract cancer, esophageal cancer, salivary cancer, and prostate cancer, and metastatic castration resistant prostate cancer.

24. The method of claim 23, wherein the cancer is selected from the group consisting of non-small cell lung cancer, colorectal cancer, pancreatic cancer, head & neck cancer, and cervical cancer.

25. The method of claim 23, wherein said compound or pharmaceutically acceptable salt thereof is administered in combination with an additional therapeutic agent.

26. The method of claim 25, wherein said additional therapeutic agent is a PD-1 antagonist.

27. The method of claim 26, wherein said PD-1 antagonist is selected from the group consisting of pembrolizumab, nivolumab, atezolizumab, durvalumab, and avelumab.

28. The method of claim 27, wherein said PD-1 antagonist is pembrolizumab.

* * * * *